US012479843B2

(12) United States Patent
Xie et al.

(10) Patent No.: US 12,479,843 B2
(45) Date of Patent: Nov. 25, 2025

(54) SPIRO RING-CONTAINING QUINAZOLINE COMPOUNDS

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Gang Cao, Shanghai (CN); Lihui Qian, Shanghai (CN)

(73) Assignee: SOOCHOW UNIVERSITY, Suzhou (CN)

( * ) Notice: Subject to any disclaimer, the term of this patent is extended or adjusted under 35 U.S.C. 154(b) by 859 days.

(21) Appl. No.: 17/767,034

(22) PCT Filed: Dec. 25, 2020

(86) PCT No.: PCT/CN2020/139530

§ 371 (c)(1),
(2) Date: Apr. 6, 2022

(87) PCT Pub. No.: WO2021/129820

PCT Pub. Date: Jul. 1, 2021

(65) Prior Publication Data

US 2023/0002382 A1 Jan. 5, 2023

(30) Foreign Application Priority Data

Dec. 27, 2019 (CN) ......................... 201911386239.6
Jun. 1, 2020 (CN) ......................... 202010486384.8

(51) Int. Cl.
*C07D 471/10* (2006.01)
*C07D 519/00* (2006.01)

(52) U.S. Cl.
CPC ......... *C07D 471/10* (2013.01); *C07D 519/00* (2013.01)

(58) Field of Classification Search
CPC ............................ C07D 471/10; C07D 519/00
(Continued)

(56) References Cited

U.S. PATENT DOCUMENTS

2019/0292182 A1 9/2019 Kuramoto et al.

FOREIGN PATENT DOCUMENTS

CN 103772411 A 5/2014
CN 108779097 A 11/2018
(Continued)

OTHER PUBLICATIONS

Vippagunta et al., Advanced Drug Reviews, 48 (2001), pp. 3-26 (Year: 2001).*

*Primary Examiner* — Kristin A Vajda
(74) *Attorney, Agent, or Firm* — SZDC Law PC

(57) ABSTRACT

The present invention relates to a spiro ring-containing quinazoline compound, a preparation method therefor, and use of the compound as a K-Ras G12C inhibitor in preparing antitumor medicaments.

(1)

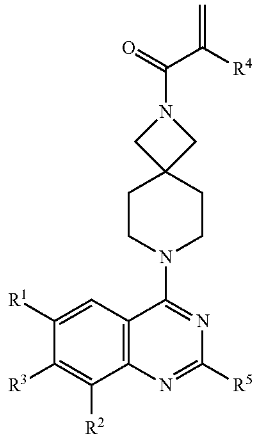

(2)

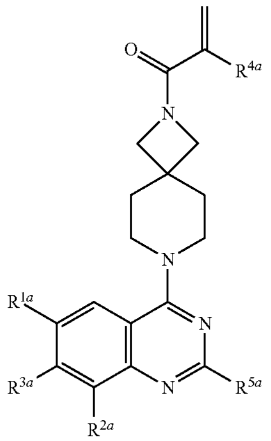

(3)

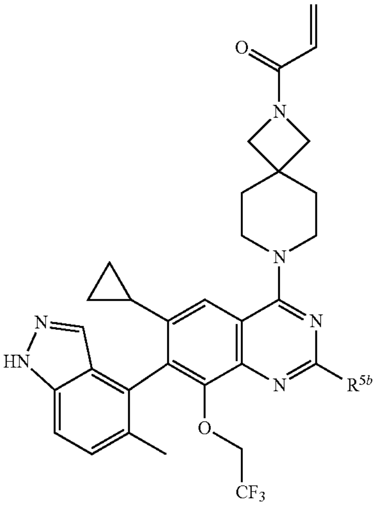

18 Claims, 1 Drawing Sheet

(58) Field of Classification Search
USPC ..................................................... 514/210.16
See application file for complete search history.

(56) References Cited

FOREIGN PATENT DOCUMENTS

| | | | |
|---|---|---|---|
| CN | 110088098 | A | 8/2019 |
| CN | 110267957 | A | 9/2019 |
| CN | 111499634 | A | 8/2020 |
| CN | 112110918 | A | 12/2020 |
| EP | 4130000 | A1 | 2/2023 |
| JP | 2018513853 | A | 5/2018 |
| JP | 2018533611 | A | 11/2018 |
| JP | 2022509830 | A | 1/2022 |
| RU | 2230062 | C2 | 6/2004 |
| WO | 2013159698 | A1 | 10/2013 |
| WO | 2016164675 | A1 | 10/2016 |
| WO | 2017087528 | A1 | 5/2017 |
| WO | 2018143315 | A1 | 8/2018 |
| WO | 2020027083 | A1 | 2/2020 |
| WO | 2020027084 | A1 | 2/2020 |
| WO | 2020113071 | A1 | 6/2020 |
| WO | 2020177629 | A1 | 9/2020 |

* cited by examiner

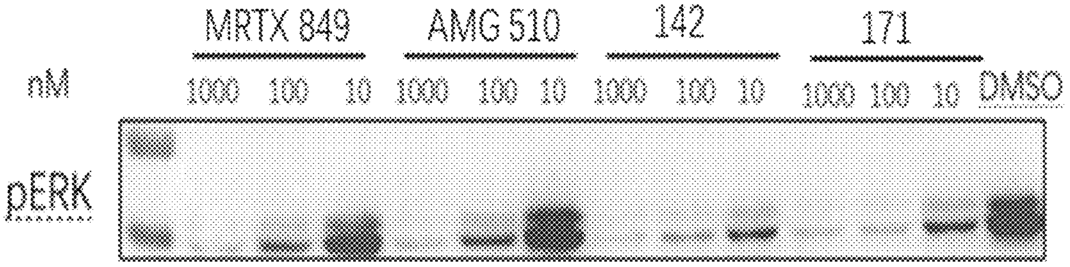
MRTX 849
AMG 510
142
171
nM
1000 100 10 1000 100 10 1000 100 10 1000 100 10 DMSO
pERK

SPIRO RING-CONTAINING QUINAZOLINE COMPOUNDS

The present application is the National Stage Application of PCT/CN2020/139530, filed on Dec. 25, 2020, which claims priority to Chinese Patent application No. CN201911386239.6 filed on Dec. 27, 2019 and Chinese Patent application No. CN202010486384.8 filed on Jun. 1, 2020, the contents of which are incorporated herein by reference in their entirety.

TECHNICAL FIELD

The present invention belongs to the field of medicinal chemistry, and particularly to a spiro ring-containing quinazoline compound, a preparation method therefor, and use of the compound as a K-Ras G12C inhibitor in preparing antitumor medicaments.

BACKGROUND

Ras protein family members are important signal transduction molecules in cells, and play an important role in the growth and development. Extensive analysis and study of in vitro tumor cells, animal models and human tumor samples indicate that the over-activation of Ras family proteins is an early event in the development of human tumors and is one of the important causes of the development and progression of many types of cancer. Targeting Ras proteins and inhibiting the Ras protein activity are therefore important means of treating related tumors.

An Ras protein exists in two forms. It is in an unactivated resting state when bound to GDP, and when a cell receives signals such as growth factor stimulation, it is bound to GTP and thus activated. Activated Ras proteins recruit a variety of signal-transducing adaptor proteins to promote phosphorylation of downstream signaling molecules such as ERK and S6, thereby activating the Ras signal transduction pathway and regulating the growth, survival, migration and differentiation of cells. Ras proteins can hydrolyze GTP back to GDP due to their GTPase activity. Besides, the GTPase-activating proteins (GAPs) in cells interact with Ras, greatly improving the GTPase activity of Ras and thereby preventing Ras proteins from being overly activated.

Mutations in the K-Ras, H-Ras and N-Ras proteins of the Ras protein family are one of the common genetic mutations in a variety of tumors, and are a major factor leading to over-activation of Ras proteins in tumors. Compared to the wild-type Ras proteins, Ras proteins with these mutations have unregulated activity; they are stably bound to GTP and constantly activated, thereby promoting the growth, migration and differentiation of tumor cells. Among these mutations, those in K-Ras proteins are the most common ones, accounting for 85% of all Ras mutations, while those in N-Ras (12%) and H-Ras (3%) are relatively rare. K-Ras mutations are very common in many types of cancer, including pancreatic cancer (95%), colorectal cancer (45%), lung cancer (25%), etc., while relatively rare (<2%) in breast cancer, ovarian cancer and brain cancer. K-Ras mutations mainly occur at position G12, and G12C mutation is the most common one. For example, in non-small cell lung cancer (NSCLC), about 50% of K-Ras mutations are K-Ras G12C, and G12V and G12D are the second most common mutations. Genomic studies show that K-Ras mutations in non-small cell lung cancer generally do not coexist with EGFR, ALK, ROS1, RET and BRAF mutations, but coexist with STK11, KEAP1, TP53 and other mutations, suggesting that K-Ras mutations may be involved in malignant transformation, proliferation and invasion of cells synergistically with STK11, KEAP1, TP53 and other mutations. In addition to tumors, abnormal activation of Ras proteins is also involved in non-tumor diseases including diabetes, neurodegenerative diseases, etc. Hence, Ras protein-targeting small-molecule compounds can benefit a large number of cancer patients with specific genetic mutations and non-cancer patients with over-activation of the Ras pathway.

Since the discovery of Ras mutations in tumors that happened forty years ago, although we have gained deeper insight into the pathogenesis involving the Ras pathway, no clinically effective therapeutic approach targeting Ras proteins has yet come onto the market for a large number of patients with Ras protein mutations and over-activation of the Ras pathway. Therefore, the development of a high-activity small-molecule inhibitor targeted at Ras proteins, particularly the K-Ras G12C protein with high frequency of mutation, is of great clinical significance.

K-Ras G12C muteins, as a leading therapeutic target, have not been extensively researched at present, and only a few compounds, such as AMG510 of Amgen and MRTX849 of Mirati, have been under clinical research. In 2018, a K-Ras G12C mutation-targeting covalent inhibitor ARS-1620 was reported in *Cell* (*Cell,* 2018, 172: 578-589). A class of spiro compounds with K-Ras G12C activity and anti-tumor activity in mice are reported in patent WO2018/143315, and a general formula A, a representative compound B (Example 35 in the patent) and a representative compound C (Example 65 in the patent) thereof are shown as the structures below (refer to the patent for the definitions of the symbols in the formula):

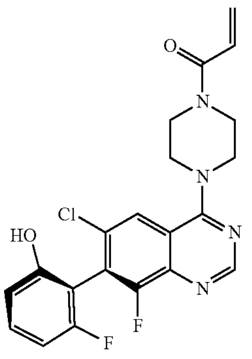

ARS-1620

A

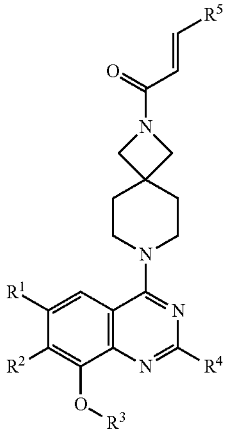

-continued

B

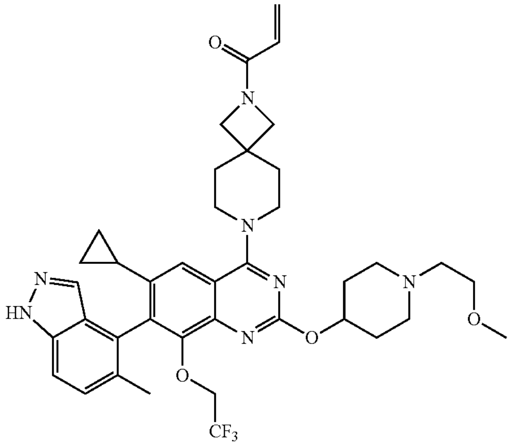

C

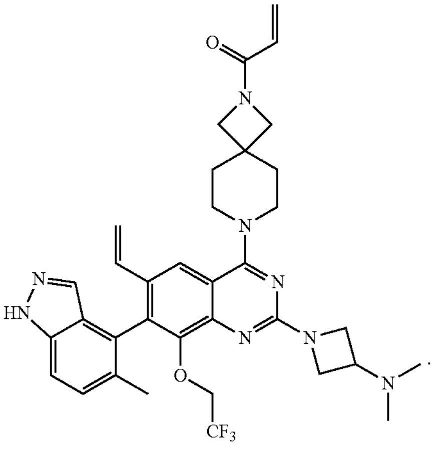

Currently, there is an urgent need to study and discover compounds with good K-Ras G12C activity and superior pharmacokinetic properties.

SUMMARY

The present invention aims to provide a compound of a structural general formula as shown in formula (1), isomers thereof, crystalline forms thereof, pharmaceutically acceptable salts thereof, hydrates thereof or solvates thereof:

(1)

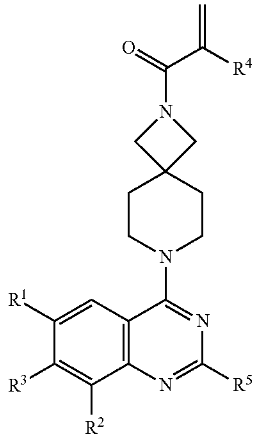

wherein in formula (1):

$R^1$ is H, halogen, C1-C3 alkyl, C2-C4 alkenyl, C2-C4 alkynyl or C3-C6 cycloalkyl;

$R^2$ is C1-C3 alkoxy, C1-C3 haloalkoxy or —$NR^aR^b$, wherein $R^a$ and $R^b$ are independently H, C1-C3 alkyl or C1-C3 haloalkyl, or $R^a$ and $R^b$, together with a N atom, form a 4-7 membered heterocycloalkyl group, wherein the heterocycloalkyl group may be substituted with 1-3 halogen atoms;

$R^3$ is

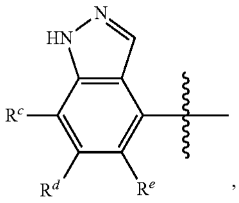,
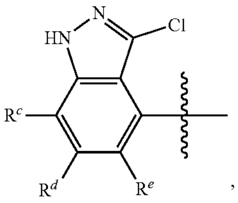,
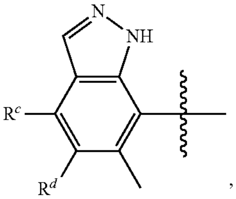,
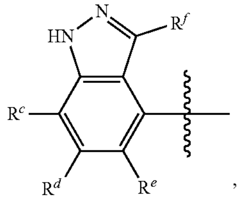,
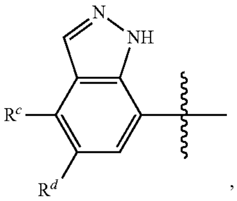,
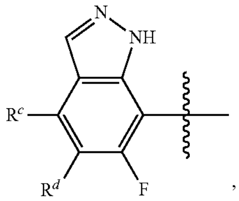,
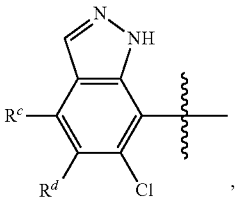,
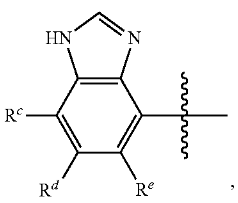, -continued

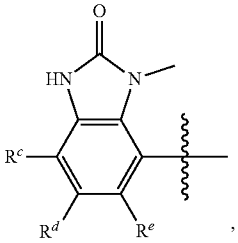
,
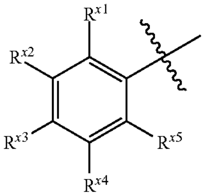
,
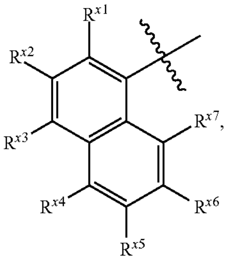
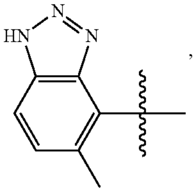
,
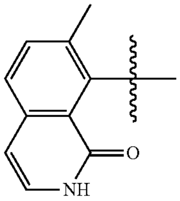
or
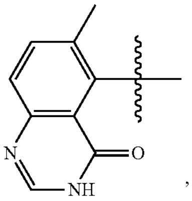
, wherein $R^c$ is H or F; $R^d$ is H, F, Cl or Me; $R^e$ is H, F, Cl or Me; $R^f$ is F, $NH_2$, Me or cyclopropyl; $R^{x1}$, $R^{x2}$, $R^{x3}$, $R^{x4}$, $R^{x5}$, $R^{x6}$ and $R^{x7}$ are independently H, F, Cl, OH, OMe, $NH_2$, $CF_3$, C1-C3 alkyl or C3-C6 cycloalkyl;

$R^4$ is H, halogen, CN, C1-C3 alkyl, C1-C3 haloalkyl or heteroaryl; and when $R^3$ is

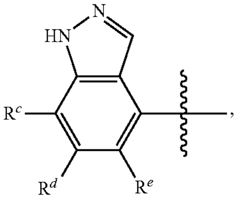
,
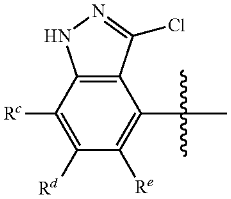
or
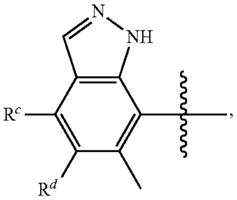

and $R^4$ is H, $R^5$ is:

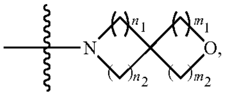
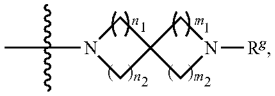

-continued

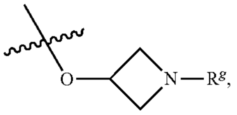
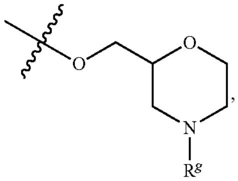
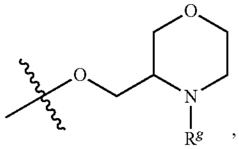
,
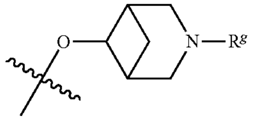
,
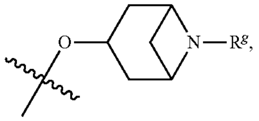
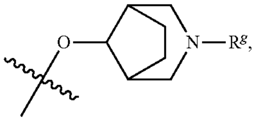
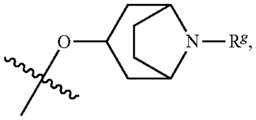
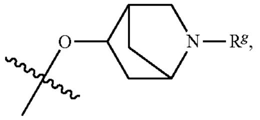
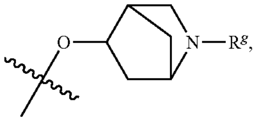
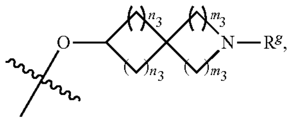
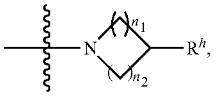
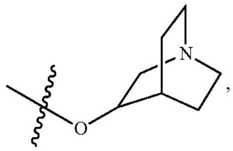
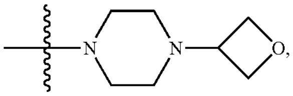
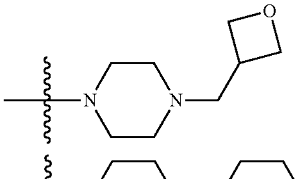
or
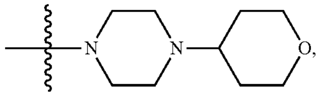

wherein $n_1$, $n_2$, $n_3$, $m_1$, $m_2$ and $m_3$ are independently integers of 1 or 2; $R^g$ is C1-C3 alkyl, C3-C6 cycloalkyl, (C1-C3) alkoxy-(C2-C3)alkyl-, (halogenated C1-C3)alkoxy-(C2-C3) alkyl-, (C3-C6)cycloalkyl-(C1-C3)alkyl-, heterocycloalkyl, heterocycloalkyl-(C1-C3)alkyl-, C1-C3 haloalkyl or cyano-substituted C1-C3 alkyl; $R^h$ is

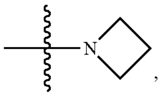
,
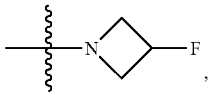
,
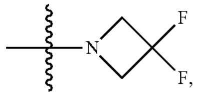
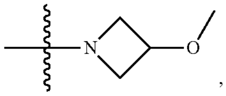
,
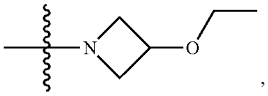
,
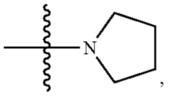
,

-continued
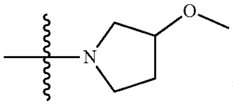, 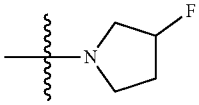, 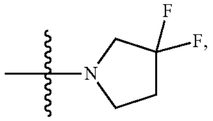 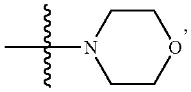, 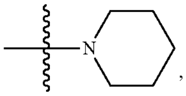, 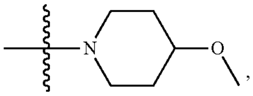, 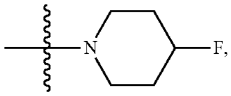 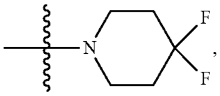, 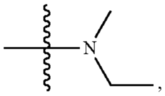, 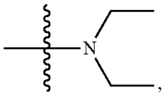, 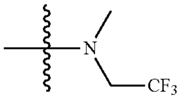 or 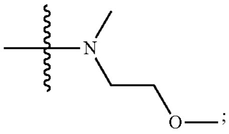;
when $R^3$ is
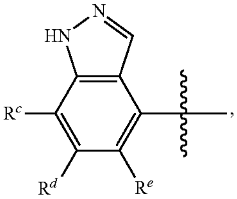, 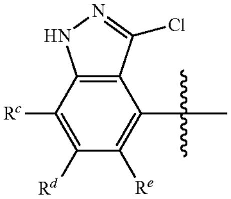 or 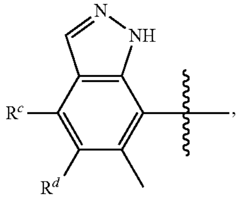,
and $R^4$ is halogen, CN, C1-C3 alkyl, C1-C3 haloalkyl or heteroaryl; or, when $R^3$ is
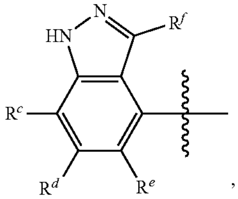, 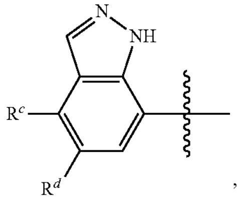, 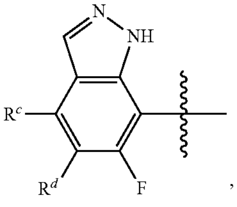, 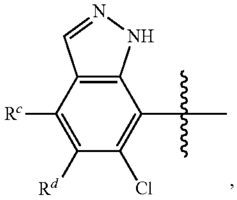,
-continued
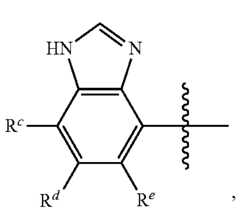, 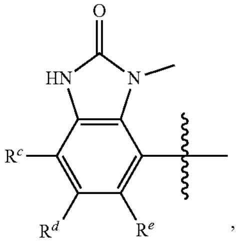, 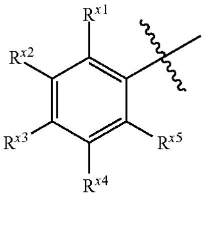, 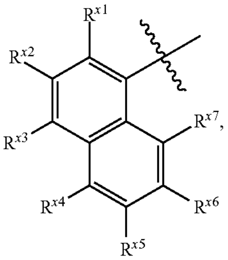 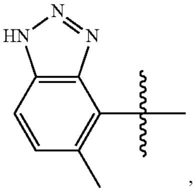, 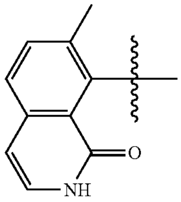 or 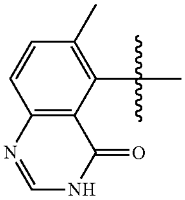, $R^5$ is: 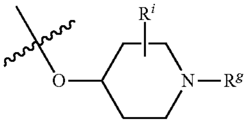, 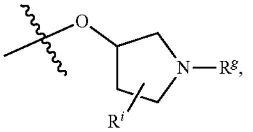 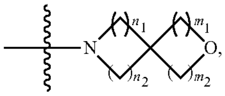 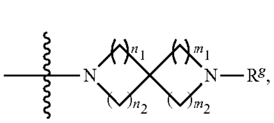 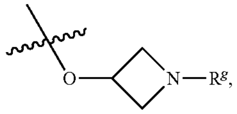 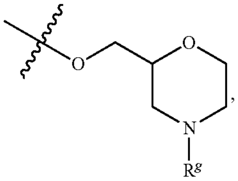, 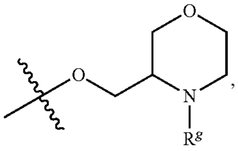, 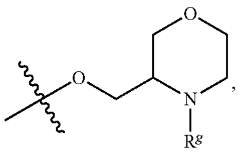, 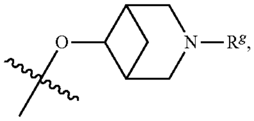 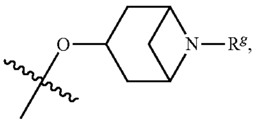 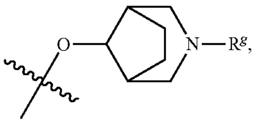

-continued

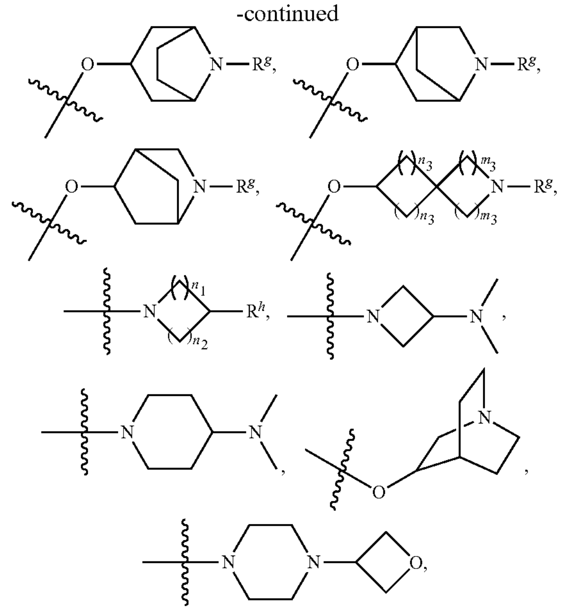

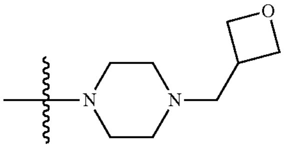

or

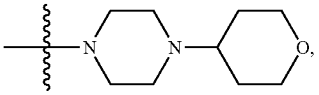

wherein $n_1$, $n_2$, $n_3$, $m_1$, $m_2$ and $m_3$ are independently integers of 1 or 2;

$R^g$ is C1-C3 alkyl, C3-C6 cycloalkyl, (C1-C3)alkoxy-(C2-C3)alkyl-, (halogenated C1-C3)alkoxy-(C2-C3)alkyl-, (C3-C6)cycloalkyl-(C1-C3)alkyl-, heterocycloalkyl, heterocycloalkyl-(C1-C3)alkyl-, C1-C3 haloalkyl or cyano-substituted C1-C3 alkyl; $R^h$ is

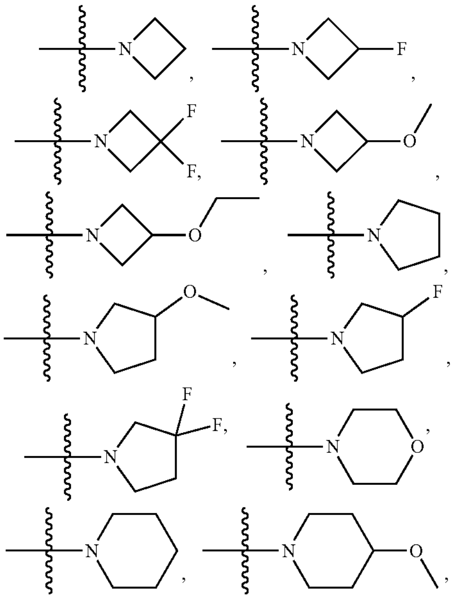

-continued

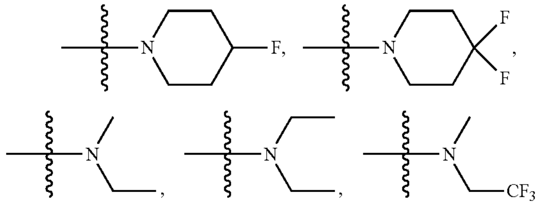

or

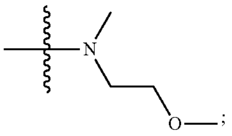

$R^i$ is H, halogen, methyl or cyano.

In another preferred embodiment, in the general formula (1), $R^1$ is H, F, Cl, Me, Et, vinyl, isopropyl, ethynyl or cyclopropyl.

In another preferred embodiment, in the general formula (1), $R^2$ is $CH_3CH_2O$—, $CF_3CH_2O$—, $CHF_2CH_2O$—,

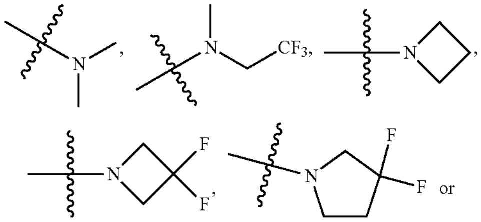

or

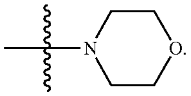

In another preferred embodiment, in the general formula (1), $R^3$ is

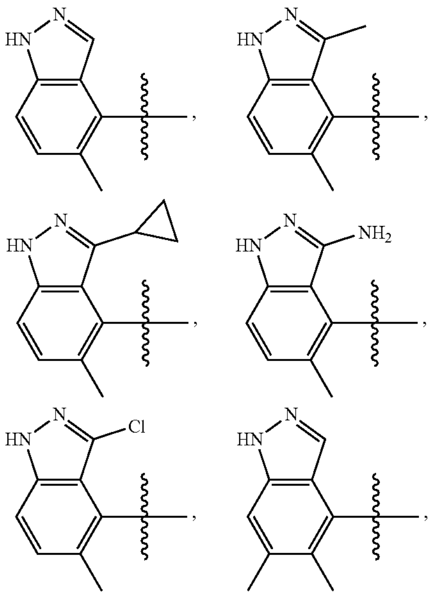

-continued
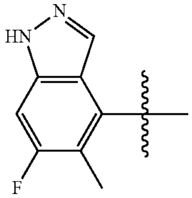, 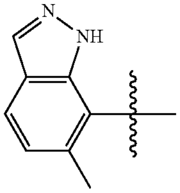,
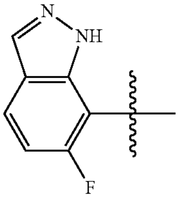, 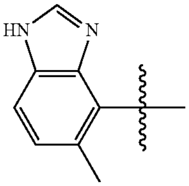,
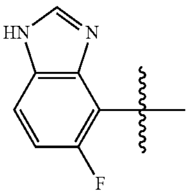, 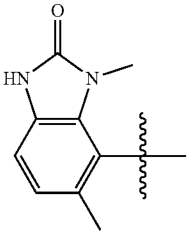,
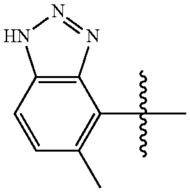, 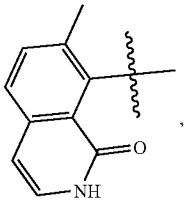,
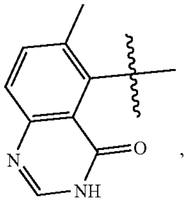, 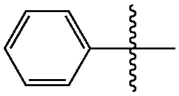,
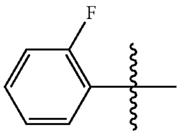, 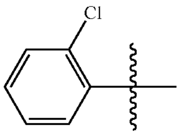, 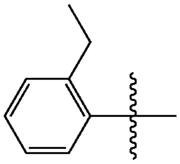,
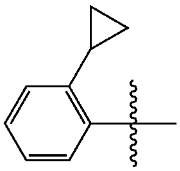, 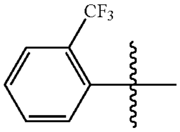, 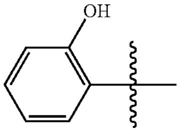,
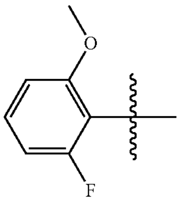, 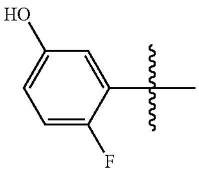,
-continued
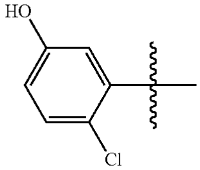, 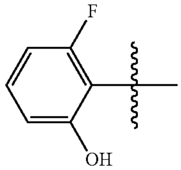,
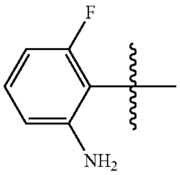, 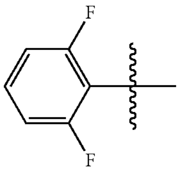,
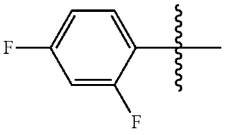, 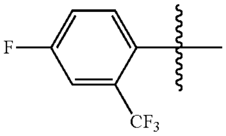,
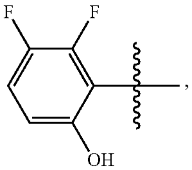, 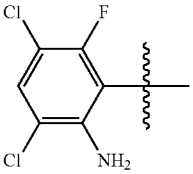,
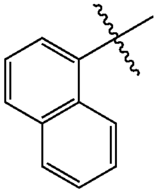, 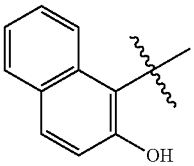 or
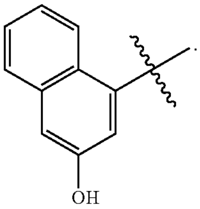.
In another preferred embodiment, in the general formula (1), $R^4$ is H, F, CN, Me, $CF_3$,
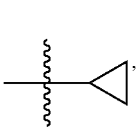, 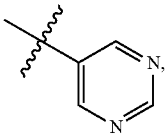, 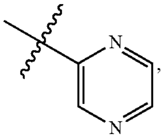,
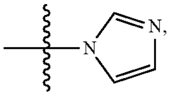, 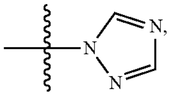, 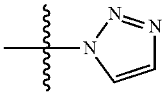 or
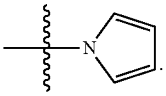.
In another preferred embodiment, in the general formula (1), when $R^3$ is

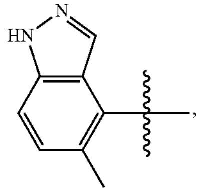
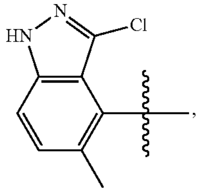
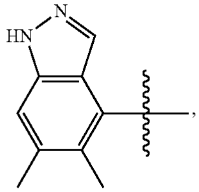
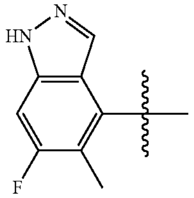
or
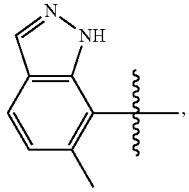
and $R^4$ is H, $R^5$ is:
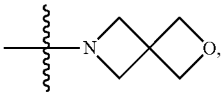
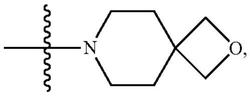
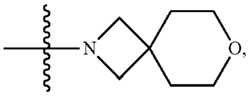
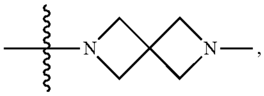
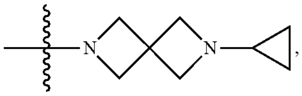
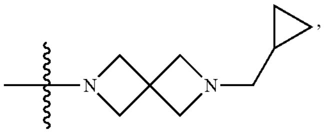
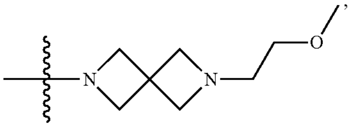
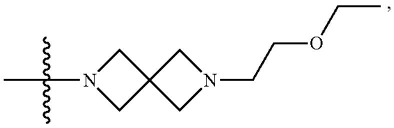
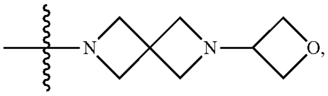
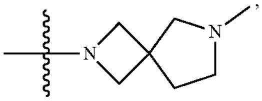
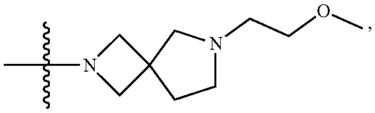
-continued
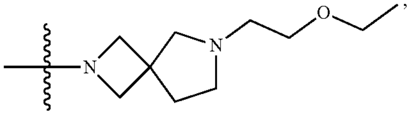
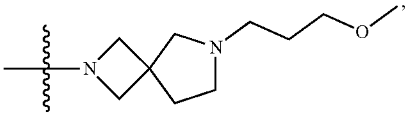
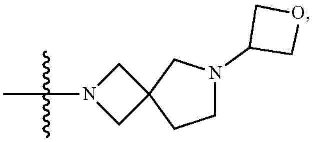
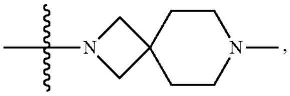
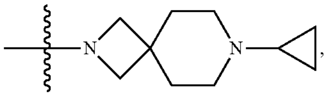
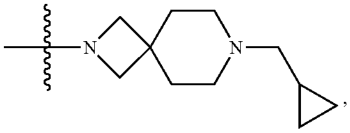
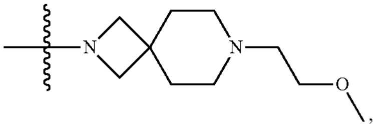
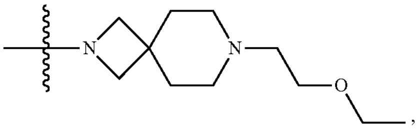
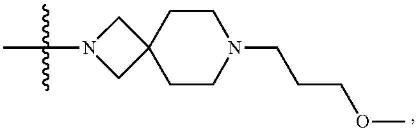
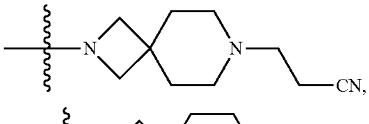
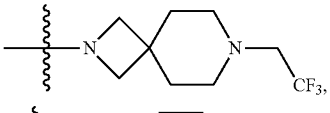
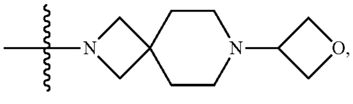
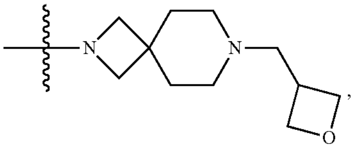
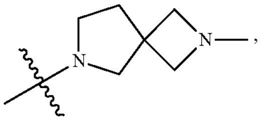

-continued
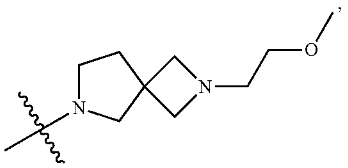,
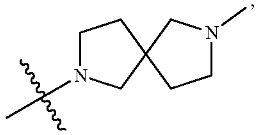,
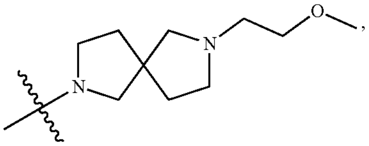,
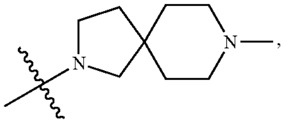,
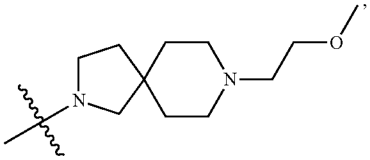,
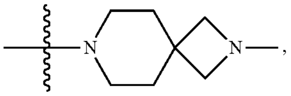,
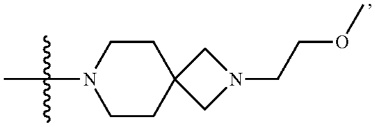,
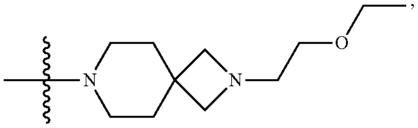,
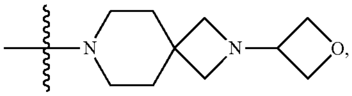,
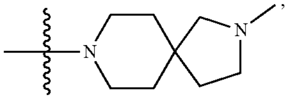,
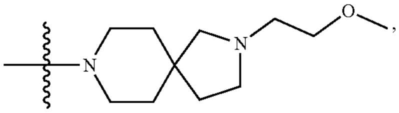,
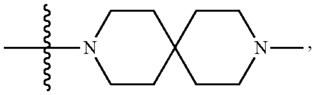,
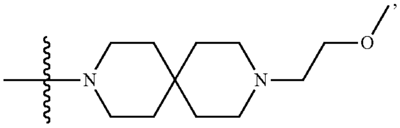,
-continued
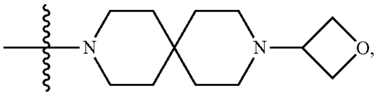,
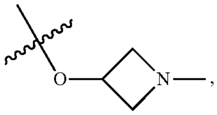,
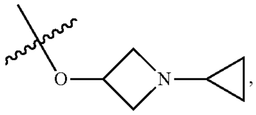,
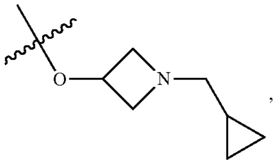,
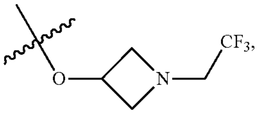,
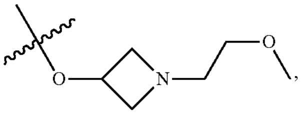,
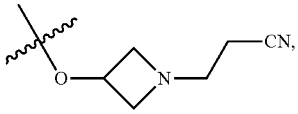,
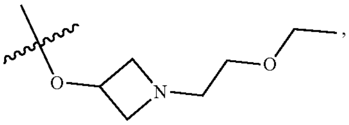,
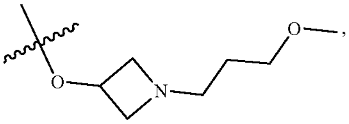,
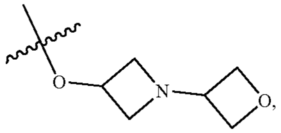,
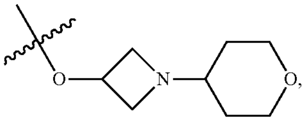,
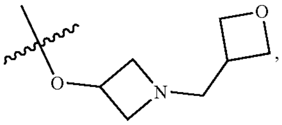,
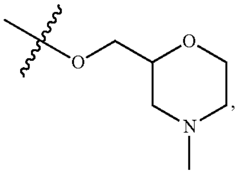,
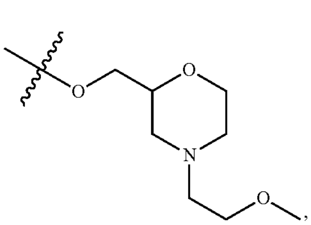,
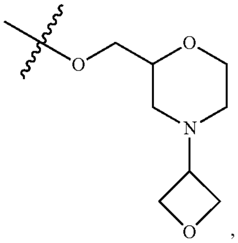,
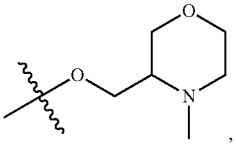,
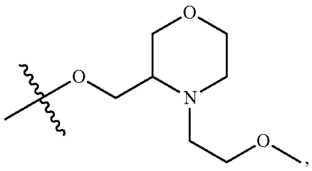, -continued
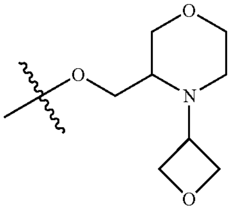
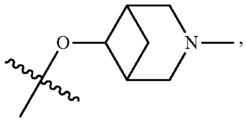
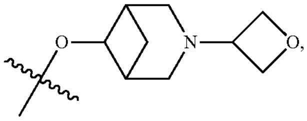
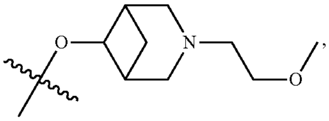
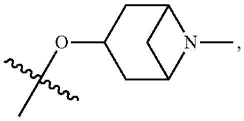
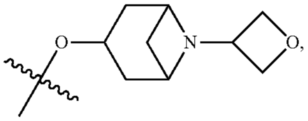
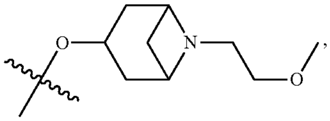
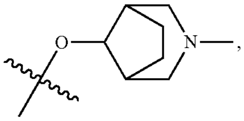
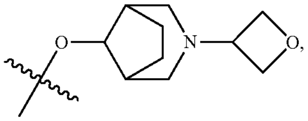
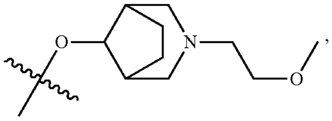
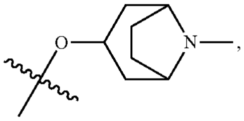
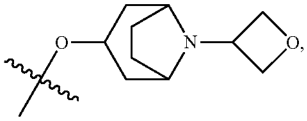
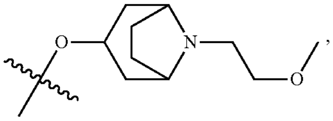
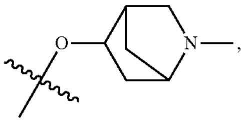
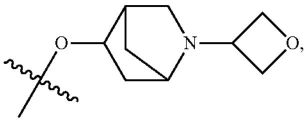
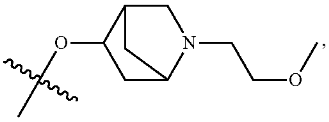
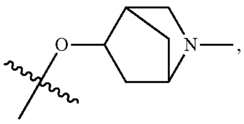
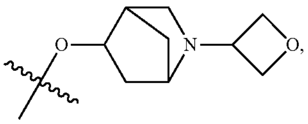
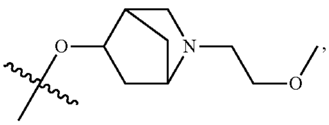
-continued
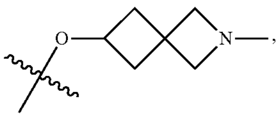
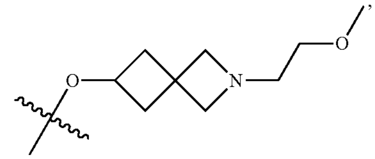
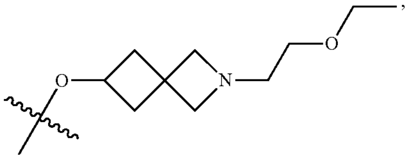
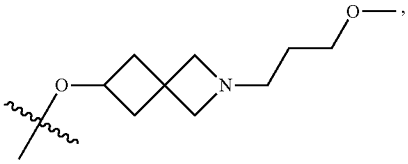
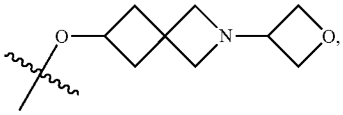
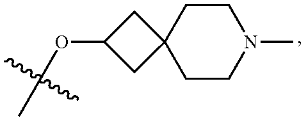
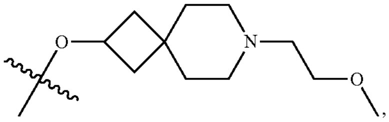
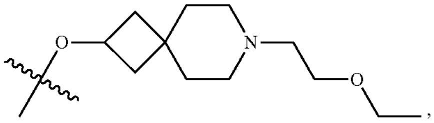
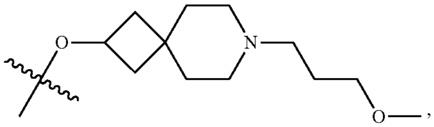
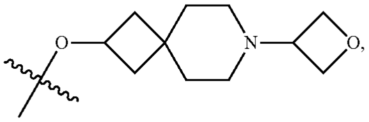
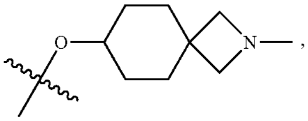
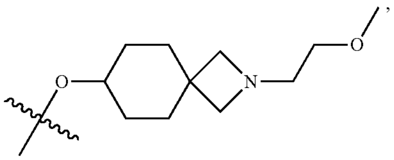

-continued
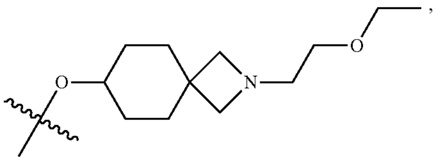
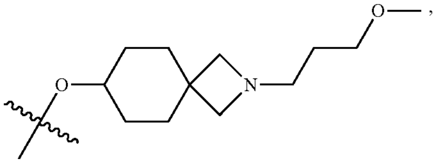
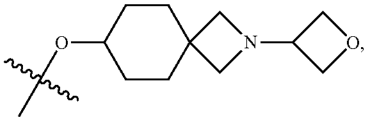
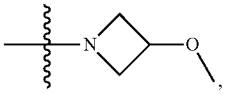
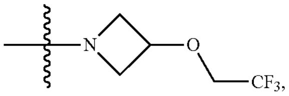
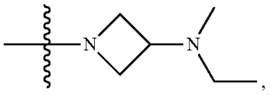
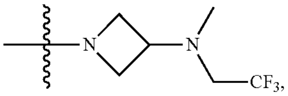
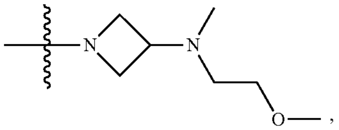
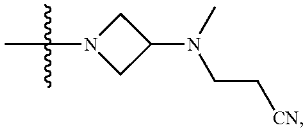
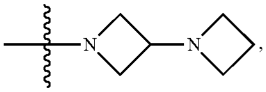
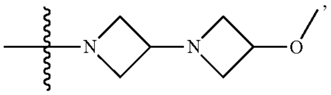
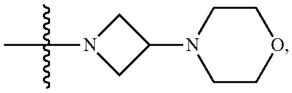
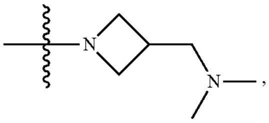
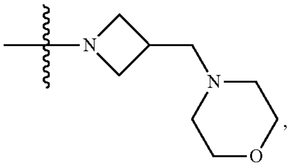
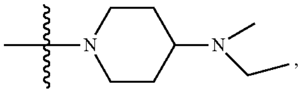
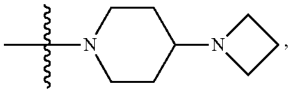
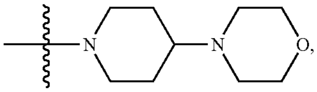
-continued
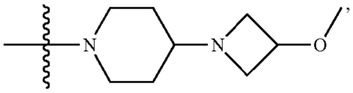
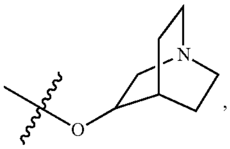
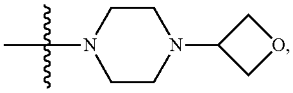
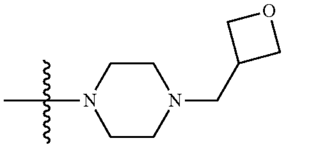
or
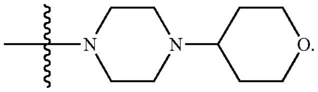
In another preferred embodiment, in the general formula (1), when $R^3$ is
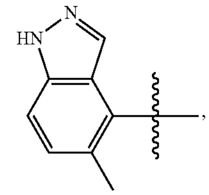
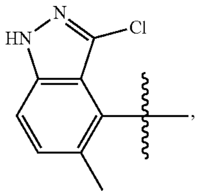
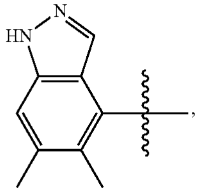
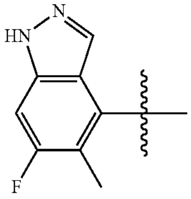
or
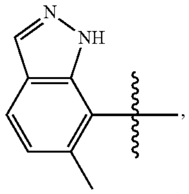
and $R^4$ is F, CN, Me, $CF_3$,
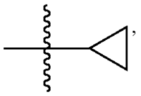
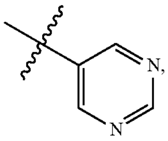
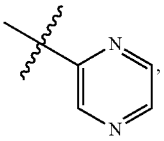
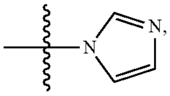
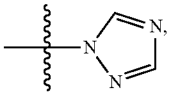
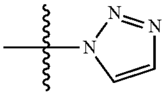
or
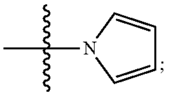
or, when $R^3$ is

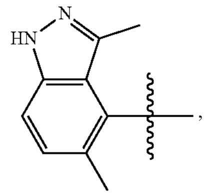, 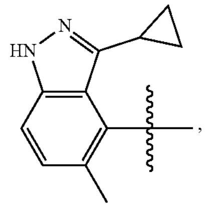,
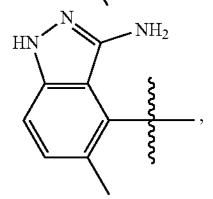, 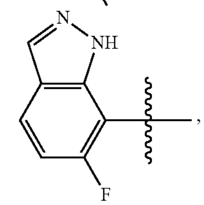,
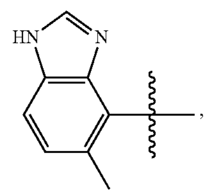, 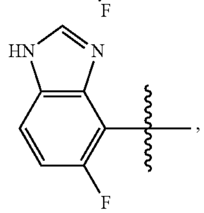,
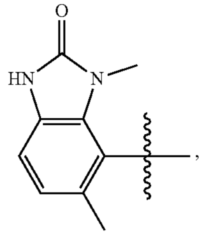, 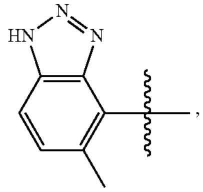,
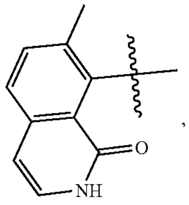, 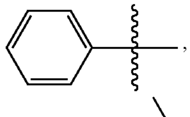,
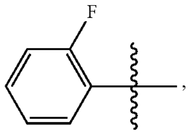, 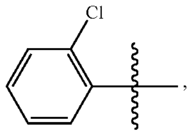, 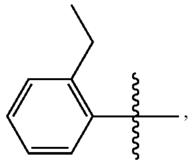,
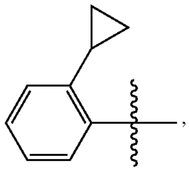, 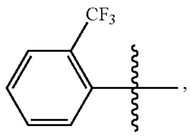, 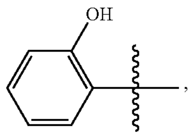,
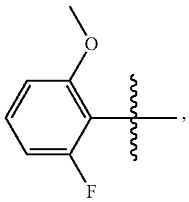, 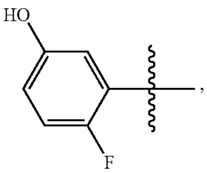,
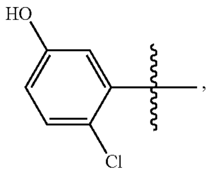, 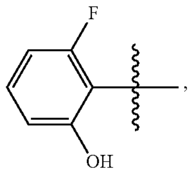,
-continued
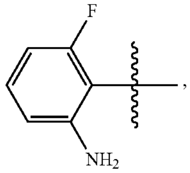, 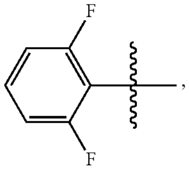,
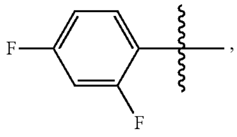, 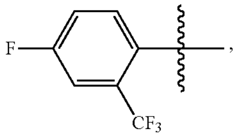,
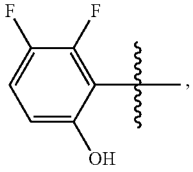, 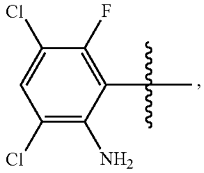,
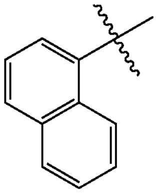, 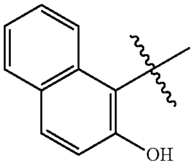 or
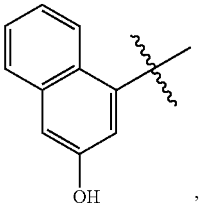 [SMILES: *c1cc(O)cc2ccccc12], $R^5$ is : 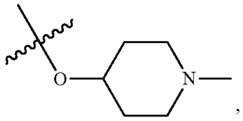,
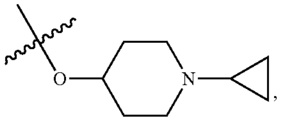,
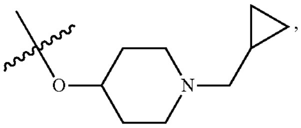,
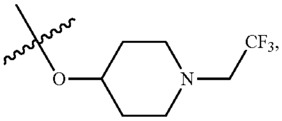,
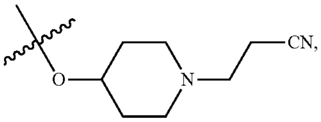,
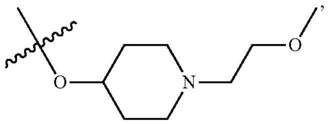,
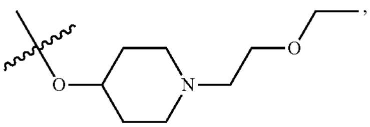, -continued
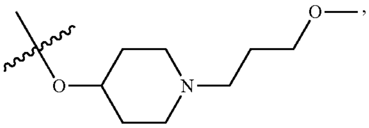
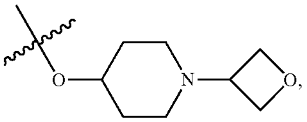
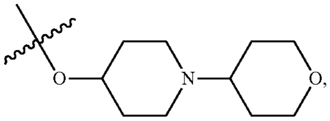
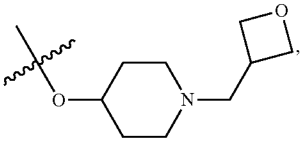
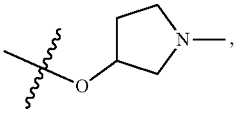
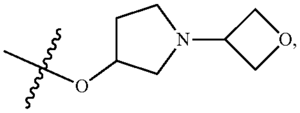
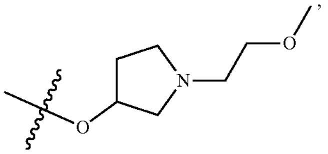
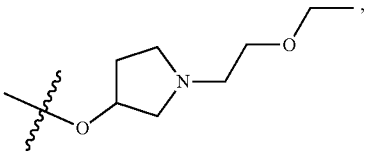
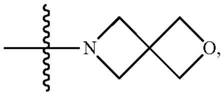
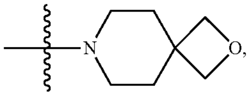
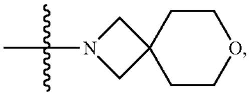
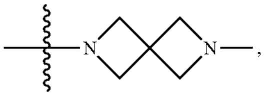
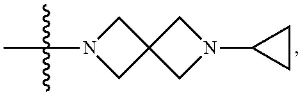
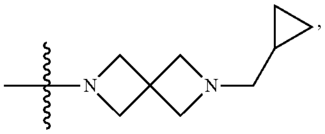
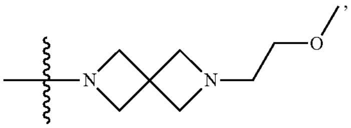
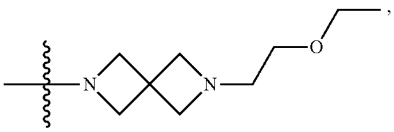
-continued
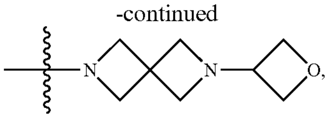
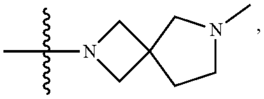
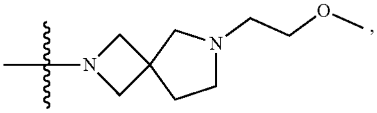
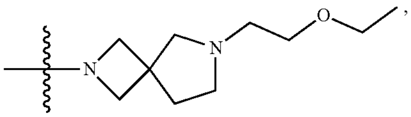
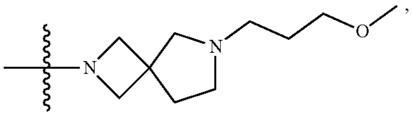
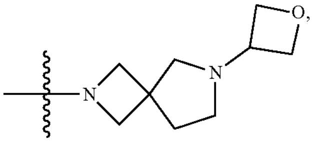
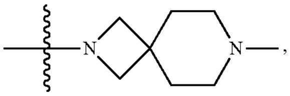
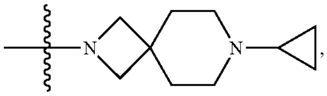
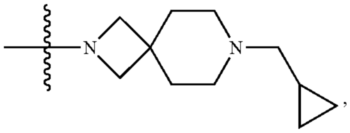
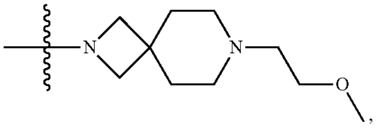
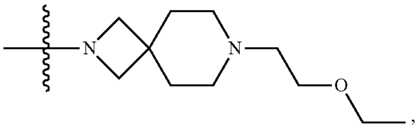
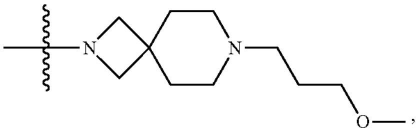
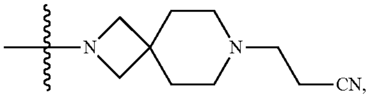
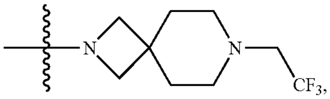
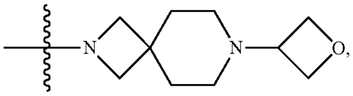

-continued
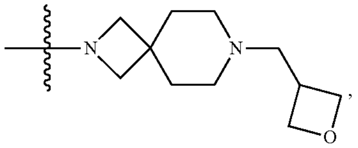
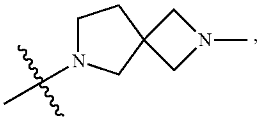
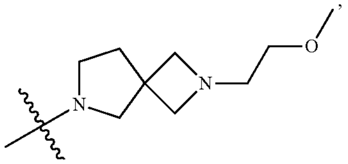
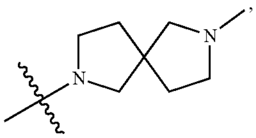
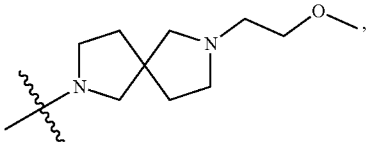
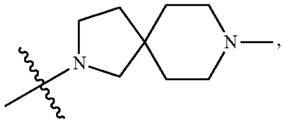
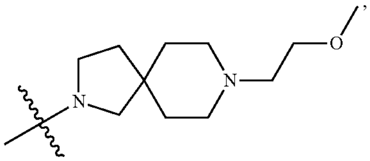
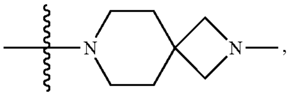
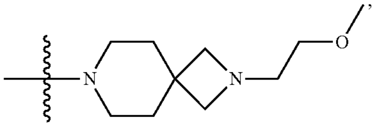
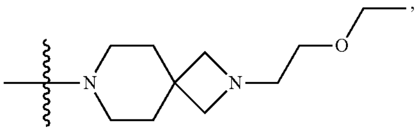
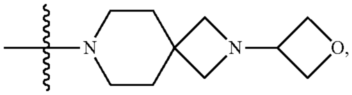
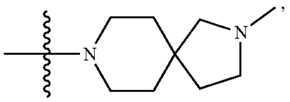
-continued
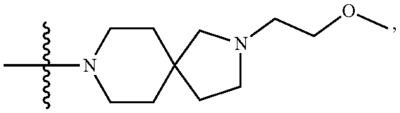
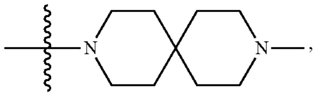
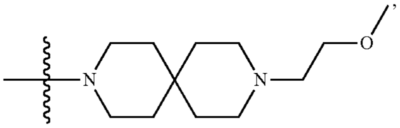
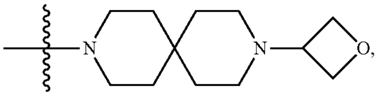
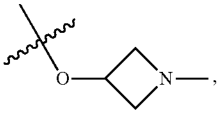
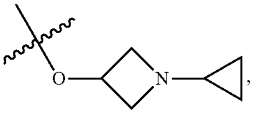
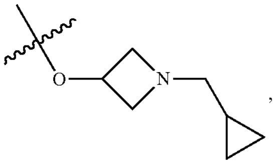
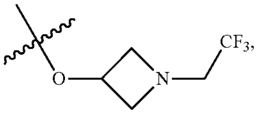
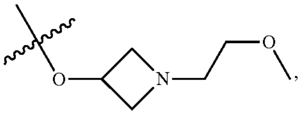
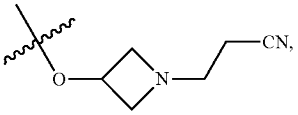
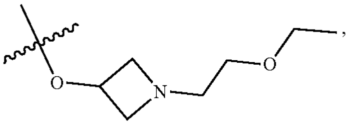
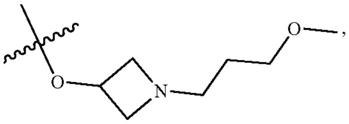
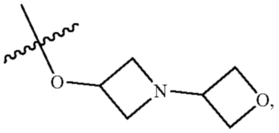
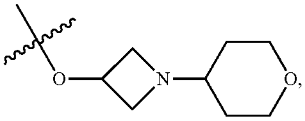
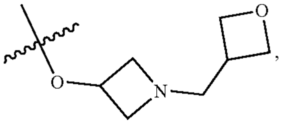
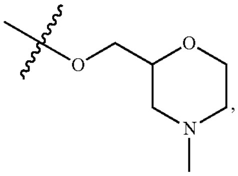

-continued
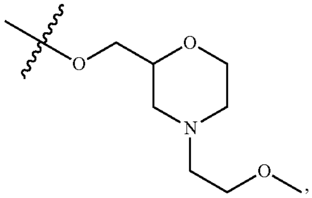,
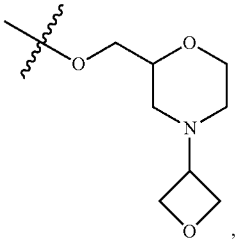,
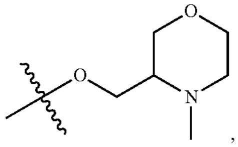,
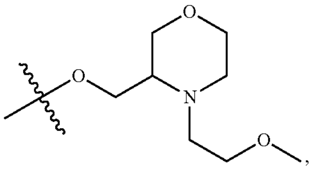,
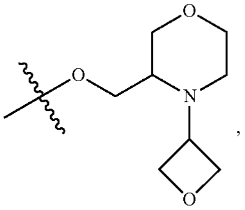,
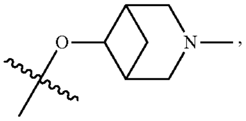,
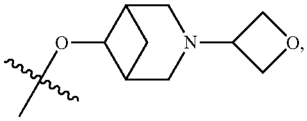,
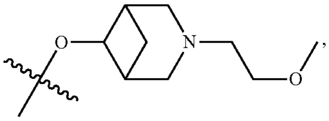,
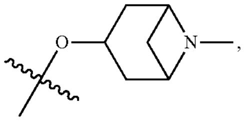,
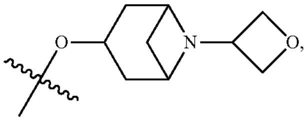,
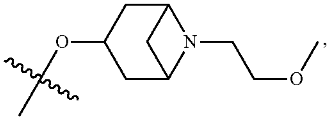,
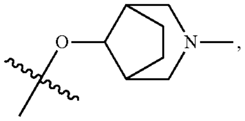,
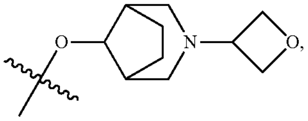,
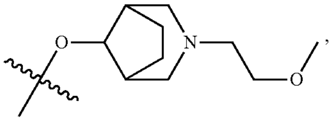,
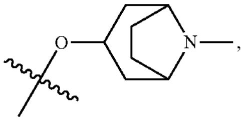,
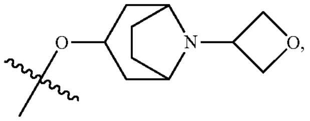,
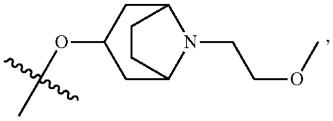,
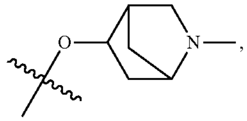,
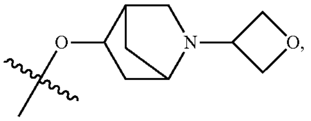,
-continued
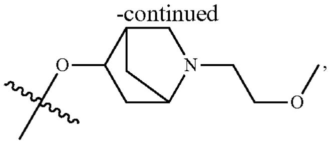,
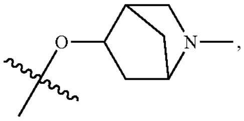,
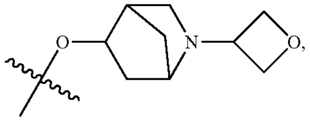,
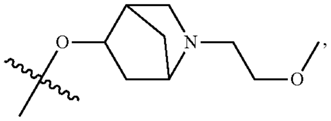,
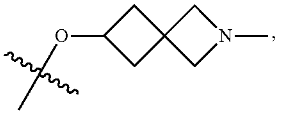,
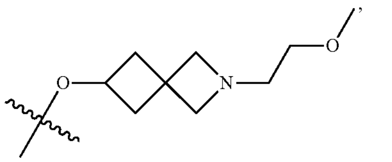,
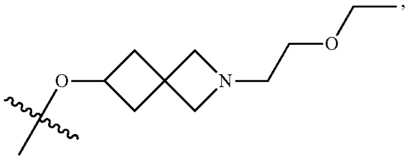,
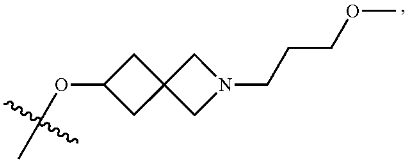,
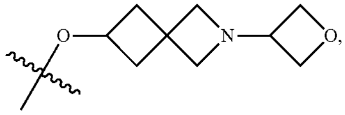,
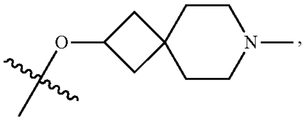,
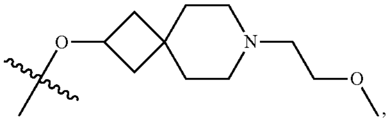,
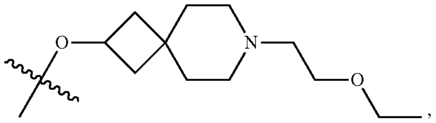,
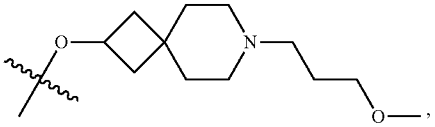,
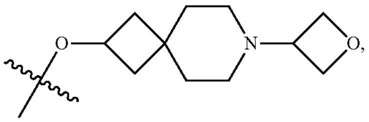, -continued
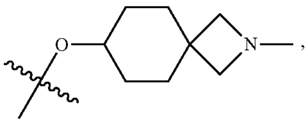
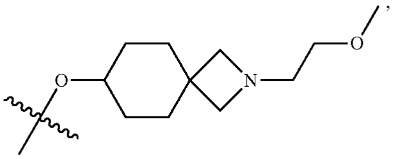
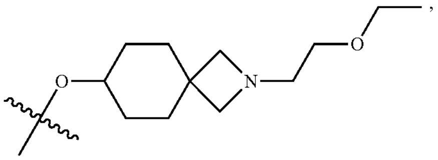
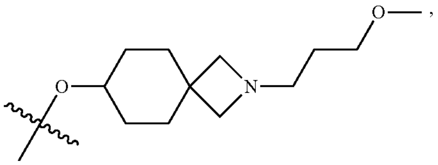
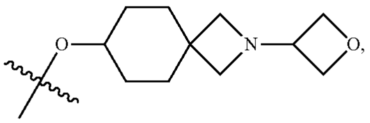
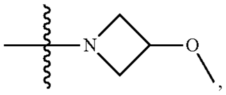
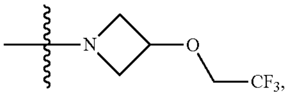
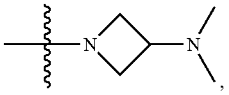
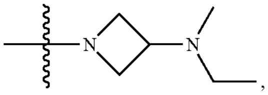
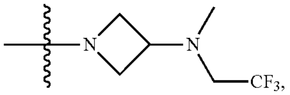
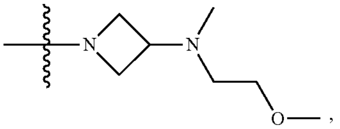
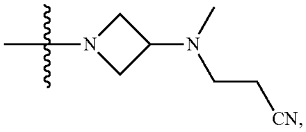
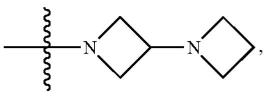
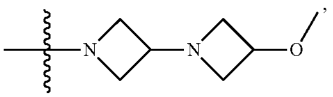
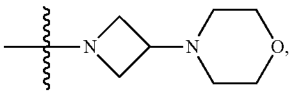
-continued
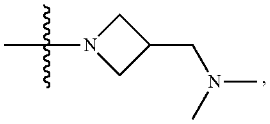
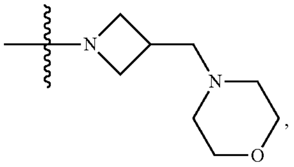
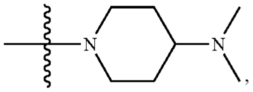
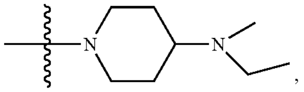
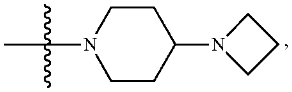
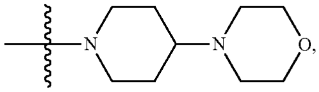
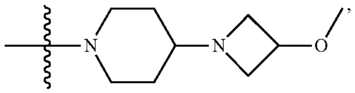
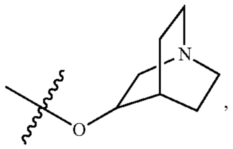
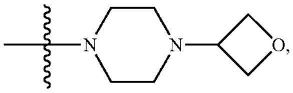
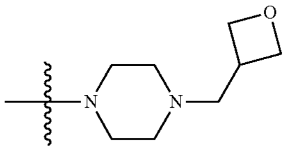
or
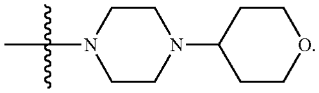
In another preferred embodiment, in the general formula (1), $R^5$ is:
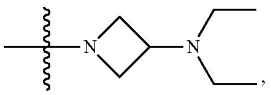
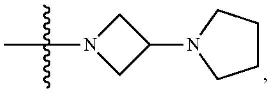
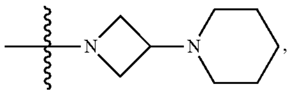
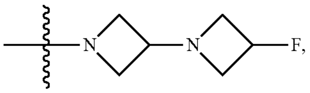
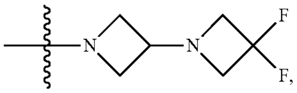
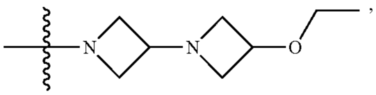
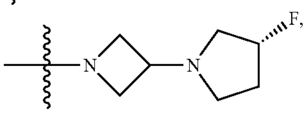

-continued
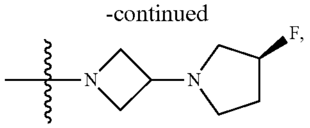
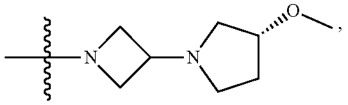
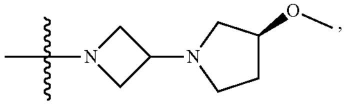
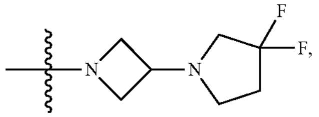
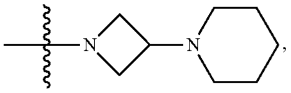
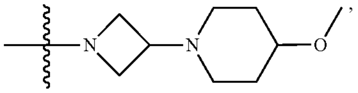
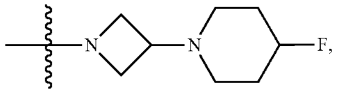
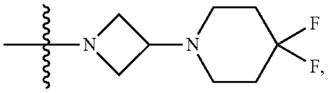
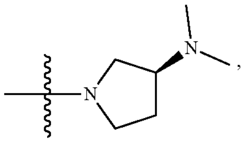
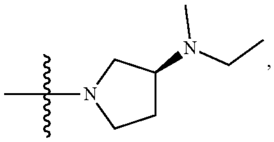
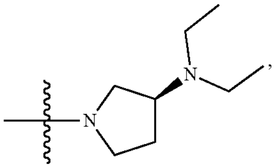
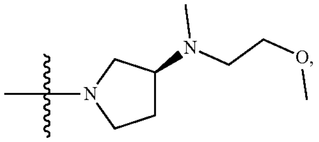
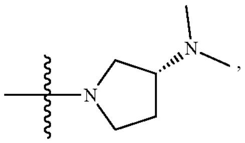
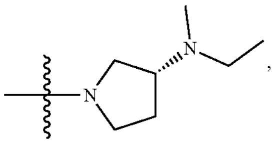
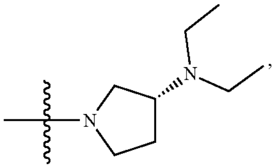
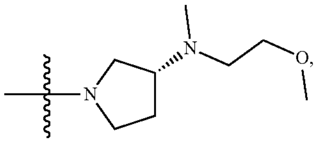
-continued
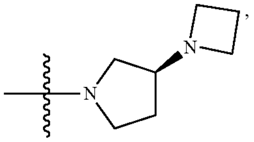
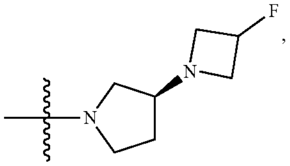
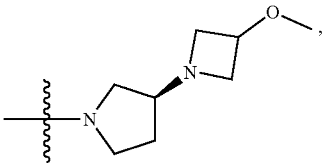
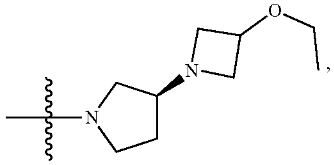
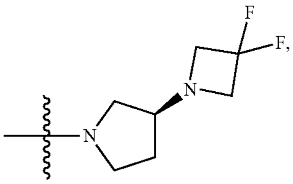
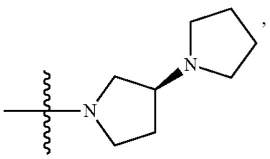
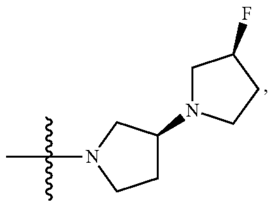
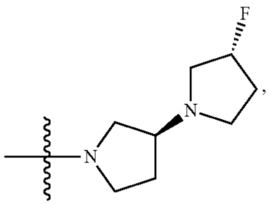
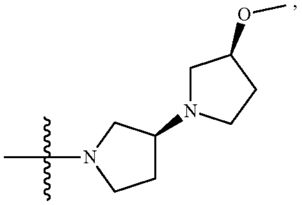
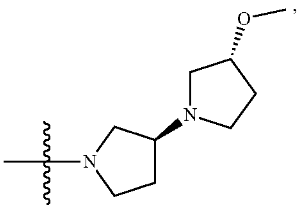
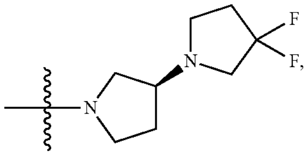
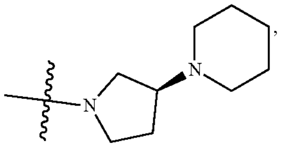
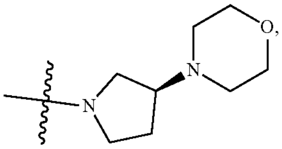

-continued
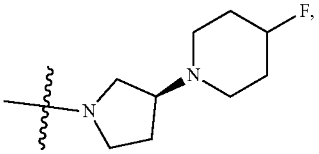
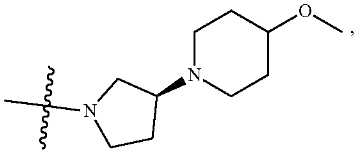
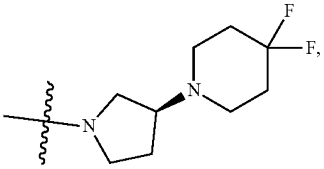
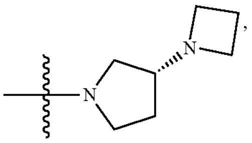
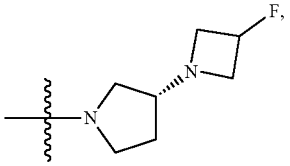
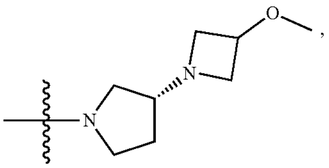
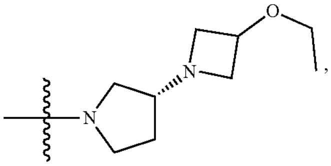
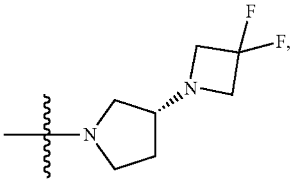
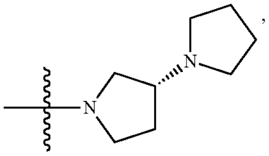
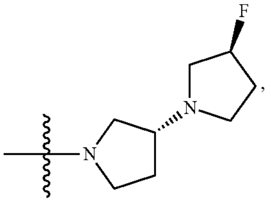
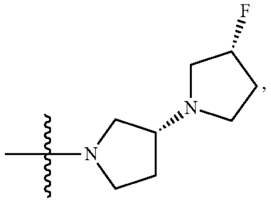
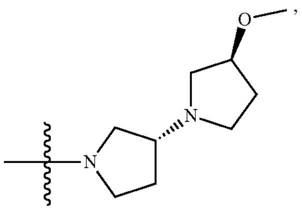
-continued
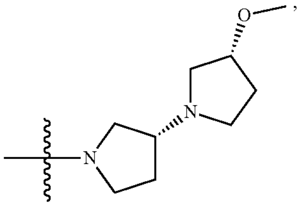
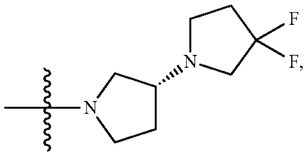
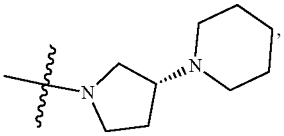
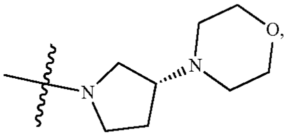
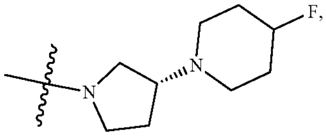
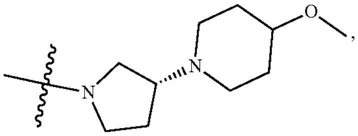
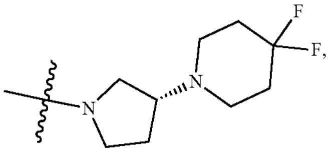
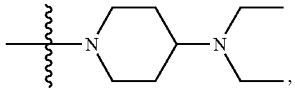
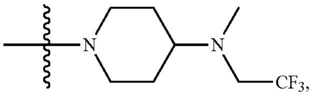
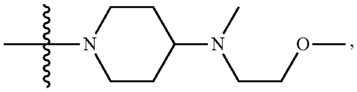
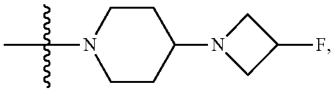
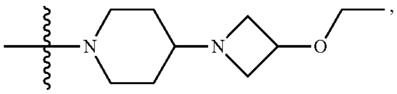
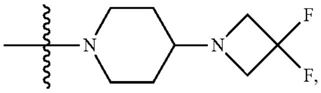
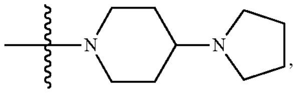
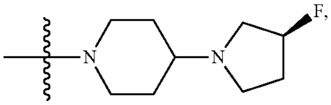

-continued
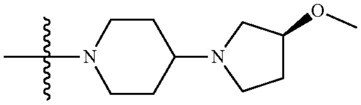
,
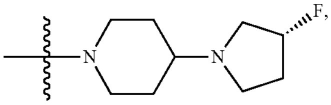
,
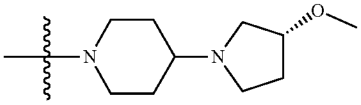
,
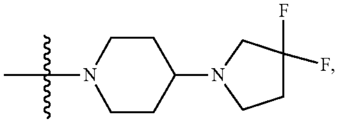
,
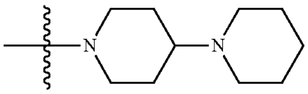
,
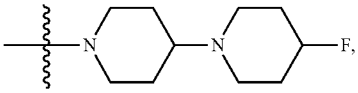
,
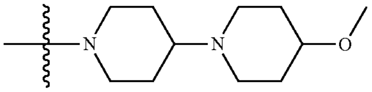
or
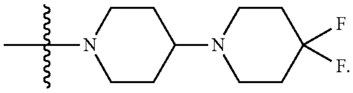
.
In various embodiments, a representative compound of general formula (1) of the present invention has one of the following structures:
1
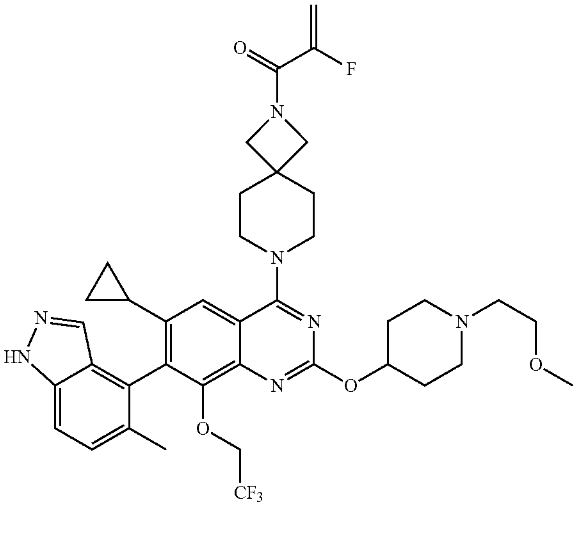
-continued
2
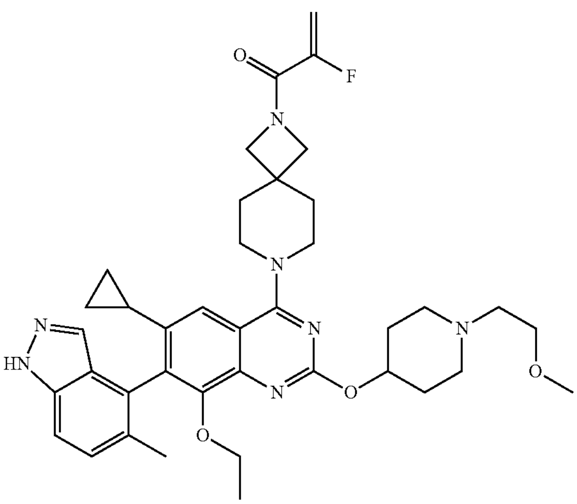
3
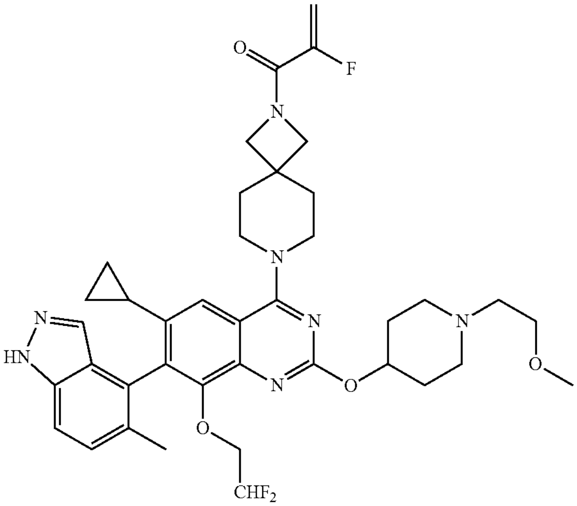
4
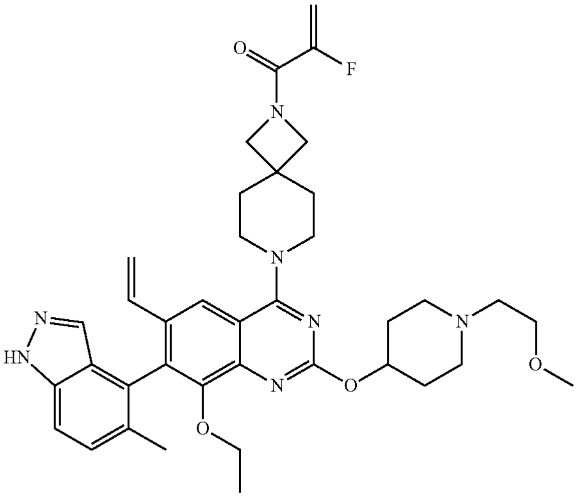

-continued
5
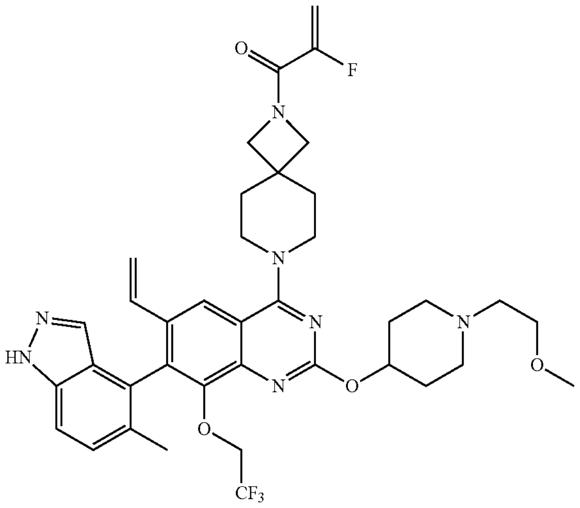
6
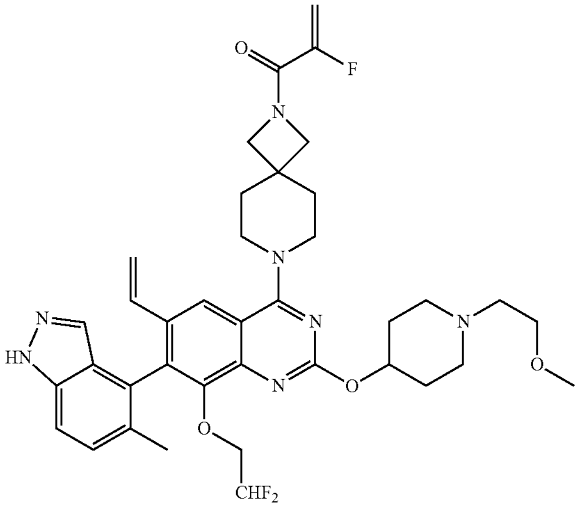
7
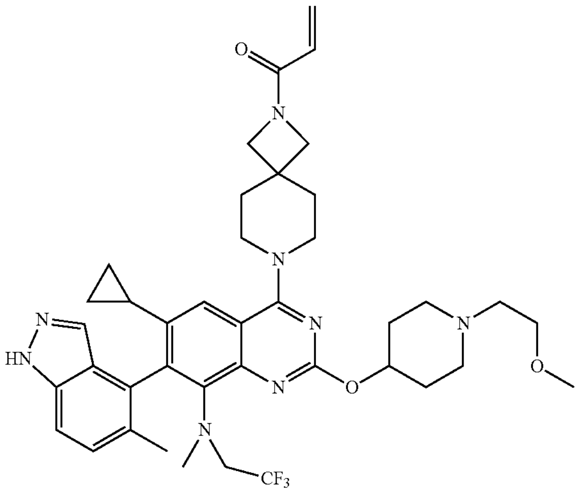
-continued
8
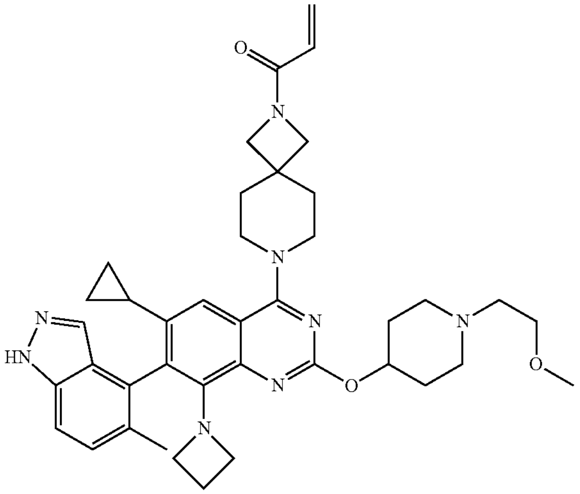
9
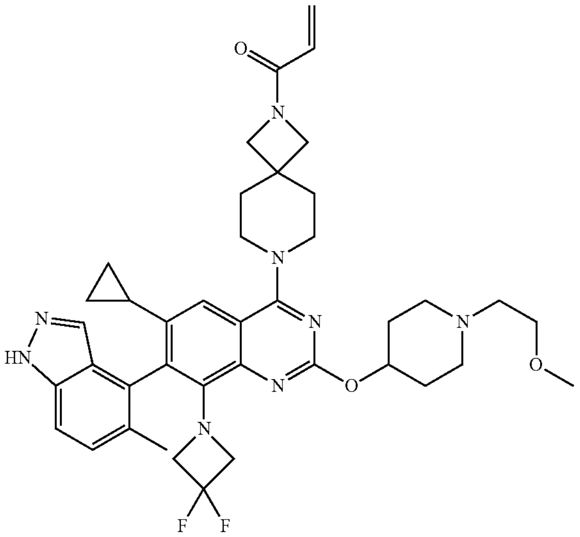
10
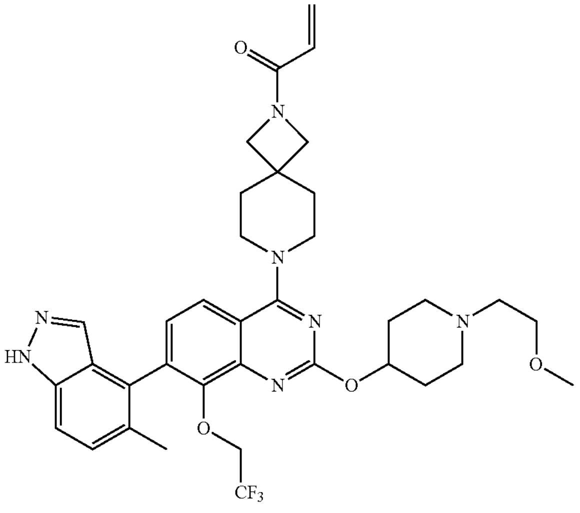

-continued
11
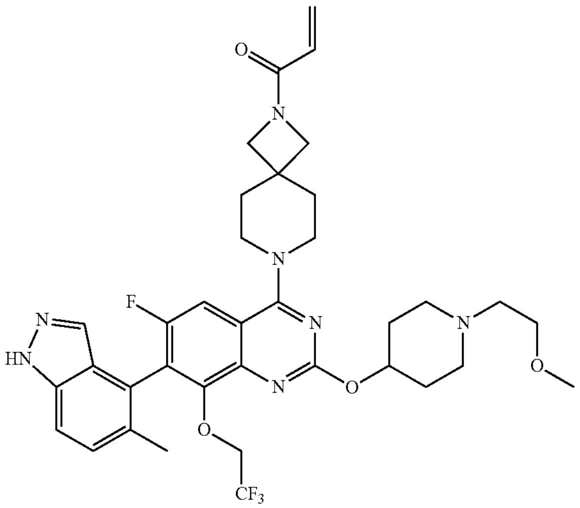
12
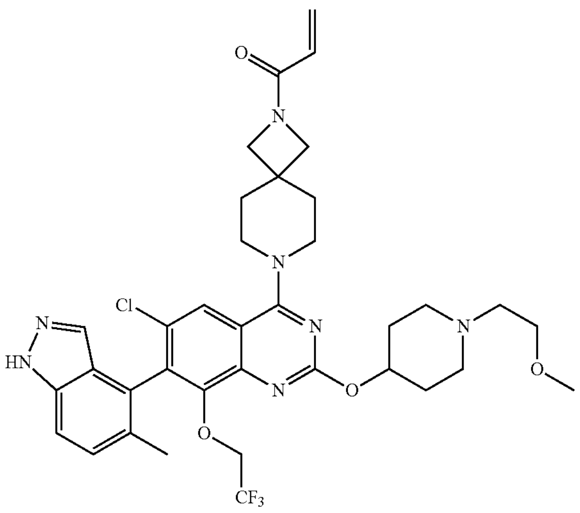
13
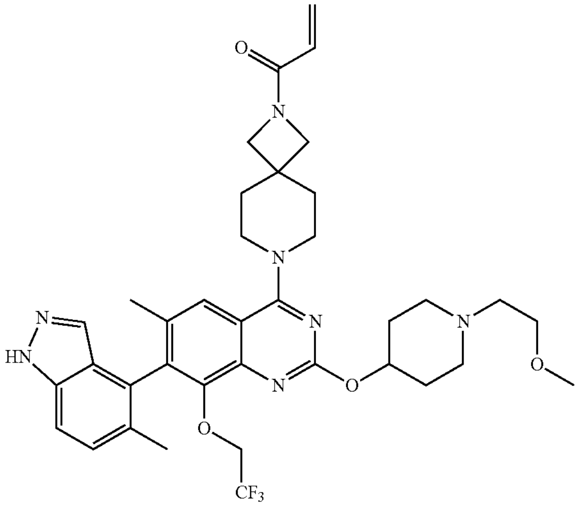
-continued
14
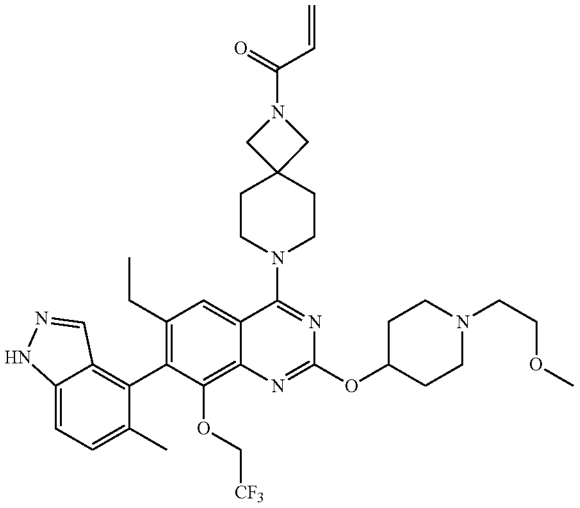
15
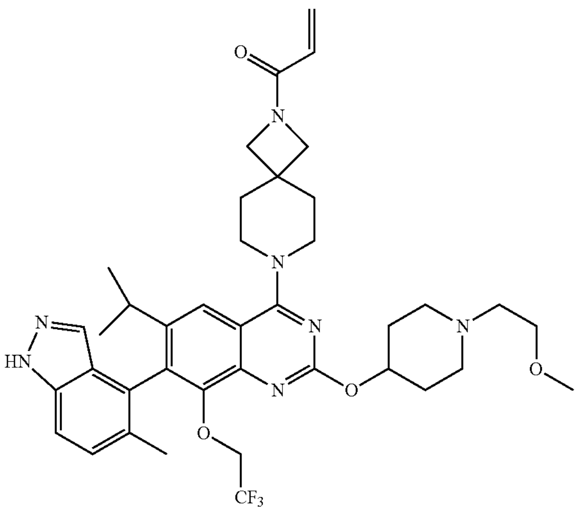
16
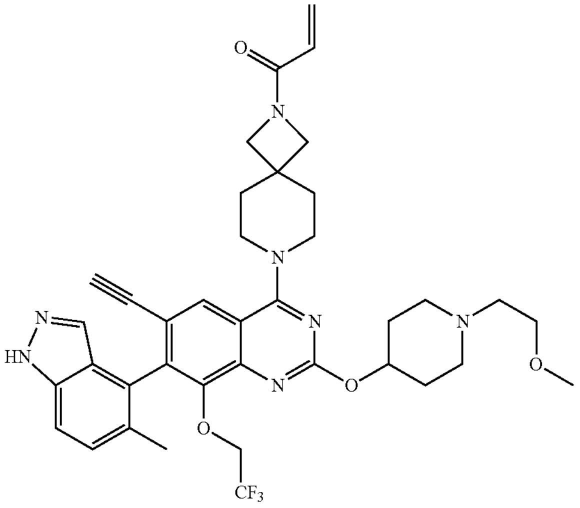

17
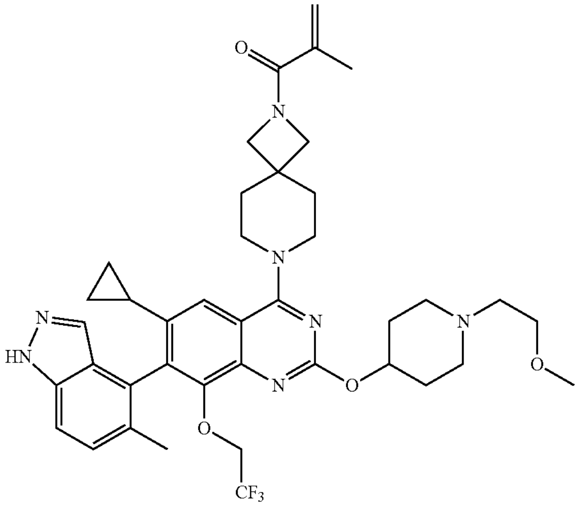
18
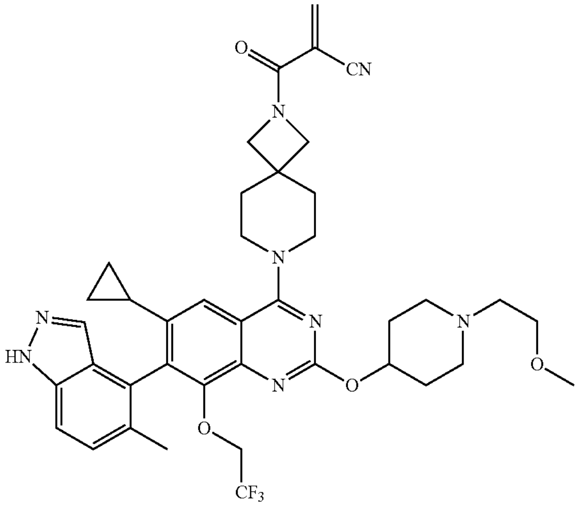
19
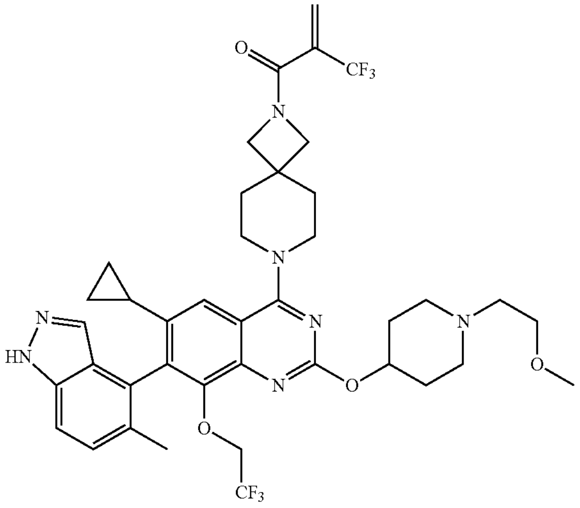
20
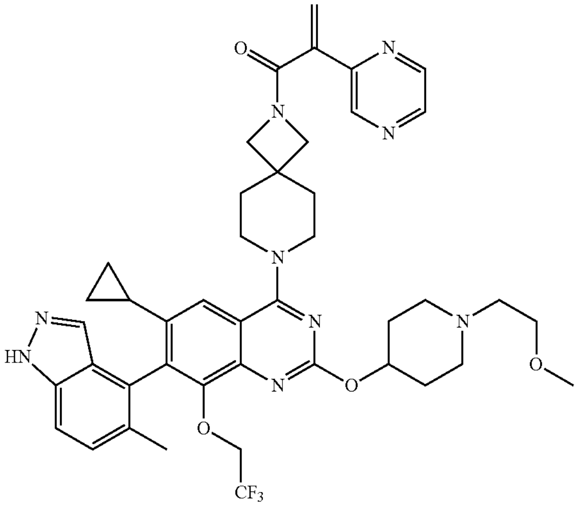
21
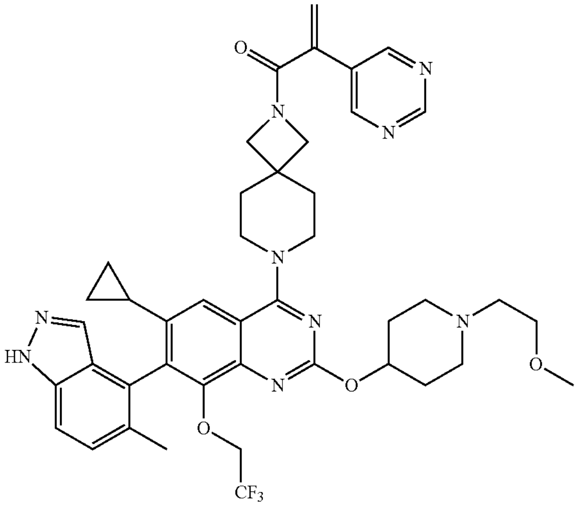
22
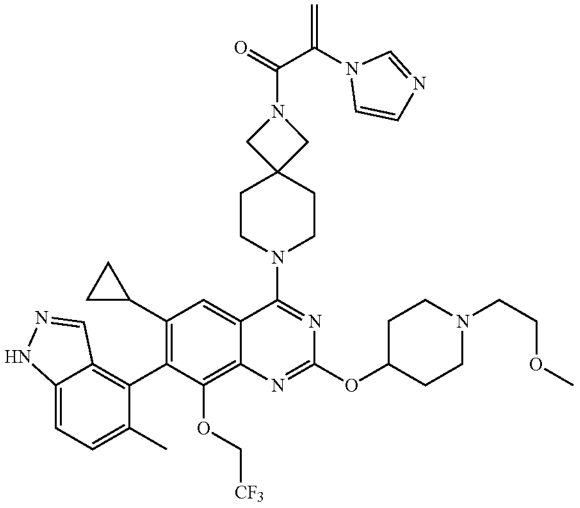

-continued
23
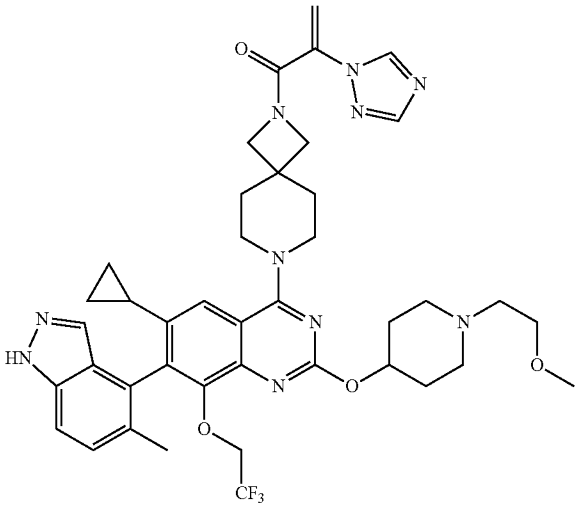
24
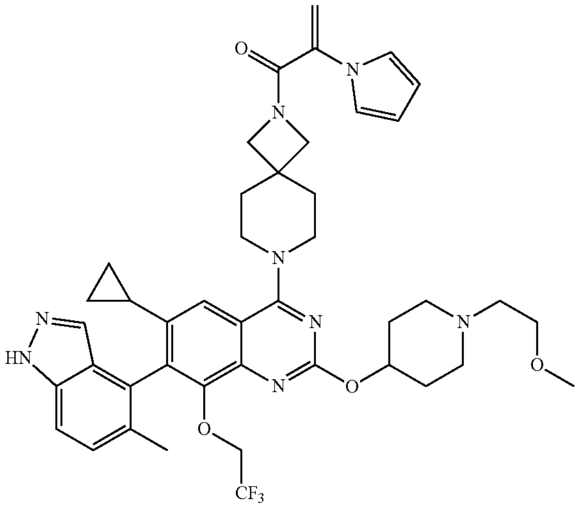
25
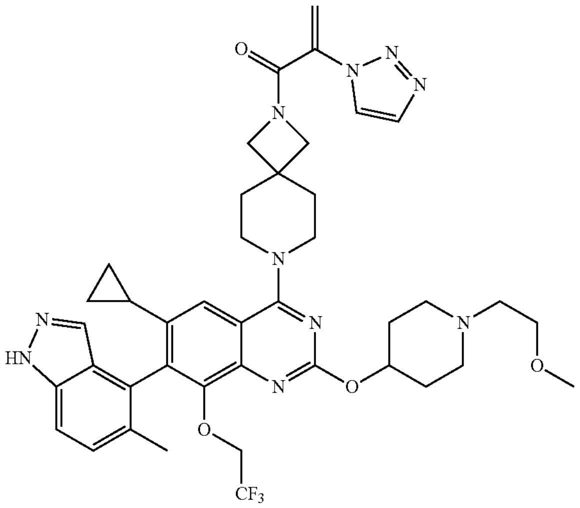
-continued
26
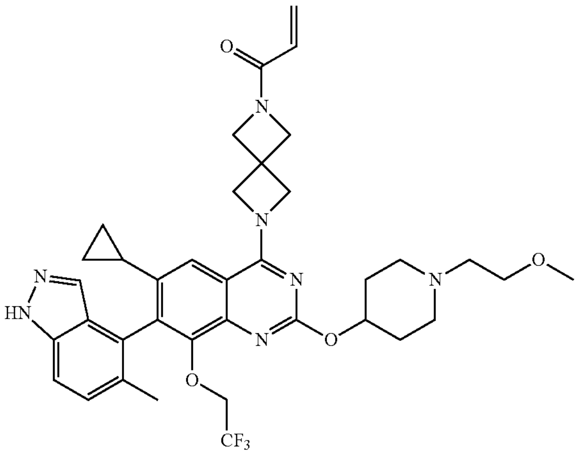
27
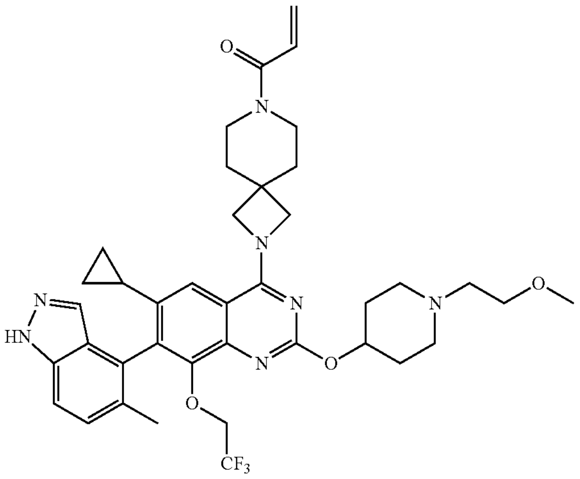
28
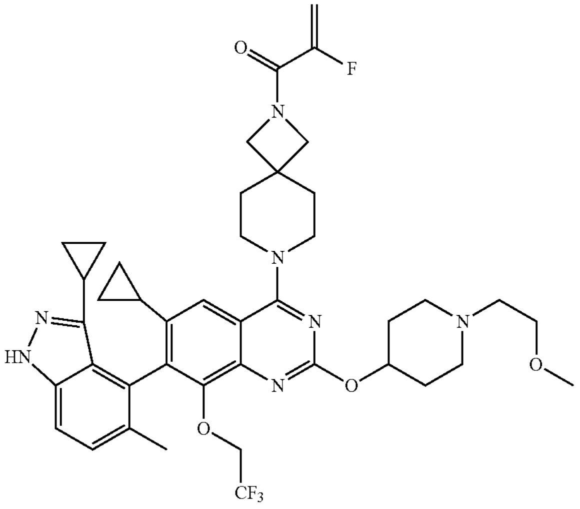

-continued
29
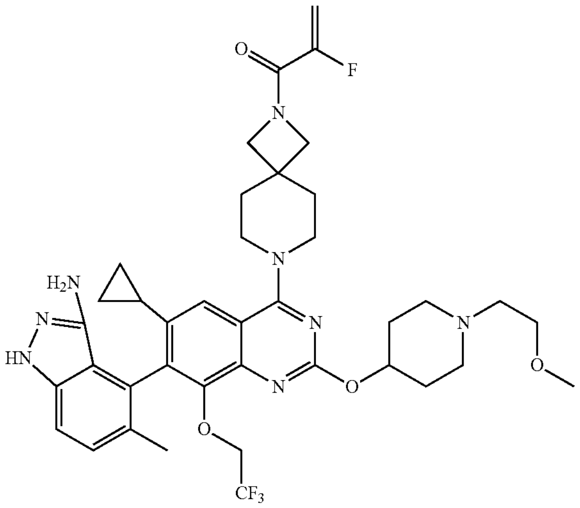
30
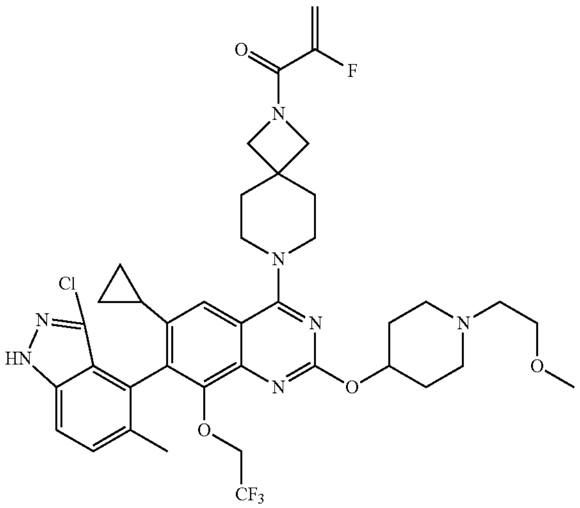
31
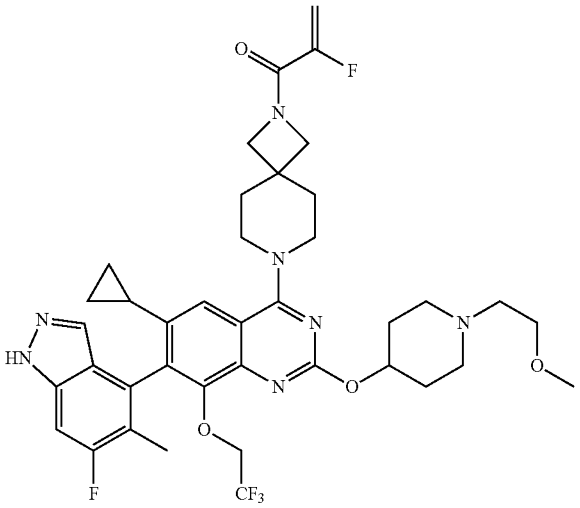
-continued
32
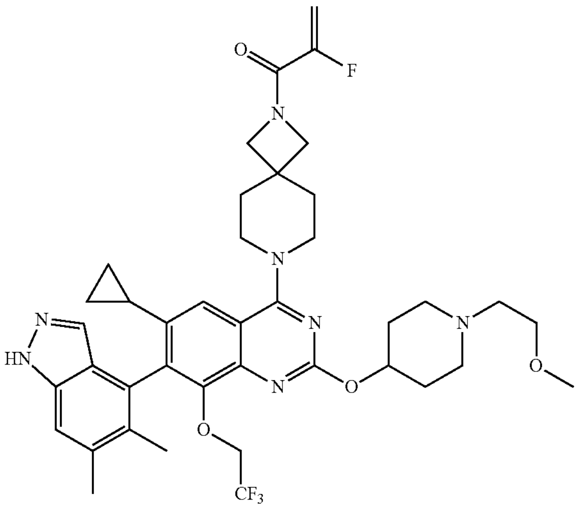
33
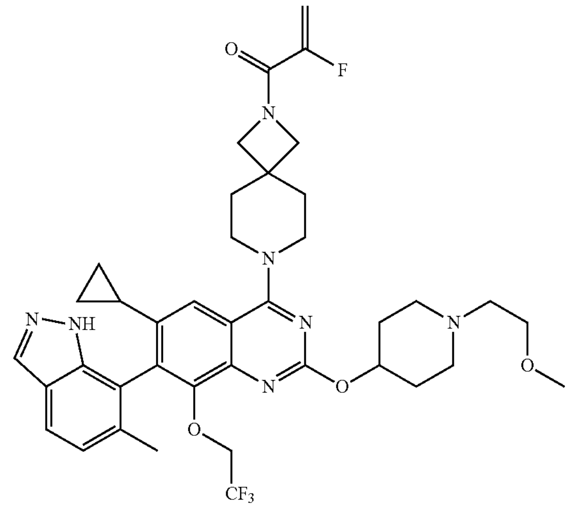
34
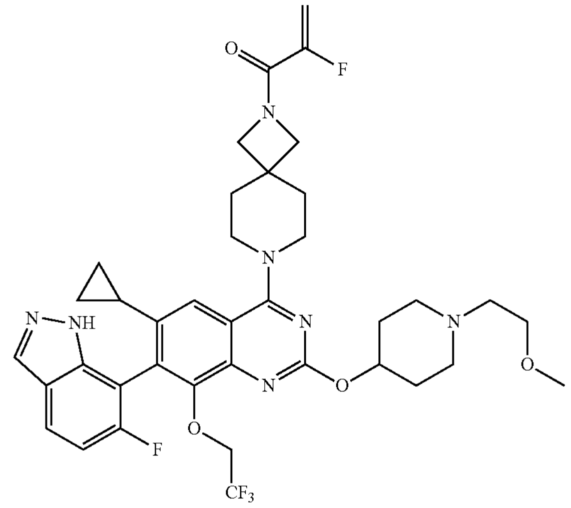

-continued
35
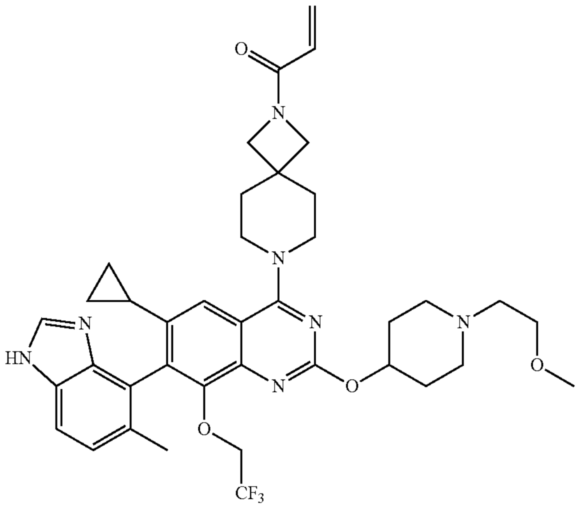
36
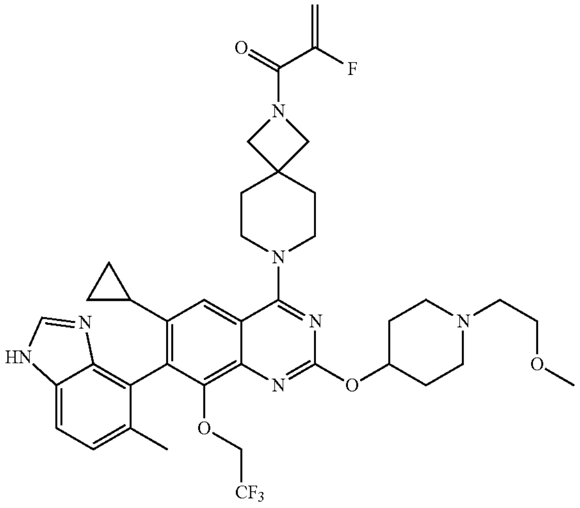
37
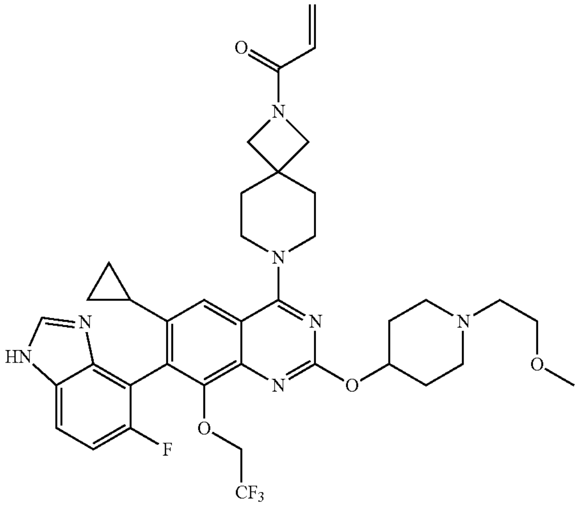
-continued
38
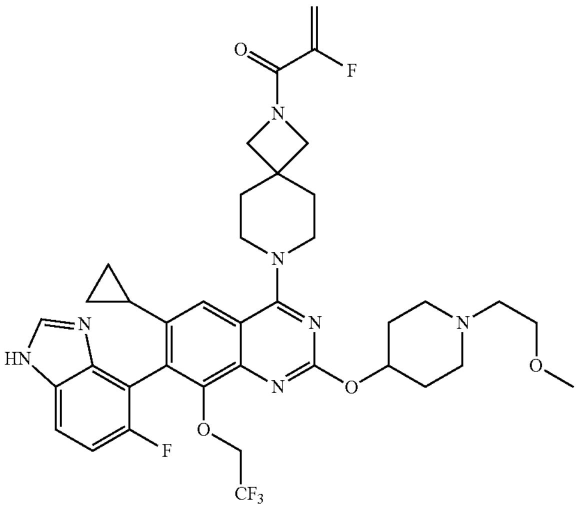
39
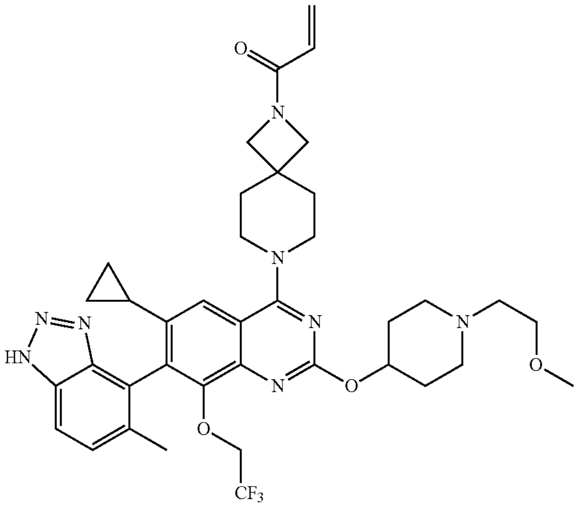
40
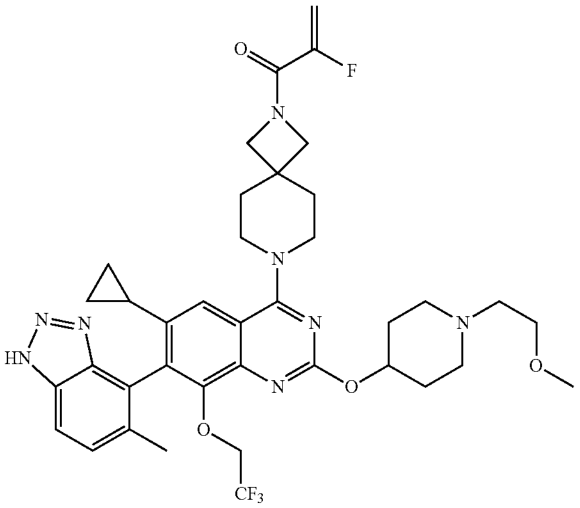

-continued
41
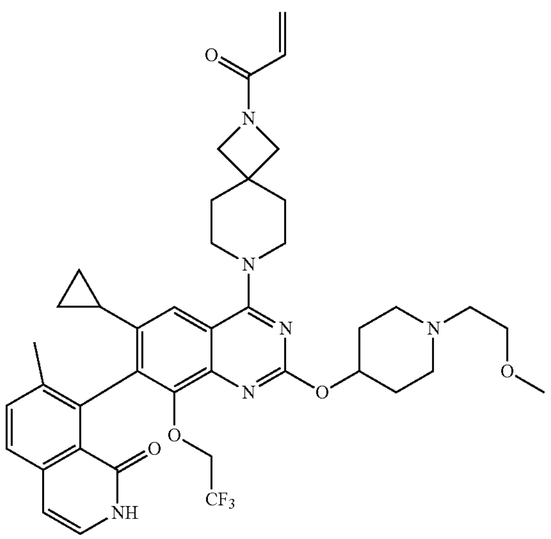
42
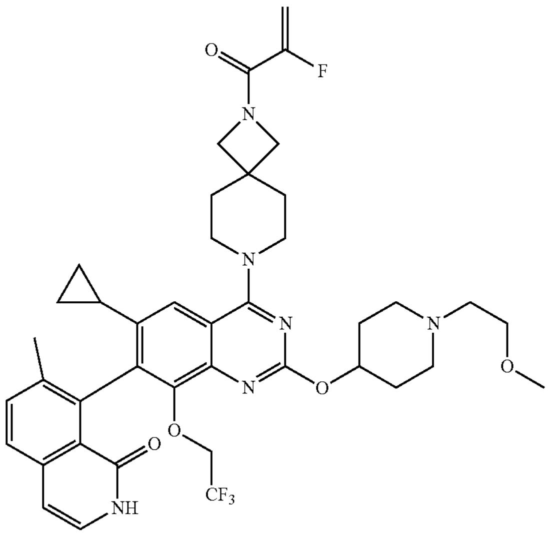
43
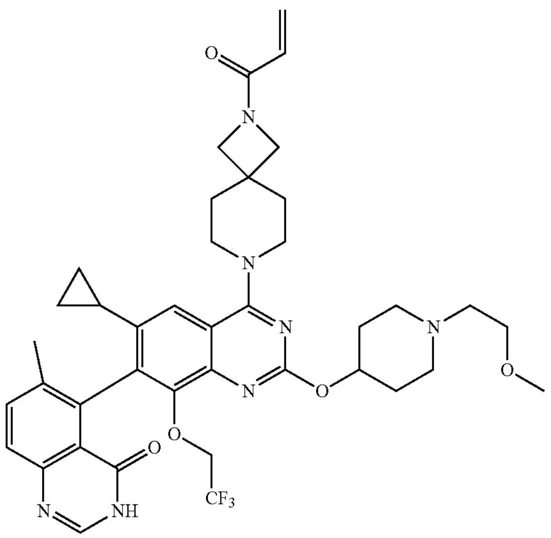
-continued
44
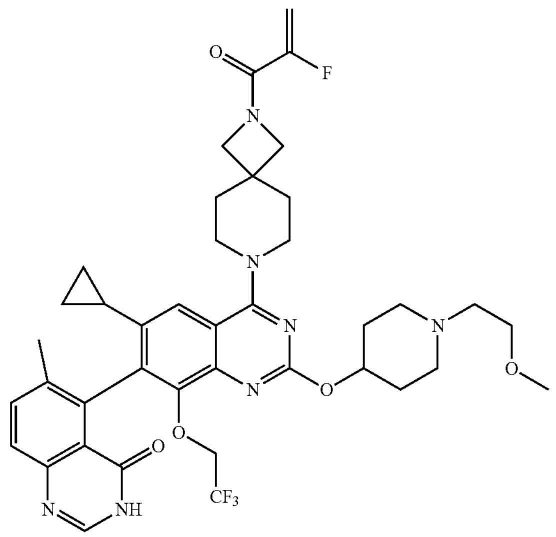
45
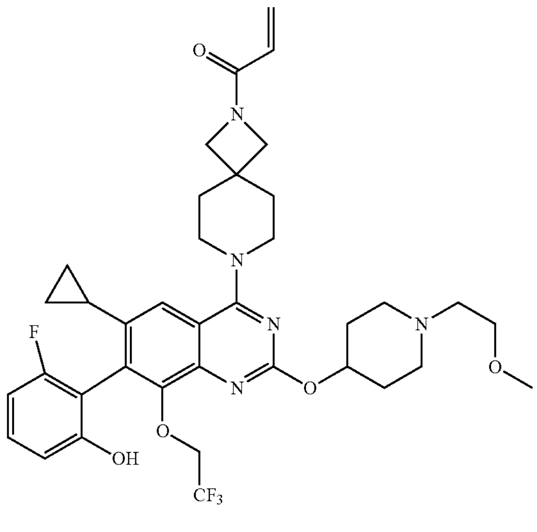
46
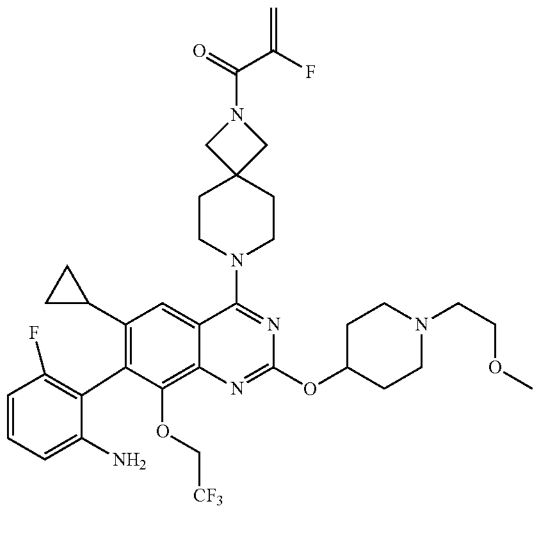

-continued
47
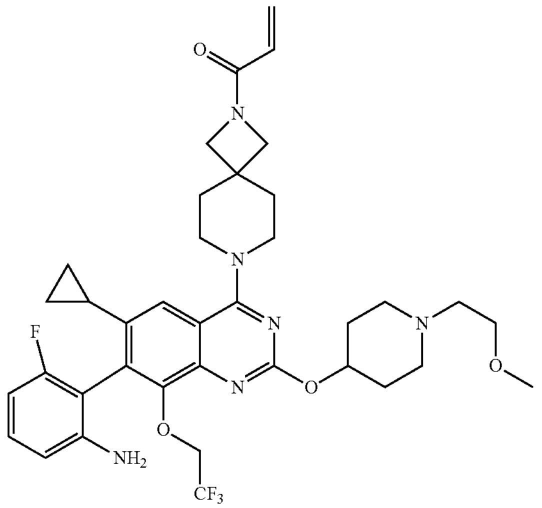
48
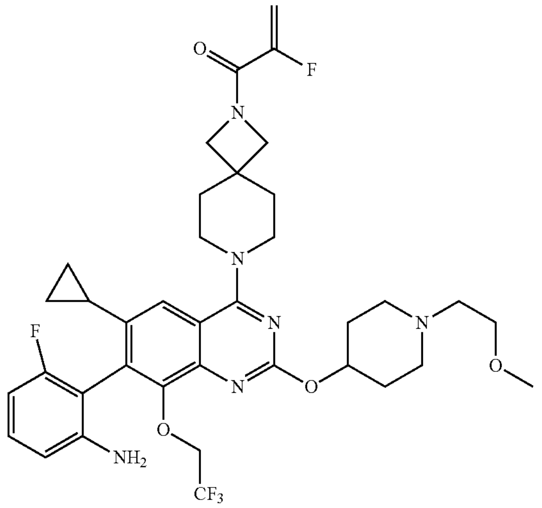
49
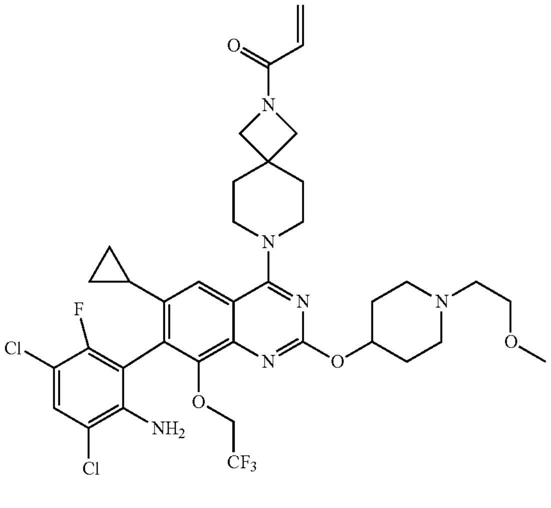
50
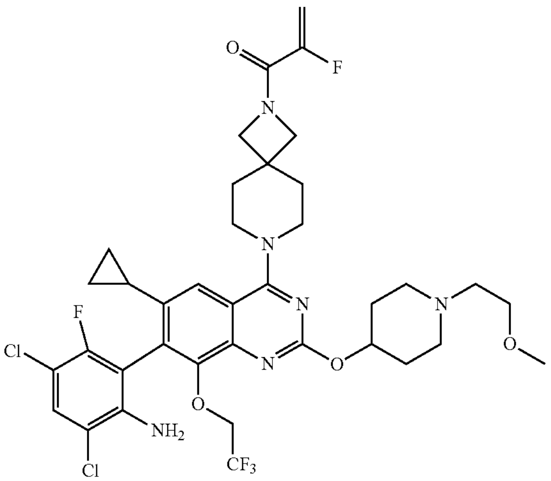
51
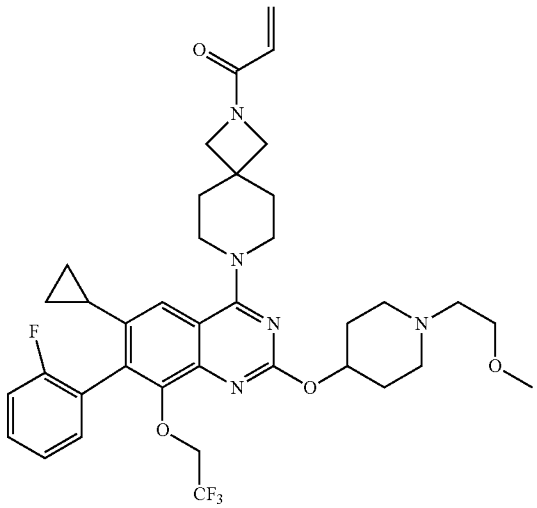
52
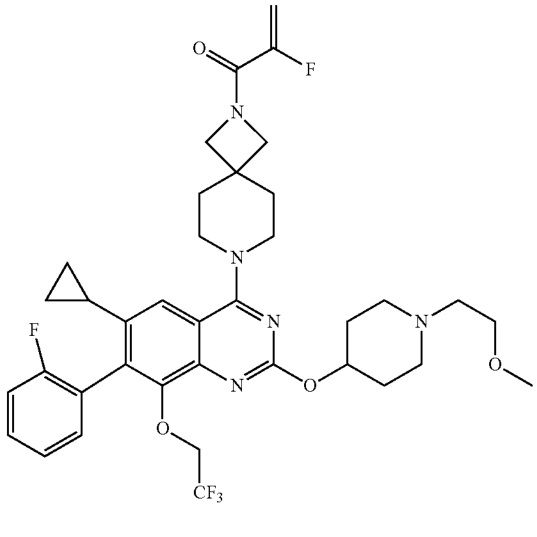

-continued
53
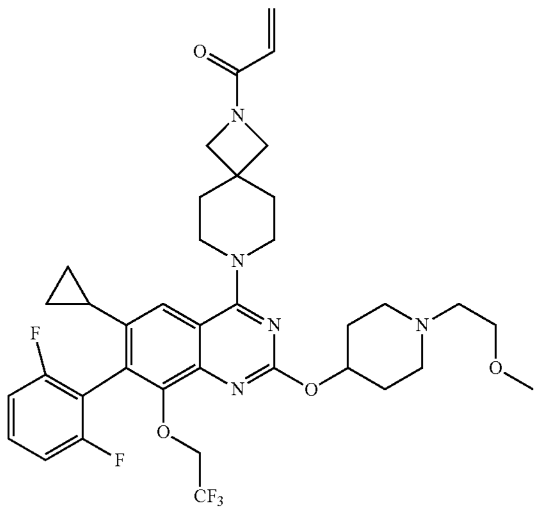
54
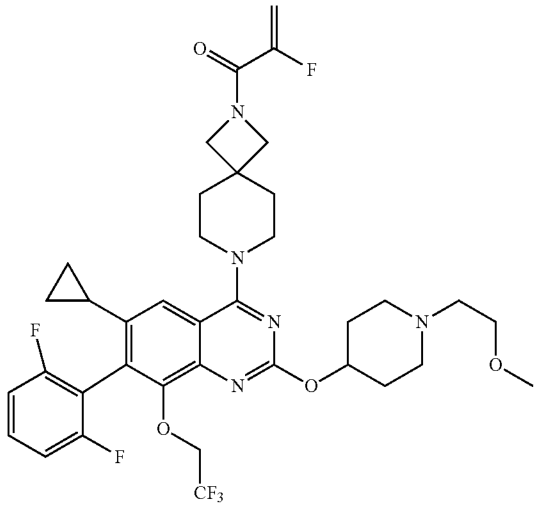
55
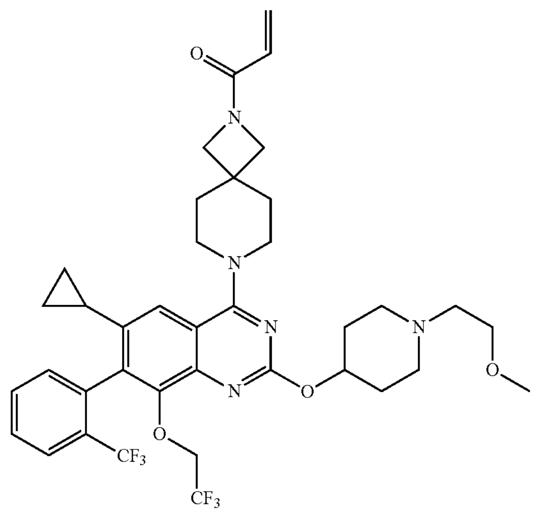
-continued
56
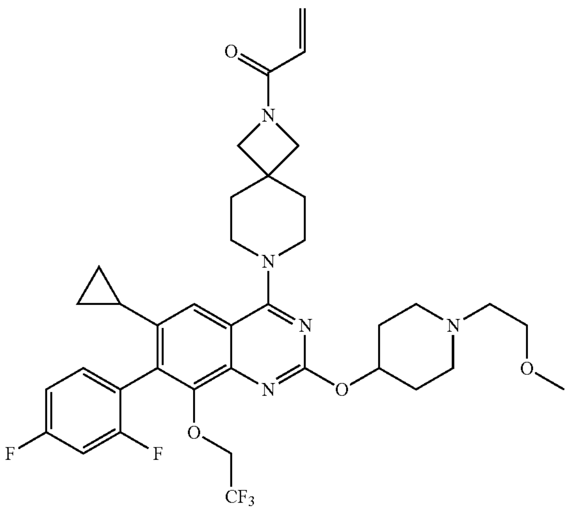
57
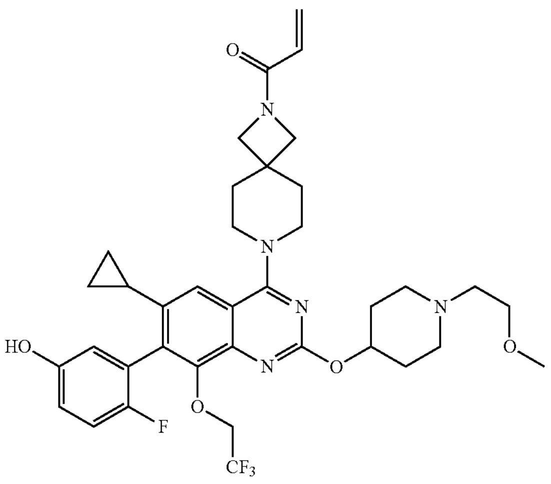
58
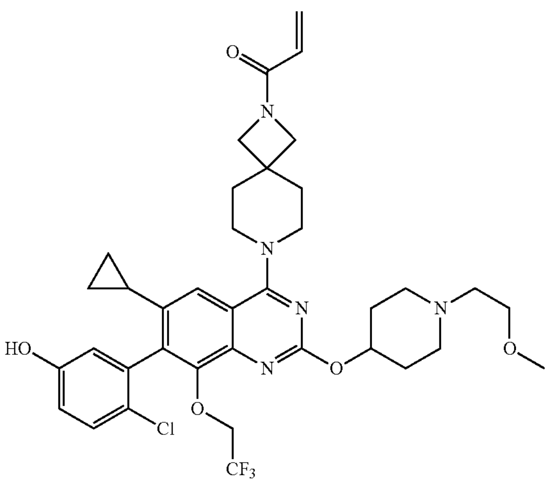

-continued
59
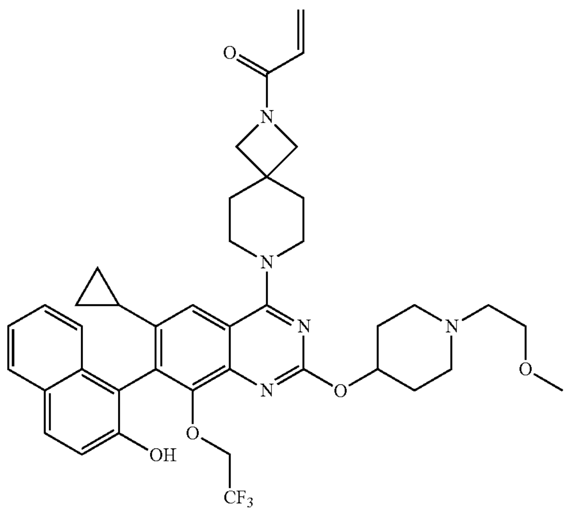
60
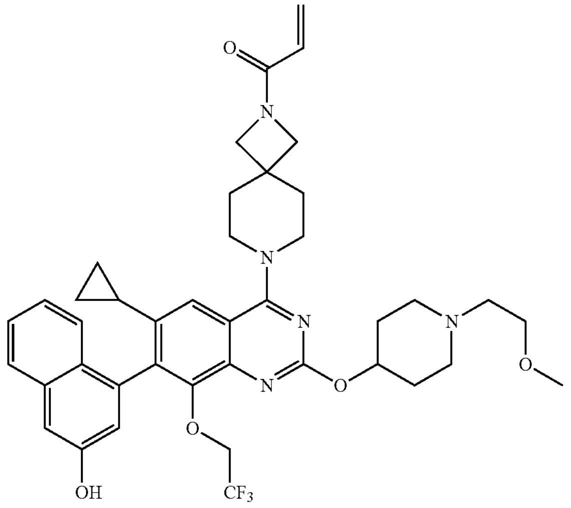
61
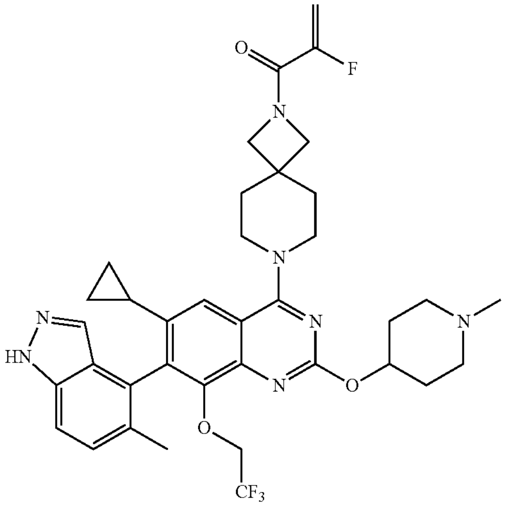
-continued
62
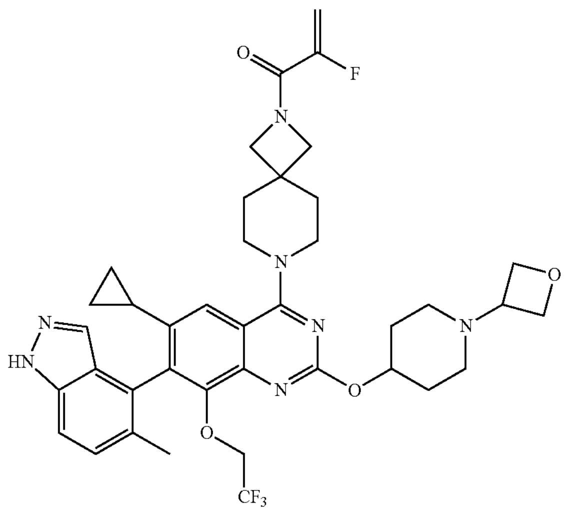
63
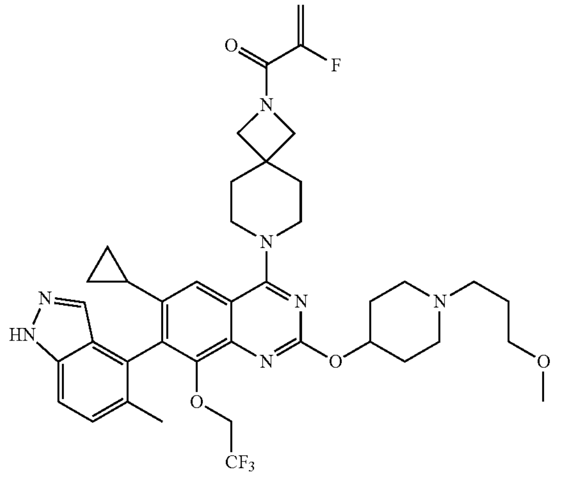
64
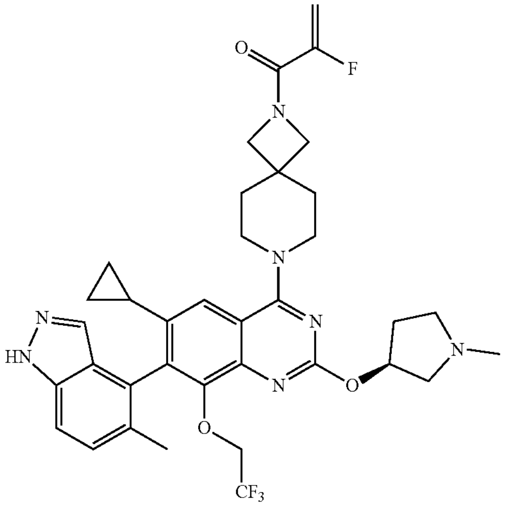

-continued
65
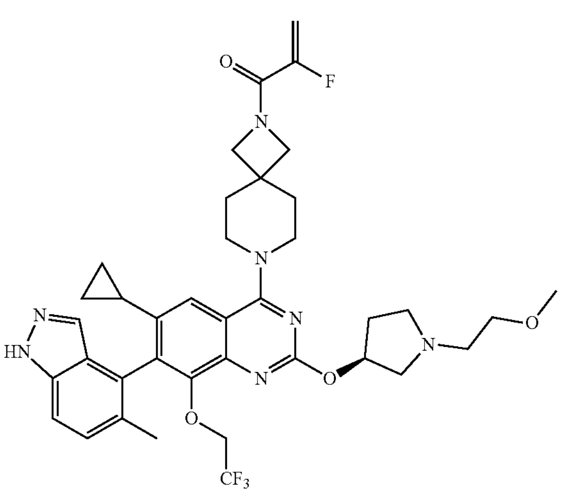
66
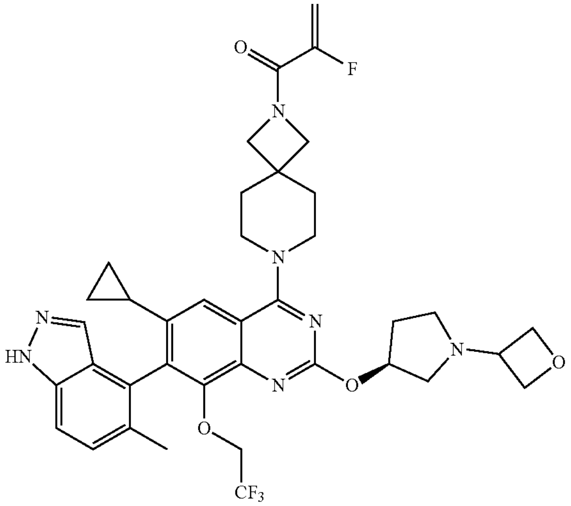
67
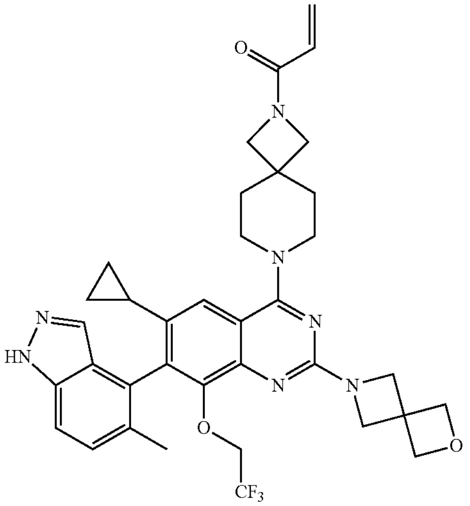
-continued
68
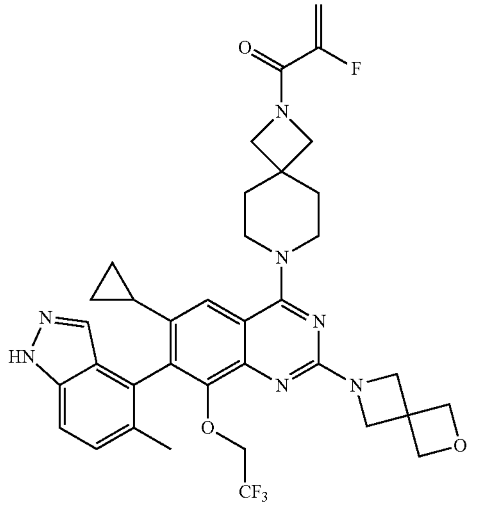
69
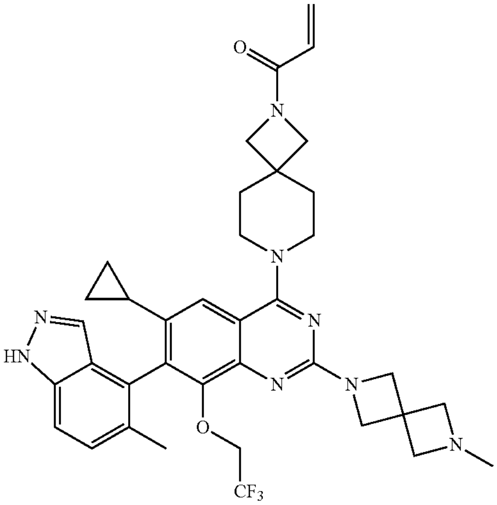
70
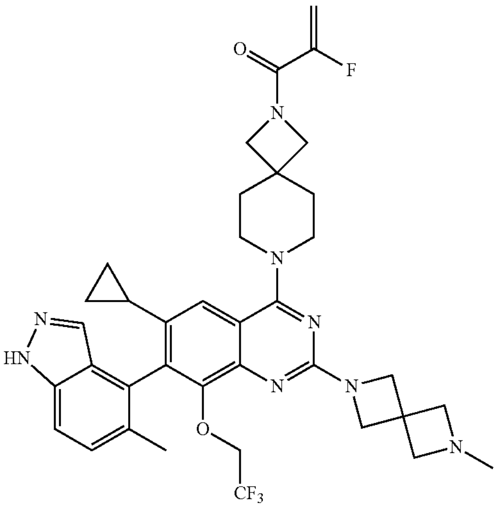

-continued
71
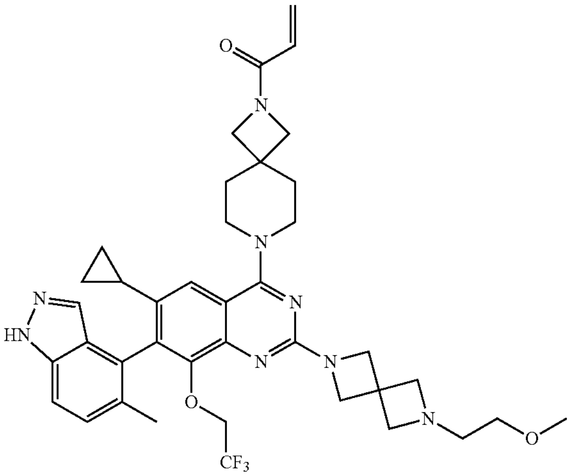
72
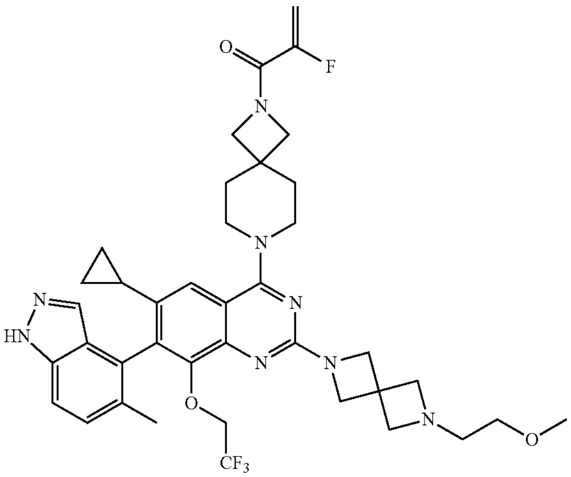
73
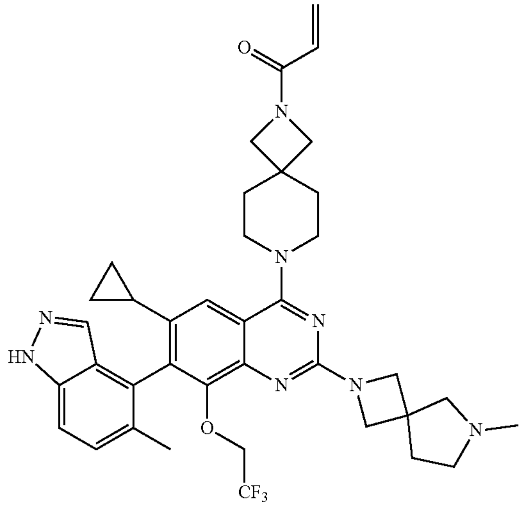
-continued
74
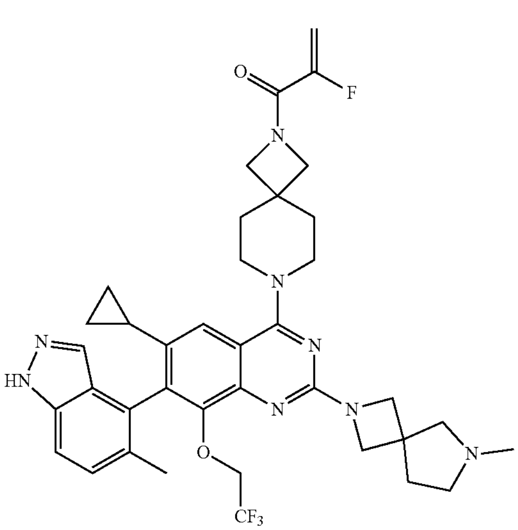
75
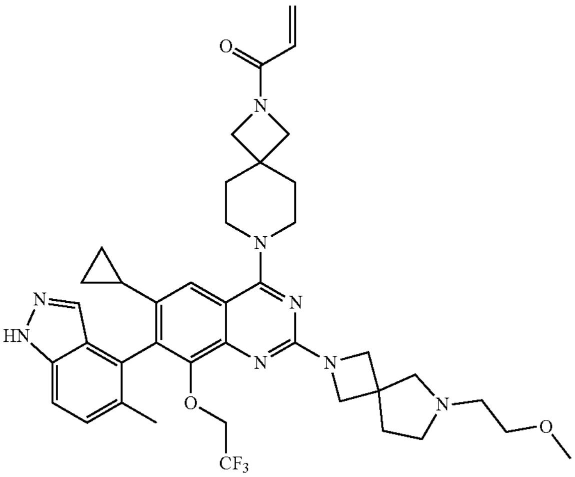
76
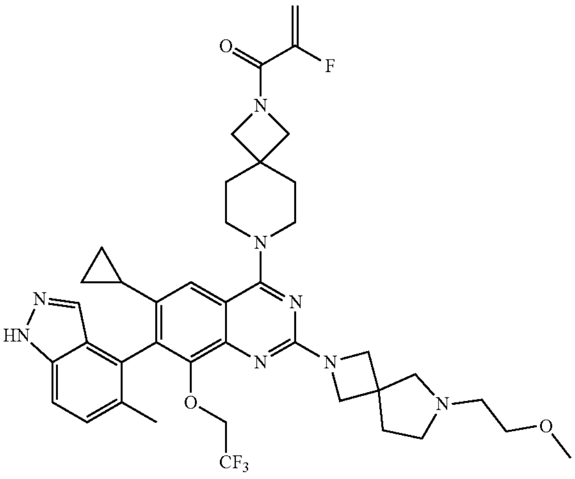

77
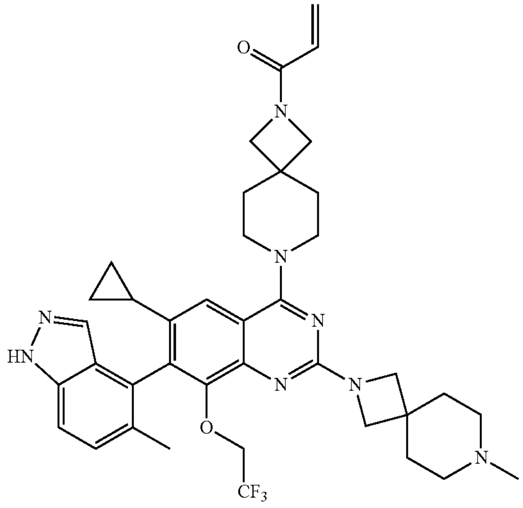
78
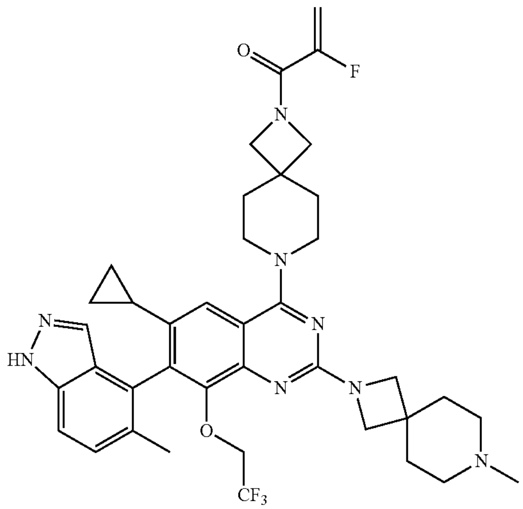
79
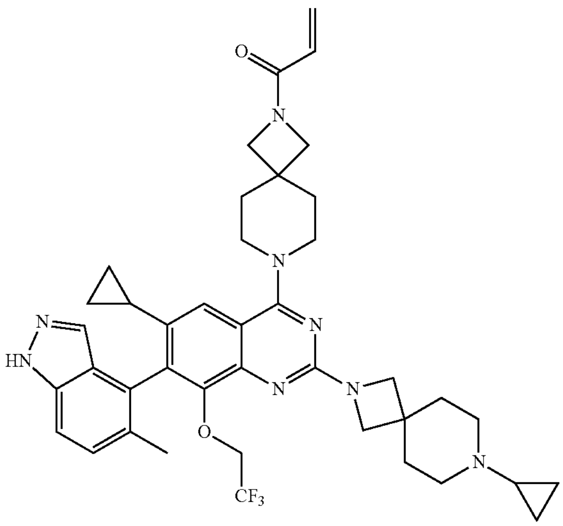
80
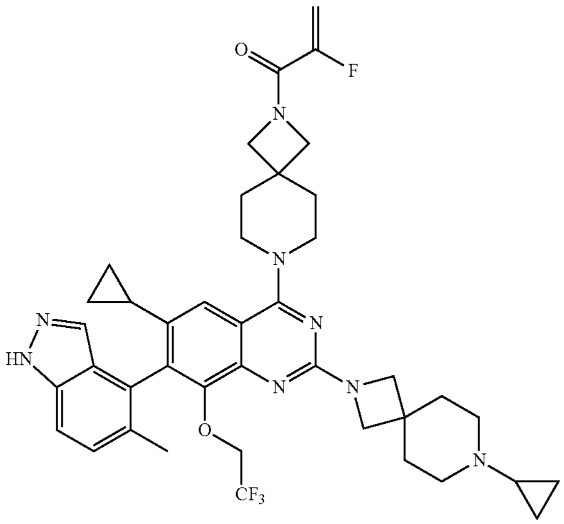
81
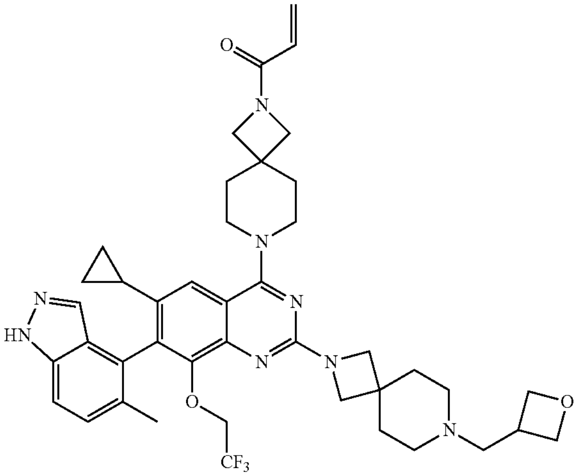
82
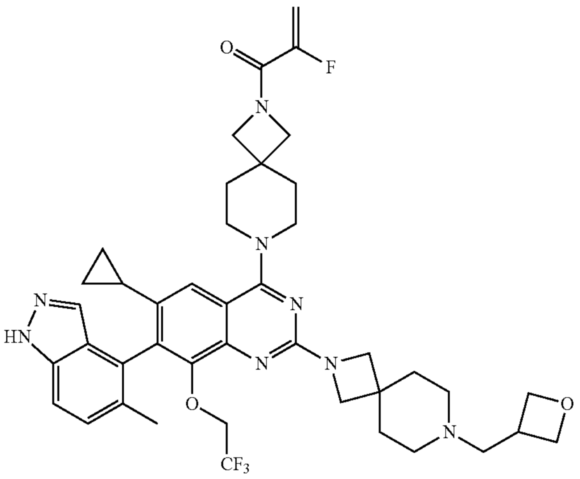

-continued
83
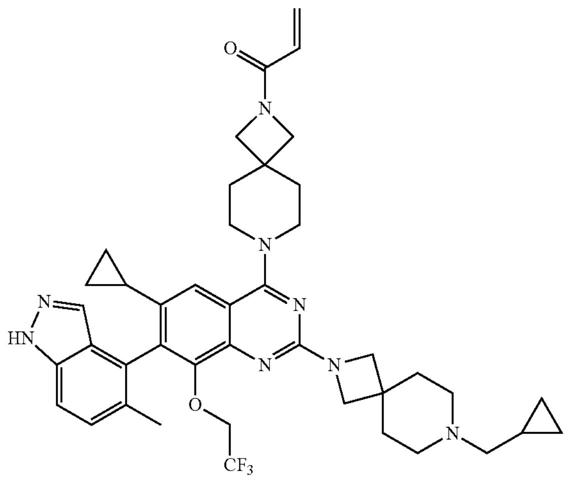
84
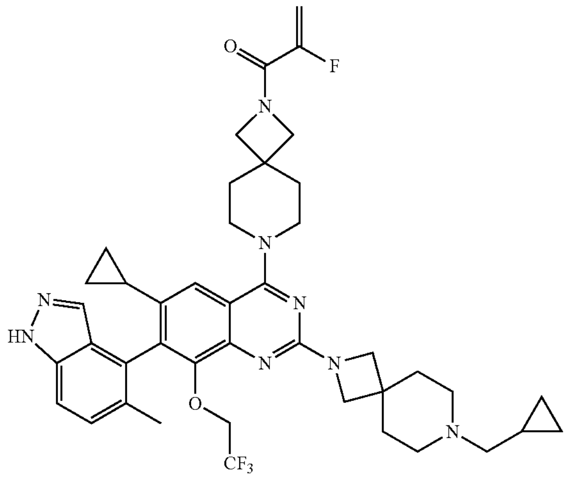
85
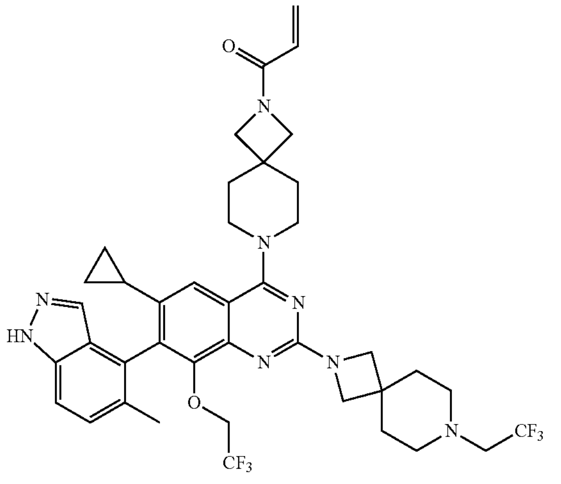
-continued
86
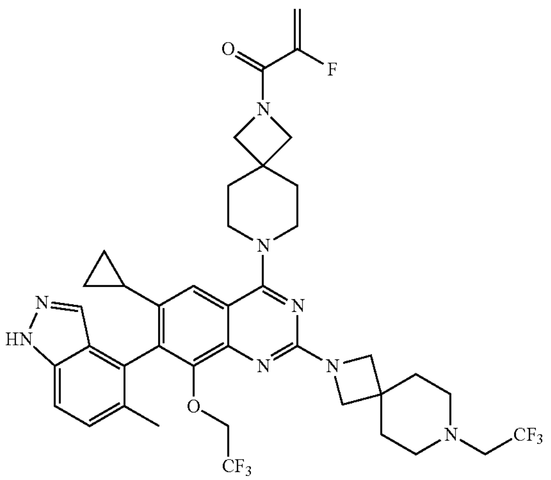
87
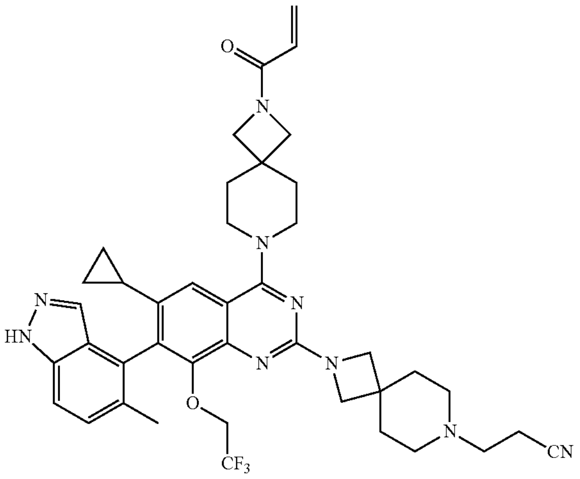
88
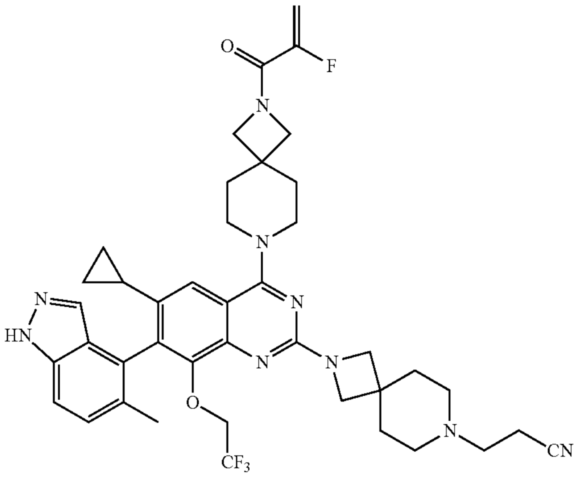

89
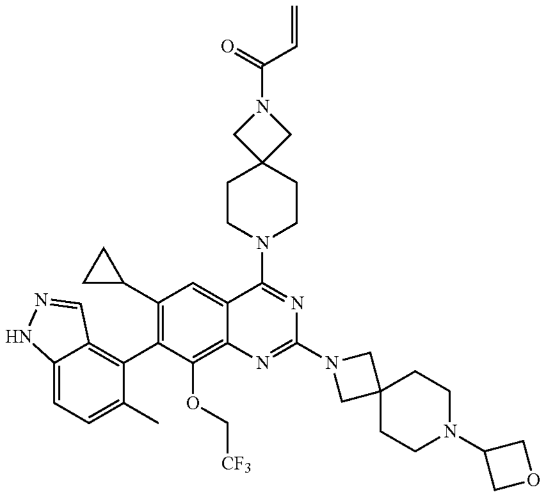
90
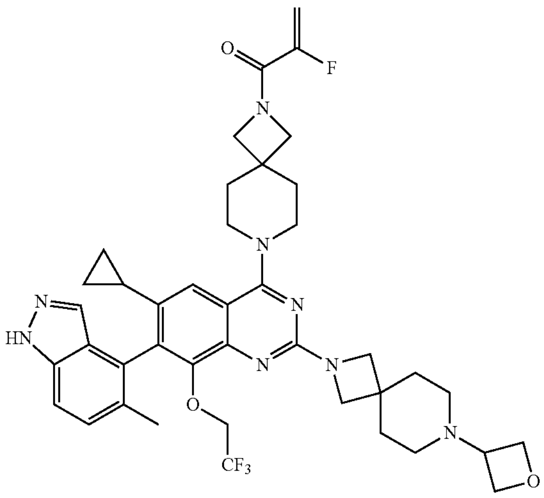
91
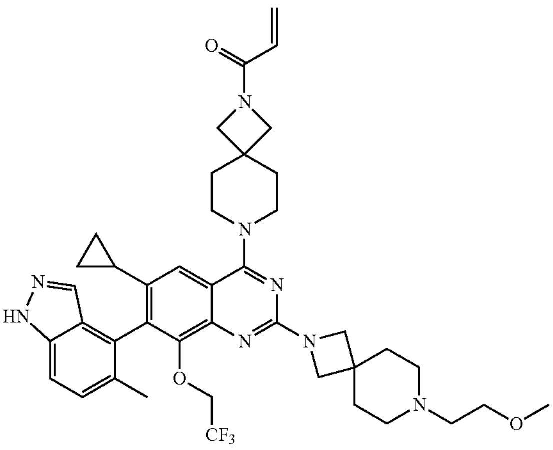
92
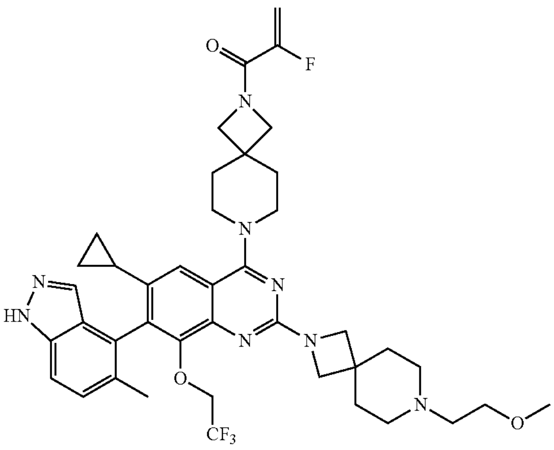
93
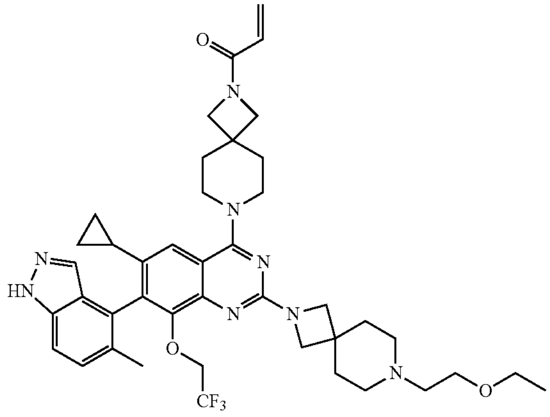
94
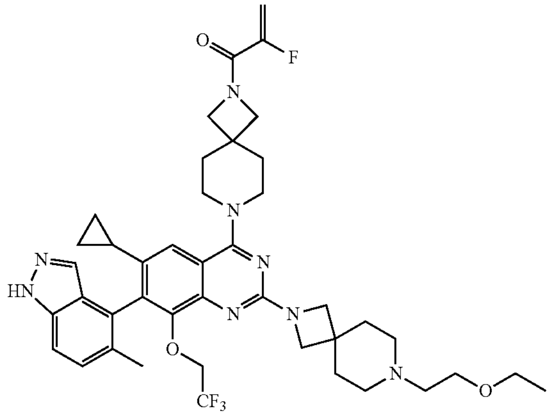

-continued
95
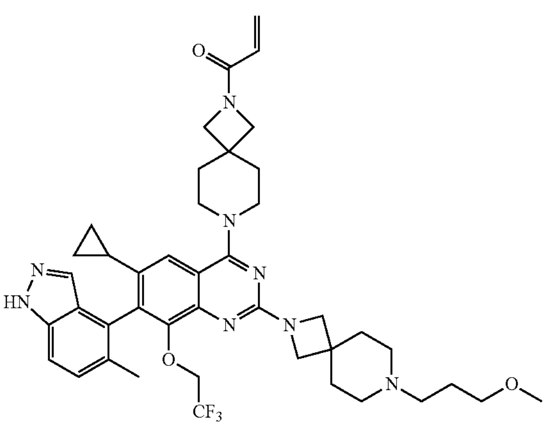
96
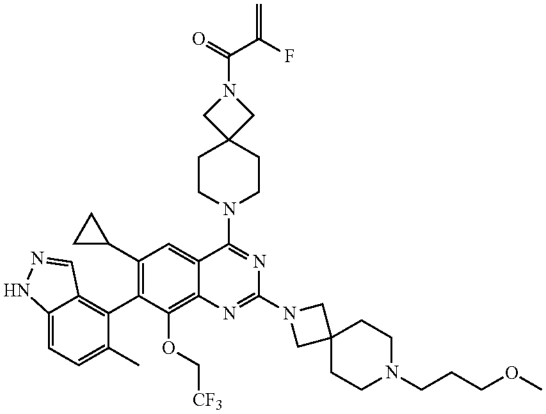
97
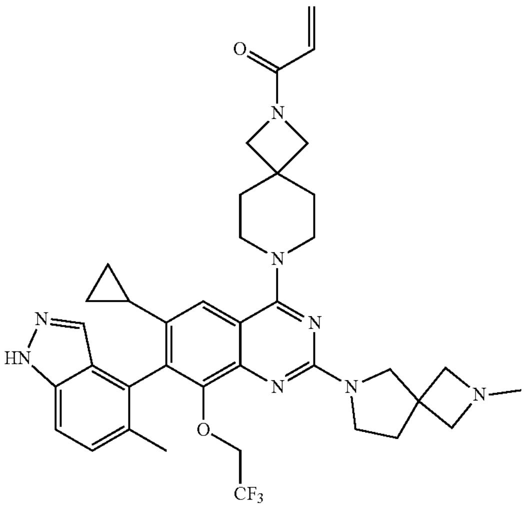
-continued
98
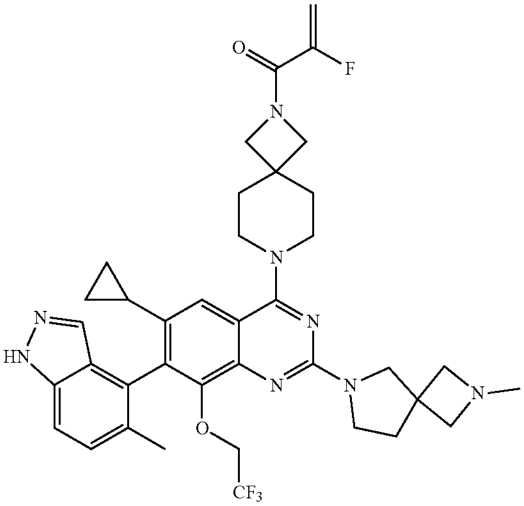
99
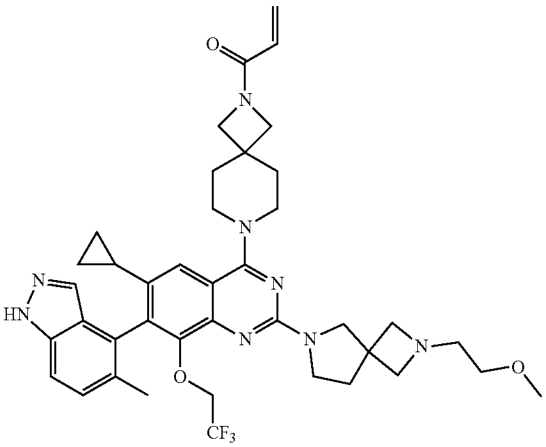
100
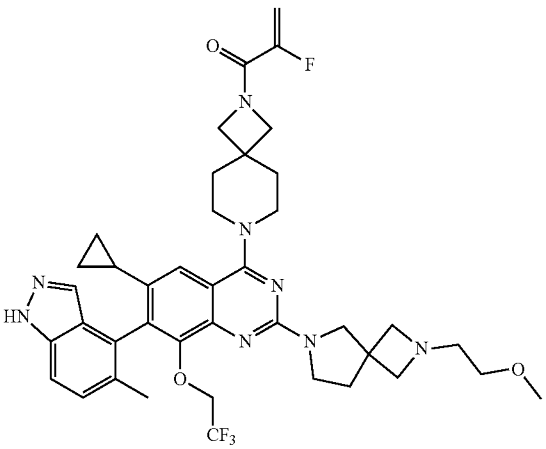

-continued
101
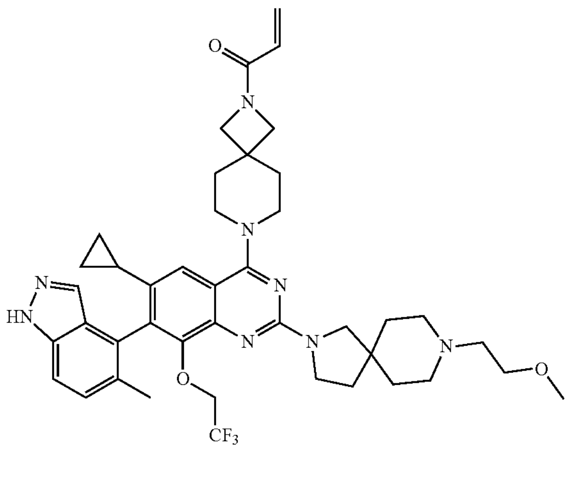
102
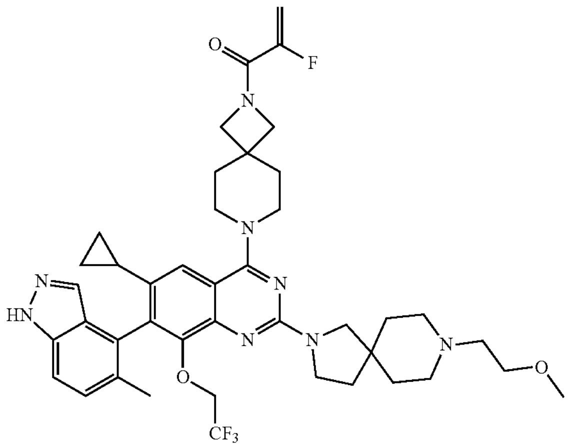
103
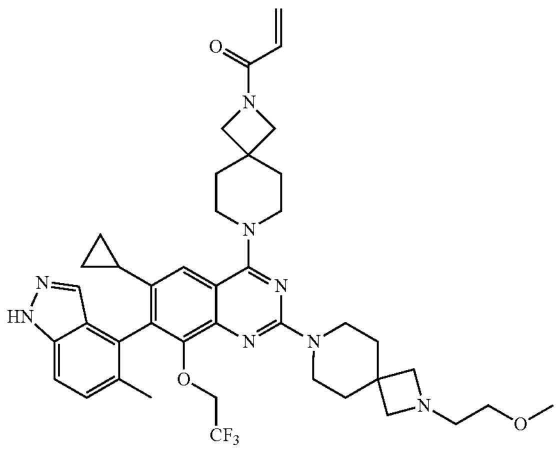
-continued
104
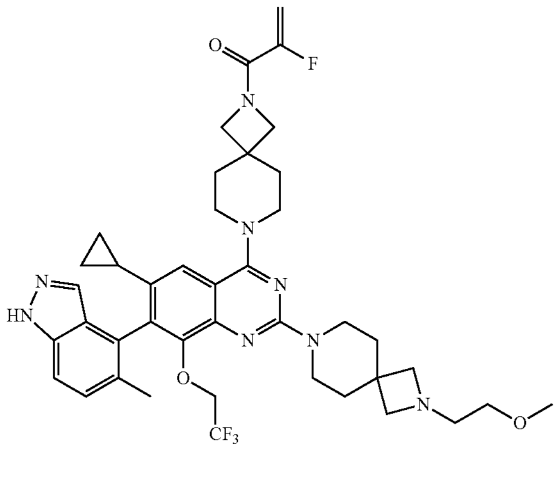
105
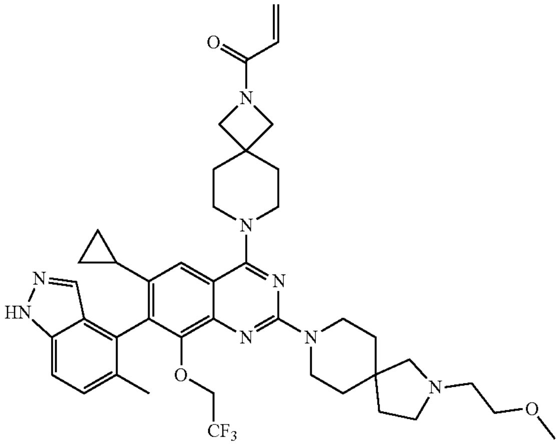
106
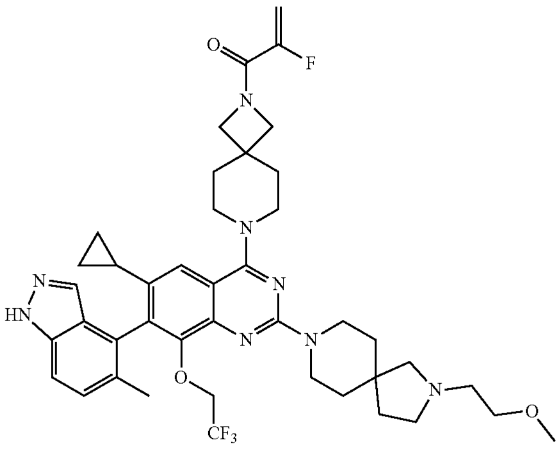

-continued
107
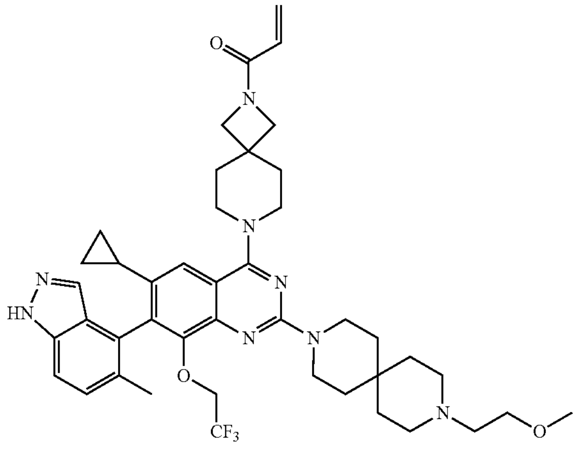
108
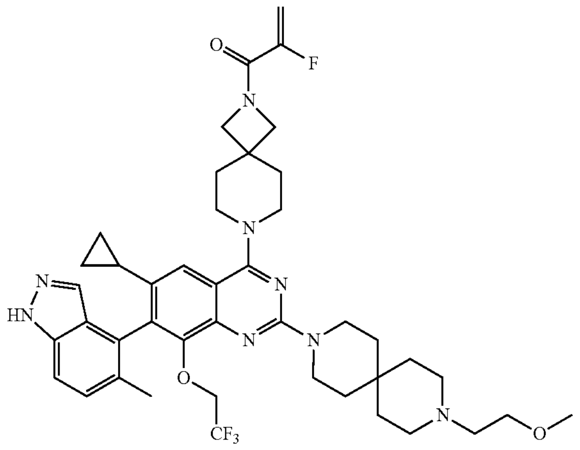
109
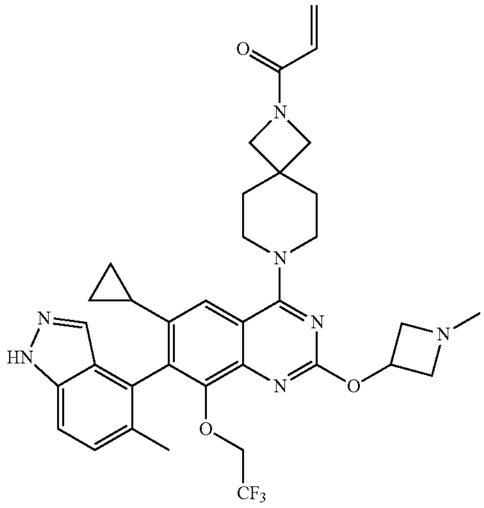
-continued
110
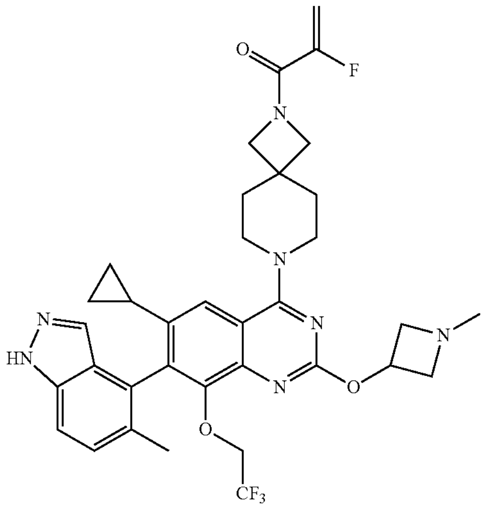
111
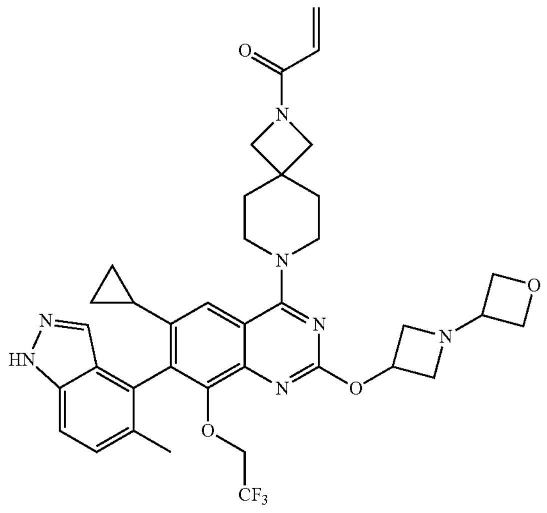
112
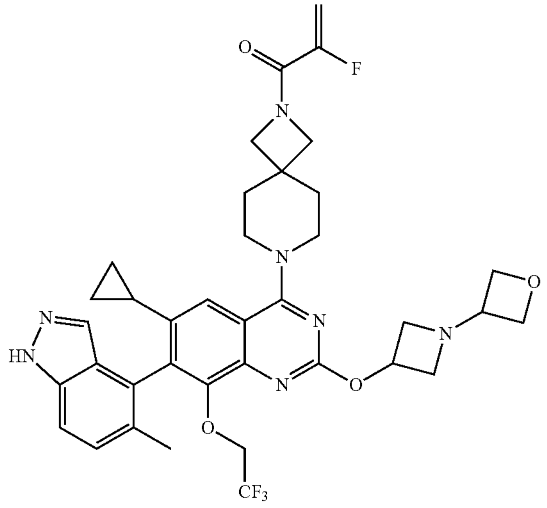

-continued
113
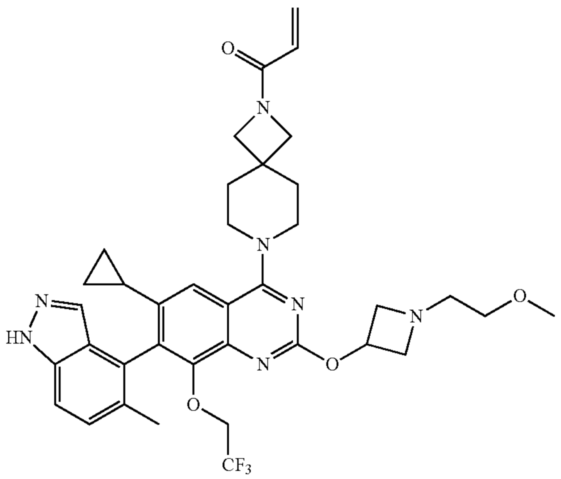
114
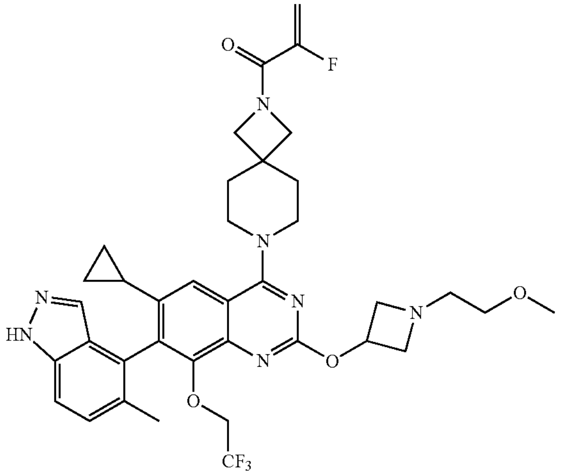
115
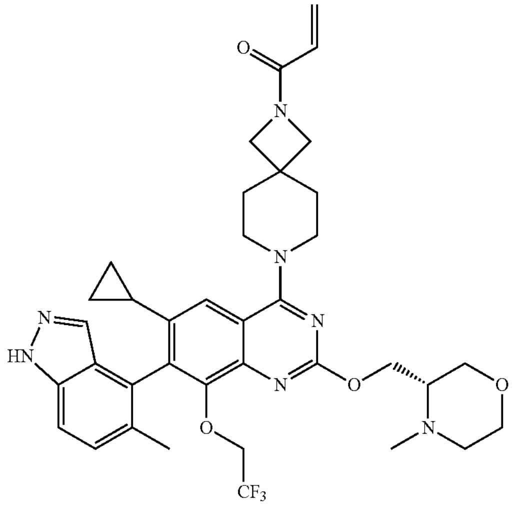
-continued
116
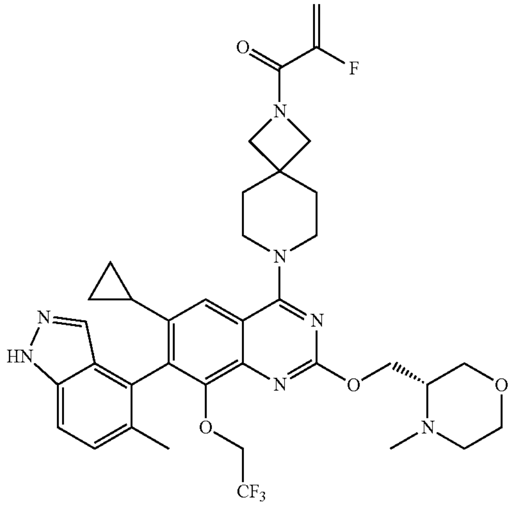
117
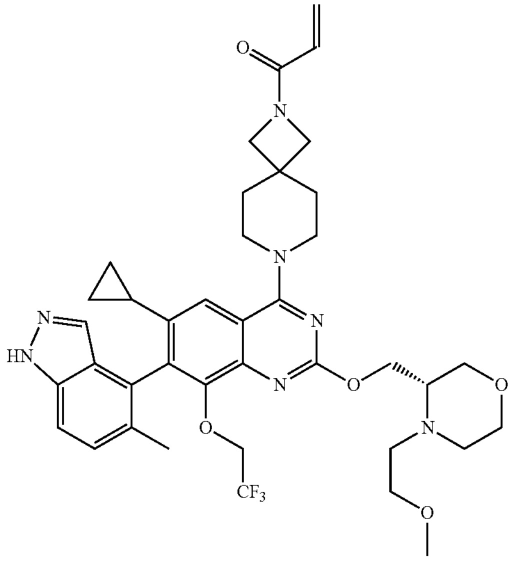
118
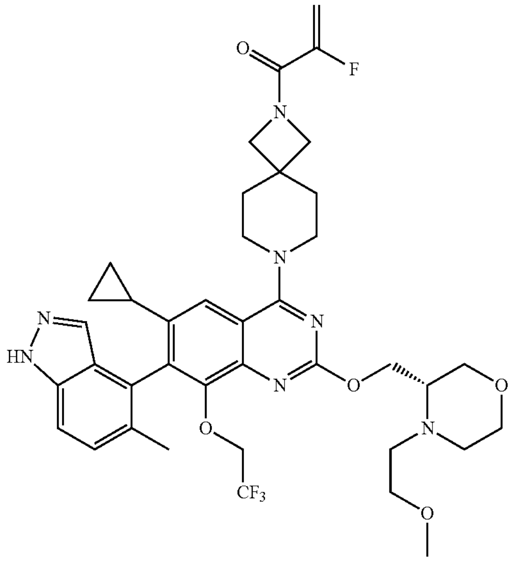

119
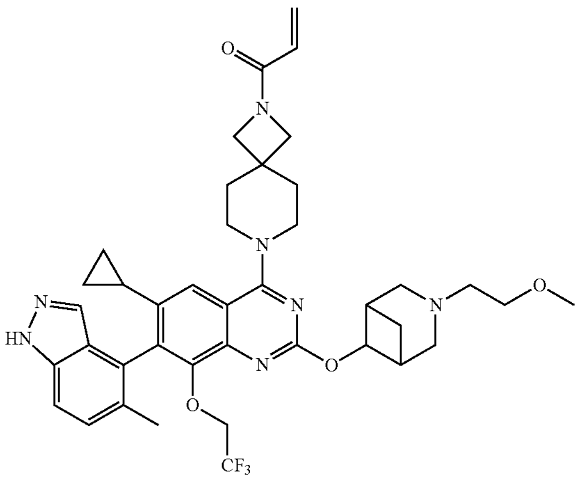
120
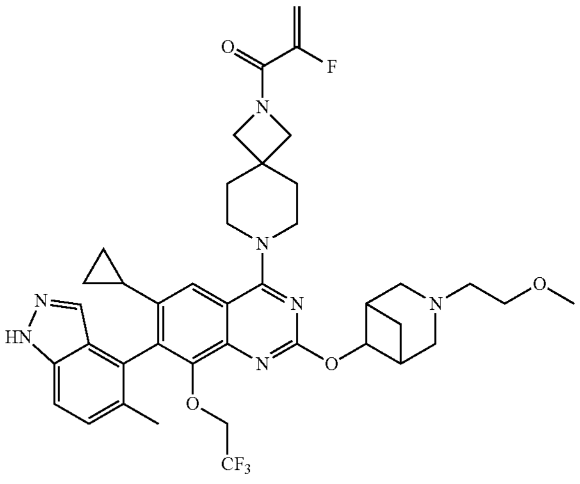
121
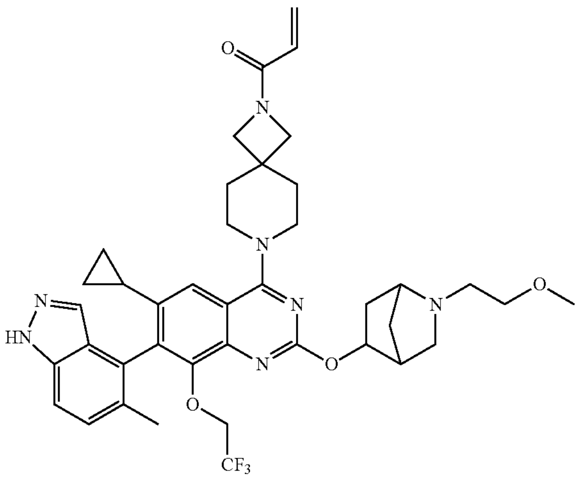
122
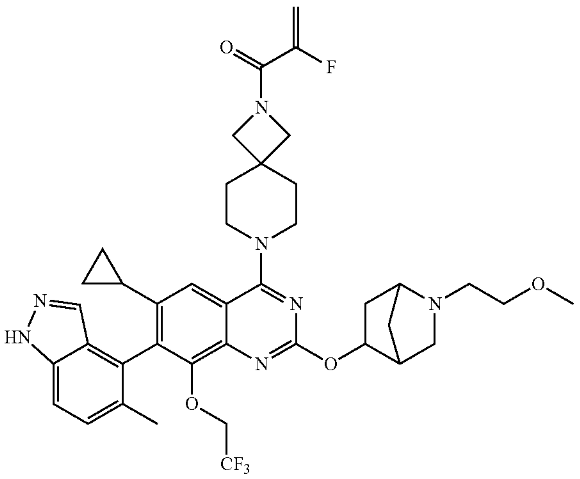
123
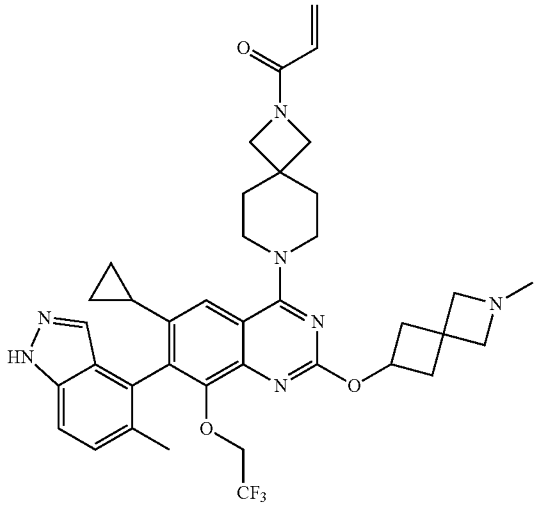
124
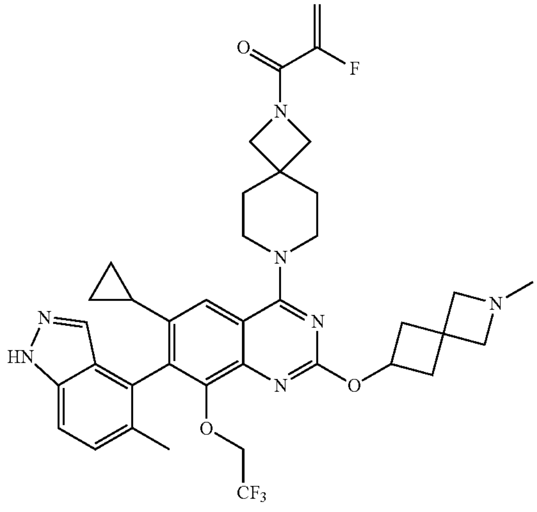

-continued
125
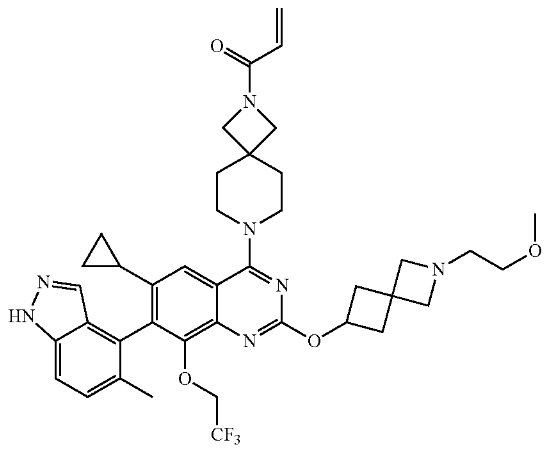
126
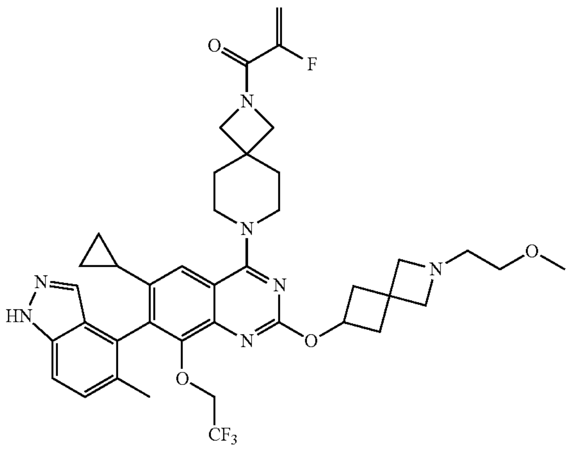
127
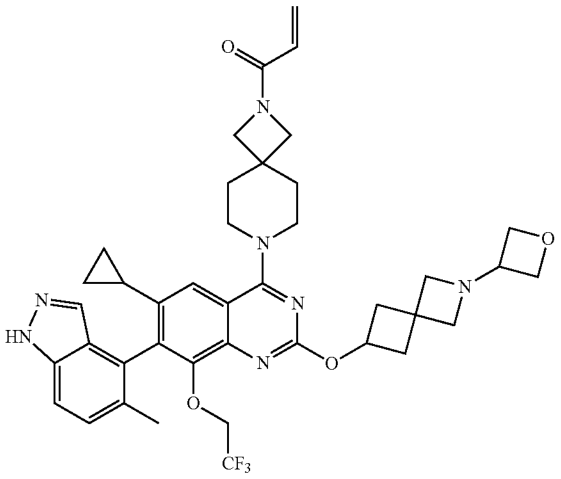
-continued
128
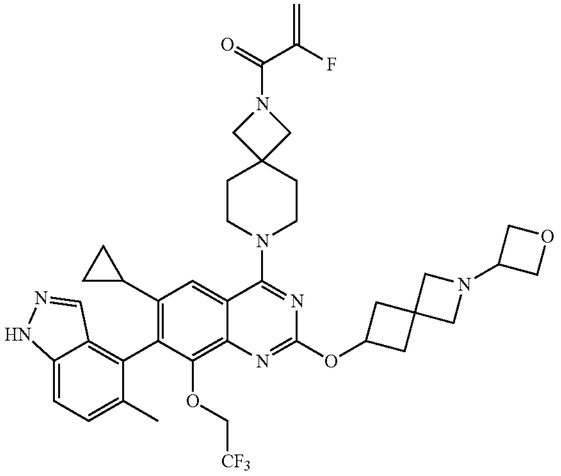
129
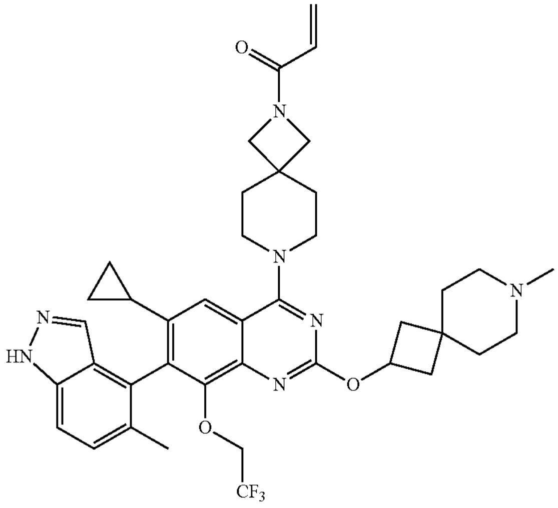
130
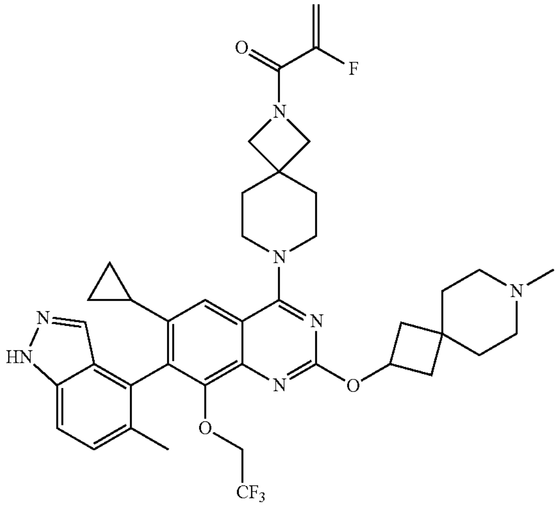

131
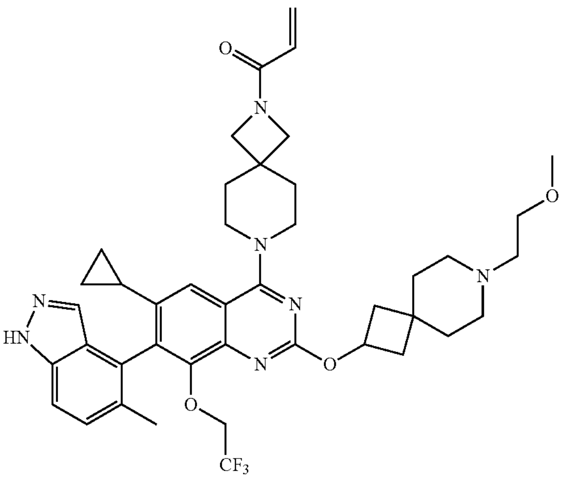
132
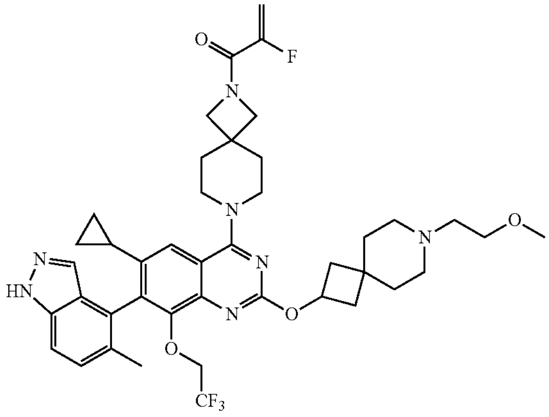
133
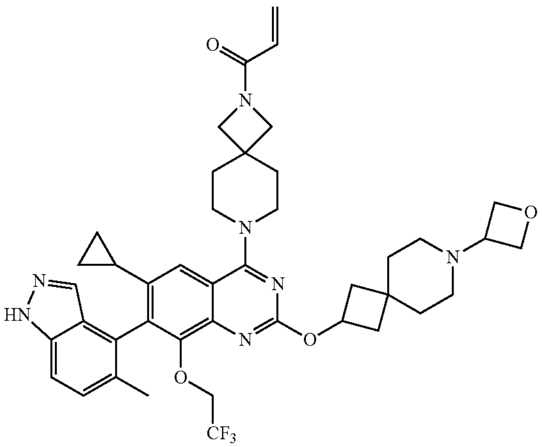
134
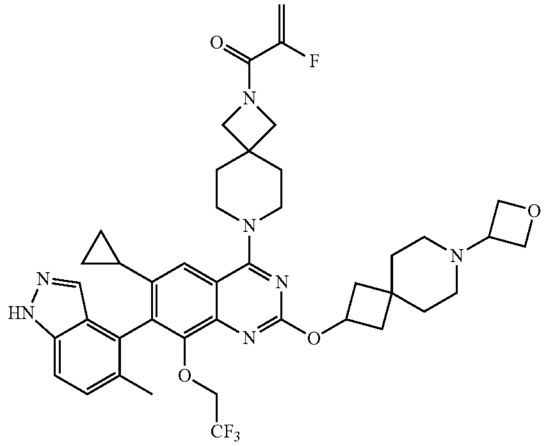
135
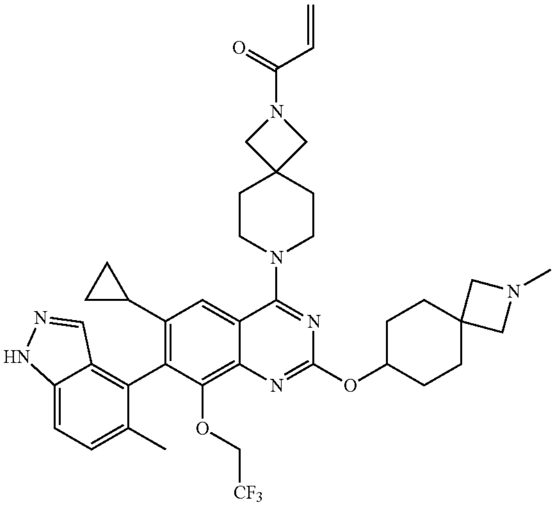
136
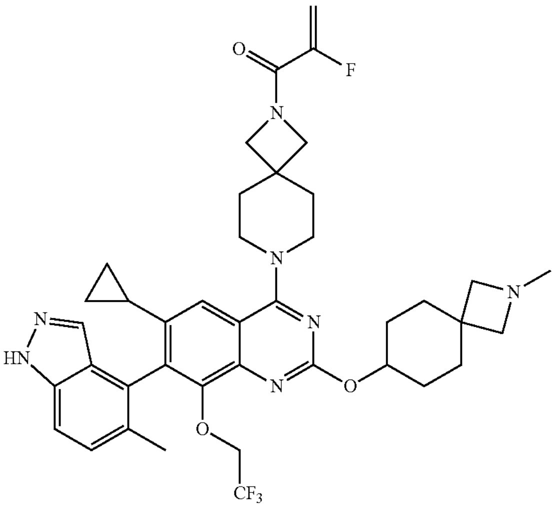

-continued
137
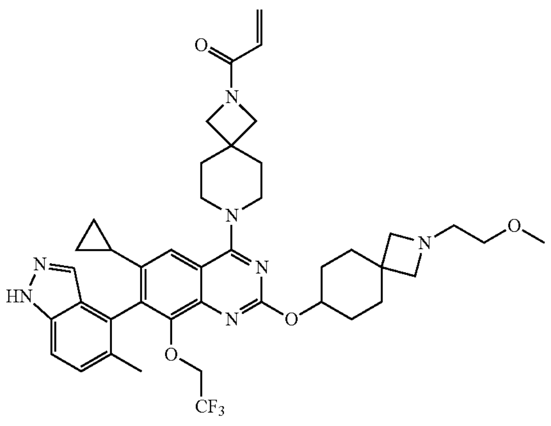
138
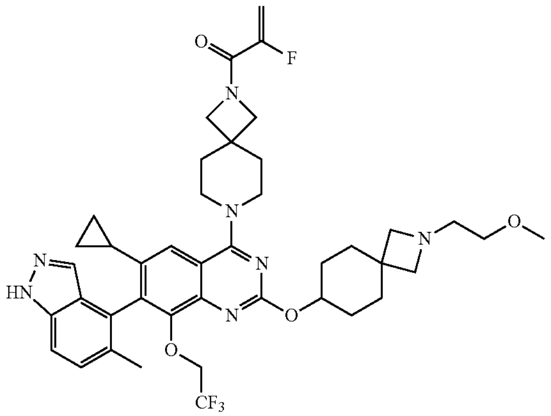
139
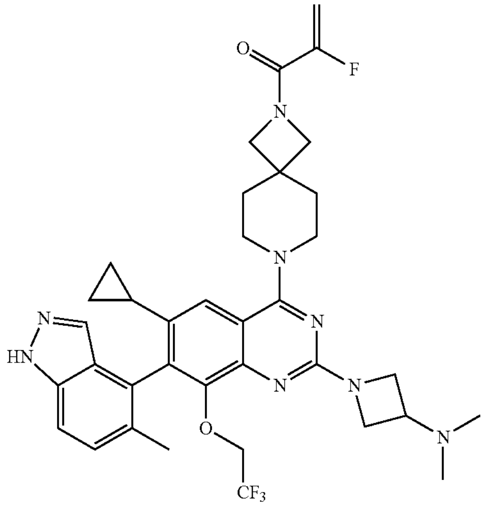
-continued
140
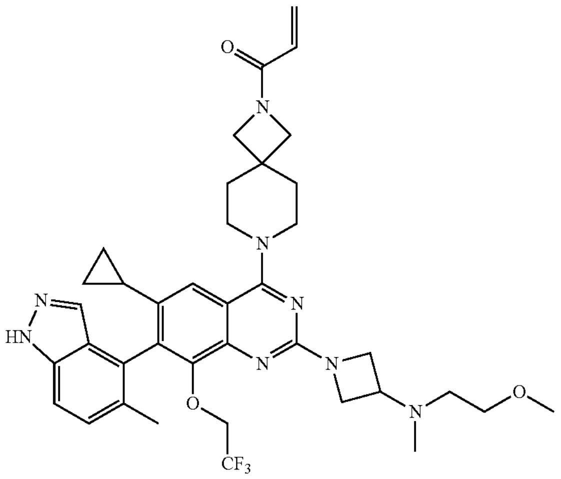
141
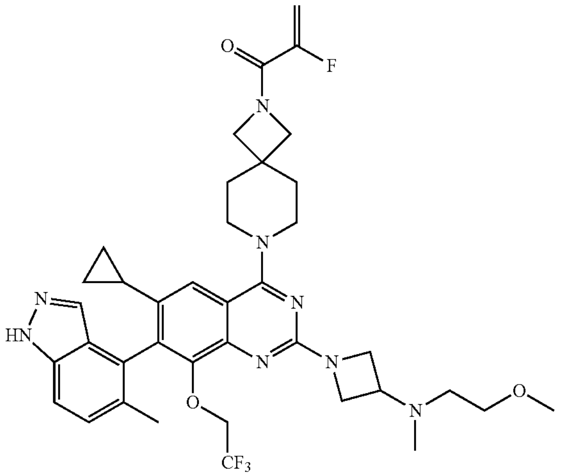
142
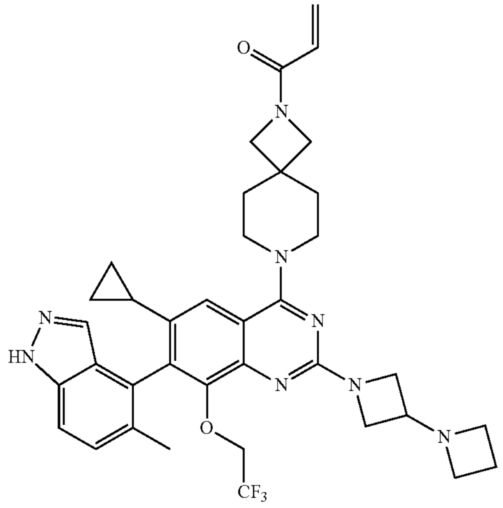

-continued
143
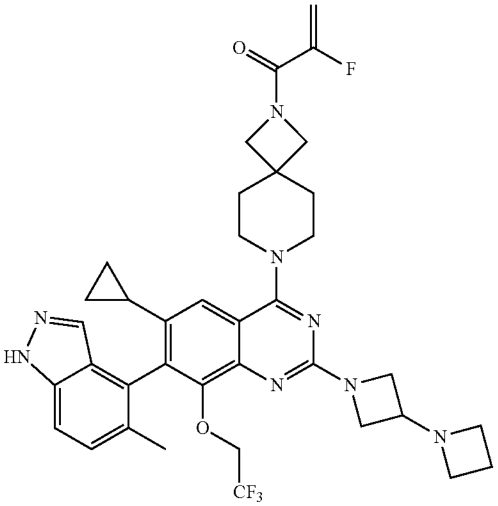
144
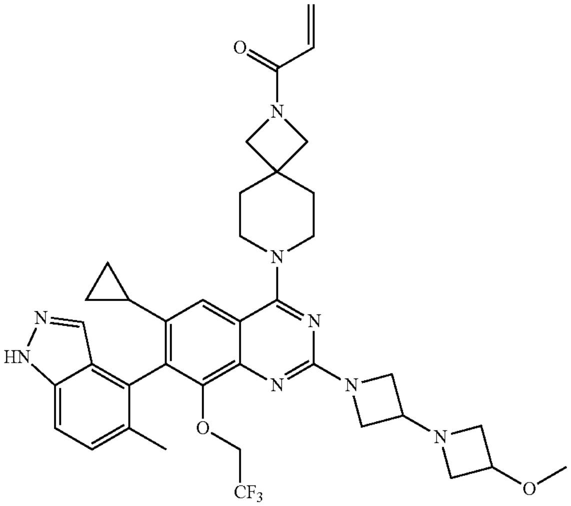
145
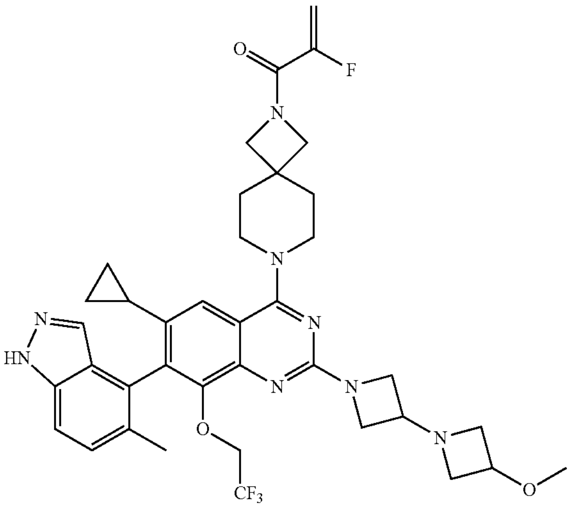
-continued
146
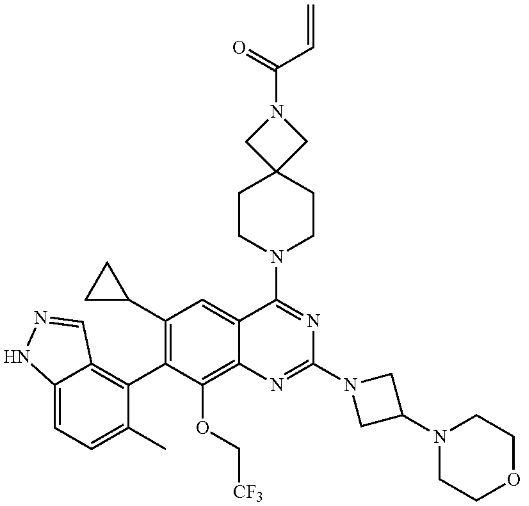
147
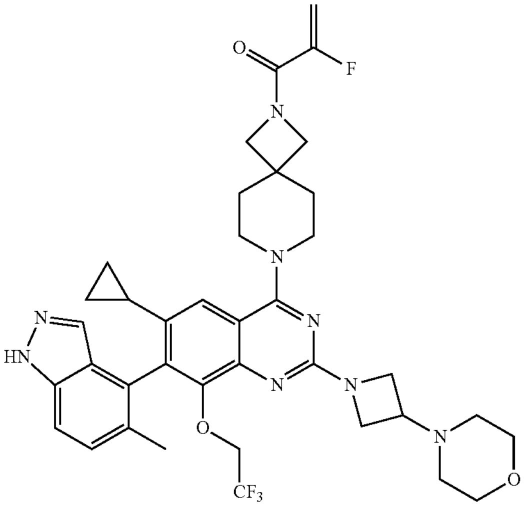
148
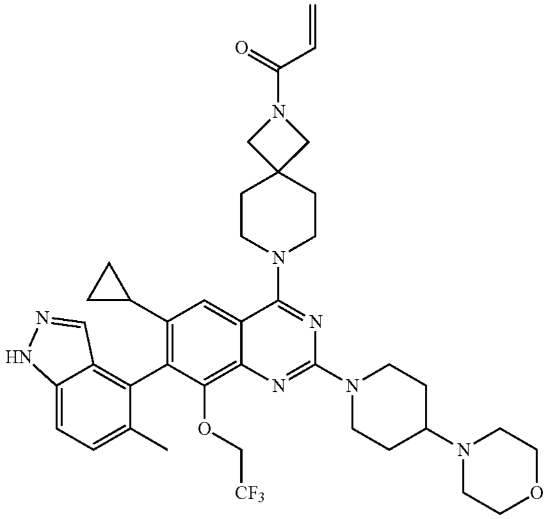

-continued
149
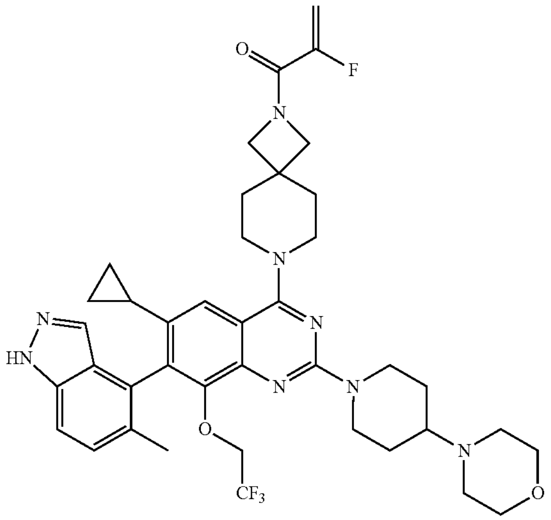
150
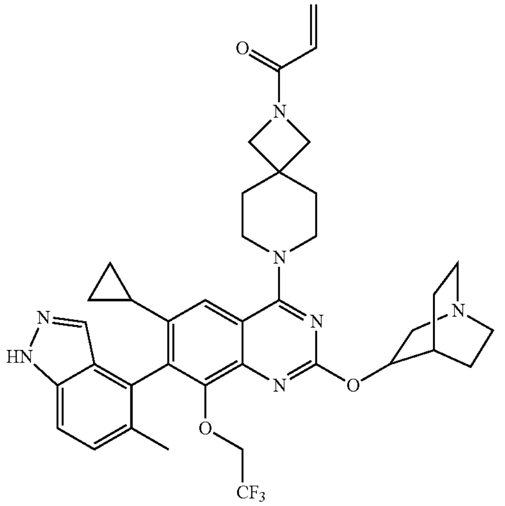
151
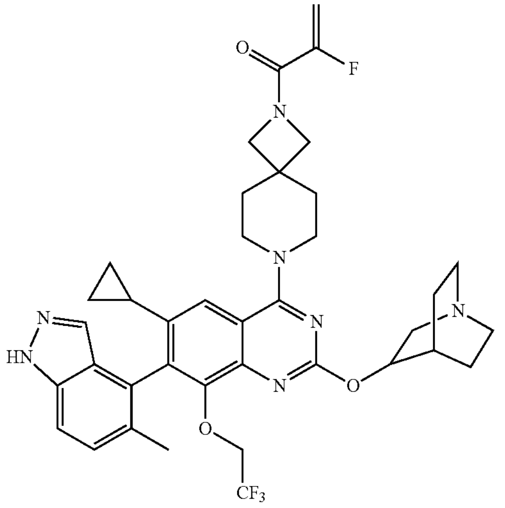
-continued
152
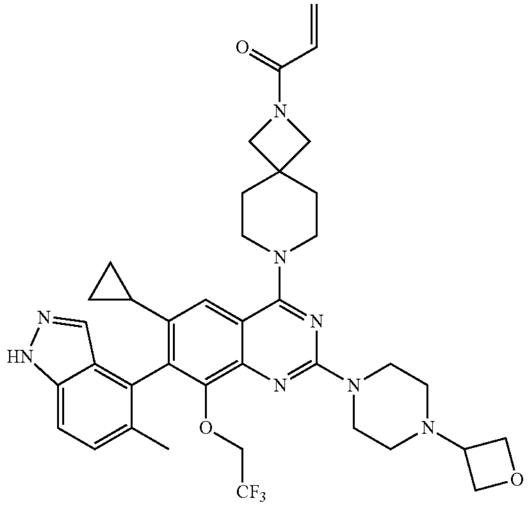
153
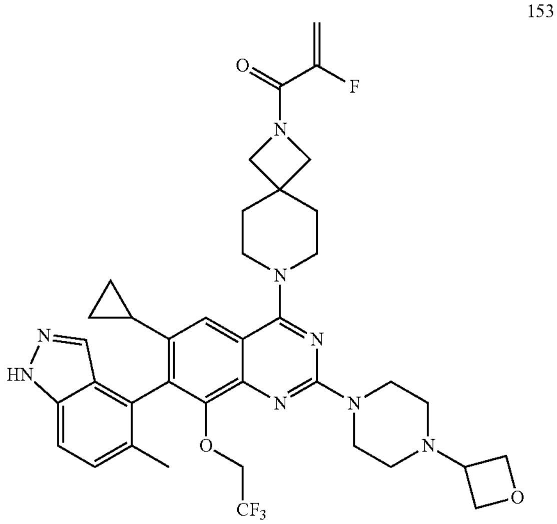
154
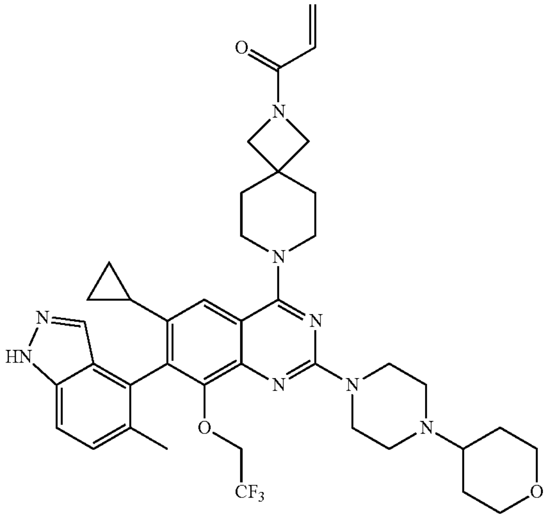

-continued
155
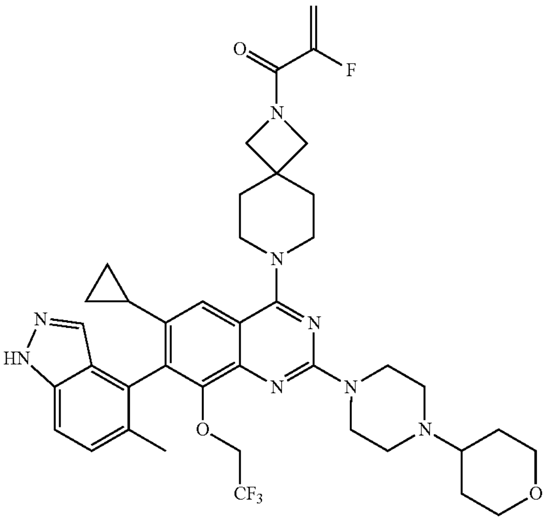
156
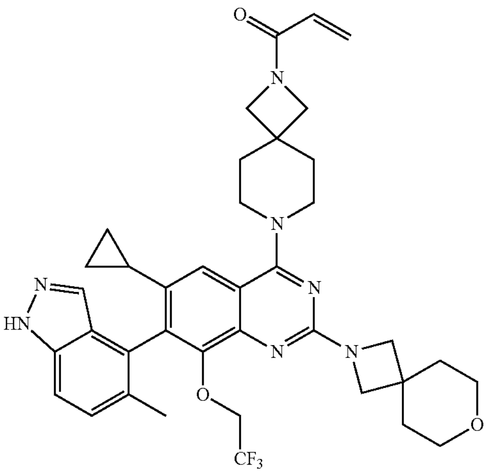
157
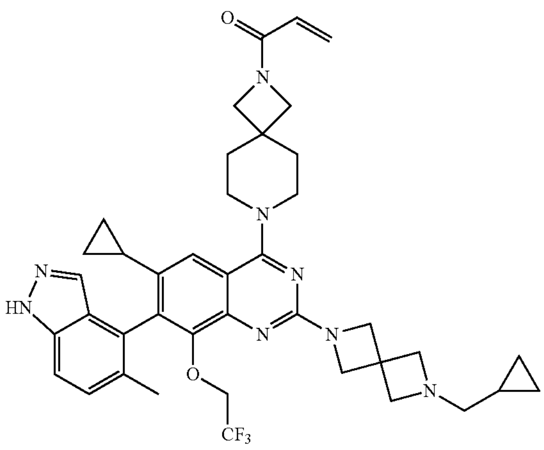
-continued
158
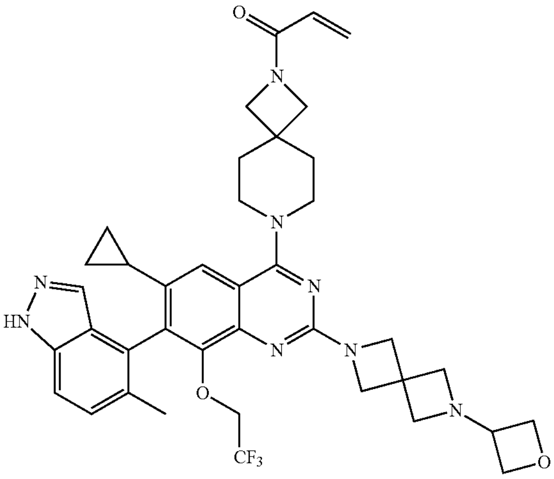
159
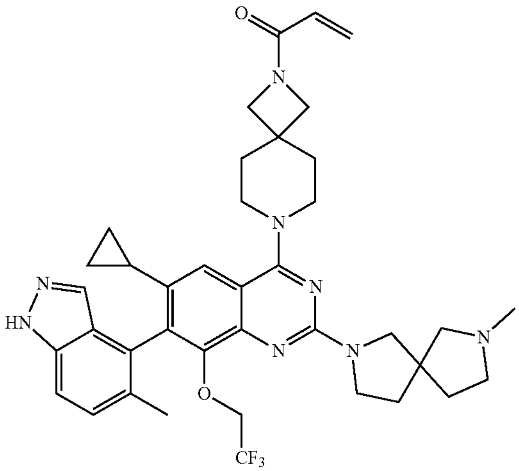
160
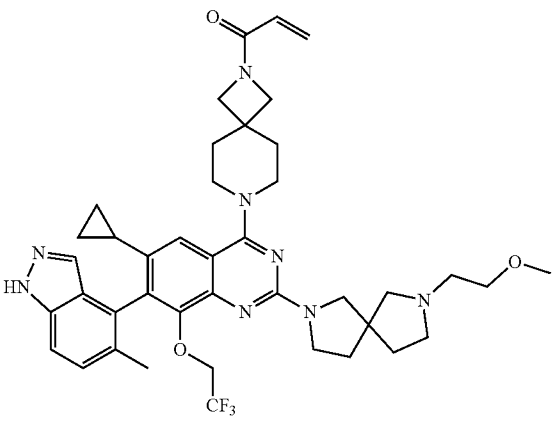

-continued
161
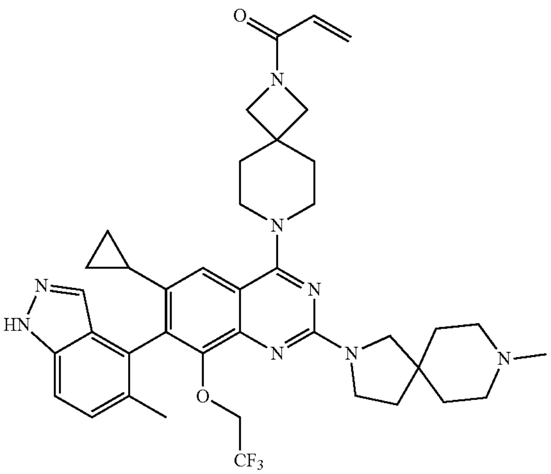
162
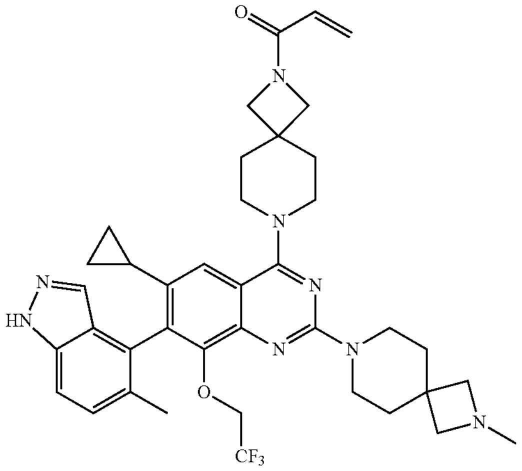
163
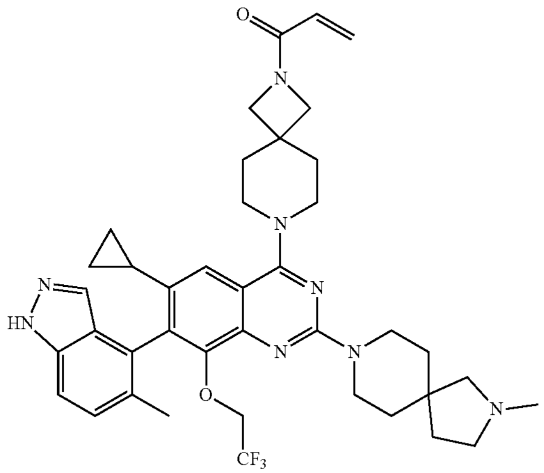
-continued
164
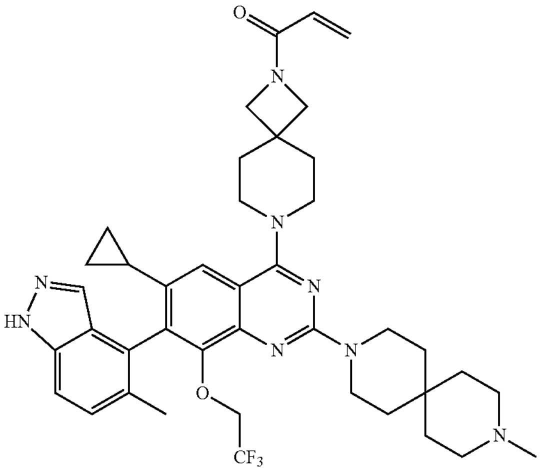
165
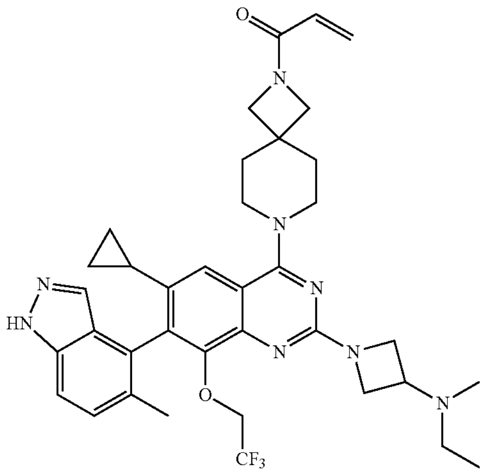
166
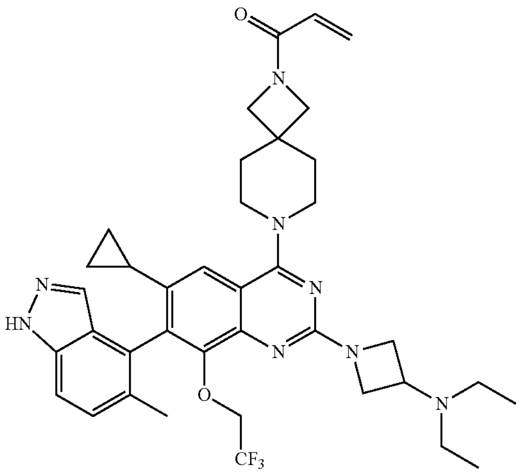

-continued
167
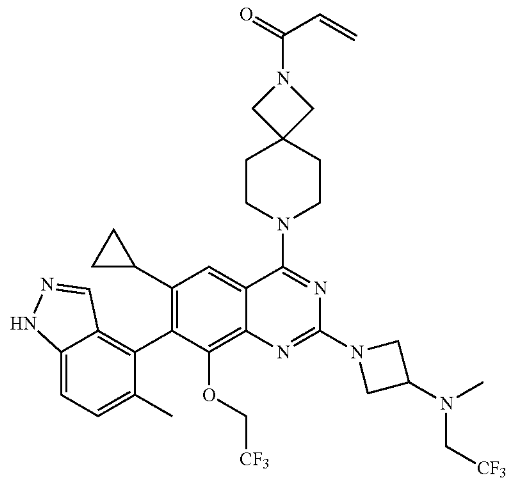
168
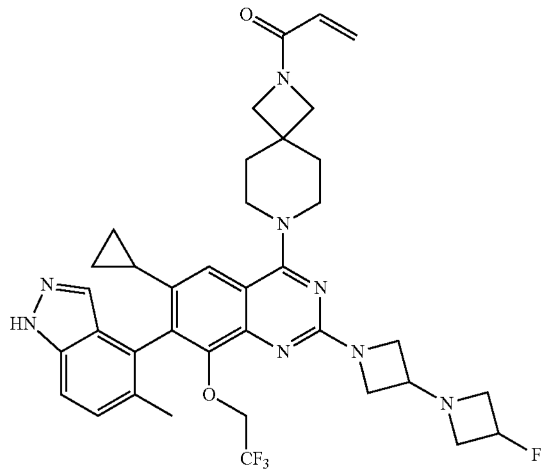
169
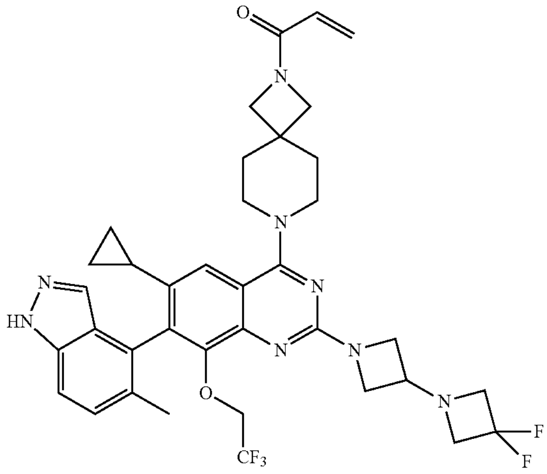
-continued
170
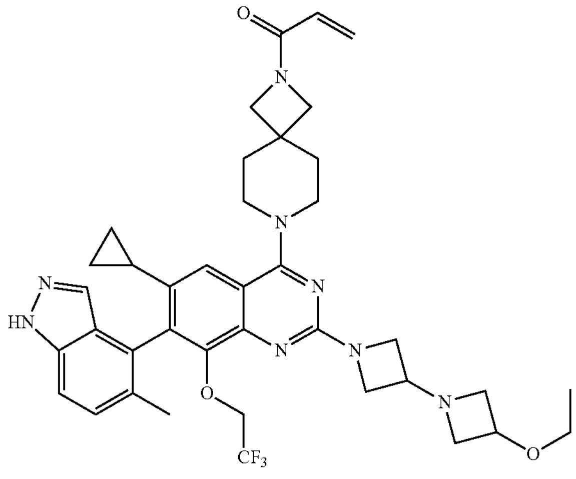
171
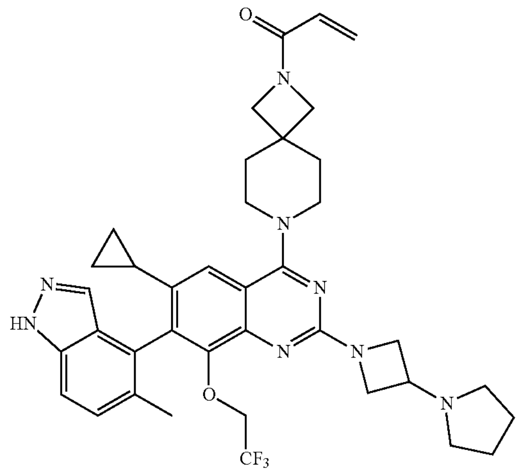
172
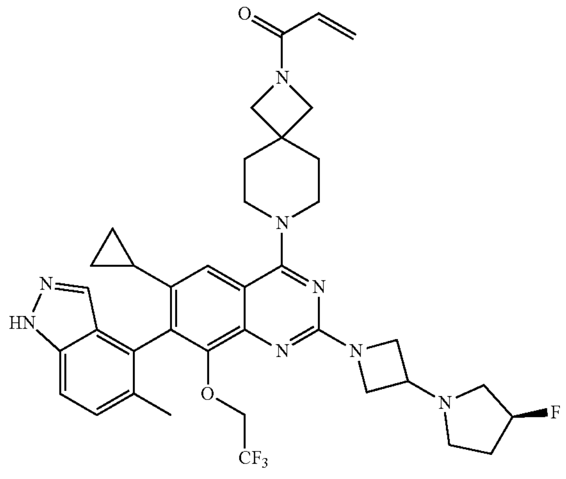

-continued
173
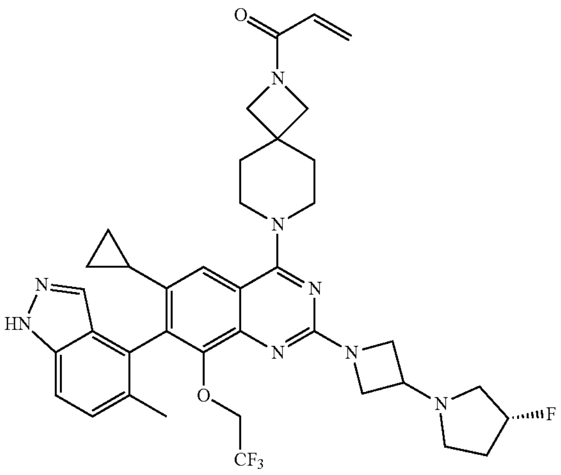
174
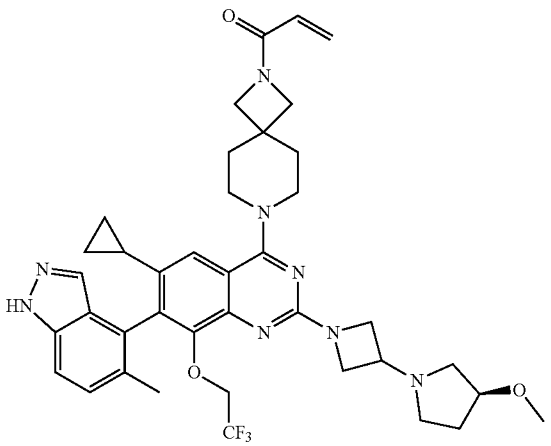
175
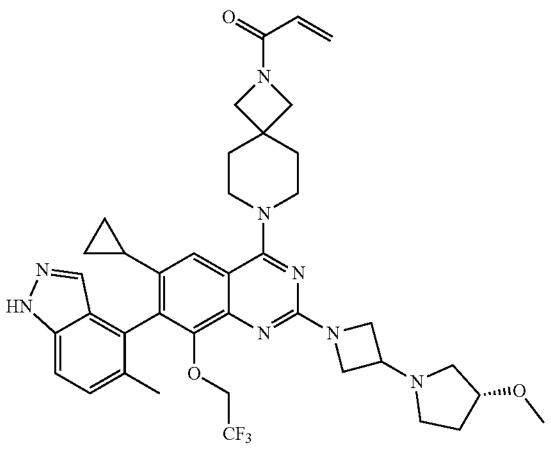
-continued
176
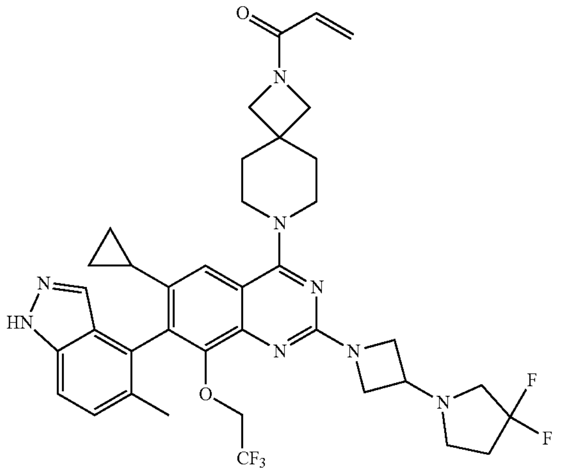
177
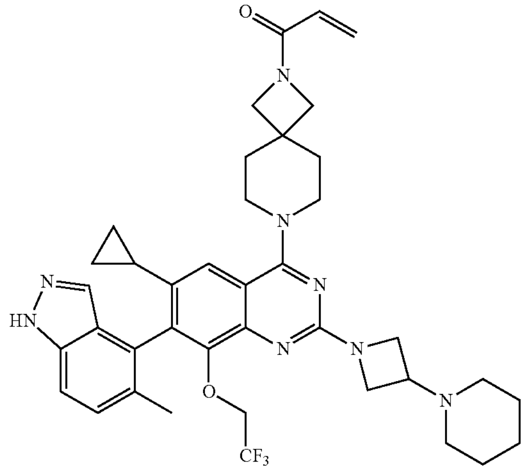
178
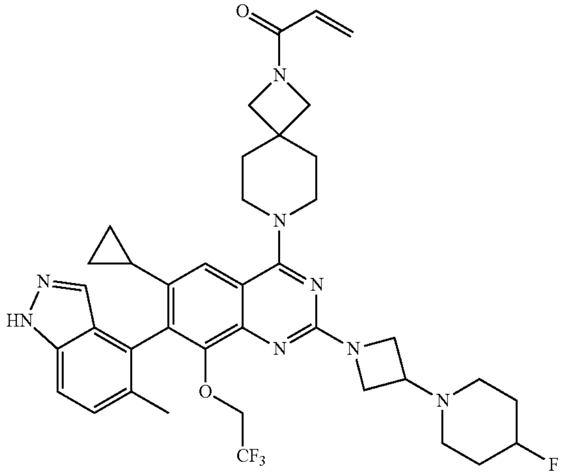

-continued
179
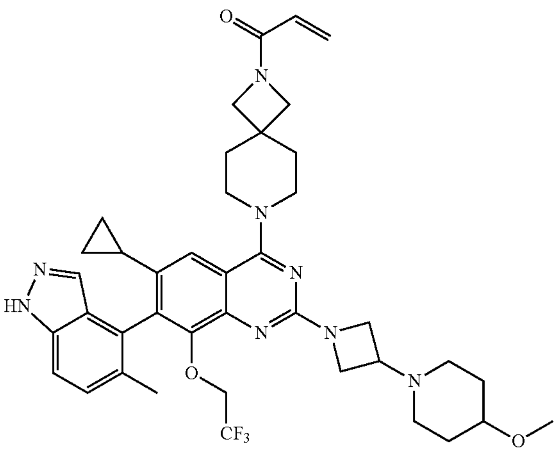
180
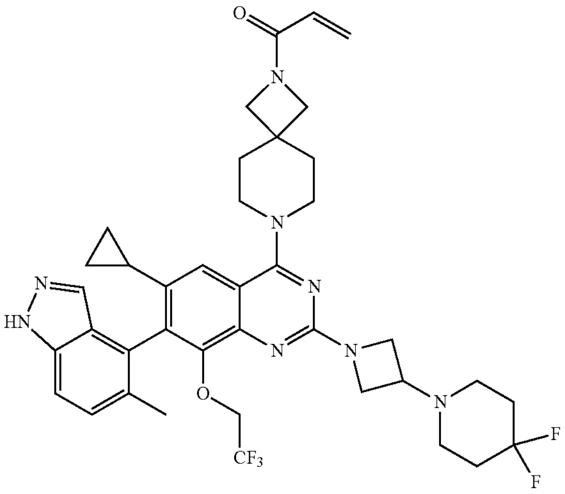
181
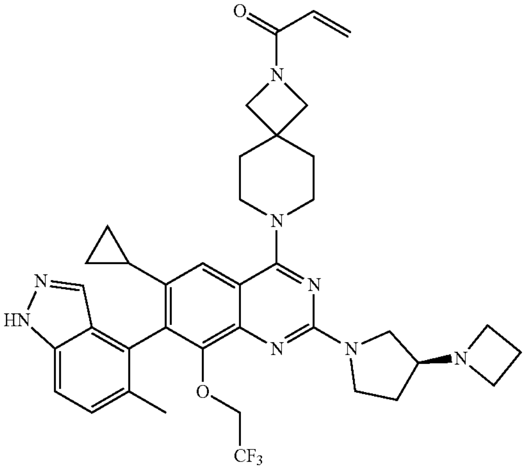
-continued
182
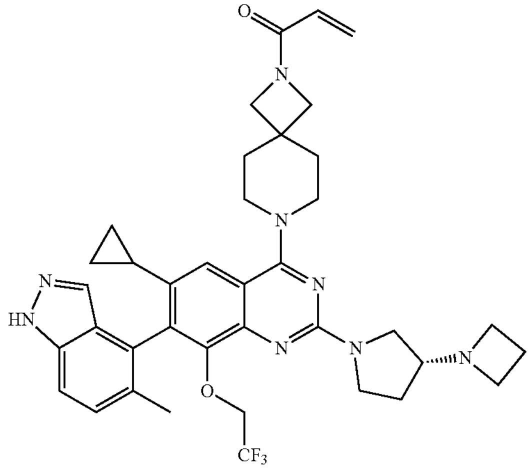
183
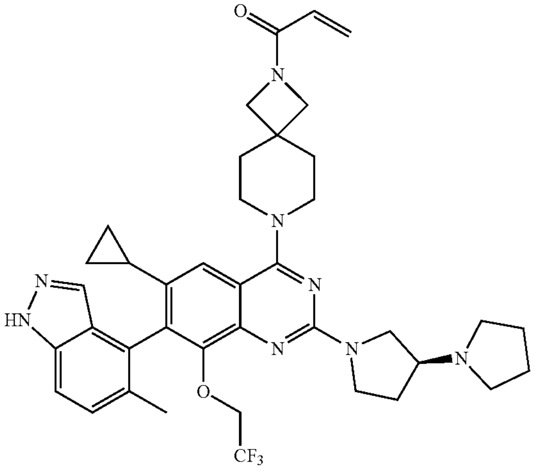
184
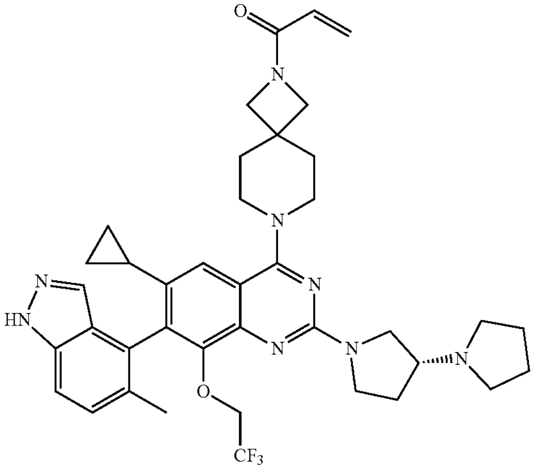

-continued
185
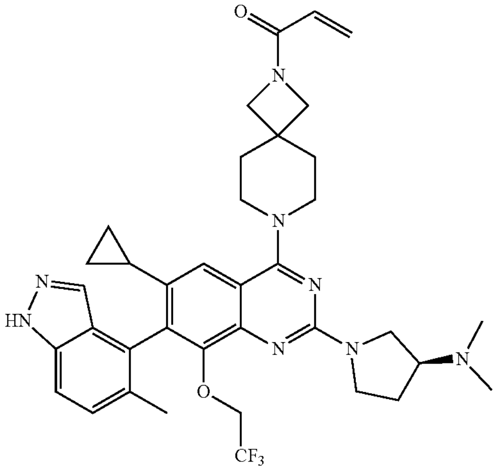
186
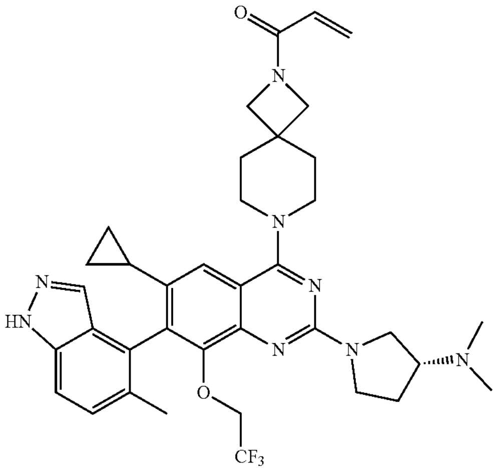
187
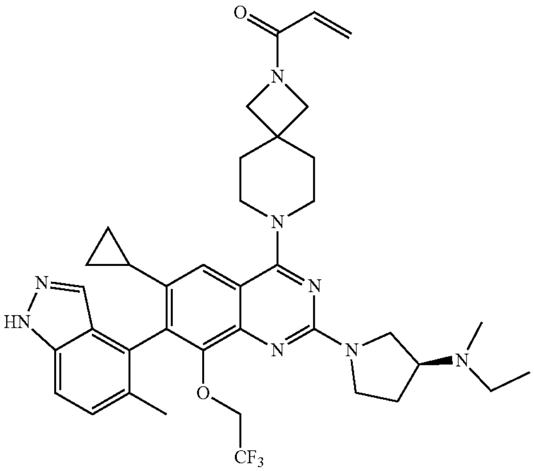
-continued
188
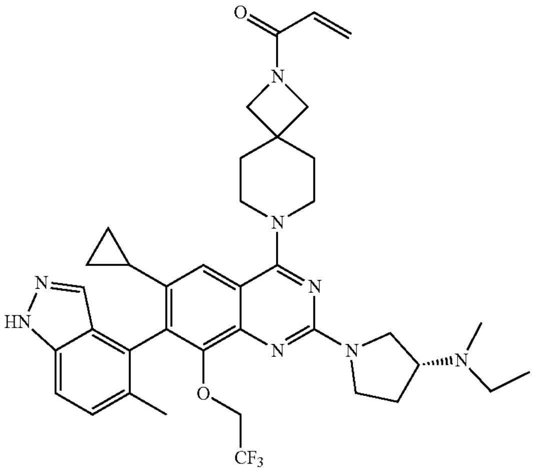
189
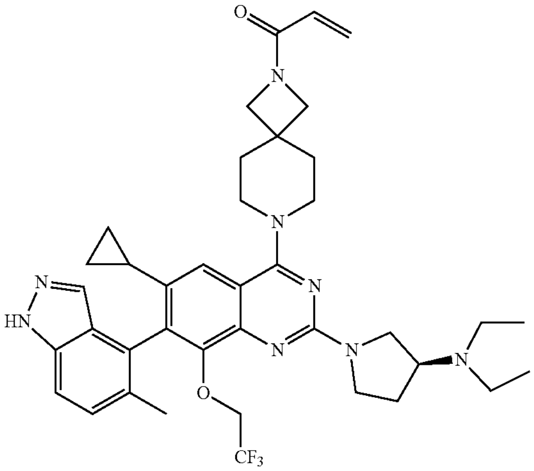
190
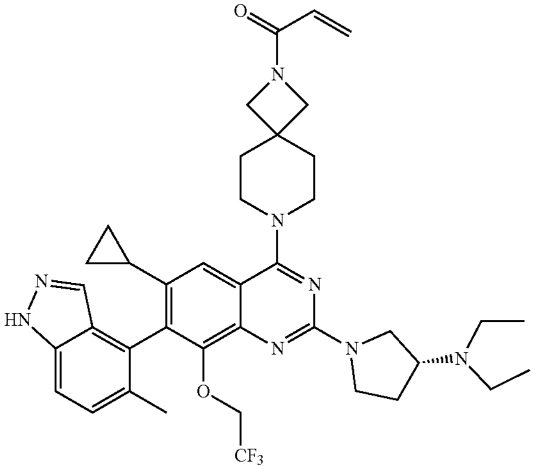

-continued
191
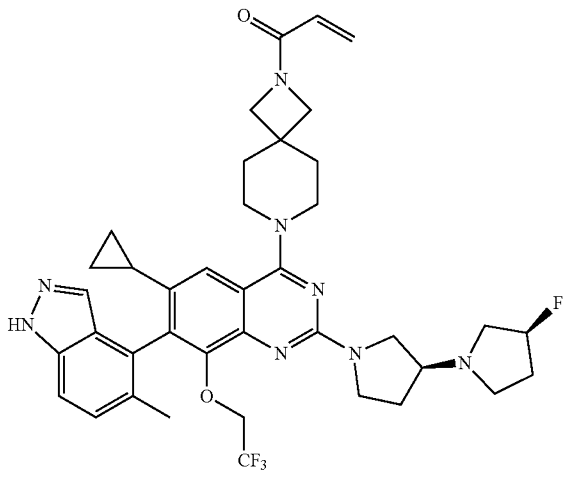
192
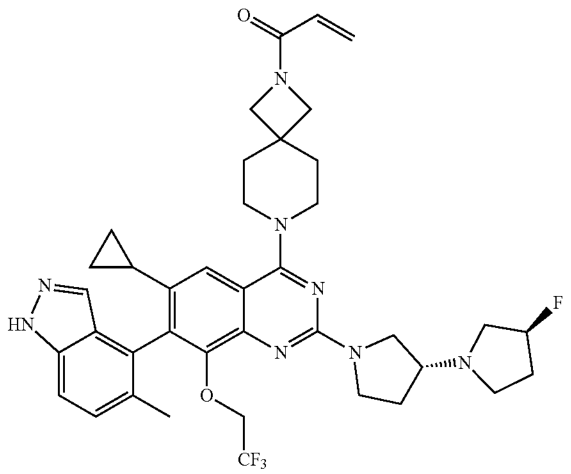
193
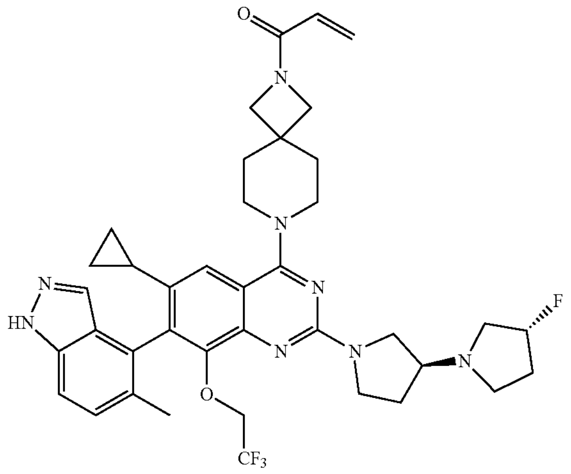
-continued
194
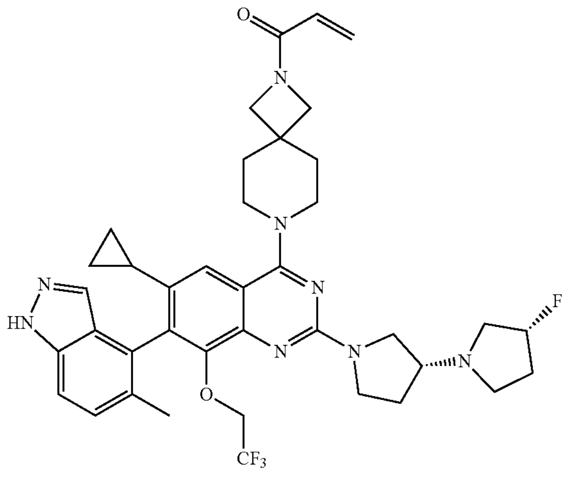
195
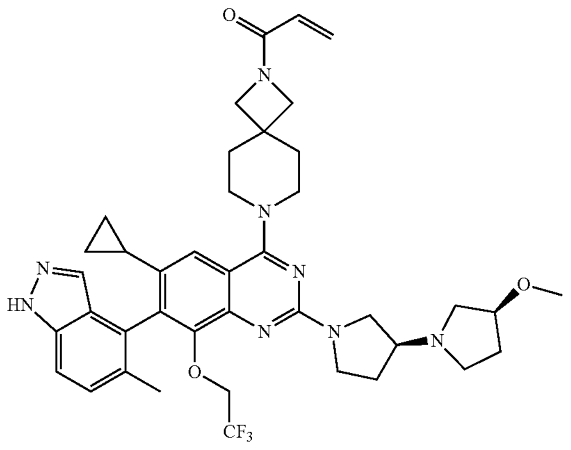
196
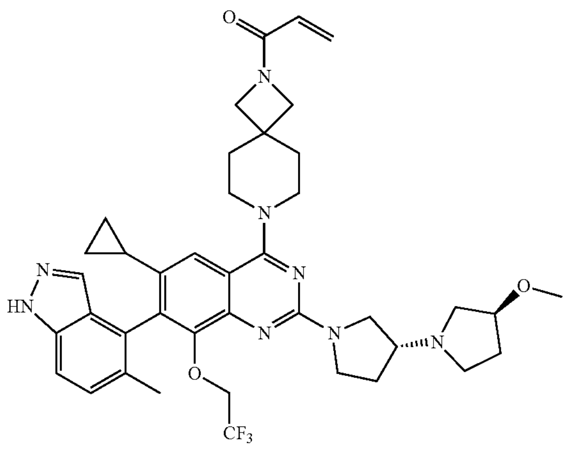

-continued
197
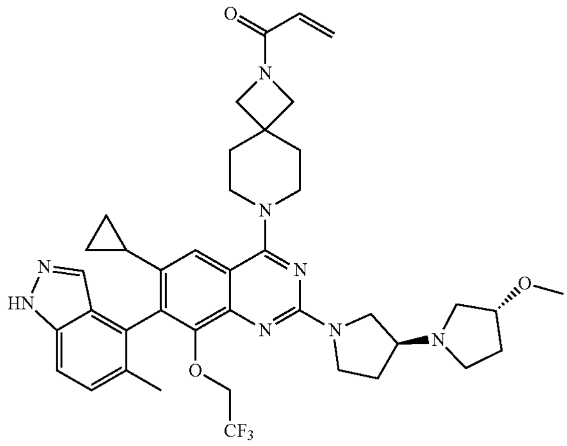
198
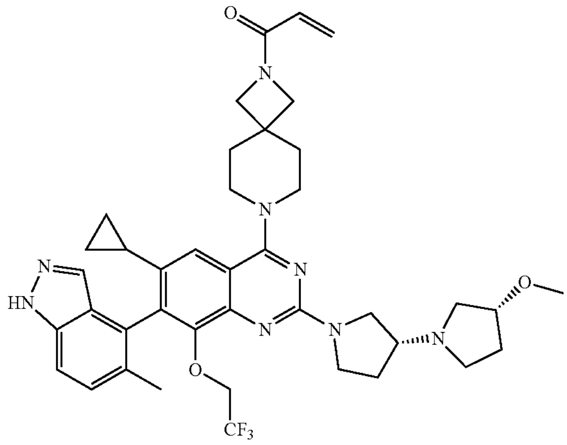
199
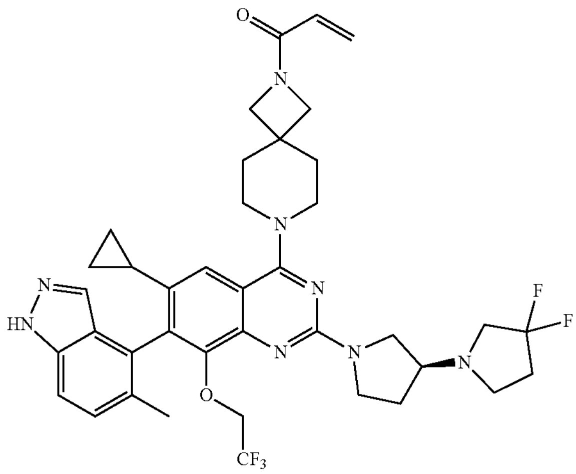
-continued
200
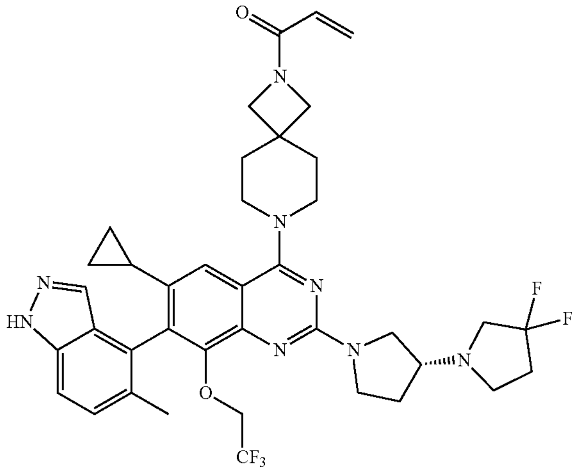
201
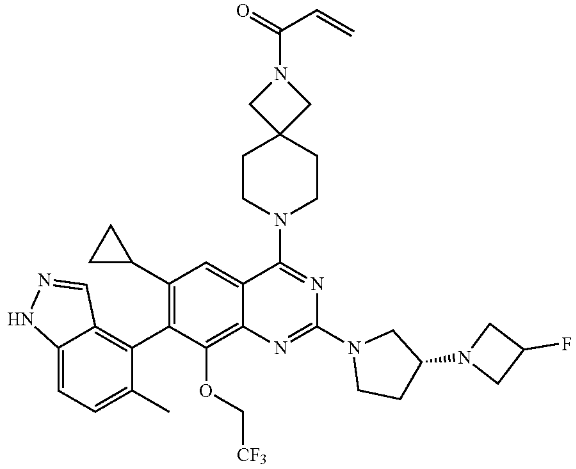
202
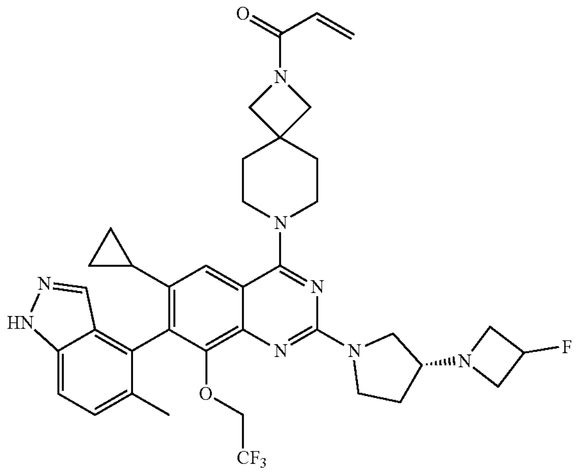

-continued
203
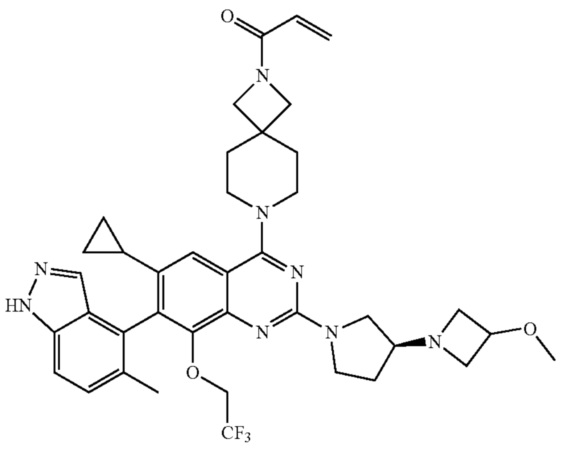
204
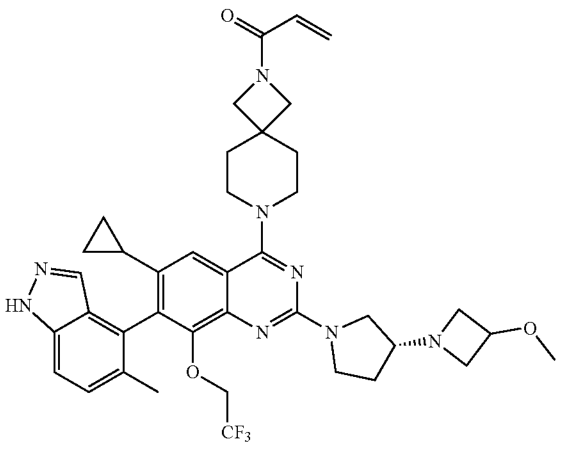
205
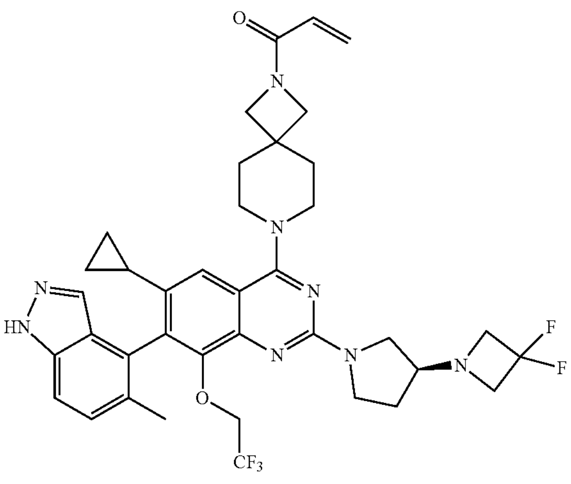
-continued
206
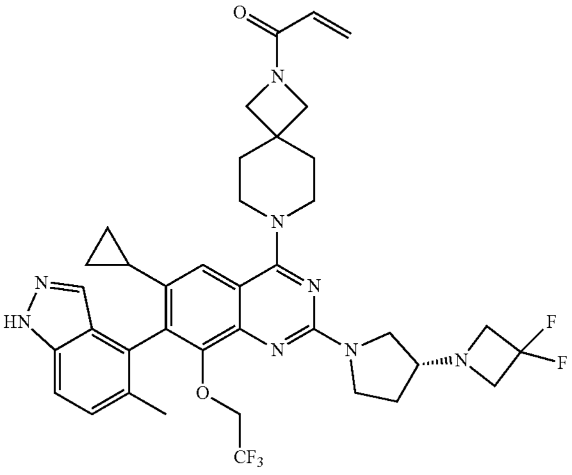
207
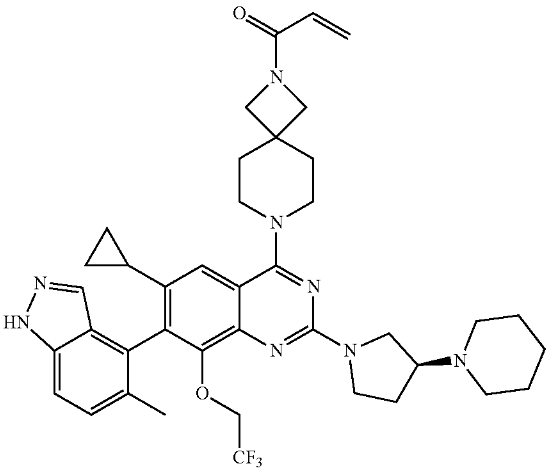
208
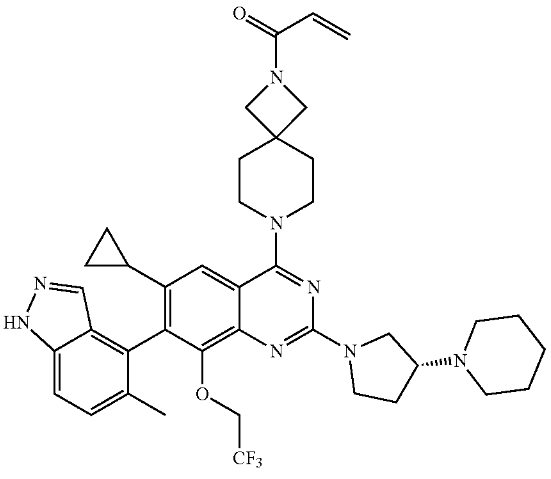

-continued
209
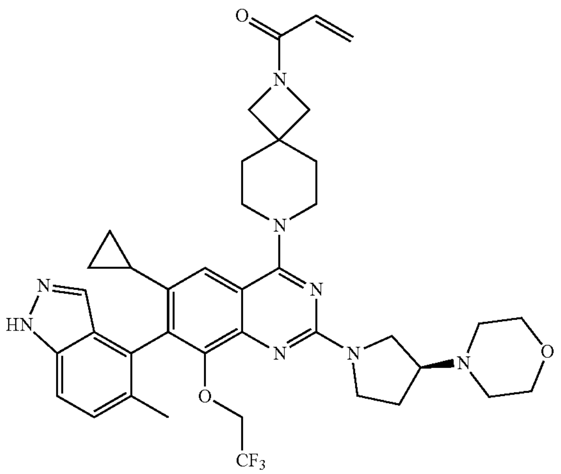
210
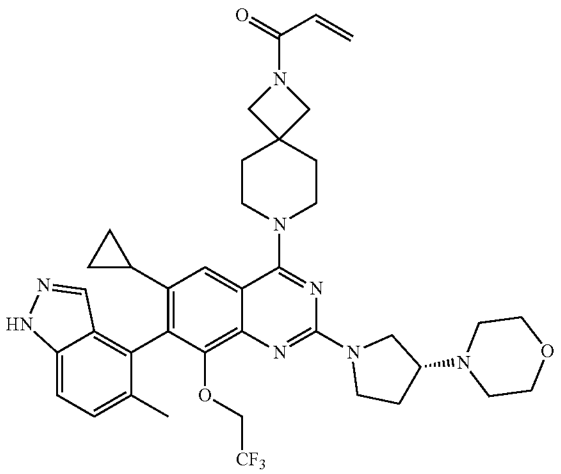
211
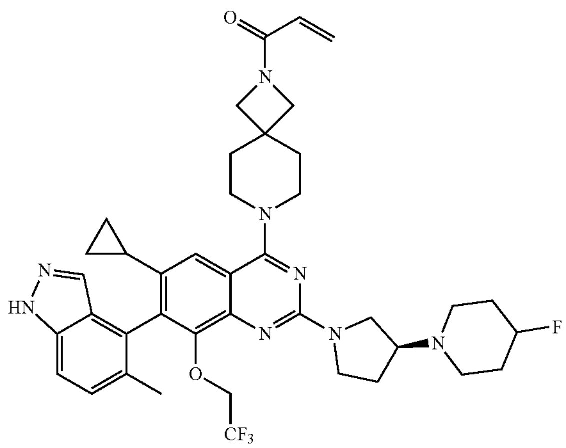
-continued
212
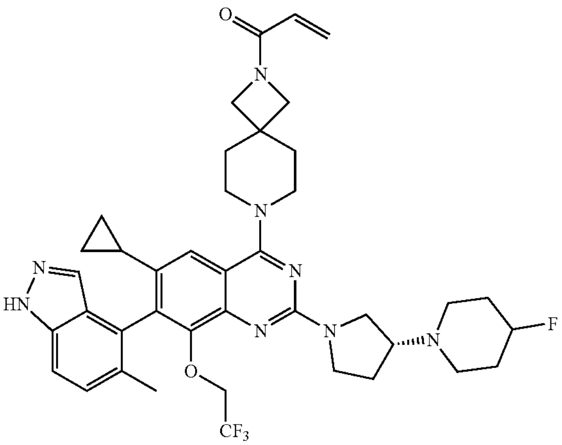
213
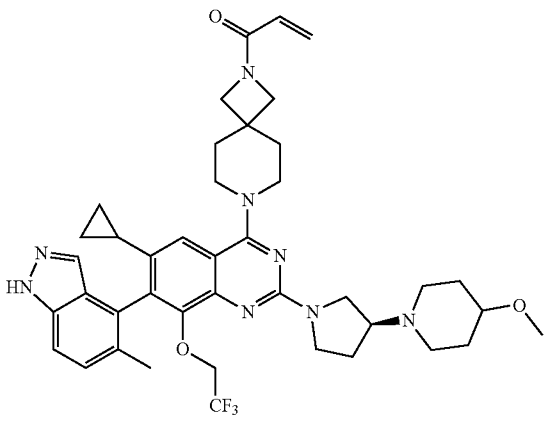
214
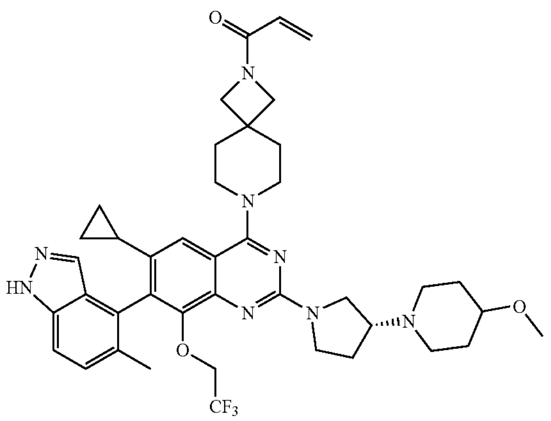

-continued
215
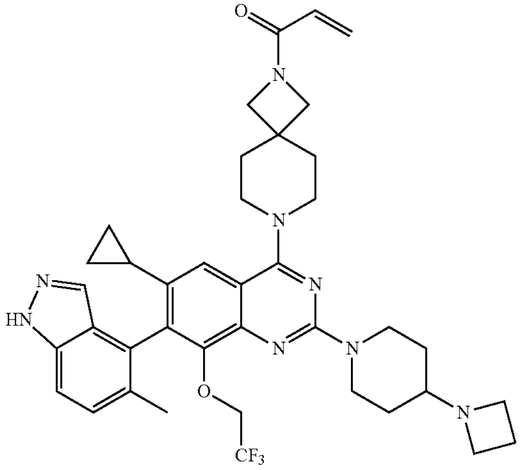
216
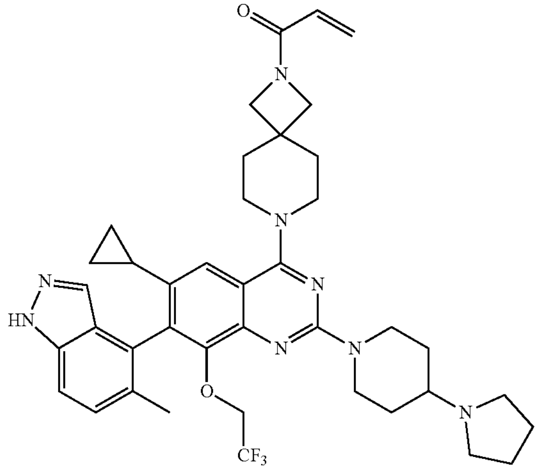
217
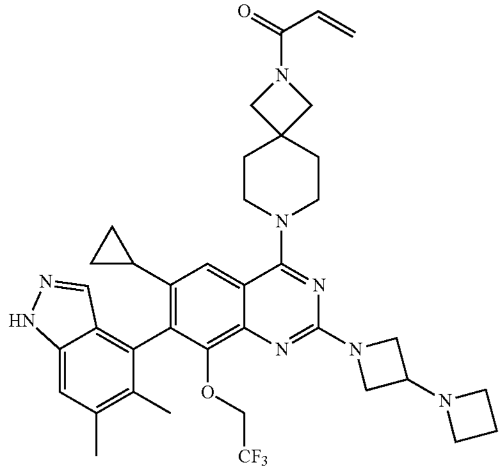
-continued
218
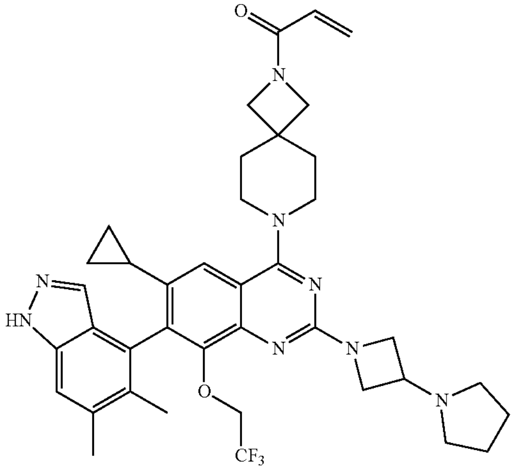
219
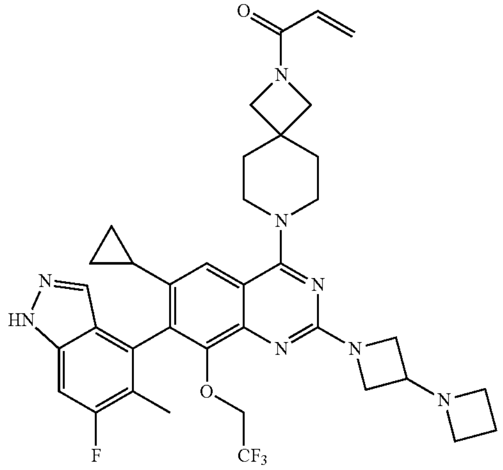
220
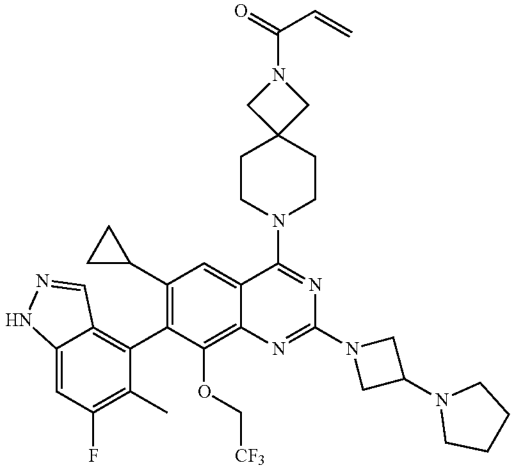

221
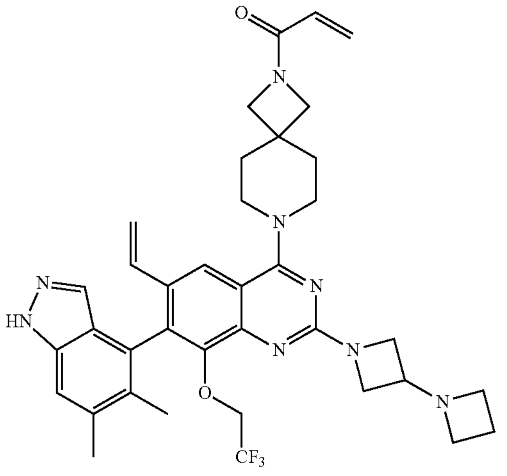
222
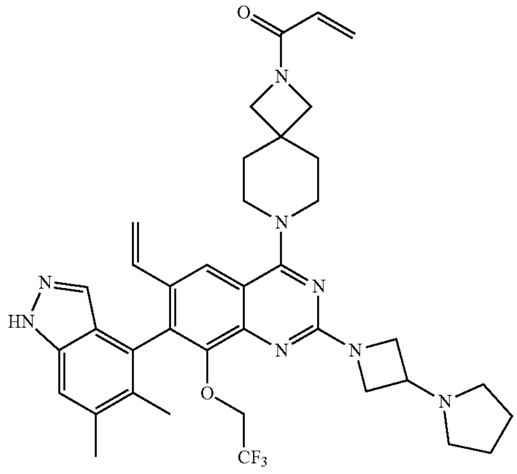
223
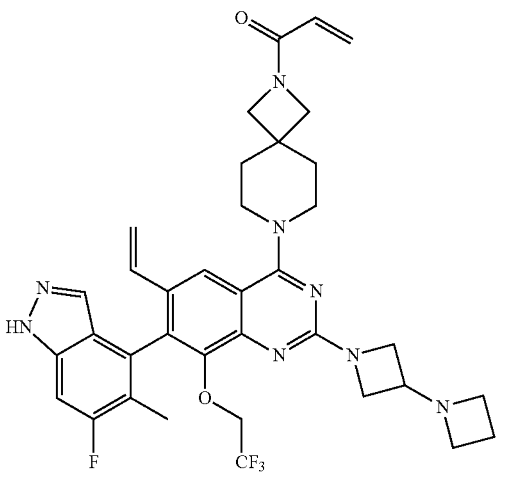
224
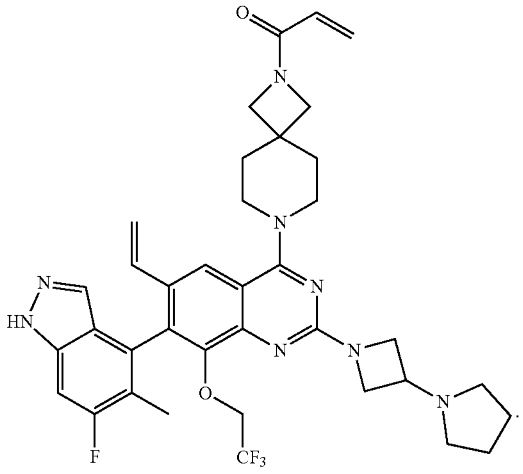
Another aspect of the present invention aims to provide a compound with a structural general formula as shown in formula (2), isomers thereof, crystalline forms thereof, pharmaceutically acceptable salts thereof, hydrates thereof or solvates thereof:
(2)
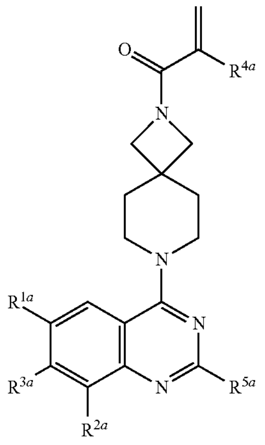
wherein in formula (2):
$R^{1a}$ is
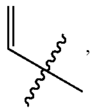 , 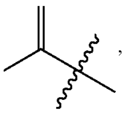 , 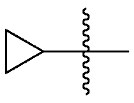 or 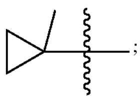 ;
$R^{2a}$ is $CH_3O$—, $CH_3CH_2O$—, $CF_3CH_2O$— or $CHF_2CH_2O$—, $R^{3a}$ is

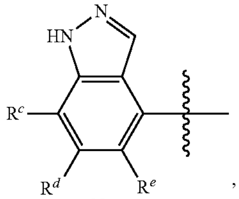

,

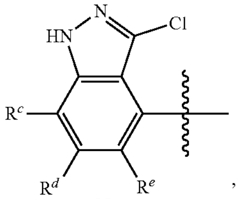

,

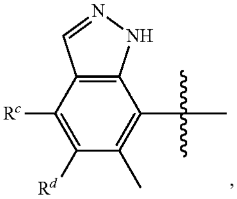

,

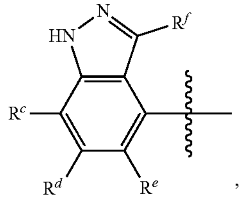

,

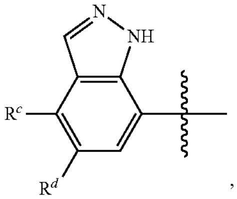

,

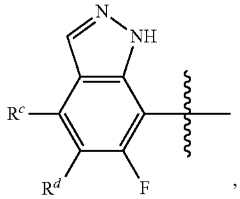

,

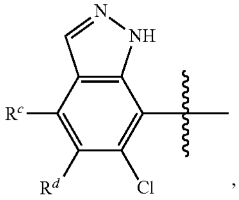

,

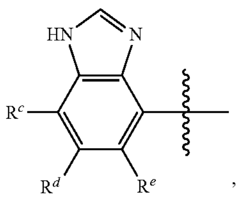

,

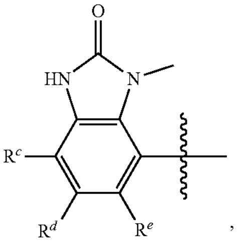

,

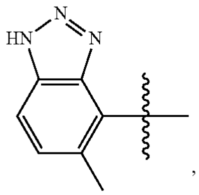

,

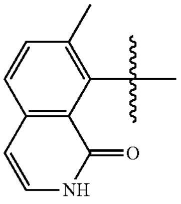

or

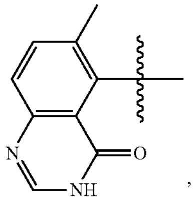

, wherein $R^c$ is H or F, $R^d$ is H, F, Cl or Me, $R^c$ is H, F, Cl or Me, and $R^f$ is F, $NH_2$, Me or cyclopropyl;

$R^{4a}$ is H or F; and $R^{5a}$ is: H,

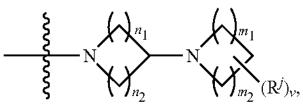

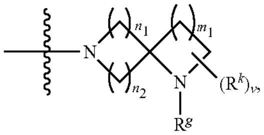

-continued

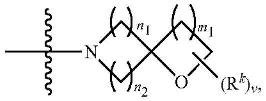

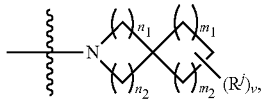

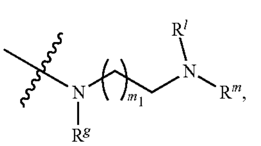

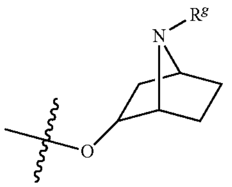

,

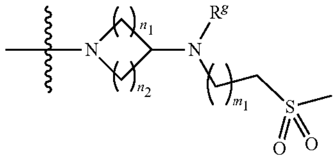

,

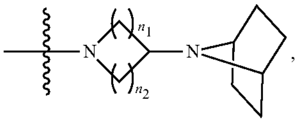

,

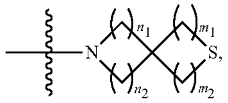

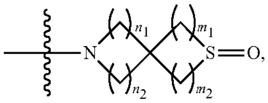

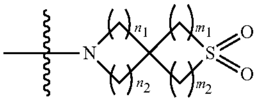

,

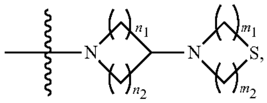

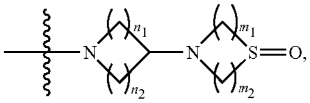

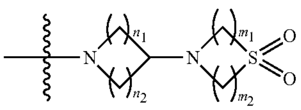

or

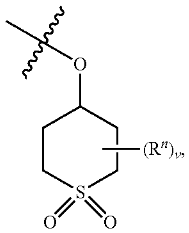

wherein $n_1$, $n_2$, $n_3$, $m_1$, $m_2$ and $m_3$ are independently integers of 1 or 2; v is an integer of 1, 2 or 3; $R^g$ is C1-C3 alkyl, C3-C6 cycloalkyl, (C1-C3)alkoxy-(C2-C3)alkyl-, (halogenated C1-C3)alkoxy-(C2-C3)alkyl-, (C3-C6)cycloalkyl-(C1-C3)alkyl-, heterocycloalkyl, heterocycloalkyl-(C1-C3) alkyl-, C1-C3 haloalkyl or cyano-substituted C1-C3 alkyl; is independently halogen, CN, $SO_2Me$, C1-C3 alkyl, C1-C3 haloalkyl, C1-C3 alkoxy, C1-C3 haloalkoxy, hydroxy-substituted C1-C3 alkyl, cyano-substituted C1-C3 alkyl, C3-C6 cycloalkyl or

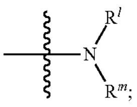

$R^k$ is independently halogen, CN, OH, C1-C3 alkyl, C1-C3 alkoxy, C3-C6 cycloalkyl or

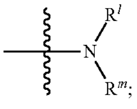

$R^n$ is independently halogen, CN, OH, C1-C3 alkyl, C1-C3 alkoxy or C3-C6 cycloalkyl, two IV groups, together with one carbon atom, form a spiro ring, or two IV groups, together with different carbon atoms, form a bridged ring; $R^l$ and $R^m$ are independently C1-C3 alkyl, C1-C3 haloalkyl, hydroxy-substituted C1-C3 alkyl, cyano-substituted C1-C3 alkyl, C3-C6 cycloalkyl, (C1-C3)alkoxy-(C2-C3)alkyl-, (halogenated C1-C3)alkoxy-(C2-C3)alkyl-, (C3-C6)cycloalkyl-(C1-C3)alkyl-, or $R^l$ and $R^m$, together with a N atom, form a 3-8 membered heterocycloalkyl group, wherein the 3-8 membered heterocycloalkyl group may be substituted with 1-3 groups selected from OH, halogen, cyano, C1-C3 alkyl, C3-C6 cycloalkyl, heterocycloalkyl, (C1-C3)alkoxy or (halogenated C1-C3)alkoxy.

In another preferred embodiment, in the general formula (2), $R^{3a}$ is

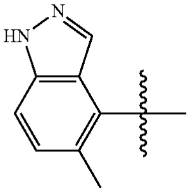 , 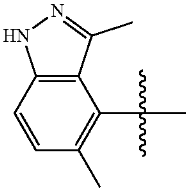 ,

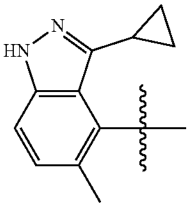 , 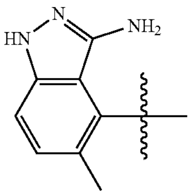 ,

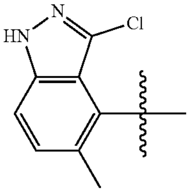 , 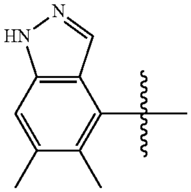 ,

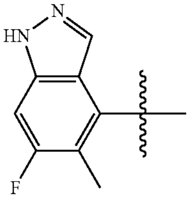 , 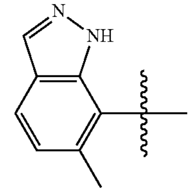 ,

-continued

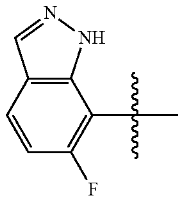 , 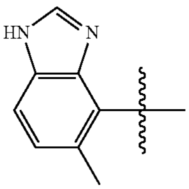 ,

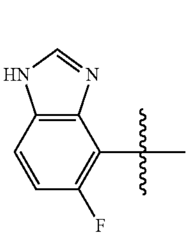 , 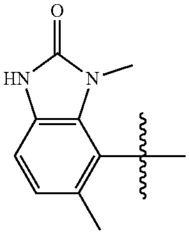 ,

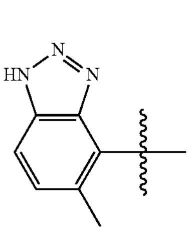 , 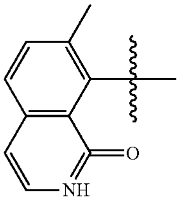 or

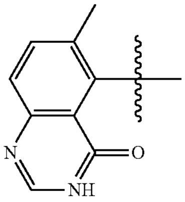 .

In another preferred embodiment, in the general formula (2), $R^{5a}$ is: H,

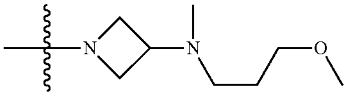 ,

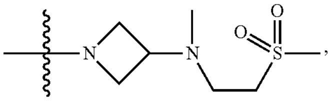 ,

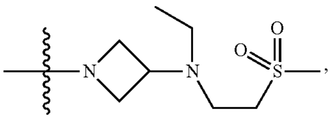 ,

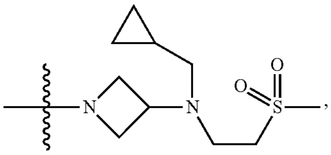 ,

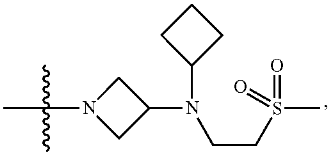 ,

-continued
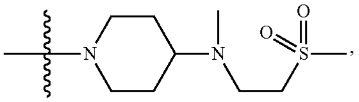
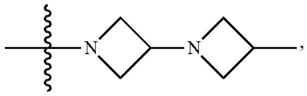
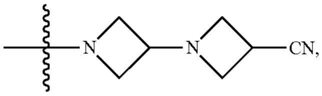
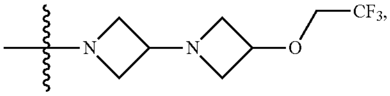
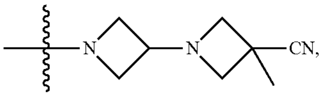
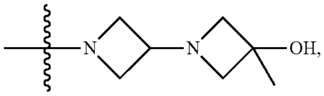
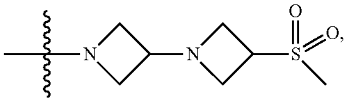
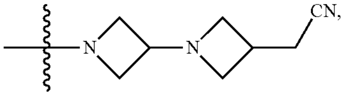
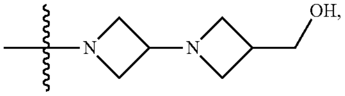
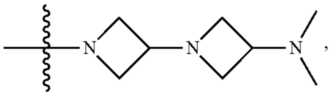
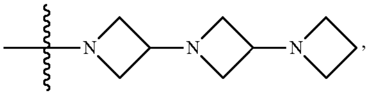
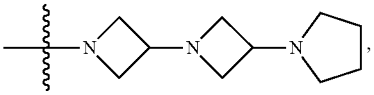
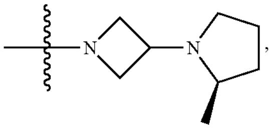 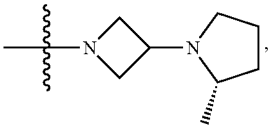
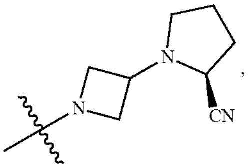 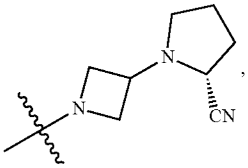
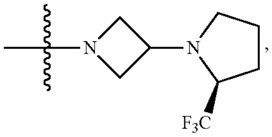 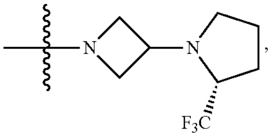
-continued
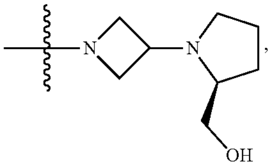 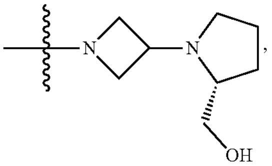
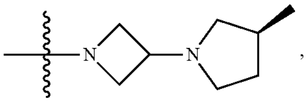
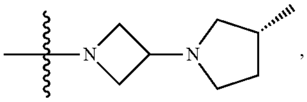
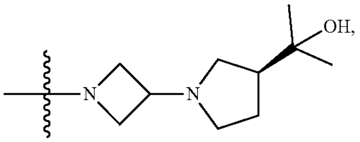
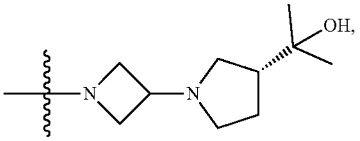
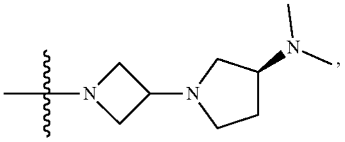
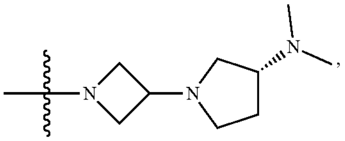
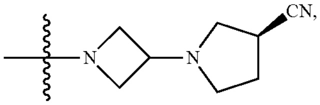
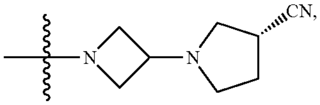
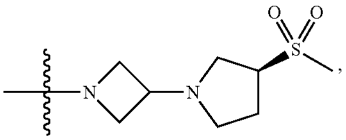
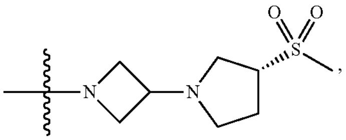
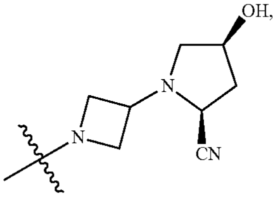

-continued
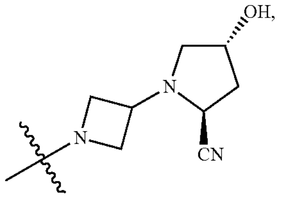
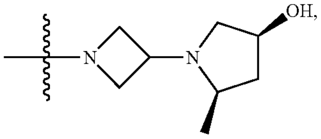
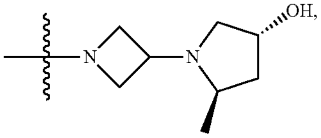
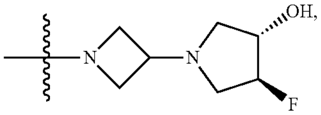
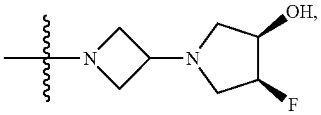
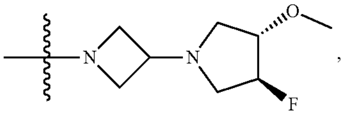
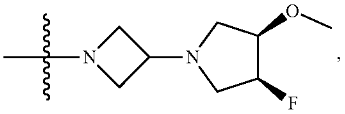
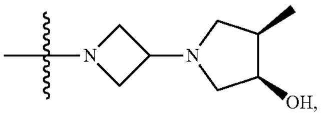
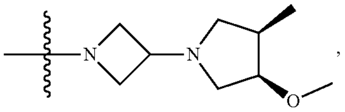
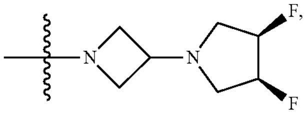
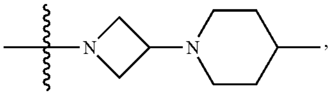
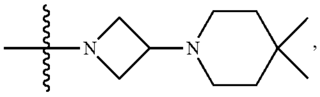
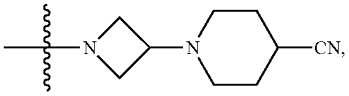
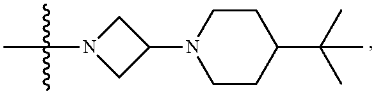
-continued
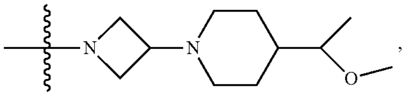
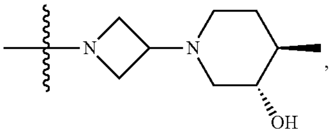
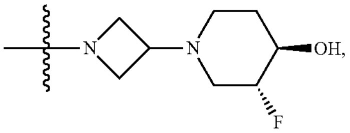
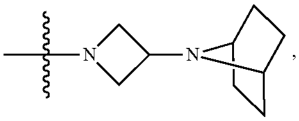
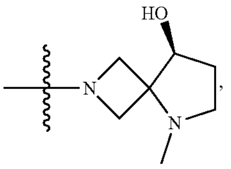
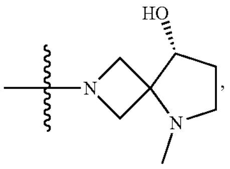
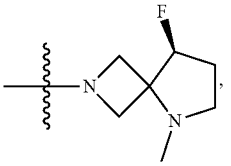
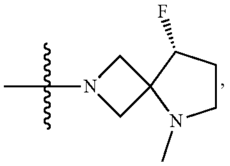
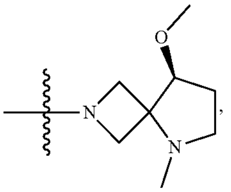
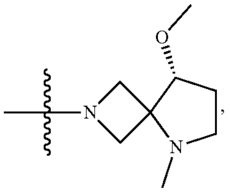
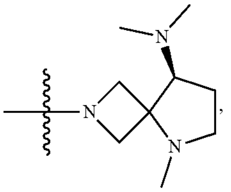
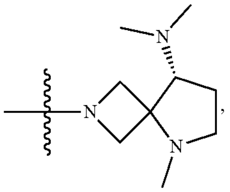
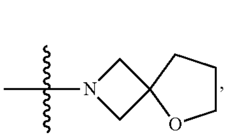
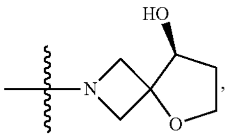
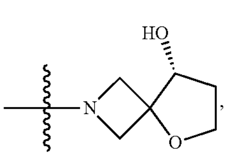
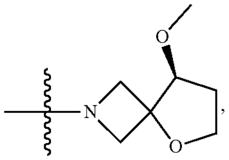
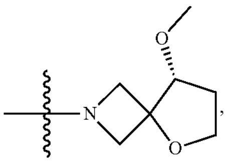
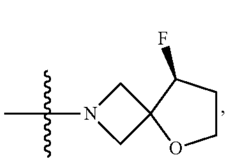

-continued
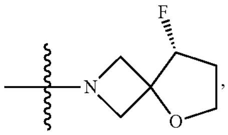, 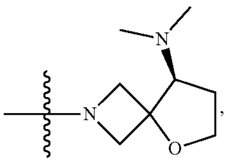,
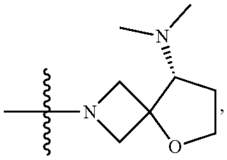, 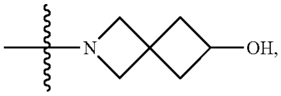
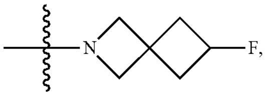 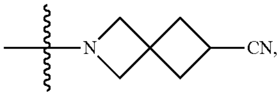
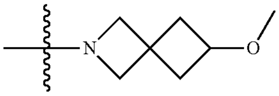,
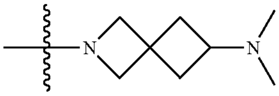,
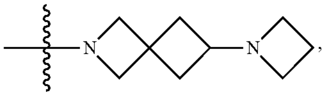,
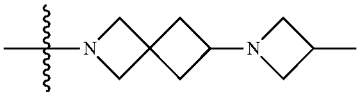,
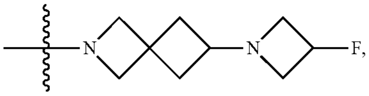
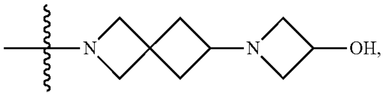
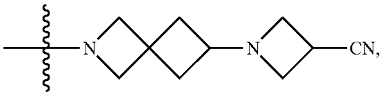
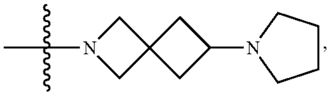,
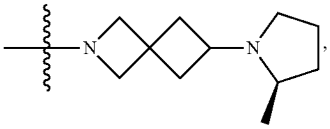,
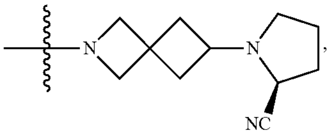,
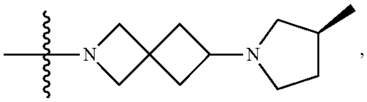,
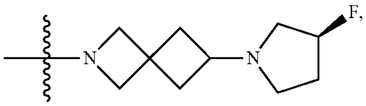
-continued
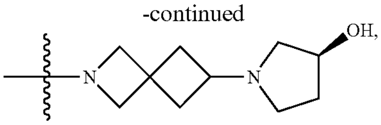
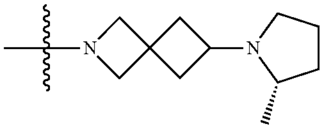,
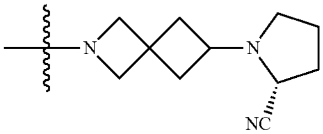,
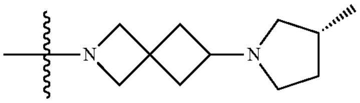,
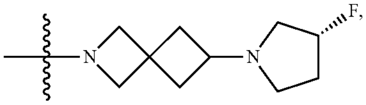
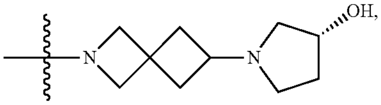
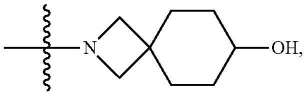
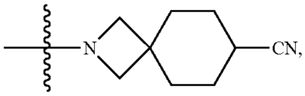
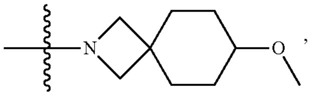,
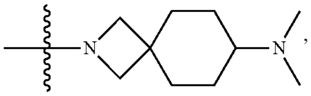,
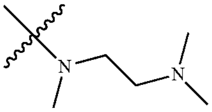, 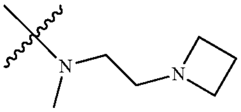,
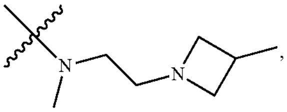,
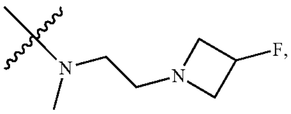
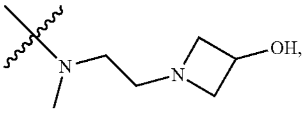
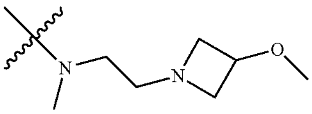,
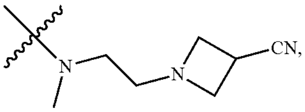

-continued
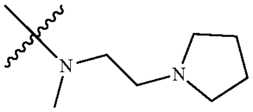,
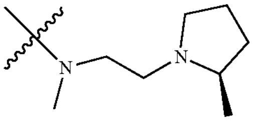, 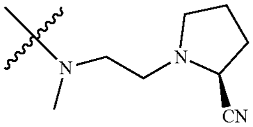,
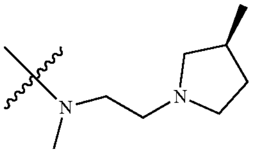,
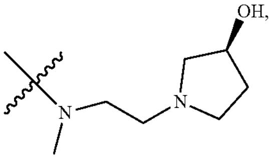
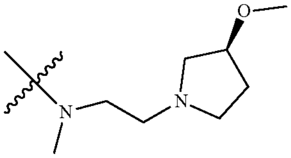,
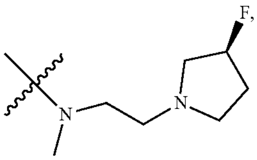
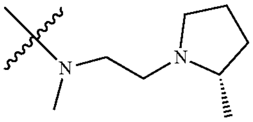, 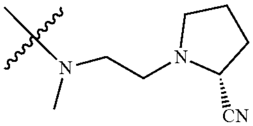,
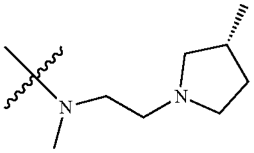,
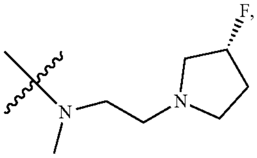 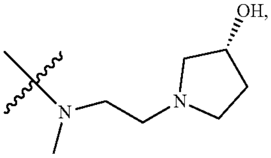
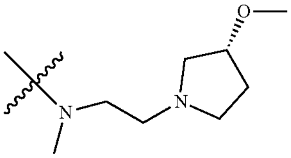,
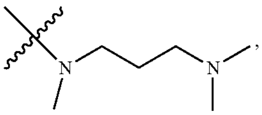, 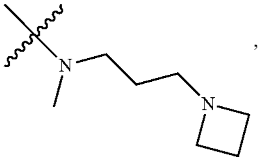,
-continued
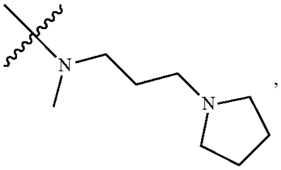, 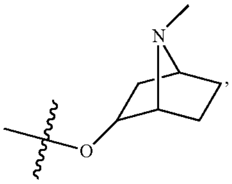,
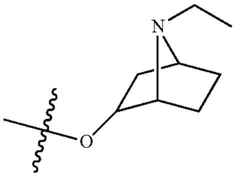,
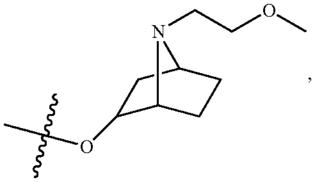,
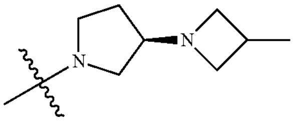,
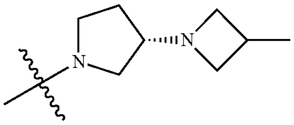,
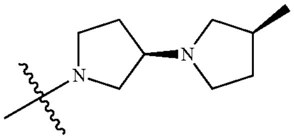,
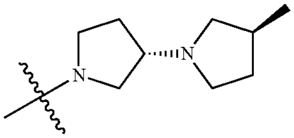,
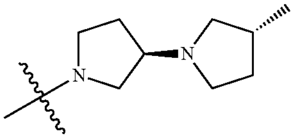,
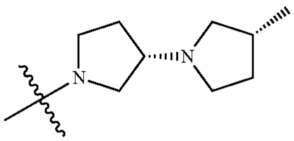,
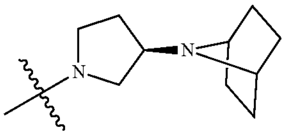,
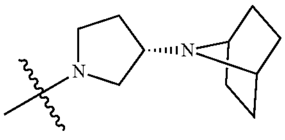,
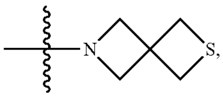 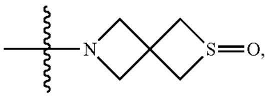

-continued
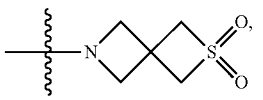
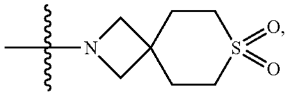
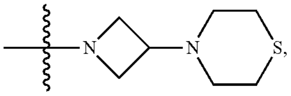
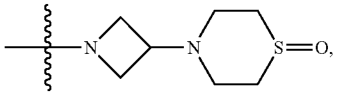
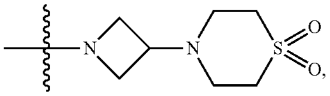
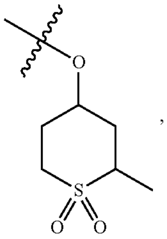
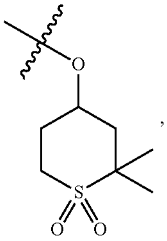
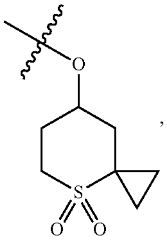
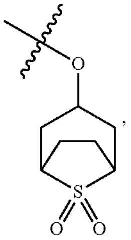
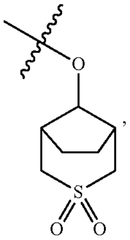
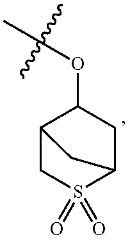
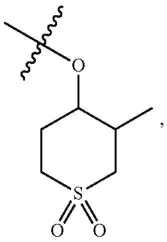
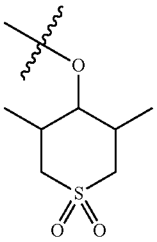
or
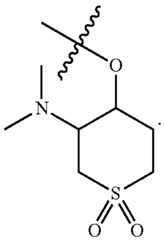
In various embodiments, a representative compound of general formula (2) of the present invention has one of the following structures:
225
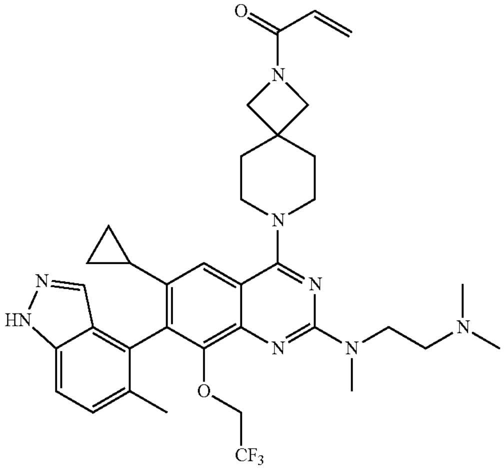
226
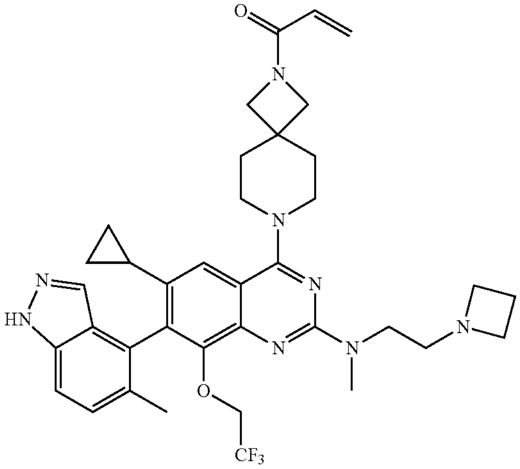
227
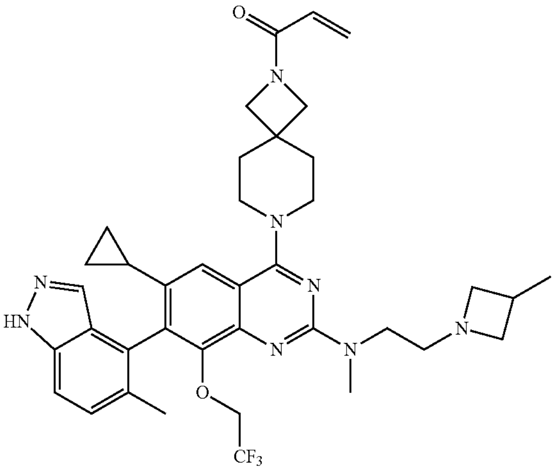

228
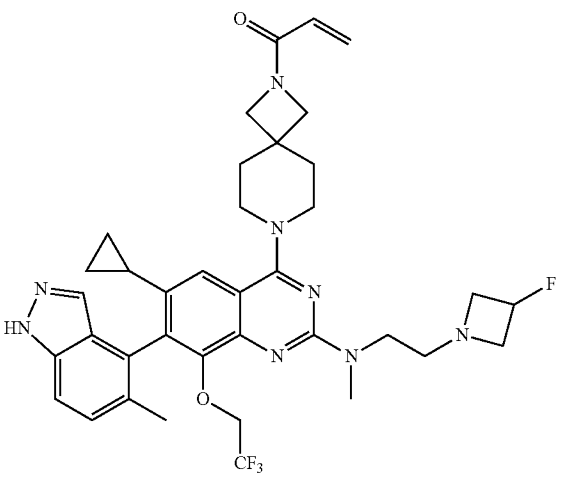
229
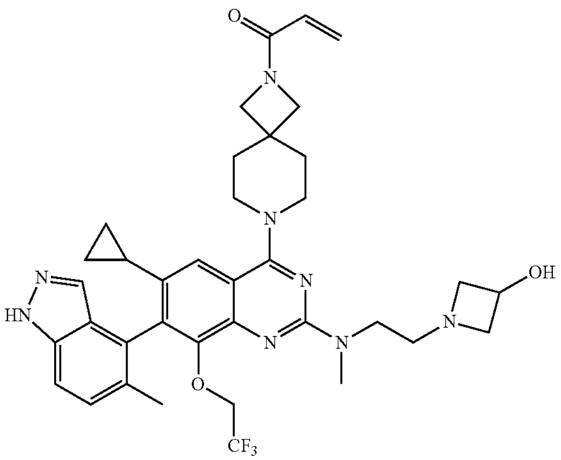
230
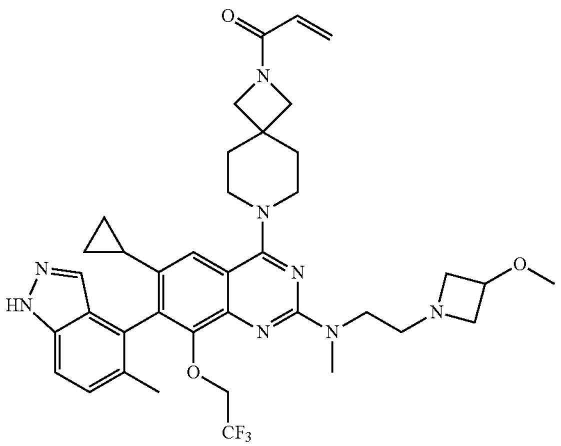
231
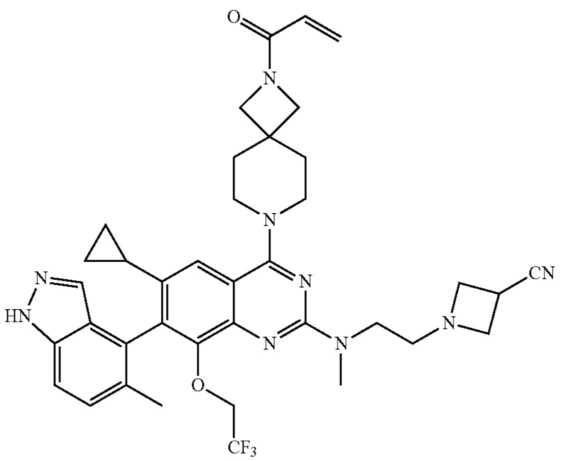
232
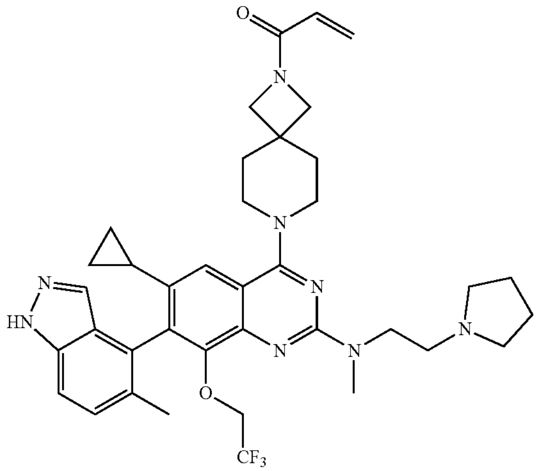
233
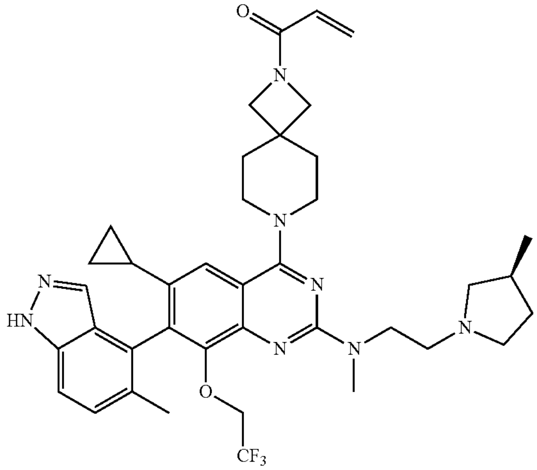

-continued
234
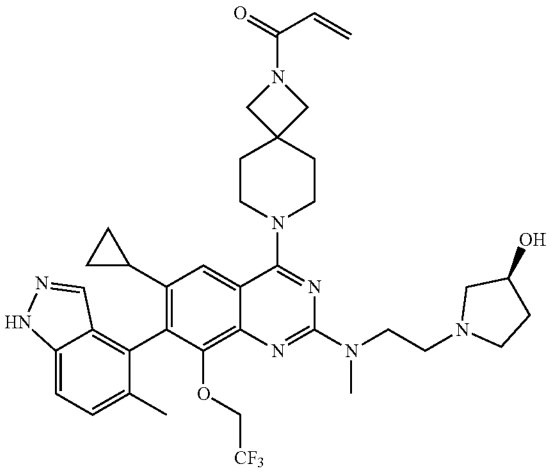
235
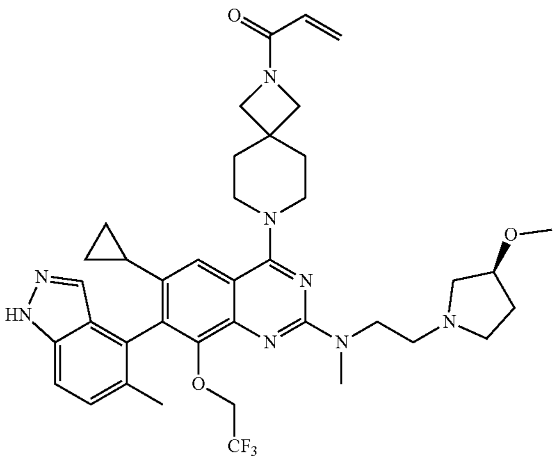
236
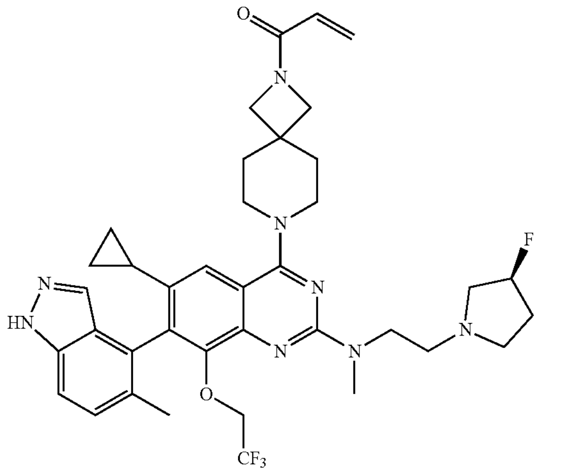
-continued
237
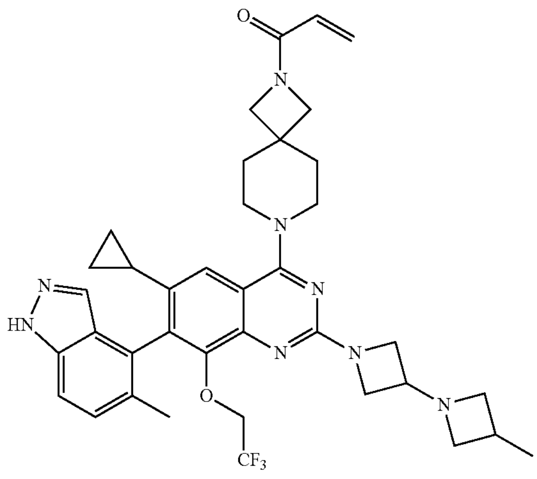
238
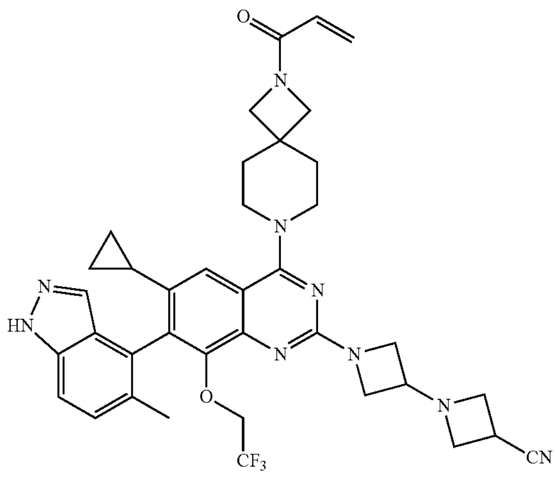
239
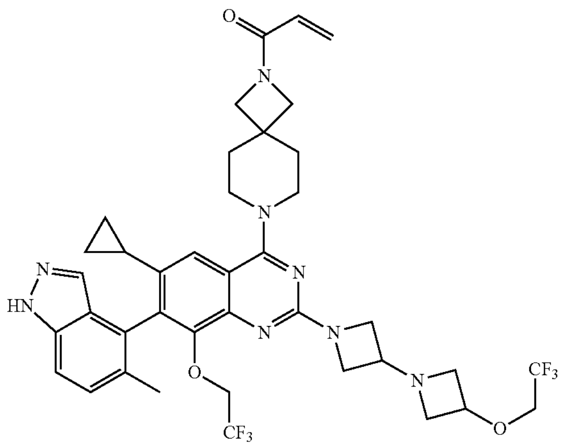

-continued
240
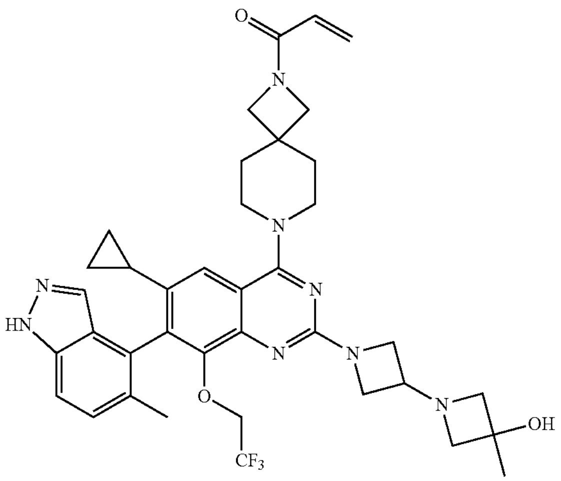
241
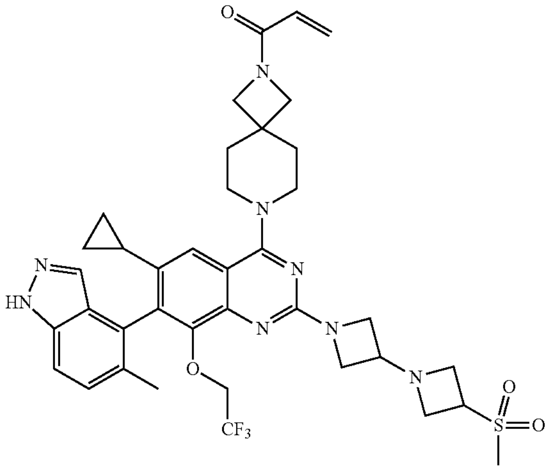
242
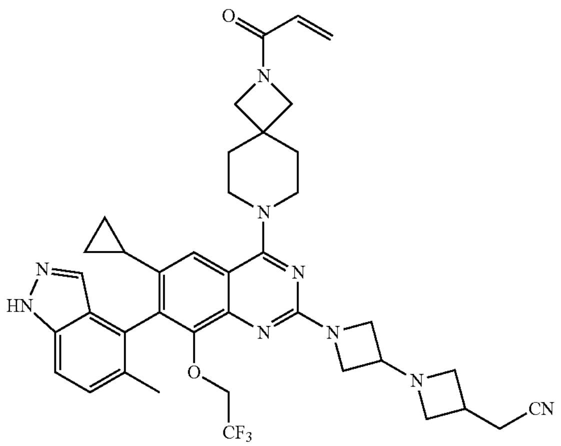
-continued
243
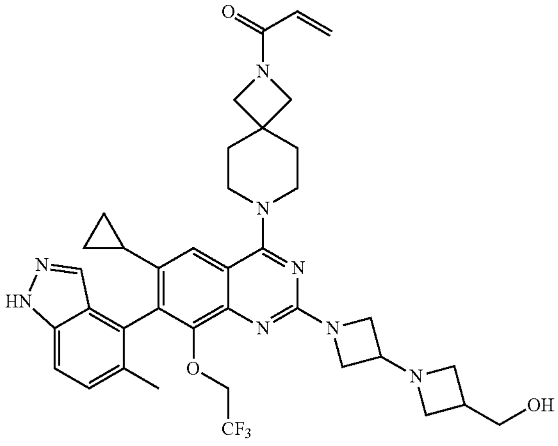
244
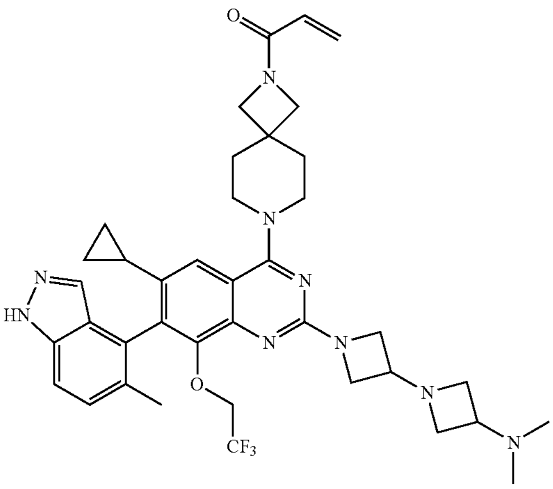
245
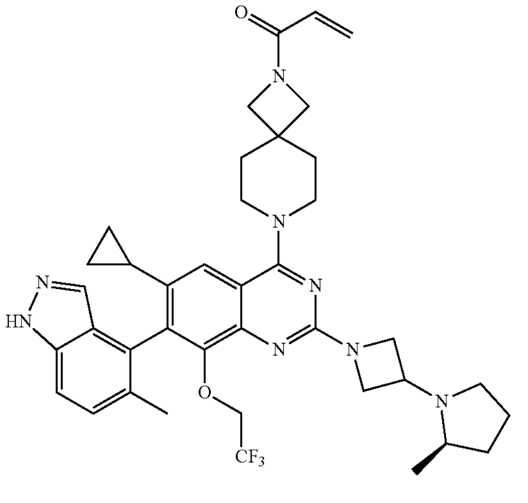

-continued
246
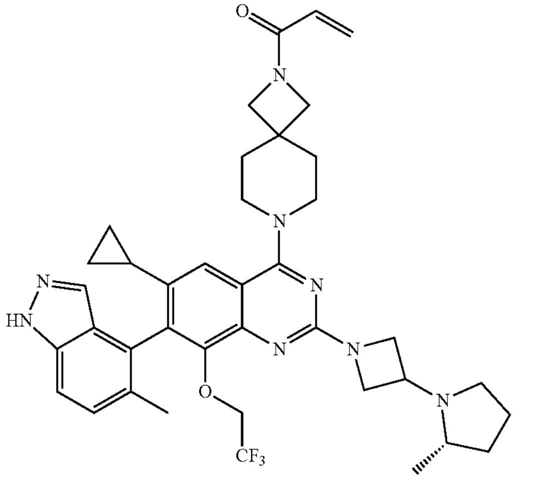
247
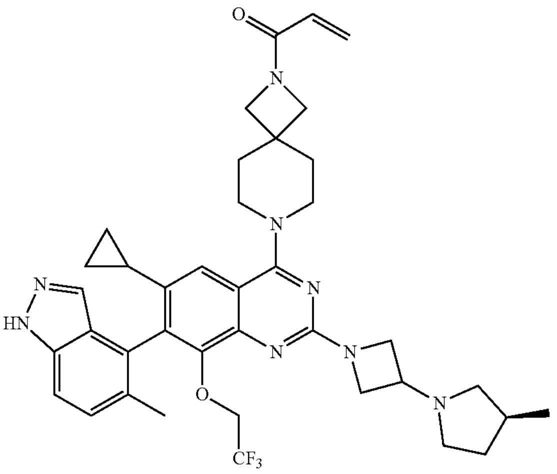
248
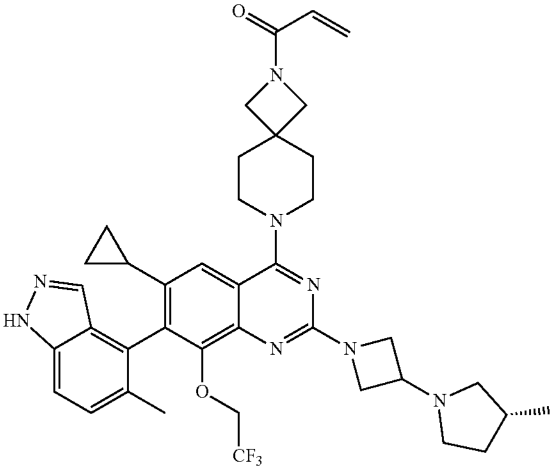
-continued
249
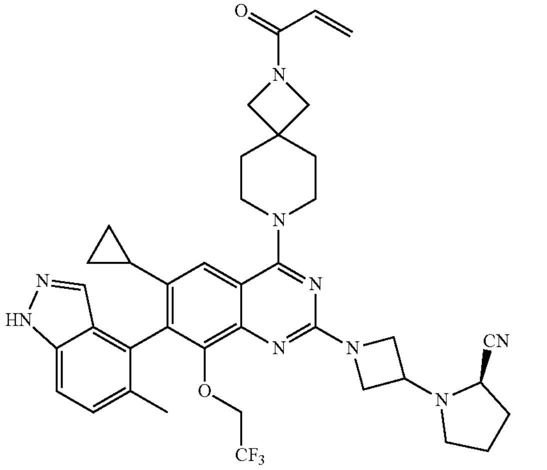
250
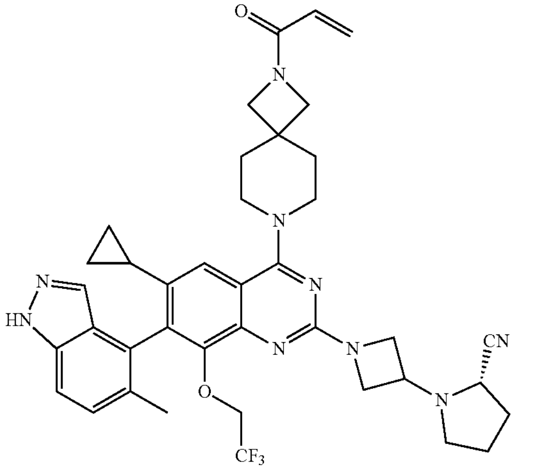
251
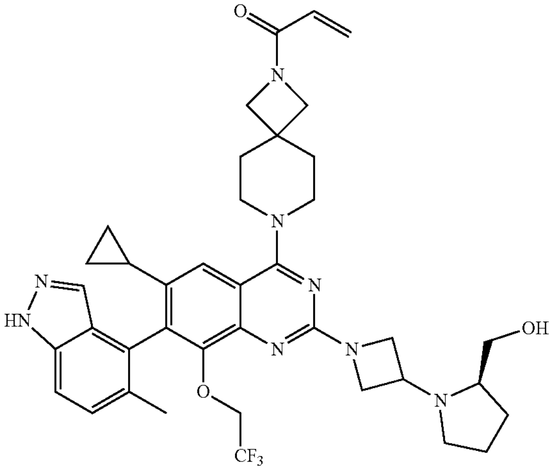

-continued
252
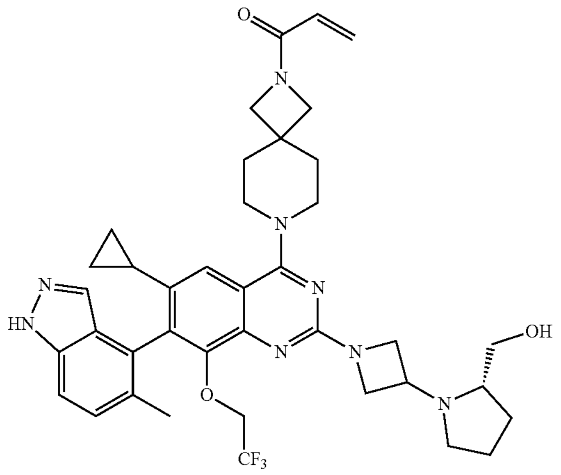
253
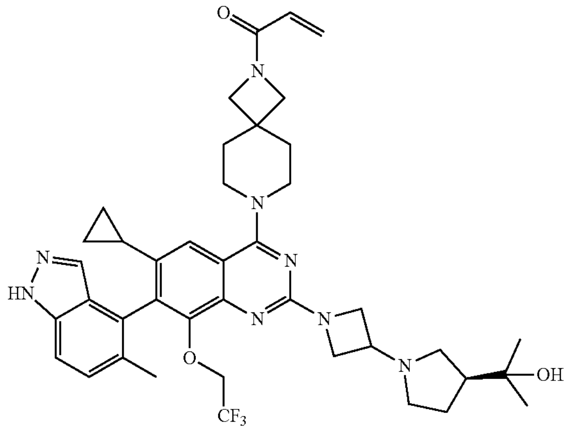
254
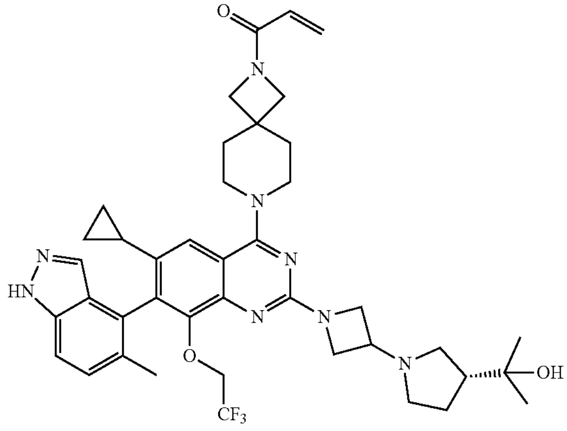
-continued
255
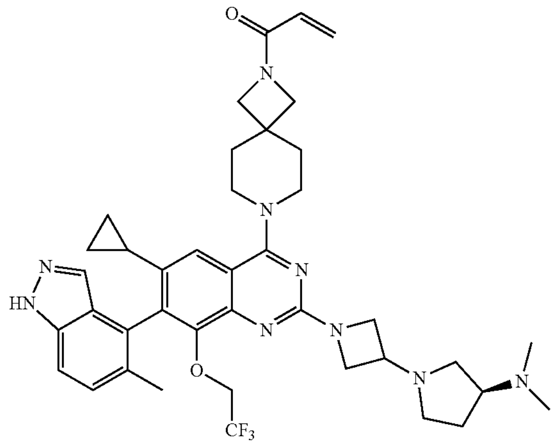
256
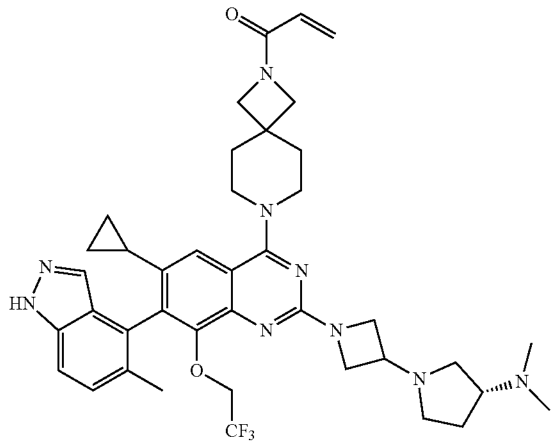
257
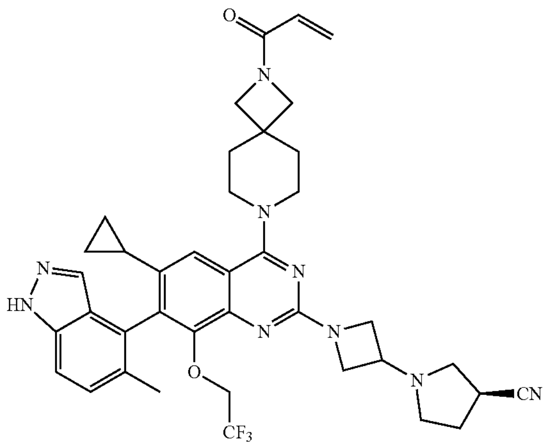

-continued
258
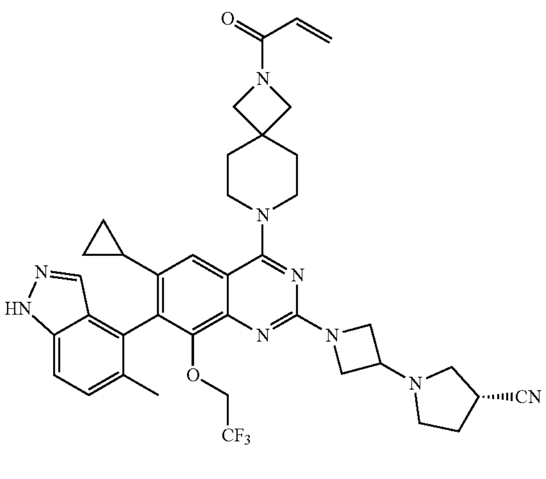
259
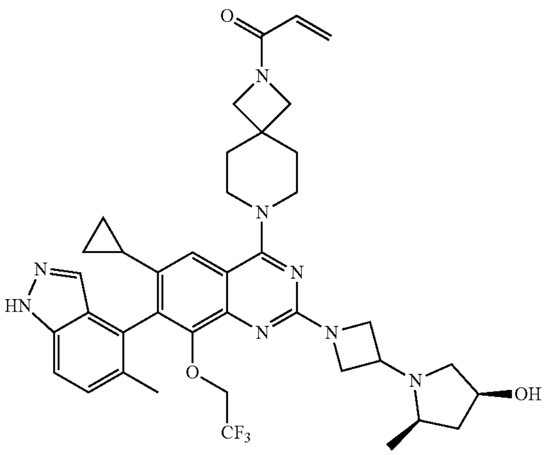
260
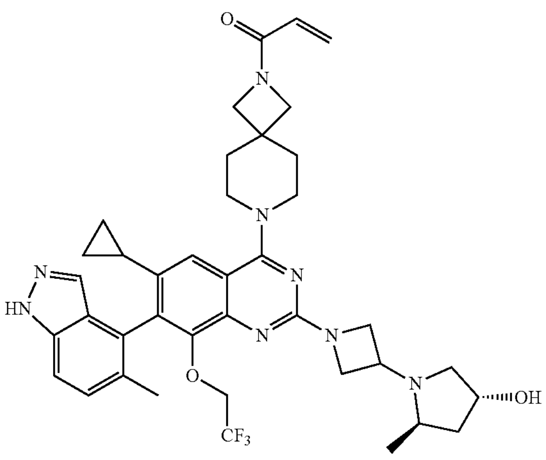
-continued
261
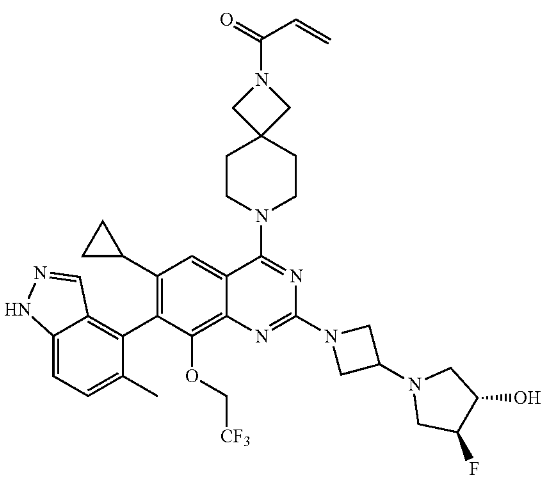
262
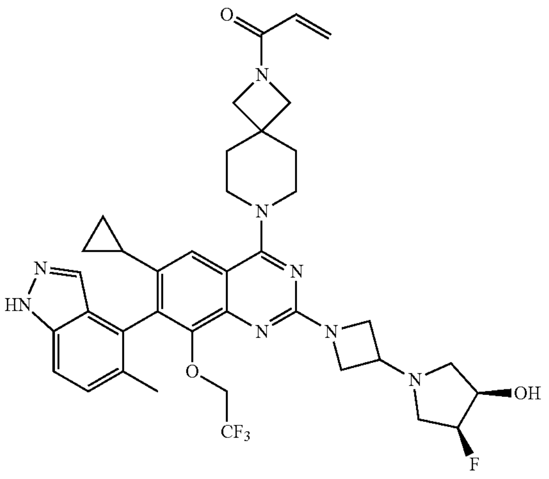
263
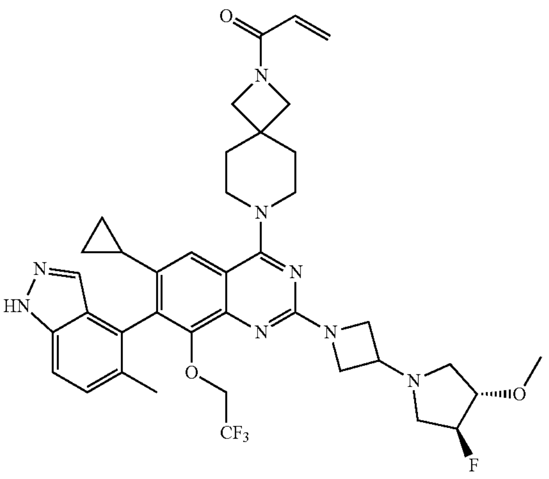

264
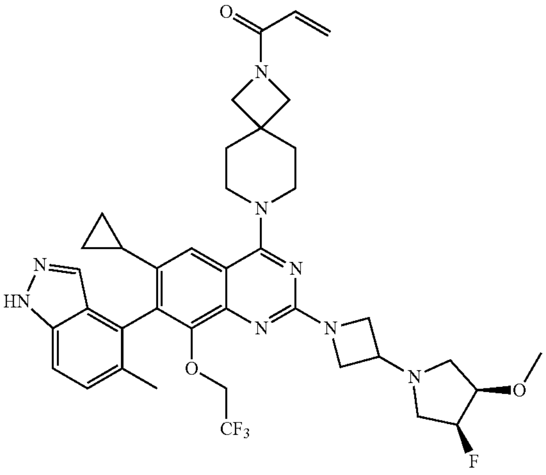
265
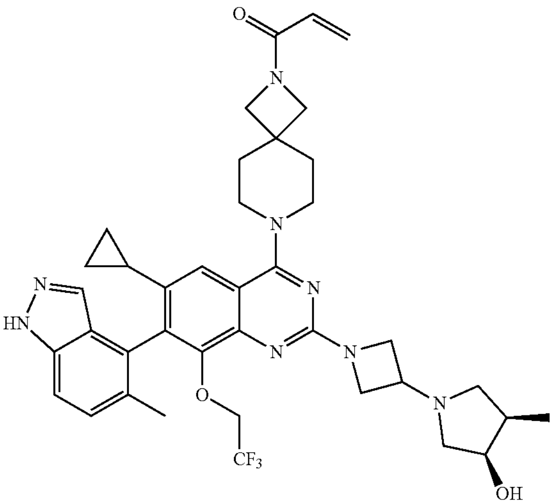
266
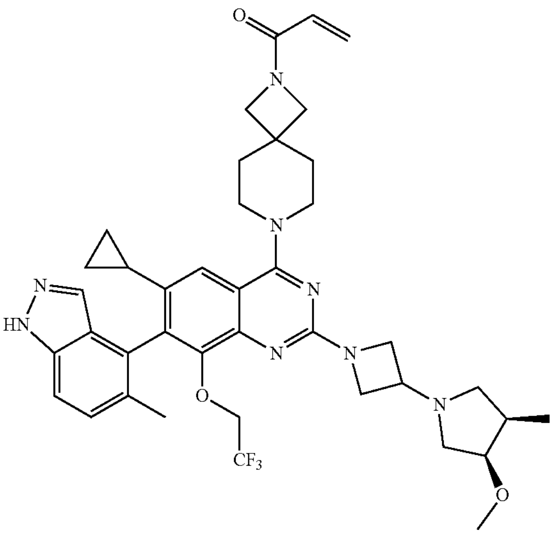
267
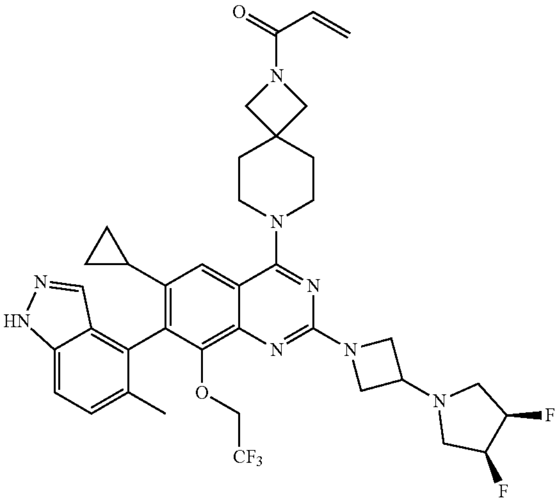
268
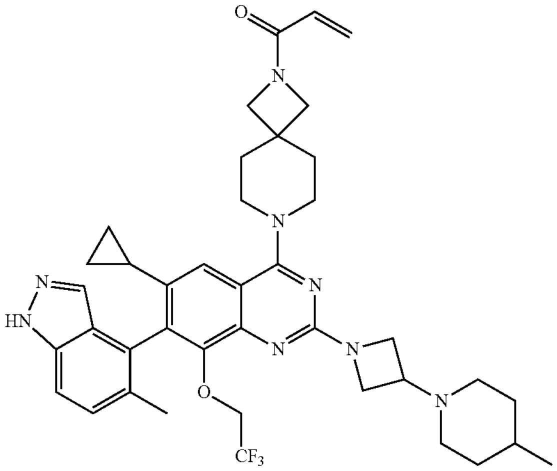
269
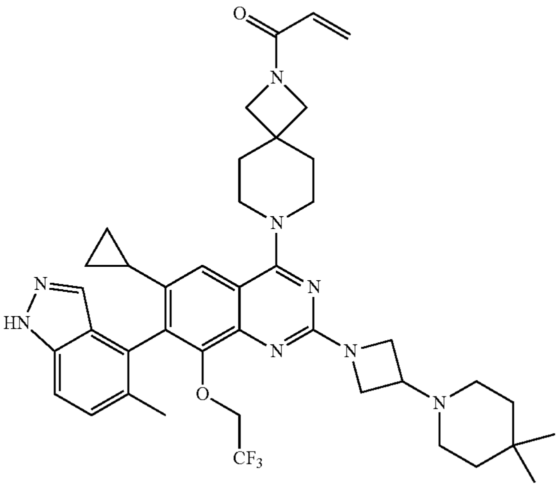

-continued
270
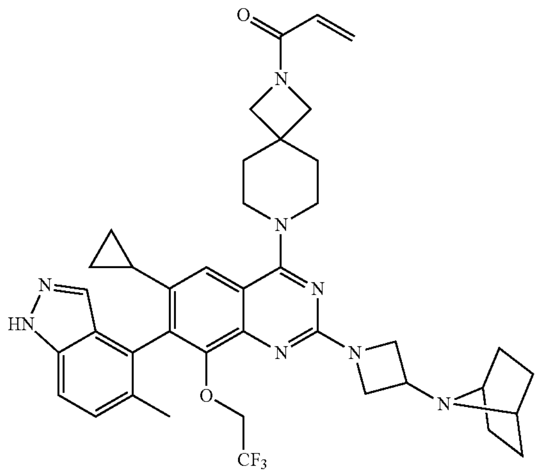
271
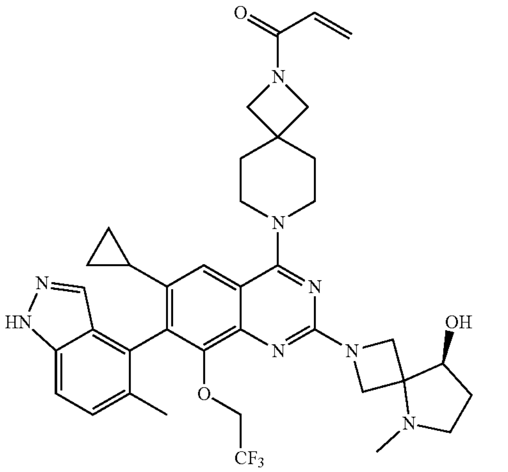
272
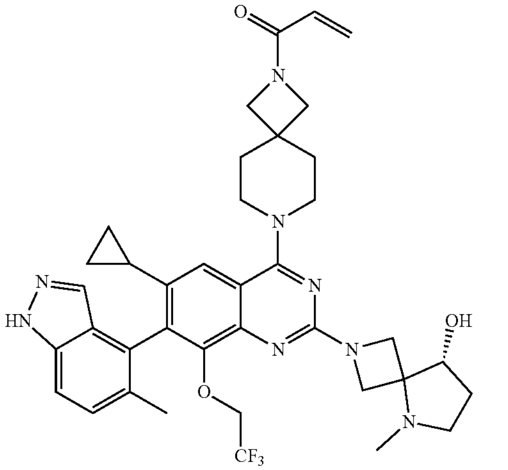
-continued
273
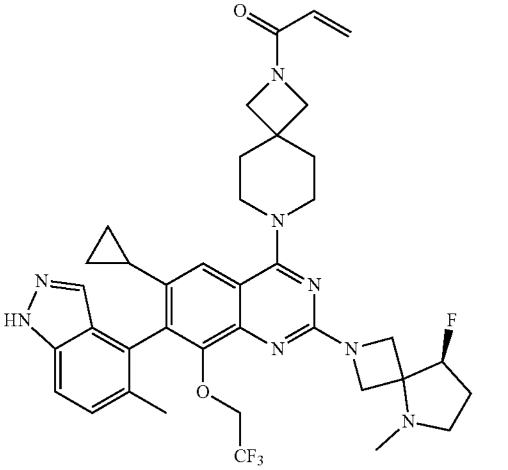
274
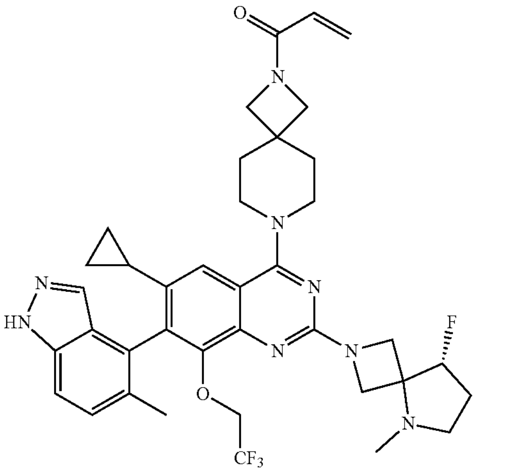
275
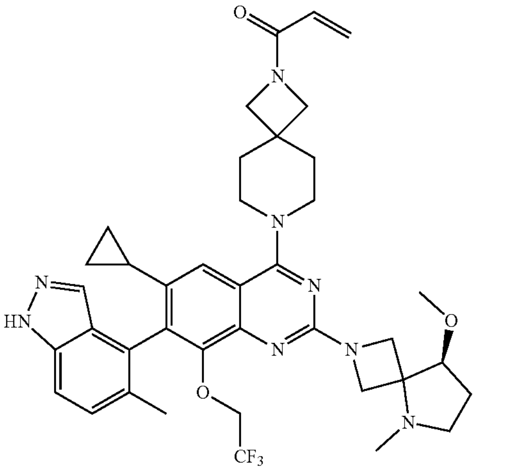

-continued
276
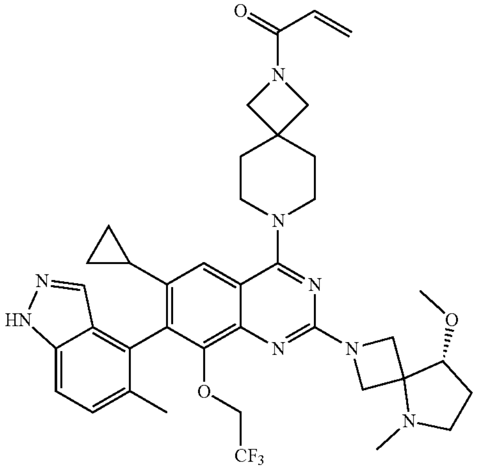
277
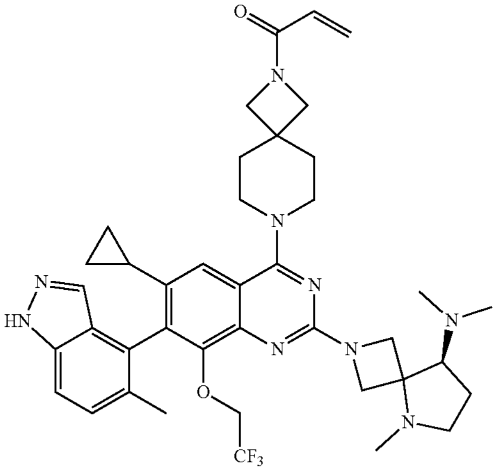
278
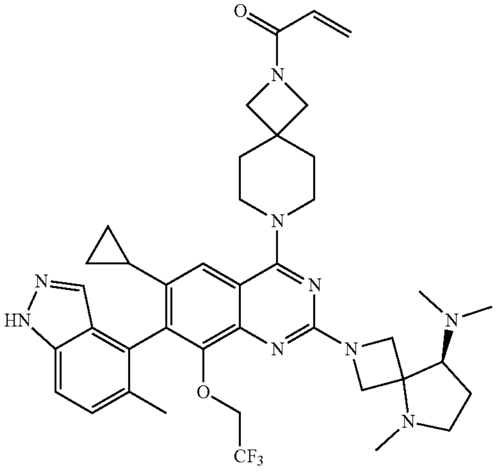
-continued
279
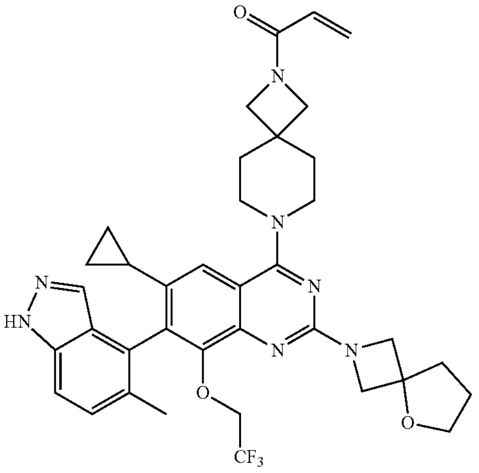
280
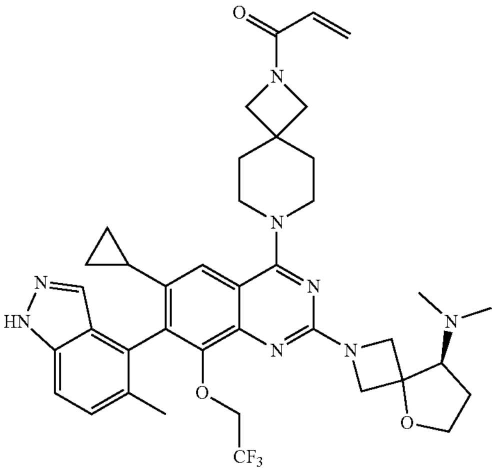
281
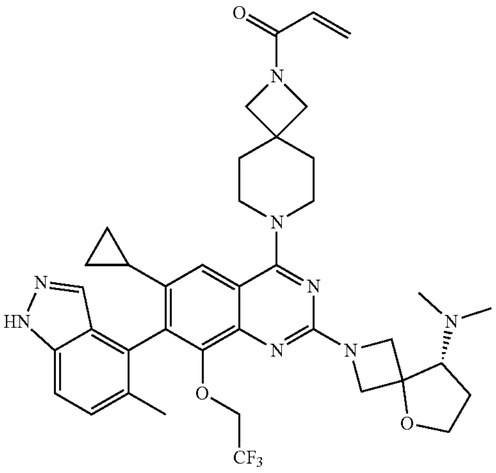

-continued
282
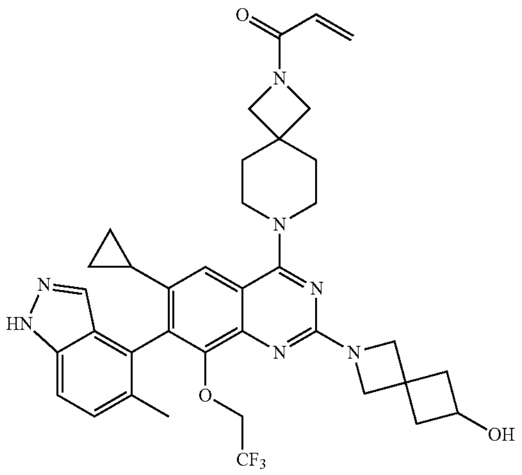
283
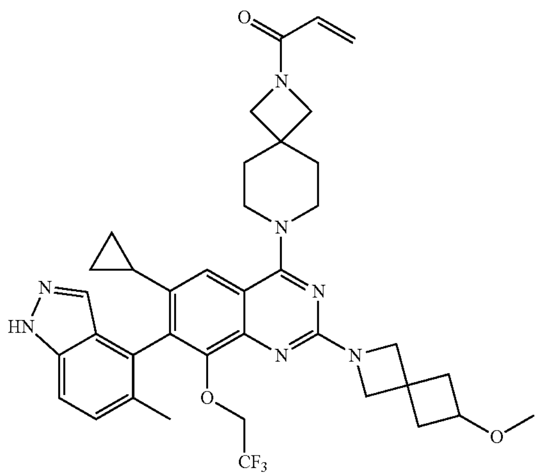
284
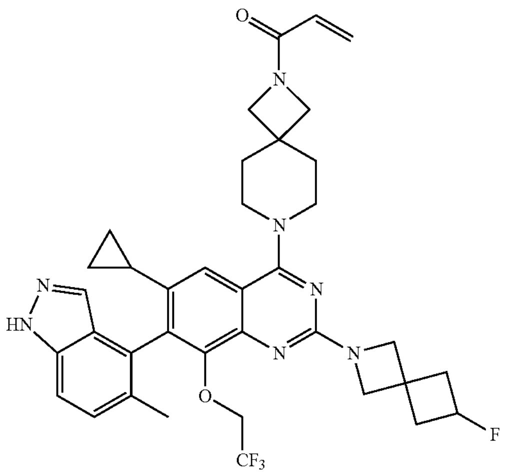
-continued
285
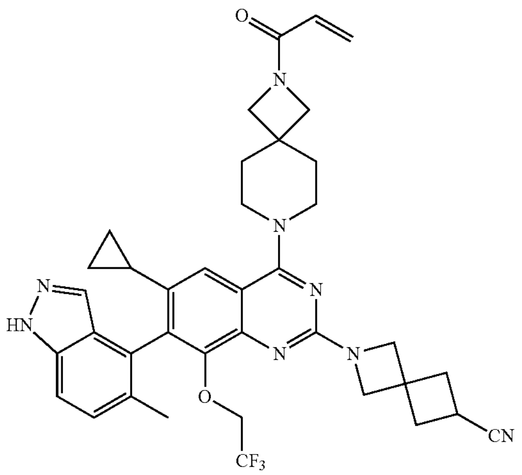
286
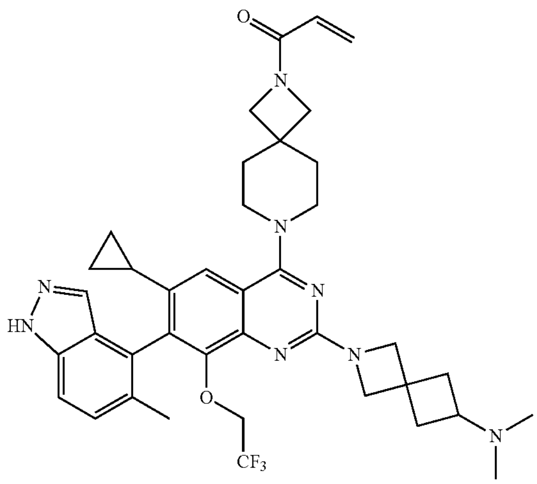
287
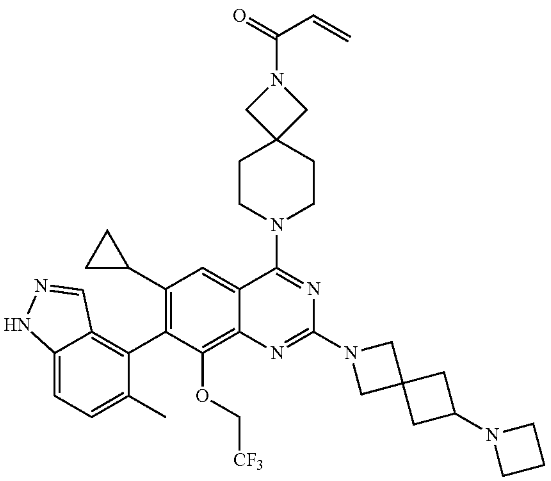

-continued
288
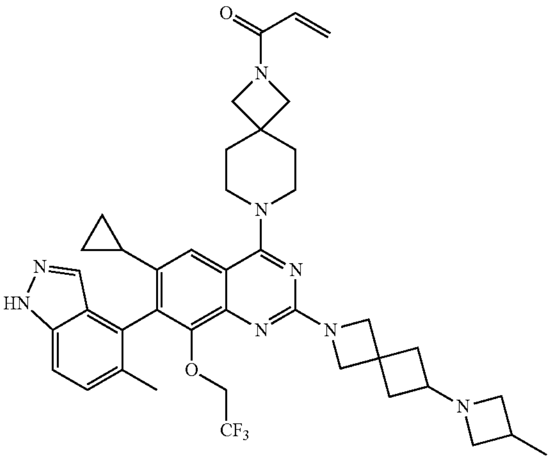
289
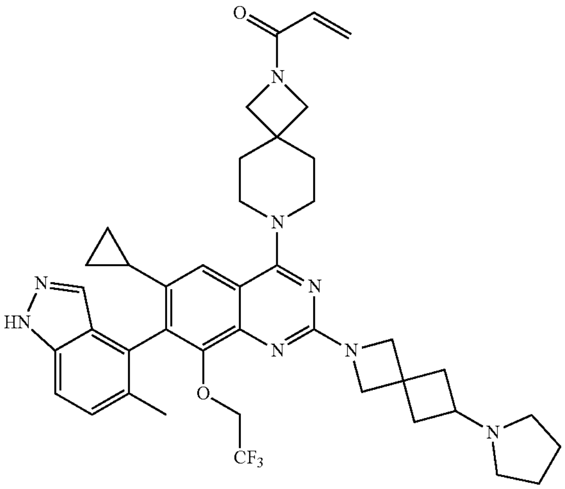
290
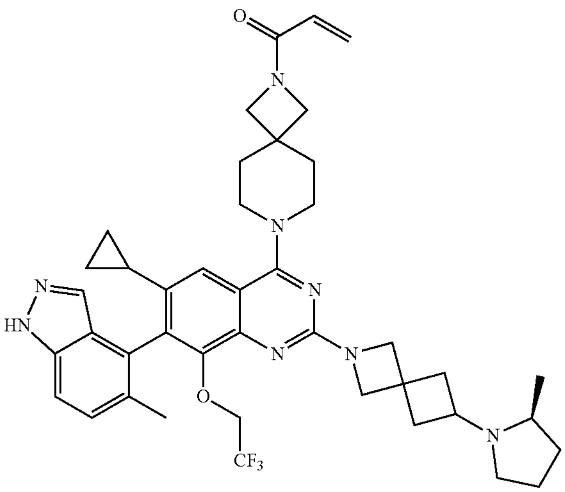
-continued
291
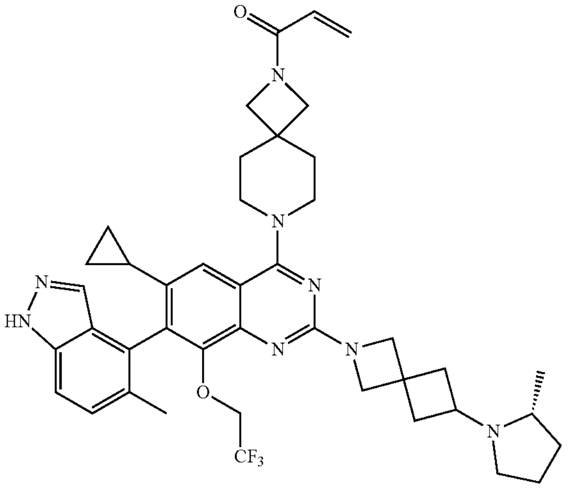
292
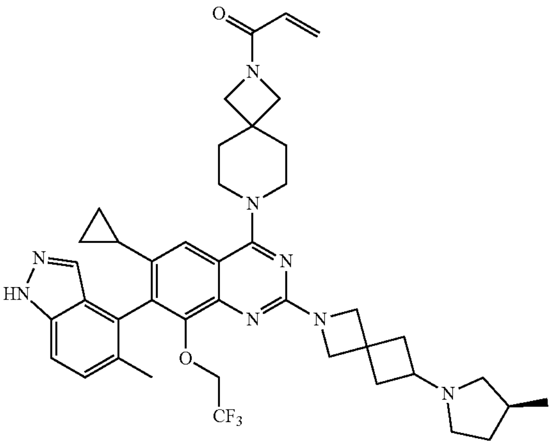
293
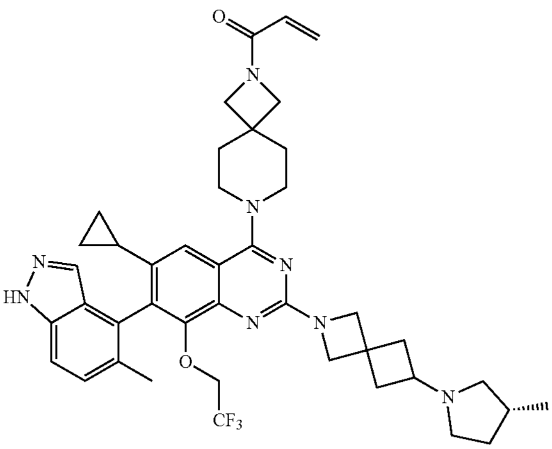

-continued
294
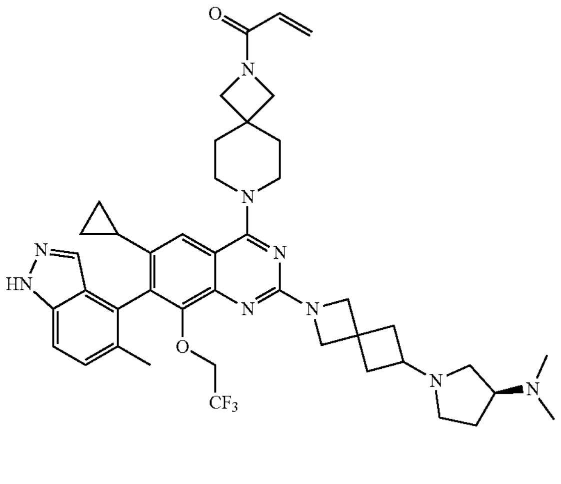
295
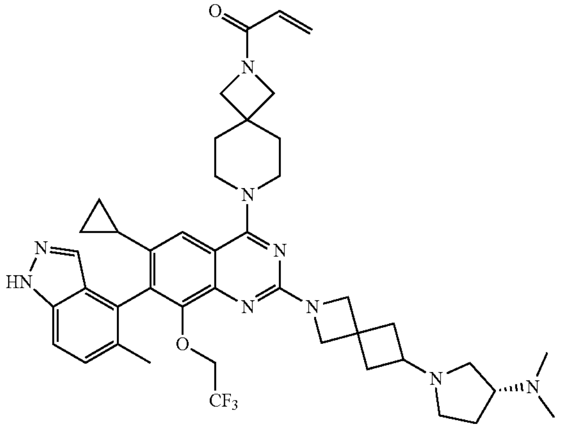
296
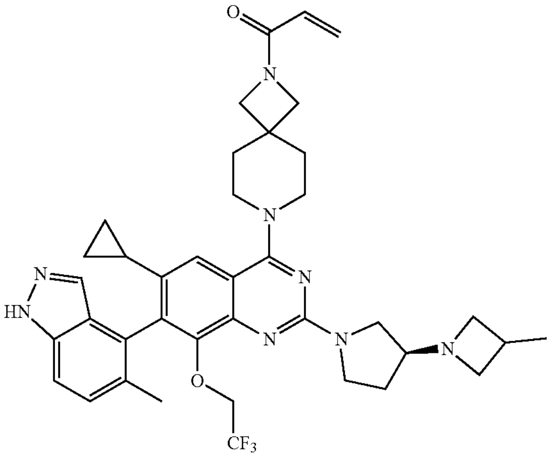
-continued
297
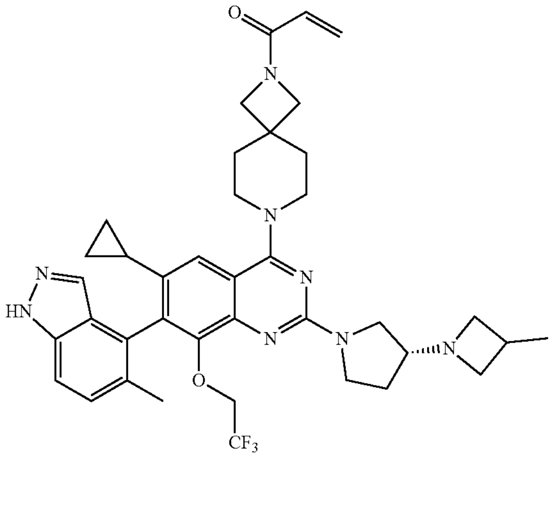
298
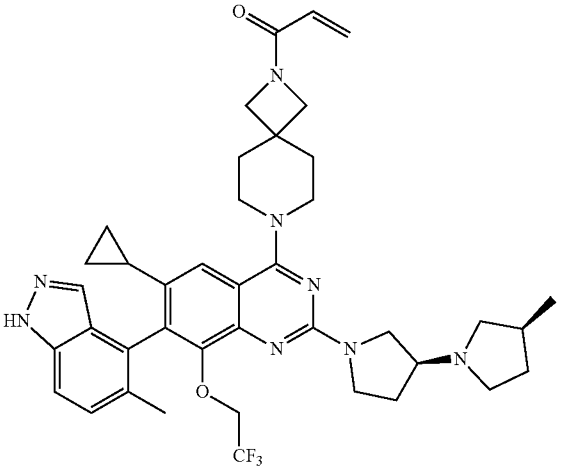
299
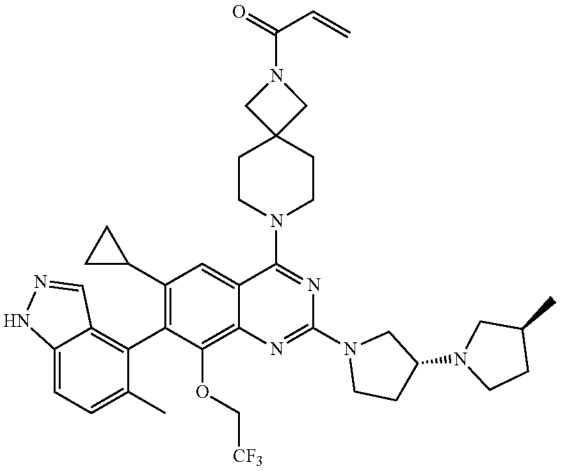

-continued
300
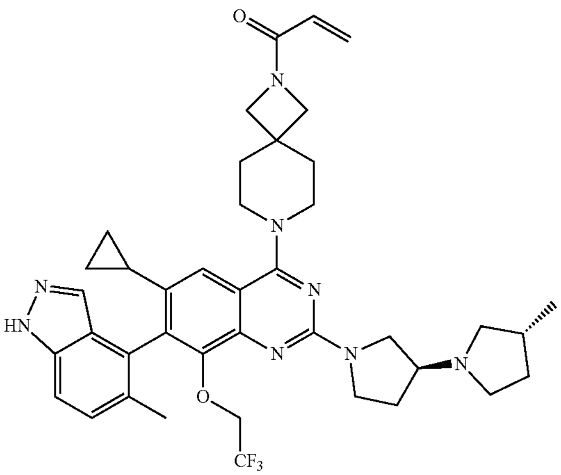
301
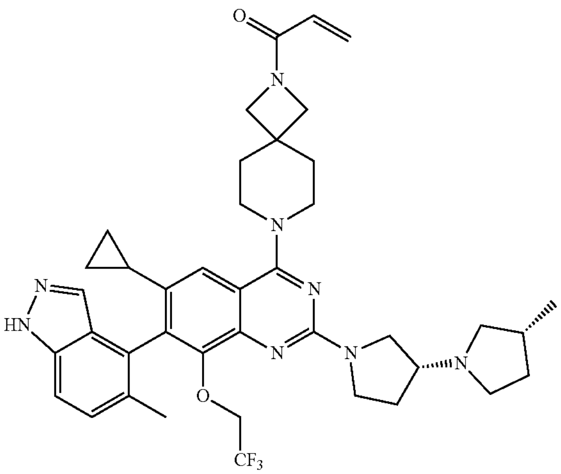
302
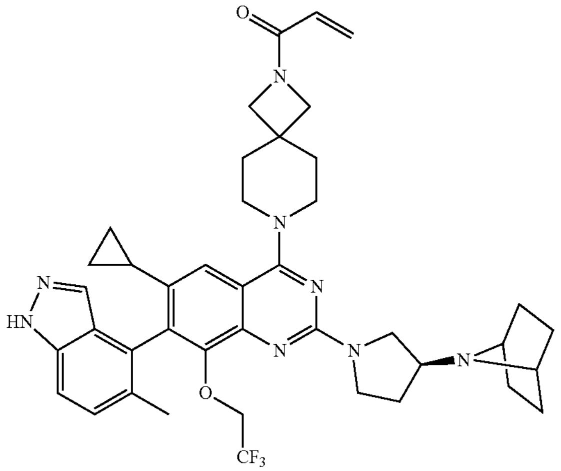
-continued
303
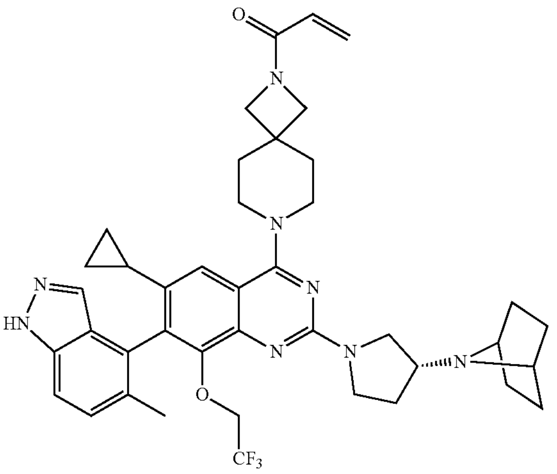
304
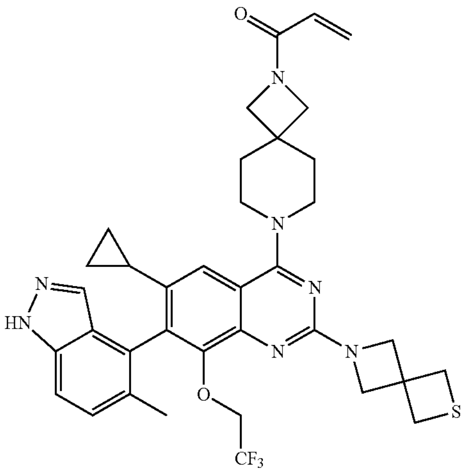
305
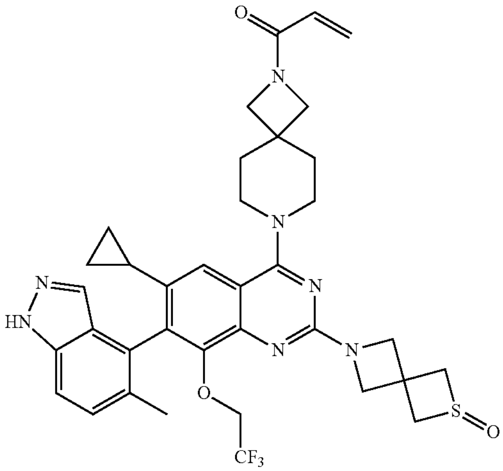

-continued
306
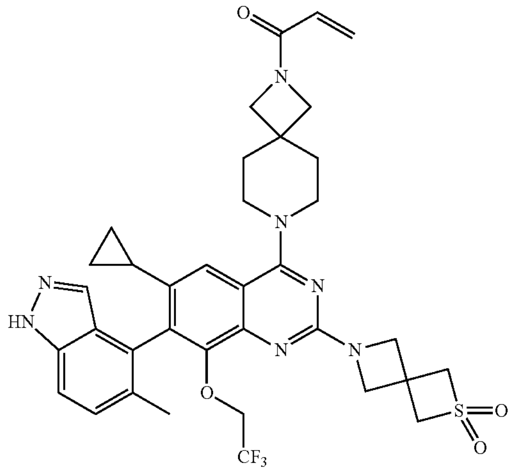
307
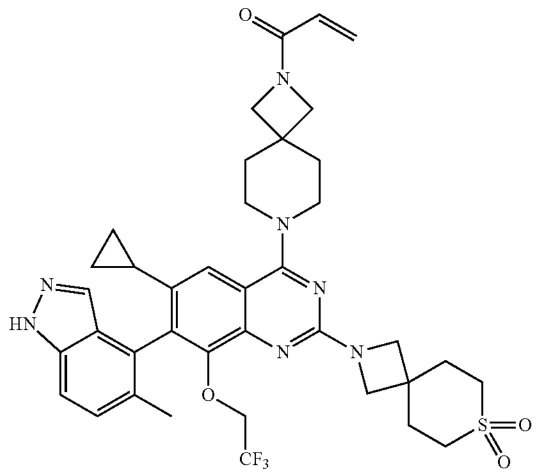
308
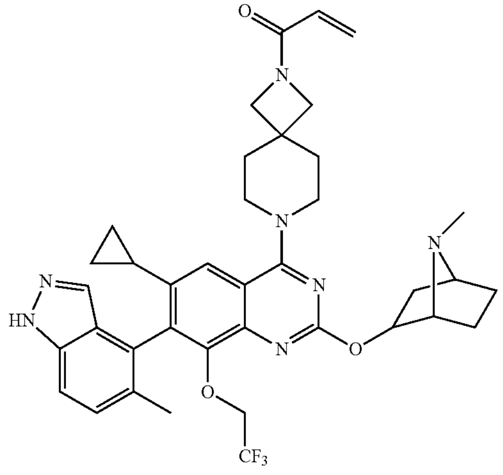
-continued
309
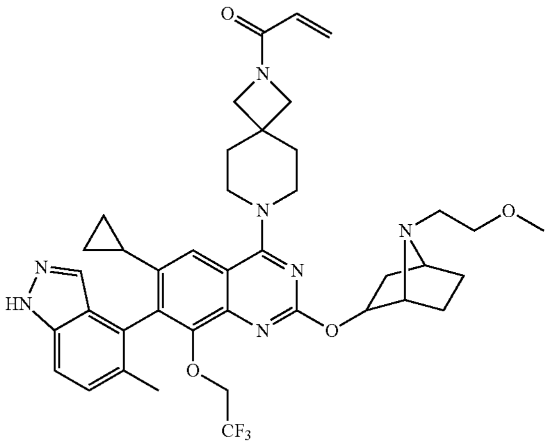
310
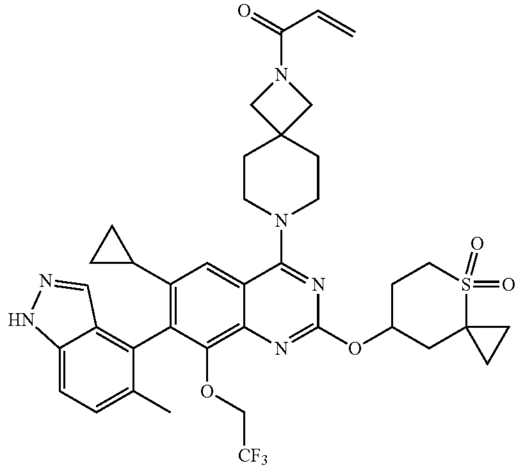
311
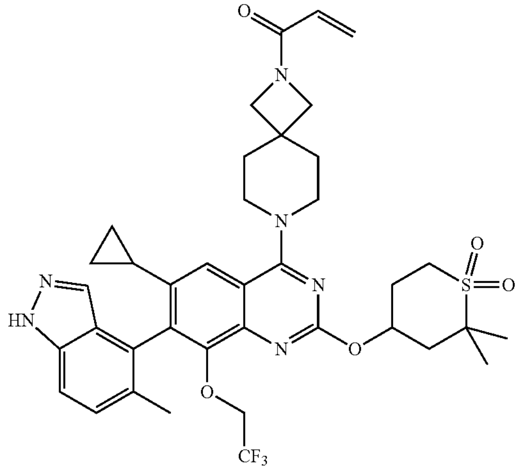

-continued
312
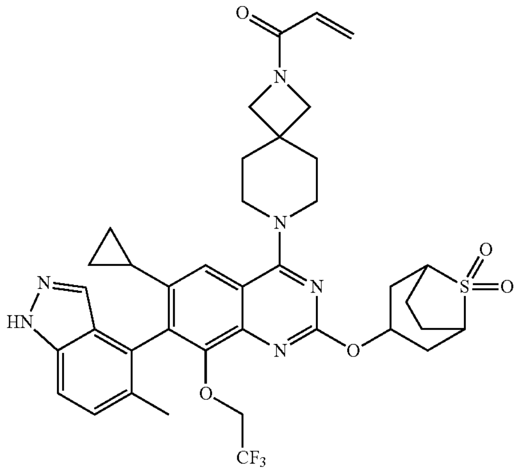
313
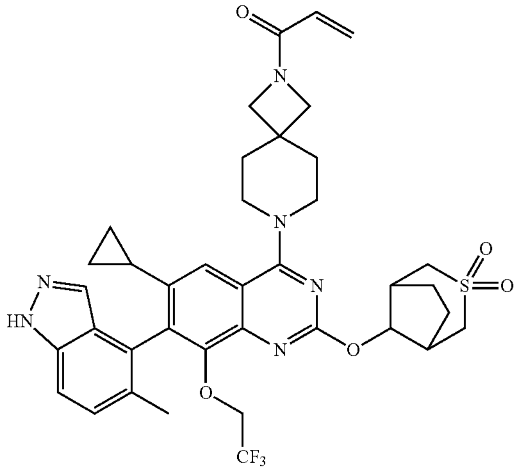
314
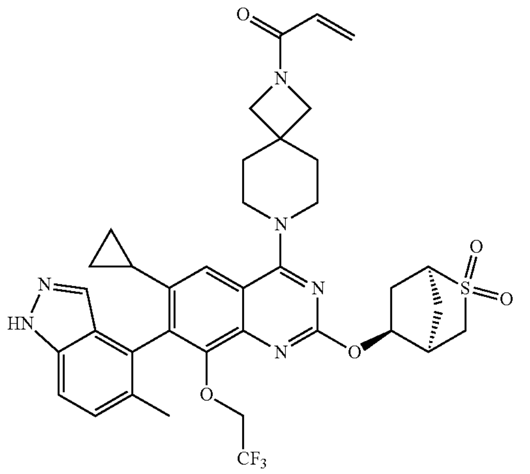
-continued
315
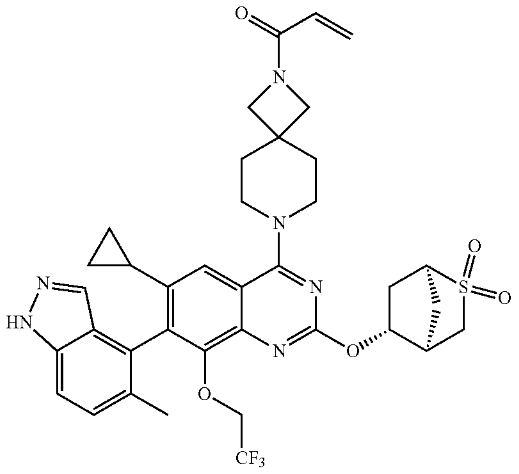
316
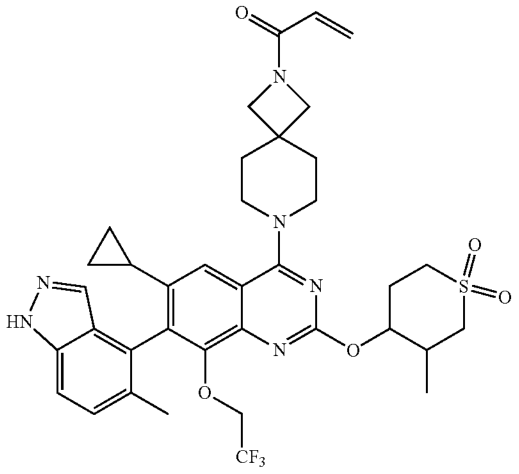
317
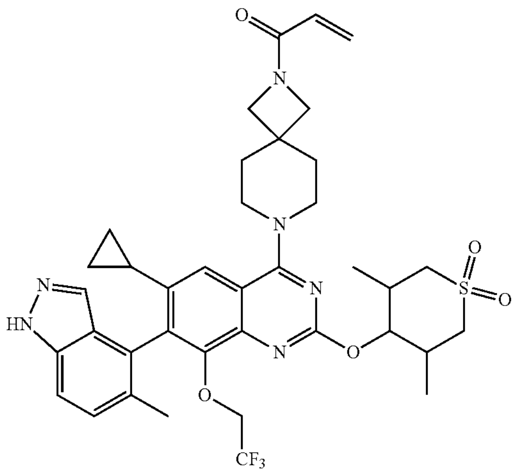

-continued
318
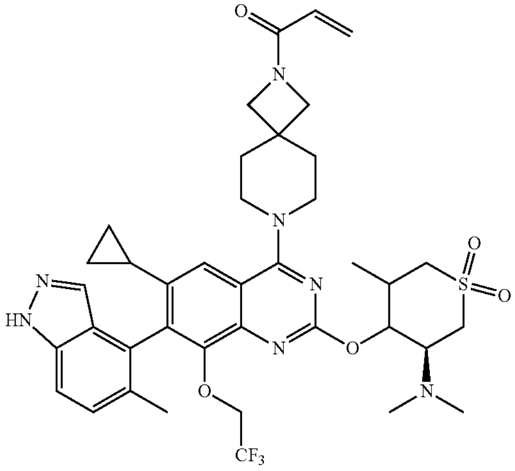
319
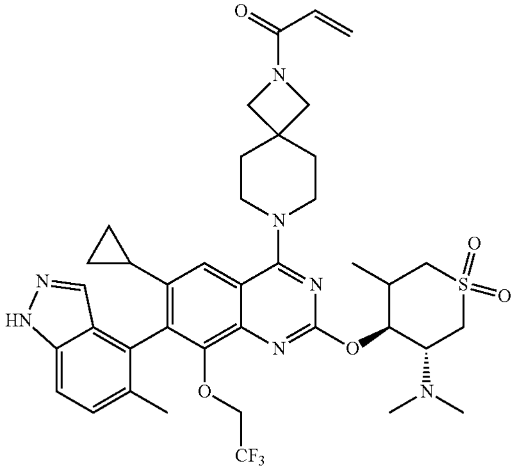
320
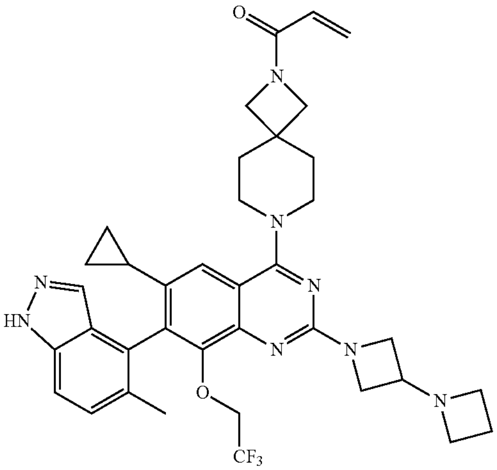
-continued
321
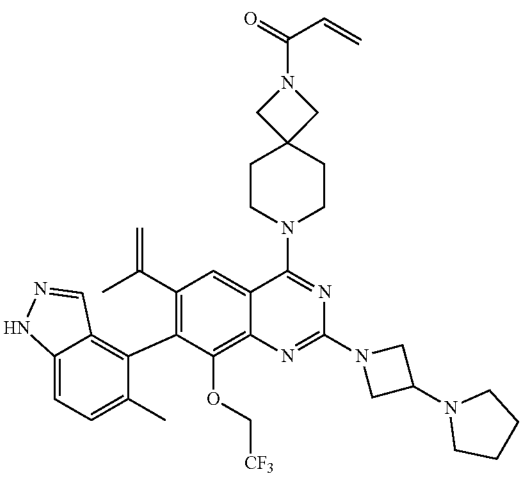
322
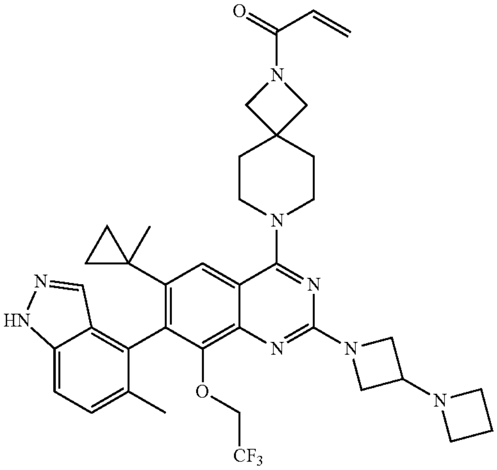
323
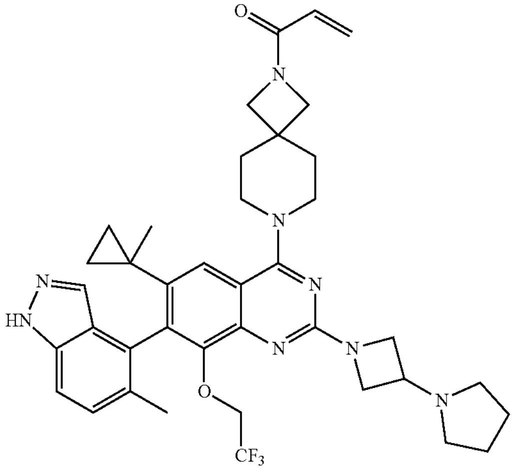

-continued
324
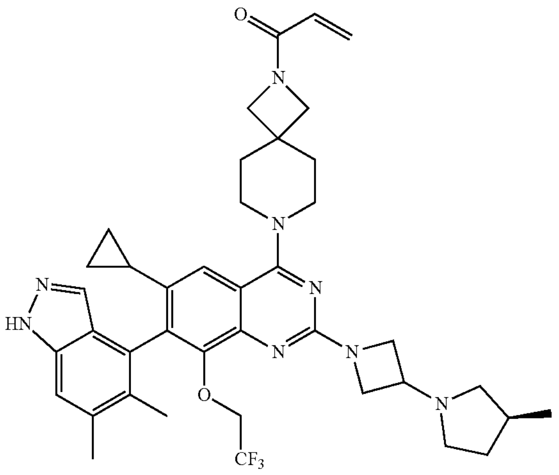
325
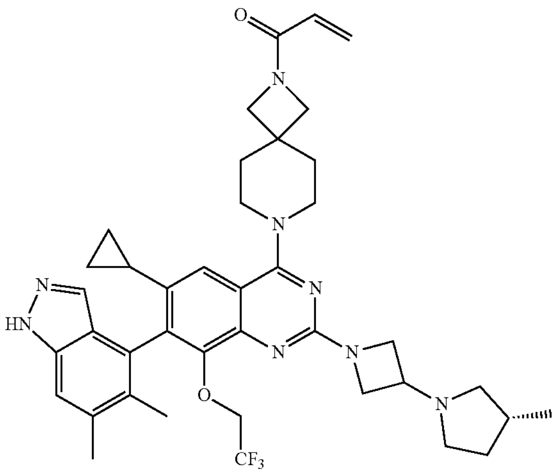
326
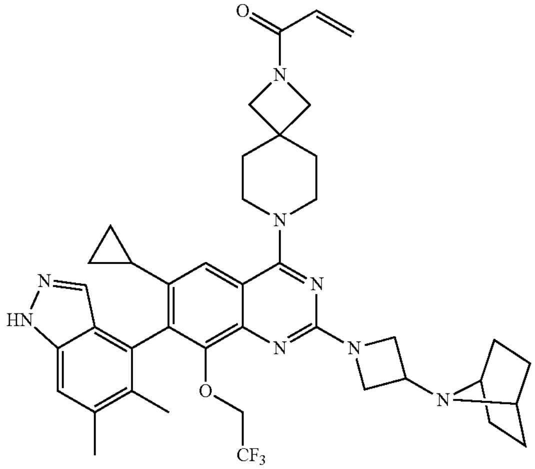
-continued
327
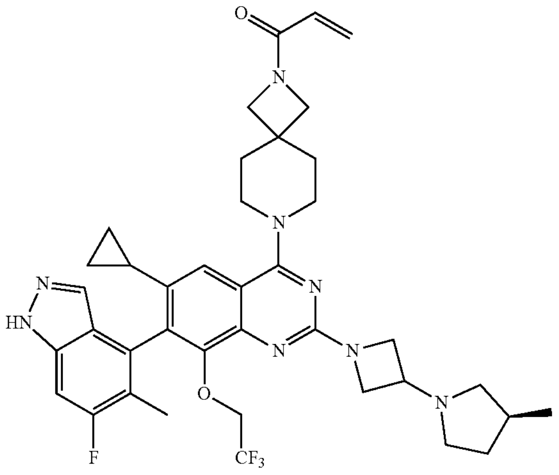
328
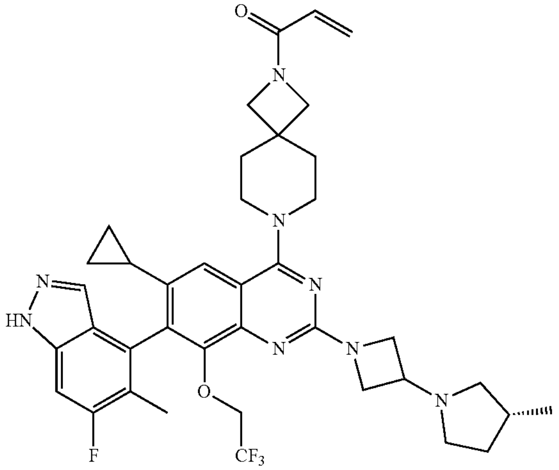
329
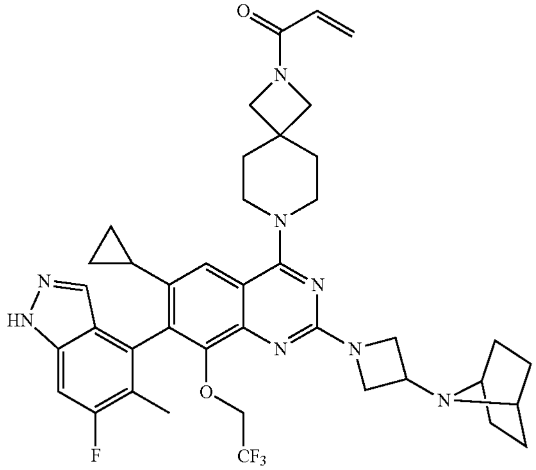

-continued
330
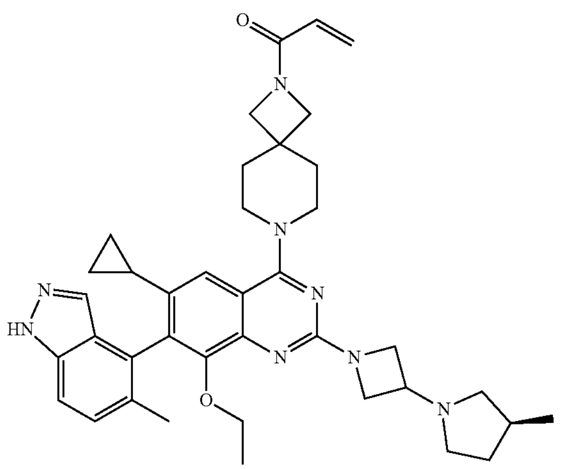
331
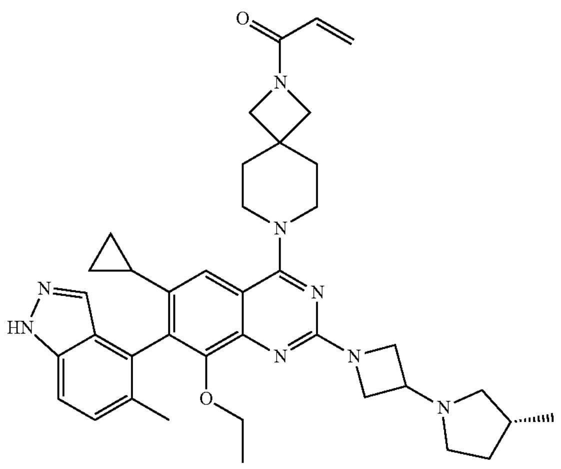
332
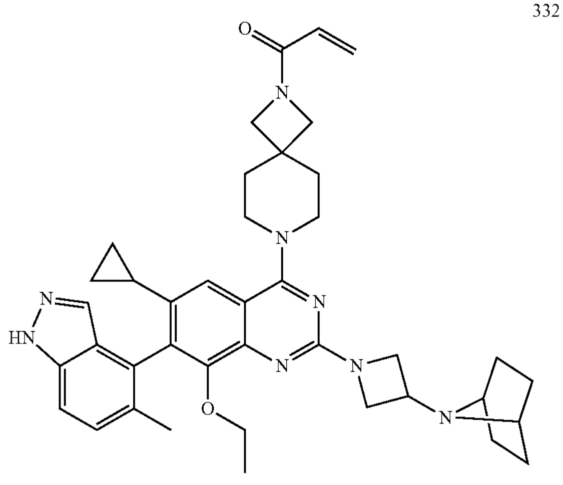
-continued
333
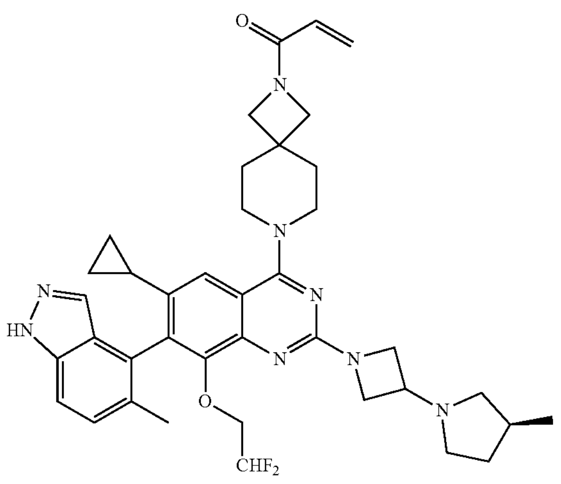
334
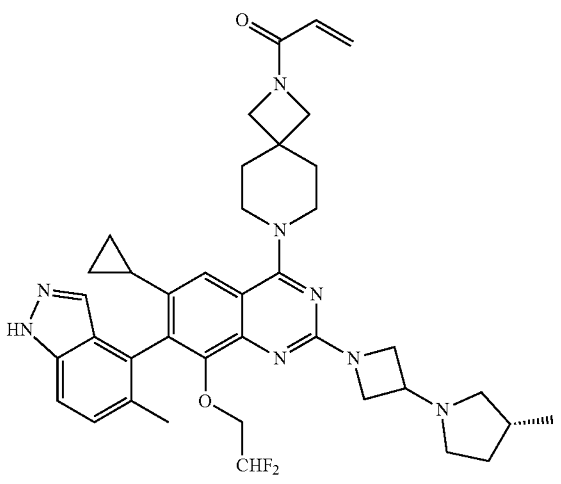
335
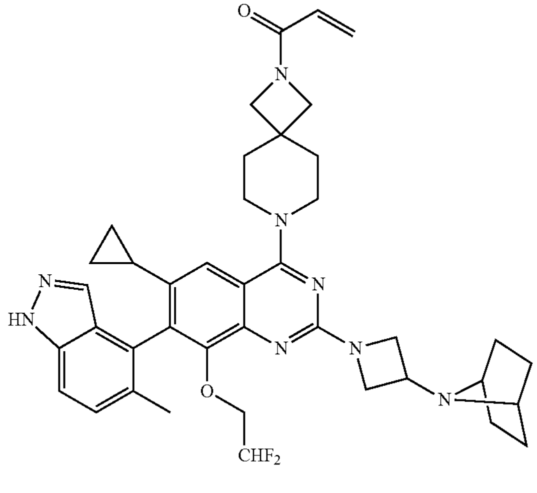

-continued
336
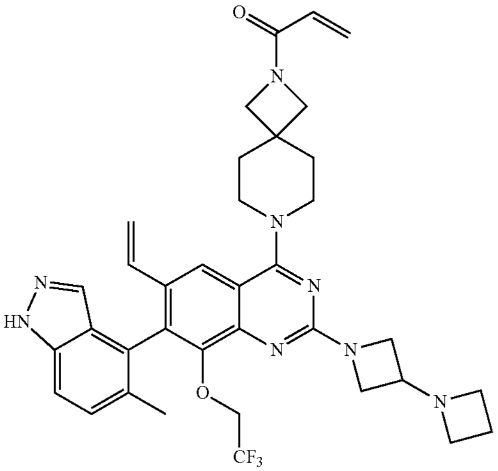
337
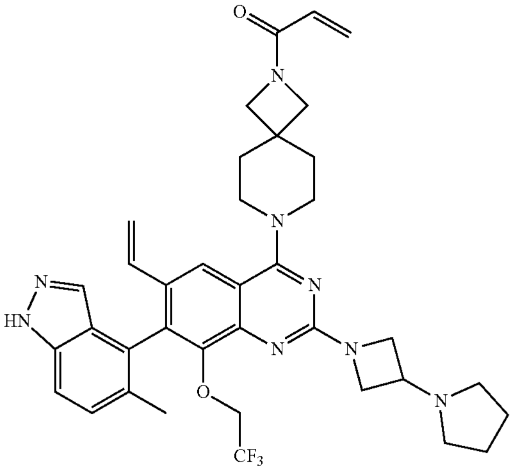
338
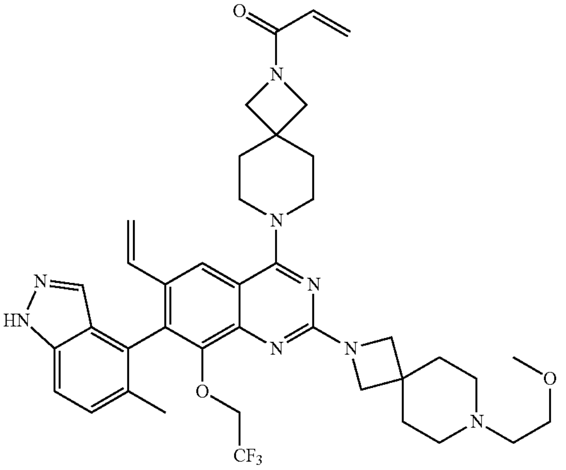
-continued
339
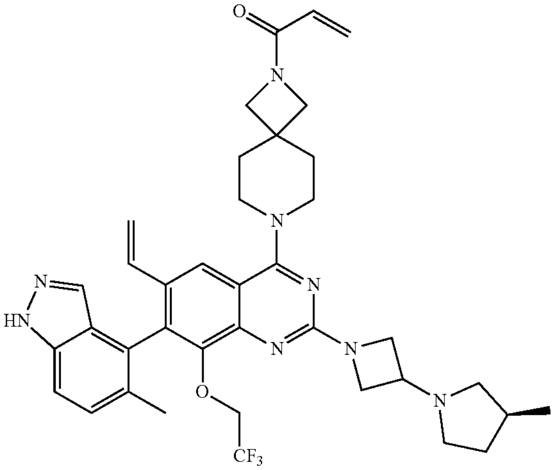
340
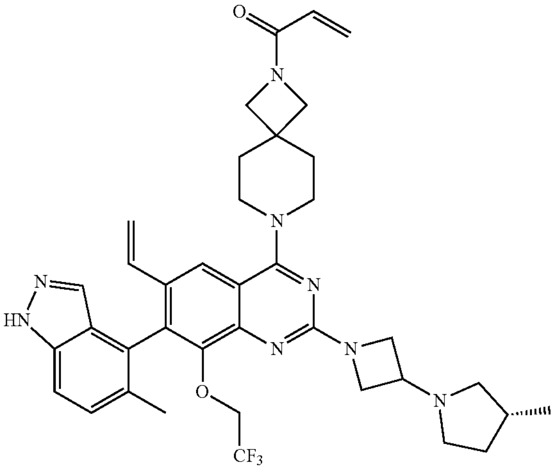
341
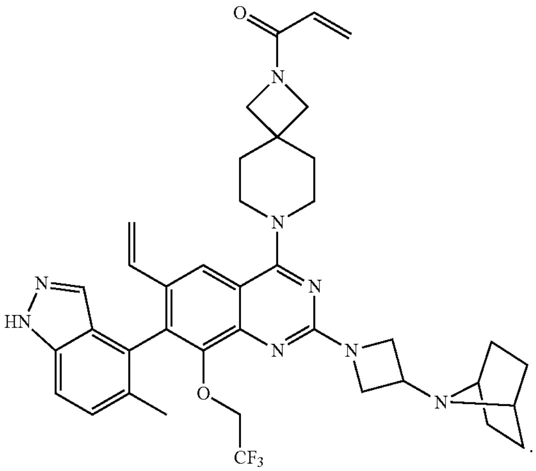
.
Another aspect of the present invention aims to provide a compound with a structure as shown in general formula (3), isomers thereof, crystalline forms thereof, pharmaceutically acceptable salts thereof, hydrates thereof or solvates thereof:

(3)
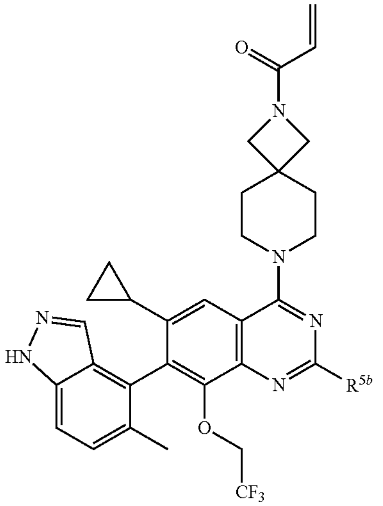
wherein, $R^{5b}$ is:
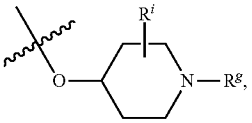, 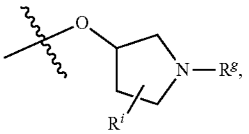, 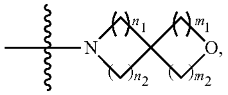, 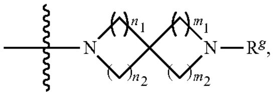, 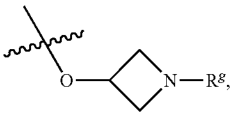, 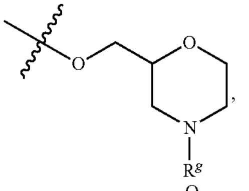, 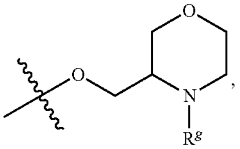, 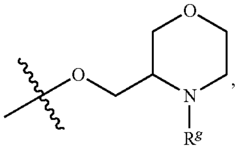, 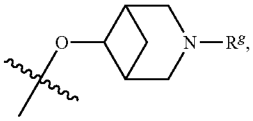, 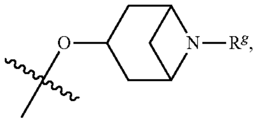, 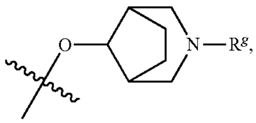, 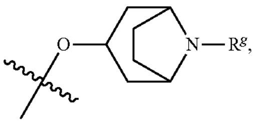, 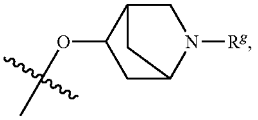, 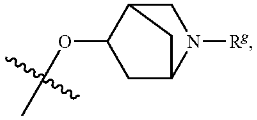, 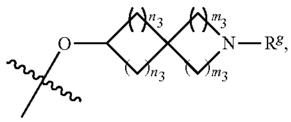, 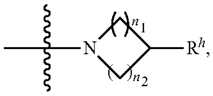,
-continued
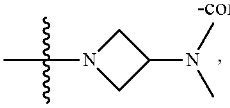, 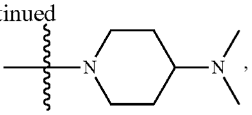, 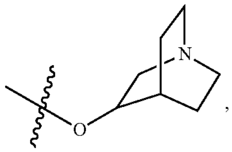, 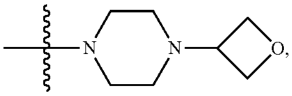, 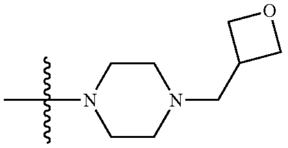 or 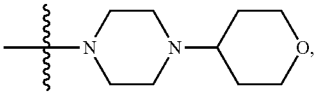,
wherein $n_1$, $n_2$, $n_3$, $m_1$, $m_2$ and $m_3$ are independently integers of 1 or 2; $R^g$ is C1-C3 alkyl, C3-C6 cycloalkyl, (C1-C3) alkoxy-(C2-C3)alkyl-, (halogenated C1-C3)alkoxy-(C2-C3) alkyl-, (C3-C6)cycloalkyl-(C1-C3)alkyl-, heterocycloalkyl, heterocycloalkyl-(C1-C3)alkyl-, C1-C3 haloalkyl or cyano-substituted C1-C3 alkyl; $R^h$ is
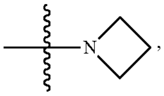, 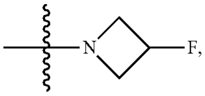, 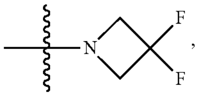, 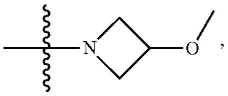, 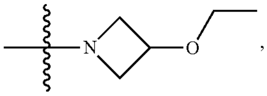, 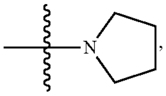, 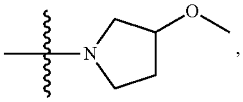, 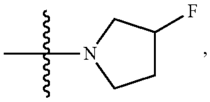, 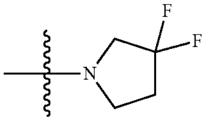, 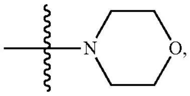, 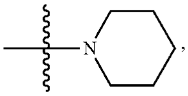, 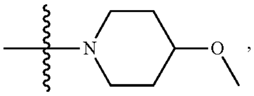, 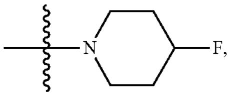, 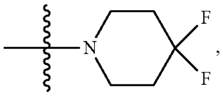, 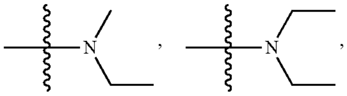, 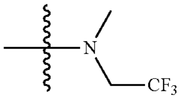 or 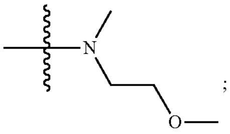;
$R^i$ is H, halogen, methyl or cyano; or $R^{5b}$ is: H,

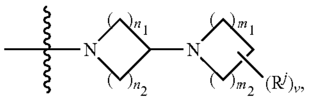

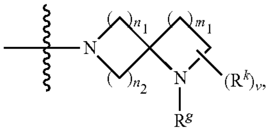

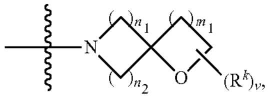

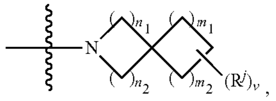

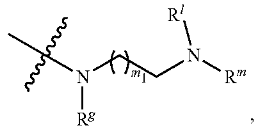

,

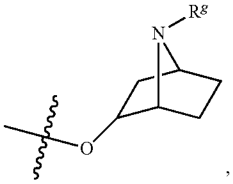

,

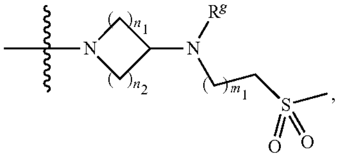

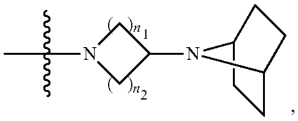

,

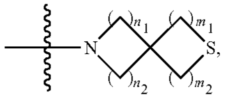

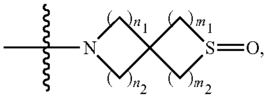

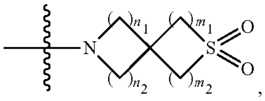

,

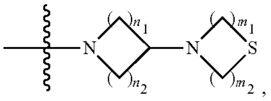

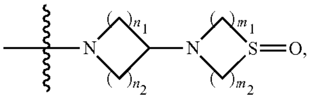

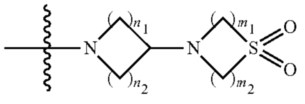

or

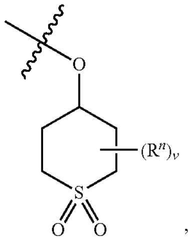

, wherein $n_1$, $n_2$, $n_3$, $m_1$, $m_2$ and $m_3$ are independently integers of 1 or 2; v is an integer of 1, 2 or 3; $R^g$ is C1-C3 alkyl, C3-C6 cycloalkyl, (C1-C3)alkoxy-(C2-C3)alkyl-, (halogenated C1-C3)alkoxy-(C2-C3)alkyl-, (C3-C6)cycloalkyl-(C1-C3)alkyl-, heterocycloalkyl, heterocycloalkyl-(C1-C3) alkyl-, C1-C3 haloalkyl or cyano-substituted C1-C3 alkyl; $R^j$ is independently halogen, CN, $SO_2Me$, C1-C3 alkyl, C1-C3 haloalkyl, C1-C3 alkoxy, C1-C3 haloalkoxy, hydroxy-substituted C1-C3 alkyl, cyano-substituted C1-C3 alkyl, C3-C6 cycloalkyl or

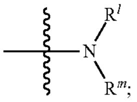

$R^k$ is independently halogen, CN, OH, C1-C3 alkyl, C1-C3 alkoxy, C3-C6 cycloalkyl or

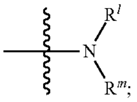

$R^n$ is independently halogen, CN, OH, C1-C3 alkyl, C1-C3 alkoxy or C3-C6 cycloalkyl, two $R^n$ groups, together with one carbon atom, form a spiro ring, or two $R^n$ groups, together with different carbon atoms, form a bridged ring; $R^l$ and $R^m$ are independently C1-C3 alkyl, C1-C3 haloalkyl, hydroxy-substituted C1-C3 alkyl, cyano-substituted C1-C3 alkyl, C3-C6 cycloalkyl, (C1-C3)alkoxy-(C2-C3)alkyl-, (halogenated C1-C3)alkoxy-(C2-C3)alkyl-, (C3-C6)cycloalkyl-(C1-C3)alkyl-, or $R^l$ and $R^m$, together with a N atom, form a 3-8 membered heterocycloalkyl group, wherein the 3-8 membered heterocycloalkyl group may be substituted with 1-3 groups selected from OH, halogen, cyano, C1-C3 alkyl, C3-C6 cycloalkyl, heterocycloalkyl, (C1-C3)alkoxy or (halogenated C1-C3)alkoxy.

In another preferred embodiment, in the general formula (3), $R^{5b}$ is: H,

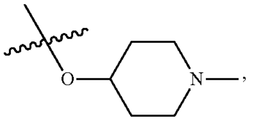

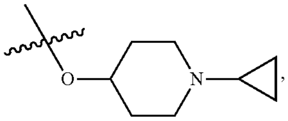

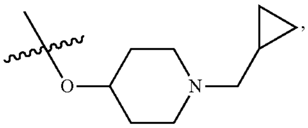

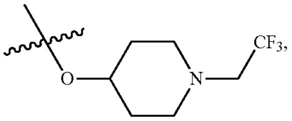

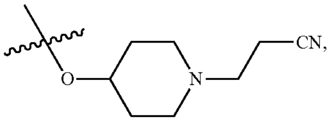

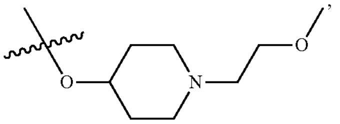

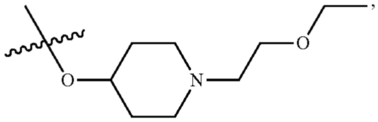

-continued
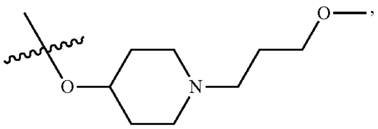
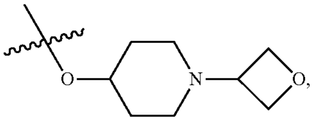
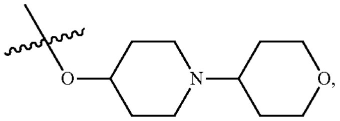
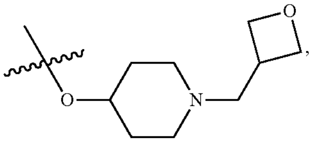
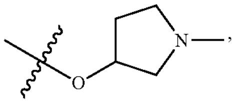
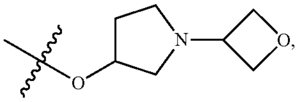
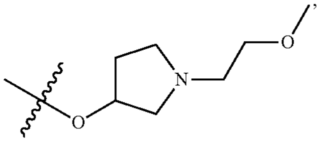
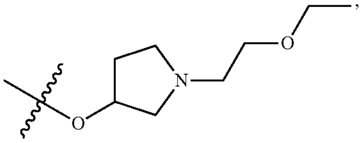
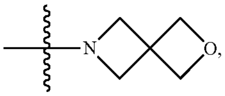
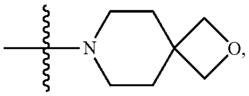
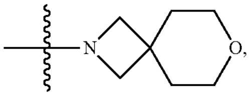
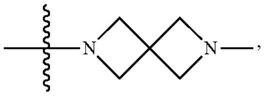
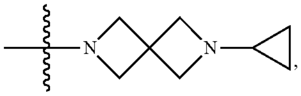
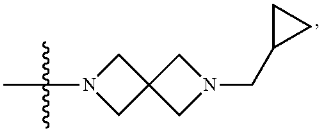
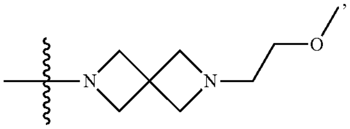
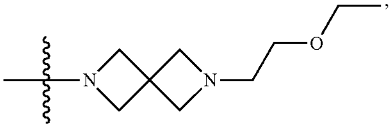
-continued
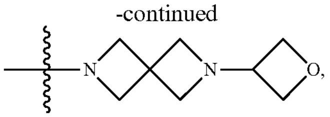
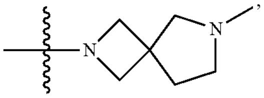
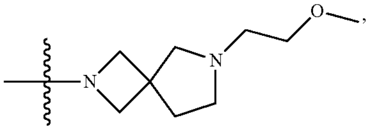
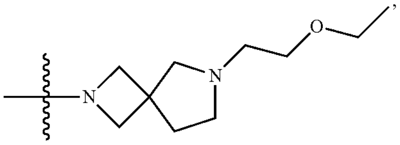
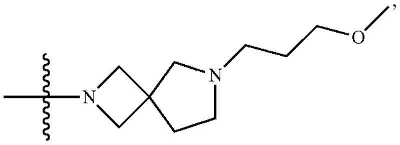
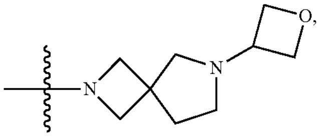
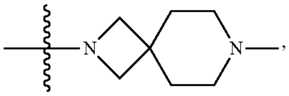
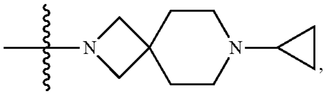
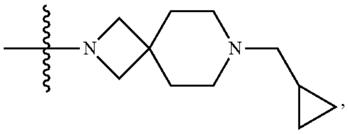
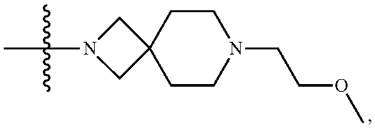
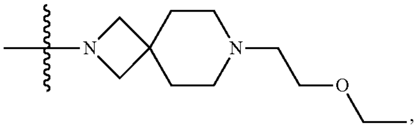
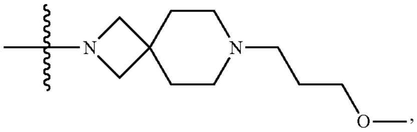
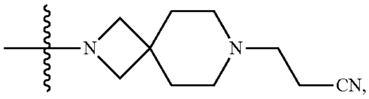
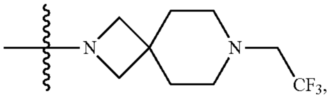

-continued
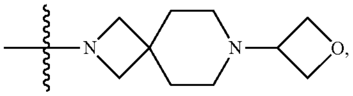
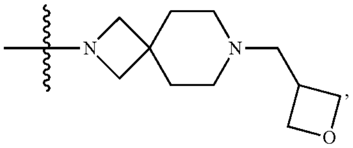
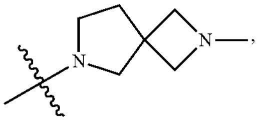
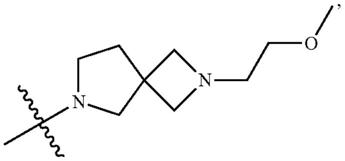
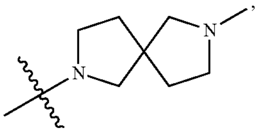
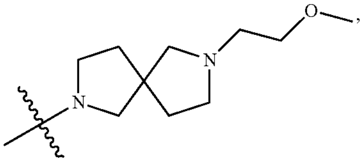
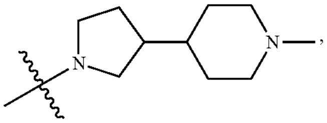
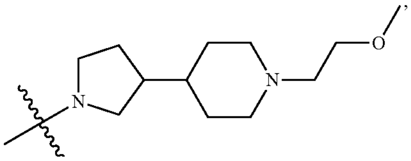
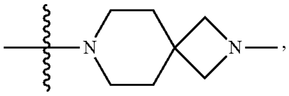
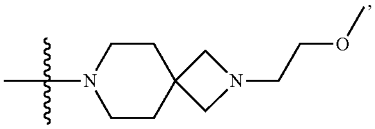
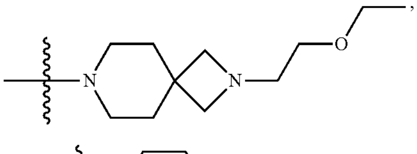
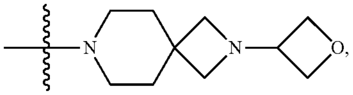
-continued
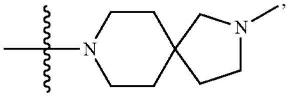
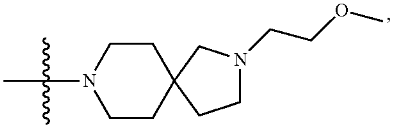
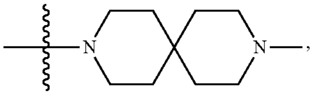
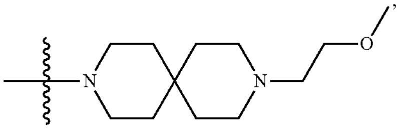
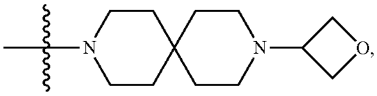
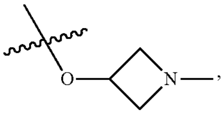
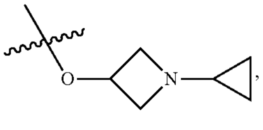
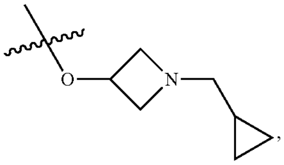
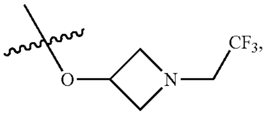
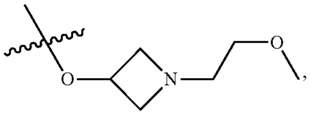
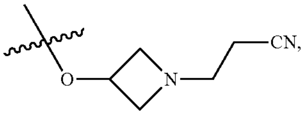
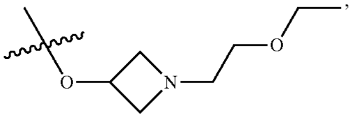
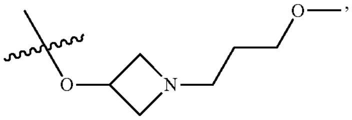
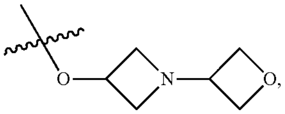
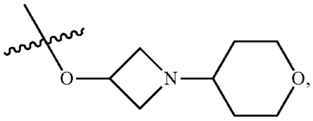

-continued
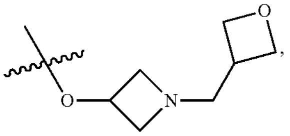
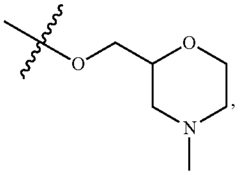
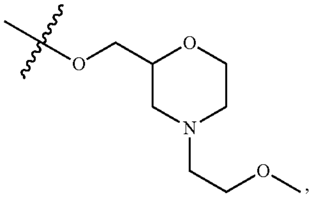
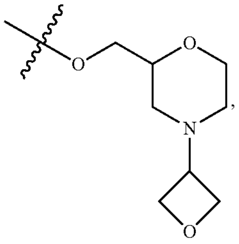
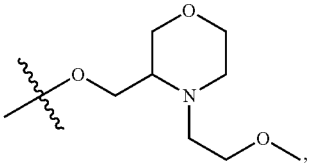
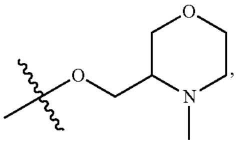
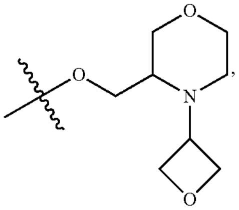
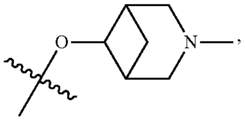
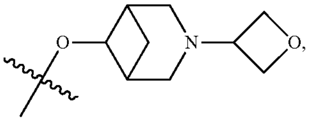
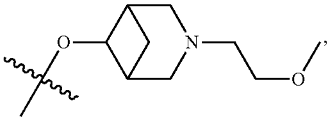
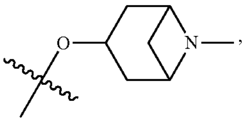
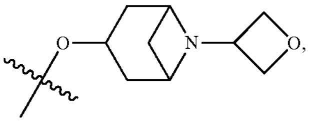
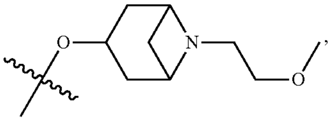
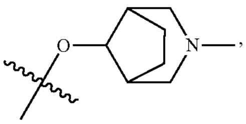
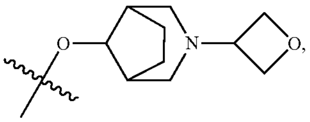
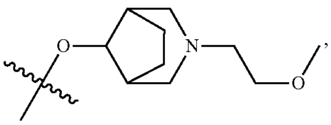
-continued
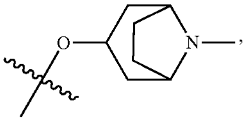
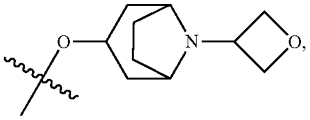
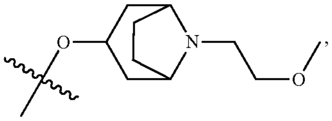
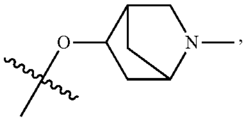
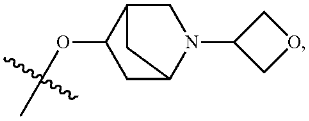
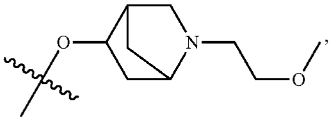
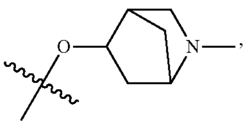
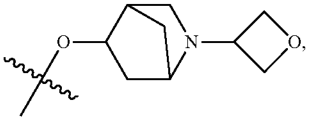
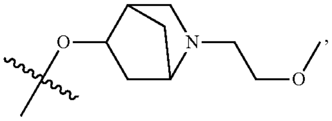
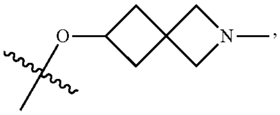
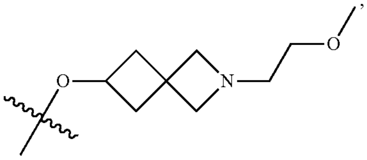
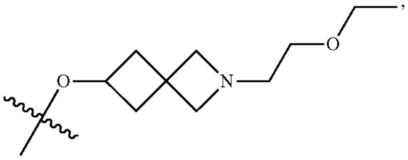
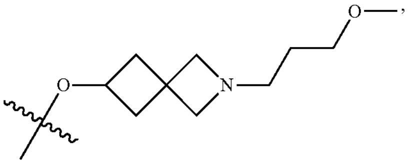
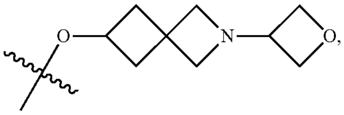
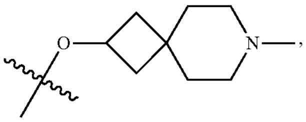
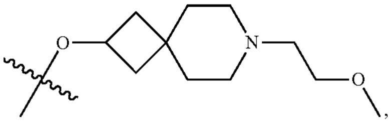

-continued
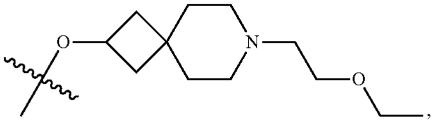,
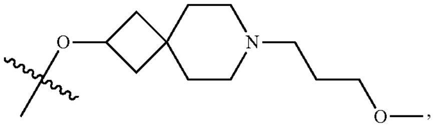,
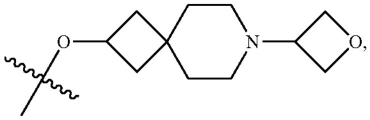,
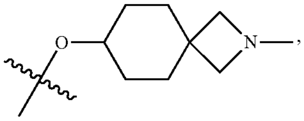,
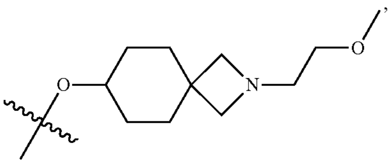,
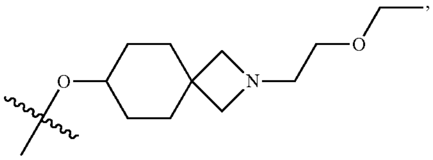,
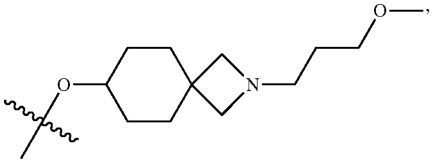,
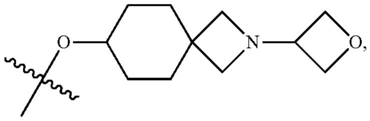,
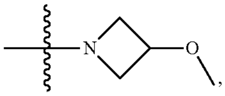, 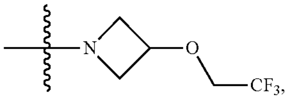,
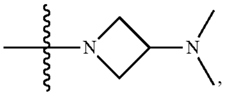, 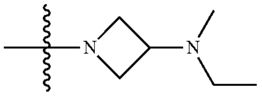,
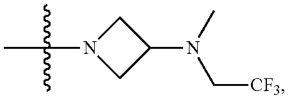,
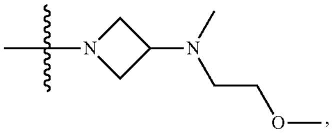,
-continued
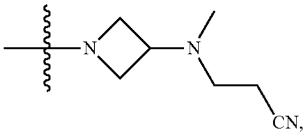, 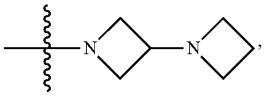,
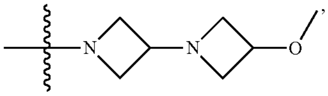,
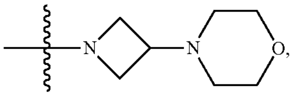, 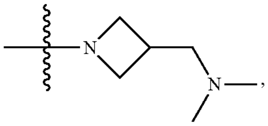,
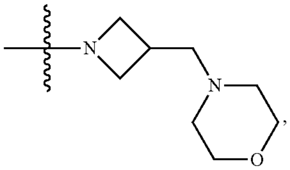, 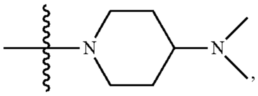,
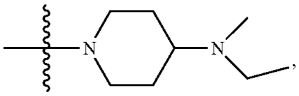,
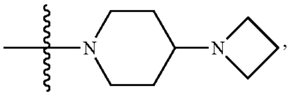,
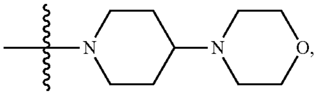,
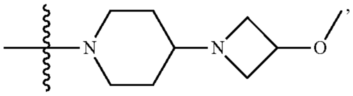,
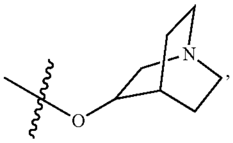, 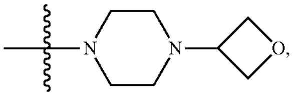,
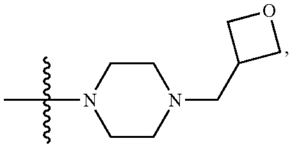,
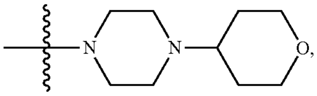,
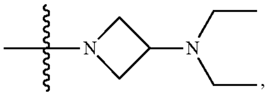, 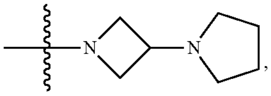,
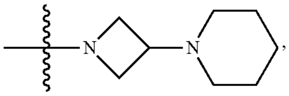,
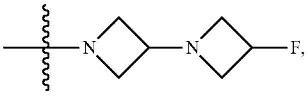, -continued
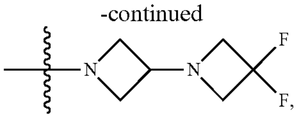
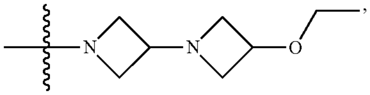
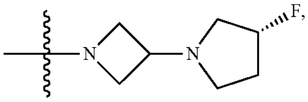
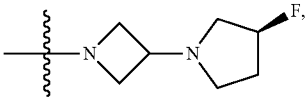
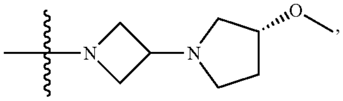
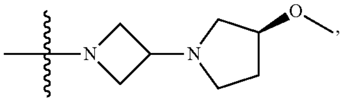
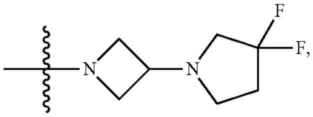
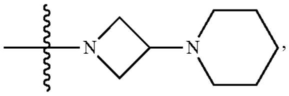
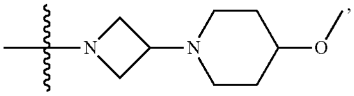
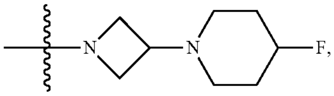
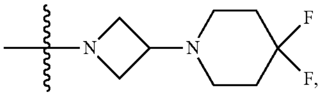
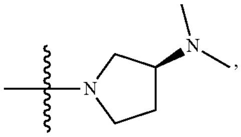
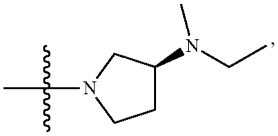
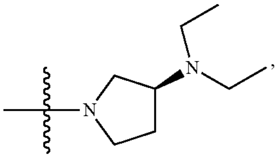
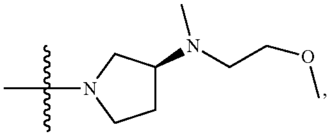
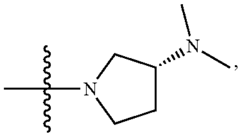
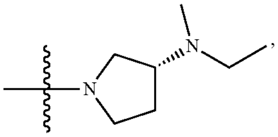
-continued
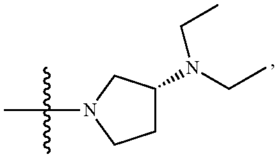
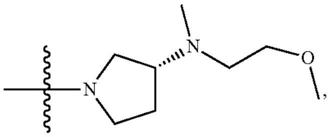
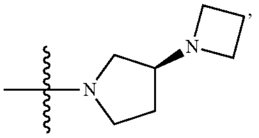
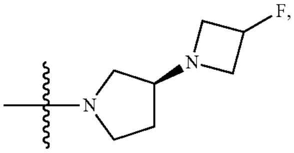
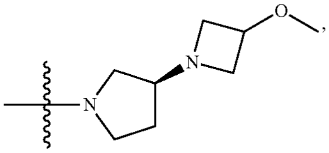
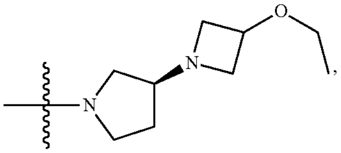
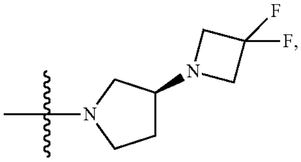
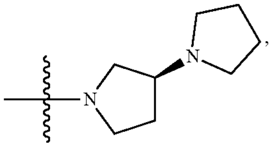
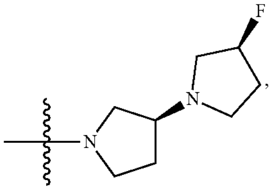
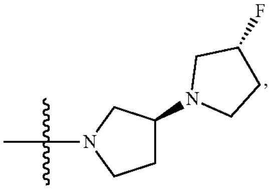
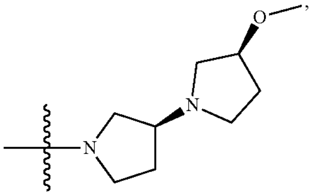
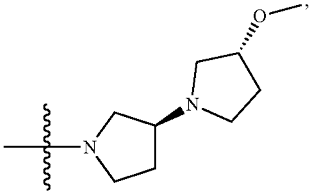
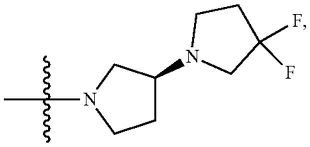

-continued
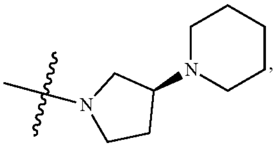
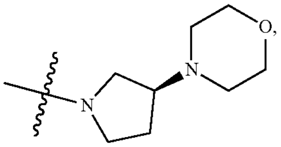
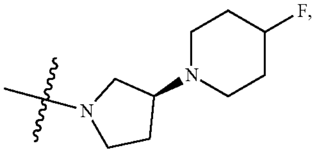
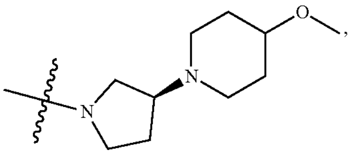
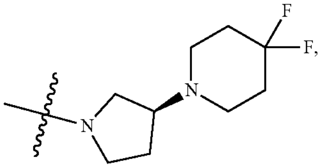
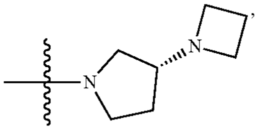
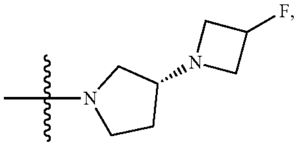
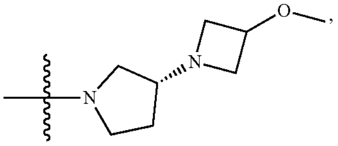
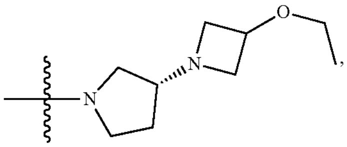
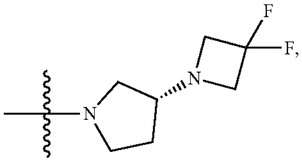
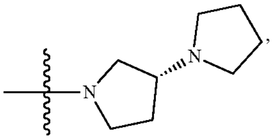
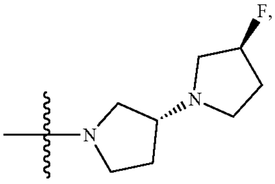
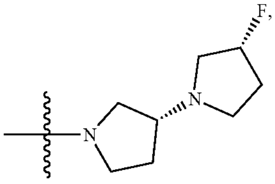
-continued
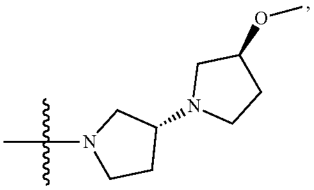
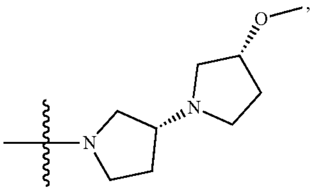
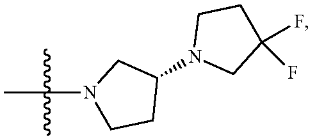
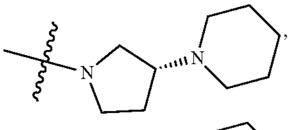
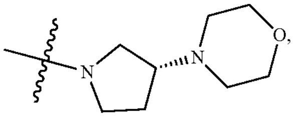
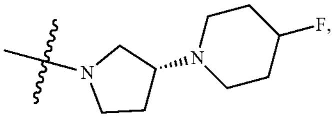
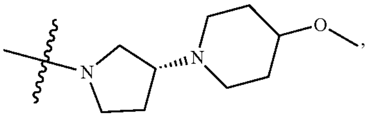
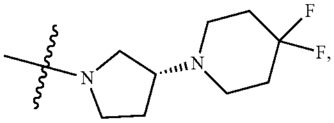
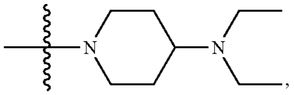
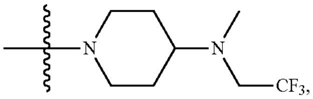
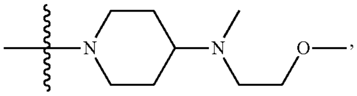
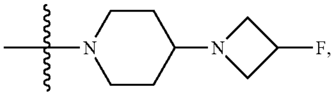
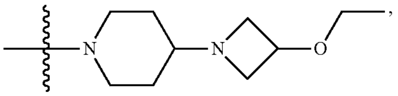
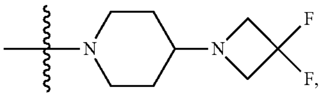

-continued
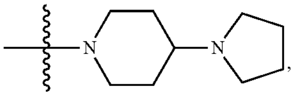
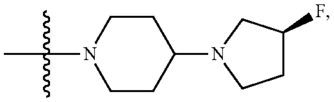
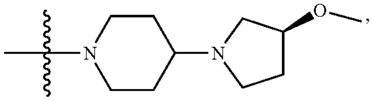
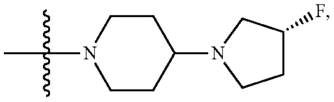
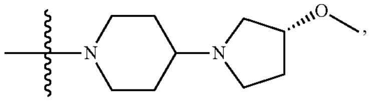
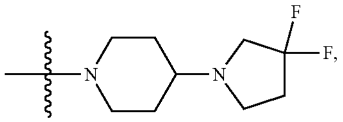
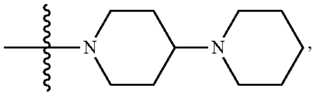
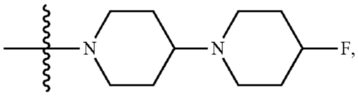
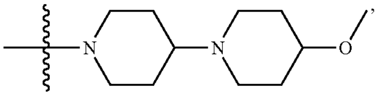
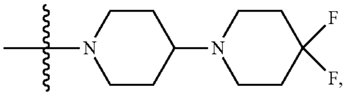
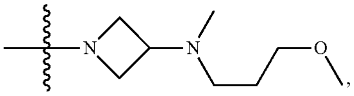
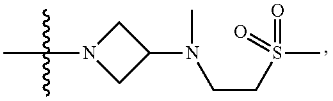
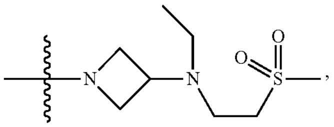
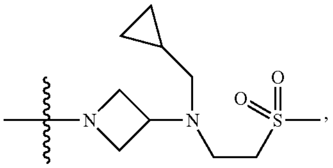
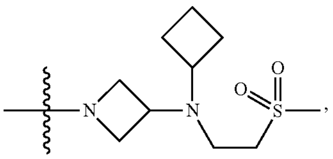
-continued
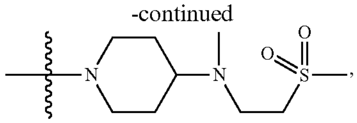
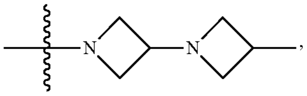
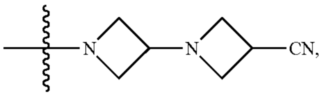
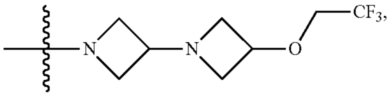
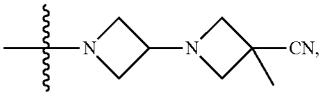
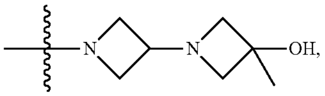
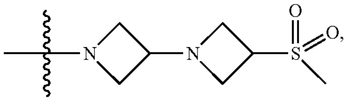
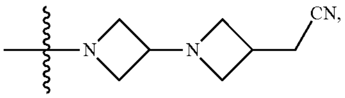
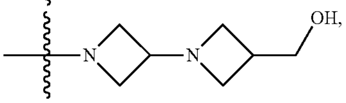
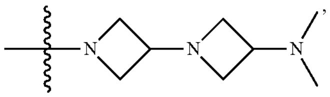
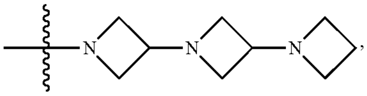
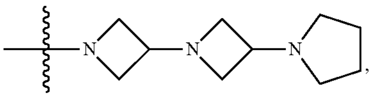
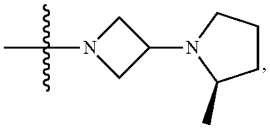
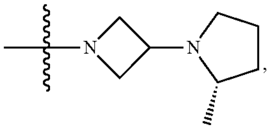
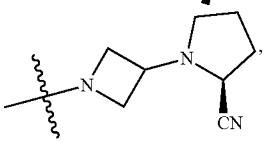
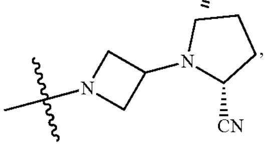
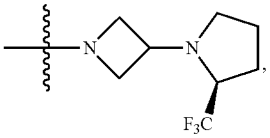
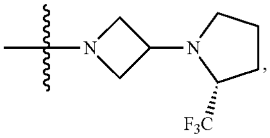
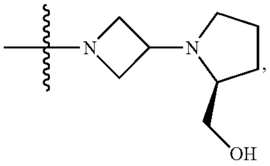
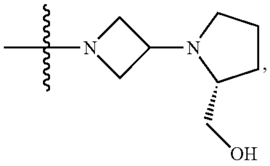

-continued
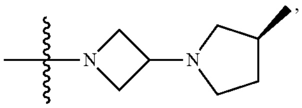
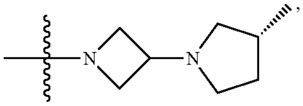
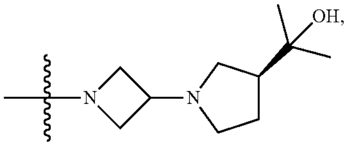
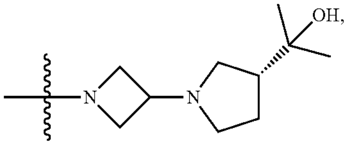
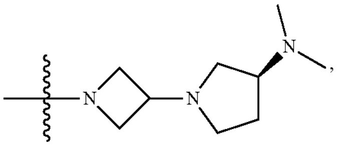
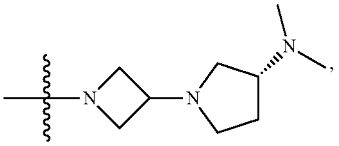
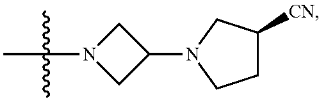
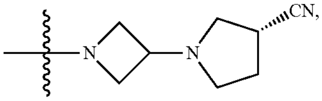
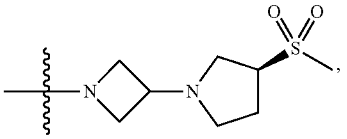
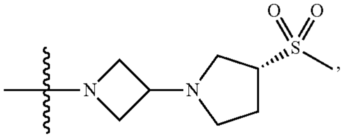
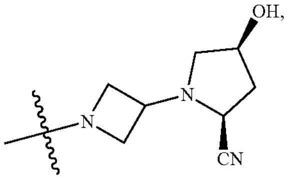
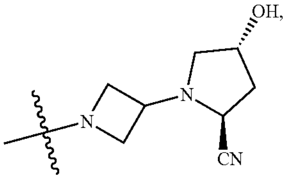
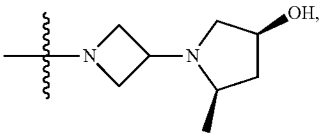
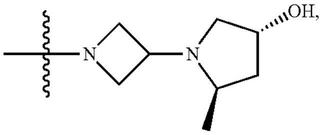
-continued
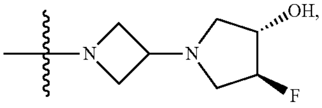
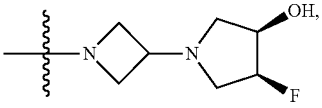
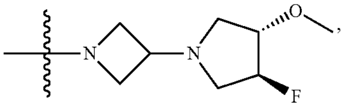
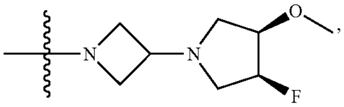
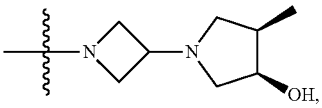
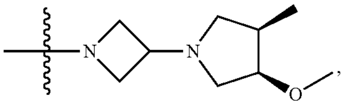
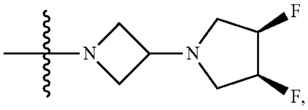
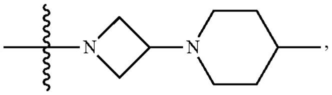
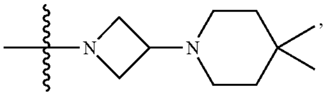
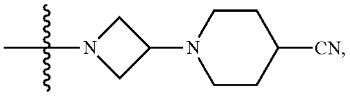
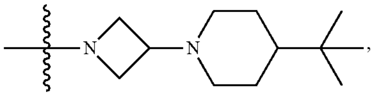
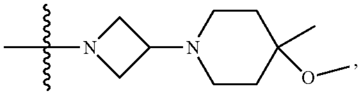
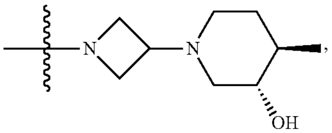
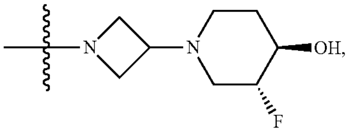
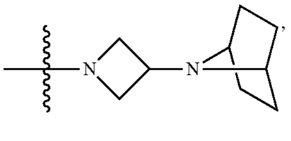
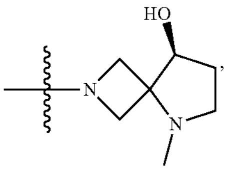

-continued
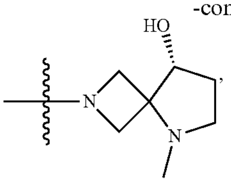,
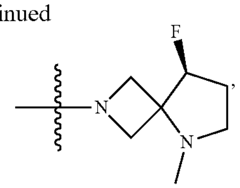,
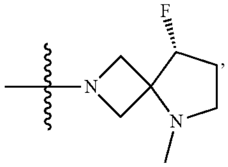,
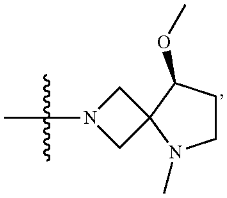,
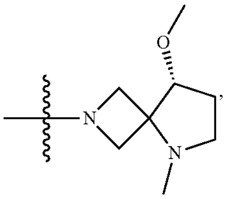,
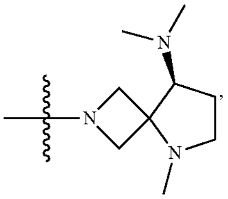,
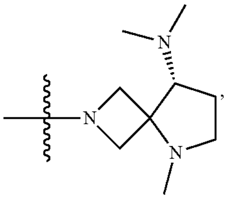,
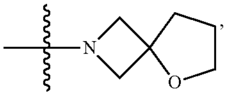,
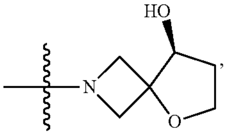,
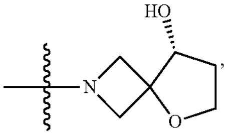,
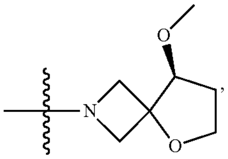,
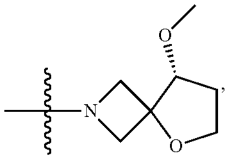,
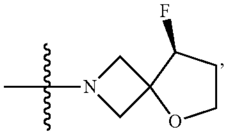,
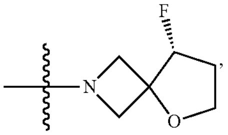,
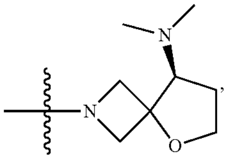,
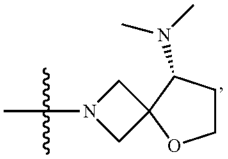,
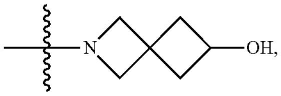,
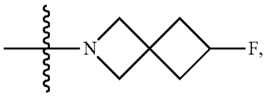,
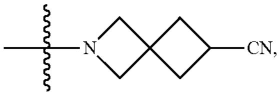,
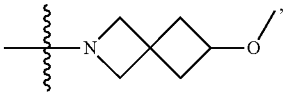,
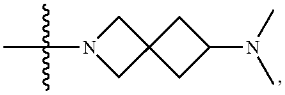,
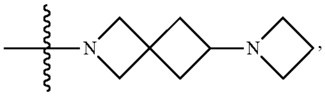,
-continued
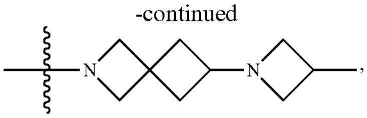,
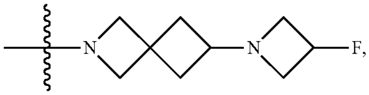,
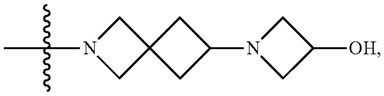,
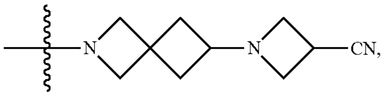,
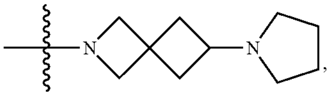,
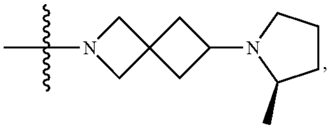,
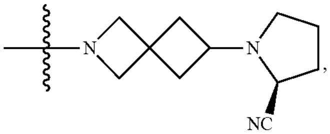,
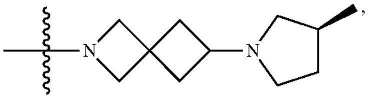,
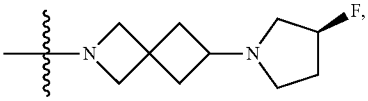,
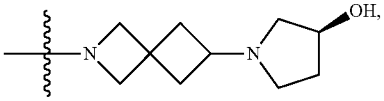,
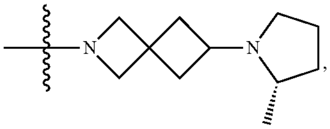,
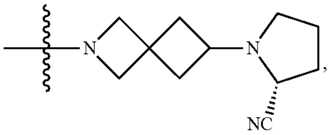,
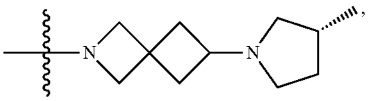,
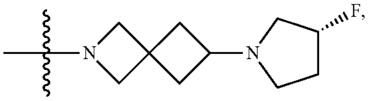,
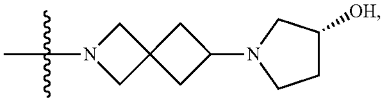,
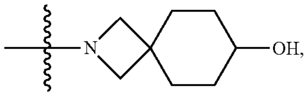, -continued
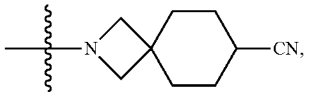
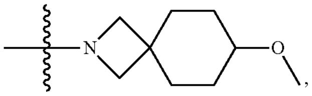
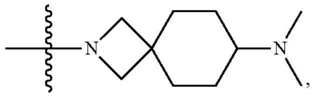
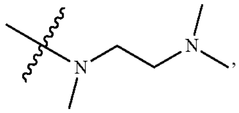
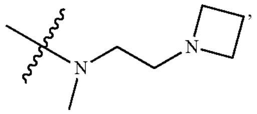
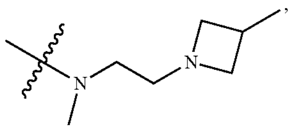
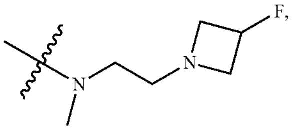
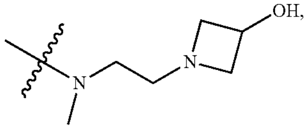
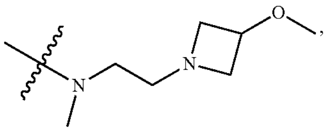
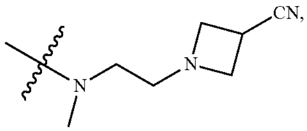
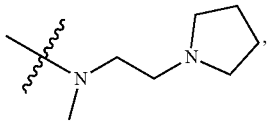
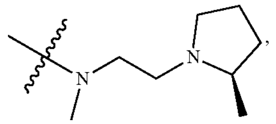
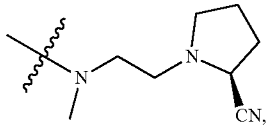
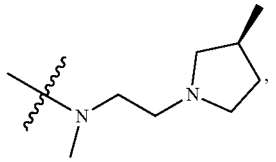
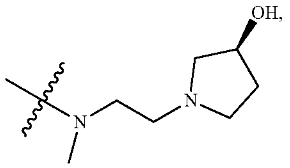
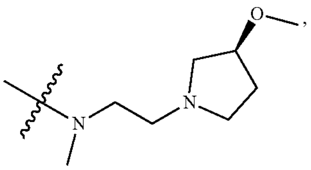
-continued
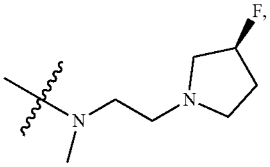
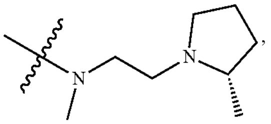
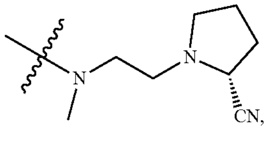
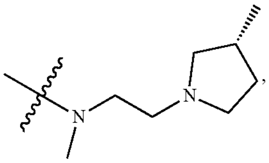
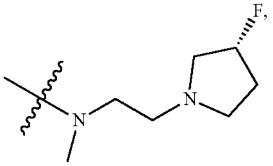
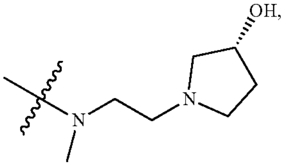
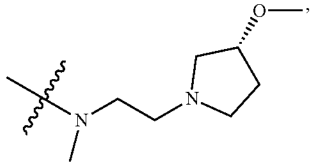
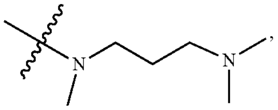
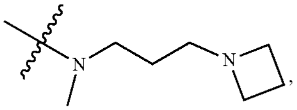
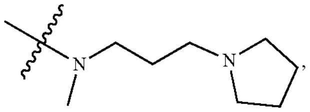
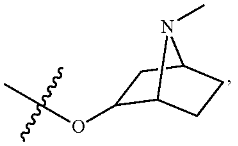
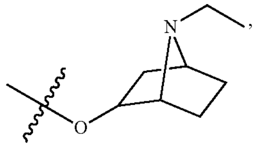
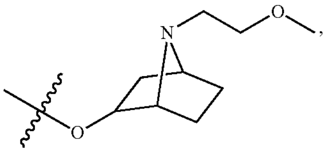
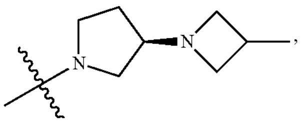
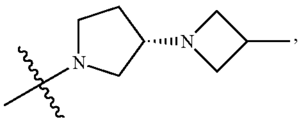
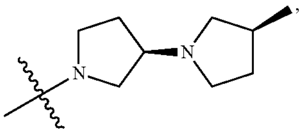

-continued

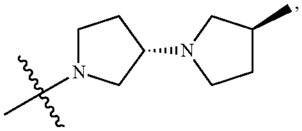
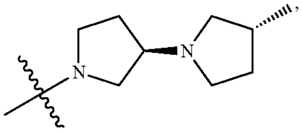
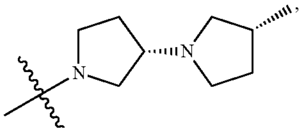
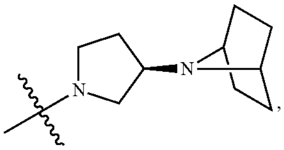
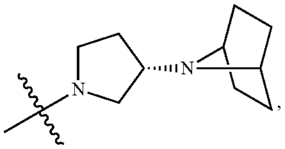
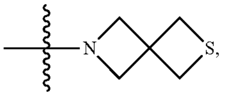
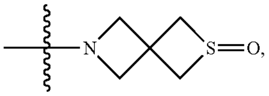
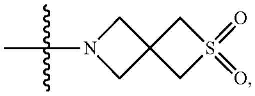
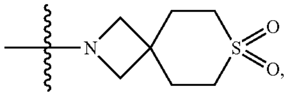
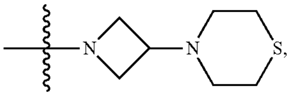
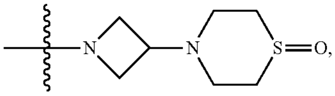
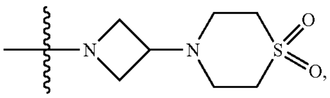
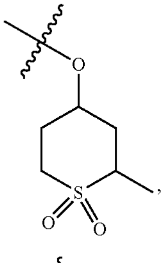
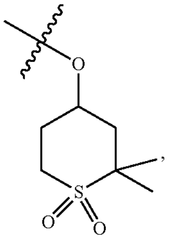
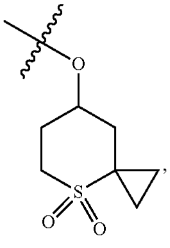
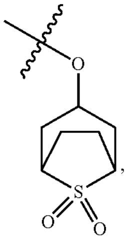

-continued

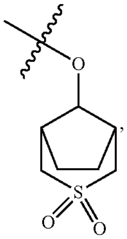
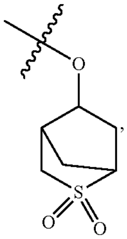
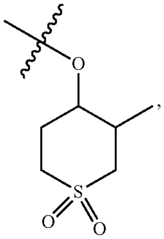
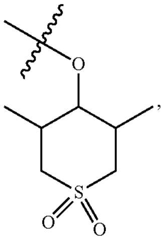
or
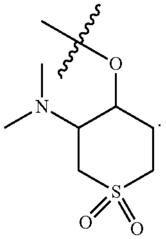

Another purpose of the present invention is to provide a pharmaceutical composition comprising a pharmaceutically acceptable excipient or carrier, and the compounds of general formulas (1) through (3), the isomers thereof, the crystalline forms thereof, the pharmaceutically acceptable salts thereof, the hydrates thereof or the solvates thereof of the present invention as active ingredients.

Still another purpose of the present invention is to provide use of the compounds, the isomers thereof, the crystalline forms thereof, the pharmaceutically acceptable salts thereof, the hydrates thereof or the solvates thereof of the present invention described above in preparing a medicament for treating RAS-associated diseases.

Through synthesis of and careful studies on various new compounds with K-RAS G12C inhibitory effects, the inventors found that in the compounds of general formulas (1) through (3), when $R^5$ (or $R^{5a}$ or $R^{5b}$) is a spiro ring or other substituted heterocyclic ring, the compounds have very high K-RAS G12C inhibitory activity, meanwhile, the pharmacokinetic properties of the compounds are greatly improved, and the in vivo activity of the compounds is enhanced. In another aspect, the inventors found that when position 2 (substituent $R^4$) of acrylamide is substituted with a F atom that is small in size, the compounds also have good K-RAS G12C inhibitory activity and pharmacokinetic properties.

It should be understood that both the above general description and the following detailed description of the present invention are exemplary and explanatory, and are intended to provide further explanation of the present invention claimed.

Synthesis of the Compounds

Methods for preparing the compounds of general formulas (1) through (3) of the present invention are hereafter described in detail, but these specific methods do not limit the present invention in any way.

The compounds of general formulas (1) through (3) described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, Advanced Organic Chemistry, 4th Ed., (Wiley 1992); Carey and Sundberg, Advanced Organic Chemistry, 4th Ed., Vols. A and B (Plenum 2000, 2001), and Green and Wuts, Protective Groups in Organic Synthesis, 3rd Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas (1) through (3), which are prepared using general reaction scheme 1 below:

General reaction scheme 1

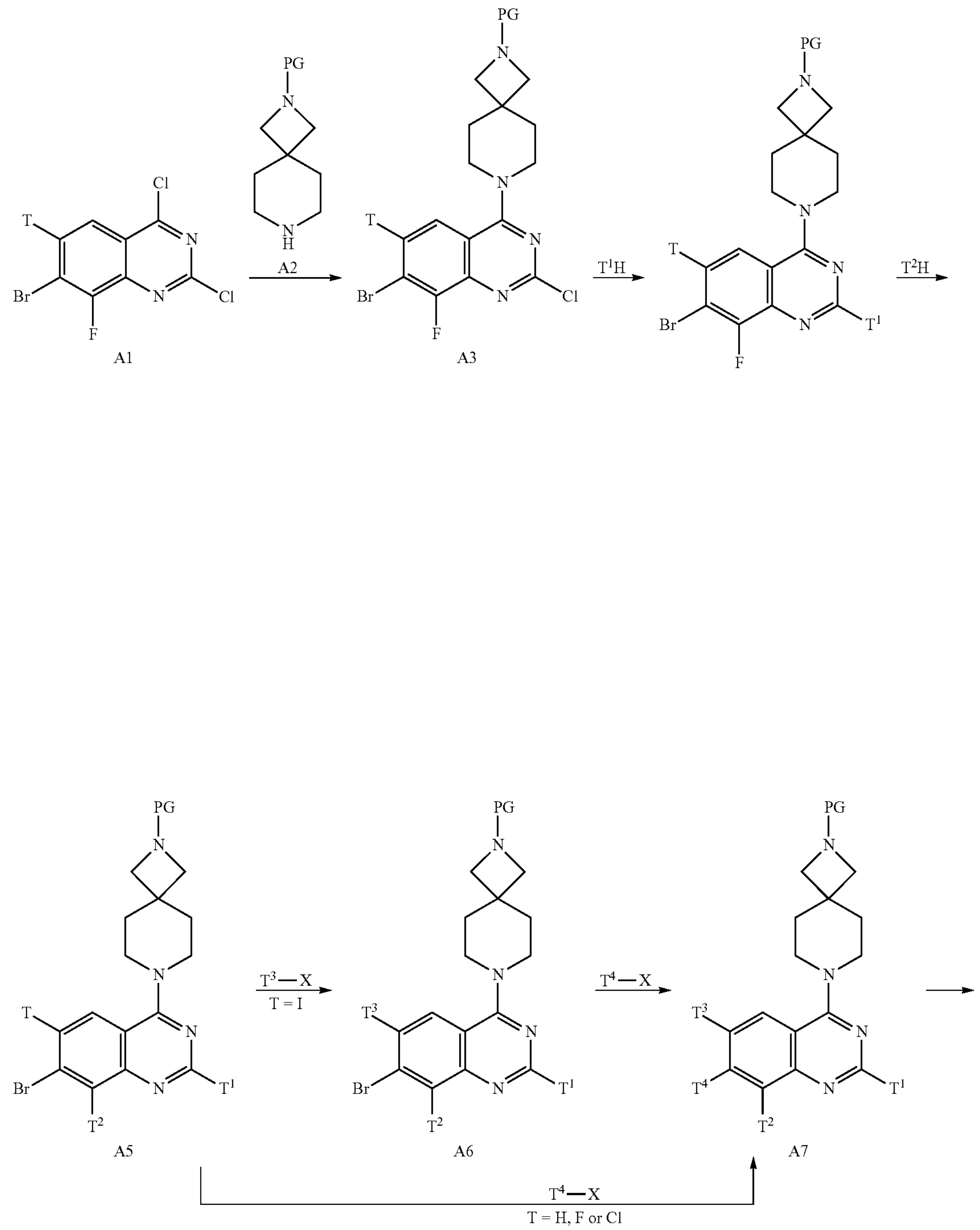

A1
A2
A3
A5
A6
A7

-continued

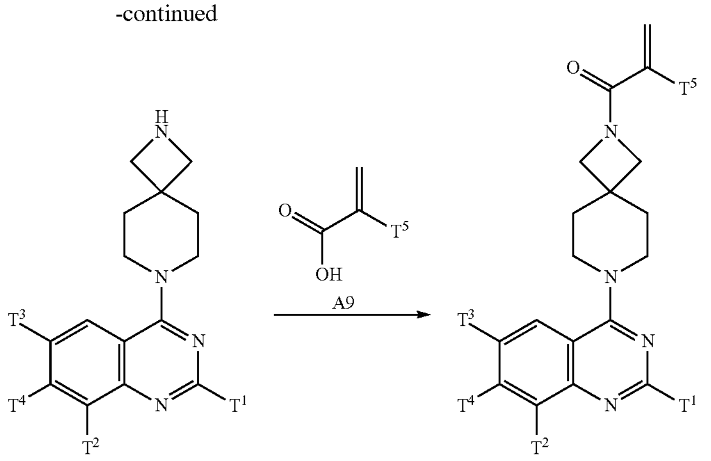

A8 A10

In an embodiment of the compound of general formula (1), the preparation may be performed according to general reaction scheme 1, wherein T represents H, F, Cl or I, $T^1$ represents $R^5$, $R^{5a}$ or $R^{5b}$, $T^2$ represents $R^3$ or $R^{3a}$, $T^3$ represents $R^1$ or $R^{1a}$, $T^4$ represents $R^2$ or $R^{2a}$, and $T^5$ represents $R^4$ or $R^{4a}$; $R^1$, $R^{1a}$, $R^2$, $R^{2a}$, $R^3$, $R^{3a}$, $R^4$, $R^{4a}$, $R^5$, $R^{5a}$ and $R^{5b}$ are defined as above, PG represents a protecting group, and X represents boric acid, a borate or a trifluoroborate. As shown in general reaction scheme 1, compound A1 (synthesized according to WO2018/143315) is reacted with compound A2 under basic conditions to give compound A3, compound A3 is reacted with $T^1H$ under basic conditions to give compound A4, compound A4 is reacted with $T^2H$ under basic conditions to give compound A5; when T=I, compound A5 and $T^3X$ are subjected to a coupling reaction to give compound A6, and compound A6 and $T^4X$ are subjected to another coupling reaction to give compound A7; when T=H, F or Cl, compound A5 and $T^4X$ are subjected to another coupling reaction to directly give compound A7; the protecting group is removed from compound A7 to give compound A8, and compound A8 is reacted with compound A9 to give the target compound A10.

Further Forms of Compounds

"Pharmaceutically acceptable" herein refers to a substance, such as a carrier or diluent, which will not cause a compound to lose its biological activity or properties. It is relatively non-toxic; for example, when an individual is given a substance, it will not cause unwanted biological effects or interact with any component contained therein in a deleterious manner.

The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by reacting the compounds of general formulas (1) through (3) with acids, e.g. inorganic acids such as hydrochloric acid, hydrobromic acid, hydrofluoric acid, sulfuric acid, phosphoric acid and nitric acid, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid and p-toluenesulfonic acid, and acidic amino acids such as aspartic acid and glutamic acid.

It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compounds of general formulas (1) through (3) are conveniently prepared or formed according to the methods described herein. For example, the hydrates of the compounds of general formulas (1) through (3) are conveniently prepared by recrystallization from a mixed solvent of water/organic solvent, wherein the organic solvent used includes, but is not limited to, tetrahydrofuran, acetone, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compounds of general formulas (1) through (3) are prepared into different forms, including but not limited to amorphous, pulverized and nanoparticle forms. In addition, the compound of general formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compounds of general formulas (1) through (3) have axial chiralities and/or chiral centers and thus occur in the form of a racemate, racemic mixture, single enantiomer, diastereomeric compound and single diastereomer. Each of these axial chiralities will independently produce two optical isomers, and all possible optical isomers, diastereomeric mixtures and pure or partially pure compounds are included within the scope of the present invention. The present invention is meant to include all such isomeric forms of these compounds.

Terminology

Unless otherwise stated, the terms used in the present application, including those in the specification and claims, are defined as follows. It must be noted that in the specification and the appended claims, the singular forms "a" and "an" include plural meanings unless the context clearly indicates otherwise. Unless otherwise stated, conventional methods of mass spectrometry, nuclear magnetic resonance spectroscopy, HPLC, protein chemistry, biochemistry, recombinant DNA technology and pharmacology are used. In the present application, "or" or "and" is used to mean "and/or" unless otherwise stated.

Unless otherwise specified, "alkyl" refers to a saturated aliphatic hydrocarbon group, including linear and branched groups containing 1 to 6 carbon atoms. Lower alkyl containing 1 to 4 carbon atoms, such as methyl, ethyl, propyl, 2-propyl, n-butyl, isobutyl or tert-butyl, is preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH$, $^{i}Pr$, $^{n}Pr$, $^{i}Bu$, $^{n}Bu$ and $^{t}Bu$.

Unless otherwise specified, "alkenyl" refers to an unsaturated aliphatic hydrocarbon group containing carbon-carbon double bonds, including linear and branched groups containing 1 to 6 carbon atoms. Lower alkenyl containing 1 to 4 carbon atoms, such as vinyl, 1-propenyl, 1-butenyl or 2-methylpropenyl, is preferred.

Unless otherwise specified, "alkynyl" refers to an unsaturated aliphatic hydrocarbon group containing carbon-carbon triple bonds, including linear and branched groups containing 1 to 6 carbon atoms. Lower alkenyl containing 1 to 4 carbon atoms, such as ethynyl, 1-propynyl or 1-butynyl, is preferred.

Unless otherwise specified, "cycloalkyl" refers to a 3- to 6-membered all-carbon monocyclic aliphatic hydrocarbon group, wherein one or more of the rings may contain one or more double bonds, but none of them has a fully conjugated π-electron system. For example, cyclopropyl, cyclobutyl, cyclopentyl, cyclohexane, and cyclohexadiene.

Unless otherwise specified, "alkoxy" refers to an alkyl group that bonds to the rest of the molecule through an ether oxygen atom. Representative alkoxy groups are ones having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}PrO$, $^{n-}PrO$, $^{i-}BuO$, $^{n-}BuO$ and $^{t-}BuO$.

Unless otherwise specified, "heteroaryl" refers to an aromatic group containing one or more heteroatoms (O, S or N) and it is monocyclic or polycyclic; for example, a monocyclic heteroaryl ring fuses with one or more carbocyclic aromatic groups or other monocyclic heterocyclyl groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, tetrazolyl, furyl, thienyl, isoxazolyl, thiazolyl, oxazolyl, isothiazolyl, pyrrolyl, indolyl, benzimidazolyl, benzofuryl, benzothiazolyl, benzothienyl, benzoxazolyl, benzopyridyl, and pyrrolopyrimidinyl.

Unless otherwise specified, "heterocycloalkyl" refers to a saturated or partially unsaturated ring system group containing one or more heteroatoms (O, S or N), wherein the nitrogen and sulfur atoms are optionally oxidized, and the nitrogen atom is optionally quaternized as a ring atom.

Unless otherwise stated, the "heterocycloalkyl" ring system may be a monocyclic, bicyclic, spiro or polycyclic ring system. "Heterocycloalkyl" may link to the rest of the molecule through one or more ring carbons or heteroatoms. Examples of "heterocycloalkyl" include, but are not limited to, pyrrolidine, piperidine, N-methylpiperidine, tetrahydroimidazole, pyrazolidine, butyrolactam, valerolactam, imidazolidinone, hydantoin, dioxolane, phthalimide, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, 2-azaspiro[3.3]heptane, etc.

Unless otherwise specified, "halogen" (or halo) refers to fluorine, chlorine, bromine, or iodine. The term "halo" (or "halogenated") before a group name indicates that the group is partially or fully halogenated, that is, substituted in any combination by F, Cl, Br or I, preferably by F or Cl.

Specific Pharmaceutical and Medical Terminology

The term "acceptable", as used herein, means that a formula component or an active ingredient does not unduly adversely affect a general therapeutic target's health.

The terms "treatment," "treatment course," or "therapy", as used herein, include alleviating, inhibiting, or ameliorating a symptom or condition of a disease; inhibiting the development of complications; ameliorating or preventing underlying metabolic syndrome; inhibiting the development of the disease or symptom, e.g., controlling the progression of the disease or condition; alleviating the disease or symptom; causing the disease or symptom to subside; alleviating a complication caused by the disease or symptom, or preventing or treating a sign caused by the disease or symptom. As used herein, a compound or pharmaceutical composition, when administered, can ameliorate a disease, symptom, or condition, particularly meaning ameliorating the severity, delaying the onset, slowing the progression, or reducing the duration of the disease. Fixed or temporary administration, or continuous or intermittent administration, may be attributed to or associated with the administration.

The "active ingredient" refers to compounds of general formulas (1) through (3), and pharmaceutically acceptable inorganic or organic salts of the compounds of general formulas (1) through (3). The compounds of the present invention may contain one or more asymmetric centers (axial chirality) and thus occur in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), is capable of inducing a desired pharmacological and/or physiological response by local and/or systemic action.

The term "administered, administering or administration" refers herein to the direct administration of the compound or composition, or the administration of a prodrug, derivative, analog or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range±10%, 5%, 1%, or 0.5%. Alternatively, the term "about" indicates that the actual value falls within the acceptable standard error of a mean, as considered by those skilled in the art. All ranges, quantities, values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be construed as the significant digits indicated or the numerical value obtained using conventional rounding rules.

Unless otherwise defined in the specification, the scientific and technical terms used herein have the same meaning as commonly understood by those skilled in the art. Furthermore, the singular nouns used in the specification encompass their plural forms, unless contradicted by context; the plural nouns used also encompass their singular forms.

Therapeutic Use

The present invention provides a method for using the compound or pharmaceutical composition of the present invention to treat diseases, including but not limited to conditions involving G12C K-Ras, G12C H-Ras and/or G12C N-Ras mutations (e.g., cancer).

In some embodiments, a method for treating cancer is provided, the method comprising administering to an individual in need thereof an effective amount of a pharmaceutical composition of any of the aforementioned compounds of structural general formulas (1) through (3) protected. In some embodiments, the cancer is mediated by K-Ras, H-Ras and/or G12C N-Ras mutations. In other embodiments, the cancer is lung cancer, pancreatic cancer, colon cancer, MYH-associated polyposis, or colorectal cancer.

Route of Administration

The compound and the pharmaceutically acceptable salt thereof of the present invention can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers.

Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances. Besides such inert diluents, the composition may also include adjuvants, such as wetting agents, emulsifiers, suspending agents, sweeteners, flavoring agents, and perfuming agents.

Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds.

When the pharmaceutical composition is used, a safe and effective amount of the compound of the present invention is administered to a mammal (such as a human) to be treated, wherein the administration dose is a pharmaceutically effective administration dose. For a human weighing 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, 1H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio.

The present invention uses the following abbreviations: $CD_3OD$ for deuterated methanol; MeCN for acetonitrile; DCM for dichloromethane; DIPEA for diisopropylethylamine; dioxane for 1,4-dioxane; DMF for dimethylformamide; $K_3PO_4$ for potassium phosphate; min for minute; MS for mass spectroscopy; NaH for sodium hydride; NMR for nuclear magnetic resonance; $Pd_2(dba)_3$ for tris(dibenzylideneacetone)dipalladium; $Pd(dppf)Cl_2$ for [1,1'-bis(diphenylphosphino)ferrocene]palladium dichloride; TFA ($CF_3COOH$) for trifluoroacetic acid; TLC for thin layer chromatography; THF for tetrahydrofuran; and Xantphos for 4,5-bis(diphenylphosphane)-9,9-dimethylxanthene.

BRIEF DESCRIPTION OF THE DRAWING

FIG. 1 shows the inhibition of the phosphorylated ERK (pERK) level in cells by compounds.

DETAILED DESCRIPTION

Example 1: Synthesis of 1-(7-(6-Cyclopropyl-8-ethoxy-2-ol-(2-methoxyethyl)piperidin-4-yl)oxy)-7-(5-methyl-1H-indazol-4-yl)quinazolin-4-yl)-2,7-diazaspiro[3.5]nonan-2-yl)-2-fluoroprop-2-en-1-one (Compound 1)

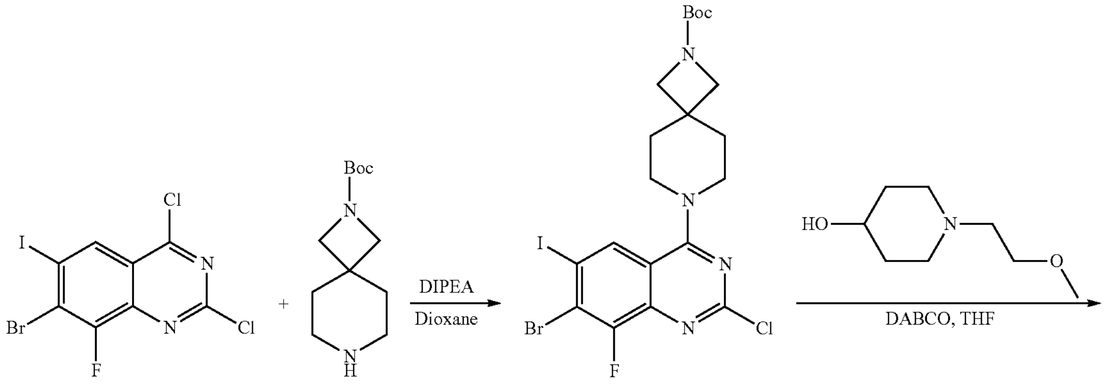

1-1 1-2 1-3

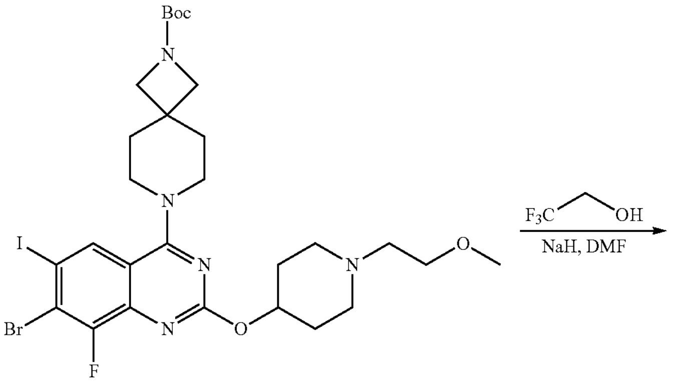

1-4

-continued
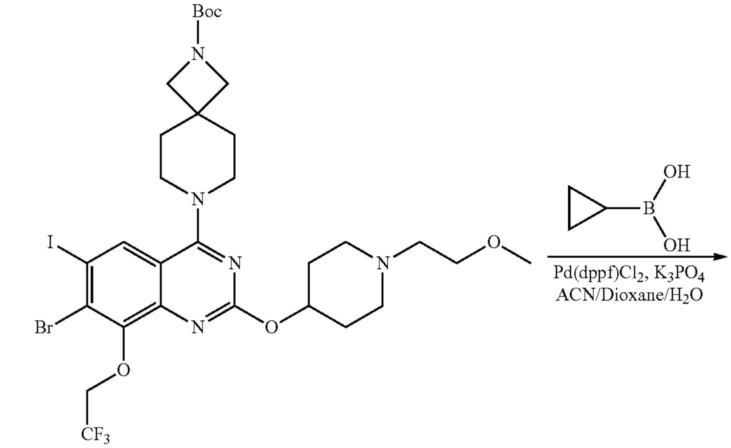
1-5
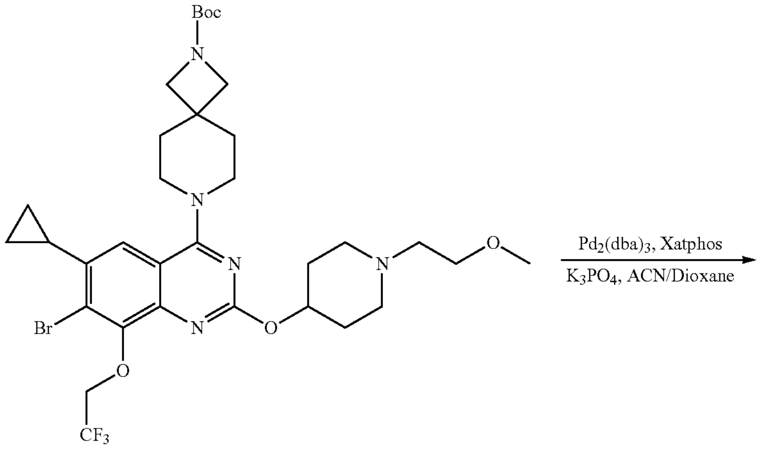
1-6
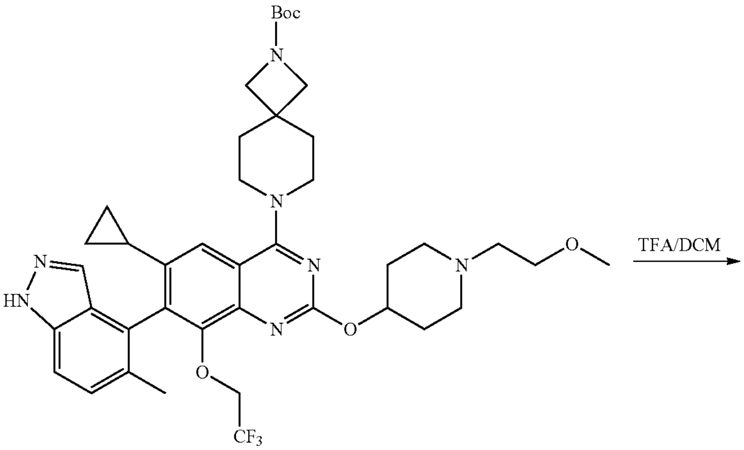
1-7

-continued

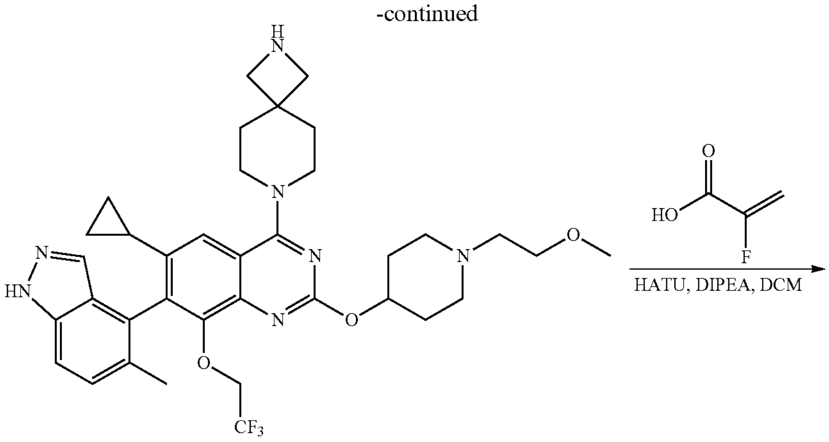

1-8

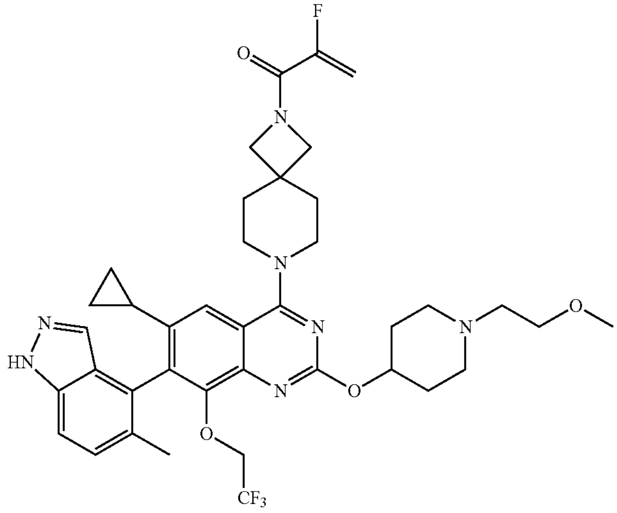

1

Step 1: Synthesis of Compound 1-3

Compound 1-1 (5.5 g, 13.1 mmol) was suspended in dioxane (80 mL). DIPEA (10.1 g, 78.6 mmol) was added under ice bath, followed by 1-2 (3.0 g, 13.1 mmol). The mixture was stirred for 30 min, and stirred at room temperature for 1 h. The reaction was completed as detected by TLC. Water was added, followed by EA for extraction. The organic phase was dried and concentrated, and the residue was slurried with EA to obtain a yellow solid 1-3 (4.5 g, 56% yield).

$^1$H NMR (400 MHz, DMSO-$d_6$) δ: 8.26 (d, J=1.5 Hz, 1H), 3.79 (s, 4H), 3.65 (s, 4H), 1.86 (t, J=5.3 Hz, 4H), 1.39 (s, 9H); MS(ESI): MS (ESI): 611.2 $[M+1]^+$.

Step 2: Synthesis of Compound 1-4

Compound 1-3 (4.5 g, 7.4 mmol) was dissolved in a mixed solution of DMF (40 mL) and THF (40 mL). 1-(2-Methoxyethyl)-4-hydroxypiperidine (2.4 g, 14.8 mmol) and DABCO (0.2 g, 1.5 mmol) were added. The mixture was stirred at room temperature overnight. After the reaction was completed, water was added, followed by EA for extraction. The organic phase was dried and concentrated, and the residue was subjected to column chromatography to obtain compound 1-4 (4.1 g, 76% yield).

$^1$H NMR (400 MHz, DMSO-$d_6$) δ: 8.14 (s, 1H), 4.99 (ddd, J=11.7, 8.5, 3.6 Hz, 1H), 3.66 (s, 9H), 3.44 (t, J=5.8 Hz, 2H), 3.24 (s, 3H), 3.17 (d, J=5.2 Hz, 1H), 2.77 (dt, J=9.5, 8.8 Hz, 2H), 2.26 (t, J=9.8 Hz, 2H), 2.00 (d, J=12.0 Hz, 2H), 1.84 (d, J=4.3 Hz, 4H), 1.74-1.61 (m, 2H), 1.39 (s, 9H); MS(ESI): 734.2 $[M+1]^+$.

Step 3: Synthesis of Compound 1-5

Trifluoroethanol (0.9 g, 8.4 mmol) was dissolved in anhydrous DMF (10 mL). NaH was added under ice bath. The mixture was stirred at room temperature for 5 min to obtain sodium trifluoroethoxide. Compound 1-4 (4.1 g, 5.6 mmol) was dissolved in anhydrous THF (40 mL). The solution of sodium trifluoroethoxide in DMF prepared above was added. The mixture was stirred at room temperature overnight. After the reaction was completed, water was added, followed by EA for extraction. The organic phase was dried and concentrated, and the residue was subjected to column chromatography to obtain compound 1-5 (4.5 g, 99% yield). MS (ESI): 814.2 $[M+1]^+$.

Step 4: Synthesis of Compound 1-6

To a single-necked flask were added compound 1-5 (4.1 g, 5.5 mmol), cyclopropylboronic acid (0.5 g, 6.1 mmol), Pd(dppf)$Cl_2$ (0.9 g, 1.1 mmol) and $K_3PO_4$ (0.4 g, 1.7 mmol), followed sequentially by MeCN (40 mL), dioxane (40 mL) and $H_2O$ (16.5 mL). The mixture was stirred under nitrogen at 100° C. for 5 h. After the reaction was completed, the mixture was subjected to column chromatography to obtain compound 1-6 (2.5 g, 62% yield). MS (ESI): 728.3 $[M+1]^+$.

Step 5: Synthesis of Compound 1-7

To a single-necked flask were added compound 1-6 (2.5 g, 3.4 mmol), 5-methyl-1H-indazole-4-boronic acid (0.9 g, 5.1 mmol), $Pd_2(dba)_3$ (0.3 g, 0.4 mmol), Xatphos (0.3 g, 0.7 mmol) and $K_3PO_4$ (2.2 g, 10.2 mmol), followed by dioxane (40 mL) and $H_2O$ (4 mL). The mixture was stirred under nitrogen at 120° C. overnight. After the reaction was completed, the mixture was subjected to column chromatography to obtain compound 1-7 (1 g, 38% yield). MS (ESI): 780.4 $[M+1]^+$.

Step 6: Synthesis of Compound 1-8

Compound 1-7 (1 g, 1.3 mmol) was dissolved in DCM (15 mL). TFA (5 mL) was added. The mixture was stirred at room temperature for 2 h. After the reaction was completed, the mixture was concentrated, basified with saturated sodium carbonate, and extracted with EA. The organic phase was dried and concentrated to obtain compound 1-8 (0.9 g, 99% yield). MS(ESI): 680.4 $[M+1]^+$.

Step 7: Synthesis of Compound 1

Compound 1-8 (150 mg, 0.2 mmol) and 2-fluoroacrylic acid (20 mg, 0.22 mmol) were dissolved in DCM (15 mL). DIPEA (52 mg, 0.4 mmol) and HATU (114 mg, 0.3 mmol) were added under ice bath. The mixture was stirred overnight. After the reaction was completed, the reaction mixture was washed with saturated brine. The organic phase was dried and concentrated, and the residue was subjected to column chromatography to obtain compound 1 (30 mg, 20% yield).

$^1$H NMR (400 MHz, $CD_3OD$) δ: 7.47-7.37 (m, 2H), 7.30 (d, J=8.6 Hz, 1H), 7.24 (s, 1H), 5.52 (d, J=3.4 Hz, 0.5H), 5.40 (d, J=3.4 Hz, 0.5H), 5.15 (d, J=3.4 Hz, 0.5H), 5.11 (d, J=3.4 Hz, 0.5H), 4.54 (dq, J=17.7, 8.8 Hz, 1H), 4.23-4.12 (m, 3H), 3.83 (s, 2H), 3.73-3.59 (m, 4H), 3.54 (t, J=5.2 Hz, 2H), 3.28 (s, 3H), 3.10 (dd, J=10.1, 6.2 Hz, 2H), 2.88 (s, 2H), 2.85-2.72 (m, 2H), 2.13 (d, J=26.2 Hz, 5H), 1.97 (dd, J=11.9, 6.8 Hz, 6H), 1.36 (dt, J=14.0, 6.6 Hz, 1H), 1.27-1.17 (m, 5H); MS (ESI): 752.4 $[M+1]^+$.

Example 2-341: Synthesis of Compound 2-341

The target compound 2-341 was obtained using different starting materials according to a synthesis method similar to that in Example 1.

TABLE 1

| Compound | Compound structure | $[M + H]^+$ |
| --- | --- | --- |
| 2 | 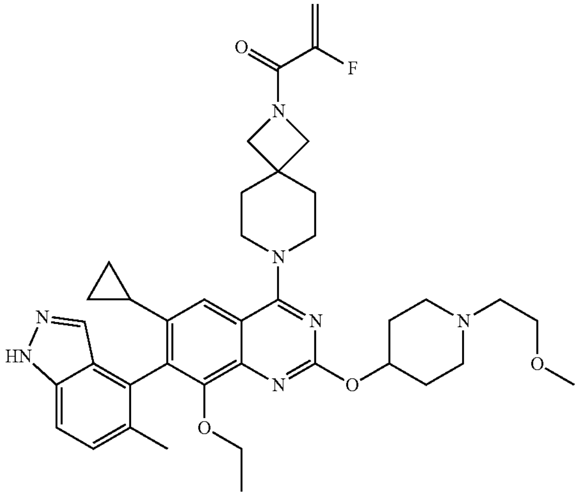 [SMILES: C=C(F)C(=O)N1CC2(CCN(c3nc(OC4CCN(CCOC)CC4)nc4c(OCC)c(-c5c(C)ccc6[nH]ncc56)c(C5CC5)cc34)CC2)C1] | 698.4 |
| 3 | 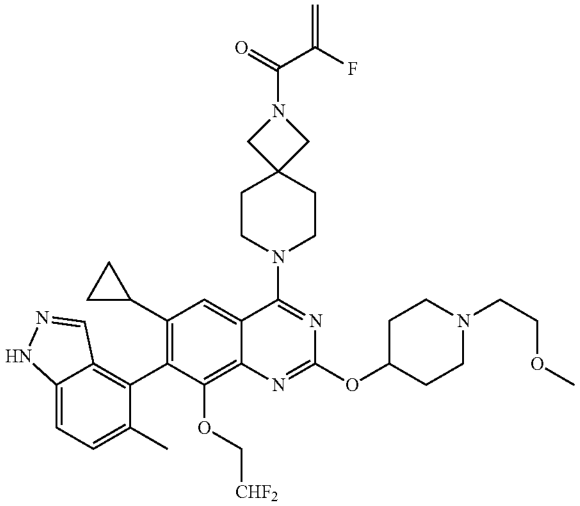 | 734.4 |

TABLE 1-continued
| Compound | Compound structure | [M + H]+ |
|---|---|---|
| 4 | 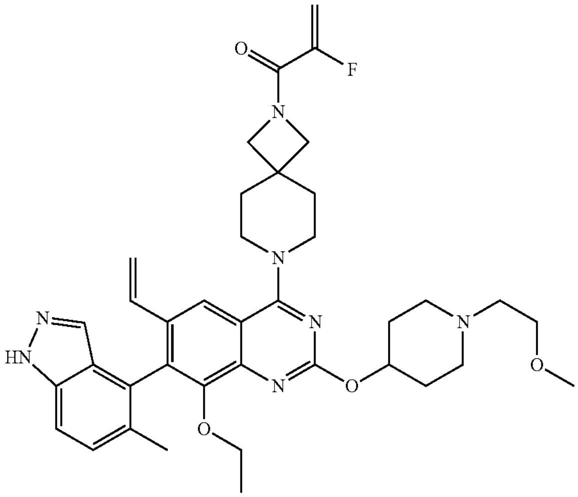 [SMILES: C=Cc1cc2c(N3CCC4(CC3)CN(C(=O)C(=C)F)C4)nc(OC3CCN(CCOC)CC3)nc2c(OCC)c1-c1c(C)ccc2[nH]ncc12] | 684.4 |
| 5 | 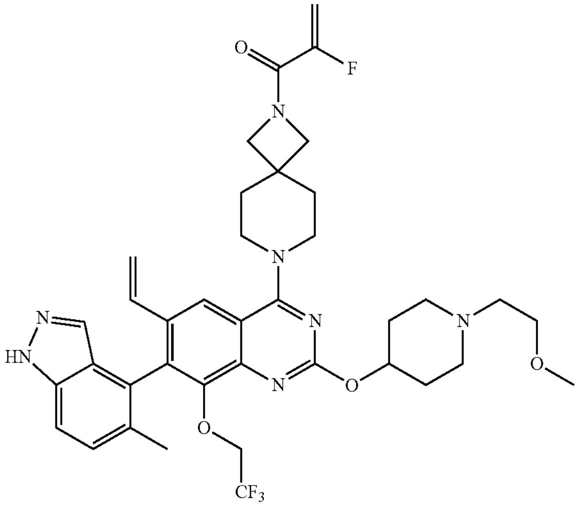 [SMILES: C=Cc1cc2c(N3CCC4(CC3)CN(C(=O)C(=C)F)C4)nc(OC3CCN(CCOC)CC3)nc2c(OCC(F)(F)F)c1-c1c(C)ccc2[nH]ncc12] | 738.3 |
| 6 | 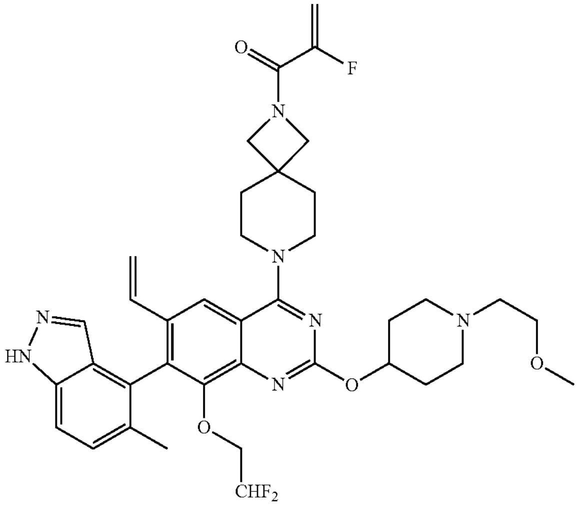 [SMILES: C=Cc1cc2c(N3CCC4(CC3)CN(C(=O)C(=C)F)C4)nc(OC3CCN(CCOC)CC3)nc2c(OCC(F)F)c1-c1c(C)ccc2[nH]ncc12] | 792.4 |

TABLE 1-continued
| Compound | Compound structure | [M + H]$^+$ |
| --- | --- | --- |
| 7 | 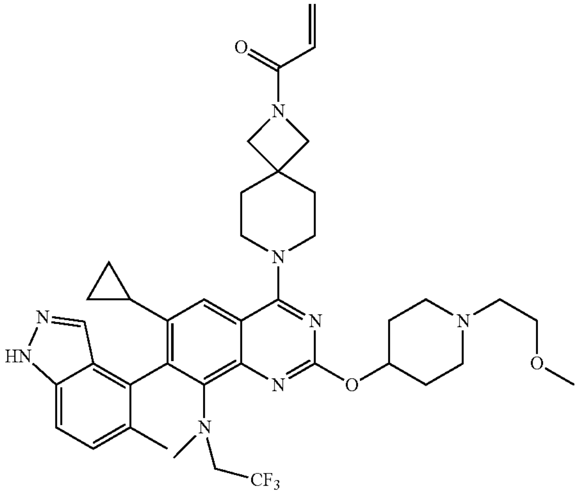 [SMILES: C=CC(=O)N1CC2(CCN(c3nc(OC4CCN(CCOC)CC4)nc4c(N(C)CC(F)(F)F)c(-c5c(C)ccc6[nH]ncc56)c(C5CC5)cc34)CC2)C1] | 747.4 |
| 8 | 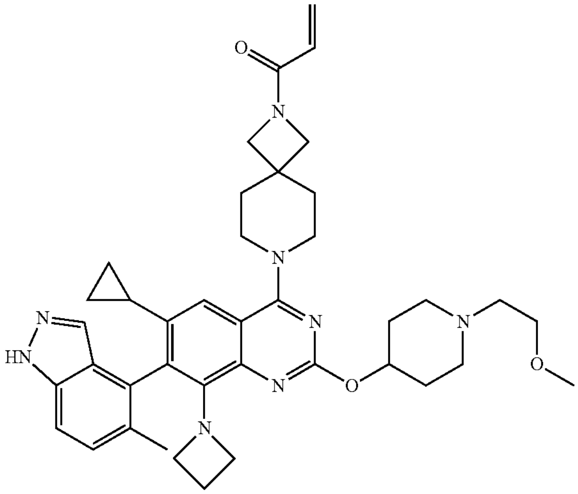 [SMILES: C=CC(=O)N1CC2(CCN(c3nc(OC4CCN(CCOC)CC4)nc4c(N5CCC5)c(-c5c(C)ccc6[nH]ncc56)c(C5CC5)cc34)CC2)C1] | 691.4 |
| 9 | 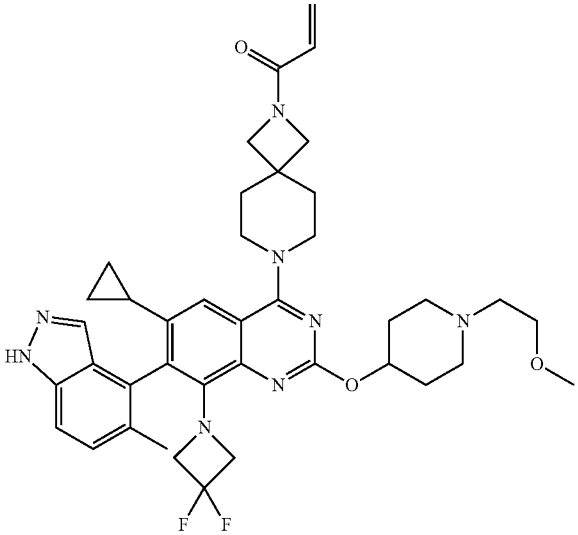 [SMILES: C=CC(=O)N1CC2(CCN(c3nc(OC4CCN(CCOC)CC4)nc4c(N5CC(F)(F)C5)c(-c5c(C)ccc6[nH]ncc56)c(C5CC5)cc34)CC2)C1] | 727.4 |

TABLE 1-continued
| Compound | Compound structure | [M + H]+ |
|---|---|---|
| 10 | 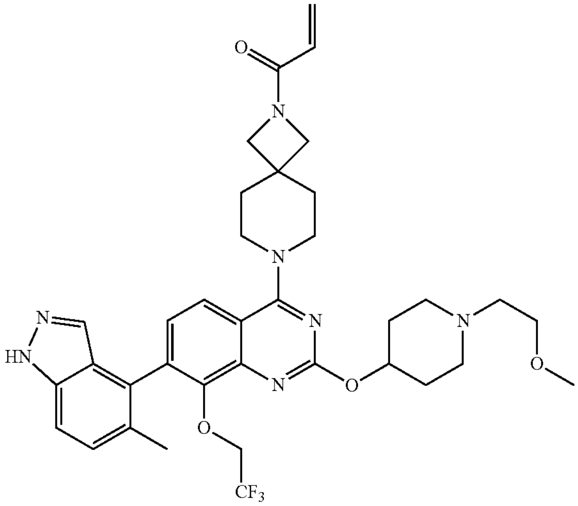 [SMILES: C=CC(=O)N1CC2(CCN(c3nc(OC4CCN(CCOC)CC4)nc4c(OCC(F)(F)F)c(-c5c(C)ccc6[nH]ncc56)ccc34)CC2)C1] | 694.3 |
| 11 | 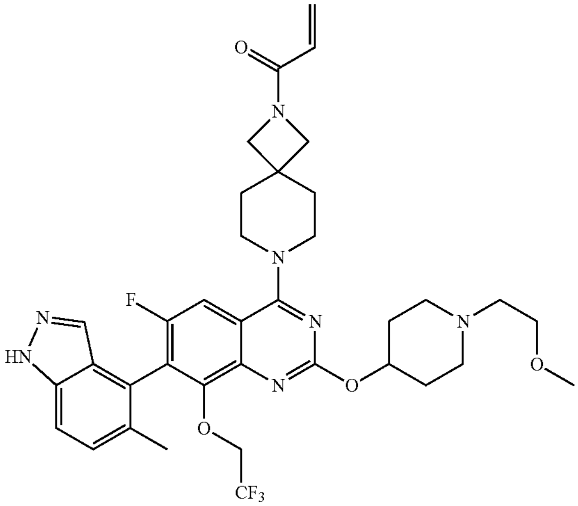 | 712.3 |
| 12 | 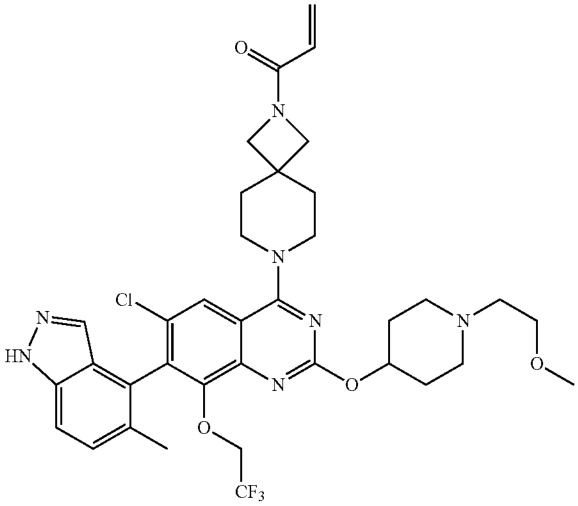 | 728.3 |

TABLE 1-continued
| Compound | Compound structure | [M + H]+ |
| --- | --- | --- |
| 13 | 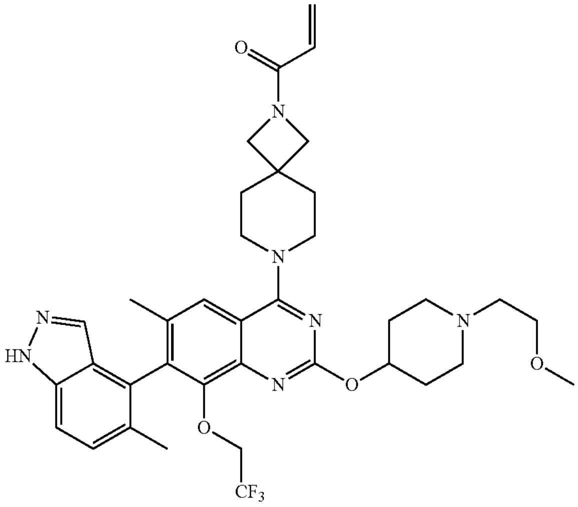 [SMILES: C=CC(=O)N1CC2(CCN(c3nc(OC4CCN(CCOC)CC4)nc4c(OCC(F)(F)F)c(-c5c(C)ccc6[nH]ncc56)c(C)cc34)CC2)C1] | 708.3 |
| 14 | 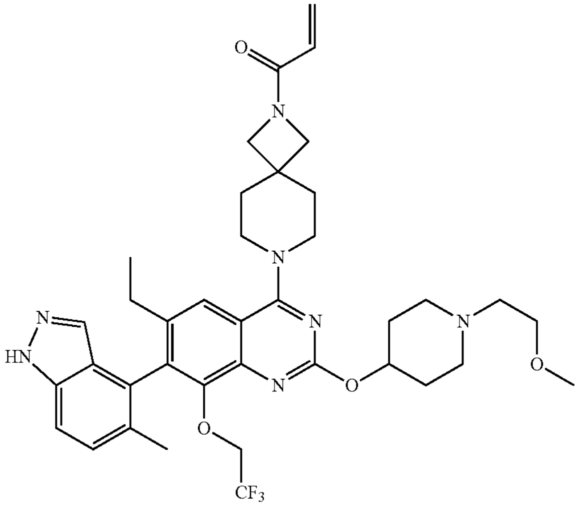 [SMILES: C=CC(=O)N1CC2(CCN(c3nc(OC4CCN(CCOC)CC4)nc4c(OCC(F)(F)F)c(-c5c(C)ccc6[nH]ncc56)c(CC)cc34)CC2)C1] | 722.4 |
| 15 | 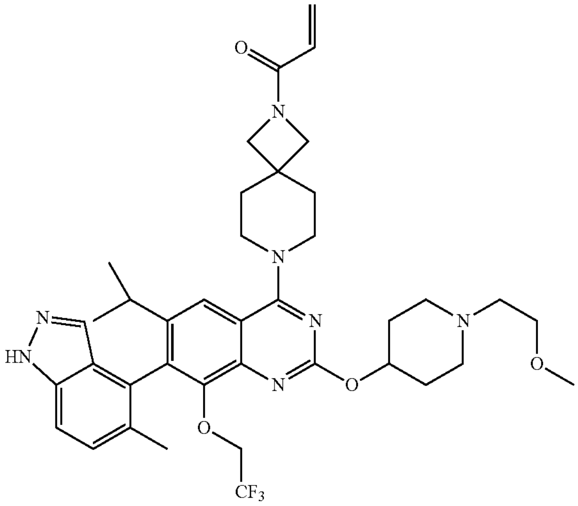 [SMILES: C=CC(=O)N1CC2(CCN(c3nc(OC4CCN(CCOC)CC4)nc4c(OCC(F)(F)F)c(-c5c(C)ccc6[nH]ncc56)c(C(C)C)cc34)CC2)C1] | 736.4 |

TABLE 1-continued
| Compound | Compound structure | [M + H]$^+$ |
|---|---|---|
| 16 | 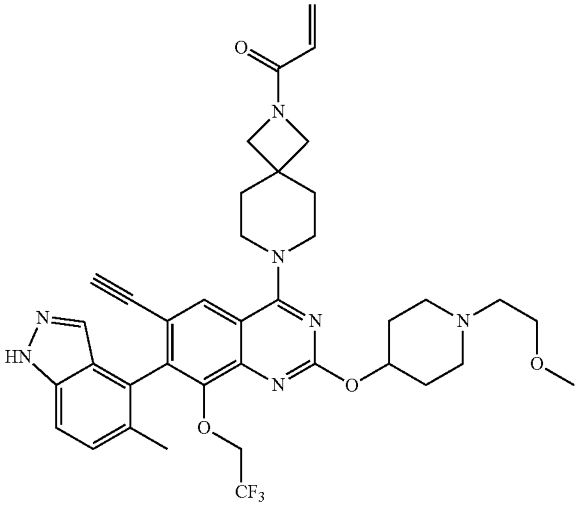 [SMILES: C#Cc1cc2c(N3CCC4(CC3)CN(C(=O)C=C)C4)nc(OC3CCN(CCOC)CC3)nc2c(OCC(F)(F)F)c1-c1c(C)ccc2[nH]ncc12] | 718.3 |
| 17 | 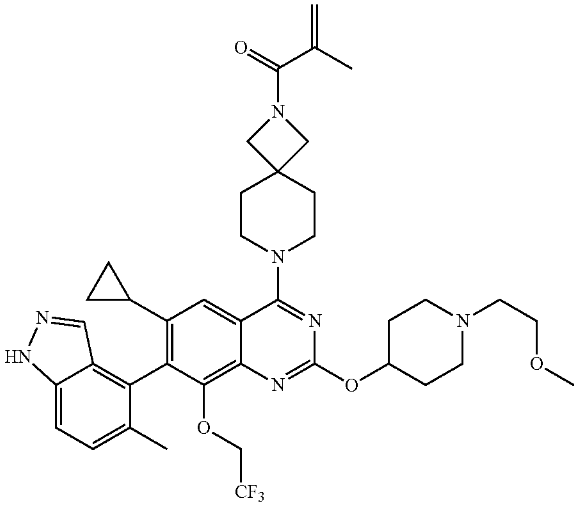 | 748.4 |
| 18 | 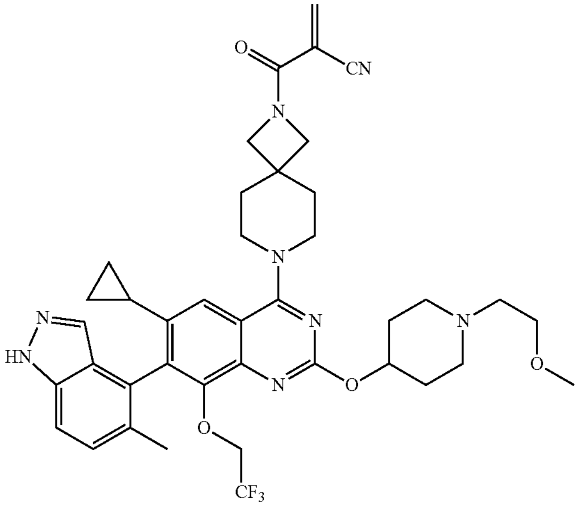 [SMILES: C=C(C(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1)C(F)(F)F] | 759.3 |

TABLE 1-continued
| Compound | Compound structure | [M + H]$^+$ |
|---|---|---|
| 19 | 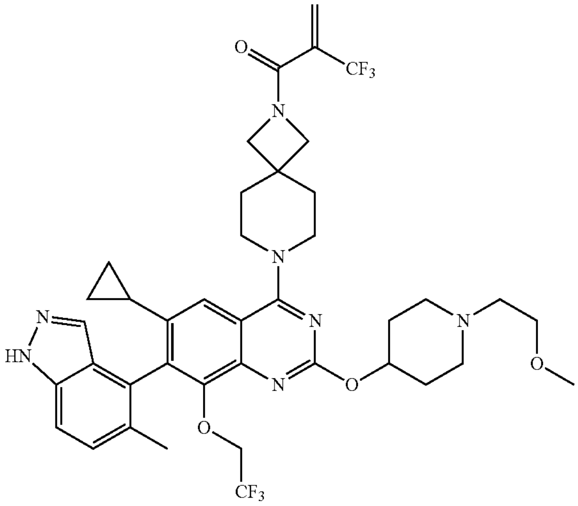 | 802.3 |
| 20 | 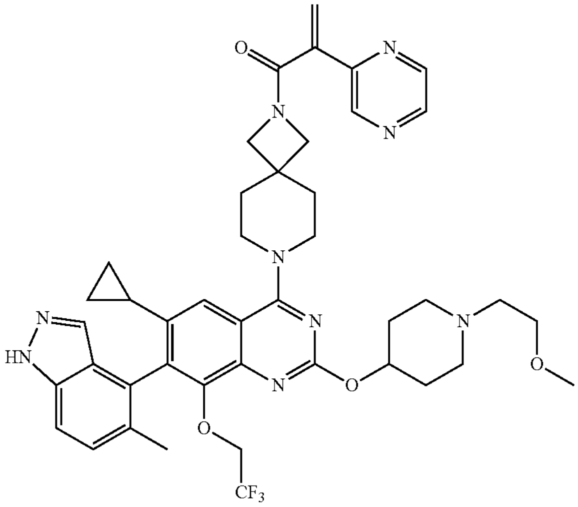 [SMILES: C=C(C(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1)c1cnccn1] | 812.4 |
| 21 | 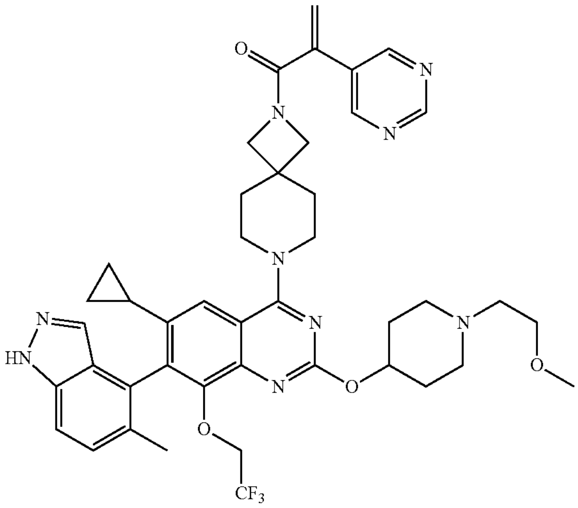 | 812.4 |

TABLE 1-continued
| Compound | Compound structure | [M + H]$^+$ |
| --- | --- | --- |
| 22 | 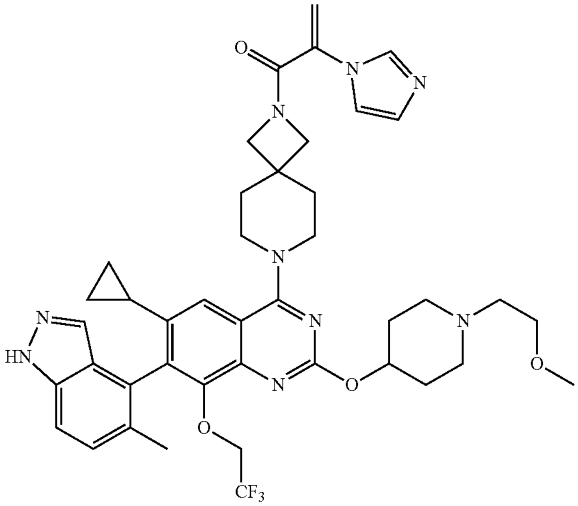 [SMILES: C=C(C(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1)n1cncn1] | 800.4 |
| 23 | 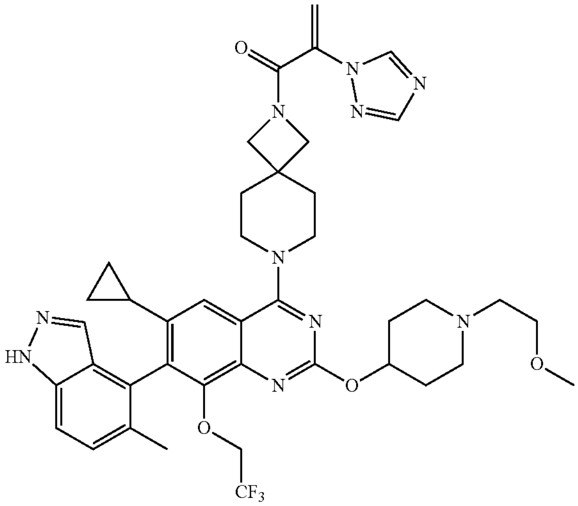 | 801.4 |
| 24 | 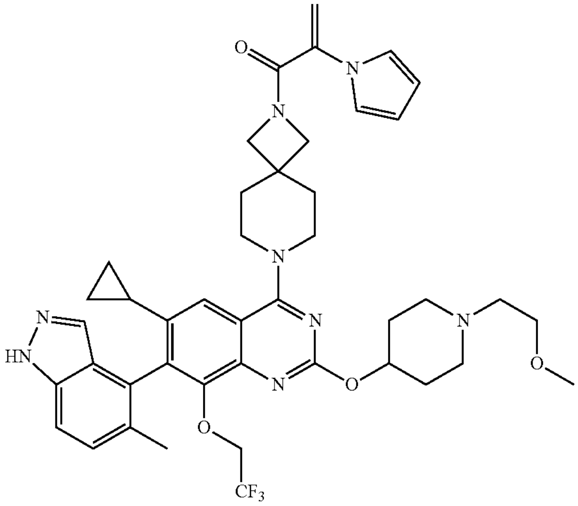 [SMILES: C=C(C(=O)N1CC2(CCN(c3nc(OC4CCN(CCOC)CC4)nc4c(OCC(F)(F)F)c(-c5c(C)ccc6[nH]ncc56)c(C5CC5)cc34)CC2)C1)n1cccc1] | 799.4 |

TABLE 1-continued
| Compound | Compound structure | [M + H]$^+$ |
| --- | --- | --- |
| 25 | 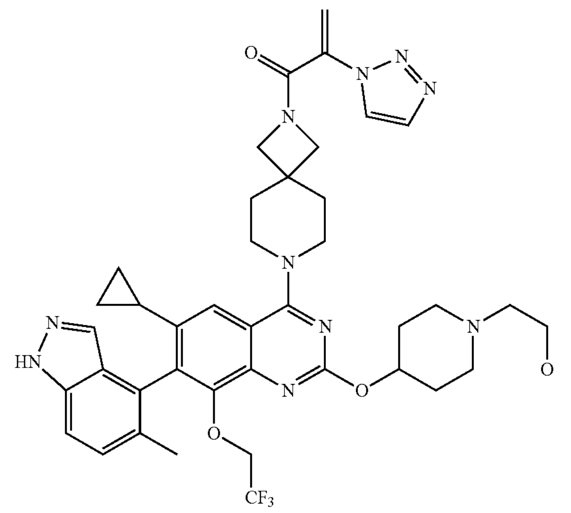 [SMILES: C=C(C(=O)N1CC2(CCN(c3nc(OC4CCN(CCO)CC4)nc4c(OCC(F)(F)F)c(-c5c(C)ccc6[nH]ncc56)c(C5CC5)cc34)CC2)C1)n1ccnn1] | 801.4 |
| 26 | 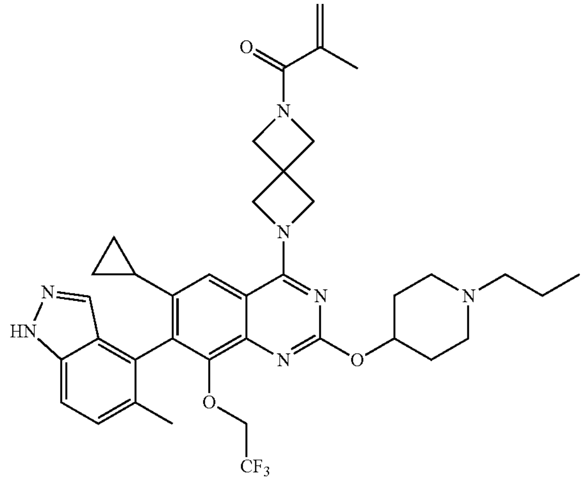 [SMILES: C=C(C)C(=O)N1CC2(C1)CN(c1nc(OC3CCN(CCC)CC3)nc3c(OCC(F)(F)F)c(-c4c(C)ccc5[nH]ncc45)c(C4CC4)cc13)C2] | 706.3 |
| 27 | 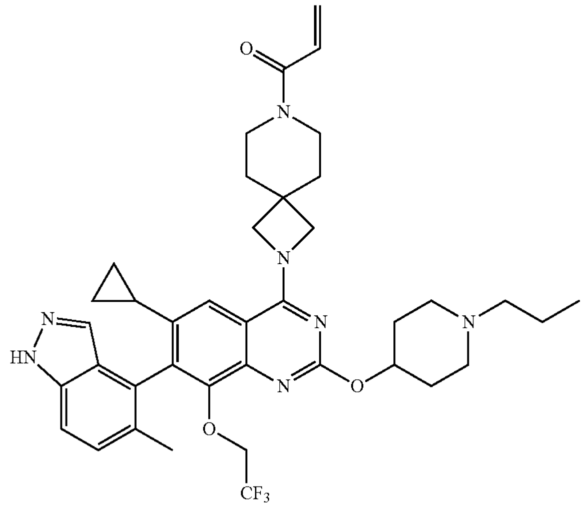 [SMILES: C=CC(=O)N1CCC2(CC1)CN(c1nc(OC3CCN(CCC)CC3)nc3c(OCC(F)(F)F)c(-c4c(C)ccc5[nH]ncc45)c(C4CC4)cc13)C2] | 734.4 |

TABLE 1-continued
| Compound | Compound structure | [M + H]+ |
| --- | --- | --- |
| 28 | 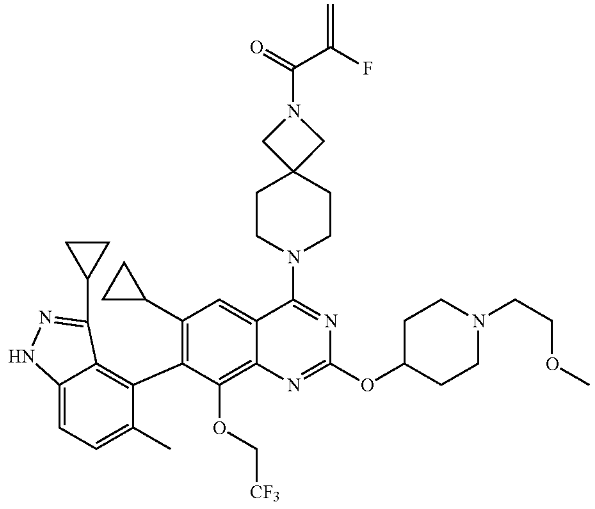 [SMILES: C=C(F)C(=O)N1CC2(CCN(c3nc(OC4CCN(CCOC)CC4)nc4c(OCC(F)(F)F)c(-c5c(C)ccc6[nH]nc(C7CC7)c56)c(C5CC5)cc34)CC2)C1] | 767.4 |
| 29 | 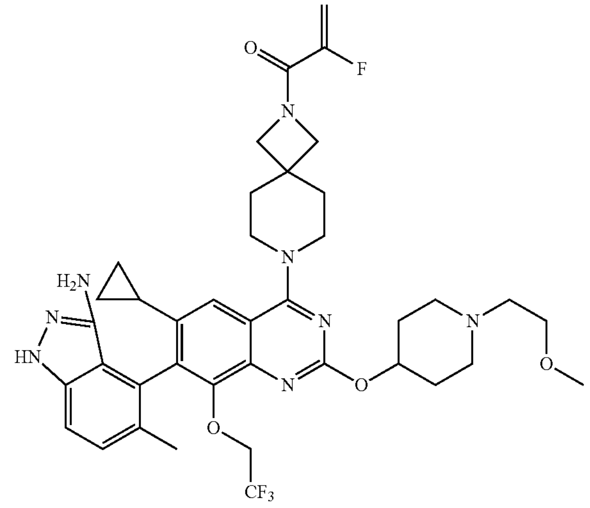 [SMILES: C=C(F)C(=O)N1CC2(CCN(c3nc(OC4CCN(CCOC)CC4)nc4c(OCC(F)(F)F)c(-c5c(C)ccc6[nH]nc(Cl)c56)c(C5CC5)cc34)CC2)C1] | 786.3 |
| 30 | 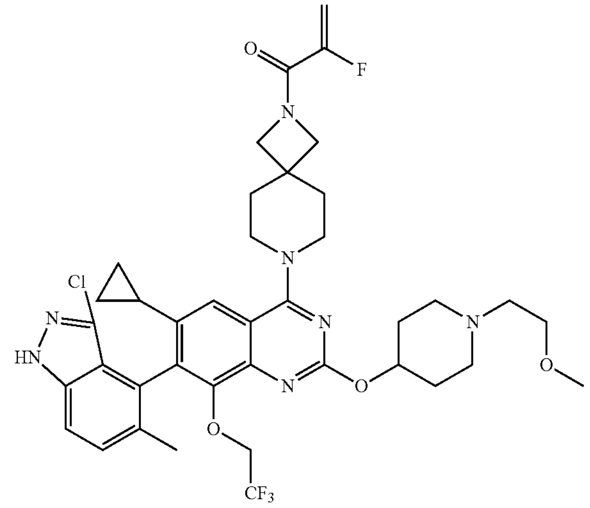 | 770.4 |

TABLE 1-continued
| Compound | Compound structure | [M + H]$^+$ |
|---|---|---|
| 31 | 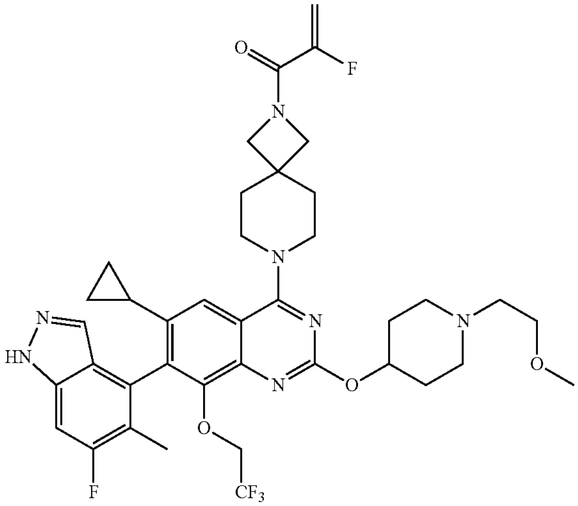 [SMILES: C=C(F)C(=O)N1CC2(CCN(c3nc(OC4CCN(CCOC)CC4)nc4c(OCC(F)(F)F)c(-c5c(C)c(F)cc6[nH]ncc56)c(C5CC5)cc34)CC2)C1] | 766.4 |
| 32 | 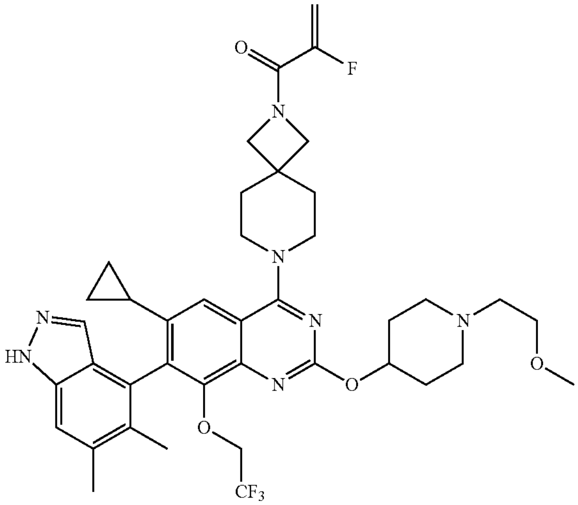 | 752.3 |
| 33 | 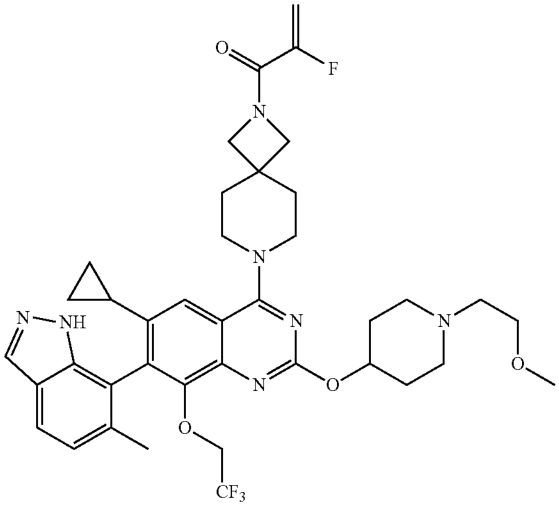 [SMILES: C=C(F)C(=O)N1CC2(CCN(c3nc(OC4CCN(CCOC)CC4)nc4c(OCC(F)(F)F)c(-c5c(C)ccc6cn[nH]c56)c(C5CC5)cc34)CC2)C1] | 756.3 |

TABLE 1-continued
| Compound | Compound structure | [M + H]$^+$ |
|---|---|---|
| 34 | 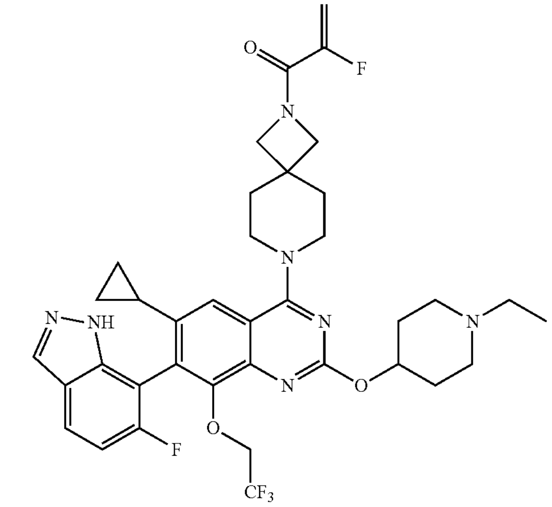 [SMILES: C=C(F)C(=O)N1CC2(CCN(c3nc(OC4CCN(CC)CC4)nc4c(OCC(F)(F)F)c(-c5c(F)ccc6cn[nH]c56)c(C5CC5)cc34)CC2)C1] | 756.3 |
| 35 | 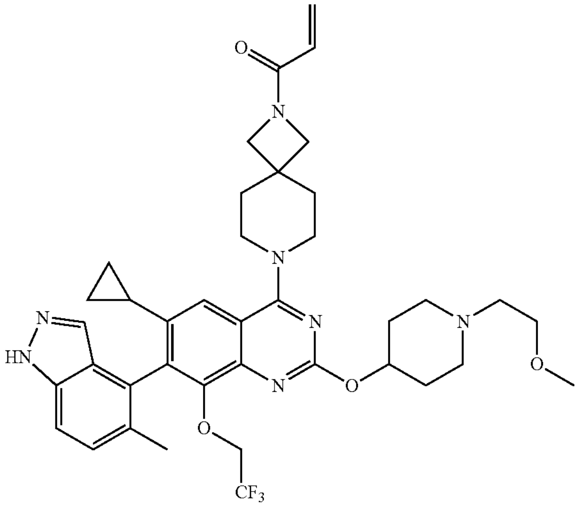 | 734.4 |
| 36 | 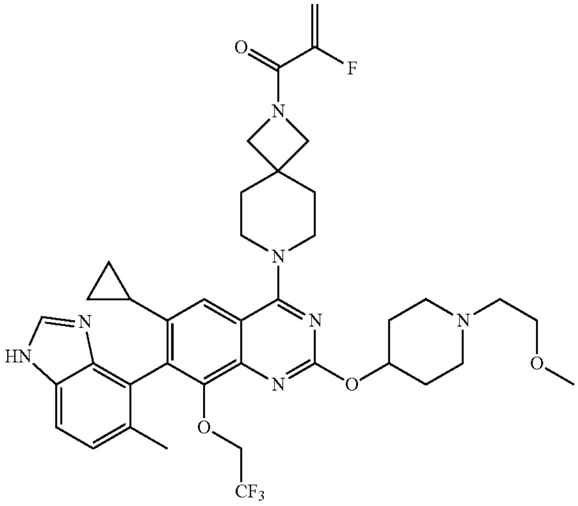 | 756.3 |

TABLE 1-continued
| Compound | Compound structure | [M + H]+ |
| --- | --- | --- |
| 37 | 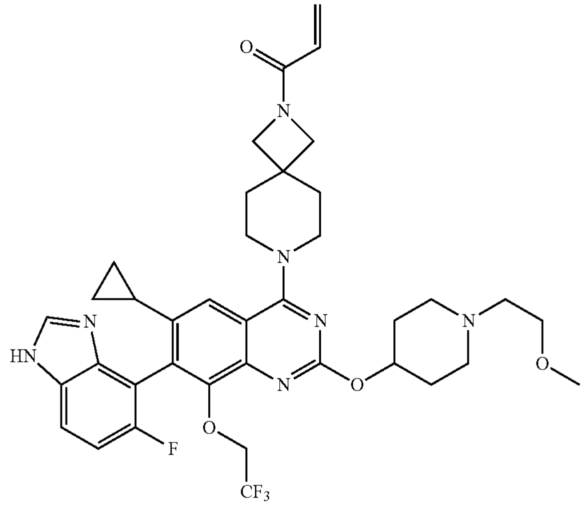 [SMILES: C=CC(=O)N1CC2(CCN(c3nc(OC4CCN(CCOC)CC4)nc4c(OCC(F)(F)F)c(-c5c(F)ccc6[nH]cnc56)c(C5CC5)cc34)CC2)C1] | 738.3 |
| 38 | 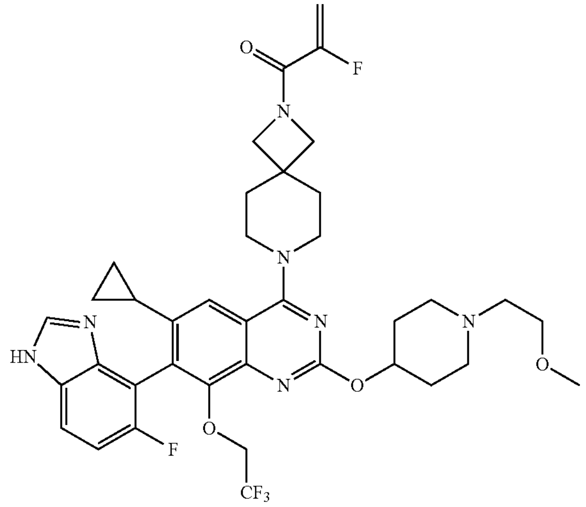 | 756.3 |
| 39 | 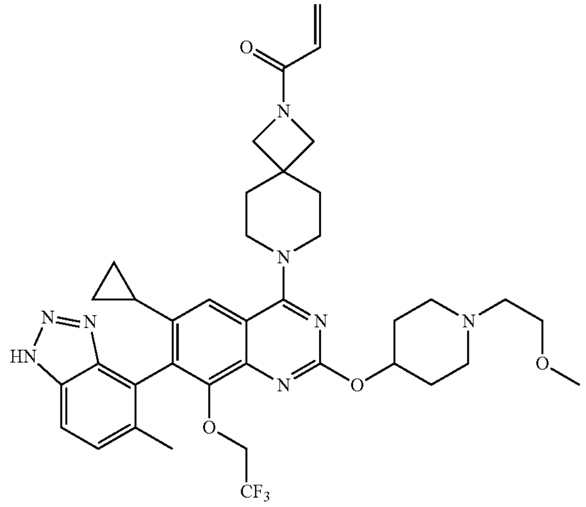 [SMILES: C=CC(=O)N1CC2(CCN(c3nc(OC4CCN(CCOC)CC4)nc4c(OCC(F)(F)F)c(-c5c(C)ccc6[nH]nnc56)c(C5CC5)cc34)CC2)C1] | 735.4 |

TABLE 1-continued
| Compound | Compound structure | [M + H]+ |
|---|---|---|
| 40 | 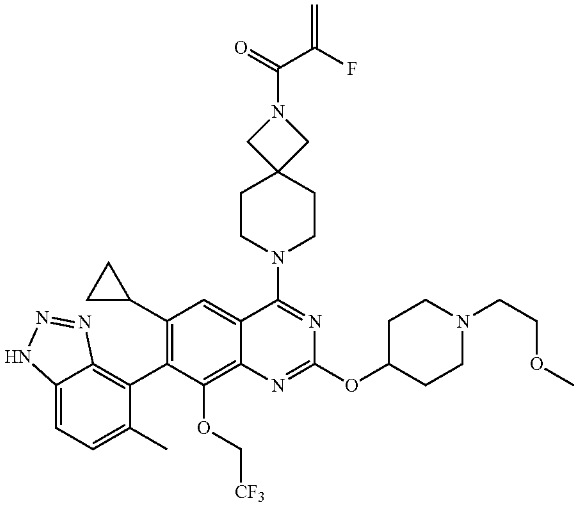 [SMILES: C=C(F)C(=O)N1CC2(CCN(c3nc(OC4CCN(CCOC)CC4)nc4c(OCC(F)(F)F)c(-c5c(C)ccc6[nH]nnc56)c(C5CC5)cc34)CC2)C1] | 753.3 |
| 41 | 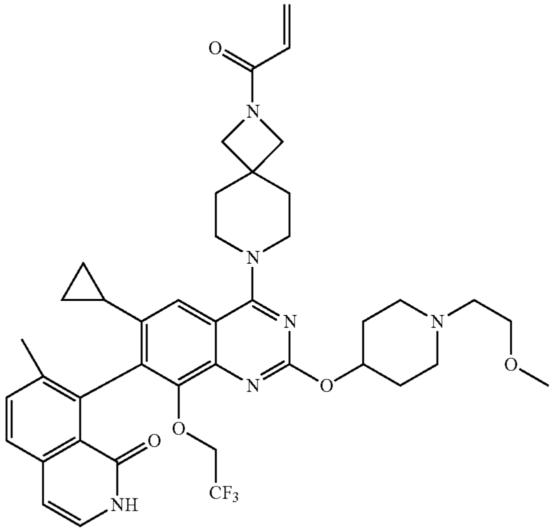 [SMILES: C=CC(=O)N1CC2(CCN(c3nc(OC4CCN(CCOC)CC4)nc4c(OCC(F)(F)F)c(-c5c(C)ccc6cc[nH]c(=O)c56)c(C5CC5)cc34)CC2)C1] | 761.3 |
| 42 | 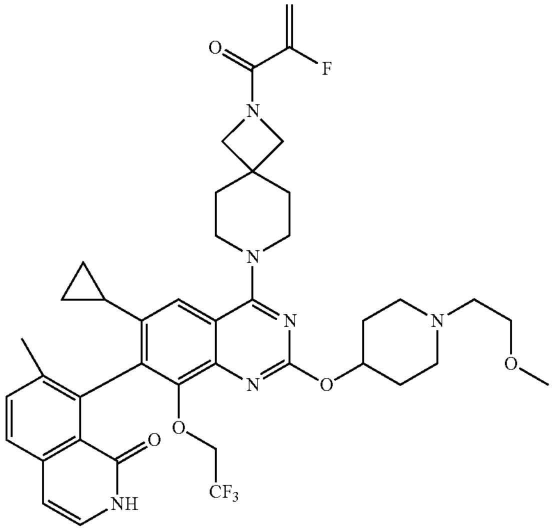 [SMILES: C=C(F)C(=O)N1CC2(CCN(c3nc(OC4CCN(CCOC)CC4)nc4c(OCC(F)(F)F)c(-c5c(C)ccc6cc[nH]c(=O)c56)c(C5CC5)cc34)CC2)C1] | 779.3 |

TABLE 1-continued
| Compound | Compound structure | [M + H]+ |
| --- | --- | --- |
| 43 | 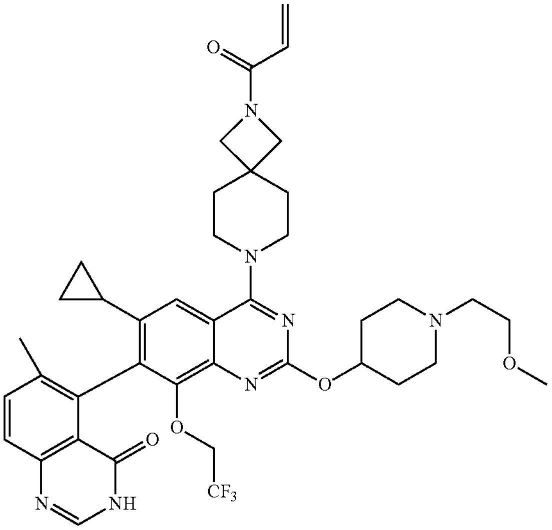 | 762.3 |
| 44 | 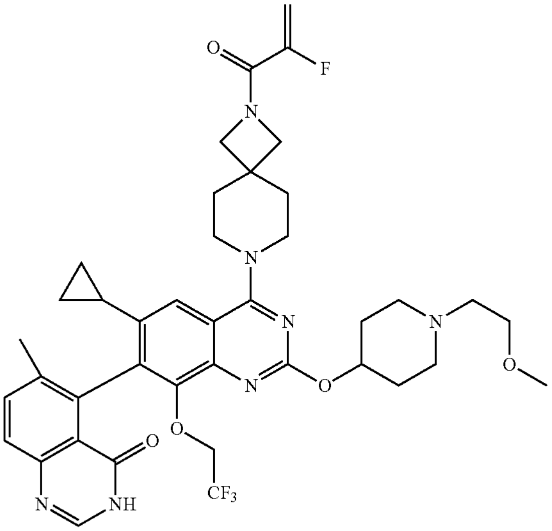 [SMILES: C=C(F)C(=O)N1CC2(CCN(c3nc(OC4CCN(CCOC)CC4)nc4c(OCC(F)(F)F)c(-c5c(C)ccc6nc[nH]c(=O)c56)c(C5CC5)cc34)CC2)C1] | 780.3 |
| 45 | 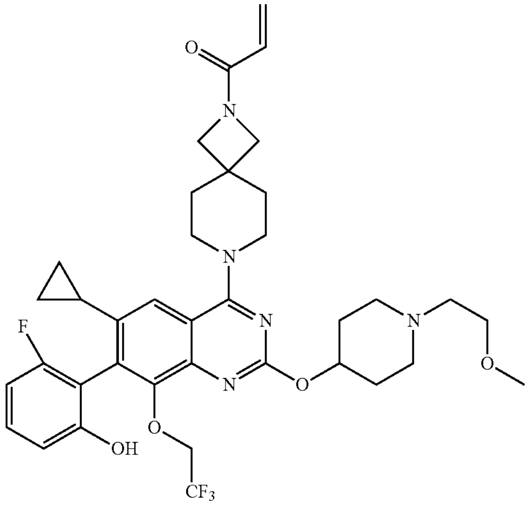 [SMILES: C=CC(=O)N1CC2(CCN(c3nc(OC4CCN(CCOC)CC4)nc4c(OCC(F)(F)F)c(-c5c(O)cccc5F)c(C5CC5)cc34)CC2)C1] | 714.3 |

TABLE 1-continued
| Compound | Compound structure | [M + H]+ |
|---|---|---|
| 46 | 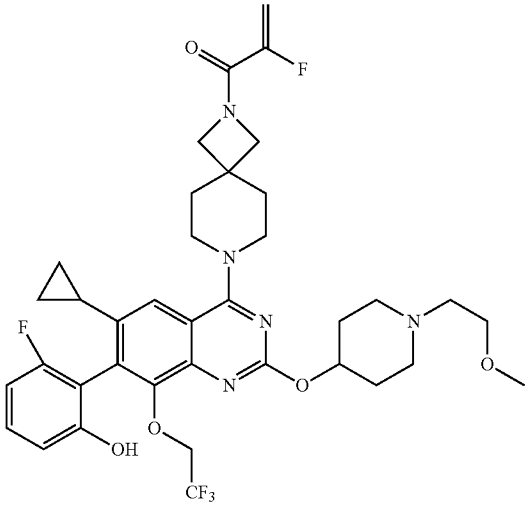 [SMILES: C=C(F)C(=O)N1CC2(CCN(c3nc(OC4CCN(CCOC)CC4)nc4c(OCC(F)(F)F)c(-c5c(O)cccc5F)c(C5CC5)cc34)CC2)C1] | 732.3 |
| 47 | 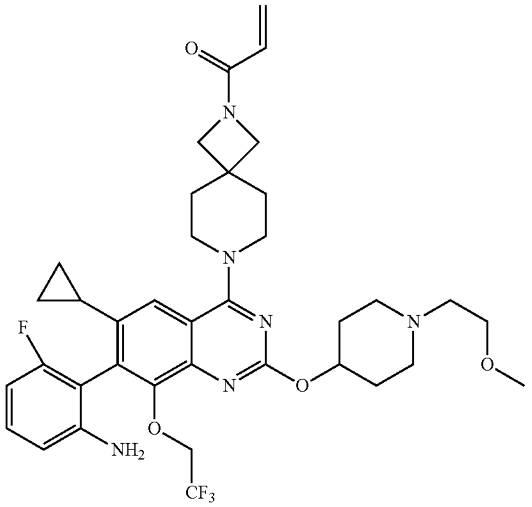 [SMILES: C=CC(=O)N1CC2(CCN(c3nc(OC4CCN(CCOC)CC4)nc4c(OCC(F)(F)F)c(-c5c(N)cccc5F)c(C5CC5)cc34)CC2)C1] | 713.4 |
| 48 | 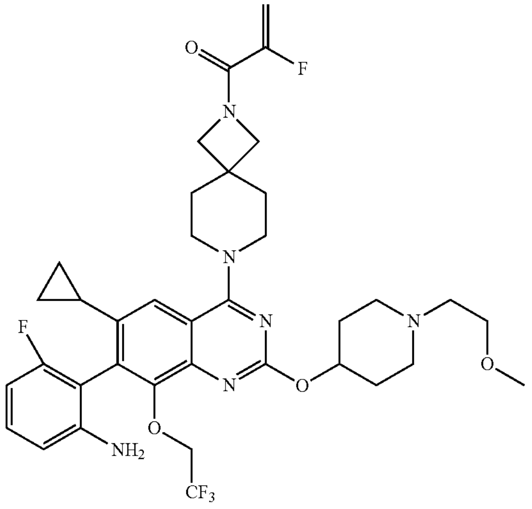 | 731.3 |

TABLE 1-continued
| Compound | Compound structure | [M + H]$^+$ |
| --- | --- | --- |
| 49 | 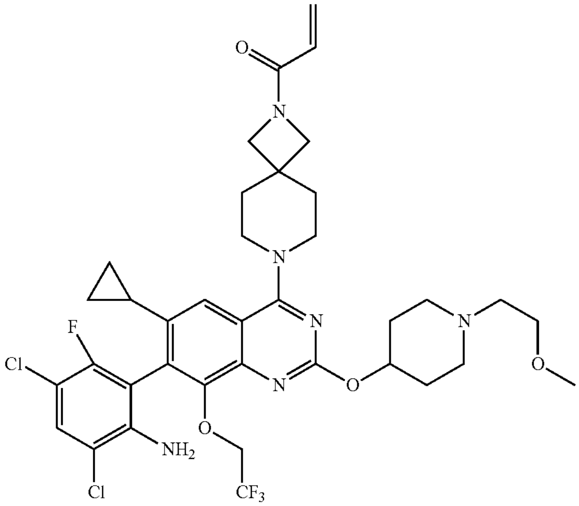 [SMILES: C=CC(=O)N1CC2(CCN(c3nc(OC4CCN(CCOC)CC4)nc4c(OCC(F)(F)F)c(-c5c(N)c(Cl)cc(Cl)c5F)c(C5CC5)cc34)CC2)C1] | 781.3 |
| 50 | 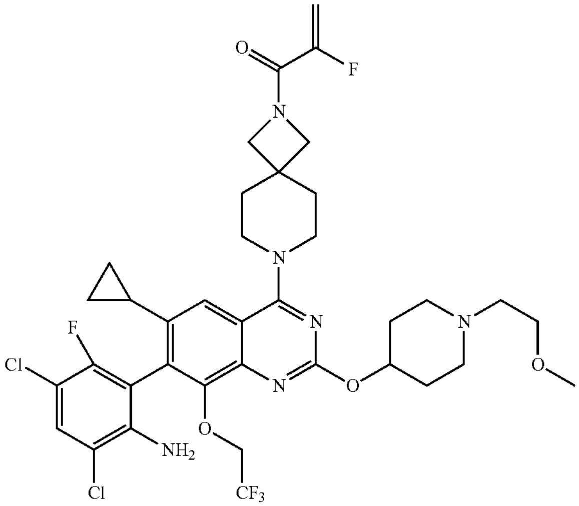 | 799.2 |
| 51 | 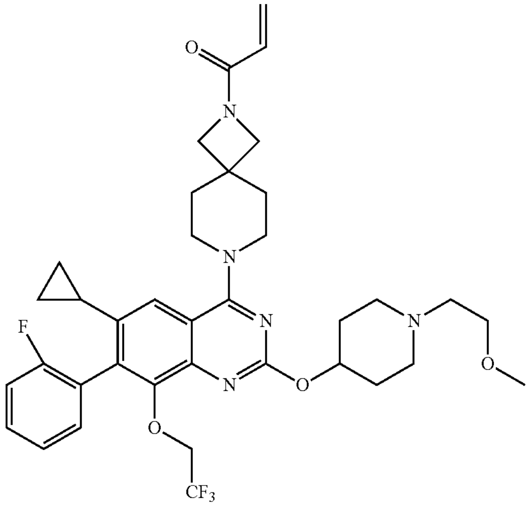 [SMILES: C=CC(=O)N1CC2(CCN(c3nc(OC4CCN(CCOC)CC4)nc4c(OCC(F)(F)F)c(-c5ccccc5F)c(C5CC5)cc34)CC2)C1] | 698.3 |

TABLE 1-continued
| Compound | Compound structure | [M + H]+ |
|---|---|---|
| 52 | 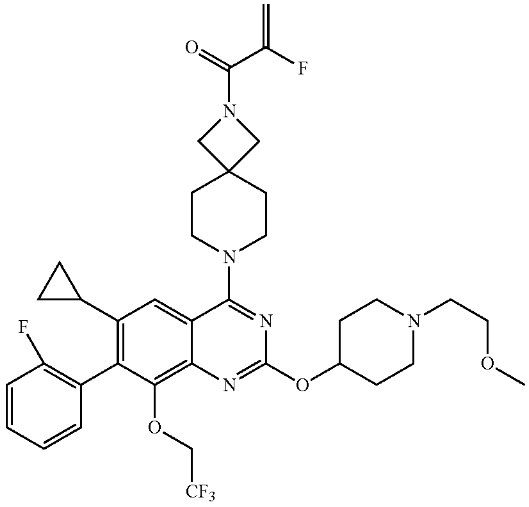 [SMILES: C=C(F)C(=O)N1CC2(CCN(c3nc(OC4CCN(CCOC)CC4)nc4c(OCC(F)(F)F)c(-c5ccccc5F)c(C5CC5)cc34)CC2)C1] | 715.3 |
| 53 | 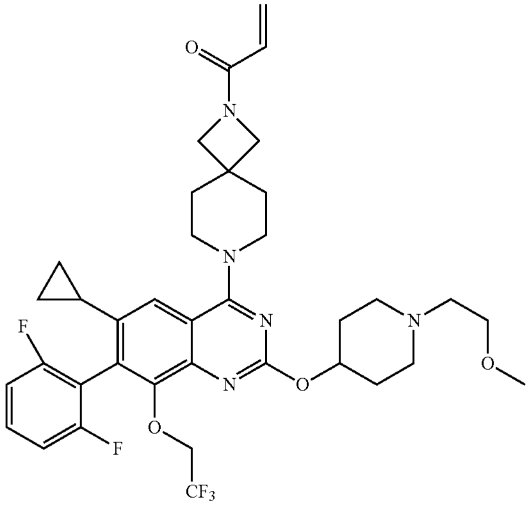 [SMILES: C=CC(=O)N1CC2(CCN(c3nc(OC4CCN(CCOC)CC4)nc4c(OCC(F)(F)F)c(-c5c(F)cccc5F)c(C5CC5)cc34)CC2)C1] | 716.3 |
| 54 | 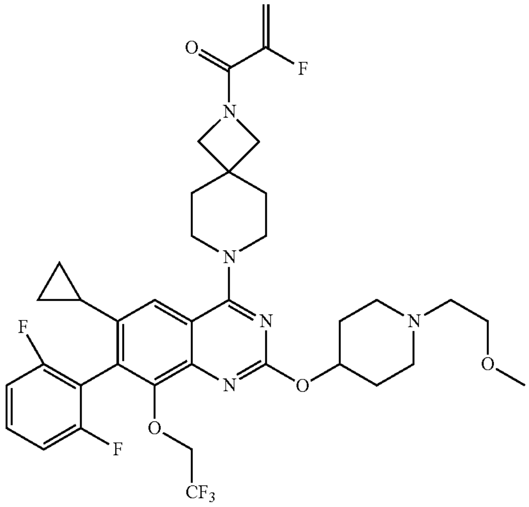 [SMILES: C=C(F)C(=O)N1CC2(CCN(c3nc(OC4CCN(CCOC)CC4)nc4c(OCC(F)(F)F)c(-c5c(F)cccc5F)c(C5CC5)cc34)CC2)C1] | 734.3 |

TABLE 1-continued
| Compound | Compound structure | [M + H]+ |
|---|---|---|
| 55 | 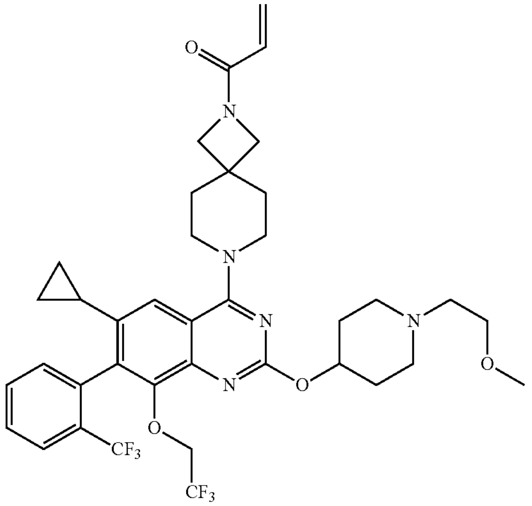 [SMILES: C=CC(=O)N1CC2(CCN(c3nc(OC4CCN(CCOC)CC4)nc4c(OCC(F)(F)F)c(-c5ccccc5C(F)(F)F)c(C5CC5)cc34)CC2)C1] | 748.3 |
| 56 | 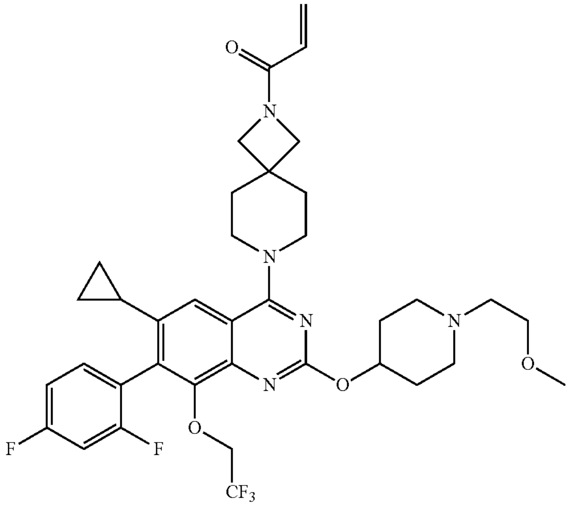 [SMILES: C=CC(=O)N1CC2(CCN(c3nc(OC4CCN(CCOC)CC4)nc4c(OCC(F)(F)F)c(-c5ccc(F)cc5F)c(C5CC5)cc34)CC2)C1] | 715.3 |
| 57 | 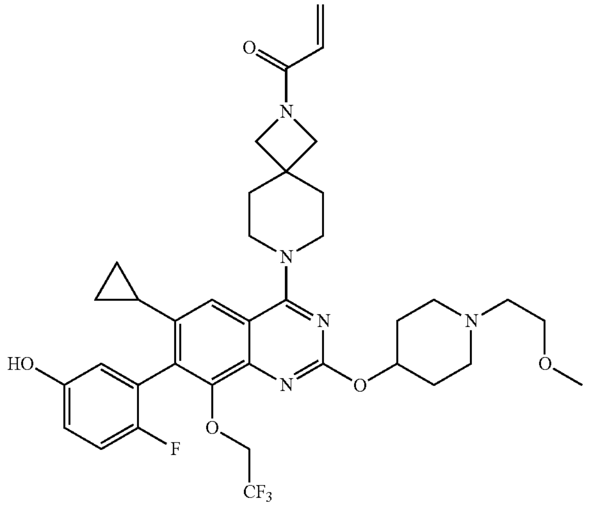 [SMILES: C=CC(=O)N1CC2(CCN(c3nc(OC4CCN(CCOC)CC4)nc4c(OCC(F)(F)F)c(-c5cc(O)ccc5Cl)c(C5CC5)cc34)CC2)C1] | 714.3 |

TABLE 1-continued
| Compound | Compound structure | [M + H]+ |
|---|---|---|
| 58 | 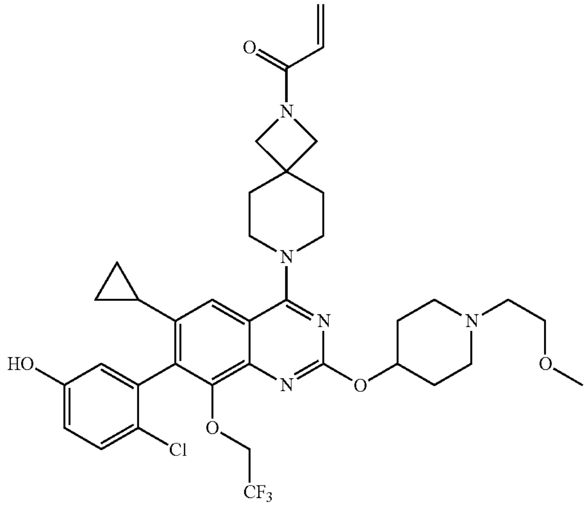 | 730.3 |
| 59 | 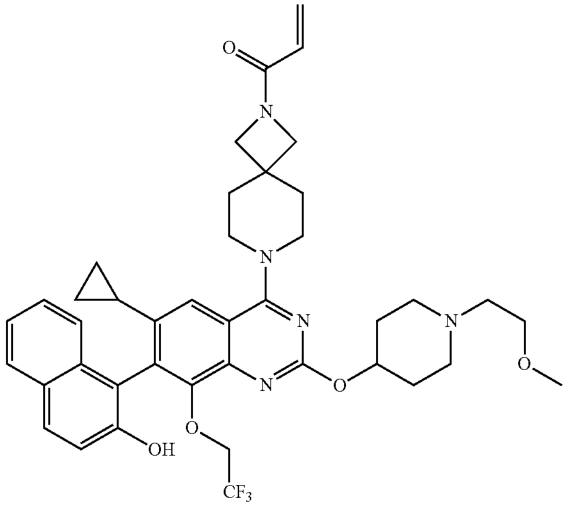 [SMILES: C=CC(=O)N1CC2(CCN(c3nc(OC4CCN(CCOC)CC4)nc4c(OCC(F)(F)F)c(-c5c(O)ccc6ccccc56)c(C5CC5)cc34)CC2)C1] | 746.3 |
| 60 | 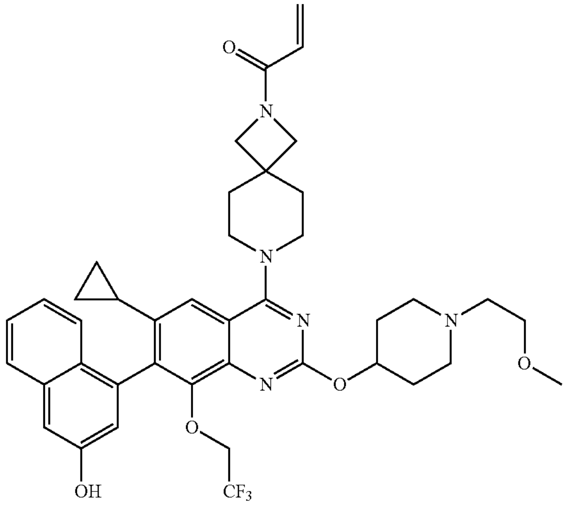 [SMILES: C=CC(=O)N1CC2(CCN(c3nc(OC4CCN(CCOC)CC4)nc4c(OCC(F)(F)F)c(-c5cc(O)cc6ccccc56)c(C5CC5)cc34)CC2)C1] | 746.3 |

TABLE 1-continued
| Compound | Compound structure | [M + H]$^+$ |
|---|---|---|
| 61 | 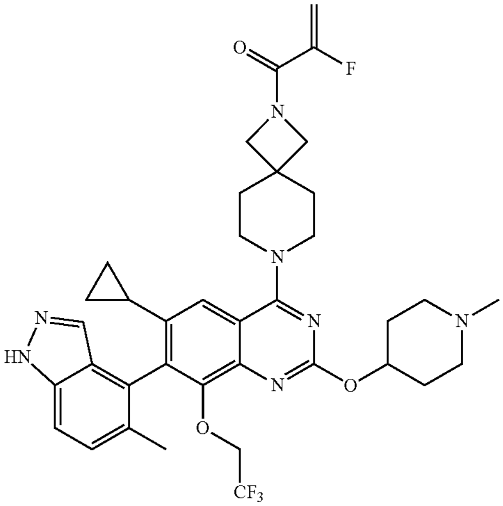 [SMILES: C=C(F)C(=O)N1CC2(CCN(c3nc(OC4CCN(C)CC4)nc4c(OCC(F)(F)F)c(-c5c(C)ccc6[nH]ncc56)c(C5CC5)cc34)CC2)C1] | 708.3 |
| 62 | 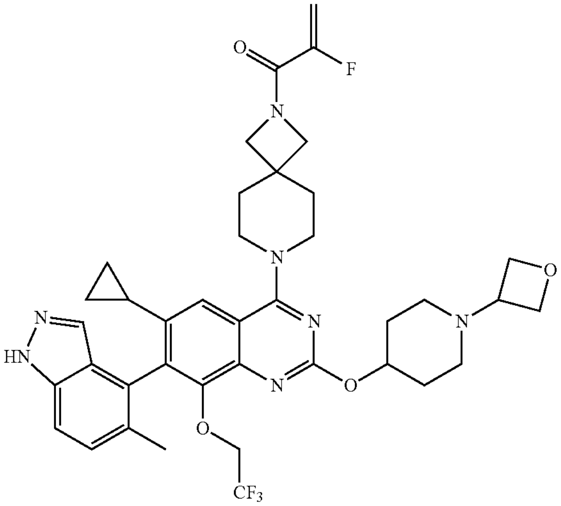 [SMILES: C=C(F)C(=O)N1CC2(CCN(c3nc(OC4CCN(C5COC5)CC4)nc4c(OCC(F)(F)F)c(-c5c(C)ccc6[nH]ncc56)c(C5CC5)cc34)CC2)C1] | 750.3 |
| 63 | 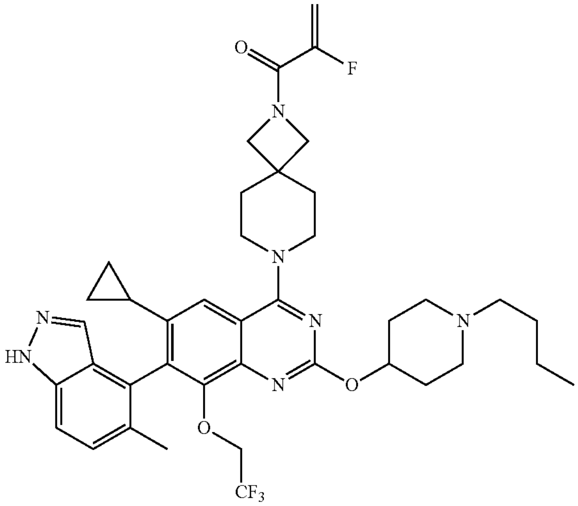 [SMILES: C=C(F)C(=O)N1CC2(CCN(c3nc(OC4CCN(CCCC)CC4)nc4c(OCC(F)(F)F)c(-c5c(C)ccc6[nH]ncc56)c(C5CC5)cc34)CC2)C1] | 766.4 |

TABLE 1-continued
| Compound | Compound structure | [M + H]+ |
| --- | --- | --- |
| 64 | 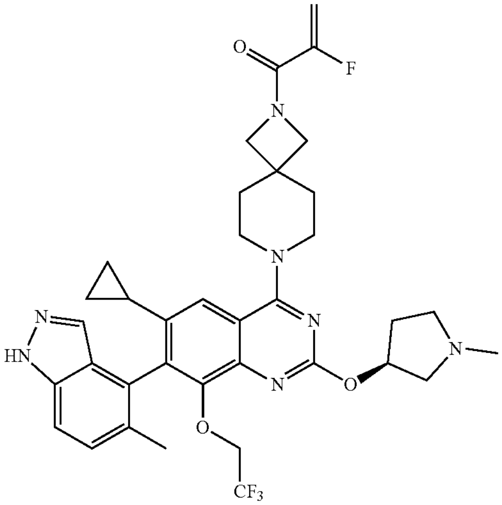 [SMILES: C=C(F)C(=O)N1CC2(CCN(c3nc(O[C@H]4CCN(C)C4)nc4c(OCC(F)(F)F)c(-c5c(C)ccc6[nH]ncc56)c(C5CC5)cc34)CC2)C1] | 694.3 |
| 65 | 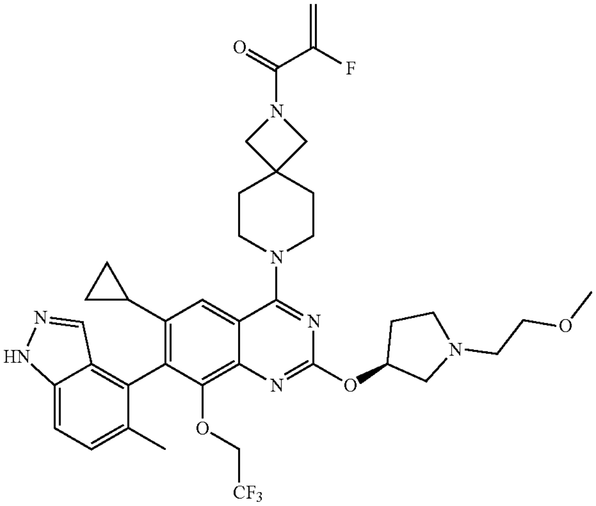 [SMILES: C=C(F)C(=O)N1CC2(CCN(c3nc(O[C@H]4CCN(CCOC)C4)nc4c(OCC(F)(F)F)c(-c5c(C)ccc6[nH]ncc56)c(C5CC5)cc34)CC2)C1] | 738.3 |
| 66 | 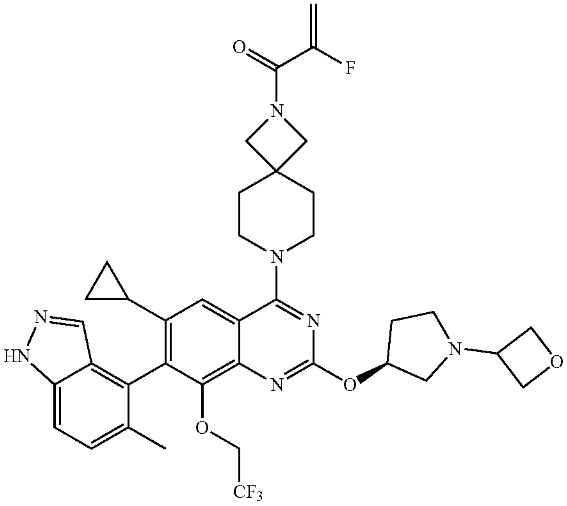 [SMILES: C=C(F)C(=O)N1CC2(CCN(c3nc(O[C@H]4CCN(C5COC5)C4)nc4c(OCC(F)(F)F)c(-c5c(C)ccc6[nH]ncc56)c(C5CC5)cc34)CC2)C1] | 736.3 |

TABLE 1-continued
| Compound | Compound structure | [M + H]+ |
| --- | --- | --- |
| 67 | 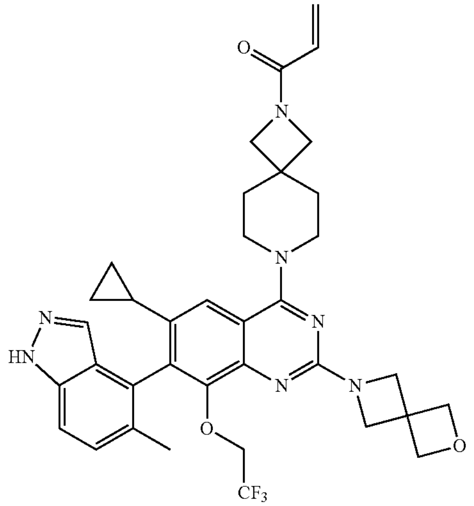 [SMILES: C=CC(=O)N1CC2(CCN(c3nc(N4CC5(COC5)C4)nc4c(OCC(F)(F)F)c(-c5c(C)ccc6[nH]ncc56)c(C5CC5)cc34)CC2)C1] | 674.3 |
| 68 | 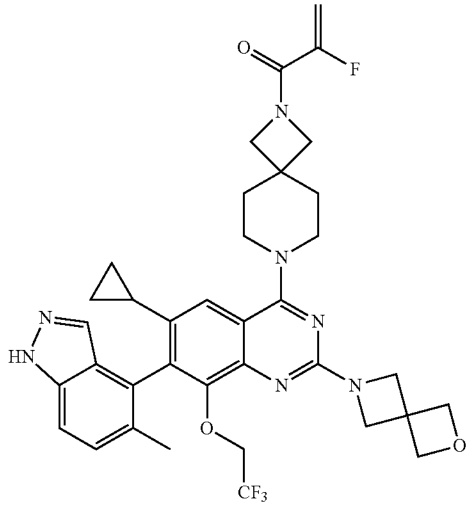 [SMILES: C=C(F)C(=O)N1CC2(CCN(c3nc(N4CC5(COC5)C4)nc4c(OCC(F)(F)F)c(-c5c(C)ccc6[nH]ncc56)c(C5CC5)cc34)CC2)C1] | 692.3 |
| 69 | 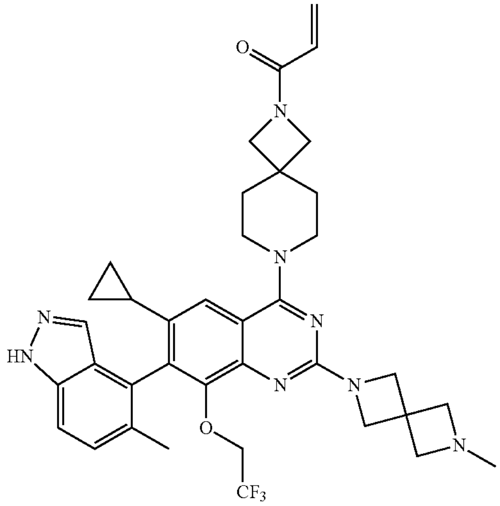 [SMILES: C=CC(=O)N1CC2(CCN(c3nc(N4CC5(CN(C)C5)C4)nc4c(OCC(F)(F)F)c(-c5c(C)ccc6[nH]ncc56)c(C5CC5)cc34)CC2)C1] | 687.3 |

TABLE 1-continued
| Compound | Compound structure | [M + H]$^+$ |
| --- | --- | --- |
| 70 | 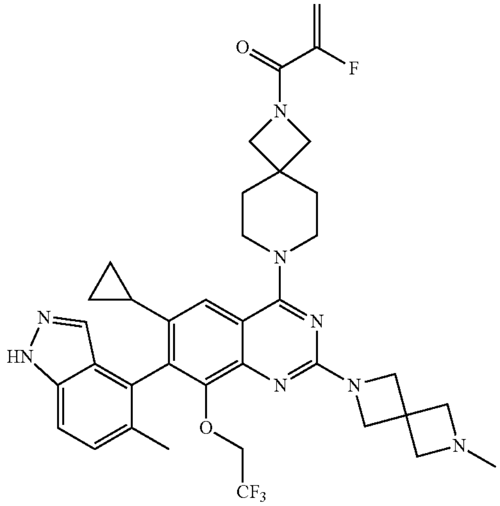 [SMILES: C=C(F)C(=O)N1CC2(CCN(c3nc(N4CC5(CN(C)C5)C4)nc4c(OCC(F)(F)F)c(-c5c(C)ccc6[nH]ncc56)c(C5CC5)cc34)CC2)C1] | 705.3 |
| 71 | 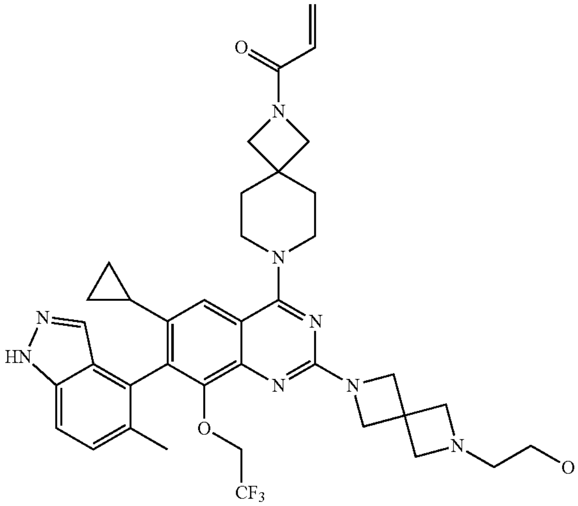 [SMILES: C=CC(=O)N1CC2(CCN(c3nc(N4CC5(CN(CCO)C5)C4)nc4c(OCC(F)(F)F)c(-c5c(C)ccc6[nH]ncc56)c(C5CC5)cc34)CC2)C1] | 731.4 |
| 72 | 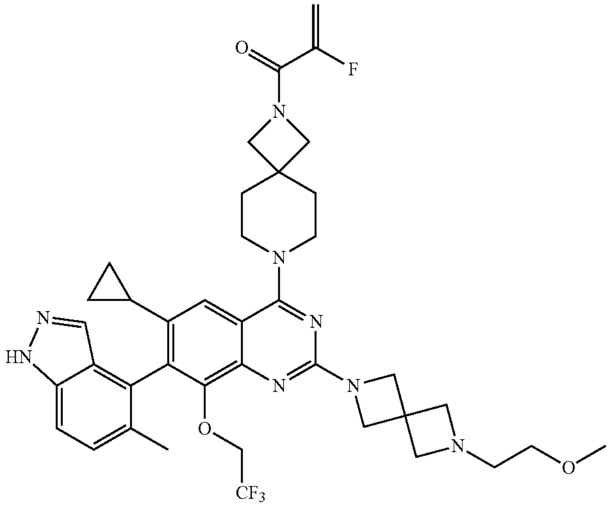 | 749.3 |

TABLE 1-continued
| Compound | Compound structure | $[M + H]^+$ |
|---|---|---|
| 73 | 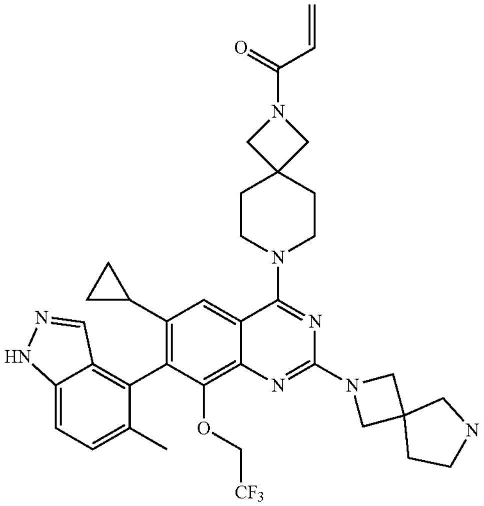 [SMILES: C=CC(=O)N1CC2(CCN(c3nc(N4CC5(CCNC5)C4)nc4c(OCC(F)(F)F)c(-c5c(C)ccc6[nH]ncc56)c(C5CC5)cc34)CC2)C1] | 701.3 |
| 74 | 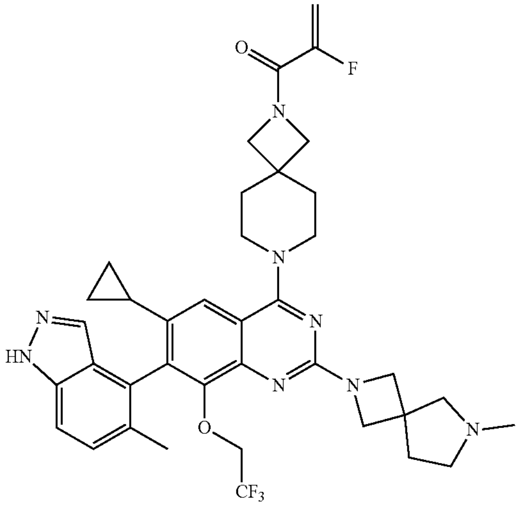 [SMILES: C=C(F)C(=O)N1CC2(CCN(c3nc(N4CC5(CCN(C)C5)C4)nc4c(OCC(F)(F)F)c(-c5c(C)ccc6[nH]ncc56)c(C5CC5)cc34)CC2)C1] | 719.3 |
| 75 | 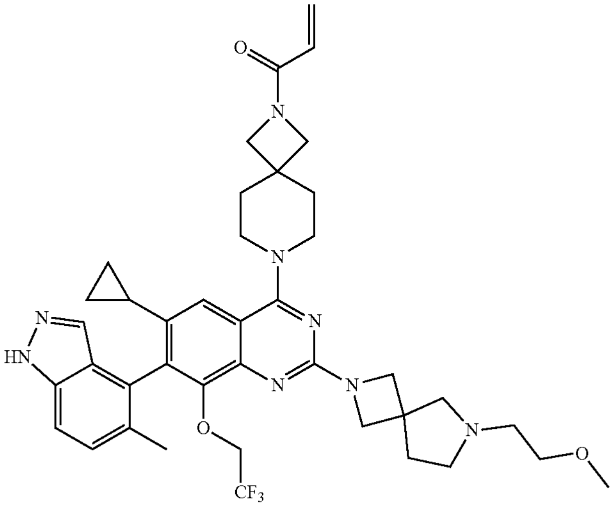 [SMILES: C=CC(=O)N1CC2(CCN(c3nc(N4CC5(CCN(CCOC)C5)C4)nc4c(OCC(F)(F)F)c(-c5c(C)ccc6[nH]ncc56)c(C5CC5)cc34)CC2)C1] | 745.4 |

TABLE 1-continued
| Compound | Compound structure | [M + H]+ |
|---|---|---|
| 76 | 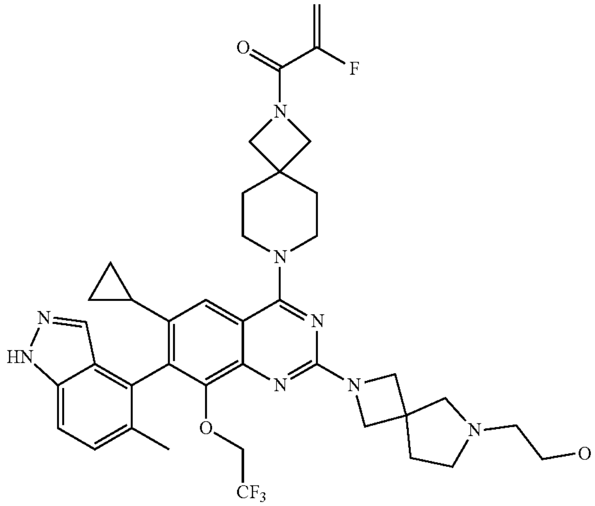 [SMILES: C=C(F)C(=O)N1CC2(CCN(c3nc(N4CC5(CCN(CCO)C5)C4)nc4c(OCC(F)(F)F)c(-c5c(C)ccc6[nH]ncc56)c(C5CC5)cc34)CC2)C1] | 763.4 |
| 77 | 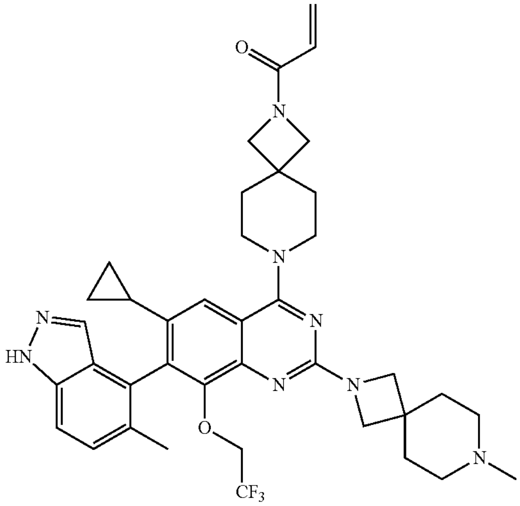 [SMILES: C=CC(=O)N1CC2(CCN(c3nc(N4CC5(CCN(C)CC5)C4)nc4c(OCC(F)(F)F)c(-c5c(C)ccc6[nH]ncc56)c(C5CC5)cc34)CC2)C1] | 715.4 |
| 78 | 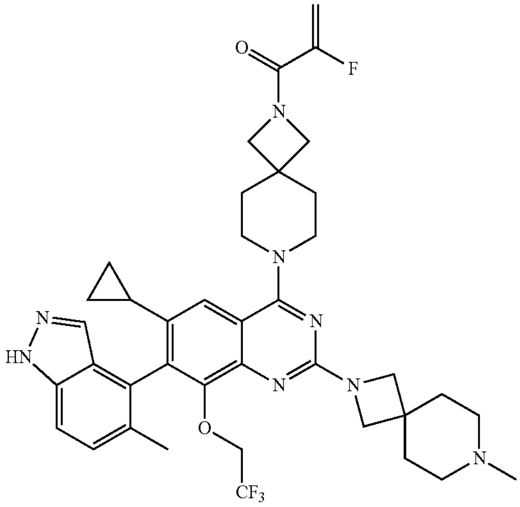 [SMILES: C=C(F)C(=O)N1CC2(CCN(c3nc(N4CC5(CCN(C)CC5)C4)nc4c(OCC(F)(F)F)c(-c5c(C)ccc6[nH]ncc56)c(C5CC5)cc34)CC2)C1] | 733.4 |

TABLE 1-continued
| Compound | Compound structure | [M + H]+ |
| --- | --- | --- |
| 79 | 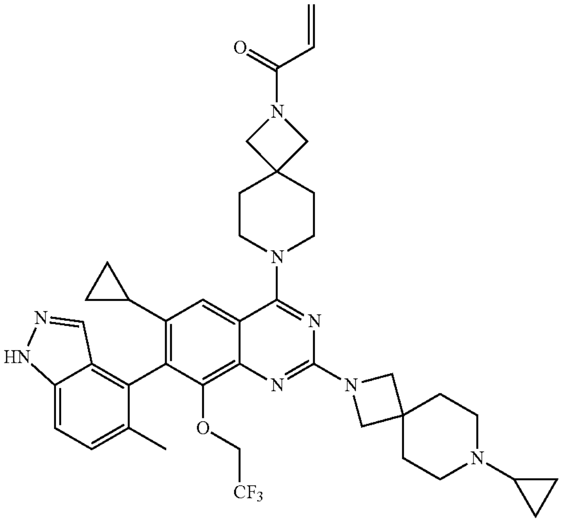 [SMILES: C=CC(=O)N1CC2(CCN(c3nc(N4CC5(CCN(C6CC6)CC5)C4)nc4c(OCC(F)(F)F)c(-c5c(C)ccc6[nH]ncc56)c(C5CC5)cc34)CC2)C1] | 741.4 |
| 80 | 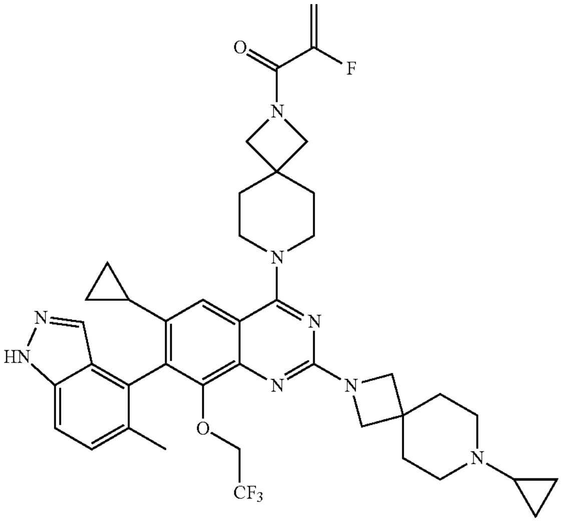 [SMILES: C=C(F)C(=O)N1CC2(CCN(c3nc(N4CC5(CCN(C6CC6)CC5)C4)nc4c(OCC(F)(F)F)c(-c5c(C)ccc6[nH]ncc56)c(C5CC5)cc34)CC2)C1] | 759.4 |
| 81 | 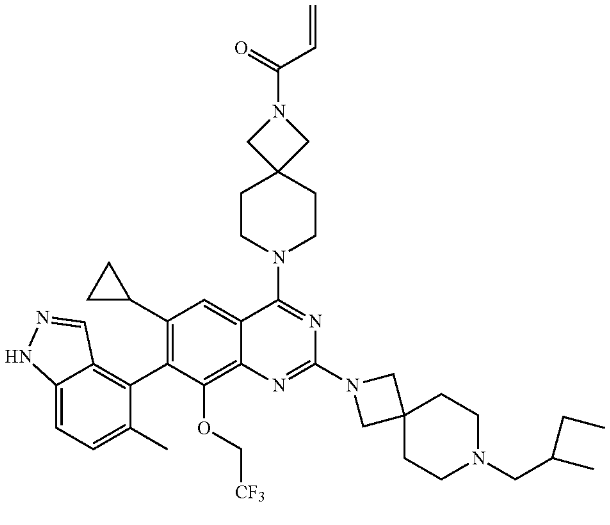 [SMILES: C=CC(=O)N1CC2(CCN(c3nc(N4CC5(CCN(CC(C)CC)CC5)C4)nc4c(OCC(F)(F)F)c(-c5c(C)ccc6[nH]ncc56)c(C5CC5)cc34)CC2)C1] | 771.4 |

TABLE 1-continued
| Compound | Compound structure | [M + H]+ |
|---|---|---|
| 82 | 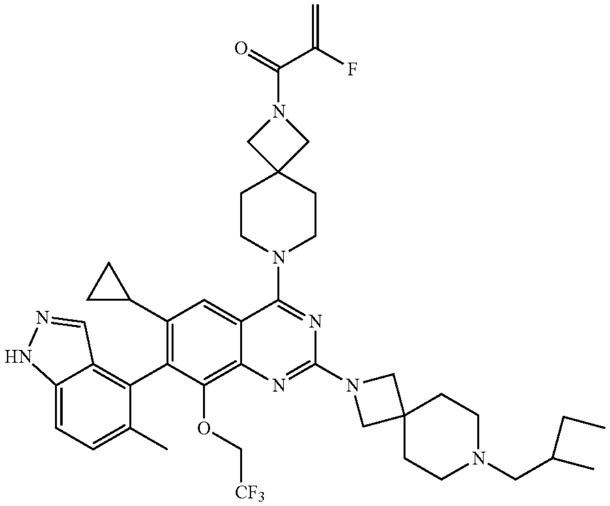 [SMILES: C=C(F)C(=O)N1CC2(CCN(c3nc(N4CC5(CCN(CC(C)CC)CC5)C4)nc4c(OCC(F)(F)F)c(-c5c(C)ccc6[nH]ncc56)c(C5CC5)cc34)CC2)C1] | 789.4 |
| 83 | 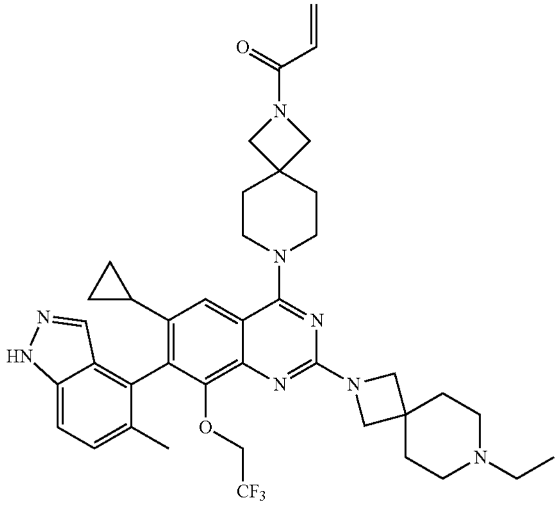 [SMILES: C=CC(=O)N1CC2(CCN(c3nc(N4CC5(CCN(CC)CC5)C4)nc4c(OCC(F)(F)F)c(-c5c(C)ccc6[nH]ncc56)c(C5CC5)cc34)CC2)C1] | 755.4 |
| 84 | 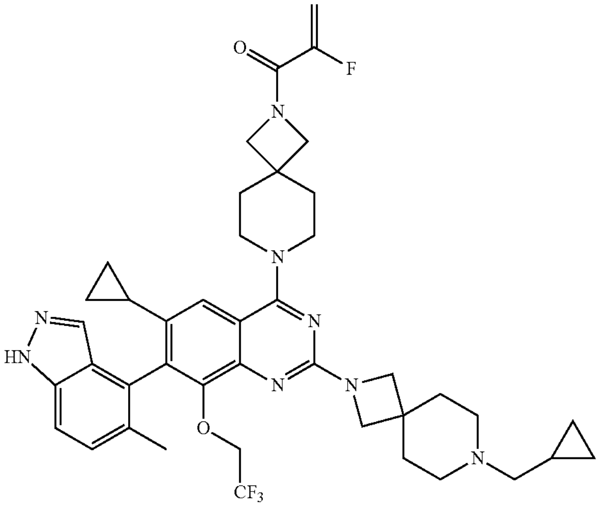 [SMILES: C=C(F)C(=O)N1CC2(CCN(c3nc(N4CC5(CCN(CC6CC6)CC5)C4)nc4c(OCC(F)(F)F)c(-c5c(C)ccc6[nH]ncc56)c(C5CC5)cc34)CC2)C1] | 773.4 |

TABLE 1-continued
| Compound | Compound structure | [M + H]$^+$ |
|---|---|---|
| 85 | 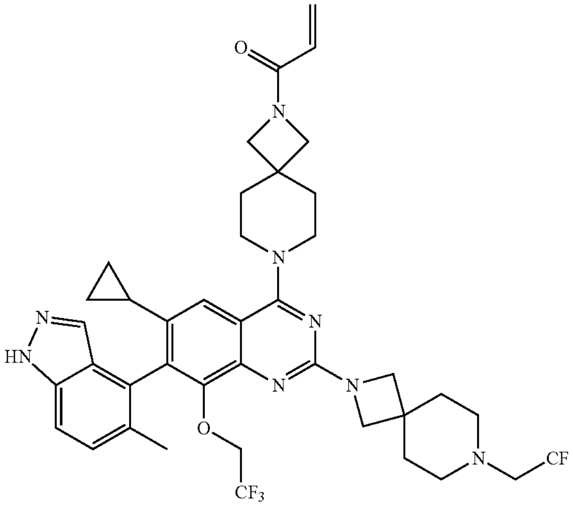 | 783.3 |
| 86 | 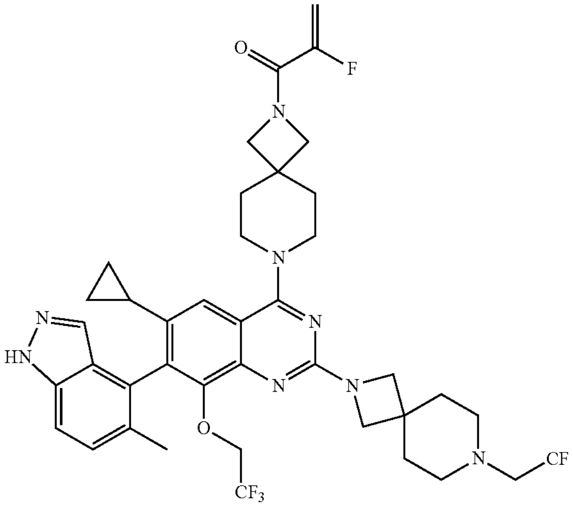 | 801.3 |
| 87 | 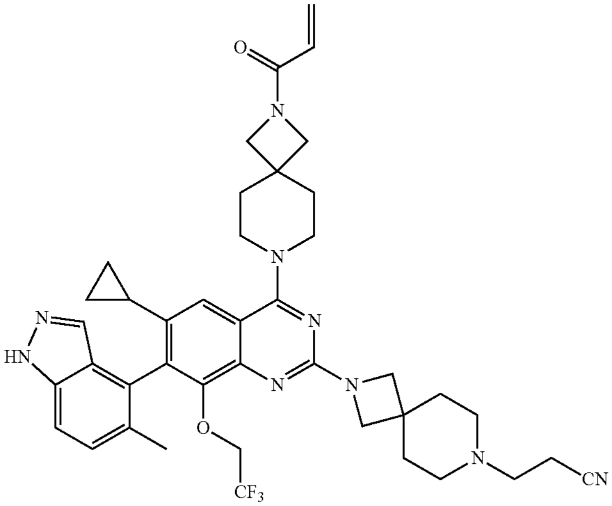 [SMILES: C=CC(=O)N1CC2(CCN(c3nc(N4CC5(CCN(CCC#N)CC5)C4)nc4c(OCC(F)(F)F)c(-c5c(C)ccc6[nH]ncc56)c(C5CC5)cc34)CC2)C1] | 754.4 |

TABLE 1-continued
| Compound | Compound structure | [M + H]+ |
| --- | --- | --- |
| 88 | 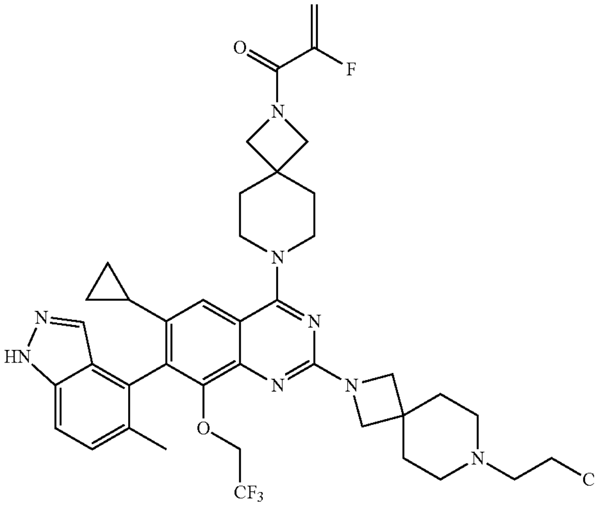 [SMILES: C=C(F)C(=O)N1CC2(CCN(c3nc(N4CC5(CCN(CCC)CC5)C4)nc4c(OCC(F)(F)F)c(-c5c(C)ccc6[nH]ncc56)c(C5CC5)cc34)CC2)C1] | 772.4 |
| 89 | 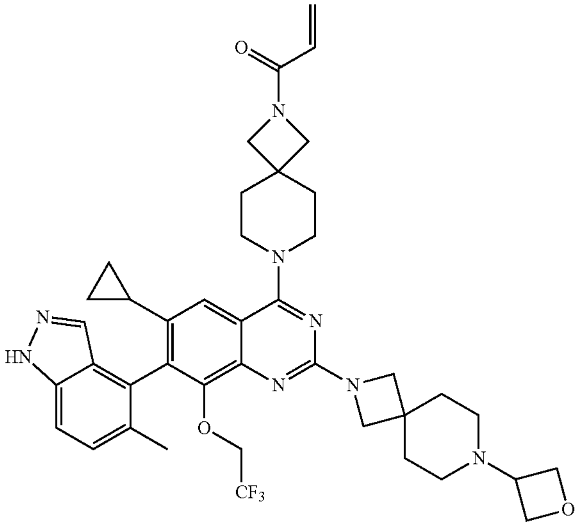 [SMILES: C=CC(=O)N1CC2(CCN(c3nc(N4CC5(CCN(C6COC6)CC5)C4)nc4c(OCC(F)(F)F)c(-c5c(C)ccc6[nH]ncc56)c(C5CC5)cc34)CC2)C1] | 757.4 |
| 90 | 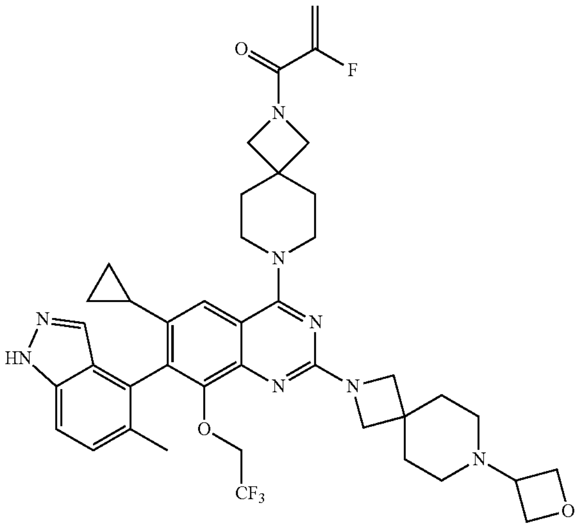 [SMILES: C=C(F)C(=O)N1CC2(CCN(c3nc(N4CC5(CCN(C6COC6)CC5)C4)nc4c(OCC(F)(F)F)c(-c5c(C)ccc6[nH]ncc56)c(C5CC5)cc34)CC2)C1] | 775.4 |

TABLE 1-continued
| Compound | Compound structure | [M + H]+ |
|---|---|---|
| 91 | 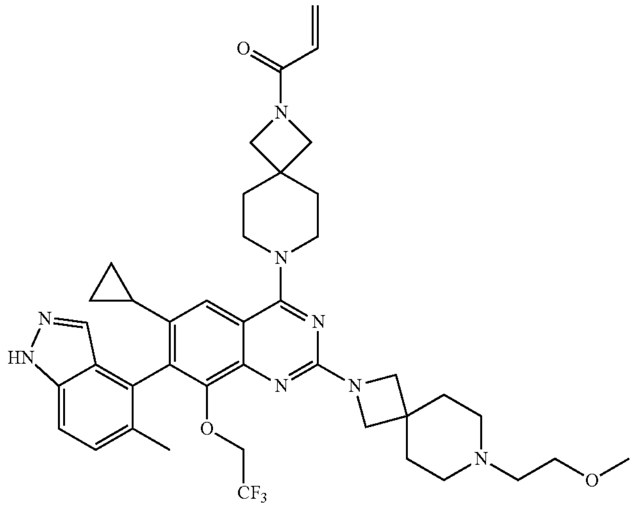 [SMILES: C=CC(=O)N1CC2(CCN(c3nc(N4CC5(CCN(CCOC)CC5)C4)nc4c(OCC(F)(F)F)c(-c5c(C)ccc6[nH]ncc56)c(C5CC5)cc34)CC2)C1] | 759.4 |
| 92 | 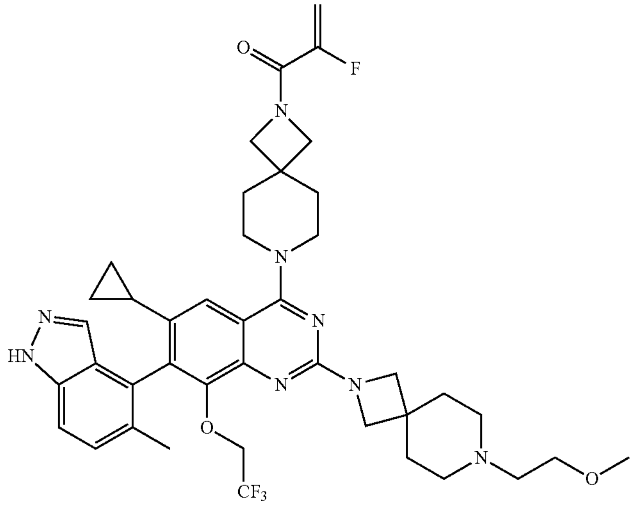 | 777.4 |
| 93 | 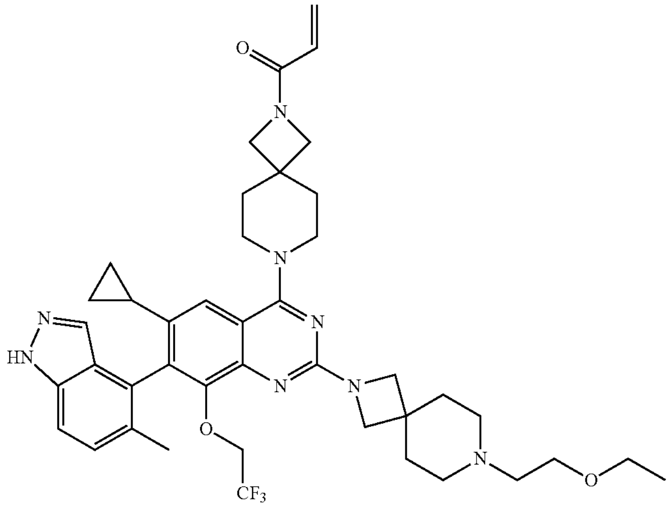 [SMILES: C=CC(=O)N1CC2(CCN(c3nc(N4CC5(CCN(CCOCC)CC5)C4)nc4c(OCC(F)(F)F)c(-c5c(C)ccc6[nH]ncc56)c(C5CC5)cc34)CC2)C1] | 773.4 |

TABLE 1-continued
| Compound | Compound structure | [M + H]+ |
|---|---|---|
| 94 | 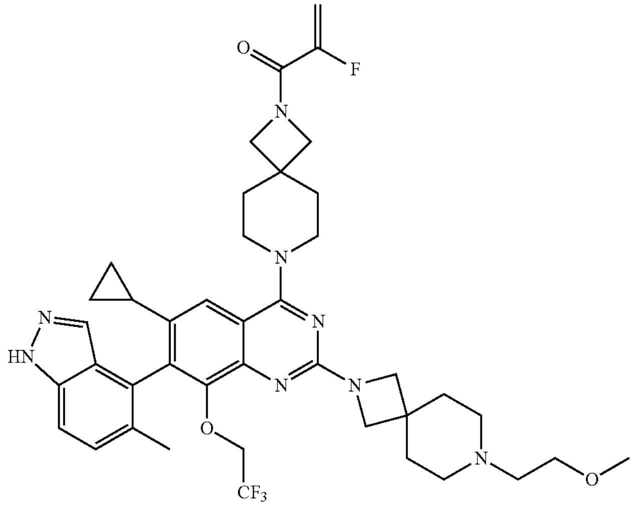 [SMILES: C=C(F)C(=O)N1CC2(CCN(c3nc(N4CC5(CCN(CCOC)CC5)C4)nc4c(OCC(F)(F)F)c(-c5c(C)ccc6[nH]ncc56)c(C5CC5)cc34)CC2)C1] | 791.4 |
| 95 | 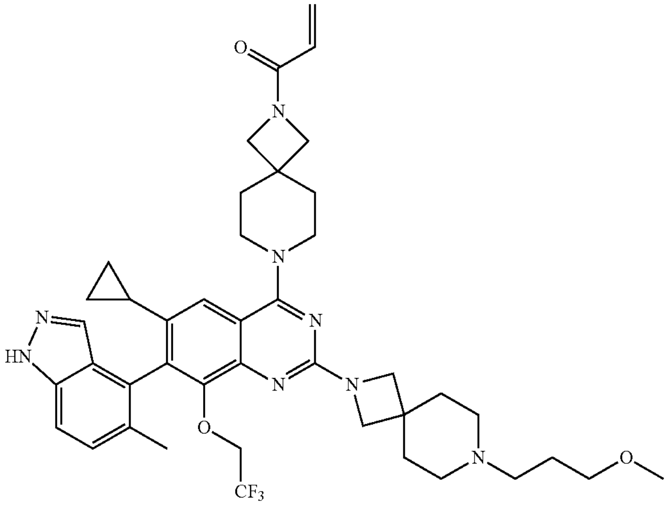 | 773.4 |
| 96 | 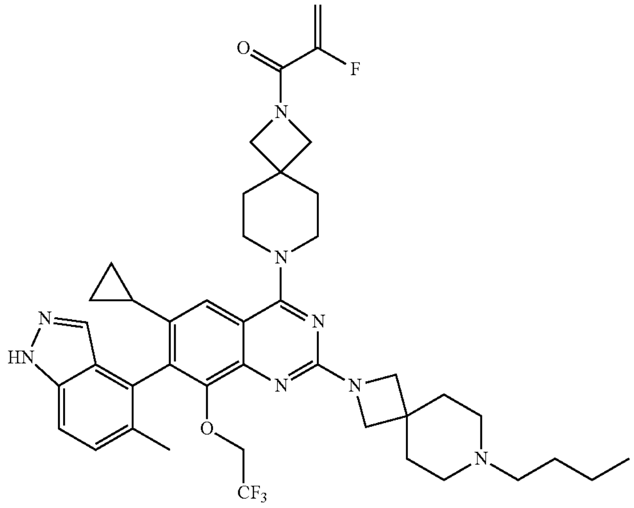 [SMILES: C=C(F)C(=O)N1CC2(CCN(c3nc(N4CC5(CCN(CCCC)CC5)C4)nc4c(OCC(F)(F)F)c(-c5c(C)ccc6[nH]ncc56)c(C5CC5)cc34)CC2)C1] | 791.4 |

TABLE 1-continued
| Compound | Compound structure | [M + H]+ |
| --- | --- | --- |
| 97 | 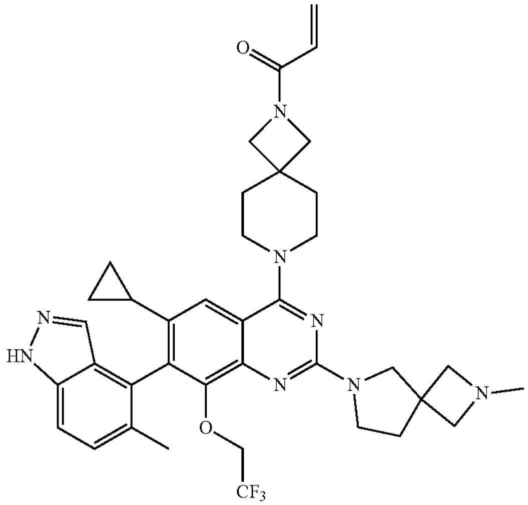 [SMILES: C=CC(=O)N1CC2(CCN(c3nc(N4CCC5(CN(C)C5)C4)nc4c(OCC(F)(F)F)c(-c5c(C)ccc6[nH]ncc56)c(C5CC5)cc34)CC2)C1] | 701.3 |
| 98 | 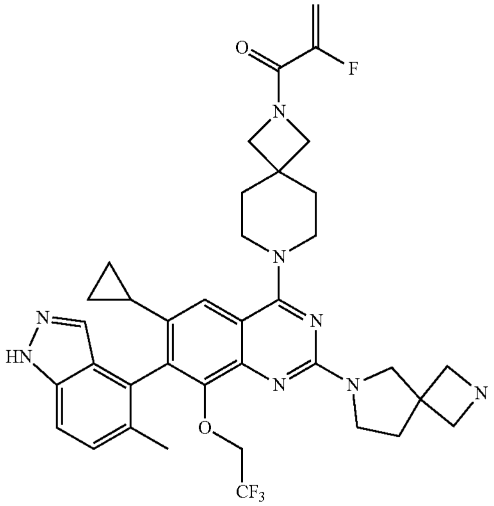 [SMILES: C=C(F)C(=O)N1CC2(CCN(c3nc(N4CCC5(CNC5)C4)nc4c(OCC(F)(F)F)c(-c5c(C)ccc6[nH]ncc56)c(C5CC5)cc34)CC2)C1] | 719.3 |
| 99 | 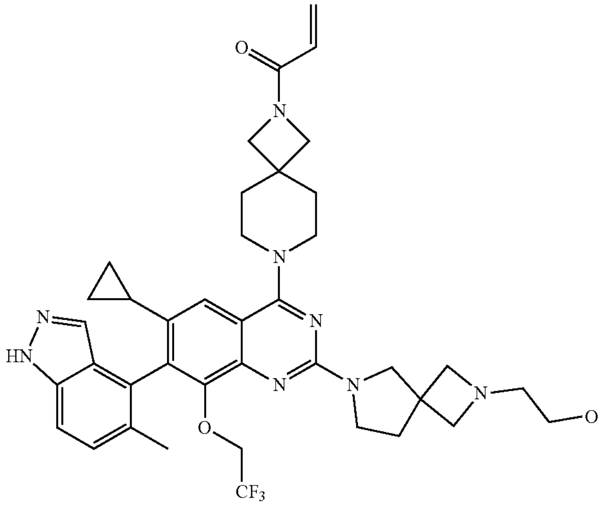 [SMILES: C=CC(=O)N1CC2(CCN(c3nc(N4CCC5(CN(CCO)C5)C4)nc4c(OCC(F)(F)F)c(-c5c(C)ccc6[nH]ncc56)c(C5CC5)cc34)CC2)C1] | 745.4 |

TABLE 1-continued
| Compound | Compound structure | [M + H]+ |
| --- | --- | --- |
| 100 | 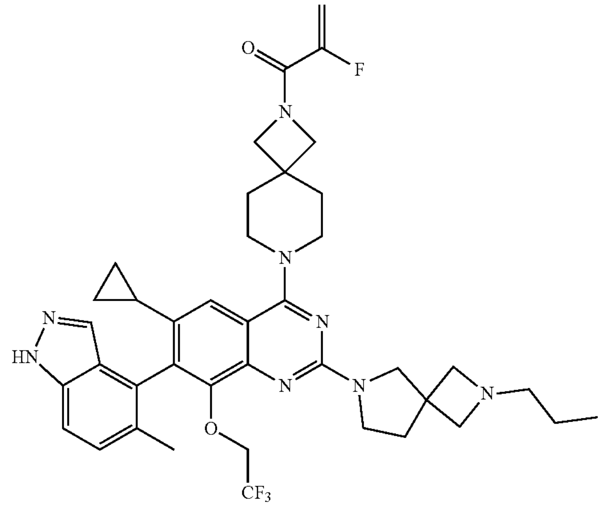 [SMILES: C=C(F)C(=O)N1CC2(CCN(c3nc(N4CCC5(CN(CCC)C5)C4)nc4c(OCC(F)(F)F)c(-c5c(C)ccc6[nH]ncc56)c(C5CC5)cc34)CC2)C1] | 763.4 |
| 101 | 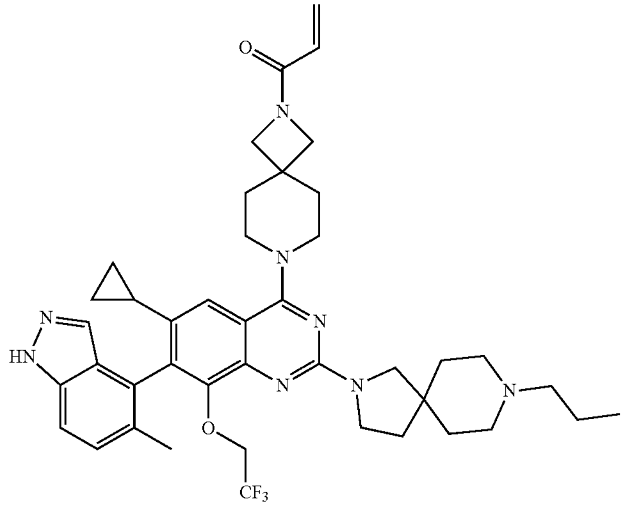 [SMILES: C=CC(=O)N1CC2(CCN(c3nc(N4CCC5(CCN(CCC)CC5)C4)nc4c(OCC(F)(F)F)c(-c5c(C)ccc6[nH]ncc56)c(C5CC5)cc34)CC2)C1] | 773.4 |
| 102 | 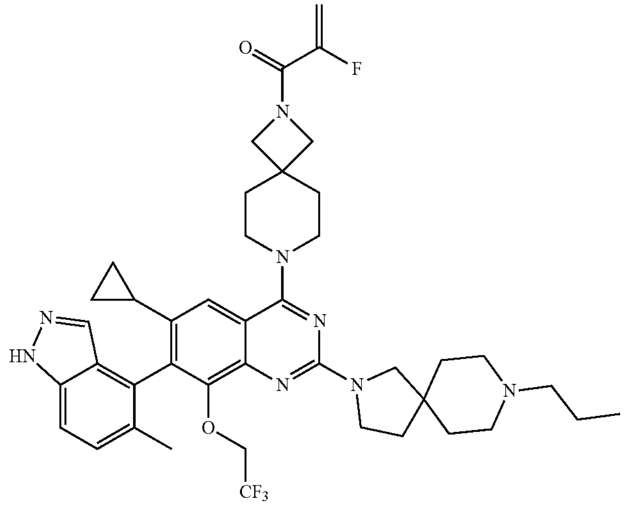 [SMILES: C=C(F)C(=O)N1CC2(CCN(c3nc(N4CCC5(CCN(CCC)CC5)C4)nc4c(OCC(F)(F)F)c(-c5c(C)ccc6[nH]ncc56)c(C5CC5)cc34)CC2)C1] | 791.4 |

TABLE 1-continued
| Compound | Compound structure | [M + H]+ |
|---|---|---|
| 103 | 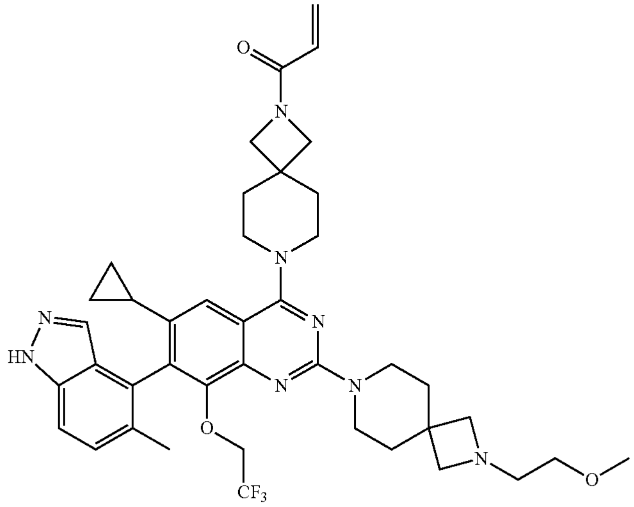 [SMILES: C=CC(=O)N1CC2(CCN(c3nc(N4CCC5(CC4)CN(CCOC)C5)nc4c(OCC(F)(F)F)c(-c5c(C)ccc6[nH]ncc56)c(C5CC5)cc34)CC2)C1] | 759.4 |
| 104 | 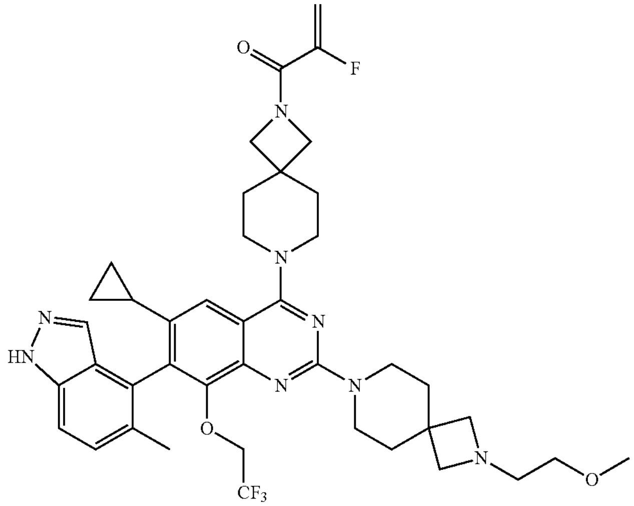 [SMILES: C=C(F)C(=O)N1CC2(CCN(c3nc(N4CCC5(CC4)CN(CCOC)C5)nc4c(OCC(F)(F)F)c(-c5c(C)ccc6[nH]ncc56)c(C5CC5)cc34)CC2)C1] | 777.4 |
| 105 | 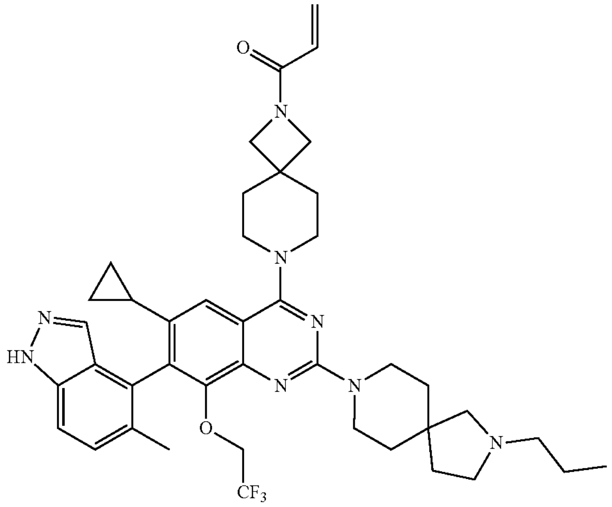 [SMILES: C=CC(=O)N1CC2(CCN(c3nc(N4CCC5(CCN(CCC)C5)CC4)nc4c(OCC(F)(F)F)c(-c5c(C)ccc6[nH]ncc56)c(C5CC5)cc34)CC2)C1] | 773.4 |

TABLE 1-continued
| Compound | Compound structure | [M + H]$^+$ |
| --- | --- | --- |
| 106 | 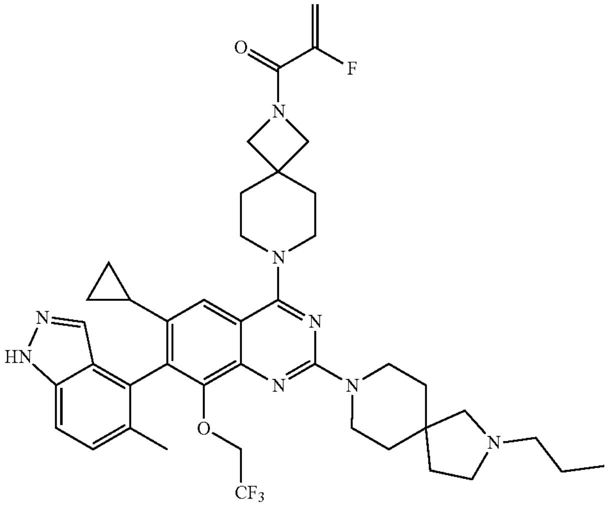 [SMILES: C=C(F)C(=O)N1CC2(CCN(c3nc(N4CCC5(CCN(CCC)C5)CC4)nc4c(OCC(F)(F)F)c(-c5c(C)ccc6[nH]ncc56)c(C5CC5)cc34)CC2)C1] | 791.4 |
| 107 | 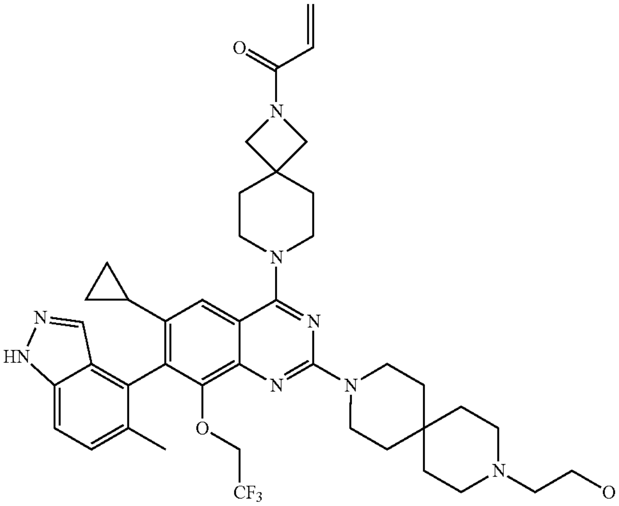 [SMILES: C=CC(=O)N1CC2(CCN(c3nc(N4CCC5(CCN(CCO)CC5)CC4)nc4c(OCC(F)(F)F)c(-c5c(C)ccc6[nH]ncc56)c(C5CC5)cc34)CC2)C1] | 787.4 |
| 108 | 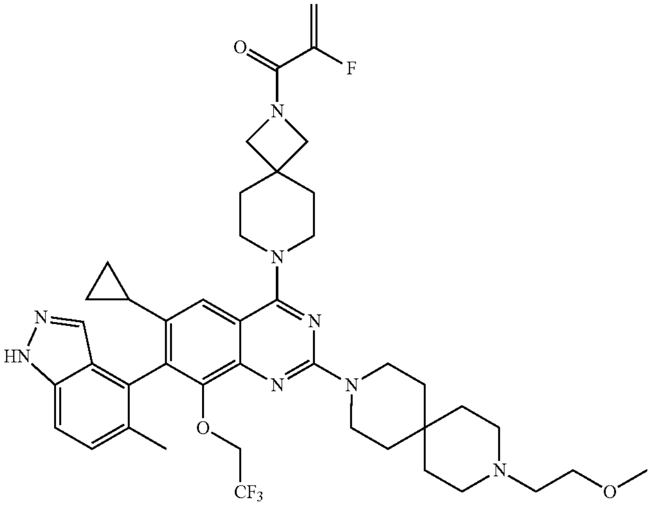 [SMILES: C=C(F)C(=O)N1CC2(CCN(c3nc(N4CCC5(CCN(CCOC)CC5)CC4)nc4c(OCC(F)(F)F)c(-c5c(C)ccc6[nH]ncc56)c(C5CC5)cc34)CC2)C1] | 805.4 |

TABLE 1-continued
| Compound | Compound structure | [M + H]+ |
| --- | --- | --- |
| 109 | 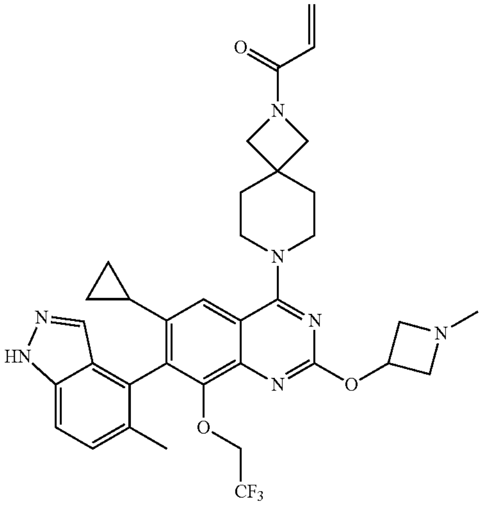 [SMILES: C=CC(=O)N1CC2(CCN(c3nc(OC4CN(C)C4)nc4c(OCC(F)(F)F)c(-c5c(C)ccc6[nH]ncc56)c(C5CC5)cc34)CC2)C1] | 662.3 |
| 110 | 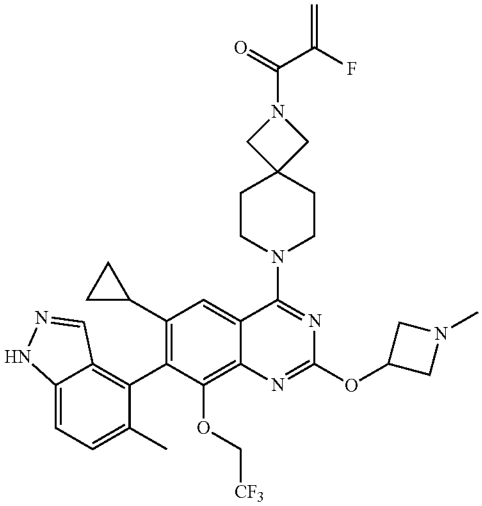 [SMILES: C=C(F)C(=O)N1CC2(CCN(c3nc(OC4CN(C)C4)nc4c(OCC(F)(F)F)c(-c5c(C)ccc6[nH]ncc56)c(C5CC5)cc34)CC2)C1] | 680.3 |
| 111 | 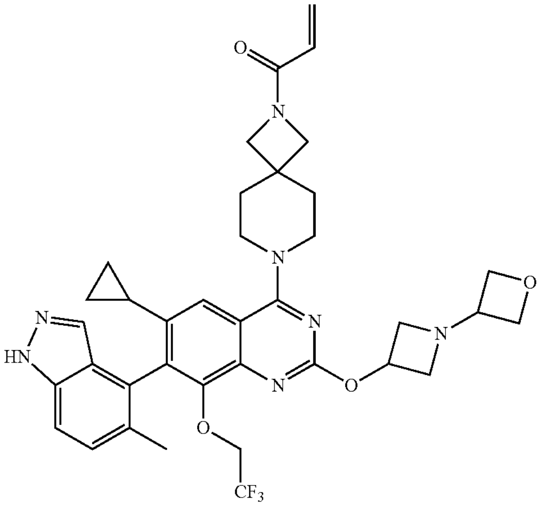 [SMILES: C=CC(=O)N1CC2(CCN(c3nc(OC4CN(C5COC5)C4)nc4c(OCC(F)(F)F)c(-c5c(C)ccc6[nH]ncc56)c(C5CC5)cc34)CC2)C1] | 704.3 |

TABLE 1-continued
| Compound | Compound structure | [M + H]+ |
|---|---|---|
| 112 | 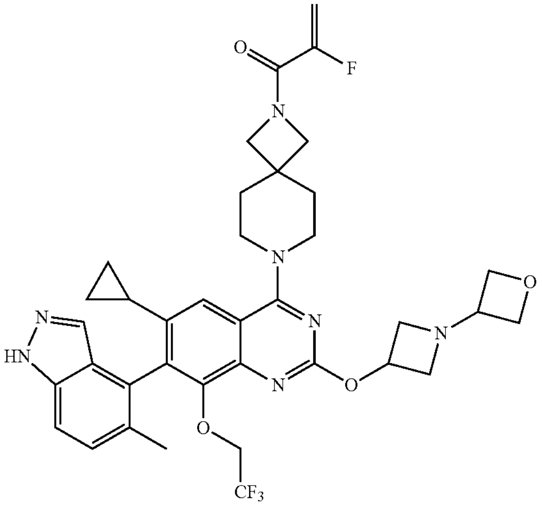 | 722.3 |
| 113 | 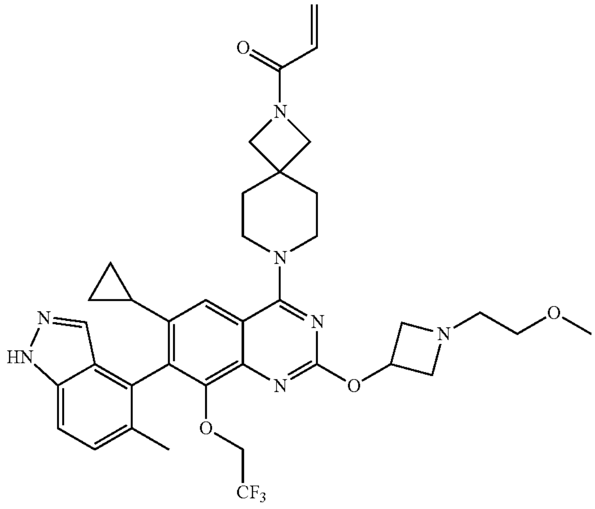 [SMILES: C=CC(=O)N1CC2(CCN(c3nc(OC4CN(CCOC)C4)nc4c(OCC(F)(F)F)c(-c5c(C)ccc6[nH]ncc56)c(C5CC5)cc34)CC2)C1] | 706.3 |
| 114 | 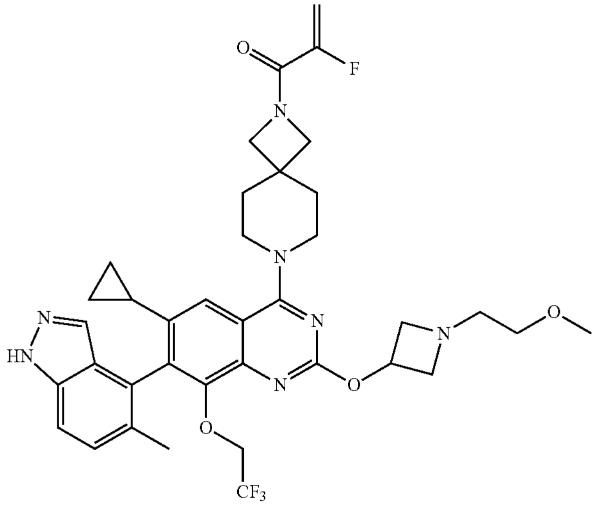 [SMILES: C=C(F)C(=O)N1CC2(CCN(c3nc(OC4CN(CCOC)C4)nc4c(OCC(F)(F)F)c(-c5c(C)ccc6[nH]ncc56)c(C5CC5)cc34)CC2)C1] | 724.3 |

TABLE 1-continued
| Compound | Compound structure | [M + H]+ |
|---|---|---|
| 115 | 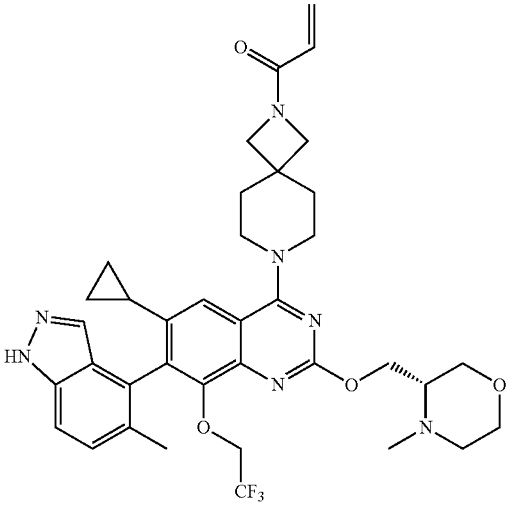 [SMILES: C=CC(=O)N1CC2(CCN(c3nc(OC[C@@H]4COCCN4C)nc4c(OCC(F)(F)F)c(-c5c(C)ccc6[nH]ncc56)c(C5CC5)cc34)CC2)C1] | 706.3 |
| 116 | 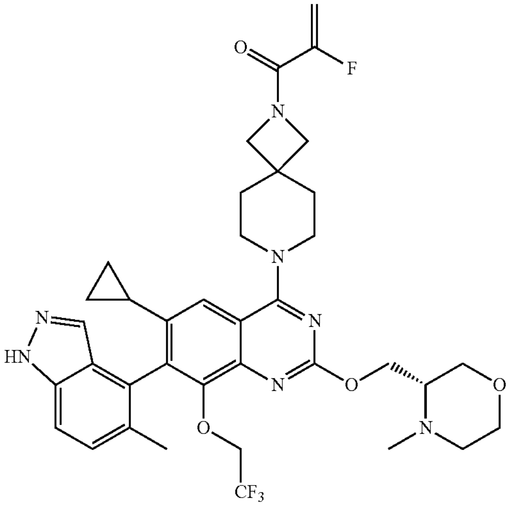 [SMILES: C=C(F)C(=O)N1CC2(CCN(c3nc(OC[C@@H]4COCCN4C)nc4c(OCC(F)(F)F)c(-c5c(C)ccc6[nH]ncc56)c(C5CC5)cc34)CC2)C1] | 723.3 |
| 117 | 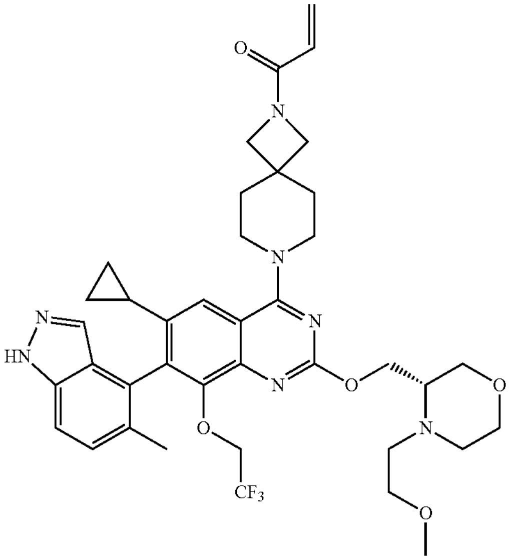 [SMILES: C=CC(=O)N1CC2(CCN(c3nc(OC[C@@H]4COCCN4CCOC)nc4c(OCC(F)(F)F)c(-c5c(C)ccc6[nH]ncc56)c(C5CC5)cc34)CC2)C1] | 750.4 |

TABLE 1-continued
| Compound | Compound structure | [M + H]+ |
|---|---|---|
| 118 | 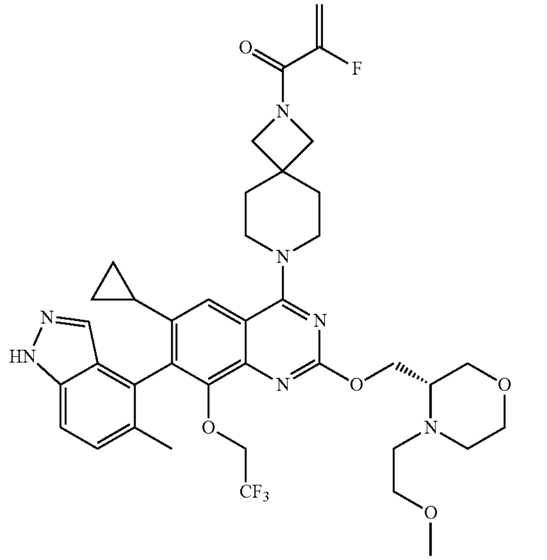 [SMILES: C=C(F)C(=O)N1CC2(CCN(c3nc(OC[C@@H]4COCCN4CCOC)nc4c(OCC(F)(F)F)c(-c5c(C)ccc6[nH]ncc56)c(C5CC5)cc34)CC2)C1] | 768.3 |
| 119 | 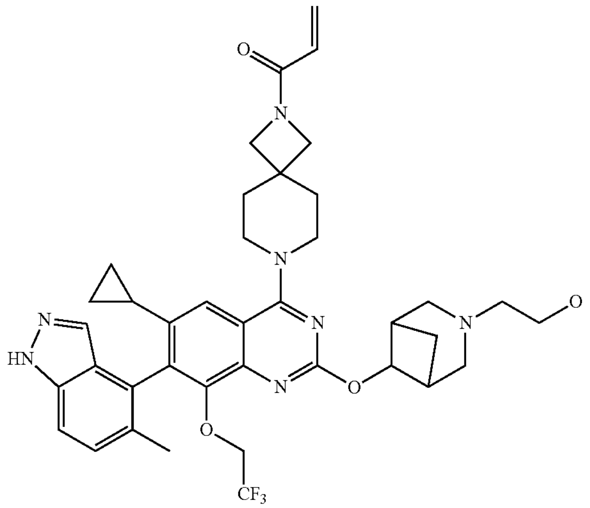 [SMILES: C=CC(=O)N1CC2(CCN(c3nc(OC4C5CC4CN(CCO)C5)nc4c(OCC(F)(F)F)c(-c5c(C)ccc6[nH]ncc56)c(C5CC5)cc34)CC2)C1] | 746.4 |
| 120 | 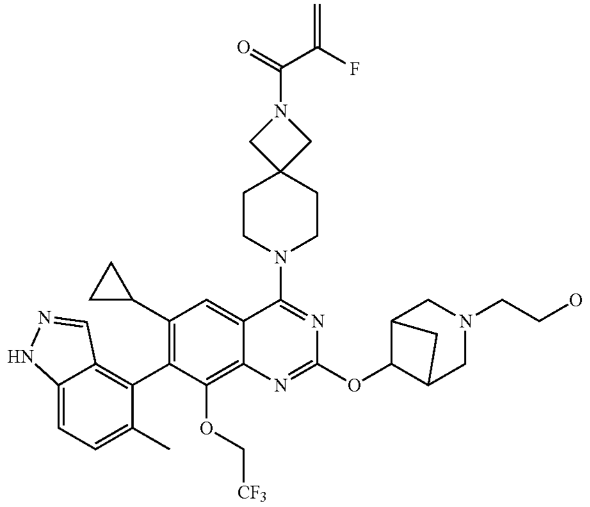 [SMILES: C=C(F)C(=O)N1CC2(CCN(c3nc(OC4C5CC4CN(CCO)C5)nc4c(OCC(F)(F)F)c(-c5c(C)ccc6[nH]ncc56)c(C5CC5)cc34)CC2)C1] | 764.4 |

TABLE 1-continued
| Compound | Compound structure | [M + H]+ |
| --- | --- | --- |
| 121 | 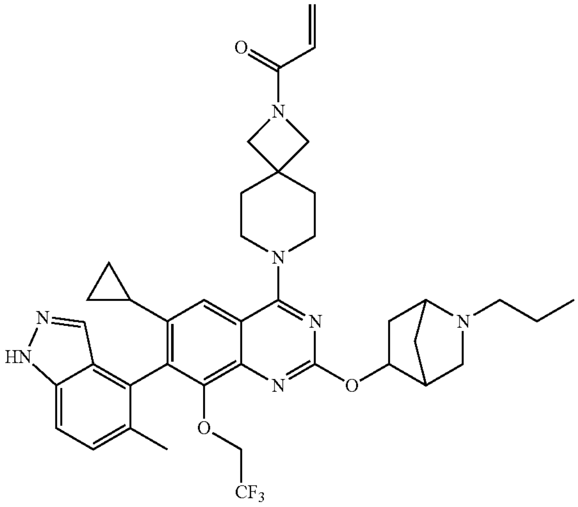 [SMILES: C=CC(=O)N1CC2(CCN(c3nc(OC4CC5CC4CN5CCC)nc4c(OCC(F)(F)F)c(-c5c(C)ccc6[nH]ncc56)c(C5CC5)cc34)CC2)C1] | 746.4 |
| 122 | 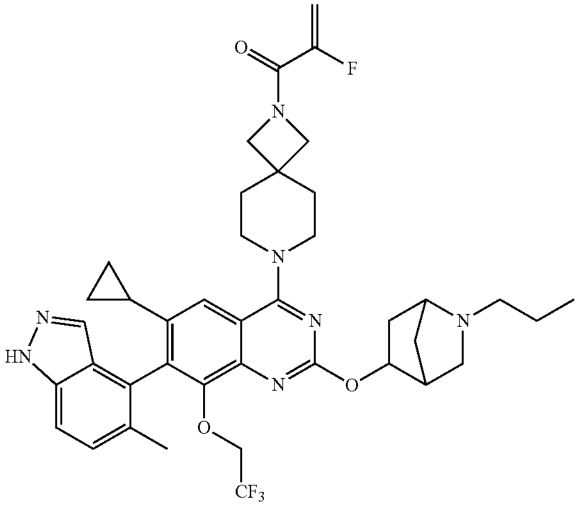 [SMILES: C=C(F)C(=O)N1CC2(CCN(c3nc(OC4CC5CC4CN5CCC)nc4c(OCC(F)(F)F)c(-c5c(C)ccc6[nH]ncc56)c(C5CC5)cc34)CC2)C1] | 764.4 |
| 123 | 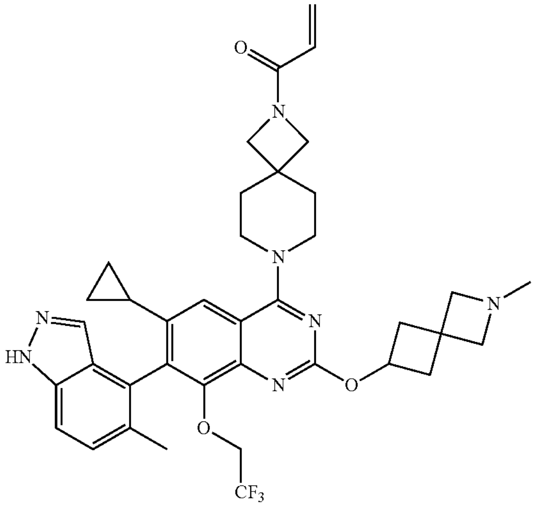 [SMILES: C=CC(=O)N1CC2(CCN(c3nc(OC4CC5(C4)CN(C)C5)nc4c(OCC(F)(F)F)c(-c5c(C)ccc6[nH]ncc56)c(C5CC5)cc34)CC2)C1] | 702.3 |

TABLE 1-continued
| Compound | Compound structure | [M + H]$^+$ |
|---|---|---|
| 124 | 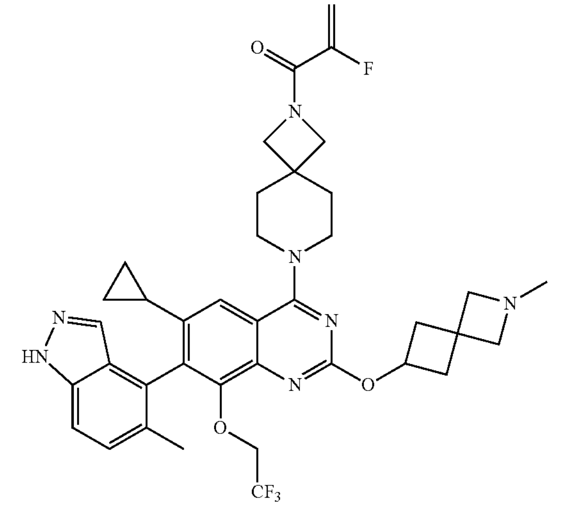 [SMILES: C=C(F)C(=O)N1CC2(CCN(c3nc(OC4CC5(C4)CN(C)C5)nc4c(OCC(F)(F)F)c(-c5c(C)ccc6[nH]ncc56)c(C5CC5)cc34)CC2)C1] | 720.3 |
| 125 | 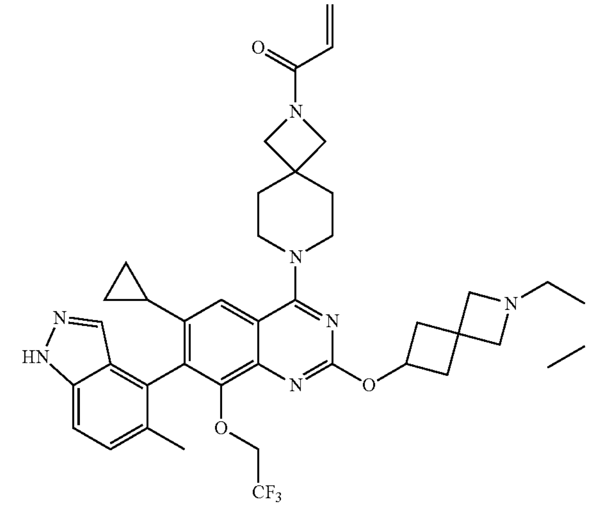 | 746.3 |
| 126 | 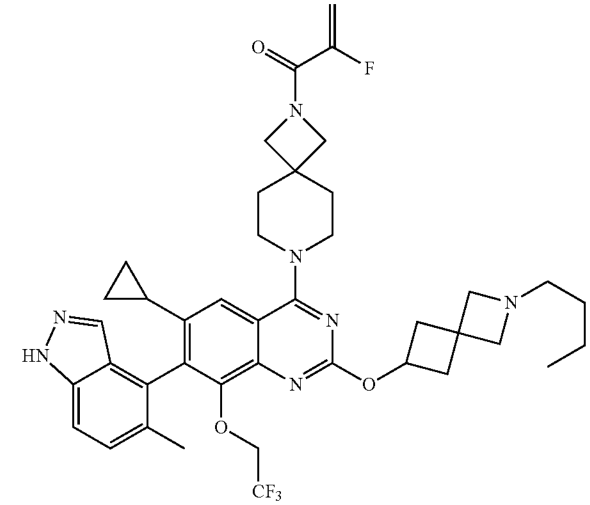 [SMILES: C=C(F)C(=O)N1CC2(CCN(c3nc(OC4CC5(C4)CN(CCCC)C5)nc4c(OCC(F)(F)F)c(-c5c(C)ccc6[nH]ncc56)c(C5CC5)cc34)CC2)C1] | 764.3 |

TABLE 1-continued
| Compound | Compound structure | [M + H]+ |
|---|---|---|
| 127 | 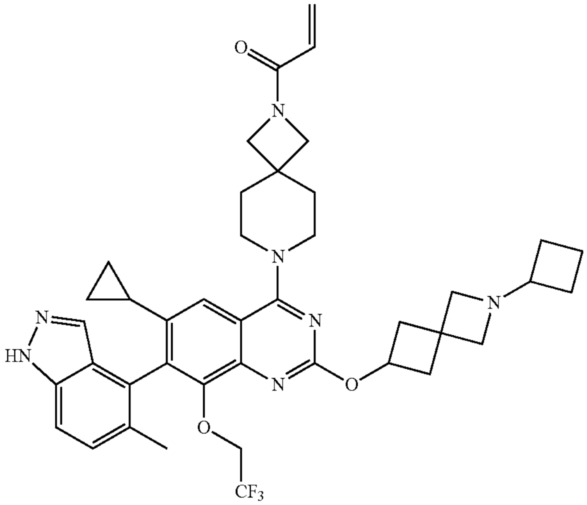 [SMILES: C=CC(=O)N1CC2(CCN(c3nc(OC4CC5(C4)CN(C4CCC4)C5)nc4c(OCC(F)(F)F)c(-c5c(C)ccc6[nH]ncc56)c(C5CC5)cc34)CC2)C1] | 744.3 |
| 128 | 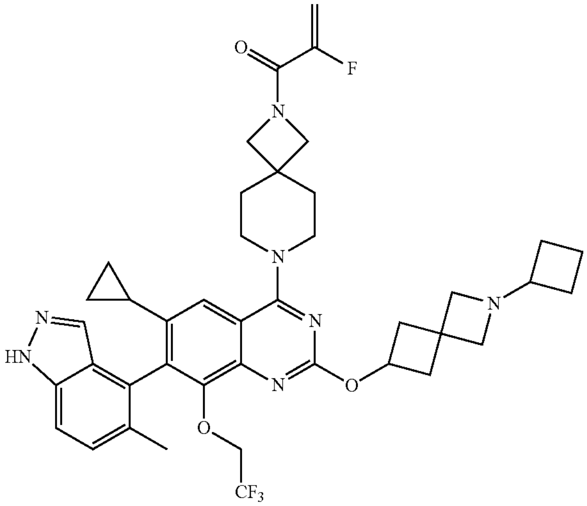 [SMILES: C=C(F)C(=O)N1CC2(CCN(c3nc(OC4CC5(C4)CN(C4CCC4)C5)nc4c(OCC(F)(F)F)c(-c5c(C)ccc6[nH]ncc56)c(C5CC5)cc34)CC2)C1] | 762.3 |
| 129 | 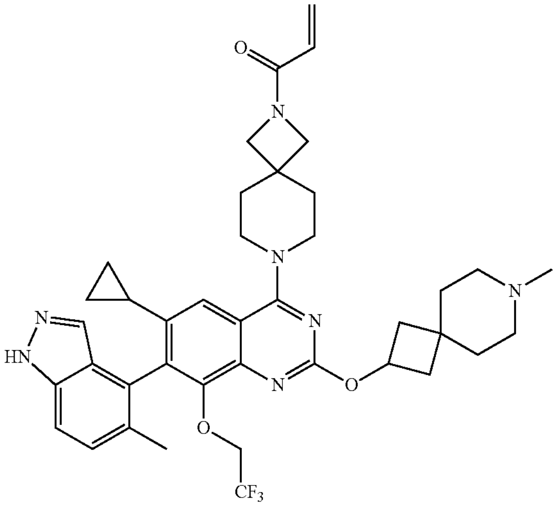 [SMILES: C=CC(=O)N1CC2(CCN(c3nc(OC4CC5(CCN(C)CC5)C4)nc4c(OCC(F)(F)F)c(-c5c(C)ccc6[nH]ncc56)c(C5CC5)cc34)CC2)C1] | 730.4 |

TABLE 1-continued
| Compound | Compound structure | [M + H]$^+$ |
| --- | --- | --- |
| 130 | 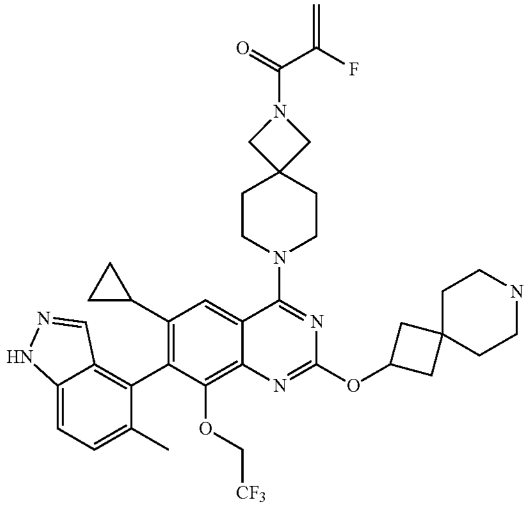 [SMILES: C=C(F)C(=O)N1CC2(CCN(c3nc(OC4CC5(CCNCC5)C4)nc4c(OCC(F)(F)F)c(-c5c(C)ccc6[nH]ncc56)c(C5CC5)cc34)CC2)C1] | 748.4 |
| 131 | 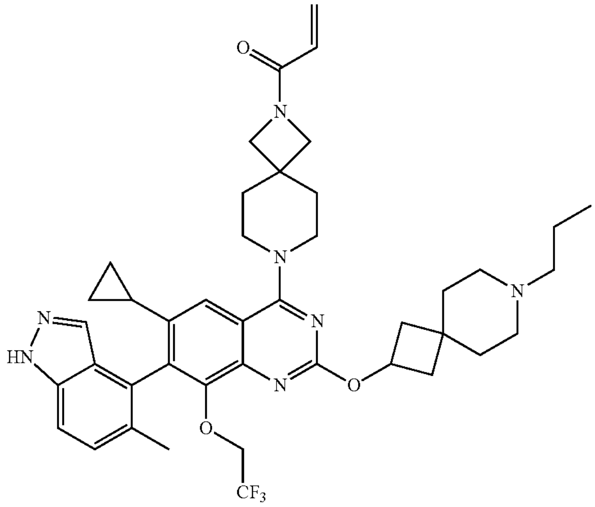 [SMILES: C=CC(=O)N1CC2(CCN(c3nc(OC4CC5(CCN(CCC)CC5)C4)nc4c(OCC(F)(F)F)c(-c5c(C)ccc6[nH]ncc56)c(C5CC5)cc34)CC2)C1] | 774.4 |
| 132 | 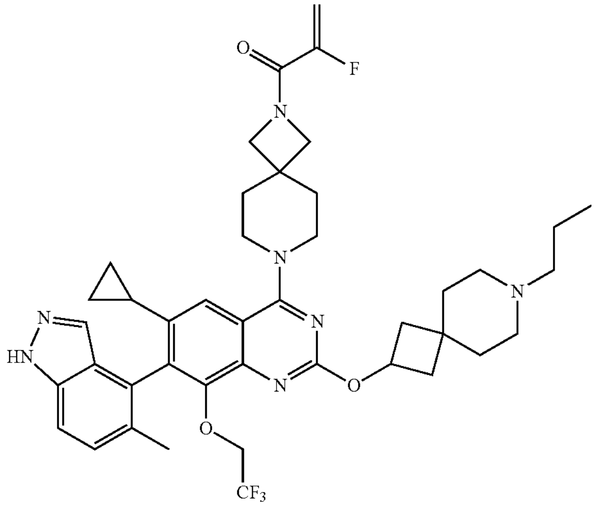 [SMILES: C=C(F)C(=O)N1CC2(CCN(c3nc(OC4CC5(CCN(CCC)CC5)C4)nc4c(OCC(F)(F)F)c(-c5c(C)ccc6[nH]ncc56)c(C5CC5)cc34)CC2)C1] | 792.4 |

TABLE 1-continued
| Compound | Compound structure | [M + H]+ |
|---|---|---|
| 133 | 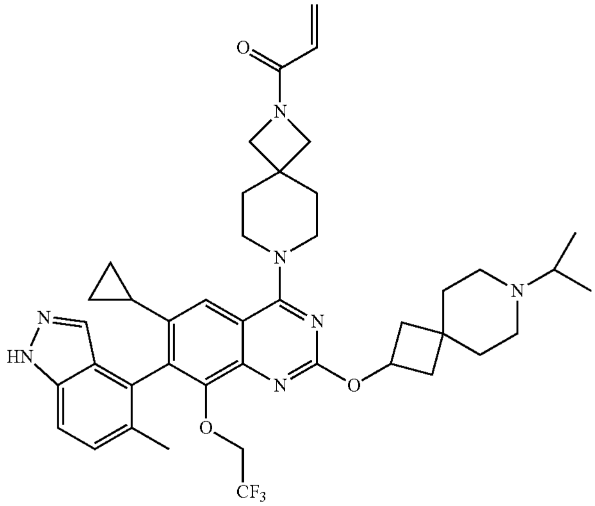 [SMILES: C=CC(=O)N1CC2(CCN(c3nc(OC4CC5(CCN(C(C)C)CC5)C4)nc4c(OCC(F)(F)F)c(-c5c(C)ccc6[nH]ncc56)c(C5CC5)cc34)CC2)C1] | 772.4 |
| 134 | 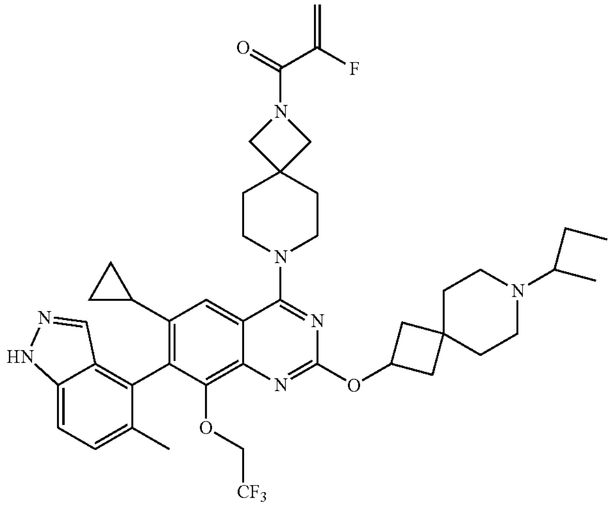 [SMILES: C=C(F)C(=O)N1CC2(CCN(c3nc(OC4CC5(CCN(C(C)CC)CC5)C4)nc4c(OCC(F)(F)F)c(-c5c(C)ccc6[nH]ncc56)c(C5CC5)cc34)CC2)C1] | 790.4 |
| 135 | 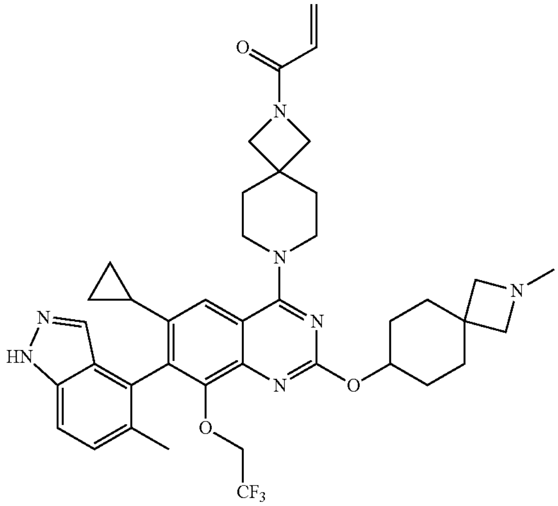 [SMILES: C=CC(=O)N1CC2(CCN(c3nc(OC4CCC5(CC4)CN(C)C5)nc4c(OCC(F)(F)F)c(-c5c(C)ccc6[nH]ncc56)c(C5CC5)cc34)CC2)C1] | 730.4 |

TABLE 1-continued
| Compound | Compound structure | [M + H]$^+$ |
| --- | --- | --- |
| 136 | 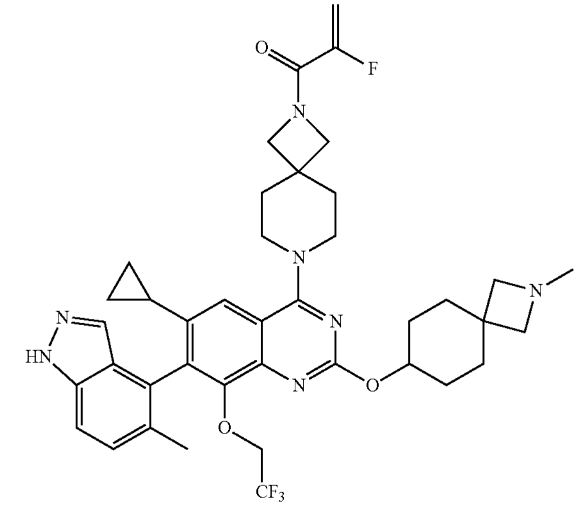 [SMILES: C=C(F)C(=O)N1CC2(CCN(c3nc(OC4CCC5(CC4)CN(C)C5)nc4c(OCC(F)(F)F)c(-c5c(C)ccc6[nH]ncc56)c(C5CC5)cc34)CC2)C1] | 748.4 |
| 137 | 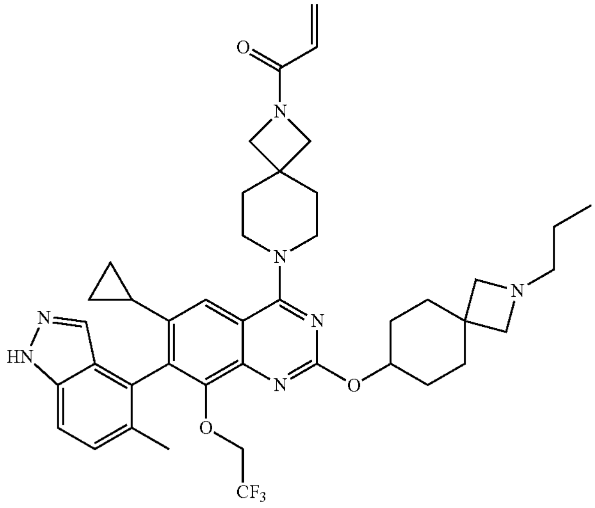 [SMILES: C=CC(=O)N1CC2(CCN(c3nc(OC4CCC5(CC4)CN(CCC)C5)nc4c(OCC(F)(F)F)c(-c5c(C)ccc6[nH]ncc56)c(C5CC5)cc34)CC2)C1] | 773.4 |
| 138 | 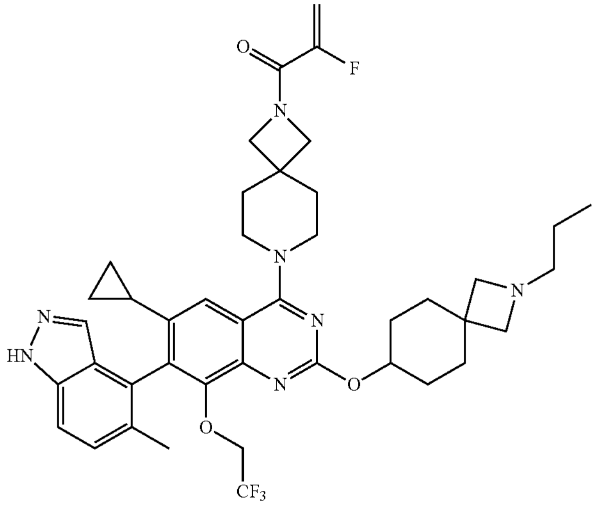 [SMILES: C=C(F)C(=O)N1CC2(CCN(c3nc(OC4CCC5(CC4)CN(CCC)C5)nc4c(OCC(F)(F)F)c(-c5c(C)ccc6[nH]ncc56)c(C5CC5)cc34)CC2)C1] | 792.4 |

TABLE 1-continued
| Compound | Compound structure | [M + H]$^+$ |
| --- | --- | --- |
| 139 | 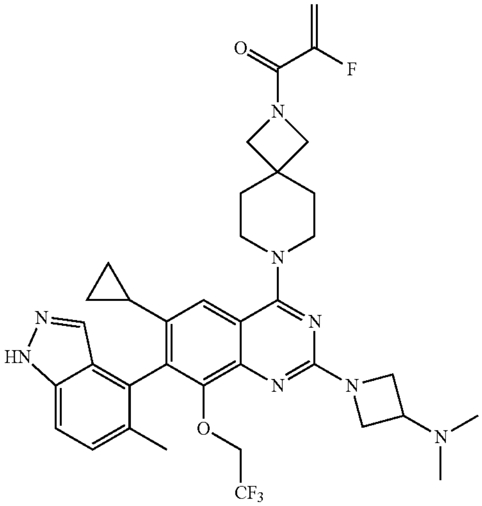 [SMILES: C=C(F)C(=O)N1CC2(CCN(c3nc(N4CC(N(C)C)C4)nc4c(OCC(F)(F)F)c(-c5c(C)ccc6[nH]ncc56)c(C5CC5)cc34)CC2)C1] | 693.3 |
| 140 | 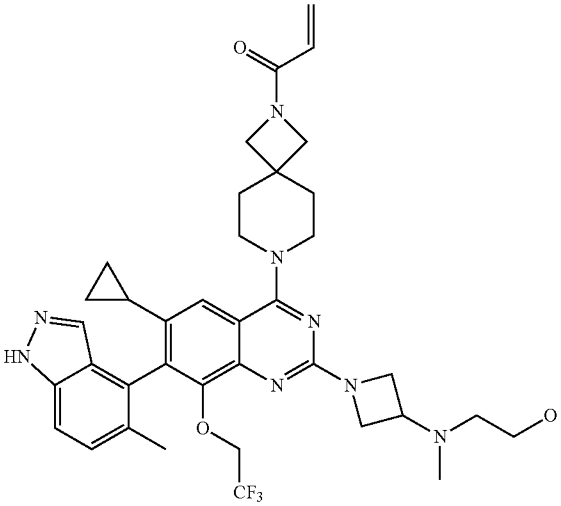 [SMILES: C=CC(=O)N1CC2(CCN(c3nc(N4CC(N(C)CCO)C4)nc4c(OCC(F)(F)F)c(-c5c(C)ccc6[nH]ncc56)c(C5CC5)cc34)CC2)C1] | 719.4 |
| 141 | 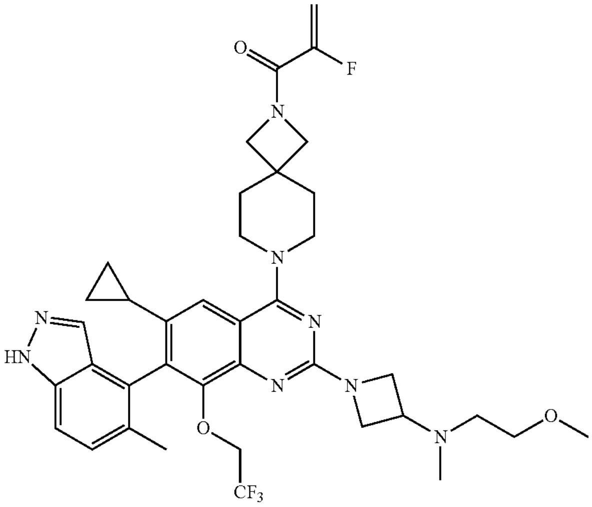 [SMILES: C=C(F)C(=O)N1CC2(CCN(c3nc(N4CC(N(C)CCOC)C4)nc4c(OCC(F)(F)F)c(-c5c(C)ccc6[nH]ncc56)c(C5CC5)cc34)CC2)C1] | 737.3 |

TABLE 1-continued
| Compound | Compound structure | [M + H]$^+$ |
|---|---|---|
| 142 | 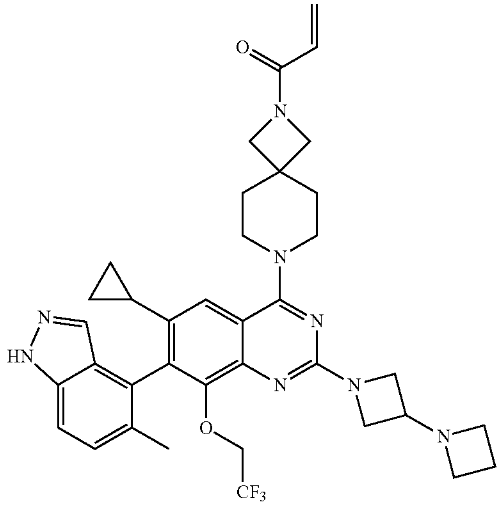 [SMILES: C=CC(=O)N1CC2(CCN(c3nc(N4CC(N5CCC5)C4)nc4c(OCC(F)(F)F)c(-c5c(C)ccc6[nH]ncc56)c(C5CC5)cc34)CC2)C1] | 687.3 |
| 143 | 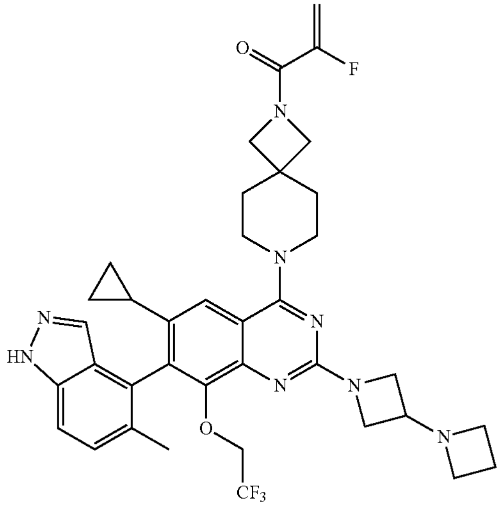 [SMILES: C=C(F)C(=O)N1CC2(CCN(c3nc(N4CC(N5CCC5)C4)nc4c(OCC(F)(F)F)c(-c5c(C)ccc6[nH]ncc56)c(C5CC5)cc34)CC2)C1] | 705.3 |
| 144 | 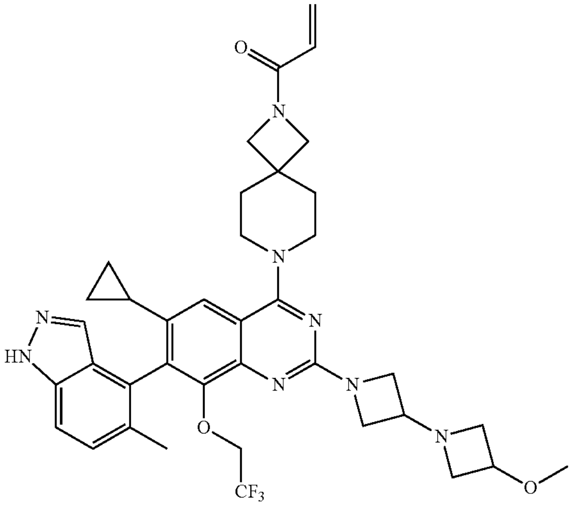 [SMILES: C=CC(=O)N1CC2(CCN(c3nc(N4CC(N5CC(OC)C5)C4)nc4c(OCC(F)(F)F)c(-c5c(C)ccc6[nH]ncc56)c(C5CC5)cc34)CC2)C1] | 717.3 |

TABLE 1-continued
| Compound | Compound structure | [M + H]+ |
| --- | --- | --- |
| 145 | 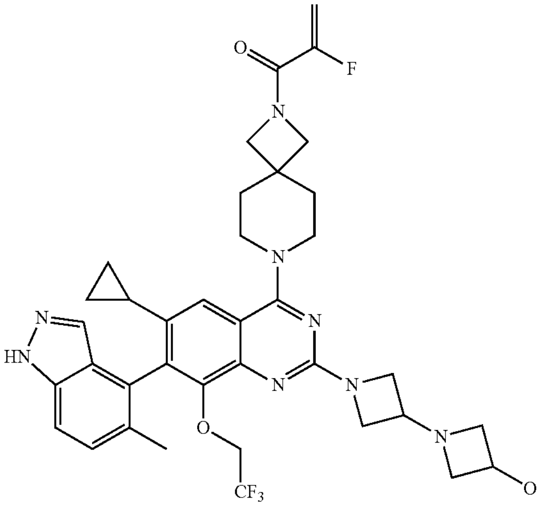 [SMILES: C=C(F)C(=O)N1CC2(CCN(c3nc(N4CC(N5CC(O)C5)C4)nc4c(OCC(F)(F)F)c(-c5c(C)ccc6[nH]ncc56)c(C5CC5)cc34)CC2)C1] | 735.3 |
| 146 | 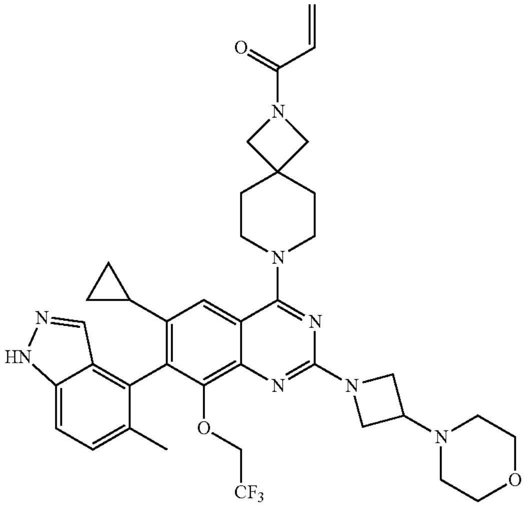 [SMILES: C=CC(=O)N1CC2(CCN(c3nc(N4CC(N5CCOCC5)C4)nc4c(OCC(F)(F)F)c(-c5c(C)ccc6[nH]ncc56)c(C5CC5)cc34)CC2)C1] | 717.3 |
| 147 | 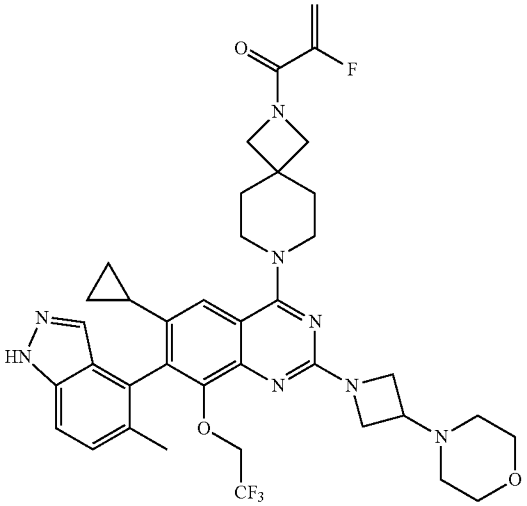 [SMILES: C=C(F)C(=O)N1CC2(CCN(c3nc(N4CC(N5CCOCC5)C4)nc4c(OCC(F)(F)F)c(-c5c(C)ccc6[nH]ncc56)c(C5CC5)cc34)CC2)C1] | 735.3 |

TABLE 1-continued
| Compound | Compound structure | [M + H]+ |
|---|---|---|
| 148 | 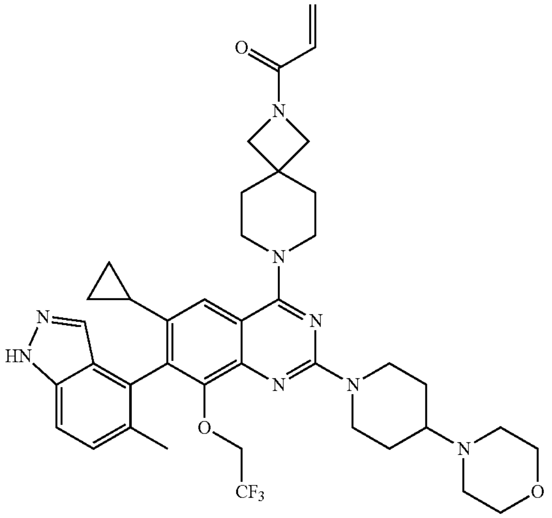 | 745.4 |
| 149 | 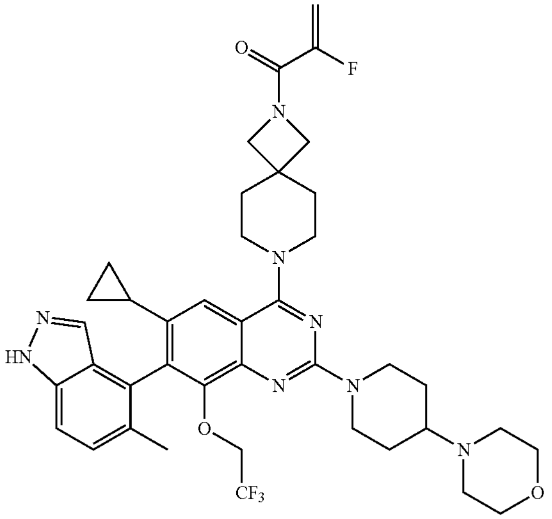 | 763.4 |
| 150 | 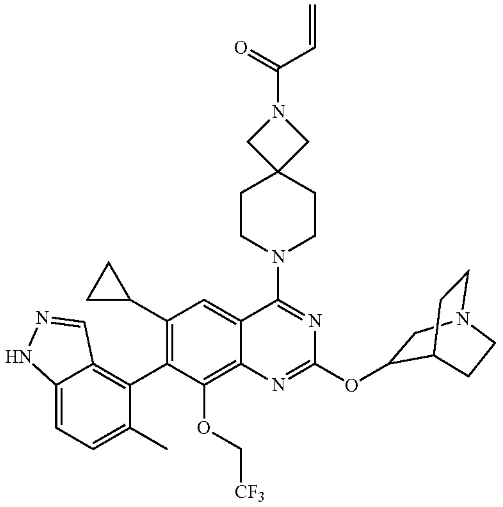 [SMILES: C=CC(=O)N1CC2(CCN(c3nc(OC4CN5CCC4CC5)nc4c(OCC(F)(F)F)c(-c5c(C)ccc6[nH]ncc56)c(C5CC5)cc34)CC2)C1] | 702.3 |

TABLE 1-continued
| Compound | Compound structure | [M + H]+ |
|---|---|---|
| 151 | 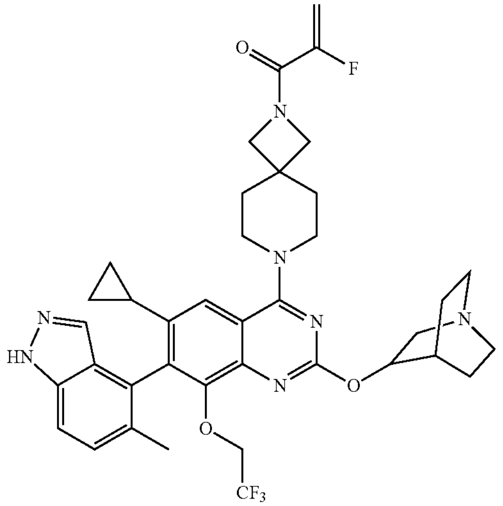 [SMILES: C=C(F)C(=O)N1CC2(CCN(c3nc(OC4CN5CCC4CC5)nc4c(OCC(F)(F)F)c(-c5c(C)ccc6[nH]ncc56)c(C5CC5)cc34)CC2)C1] | 720.3 |
| 152 | 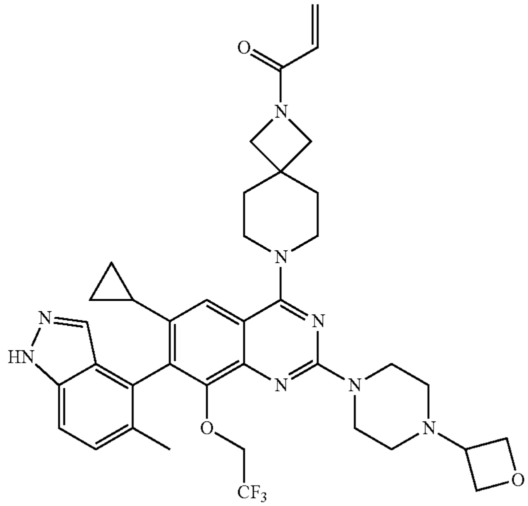 [SMILES: C=CC(=O)N1CC2(CCN(c3nc(N4CCN(C5COC5)CC4)nc4c(OCC(F)(F)F)c(-c5c(C)ccc6[nH]ncc56)c(C5CC5)cc34)CC2)C1] | 717.3 |
| 153 | 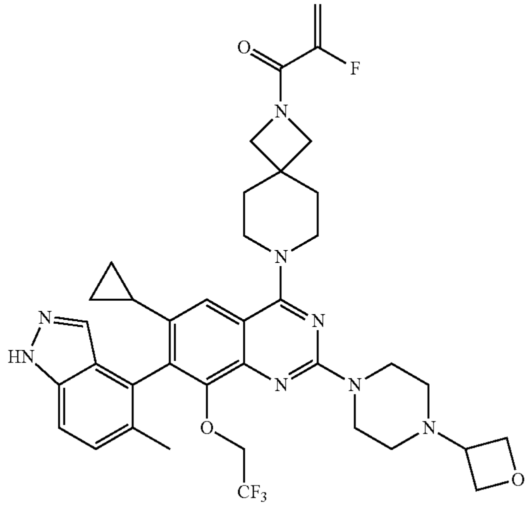 [SMILES: C=C(F)C(=O)N1CC2(CCN(c3nc(N4CCN(C5COC5)CC4)nc4c(OCC(F)(F)F)c(-c5c(C)ccc6[nH]ncc56)c(C5CC5)cc34)CC2)C1] | 735.3 |

TABLE 1-continued
| Compound | Compound structure | [M + H]+ |
|---|---|---|
| 154 | 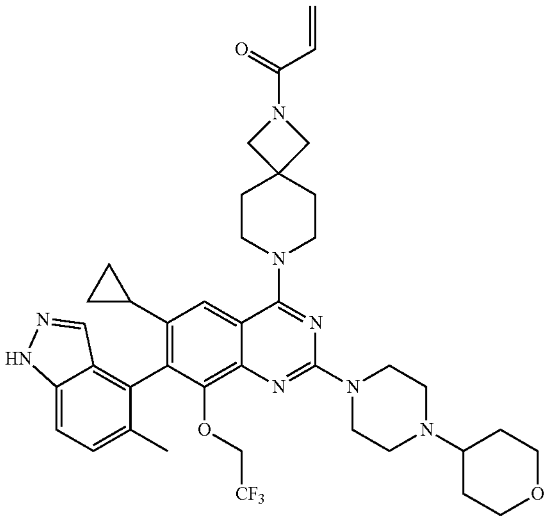 [SMILES: C=CC(=O)N1CC2(CCN(c3nc(N4CCN(C5CCOCC5)CC4)nc4c(OCC(F)(F)F)c(-c5c(C)ccc6[nH]ncc56)c(C5CC5)cc34)CC2)C1] | 745.4 |
| 155 | 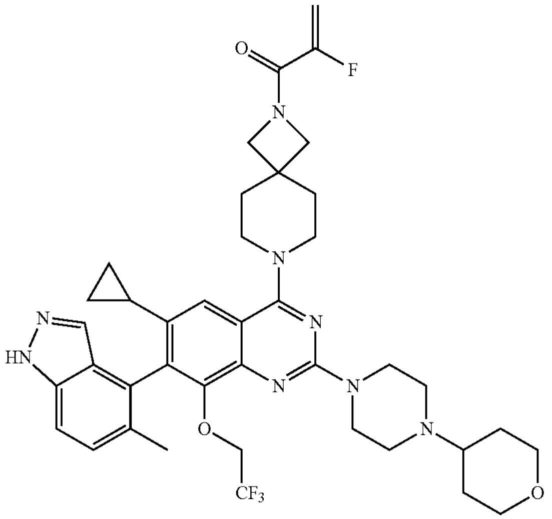 [SMILES: C=C(F)C(=O)N1CC2(CCN(c3nc(N4CCN(C5CCOCC5)CC4)nc4c(OCC(F)(F)F)c(-c5c(C)ccc6[nH]ncc56)c(C5CC5)cc34)CC2)C1] | 763.4 |
| 156 | 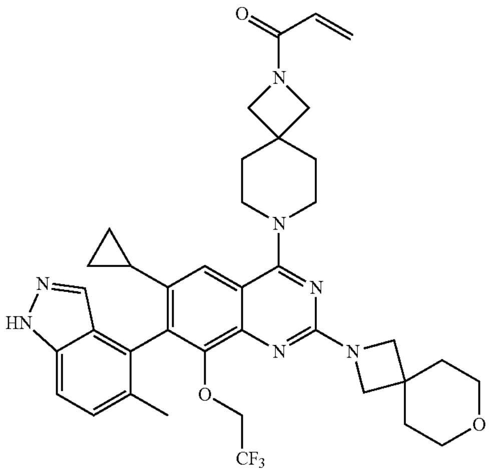 [SMILES: C=CC(=O)N1CC2(CCN(c3nc(N4CC5(CCOCC5)C4)nc4c(OCC(F)(F)F)c(-c5c(C)ccc6[nH]ncc56)c(C5CC5)cc34)CC2)C1] | 702.3 |

TABLE 1-continued
| Compound | Compound structure | [M + H]+ |
| --- | --- | --- |
| 157 | 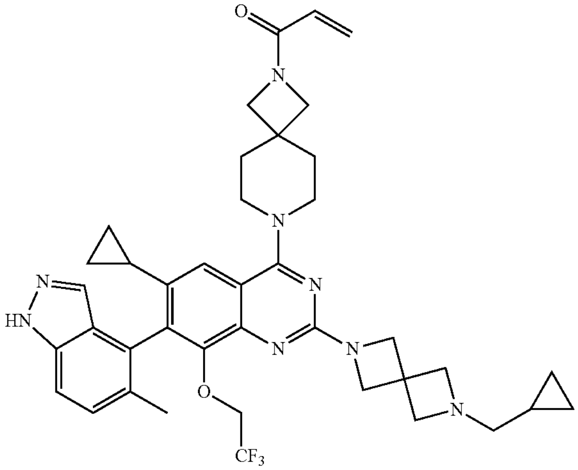 [SMILES: C=CC(=O)N1CC2(CCN(c3nc(N4CC5(CN(CC6CC6)C5)C4)nc4c(OCC(F)(F)F)c(-c5c(C)ccc6[nH]ncc56)c(C5CC5)cc34)CC2)C1] | 727.4 |
| 158 | 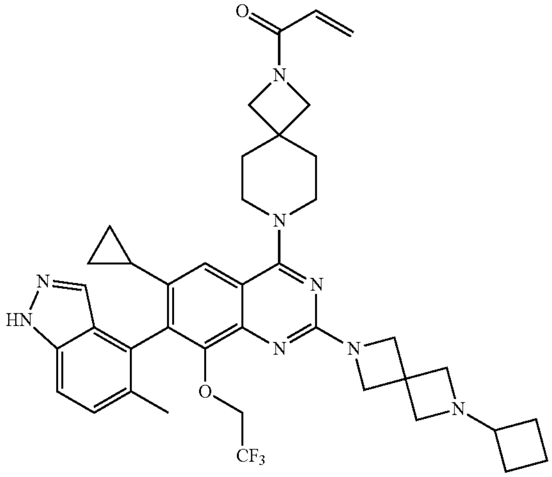 [SMILES: C=CC(=O)N1CC2(CCN(c3nc(N4CC5(C4)CN(C4CCC4)C5)nc4c(OCC(F)(F)F)c(-c5c(C)ccc6[nH]ncc56)c(C5CC5)cc34)CC2)C1] | 729.3 |
| 159 | 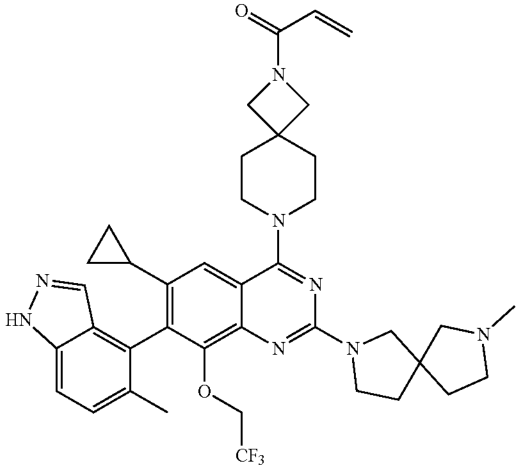 [SMILES: C=CC(=O)N1CC2(CCN(c3nc(N4CCC5(CCN(C)C5)C4)nc4c(OCC(F)(F)F)c(-c5c(C)ccc6[nH]ncc56)c(C5CC5)cc34)CC2)C1] | 715.4 |

TABLE 1-continued
| Compound | Compound structure | [M + H]+ |
| --- | --- | --- |
| 160 | 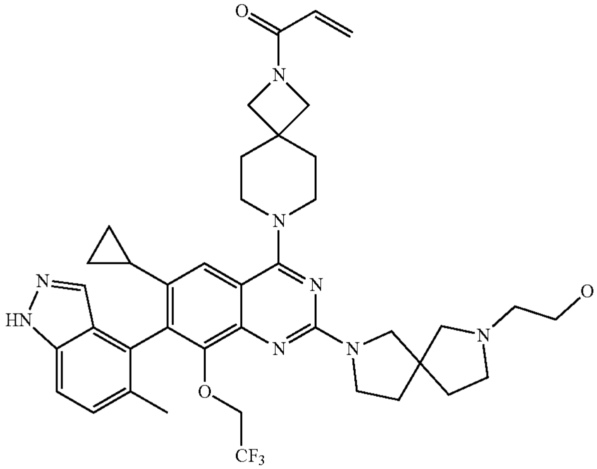 [SMILES: C=CC(=O)N1CC2(CCN(c3nc(N4CCC5(CCN(CCO)C5)C4)nc4c(OCC(F)(F)F)c(-c5c(C)ccc6[nH]ncc56)c(C5CC5)cc34)CC2)C1] | 759.4 |
| 161 | 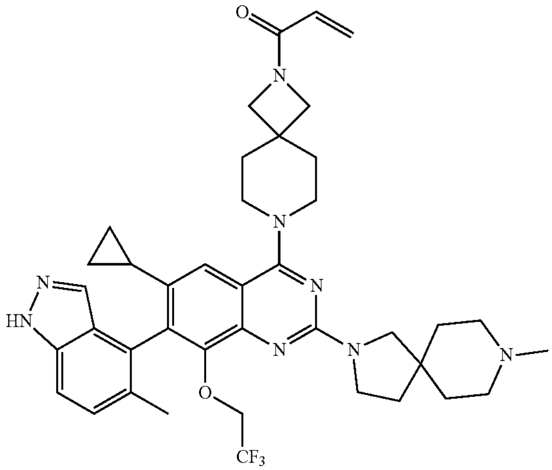 [SMILES: C=CC(=O)N1CC2(CCN(c3nc(N4CCC5(CCN(C)CC5)C4)nc4c(OCC(F)(F)F)c(-c5c(C)ccc6[nH]ncc56)c(C5CC5)cc34)CC2)C1] | 729.4 |
| 162 | 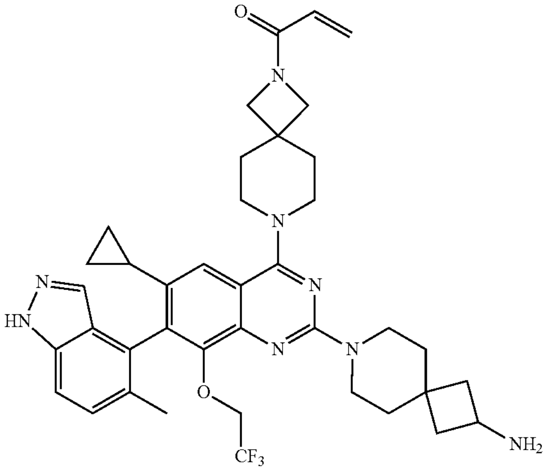 [SMILES: C=CC(=O)N1CC2(CCN(c3nc(N4CCC5(CC4)CC(N)C5)nc4c(OCC(F)(F)F)c(-c5c(C)ccc6[nH]ncc56)c(C5CC5)cc34)CC2)C1] | 715.4 |

TABLE 1-continued
| Compound | Compound structure | [M + H]+ |
|---|---|---|
| 163 | 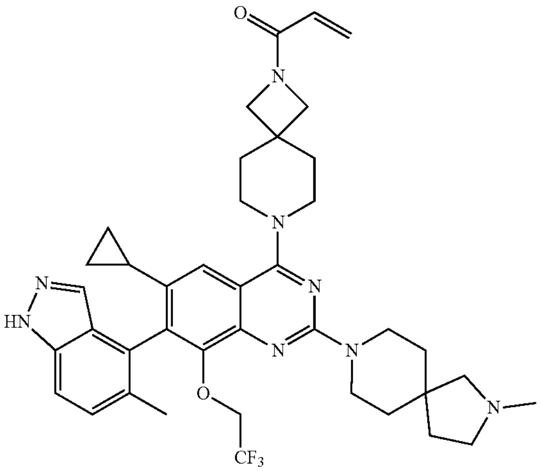 [SMILES: C=CC(=O)N1CC2(CCN(c3nc(N4CCC5(CCN(C)C5)CC4)nc4c(OCC(F)(F)F)c(-c5c(C)ccc6[nH]ncc56)c(C5CC5)cc34)CC2)C1] | 729.4 |
| 164 | 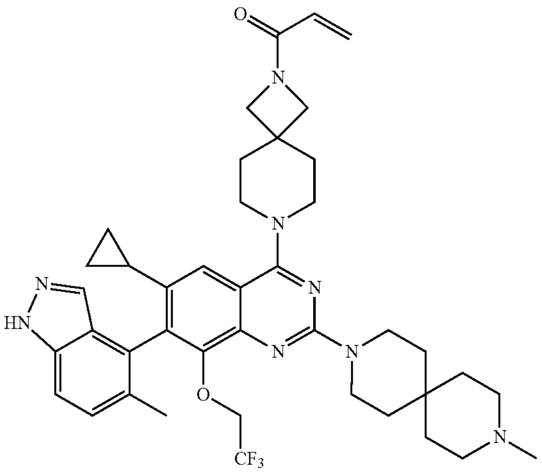 [SMILES: C=CC(=O)N1CC2(CCN(c3nc(N4CCC5(CCN(C)CC5)CC4)nc4c(OCC(F)(F)F)c(-c5c(C)ccc6[nH]ncc56)c(C5CC5)cc34)CC2)C1] | 743.4 |
| 165 | 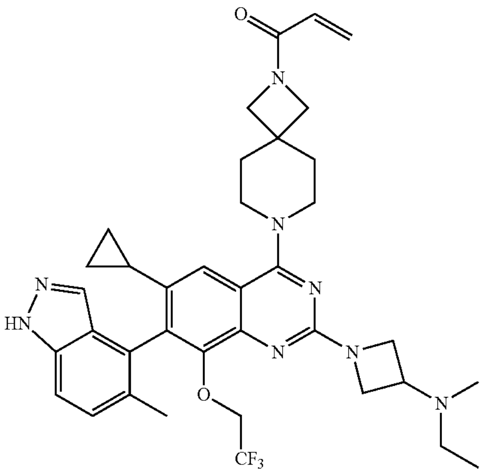 [SMILES: C=CC(=O)N1CC2(CCN(c3nc(N4CC(N(C)CC)C4)nc4c(OCC(F)(F)F)c(-c5c(C)ccc6[nH]ncc56)c(C5CC5)cc34)CC2)C1] | 689.3 |

TABLE 1-continued
| Compound | Compound structure | [M + H]$^+$ |
|---|---|---|
| 166 | 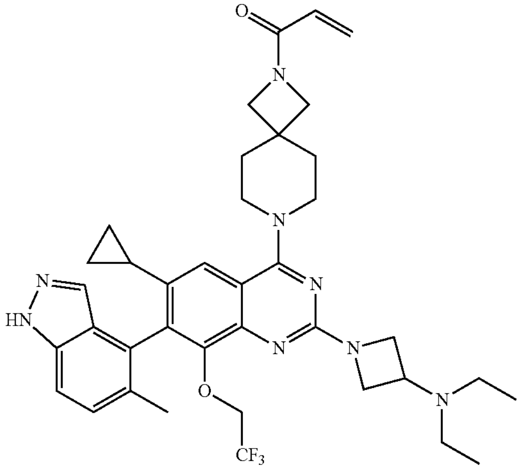 [SMILES: C=CC(=O)N1CC2(CCN(c3nc(N4CC(N(CC)CC)C4)nc4c(OCC(F)(F)F)c(-c5c(C)ccc6[nH]ncc56)c(C5CC5)cc34)CC2)C1] | 703.4 |
| 167 | 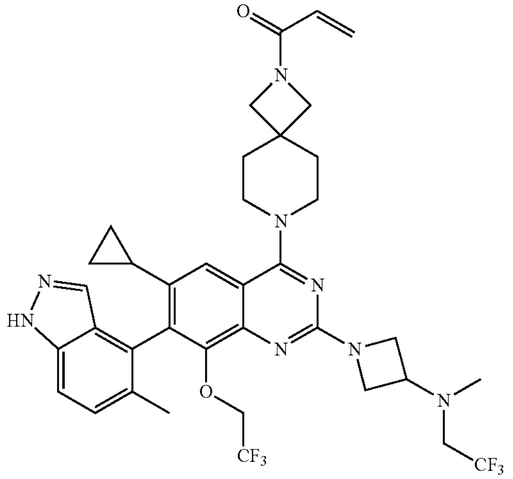 [SMILES: C=CC(=O)N1CC2(CCN(c3nc(N4CC(N(C)CC(F)(F)F)C4)nc4c(OCC(F)(F)F)c(-c5c(C)ccc6[nH]ncc56)c(C5CC5)cc34)CC2)C1] | 743.3 |
| 168 | 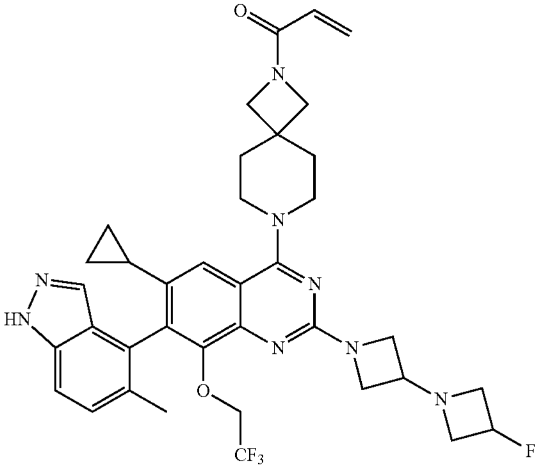 [SMILES: C=CC(=O)N1CC2(CCN(c3nc(N4CC(N5CC(F)C5)C4)nc4c(OCC(F)(F)F)c(-c5c(C)ccc6[nH]ncc56)c(C5CC5)cc34)CC2)C1] | 705.3 |

TABLE 1-continued
| Compound | Compound structure | [M + H]+ |
|---|---|---|
| 169 | 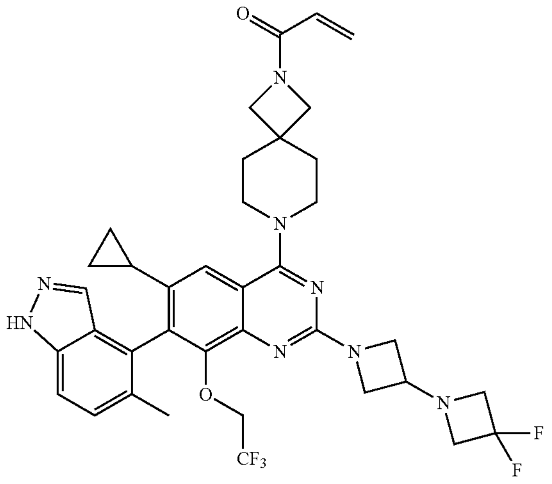 [SMILES: C=CC(=O)N1CC2(CCN(c3nc(N4CC(N5CC(F)(F)C5)C4)nc4c(OCC(F)(F)F)c(-c5c(C)ccc6[nH]ncc56)c(C5CC5)cc34)CC2)C1] | 723.3 |
| 170 | 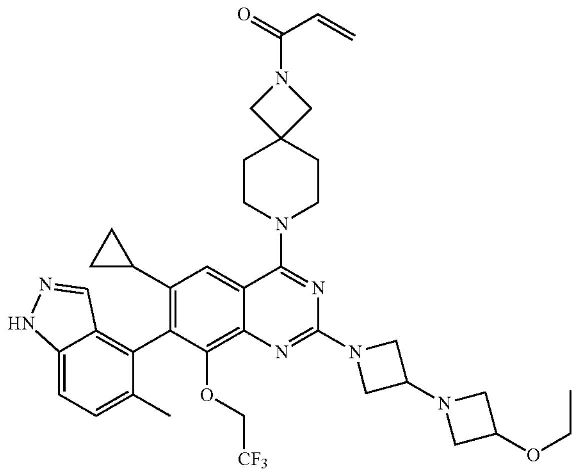 [SMILES: C=CC(=O)N1CC2(CCN(c3nc(N4CC(N5CC(OCC)C5)C4)nc4c(OCC(F)(F)F)c(-c5c(C)ccc6[nH]ncc56)c(C5CC5)cc34)CC2)C1] | 731.4 |
| 171 | 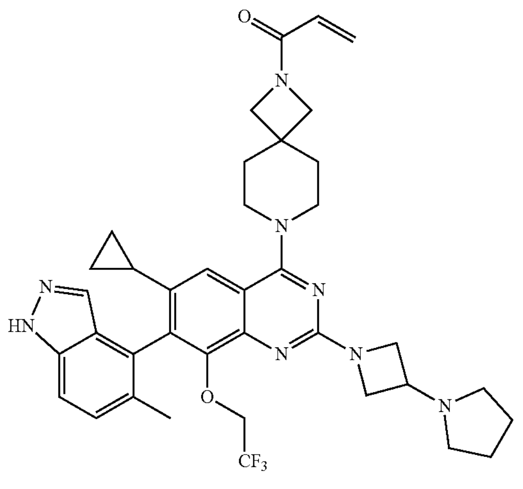 [SMILES: C=CC(=O)N1CC2(CCN(c3nc(N4CC(N5CCCC5)C4)nc4c(OCC(F)(F)F)c(-c5c(C)ccc6[nH]ncc56)c(C5CC5)cc34)CC2)C1] | 700.4 |

TABLE 1-continued
| Compound | Compound structure | [M + H]+ |
| --- | --- | --- |
| 172 | 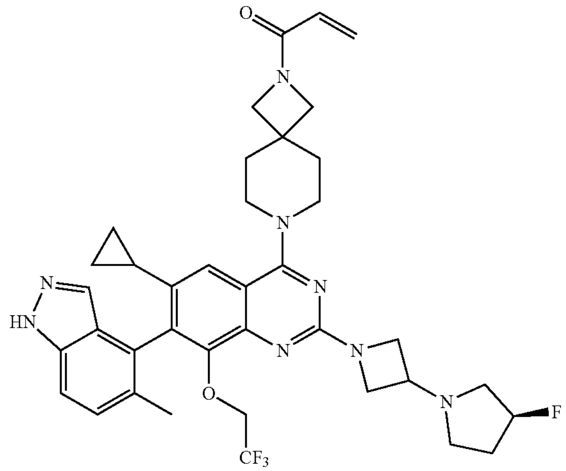 [SMILES: C=CC(=O)N1CC2(CCN(c3nc(N4CC(N5CC[C@H](F)C5)C4)nc4c(OCC(F)(F)F)c(-c5c(C)ccc6[nH]ncc56)c(C5CC5)cc34)CC2)C1] | 719.3 |
| 173 | 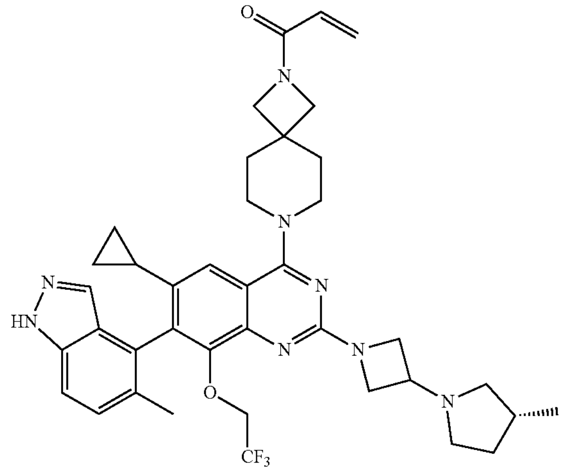 | 719.3 |
| 174 | 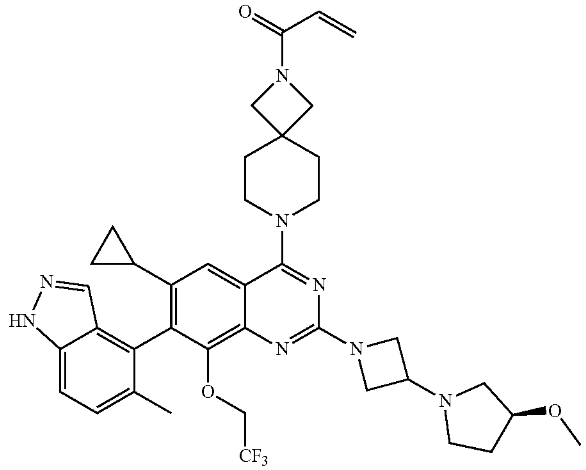 [SMILES: C=CC(=O)N1CC2(CCN(c3nc(N4CC(N5CC[C@H](OC)C5)C4)nc4c(OCC(F)(F)F)c(-c5c(C)ccc6[nH]ncc56)c(C5CC5)cc34)CC2)C1] | 731.4 |

TABLE 1-continued
| Compound | Compound structure | [M + H]+ |
| --- | --- | --- |
| 175 | 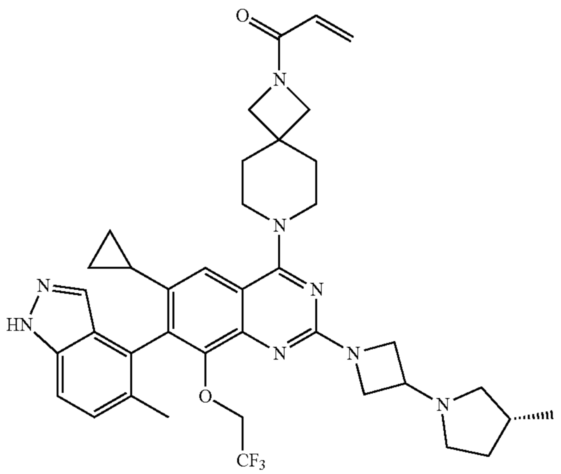 [SMILES: C=CC(=O)N1CC2(CCN(c3nc(N4CC(N5CC[C@@H](C)C5)C4)nc4c(OCC(F)(F)F)c(-c5c(C)ccc6[nH]ncc56)c(C5CC5)cc34)CC2)C1] | 731.4 |
| 176 | 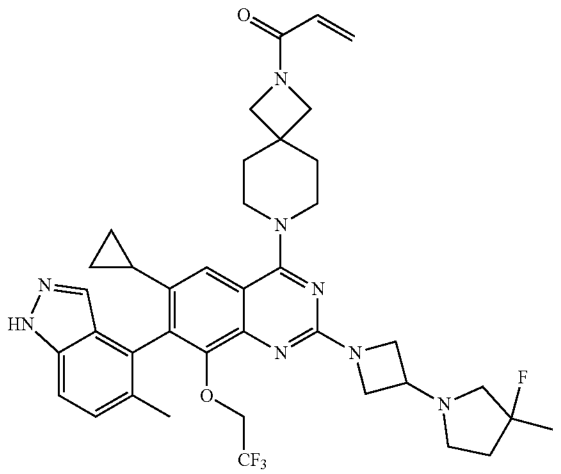 [SMILES: C=CC(=O)N1CC2(CCN(c3nc(N4CC(N5CCC(C)(F)C5)C4)nc4c(OCC(F)(F)F)c(-c5c(C)ccc6[nH]ncc56)c(C5CC5)cc34)CC2)C1] | 737.3 |
| 177 | 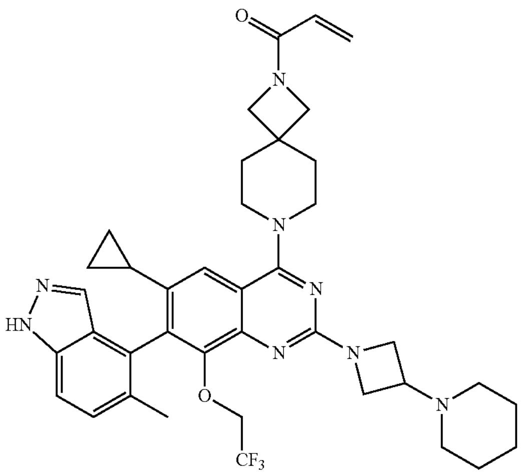 [SMILES: C=CC(=O)N1CC2(CCN(c3nc(N4CC(N5CCCCC5)C4)nc4c(OCC(F)(F)F)c(-c5c(C)ccc6[nH]ncc56)c(C5CC5)cc34)CC2)C1] | 715.4 |

TABLE 1-continued
| Compound | Compound structure | [M + H]+ |
| --- | --- | --- |
| 178 | 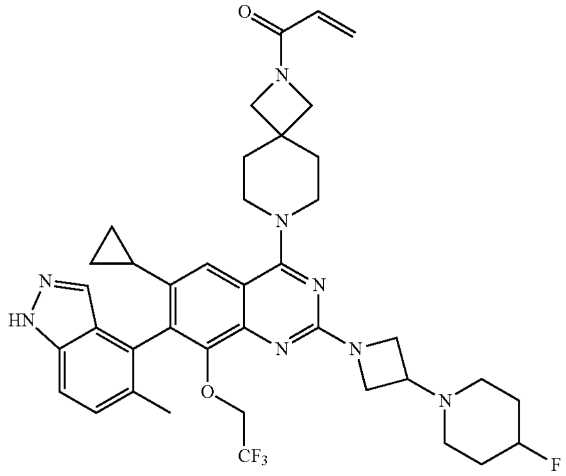 [SMILES: C=CC(=O)N1CC2(CCN(c3nc(N4CC(N5CCC(O)CC5)C4)nc4c(OCC(F)(F)F)c(-c5c(C)ccc6[nH]ncc56)c(C5CC5)cc34)CC2)C1] | 733.3 |
| 179 | 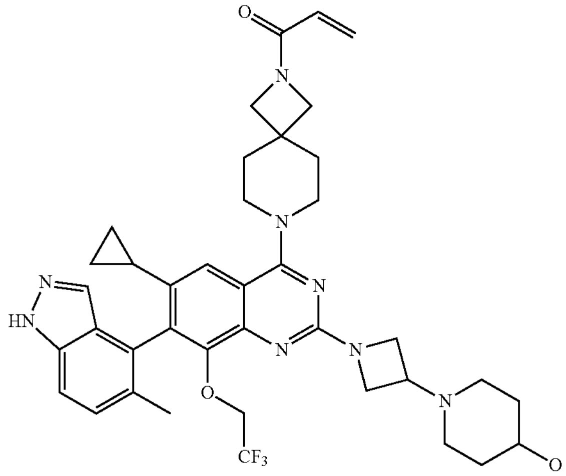 | 745.4 |
| 180 | 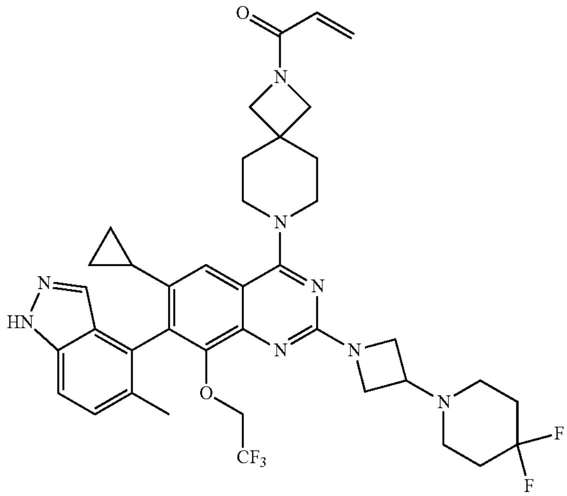 [SMILES: C=CC(=O)N1CC2(CCN(c3nc(N4CC(N5CCC(F)(F)CC5)C4)nc4c(OCC(F)(F)F)c(-c5c(C)ccc6[nH]ncc56)c(C5CC5)cc34)CC2)C1] | 751.3 |

TABLE 1-continued
| Compound | Compound structure | [M + H]+ |
|---|---|---|
| 181 | 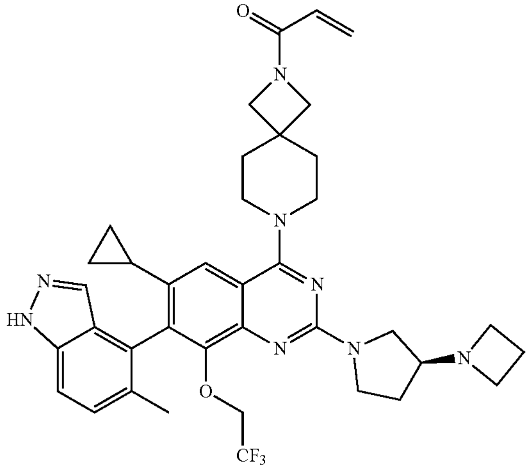 [SMILES: C=CC(=O)N1CC2(CCN(c3nc(N4CC[C@H](N5CCC5)C4)nc4c(OCC(F)(F)F)c(-c5c(C)ccc6[nH]ncc56)c(C5CC5)cc34)CC2)C1] | 700.4 |
| 182 | 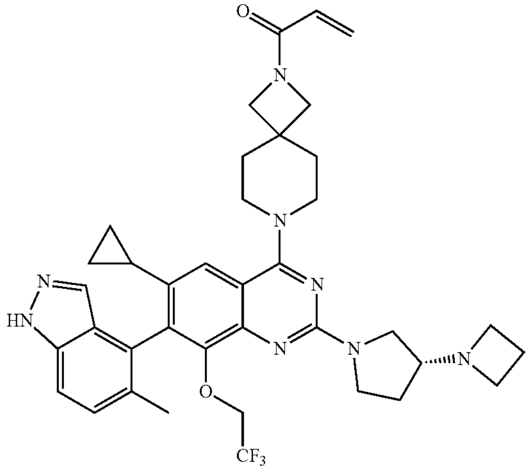 [SMILES: C=CC(=O)N1CC2(CCN(c3nc(N4CC[C@@H](N5CCC5)C4)nc4c(OCC(F)(F)F)c(-c5c(C)ccc6[nH]ncc56)c(C5CC5)cc34)CC2)C1] | 700.4 |
| 183 | 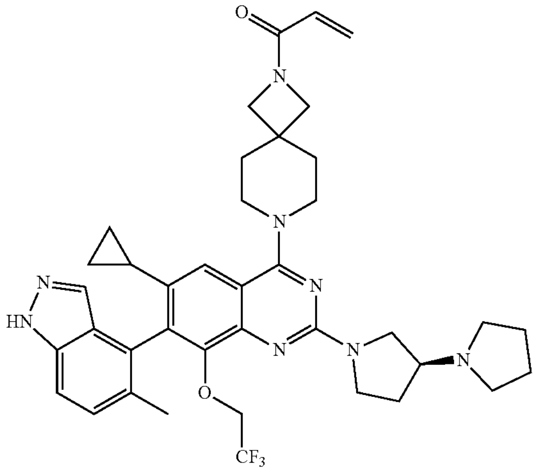 | 715.4 |

TABLE 1-continued
| Compound | Compound structure | [M + H]+ |
|---|---|---|
| 184 | 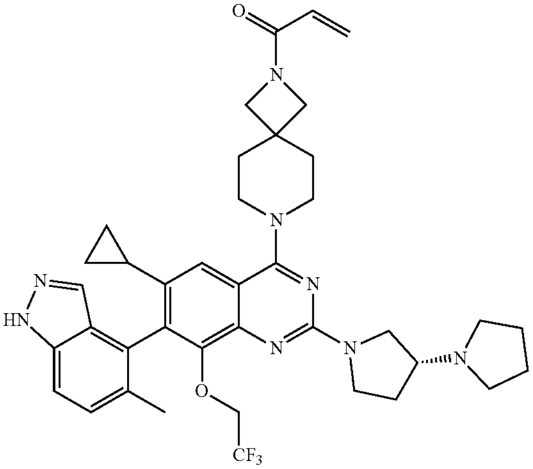 [SMILES: C=CC(=O)N1CC2(CCN(c3nc(N4CC[C@@H](N5CCCC5)C4)nc4c(OCC(F)(F)F)c(-c5c(C)ccc6[nH]ncc56)c(C5CC5)cc34)CC2)C1] | 715.4 |
| 185 | 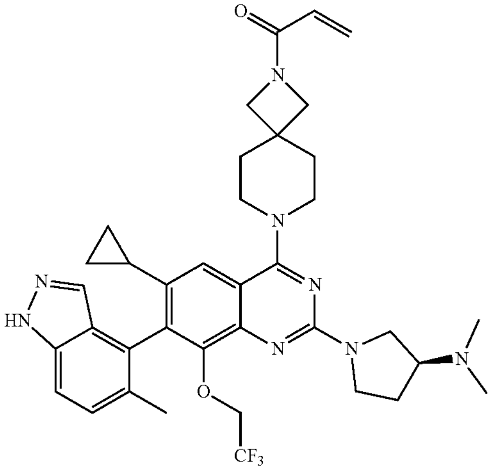 | 689.4 |
| 186 | 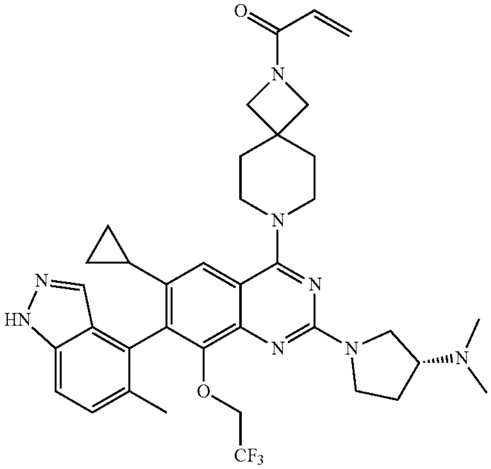 [SMILES: C=CC(=O)N1CC2(CCN(c3nc(N4CC[C@@H](N(C)C)C4)nc4c(OCC(F)(F)F)c(-c5c(C)ccc6[nH]ncc56)c(C5CC5)cc34)CC2)C1] | 689.4 |

TABLE 1-continued
| Compound | Compound structure | [M + H]+ |
|---|---|---|
| 187 | 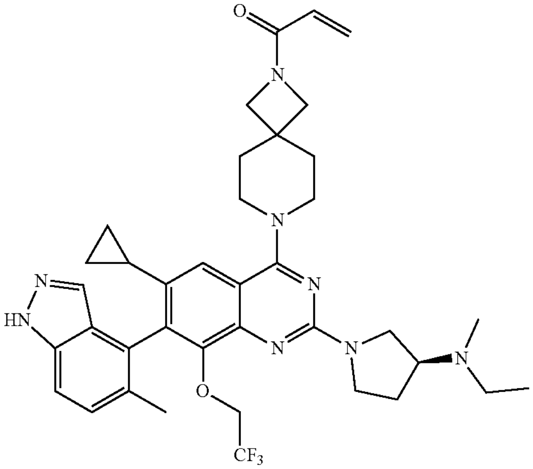 [SMILES: C=CC(=O)N1CC2(CCN(c3nc(N4CC[C@H](N(C)CC)C4)nc4c(OCC(F)(F)F)c(-c5c(C)ccc6[nH]ncc56)c(C5CC5)cc34)CC2)C1] | 703.4 |
| 188 | 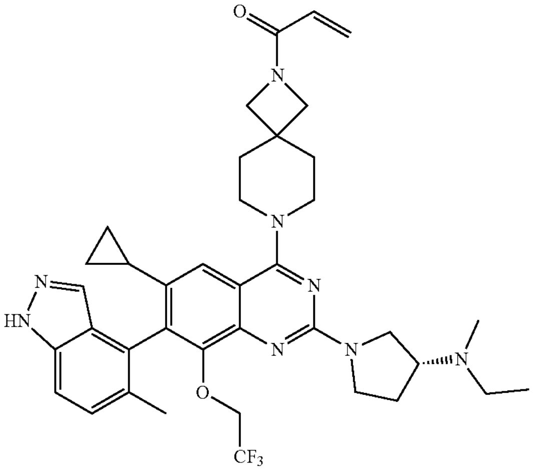 | 703.4 |
| 189 | 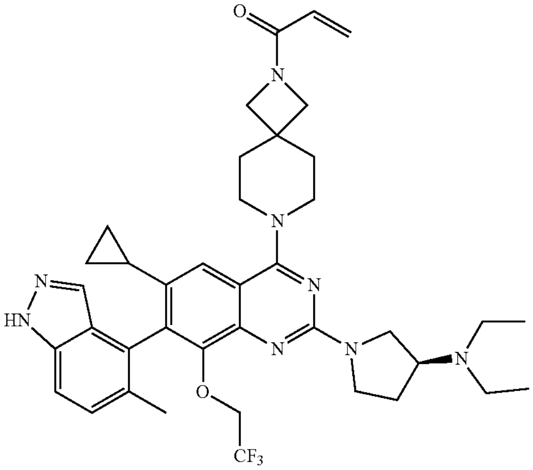 | 717.4 |

TABLE 1-continued
| Compound | Compound structure | [M + H]+ |
| --- | --- | --- |
| 190 | 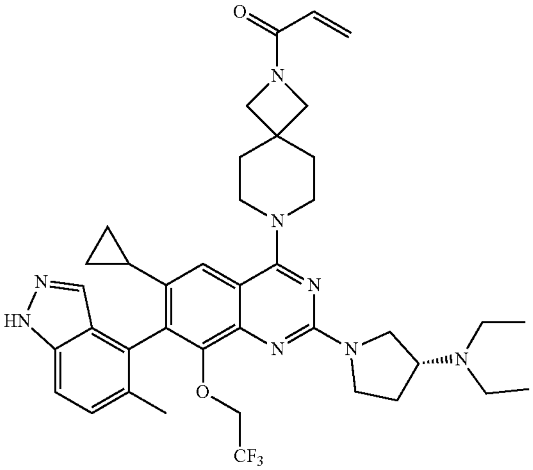 [SMILES: C=CC(=O)N1CC2(CCN(c3nc(N4CC[C@@H](N(CC)CC)C4)nc4c(OCC(F)(F)F)c(-c5c(C)ccc6[nH]ncc56)c(C5CC5)cc34)CC2)C1] | 717.4 |
| 191 | 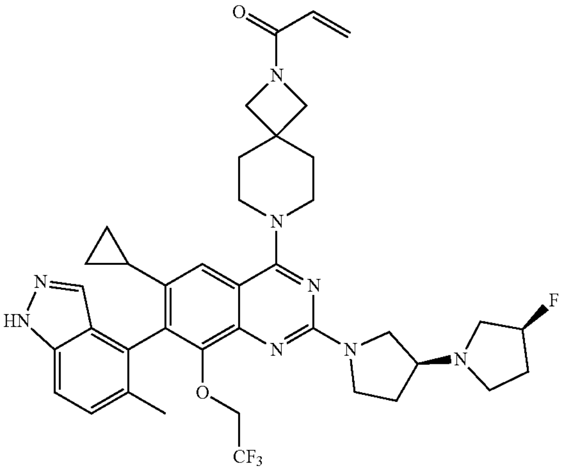 | 733.4 |
| 192 | 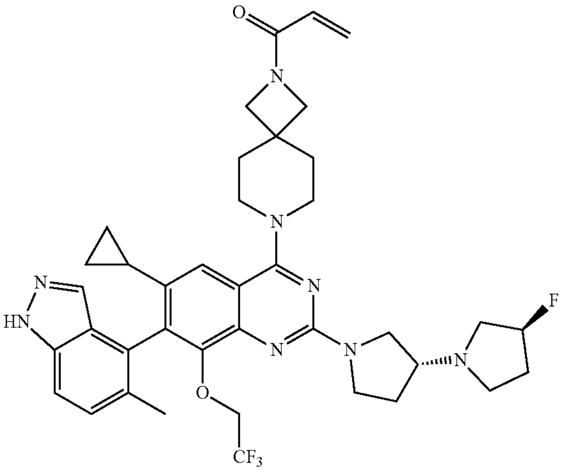 [SMILES: C=CC(=O)N1CC2(CCN(c3nc(N4CC[C@@H](N5CC[C@H](F)C5)C4)nc4c(OCC(F)(F)F)c(-c5c(C)ccc6[nH]ncc56)c(C5CC5)cc34)CC2)C1] | 733.4 |

TABLE 1-continued
| Compound | Compound structure | [M + H]+ |
|---|---|---|
| 193 | 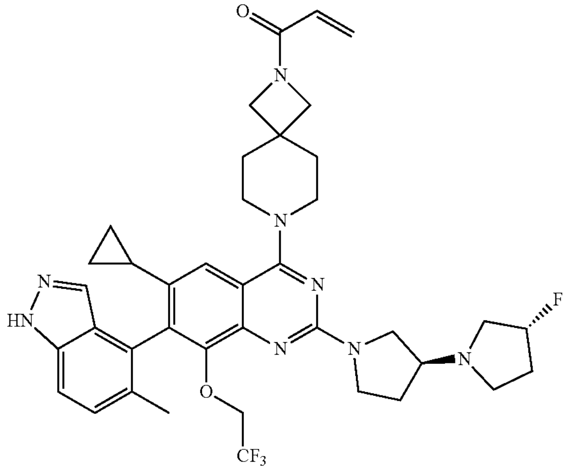 | 733.4 |
| 194 | 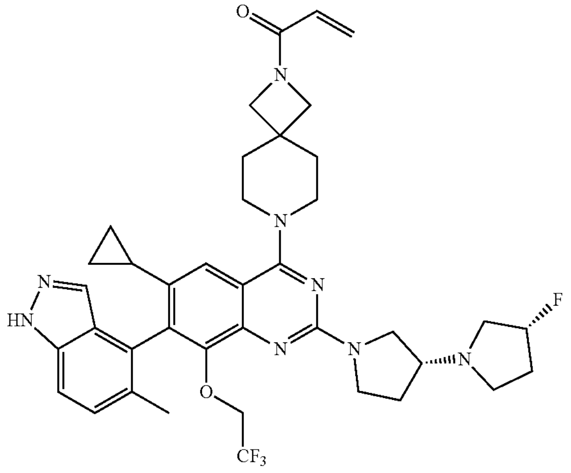 [SMILES: C=CC(=O)N1CC2(CCN(c3nc(N4CC[C@@H](N5CC[C@@H](F)C5)C4)nc4c(OCC(F)(F)F)c(-c5c(C)ccc6[nH]ncc56)c(C5CC5)cc34)CC2)C1] | 733.4 |
| 195 | 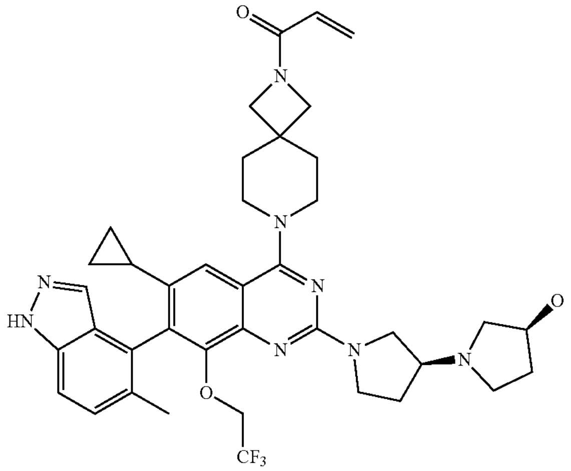 [SMILES: C=CC(=O)N1CC2(CCN(c3nc(N4CC[C@H](N5CC[C@H](O)C5)C4)nc4c(OCC(F)(F)F)c(-c5c(C)ccc6[nH]ncc56)c(C5CC5)cc34)CC2)C1] | 745.4 |

TABLE 1-continued
| Compound | Compound structure | [M + H]+ |
|---|---|---|
| 196 | 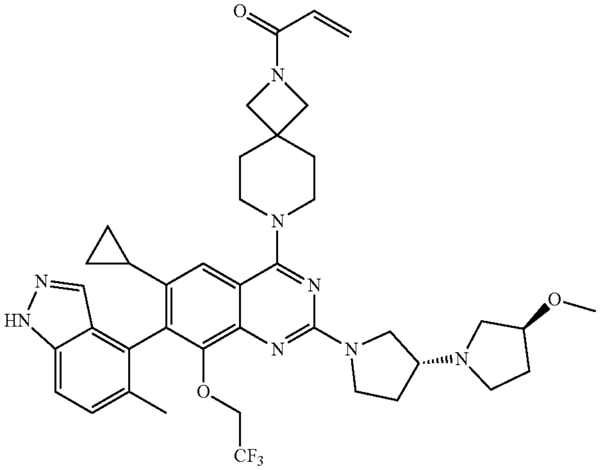 | 745.4 |
| 197 | 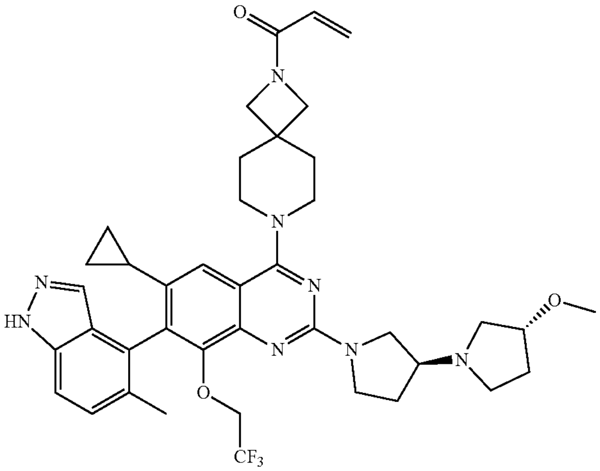 [SMILES: C=CC(=O)N1CC2(CCN(c3nc(N4CC[C@H](N5CC[C@@H](OC)C5)C4)nc4c(OCC(F)(F)F)c(-c5c(C)ccc6[nH]ncc56)c(C5CC5)cc34)CC2)C1] | 745.4 |
| 198 | 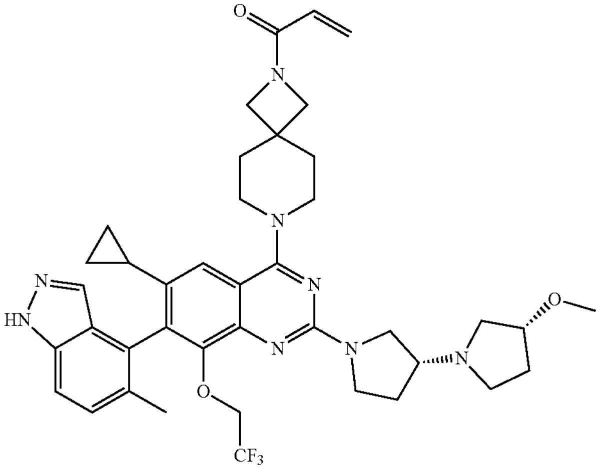 [SMILES: C=CC(=O)N1CC2(CCN(c3nc(N4CC[C@@H](N5CC[C@@H](OC)C5)C4)nc4c(OCC(F)(F)F)c(-c5c(C)ccc6[nH]ncc56)c(C5CC5)cc34)CC2)C1] | 745.4 |

TABLE 1-continued
| Compound | Compound structure | [M + H]+ |
|---|---|---|
| 199 | 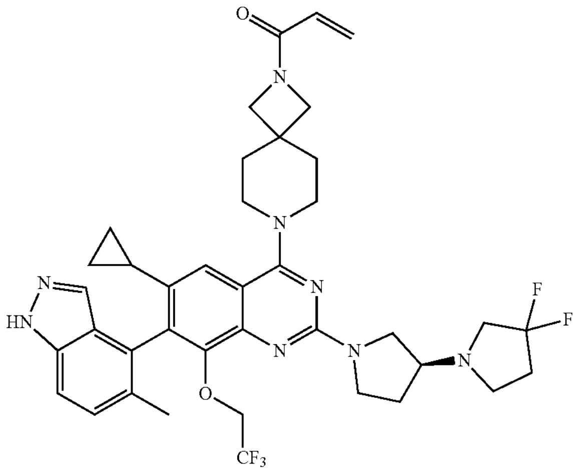 [SMILES: C=CC(=O)N1CC2(CCN(c3nc(N4CC[C@H](N5CCC(F)(F)C5)C4)nc4c(OCC(F)(F)F)c(-c5c(C)ccc6[nH]ncc56)c(C5CC5)cc34)CC2)C1] | 751.3 |
| 200 | 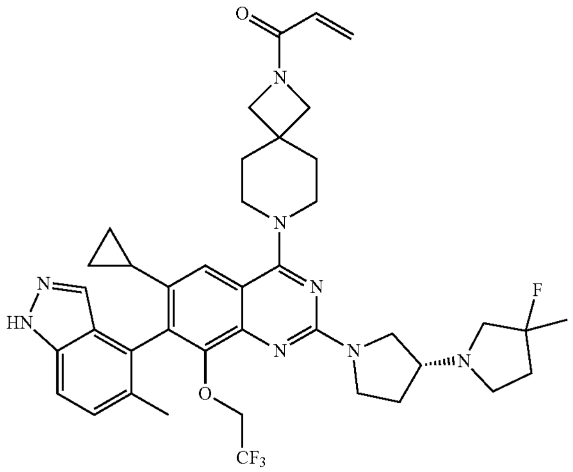 [SMILES: C=CC(=O)N1CC2(CCN(c3nc(N4CC[C@@H](N5CCC(C)(F)C5)C4)nc4c(OCC(F)(F)F)c(-c5c(C)ccc6[nH]ncc56)c(C5CC5)cc34)CC2)C1] | 751.3 |
| 201 | 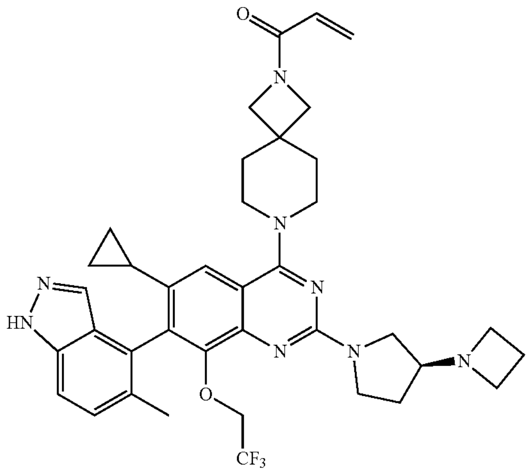 [SMILES: C=CC(=O)N1CC2(CCN(c3nc(N4CC[C@H](N5CCC5)C4)nc4c(OCC(F)(F)F)c(-c5c(C)ccc6[nH]ncc56)c(C5CC5)cc34)CC2)C1] | 719.3 |

TABLE 1-continued
| Compound | Compound structure | [M + H]+ |
|---|---|---|
| 202 | 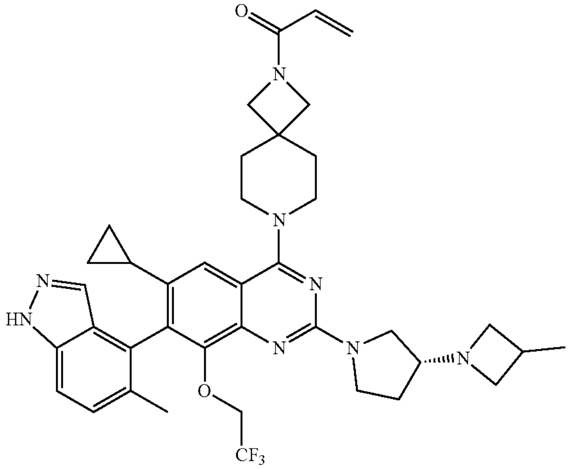 [SMILES: C=CC(=O)N1CC2(CCN(c3nc(N4CC[C@@H](N5CC(C)C5)C4)nc4c(OCC(F)(F)F)c(-c5c(C)ccc6[nH]ncc56)c(C5CC5)cc34)CC2)C1] | 719.3 |
| 203 | 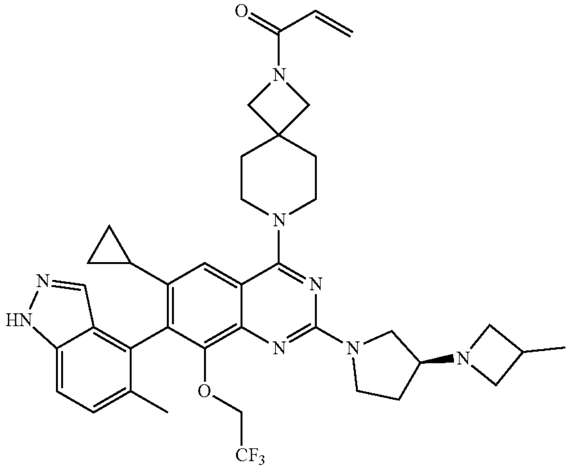 [SMILES: C=CC(=O)N1CC2(CCN(c3nc(N4CC[C@H](N5CC(C)C5)C4)nc4c(OCC(F)(F)F)c(-c5c(C)ccc6[nH]ncc56)c(C5CC5)cc34)CC2)C1] | 731.4 |
| 204 | 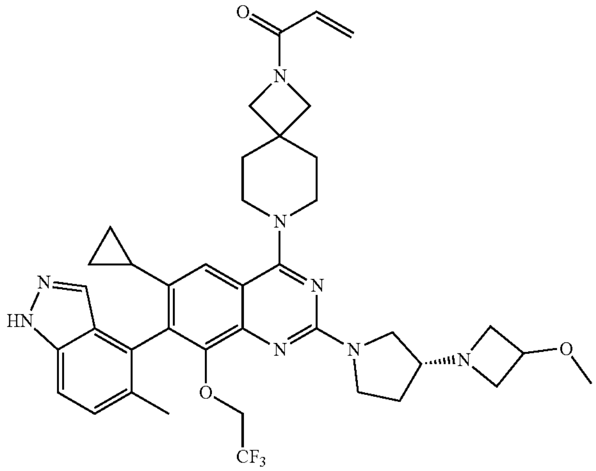 [SMILES: C=CC(=O)N1CC2(CCN(c3nc(N4CC[C@@H](N5CC(OC)C5)C4)nc4c(OCC(F)(F)F)c(-c5c(C)ccc6[nH]ncc56)c(C5CC5)cc34)CC2)C1] | 731.3 |

TABLE 1-continued
| Compound | Compound structure | [M + H]+ |
|---|---|---|
| 205 | 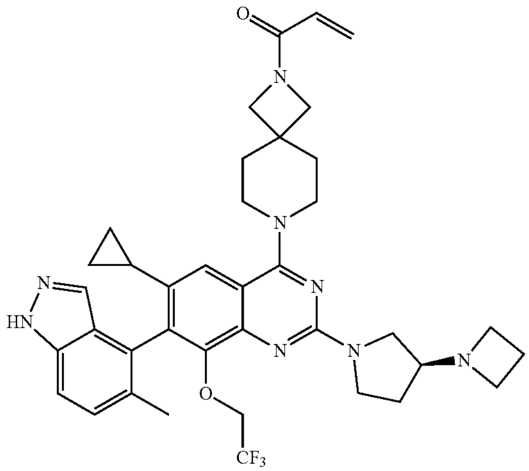 [SMILES: C=CC(=O)N1CC2(CCN(c3nc(N4CC[C@H](N5CCC5)C4)nc4c(OCC(F)(F)F)c(-c5c(C)ccc6[nH]ncc56)c(C5CC5)cc34)CC2)C1] | 737.3 |
| 206 | 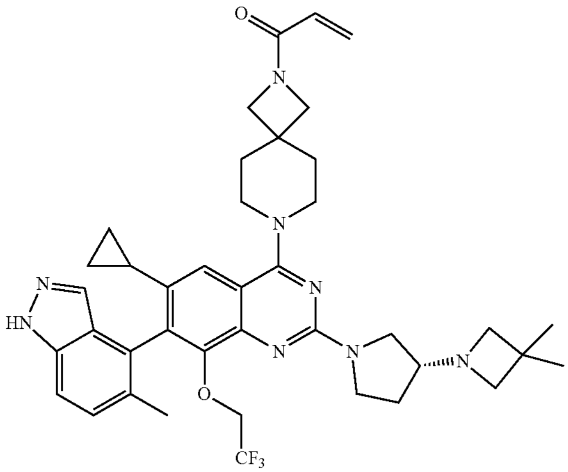 | 737.3 |
| 207 | 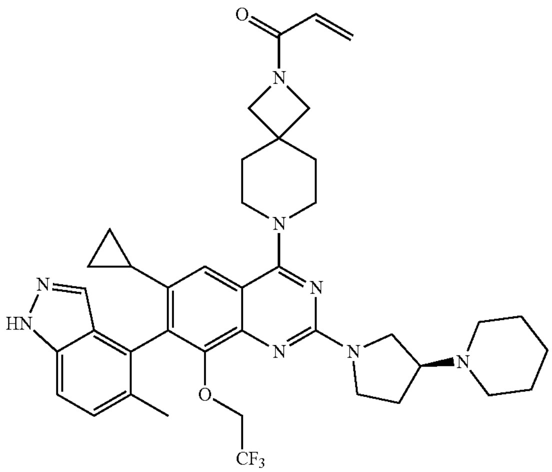 | 729.4 |

TABLE 1-continued
| Compound | Compound structure | [M + H]+ |
|---|---|---|
| 208 | 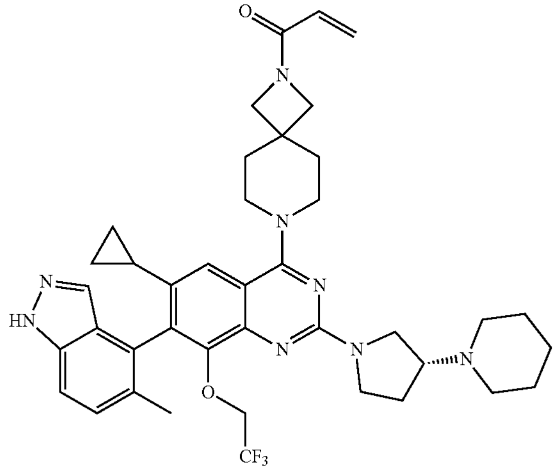 [SMILES: C=CC(=O)N1CC2(CCN(c3nc(N4CC[C@@H](N5CCCCC5)C4)nc4c(OCC(F)(F)F)c(-c5c(C)ccc6[nH]ncc56)c(C5CC5)cc34)CC2)C1] | 729.4 |
| 209 | 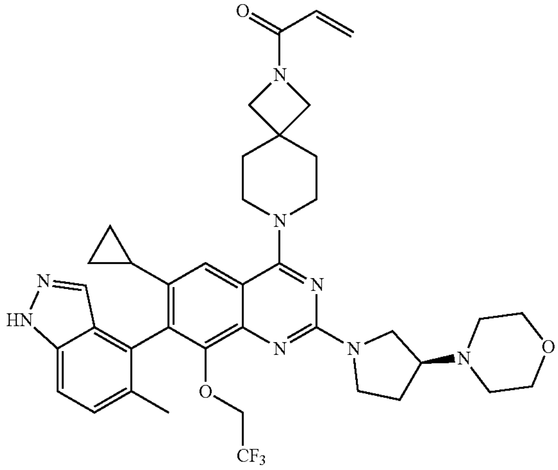 [SMILES: C=CC(=O)N1CC2(CCN(c3nc(N4CC[C@H](N5CCOCC5)C4)nc4c(OCC(F)(F)F)c(-c5c(C)ccc6[nH]ncc56)c(C5CC5)cc34)CC2)C1] | 731.4 |
| 210 | 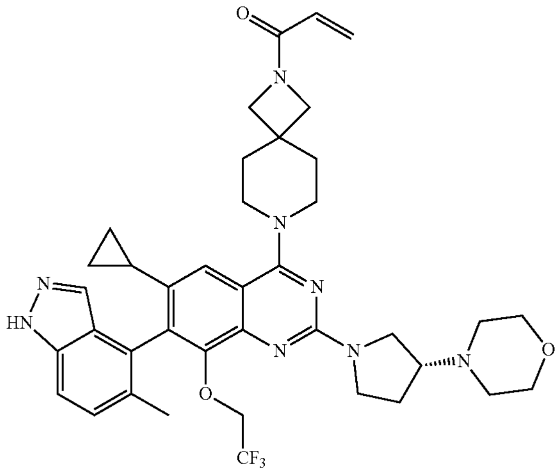 [SMILES: C=CC(=O)N1CC2(CCN(c3nc(N4CC[C@@H](N5CCOCC5)C4)nc4c(OCC(F)(F)F)c(-c5c(C)ccc6[nH]ncc56)c(C5CC5)cc34)CC2)C1] | 731.4 |

TABLE 1-continued
| Compound | Compound structure | [M + H]$^+$ |
|---|---|---|
| 211 | 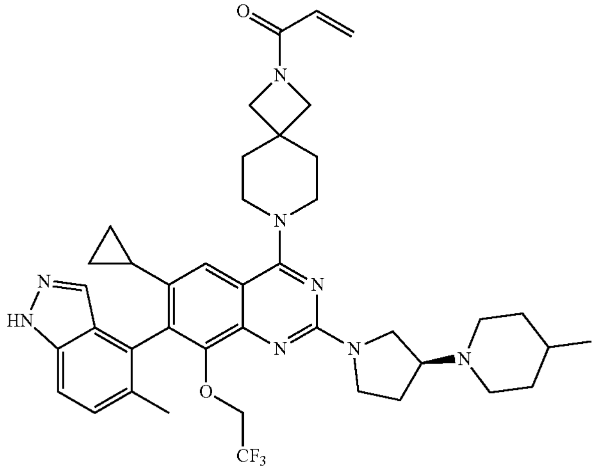 | 747.4 |
| 212 | 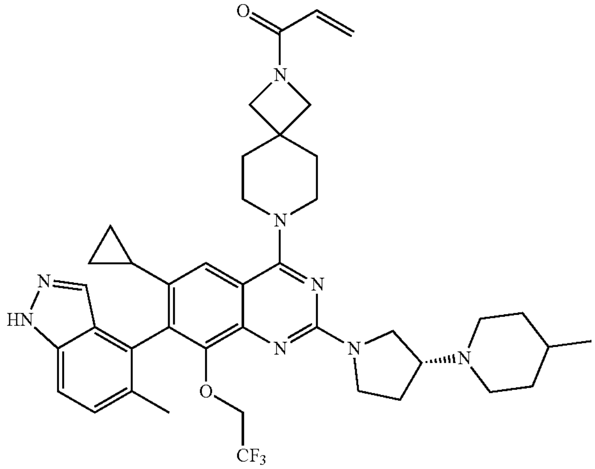 [SMILES: C=CC(=O)N1CC2(CCN(c3nc(N4CC[C@@H](N5CCC(C)CC5)C4)nc4c(OCC(F)(F)F)c(-c5c(C)ccc6[nH]ncc56)c(C5CC5)cc34)CC2)C1] | 747.4 |
| 213 | 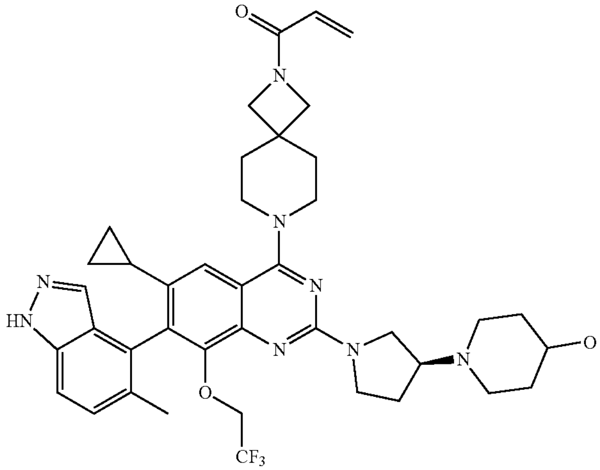 | 759.4 |

TABLE 1-continued
| Compound | Compound structure | [M + H]+ |
| --- | --- | --- |
| 214 | 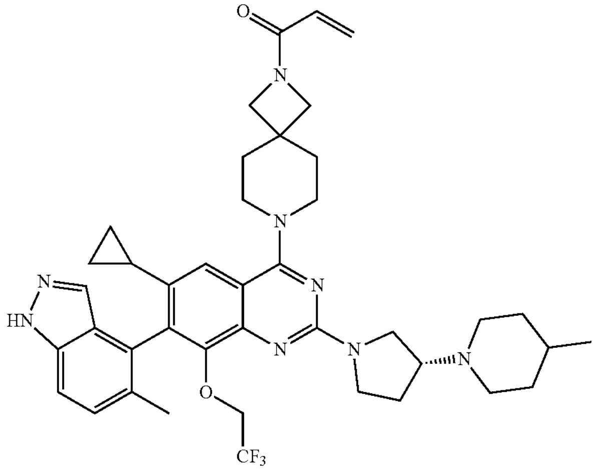 | 759.4 |
| 215 | 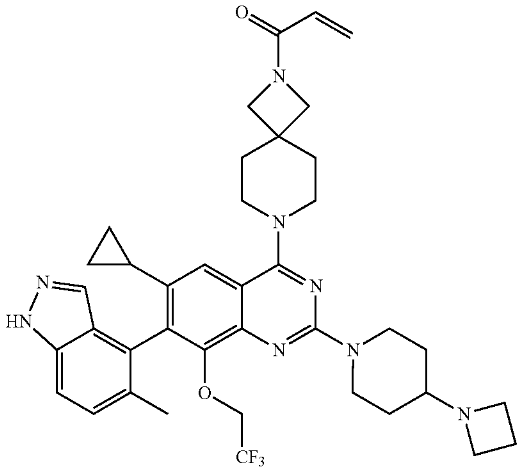 [SMILES: C=CC(=O)N1CC2(CCN(c3nc(N4CCC(N5CCC5)CC4)nc4c(OCC(F)(F)F)c(-c5c(C)ccc6[nH]ncc56)c(C5CC5)cc34)CC2)C1] | 715.4 |
| 216 | 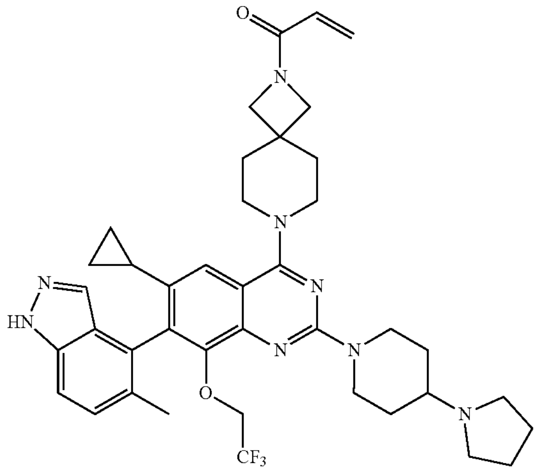 [SMILES: C=CC(=O)N1CC2(CCN(c3nc(N4CCC(N5CCCC5)CC4)nc4c(OCC(F)(F)F)c(-c5c(C)ccc6[nH]ncc56)c(C5CC5)cc34)CC2)C1] | 729.4 |

TABLE 1-continued
| Compound | Compound structure | [M + H]+ |
| --- | --- | --- |
| 217 | 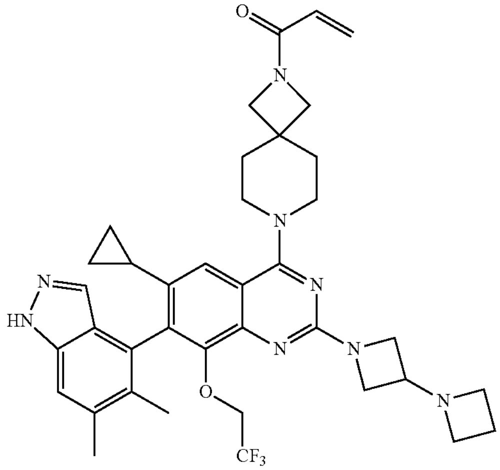 [SMILES: C=CC(=O)N1CC2(CCN(c3nc(N4CC(N5CCC5)C4)nc4c(OCC(F)(F)F)c(-c5c(C)c(C)cc6[nH]ncc56)c(C5CC5)cc34)CC2)C1] | 701.4 |
| 218 | 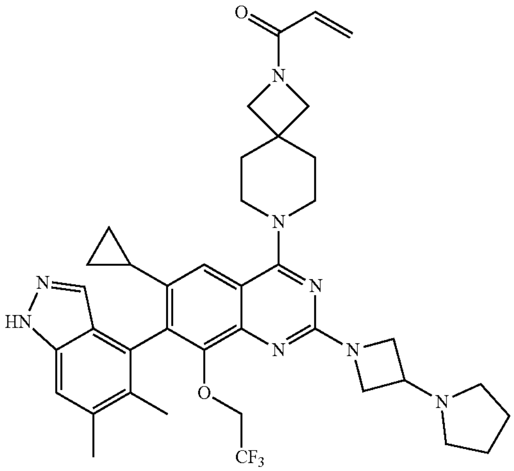 [SMILES: C=CC(=O)N1CC2(CCN(c3nc(N4CC(N5CCCC5)C4)nc4c(OCC(F)(F)F)c(-c5c(C)c(F)cc6[nH]ncc56)c(C5CC5)cc34)CC2)C1] | 715.4 |
| 219 | 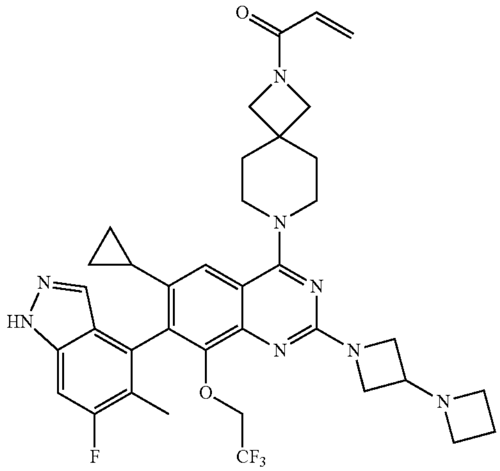 | 705.3 |

TABLE 1-continued
| Compound | Compound structure | [M + H]+ |
|---|---|---|
| 220 | 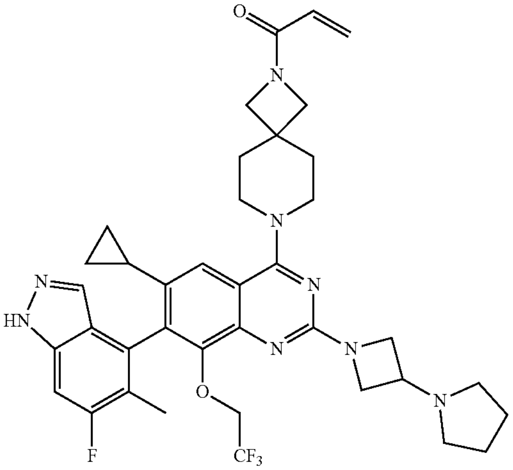 | 719.3 |
| 221 | 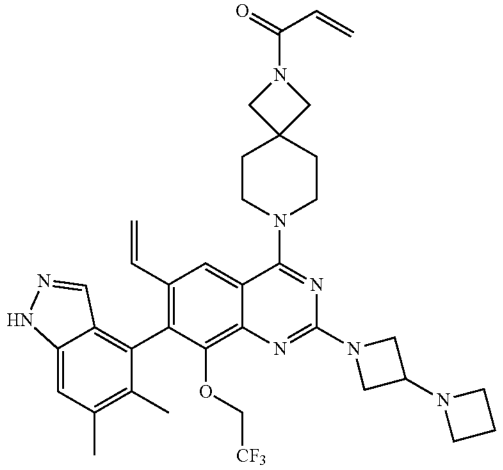 | 687.3 |
| 222 | 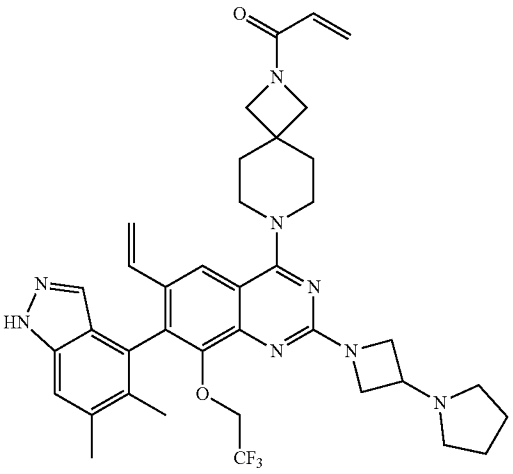 | 701.4 |

TABLE 1-continued
| Compound | Compound structure | [M + H]+ |
| --- | --- | --- |
| 223 | 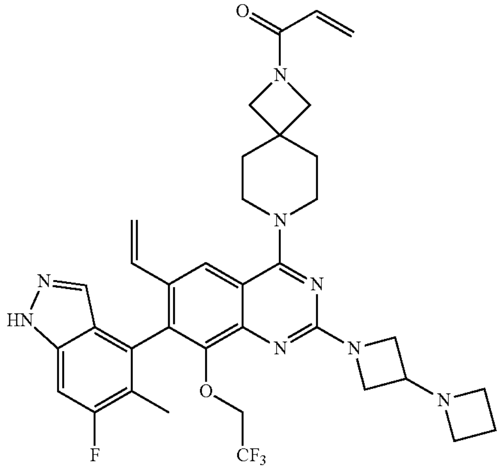 [SMILES: C=CC(=O)N1CC2(CCN(c3nc(N4CC(N5CCC5)C4)nc4c(OCC(F)(F)F)c(-c5c(C)c(C)cc6[nH]ncc56)c(C=C)cc34)CC2)C1] | 691.3 |
| 224 | 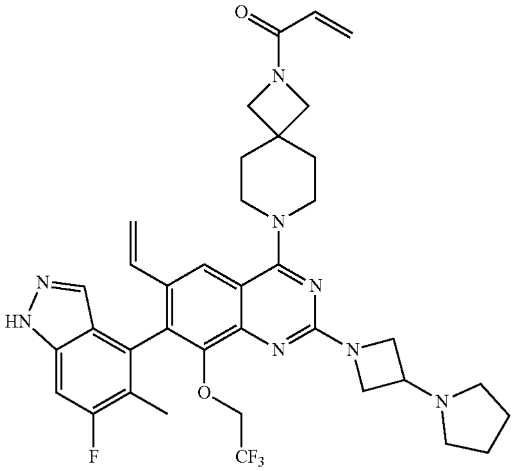 | 705.3 |
| 225 | 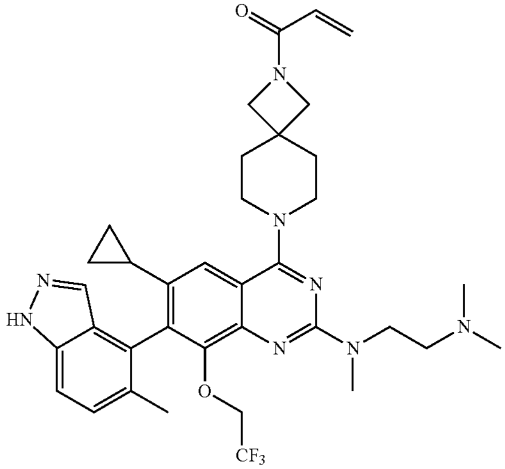 | 677.4 |

TABLE 1-continued
| Compound | Compound structure | [M + H]+ |
| --- | --- | --- |
| 226 | 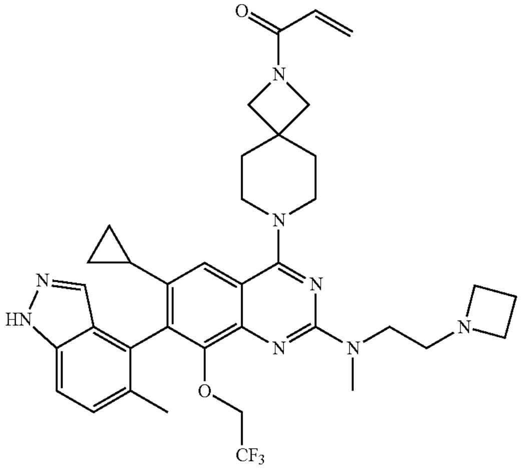 [SMILES: C=CC(=O)N1CC2(CCN(c3nc(N(C)CCN4CCC4)nc4c(OCC(F)(F)F)c(-c5c(C)ccc6[nH]ncc56)c(C5CC5)cc34)CC2)C1] | 688.4 |
| 227 | 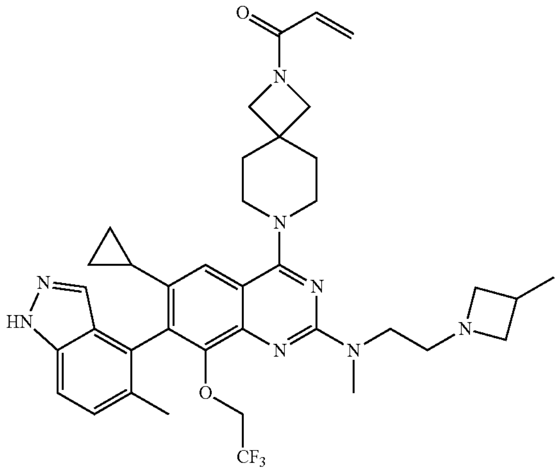 [SMILES: C=CC(=O)N1CC2(CCN(c3nc(N(C)CCN4CC(C)C4)nc4c(OCC(F)(F)F)c(-c5c(C)ccc6[nH]ncc56)c(C5CC5)cc34)CC2)C1] | 703.4 |
| 228 | 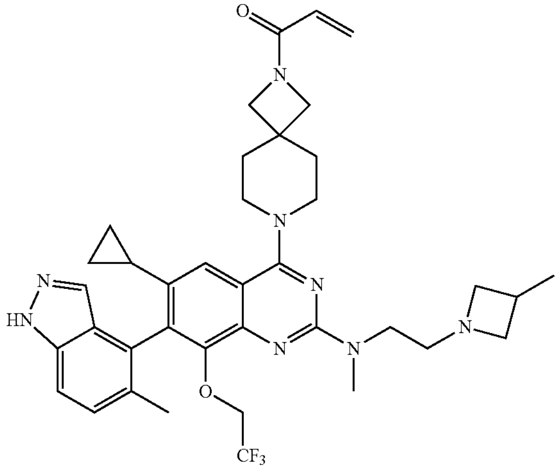 [SMILES: C=CC(=O)N1CC2(CCN(c3nc(N(C)CCN4CC(C)C4)nc4c(OCC(F)(F)F)c(-c5c(C)ccc6[nH]ncc56)c(C5CC5)cc34)CC2)C1] | 707.3 |

TABLE 1-continued
| Compound | Compound structure | [M + H]+ |
|---|---|---|
| 229 | 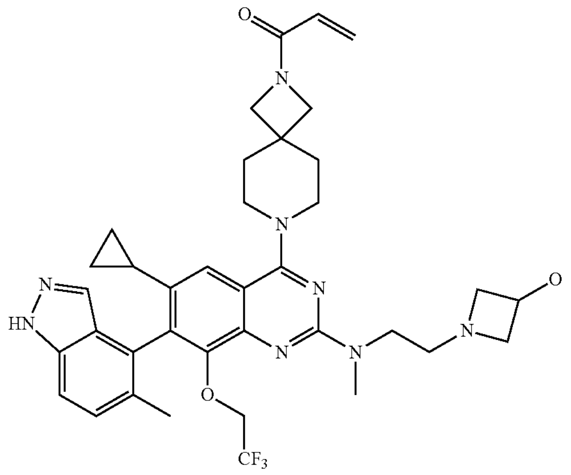 [SMILES: C=CC(=O)N1CC2(CCN(c3nc(N(C)CCN4CC(O)C4)nc4c(OCC(F)(F)F)c(-c5c(C)ccc6[nH]ncc56)c(C5CC5)cc34)CC2)C1] | 705.3 |
| 230 | 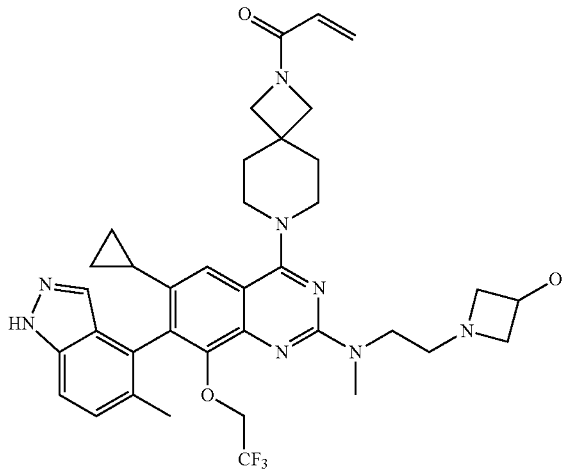 | 719.4 |
| 231 | 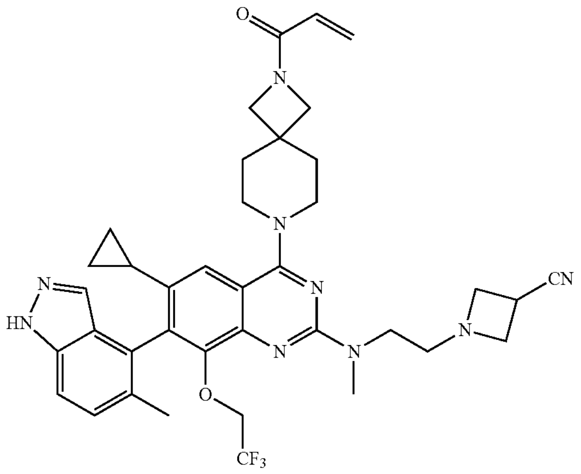 [SMILES: C=CC(=O)N1CC2(CCN(c3nc(N(C)CCN4CC(C#N)C4)nc4c(OCC(F)(F)F)c(-c5c(C)ccc6[nH]ncc56)c(C5CC5)cc34)CC2)C1] | 714.3 |

TABLE 1-continued
| Compound | Compound structure | [M + H]+ |
|---|---|---|
| 232 | 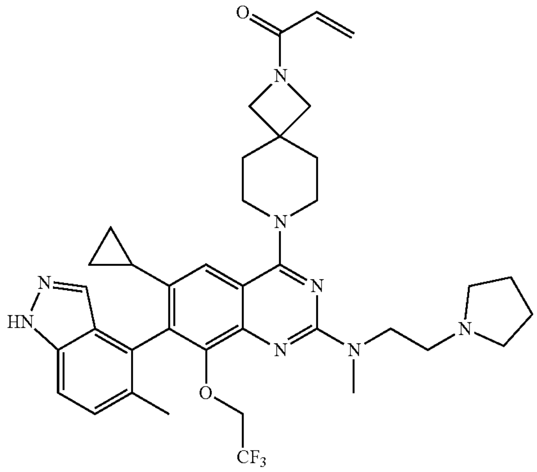 [SMILES: C=CC(=O)N1CC2(CCN(c3nc(N(C)CCN4CCCC4)nc4c(OCC(F)(F)F)c(-c5c(C)ccc6[nH]ncc56)c(C5CC5)cc34)CC2)C1] | 703.4 |
| 233 | 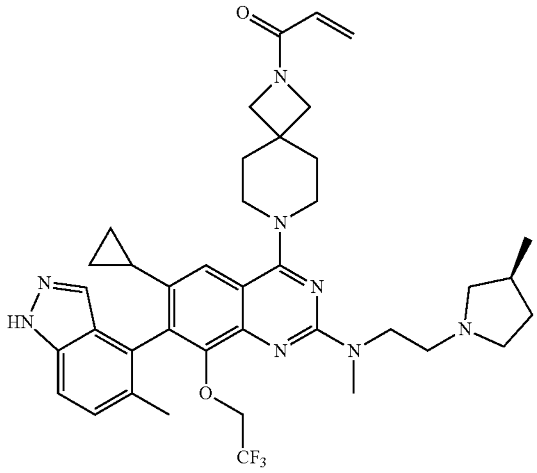 [SMILES: C=CC(=O)N1CC2(CCN(c3nc(N(C)CCN4CC[C@H](C)C4)nc4c(OCC(F)(F)F)c(-c5c(C)ccc6[nH]ncc56)c(C5CC5)cc34)CC2)C1] | 717.4 |
| 234 | 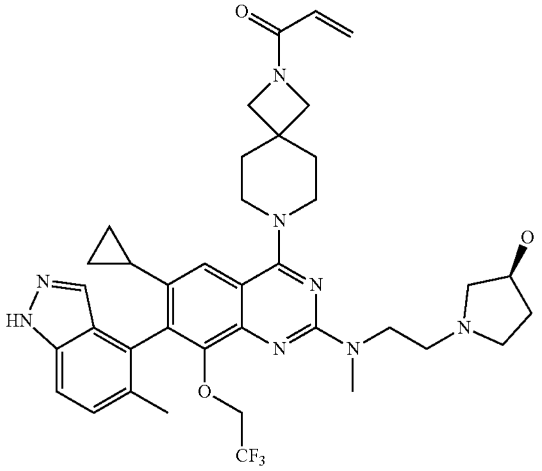 | 719.4 |

TABLE 1-continued
| Compound | Compound structure | [M + H]+ |
|---|---|---|
| 235 | 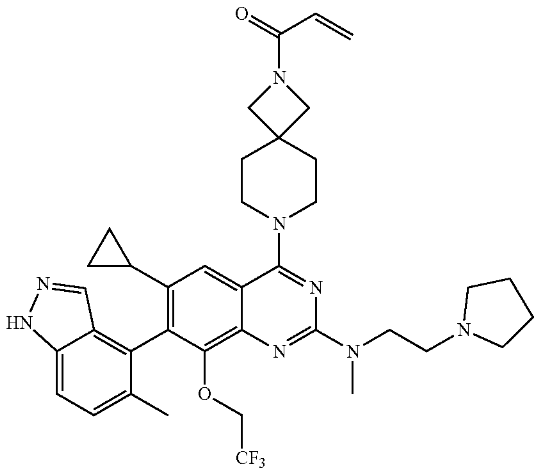 [SMILES: C=CC(=O)N1CC2(CCN(c3nc(N(C)CCN4CCCC4)nc4c(OCC(F)(F)F)c(-c5c(C)ccc6[nH]ncc56)c(C5CC5)cc34)CC2)C1] | 733.4 |
| 236 | 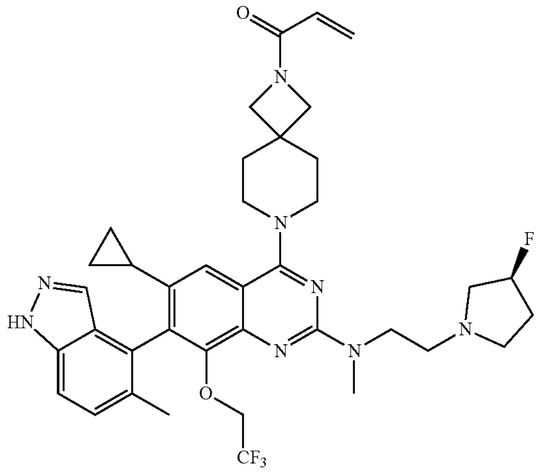 [SMILES: C=CC(=O)N1CC2(CCN(c3nc(N(C)CCN4CC[C@H](F)C4)nc4c(OCC(F)(F)F)c(-c5c(C)ccc6[nH]ncc56)c(C5CC5)cc34)CC2)C1] | 721.4 |
| 237 | 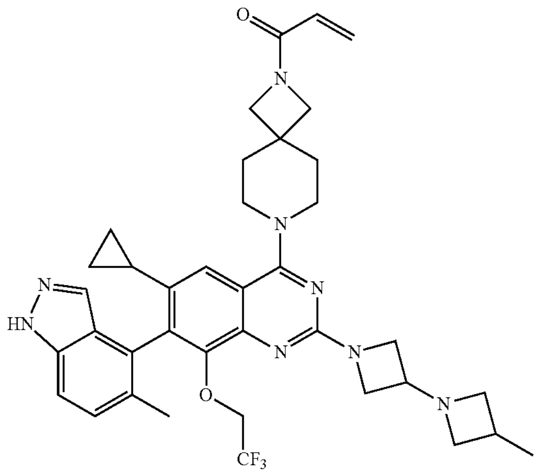 [SMILES: C=CC(=O)N1CC2(CCN(c3nc(N4CC(N5CC(C)C5)C4)nc4c(OCC(F)(F)F)c(-c5c(C)ccc6[nH]ncc56)c(C5CC5)cc34)CC2)C1] | 701.4 |

TABLE 1-continued
| Compound | Compound structure | [M + H]+ |
|---|---|---|
| 238 | 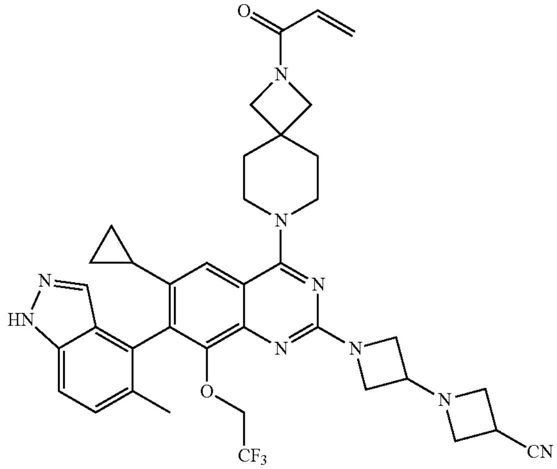 [SMILES: C=CC(=O)N1CC2(CCN(c3nc(N4CC(N5CC(C#N)C5)C4)nc4c(OCC(F)(F)F)c(-c5c(C)ccc6[nH]ncc56)c(C5CC5)cc34)CC2)C1] | 712.3 |
| 239 | 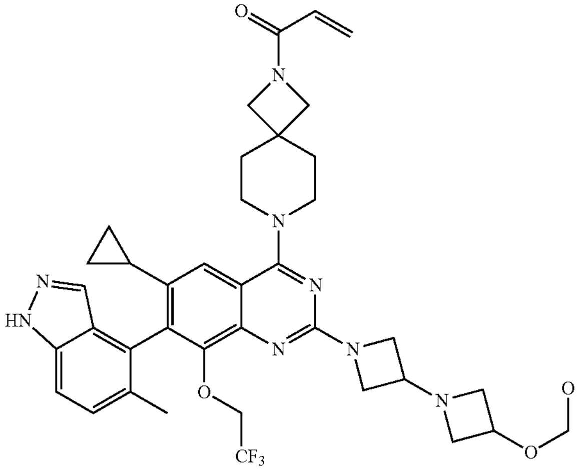 [SMILES: C=CC(=O)N1CC2(CCN(c3nc(N4CC(N5CC(OCO)C5)C4)nc4c(OCC(F)(F)F)c(-c5c(C)ccc6[nH]ncc56)c(C5CC5)cc34)CC2)C1] | 785.3 |
| 240 | 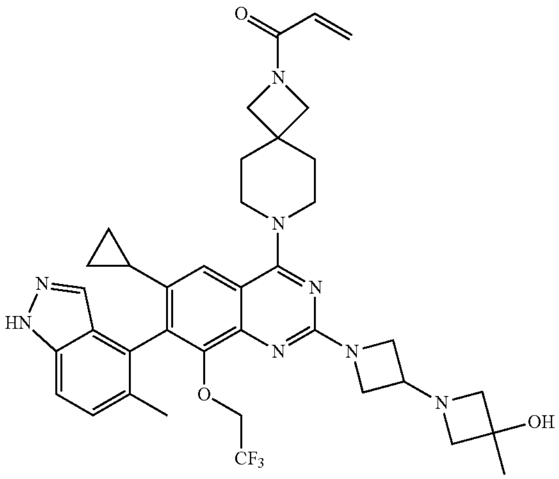 [SMILES: C=CC(=O)N1CC2(CCN(c3nc(N4CC(N5CC(C)(O)C5)C4)nc4c(OCC(F)(F)F)c(-c5c(C)ccc6[nH]ncc56)c(C5CC5)cc34)CC2)C1] | 717.3 |

TABLE 1-continued
| Compound | Compound structure | [M + H]+ |
| --- | --- | --- |
| 241 | 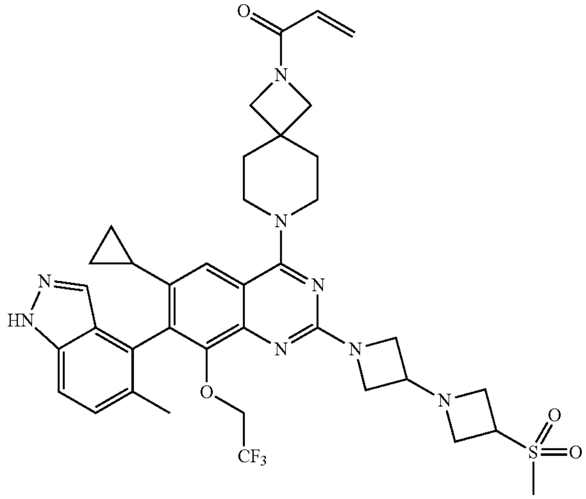 [SMILES: C=CC(=O)N1CC2(CCN(c3nc(N4CC(N5CC(S(C)(=O)=O)C5)C4)nc4c(OCC(F)(F)F)c(-c5c(C)ccc6[nH]ncc56)c(C5CC5)cc34)CC2)C1] | 765.3 |
| 242 | 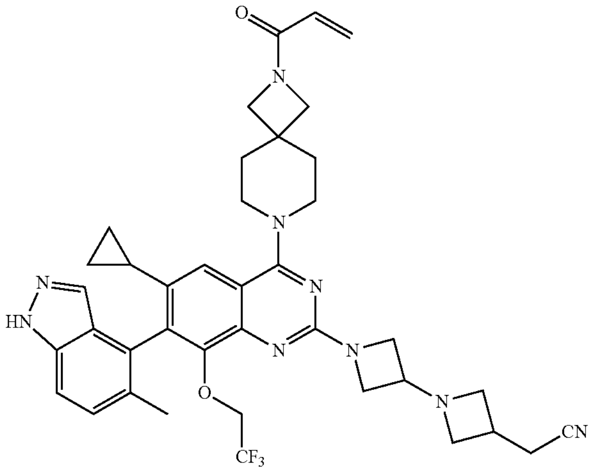 | 726.3 |
| 243 | 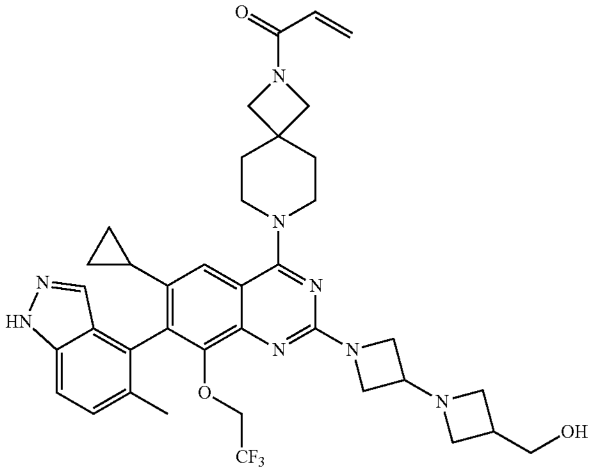 [SMILES: C=CC(=O)N1CC2(CCN(c3nc(N4CC(N5CC(CO)C5)C4)nc4c(OCC(F)(F)F)c(-c5c(C)ccc6[nH]ncc56)c(C5CC5)cc34)CC2)C1] | 717.3 |

TABLE 1-continued
| Compound | Compound structure | [M + H]+ |
| --- | --- | --- |
| 244 | 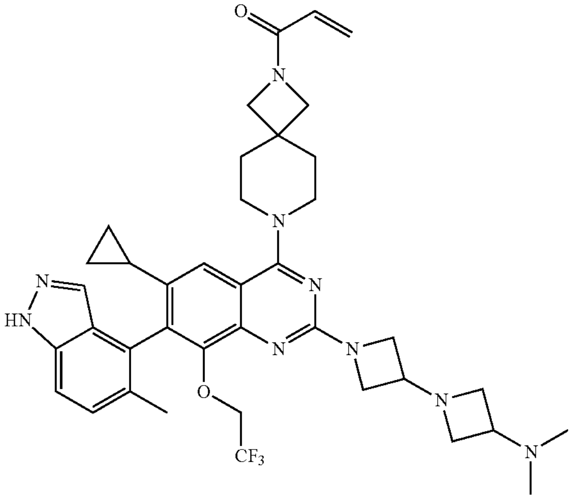 [SMILES: C=CC(=O)N1CC2(CCN(c3nc(N4CC(N5CC(N(C)C)C5)C4)nc4c(OCC(F)(F)F)c(-c5c(C)ccc6[nH]ncc56)c(C5CC5)cc34)CC2)C1] | 730.4 |
| 245 | 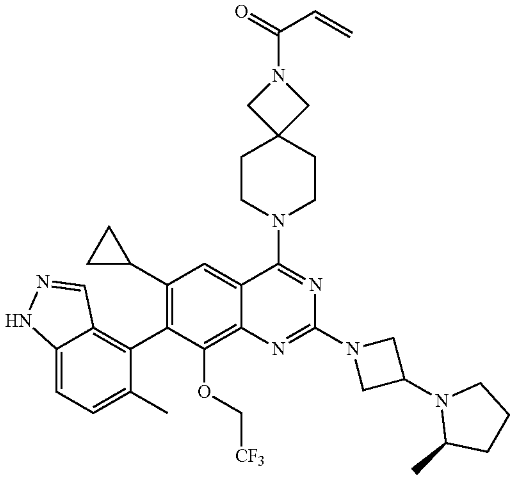 [SMILES: C=CC(=O)N1CC2(CCN(c3nc(N4CC(N5CCC[C@H]5C)C4)nc4c(OCC(F)(F)F)c(-c5c(C)ccc6[nH]ncc56)c(C5CC5)cc34)CC2)C1] | 715.4 |
| 246 | 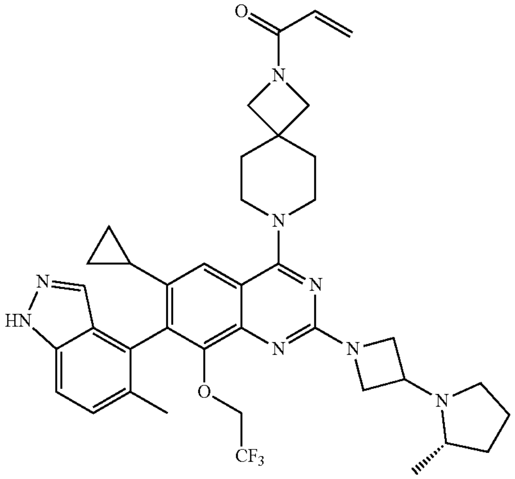 [SMILES: C=CC(=O)N1CC2(CCN(c3nc(N4CC(N5CCC[C@@H]5C)C4)nc4c(OCC(F)(F)F)c(-c5c(C)ccc6[nH]ncc56)c(C5CC5)cc34)CC2)C1] | 715.4 |

TABLE 1-continued
| Compound | Compound structure | [M + H]+ |
|---|---|---|
| 247 | 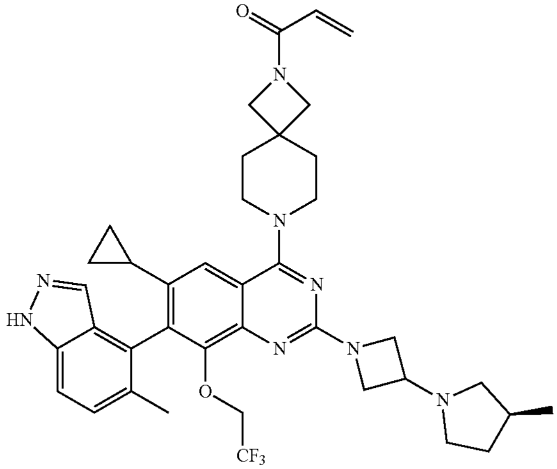 | 715.4 |
| 248 | 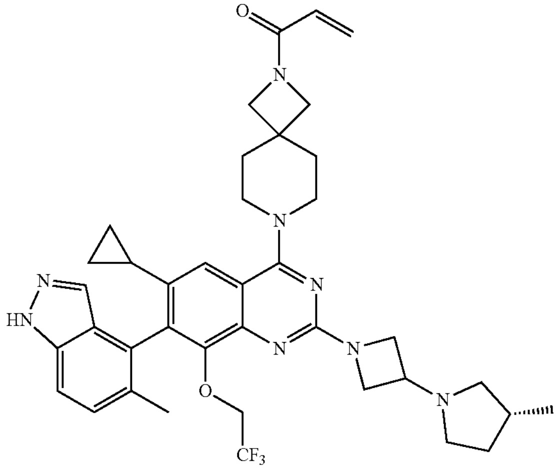 [SMILES: C=CC(=O)N1CC2(CCN(c3nc(N4CC(N5CC[C@@H](C)C5)C4)nc4c(OCC(F)(F)F)c(-c5c(C)ccc6[nH]ncc56)c(C5CC5)cc34)CC2)C1] | 715.4 |
| 249 | 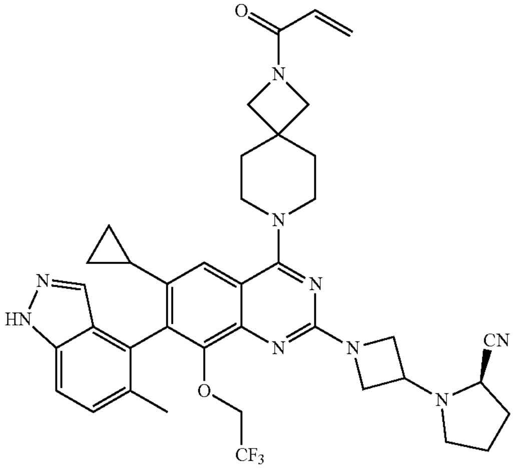 | 726.3 |

TABLE 1-continued
| Compound | Compound structure | [M + H]+ |
|---|---|---|
| 250 | 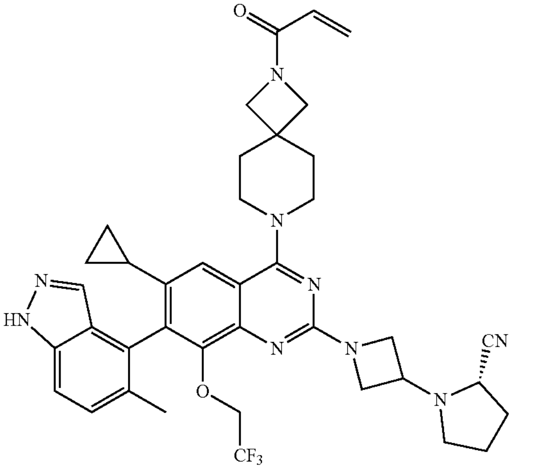 [SMILES: C=CC(=O)N1CC2(CCN(c3nc(N4CC(N5CCC[C@H]5C#N)C4)nc4c(OCC(F)(F)F)c(-c5c(C)ccc6[nH]ncc56)c(C5CC5)cc34)CC2)C1] | 726.3 |
| 251 | 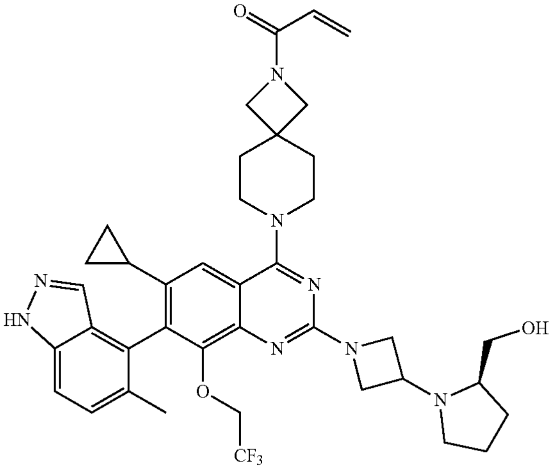 [SMILES: C=CC(=O)N1CC2(CCN(c3nc(N4CC(N5CCC[C@@H]5CO)C4)nc4c(OCC(F)(F)F)c(-c5c(C)ccc6[nH]ncc56)c(C5CC5)cc34)CC2)C1] | 731.4 |
| 252 | 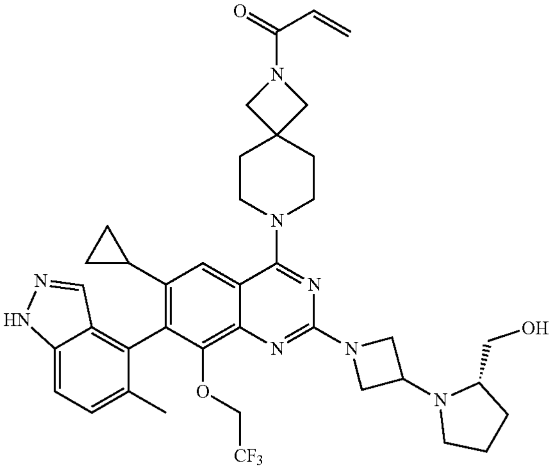 [SMILES: C=CC(=O)N1CC2(CCN(c3nc(N4CC(N5CCC[C@H]5CO)C4)nc4c(OCC(F)(F)F)c(-c5c(C)ccc6[nH]ncc56)c(C5CC5)cc34)CC2)C1] | 731.4 |

TABLE 1-continued
| Compound | Compound structure | [M + H]+ |
|---|---|---|
| 253 | 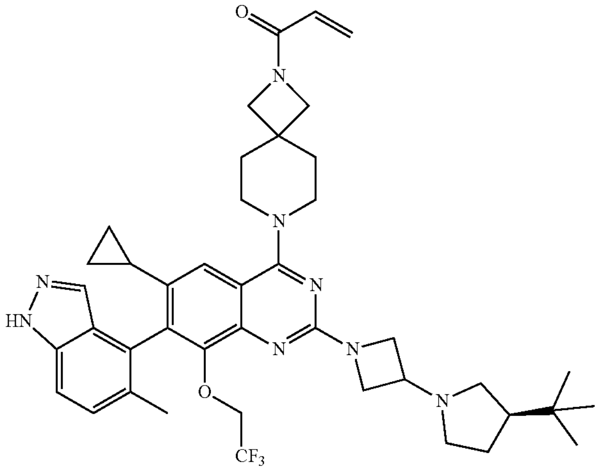 [SMILES: C=CC(=O)N1CC2(CCN(c3nc(N4CC(N5CC[C@H](C(C)(C)C)C5)C4)nc4c(OCC(F)(F)F)c(-c5c(C)ccc6[nH]ncc56)c(C5CC5)cc34)CC2)C1] | 759.4 |
| 254 | 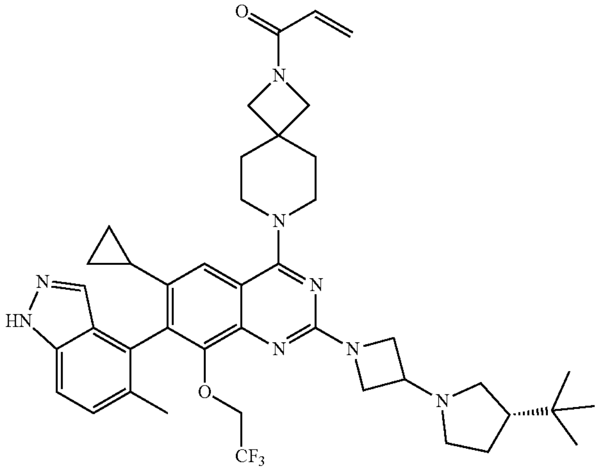 [SMILES: C=CC(=O)N1CC2(CCN(c3nc(N4CC(N5CC[C@@H](C(C)(C)C)C5)C4)nc4c(OCC(F)(F)F)c(-c5c(C)ccc6[nH]ncc56)c(C5CC5)cc34)CC2)C1] | 759.4 |
| 255 | 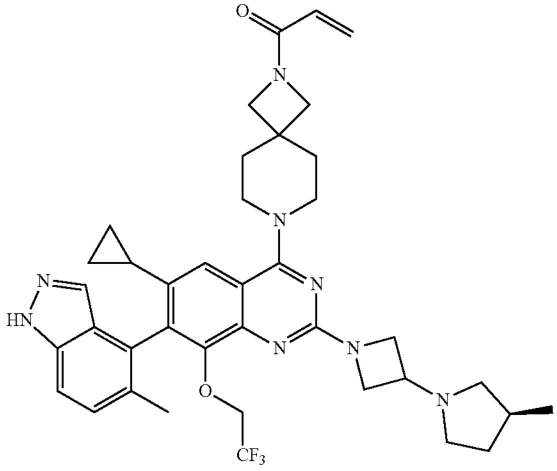 | 744.4 |

TABLE 1-continued
| Compound | Compound structure | [M + H]+ |
| --- | --- | --- |
| 256 | 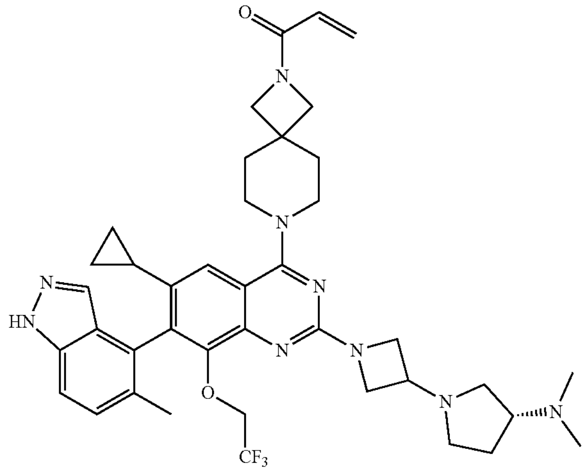 [SMILES: C=CC(=O)N1CC2(CCN(c3nc(N4CC(N5CC[C@@H](N(C)C)C5)C4)nc4c(OCC(F)(F)F)c(-c5c(C)ccc6[nH]ncc56)c(C5CC5)cc34)CC2)C1] | 744.4 |
| 257 | 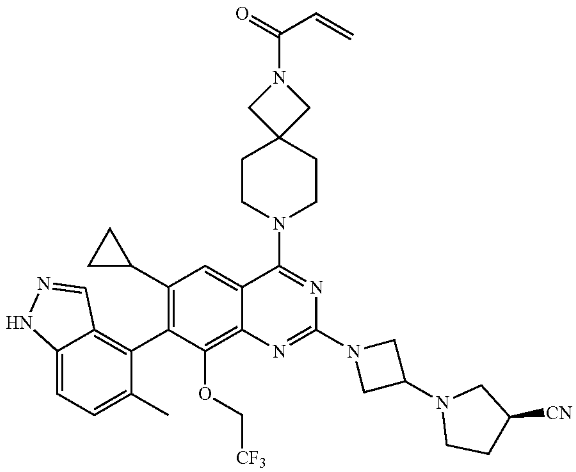 [SMILES: C=CC(=O)N1CC2(CCN(c3nc(N4CC(N5CC[C@H](C#N)C5)C4)nc4c(OCC(F)(F)F)c(-c5c(C)ccc6[nH]ncc56)c(C5CC5)cc34)CC2)C1] | 726.3 |
| 258 | 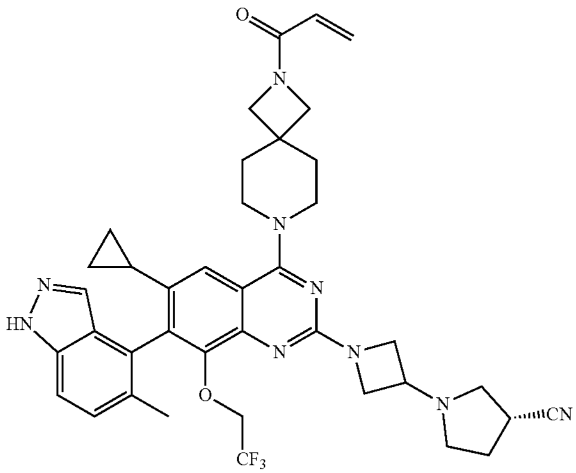 [SMILES: C=CC(=O)N1CC2(CCN(c3nc(N4CC(N5CC[C@@H](C#N)C5)C4)nc4c(OCC(F)(F)F)c(-c5c(C)ccc6[nH]ncc56)c(C5CC5)cc34)CC2)C1] | 726.3 |

TABLE 1-continued
| Compound | Compound structure | [M + H]+ |
| --- | --- | --- |
| 259 | 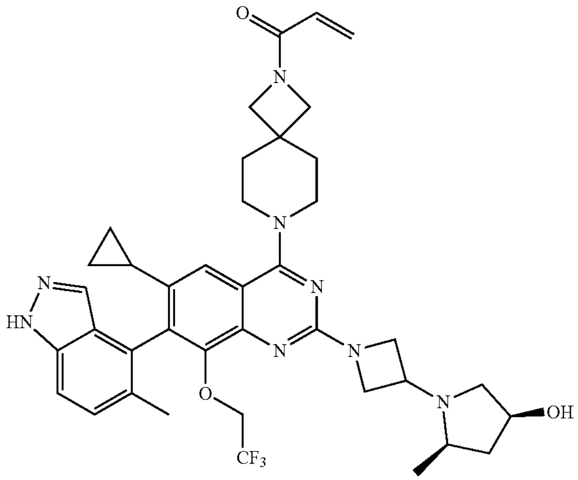 [SMILES: C=CC(=O)N1CC2(CCN(c3nc(N4CC(N5C[C@@H](O)C[C@H]5C)C4)nc4c(OCC(F)(F)F)c(-c5c(C)ccc6[nH]ncc56)c(C5CC5)cc34)CC2)C1] | 731.4 |
| 260- | 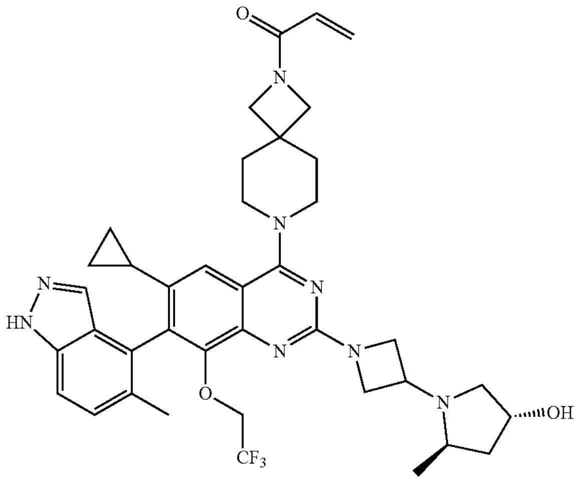 [SMILES: C=CC(=O)N1CC2(CCN(c3nc(N4CC(N5C[C@H](O)C[C@H]5C)C4)nc4c(OCC(F)(F)F)c(-c5c(C)ccc6[nH]ncc56)c(C5CC5)cc34)CC2)C1] | 731.4 |
| 261 | 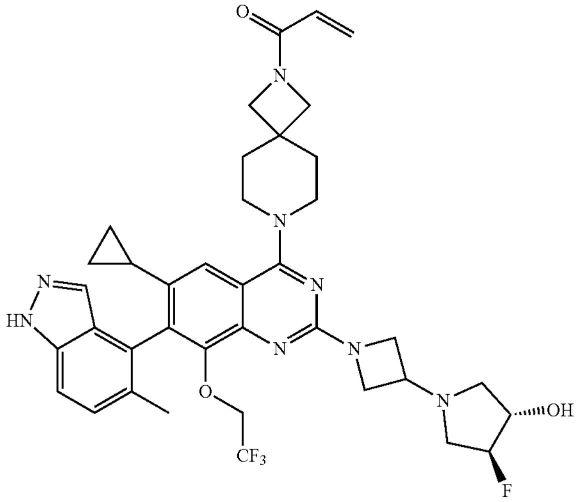 [SMILES: C=CC(=O)N1CC2(CCN(c3nc(N4CC(N5C[C@H](O)[C@@H](F)C5)C4)nc4c(OCC(F)(F)F)c(-c5c(C)ccc6[nH]ncc56)c(C5CC5)cc34)CC2)C1] | 735.3 |

TABLE 1-continued
| Compound | Compound structure | [M + H]+ |
| --- | --- | --- |
| 262 | 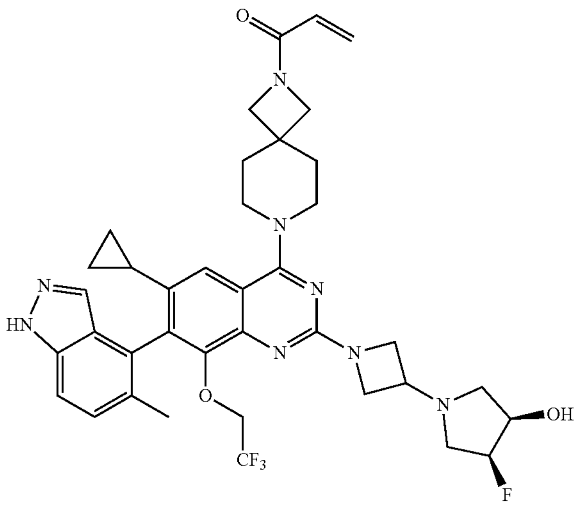 [SMILES: C=CC(=O)N1CC2(CCN(c3nc(N4CC(N5C[C@@H](O)[C@@H](F)C5)C4)nc4c(OCC(F)(F)F)c(-c5c(C)ccc6[nH]ncc56)c(C5CC5)cc34)CC2)C1] | 735.3 |
| 263 | 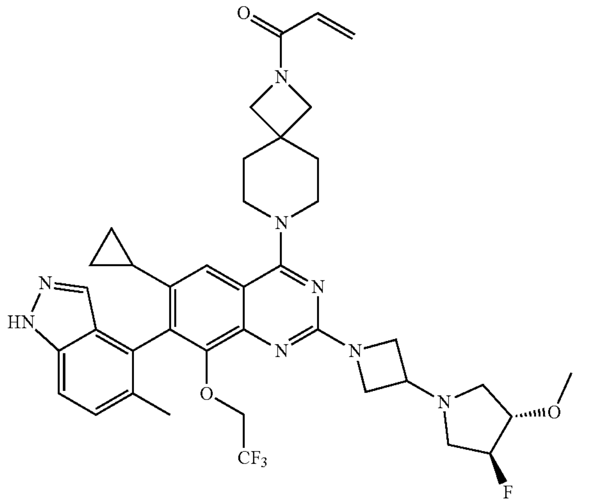 [SMILES: C=CC(=O)N1CC2(CCN(c3nc(N4CC(N5C[C@H](OC)[C@@H](F)C5)C4)nc4c(OCC(F)(F)F)c(-c5c(C)ccc6[nH]ncc56)c(C5CC5)cc34)CC2)C1] | 749.4 |
| 264 | 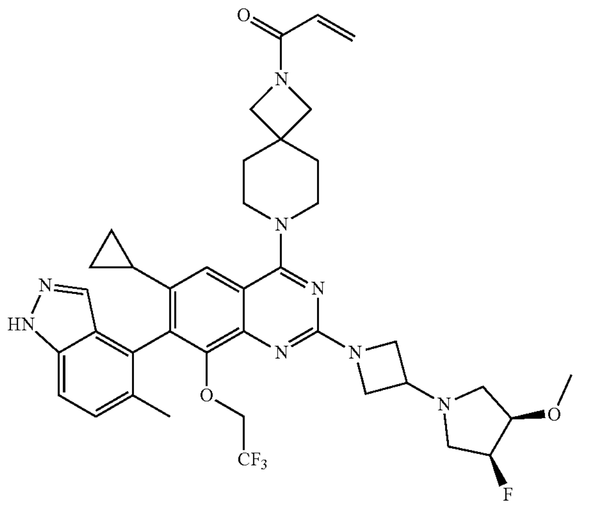 [SMILES: C=CC(=O)N1CC2(CCN(c3nc(N4CC(N5C[C@H](F)[C@H](OC)C5)C4)nc4c(OCC(F)(F)F)c(-c5c(C)ccc6[nH]ncc56)c(C5CC5)cc34)CC2)C1] | 749.4 |

TABLE 1-continued
| Compound | Compound structure | [M + H]+ |
|---|---|---|
| 265 | 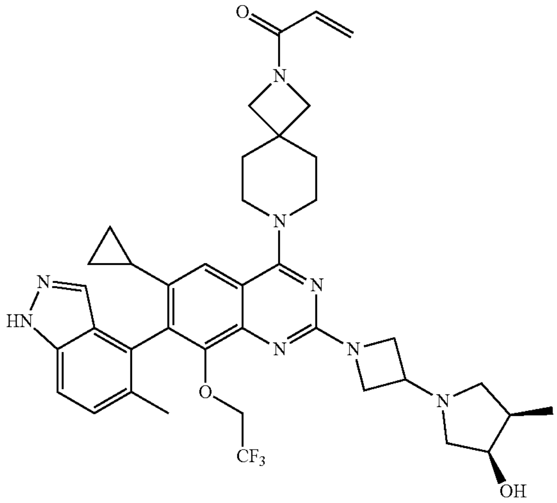 [SMILES: C=CC(=O)N1CC2(CCN(c3nc(N4CC(N5C[C@@H](C)[C@@H](O)C5)C4)nc4c(OCC(F)(F)F)c(-c5c(C)ccc6[nH]ncc56)c(C5CC5)cc34)CC2)C1] | 731.4 |
| 266 | 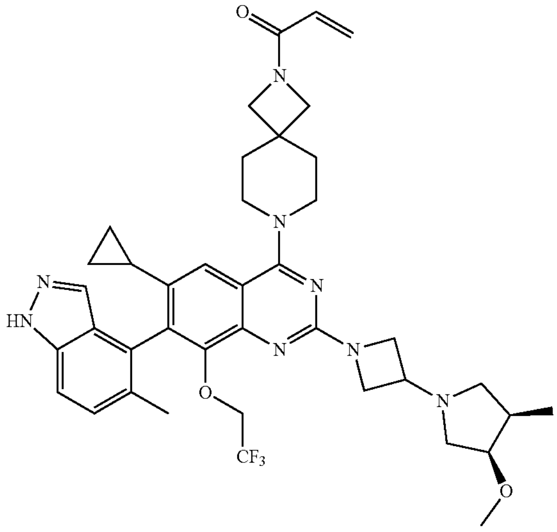 [SMILES: C=CC(=O)N1CC2(CCN(c3nc(N4CC(N5C[C@@H](C)[C@@H](OC)C5)C4)nc4c(OCC(F)(F)F)c(-c5c(C)ccc6[nH]ncc56)c(C5CC5)cc34)CC2)C1] | 745.4 |
| 267 | 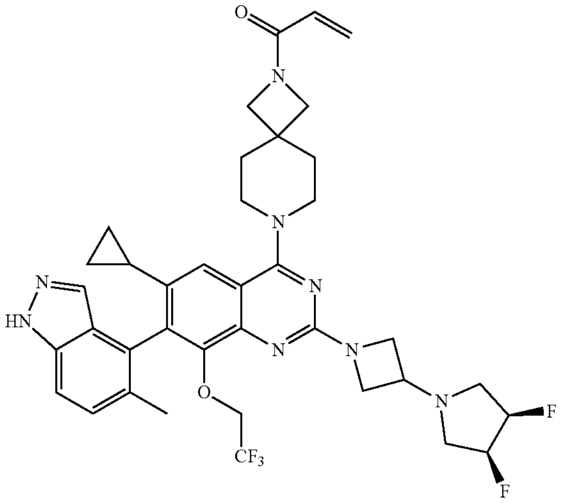 [SMILES: C=CC(=O)N1CC2(CCN(c3nc(N4CC(N5C[C@@H](F)[C@@H](F)C5)C4)nc4c(OCC(F)(F)F)c(-c5c(C)ccc6[nH]ncc56)c(C5CC5)cc34)CC2)C1] | 737.3 |

TABLE 1-continued
| Compound | Compound structure | [M + H]+ |
|---|---|---|
| 268 | 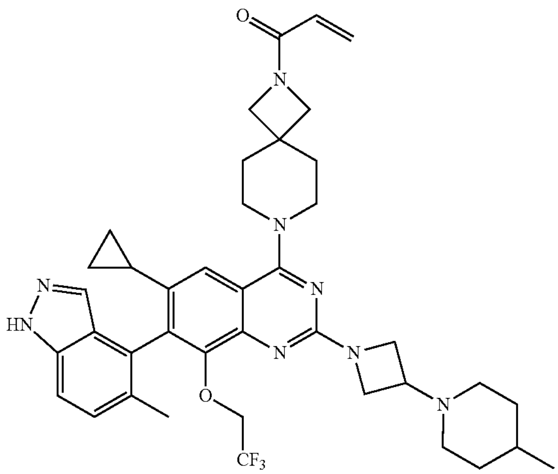 [SMILES: C=CC(=O)N1CC2(CCN(c3nc(N4CC(N5CCC(C)CC5)C4)nc4c(OCC(F)(F)F)c(-c5c(C)ccc6[nH]ncc56)c(C5CC5)cc34)CC2)C1] | 729.4 |
| 269 | 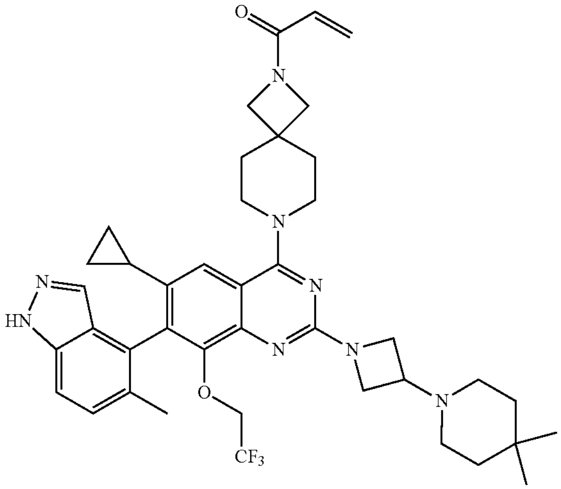 [SMILES: C=CC(=O)N1CC2(CCN(c3nc(N4CC(N5CCC(C)(C)CC5)C4)nc4c(OCC(F)(F)F)c(-c5c(C)ccc6[nH]ncc56)c(C5CC5)cc34)CC2)C1] | 743.4 |
| 270 | 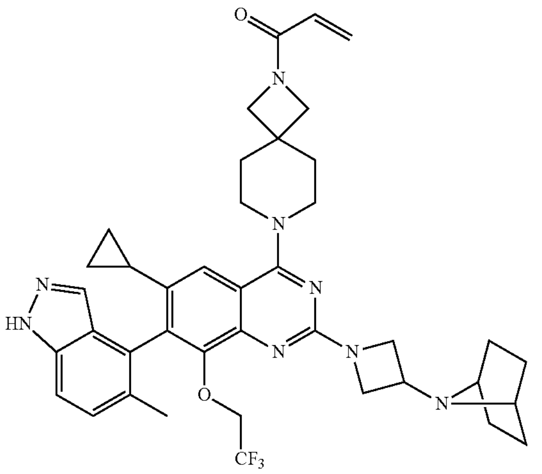 | 727.4 |

TABLE 1-continued
| Compound | Compound structure | [M + H]+ |
|---|---|---|
| 271 | 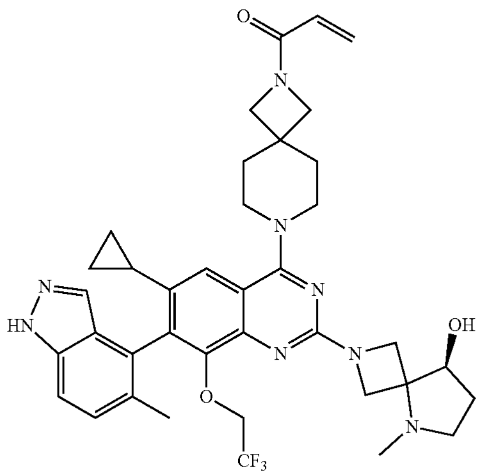 [SMILES: C=CC(=O)N1CC2(CCN(c3nc(N4CC5(C4)[C@@H](O)CCN5C)nc4c(OCC(F)(F)F)c(-c5c(C)ccc6[nH]ncc56)c(C5CC5)cc34)CC2)C1] | 717.3 |
| 272 | 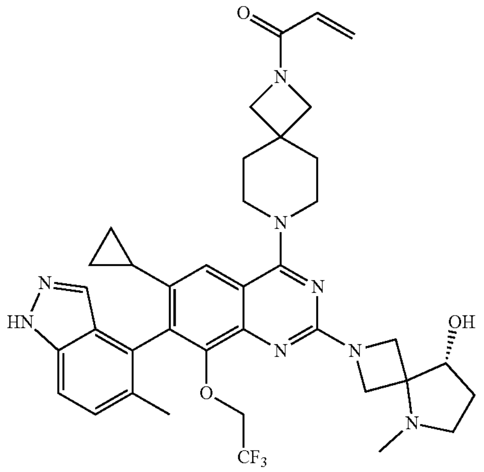 | 717.3 |
| 273 | 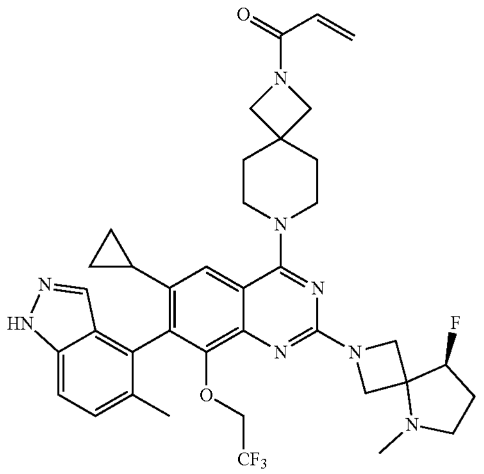 | 719.3 |

TABLE 1-continued
| Compound | Compound structure | [M + H]+ |
| --- | --- | --- |
| 274 | 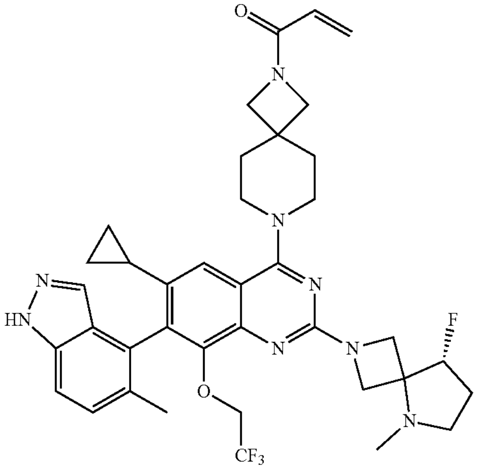 [SMILES: C=CC(=O)N1CC2(CCN(c3nc(N4CC5(C4)[C@H](F)CCN5C)nc4c(OCC(F)(F)F)c(-c5c(C)ccc6[nH]ncc56)c(C5CC5)cc34)CC2)C1] | 719.3 |
| 275 | 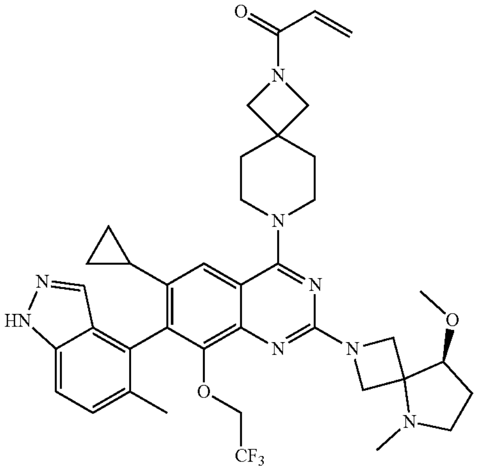 [SMILES: C=CC(=O)N1CC2(CCN(c3nc(N4CC5(C4)[C@@H](OC)CCN5C)nc4c(OCC(F)(F)F)c(-c5c(C)ccc6[nH]ncc56)c(C5CC5)cc34)CC2)C1] | 731.4 |
| 276 | 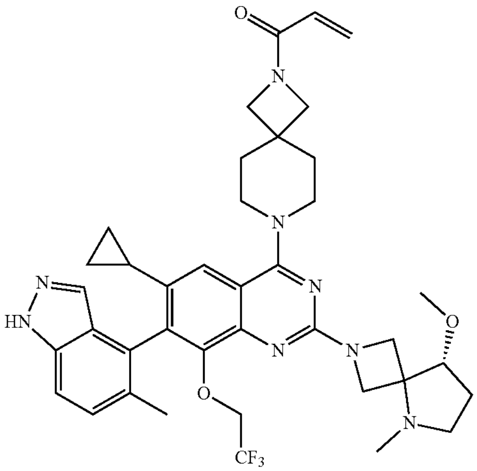 [SMILES: C=CC(=O)N1CC2(CCN(c3nc(N4CC5(C4)[C@H](OC)CCN5C)nc4c(OCC(F)(F)F)c(-c5c(C)ccc6[nH]ncc56)c(C5CC5)cc34)CC2)C1] | 731.4 |

TABLE 1-continued
| Compound | Compound structure | [M + H]+ |
|---|---|---|
| 277 | 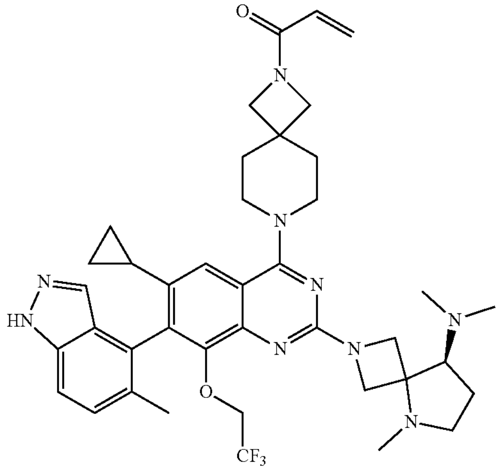 [SMILES: C=CC(=O)N1CC2(CCN(c3nc(N4CC5(C4)[C@@H](N(C)C)CCN5C)nc4c(OCC(F)(F)F)c(-c5c(C)ccc6[nH]ncc56)c(C5CC5)cc34)CC2)C1] | 744.4 |
| 278 | 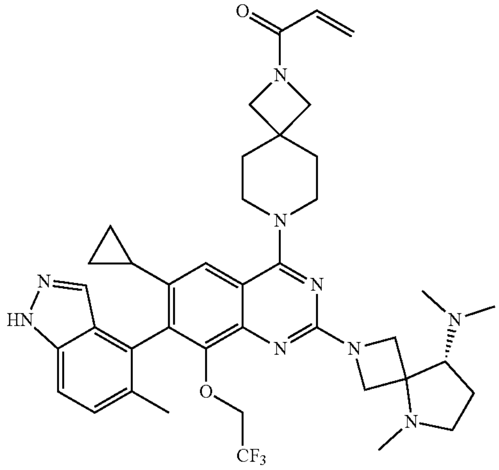 | 744.4 |
| 279 | 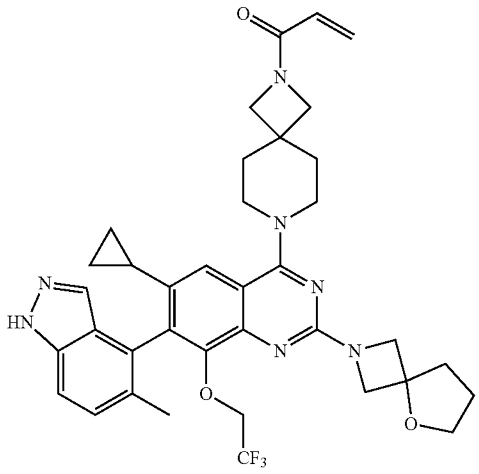 [SMILES: C=CC(=O)N1CC2(CCN(c3nc(N4CC5(CCCO5)C4)nc4c(OCC(F)(F)F)c(-c5c(C)ccc6[nH]ncc56)c(C5CC5)cc34)CC2)C1] | 688.3 |

TABLE 1-continued
| Compound | Compound structure | [M + H]+ |
|---|---|---|
| 280 | 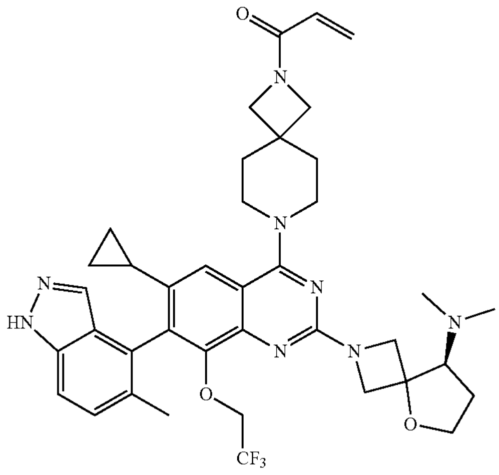 [SMILES: C=CC(=O)N1CC2(CCN(c3nc(N4CC5(C4)OCC[C@@H]5N(C)C)nc4c(OCC(F)(F)F)c(-c5c(C)ccc6[nH]ncc56)c(C5CC5)cc34)CC2)C1] | 731.4 |
| 281 | 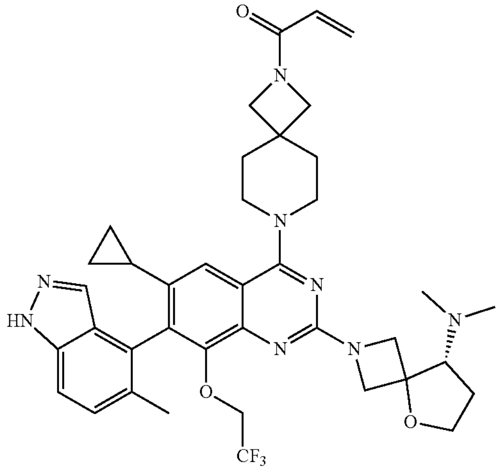 [SMILES: C=CC(=O)N1CC2(CCN(c3nc(N4CC5(C4)OCC[C@H]5N(C)C)nc4c(OCC(F)(F)F)c(-c5c(C)ccc6[nH]ncc56)c(C5CC5)cc34)CC2)C1] | 731.4 |
| 282 | 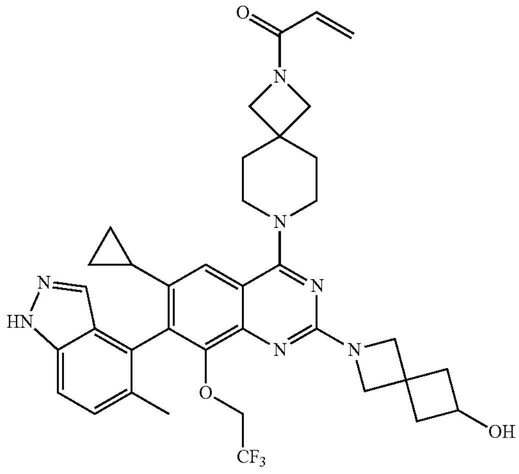 | 688.3 |

TABLE 1-continued
| Compound | Compound structure | [M + H]+ |
|---|---|---|
| 283 | 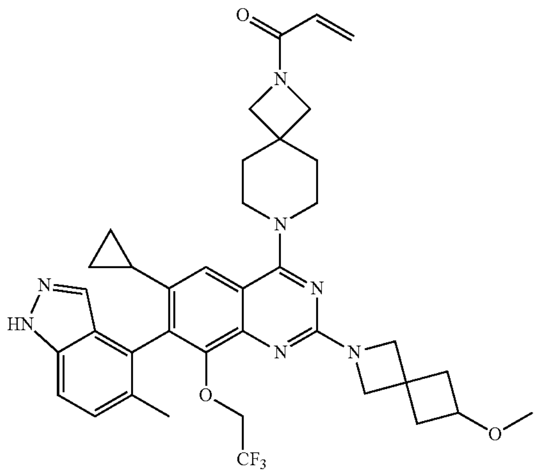 [SMILES: C=CC(=O)N1CC2(CCN(c3nc(N4CC5(CC(OC)C5)C4)nc4c(OCC(F)(F)F)c(-c5c(C)ccc6[nH]ncc56)c(C5CC5)cc34)CC2)C1] | 702.3 |
| 284 | 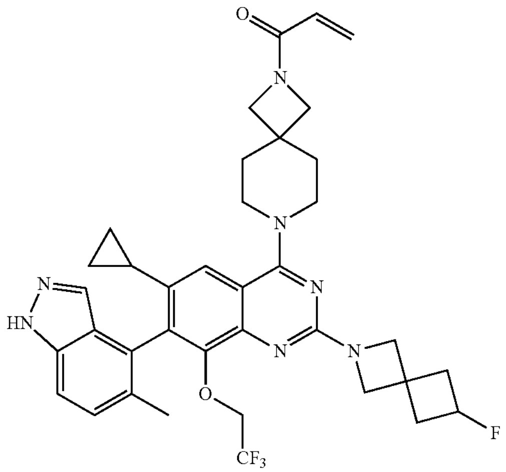 | 690.3 |
| 285 | 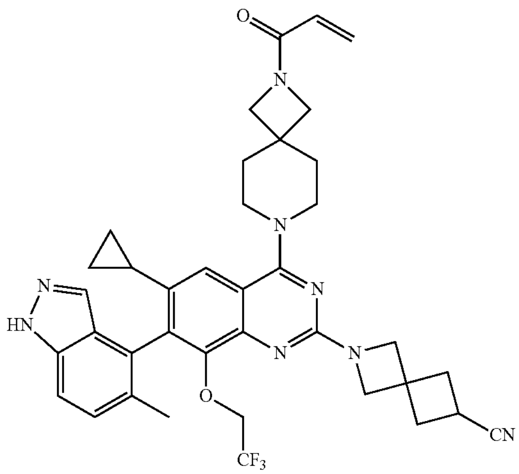 [SMILES: C=CC(=O)N1CC2(CCN(c3nc(N4CC5(CC(C#N)C5)C4)nc4c(OCC(F)(F)F)c(-c5c(C)ccc6[nH]ncc56)c(C5CC5)cc34)CC2)C1] | 697.3 |

TABLE 1-continued
| Compound | Compound structure | [M + H]+ |
| --- | --- | --- |
| 286 | 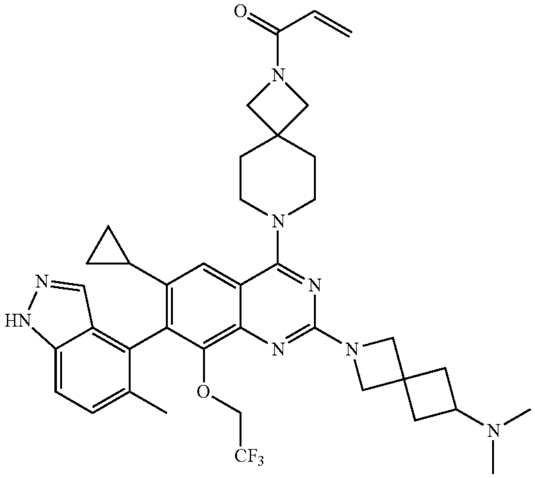 [SMILES: C=CC(=O)N1CC2(CCN(c3nc(N4CC5(CC(N(C)C)C5)C4)nc4c(OCC(F)(F)F)c(-c5c(C)ccc6[nH]ncc56)c(C5CC5)cc34)CC2)C1] | 715.4 |
| 287 | 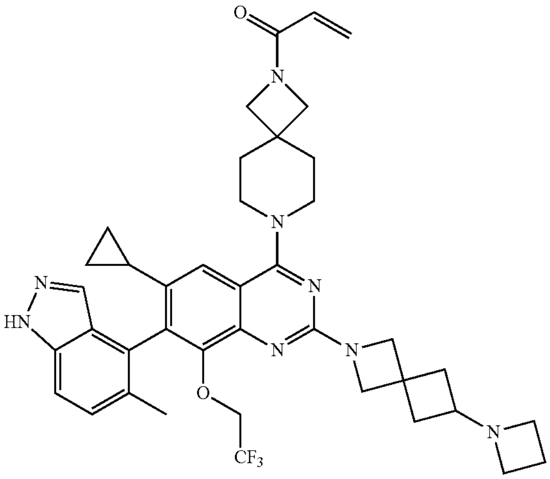 [SMILES: C=CC(=O)N1CC2(CCN(c3nc(N4CC5(CC(N6CCC6)C5)C4)nc4c(OCC(F)(F)F)c(-c5c(C)ccc6[nH]ncc56)c(C5CC5)cc34)CC2)C1] | 727.4 |
| 288 | 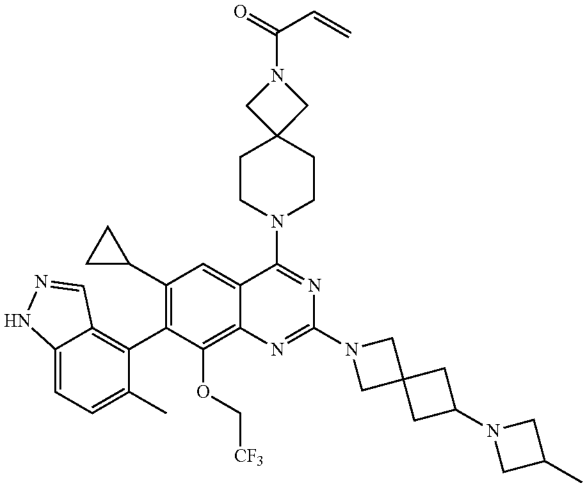 [SMILES: C=CC(=O)N1CC2(CCN(c3nc(N4CC5(CC(N6CC(C)C6)C5)C4)nc4c(OCC(F)(F)F)c(-c5c(C)ccc6[nH]ncc56)c(C5CC5)cc34)CC2)C1] | 741.4 |

TABLE 1-continued
| Compound | Compound structure | [M + H]+ |
| --- | --- | --- |
| 289 | 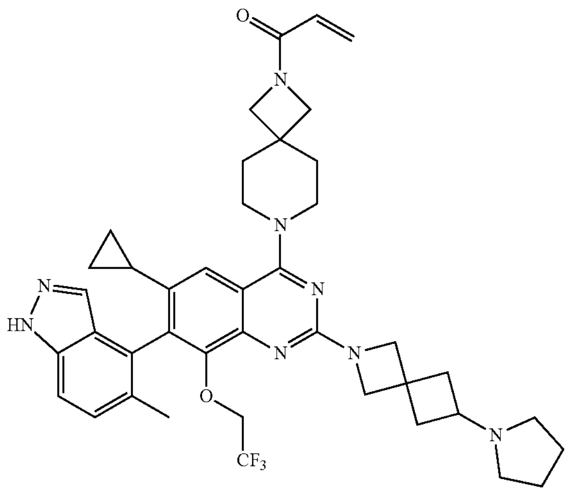 [SMILES: C=CC(=O)N1CC2(CCN(c3nc(N4CC5(CC(N6CCCC6)C5)C4)nc4c(OCC(F)(F)F)c(-c5c(C)ccc6[nH]ncc56)c(C5CC5)cc34)CC2)C1] | 741.4 |
| 290 | 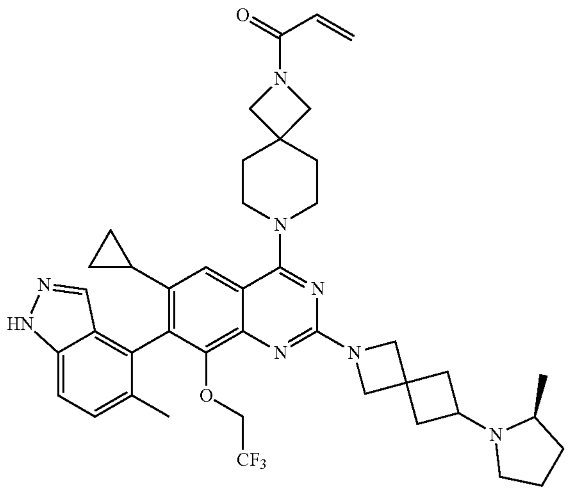 [SMILES: C=CC(=O)N1CC2(CCN(c3nc(N4CC5(CC(N6CCC[C@@H]6C)C5)C4)nc4c(OCC(F)(F)F)c(-c5c(C)ccc6[nH]ncc56)c(C5CC5)cc34)CC2)C1] | 755.4 |
| 291 | 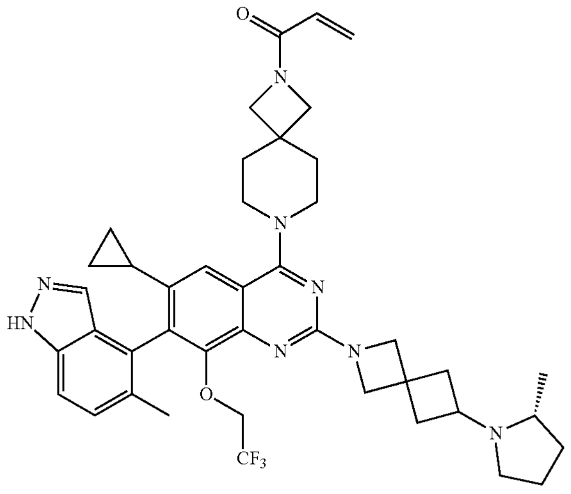 [SMILES: C=CC(=O)N1CC2(CCN(c3nc(N4CC5(CC(N6CCC[C@H]6C)C5)C4)nc4c(OCC(F)(F)F)c(-c5c(C)ccc6[nH]ncc56)c(C5CC5)cc34)CC2)C1] | 755.4 |

TABLE 1-continued
| Compound | Compound structure | [M + H]+ |
|---|---|---|
| 292 | 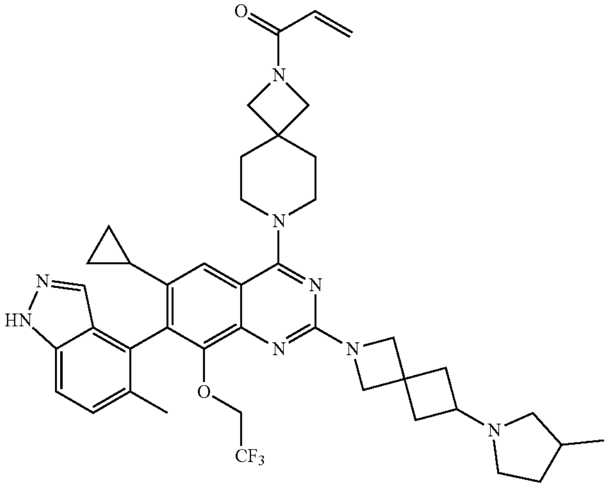 [SMILES: C=CC(=O)N1CC2(CCN(c3nc(N4CC5(CC(N6CC[C@@H](C)C6)C5)C4)nc4c(OCC(F)(F)F)c(-c5c(C)ccc6[nH]ncc56)c(C5CC5)cc34)CC2)C1] | 755.4 |
| 293 | 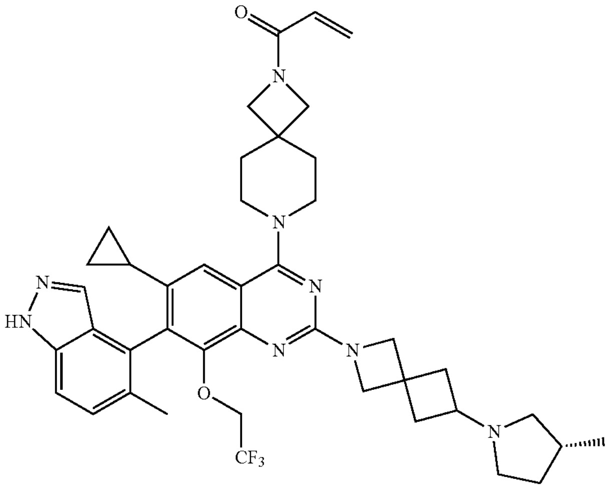 | 755.4 |
| 294 | 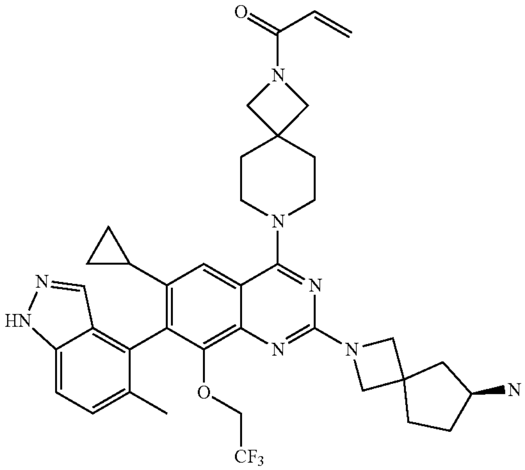 [SMILES: C=CC(=O)N1CC2(CCN(c3nc(N4CC5(CC[C@H](N)C5)C4)nc4c(OCC(F)(F)F)c(-c5c(C)ccc6[nH]ncc56)c(C5CC5)cc34)CC2)C1] | 729.4 |

TABLE 1-continued
| Compound | Compound structure | [M + H]+ |
|---|---|---|
| 295 | 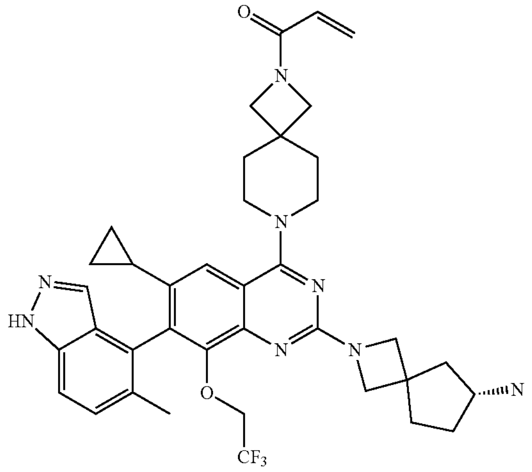 [SMILES: C=CC(=O)N1CC2(CCN(c3nc(N4CC5(CC[C@@H](N)C5)C4)nc4c(OCC(F)(F)F)c(-c5c(C)ccc6[nH]ncc56)c(C5CC5)cc34)CC2)C1] | 729.4 |
| 296 | 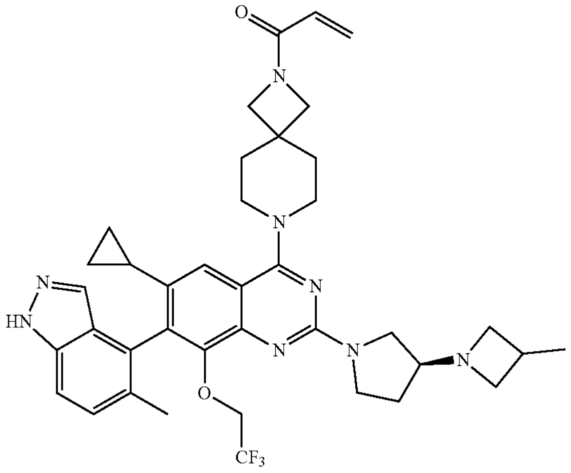 | 715.4 |
| 297 | 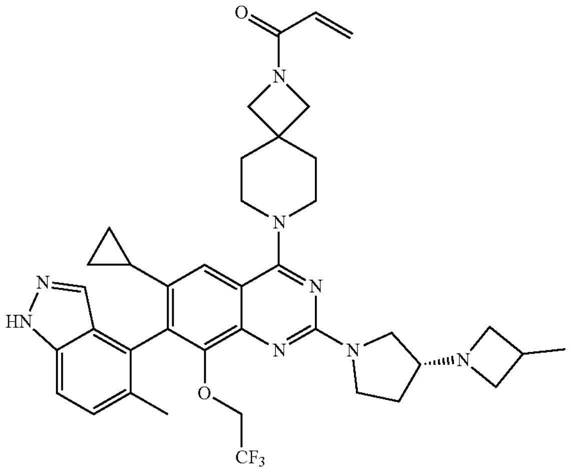 [SMILES: C=CC(=O)N1CC2(CCN(c3nc(N4CC[C@@H](N5CC(C)C5)C4)nc4c(OCC(F)(F)F)c(-c5c(C)ccc6[nH]ncc56)c(C5CC5)cc34)CC2)C1] | 715.4 |

TABLE 1-continued
| Compound | Compound structure | [M + H]+ |
| --- | --- | --- |
| 298 | 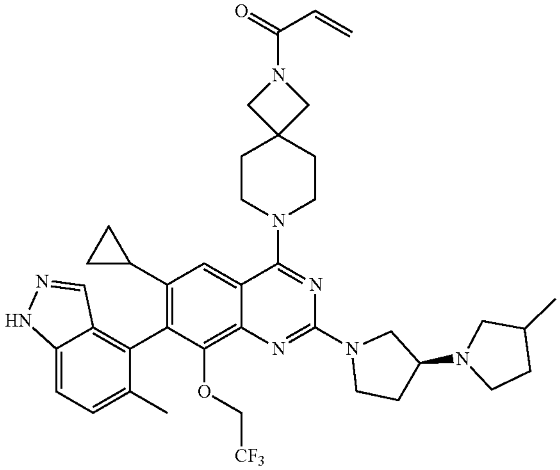 | 729.4 |
| 299 | 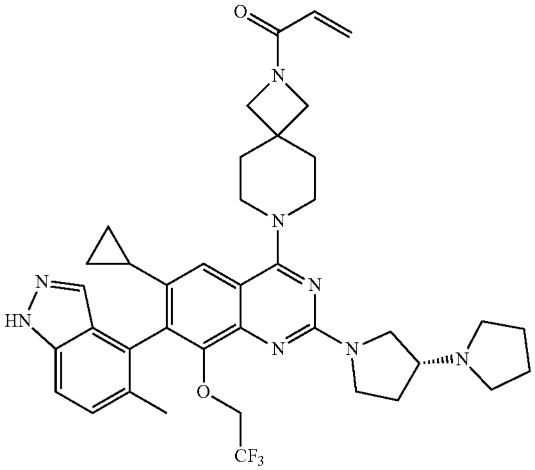 [SMILES: C=CC(=O)N1CC2(CCN(c3nc(N4CC[C@@H](N5CCCC5)C4)nc4c(OCC(F)(F)F)c(-c5c(C)ccc6[nH]ncc56)c(C5CC5)cc34)CC2)C1] | 729.4 |
| 300 | 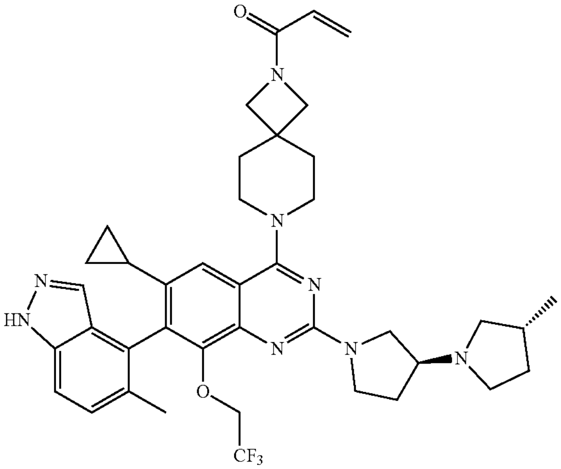 | 729.4 |

TABLE 1-continued
| Compound | Compound structure | [M + H]+ |
| --- | --- | --- |
| 301 | 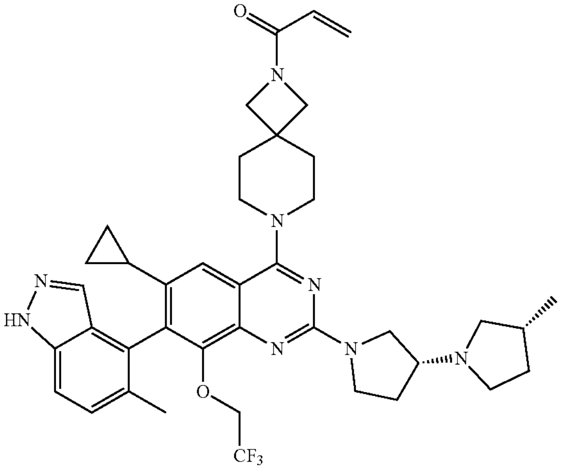 | 729.4 |
| 302 | 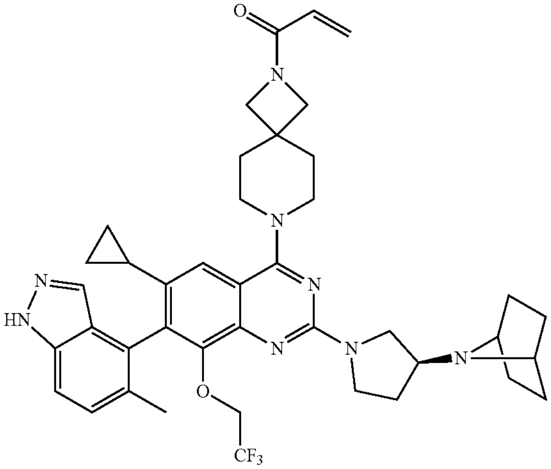 [SMILES: C=CC(=O)N1CC2(CCN(c3nc(N4CC[C@H](N5C6CCC5CC6)C4)nc4c(OCC(F)(F)F)c(-c5c(C)ccc6[nH]ncc56)c(C5CC5)cc34)CC2)C1] | 741.4 |
| 303 | 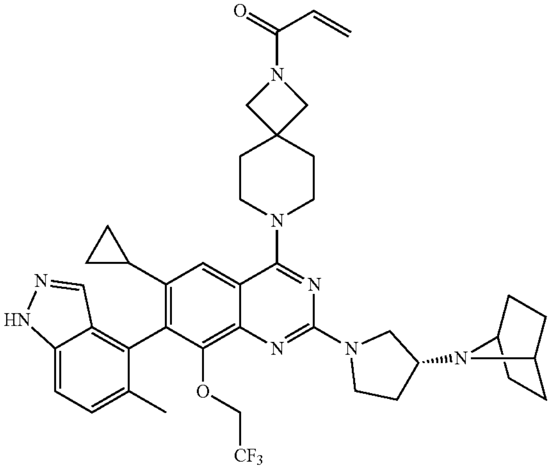 [SMILES: C=CC(=O)N1CC2(CCN(c3nc(N4CC[C@@H](N5C6CCC5CC6)C4)nc4c(OCC(F)(F)F)c(-c5c(C)ccc6[nH]ncc56)c(C5CC5)cc34)CC2)C1] | 741.4 |

TABLE 1-continued
| Compound | Compound structure | [M + H]+ |
| --- | --- | --- |
| 304 | 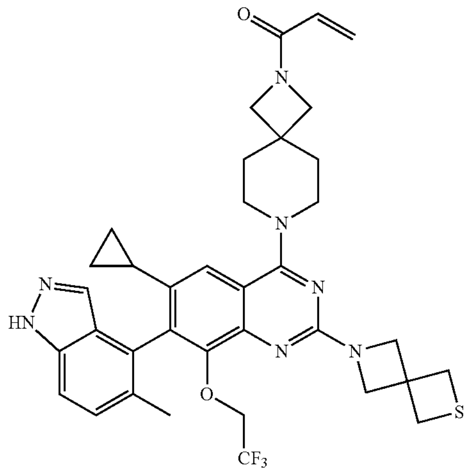 [SMILES: C=CC(=O)N1CC2(CCN(c3nc(N4CC5(CSC5)C4)nc4c(OCC(F)(F)F)c(-c5c(C)ccc6[nH]ncc56)c(C5CC5)cc34)CC2)C1] | 690.3 |
| 305 | 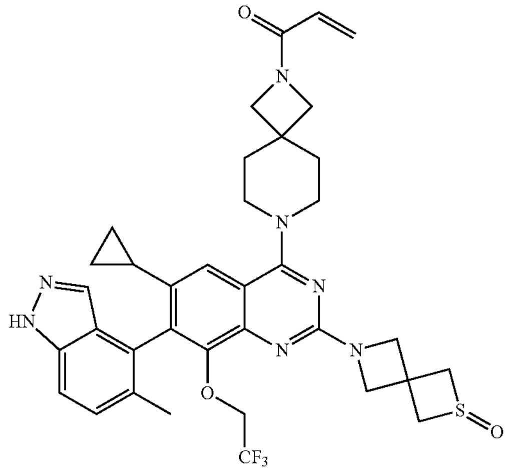 [SMILES: C=CC(=O)N1CC2(CCN(c3nc(N4CC5(C4)CS(=O)C5)nc4c(OCC(F)(F)F)c(-c5c(C)ccc6[nH]ncc56)c(C5CC5)cc34)CC2)C1] | 706.3 |
| 306 | 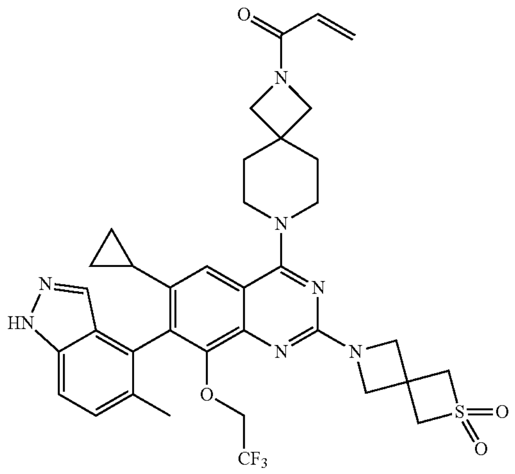 [SMILES: C=CC(=O)N1CC2(CCN(c3nc(N4CC5(C4)CS(=O)(=O)C5)nc4c(OCC(F)(F)F)c(-c5c(C)ccc6[nH]ncc56)c(C5CC5)cc34)CC2)C1] | 721.3 |

TABLE 1-continued
| Compound | Compound structure | [M + H]+ |
|---|---|---|
| 307 | 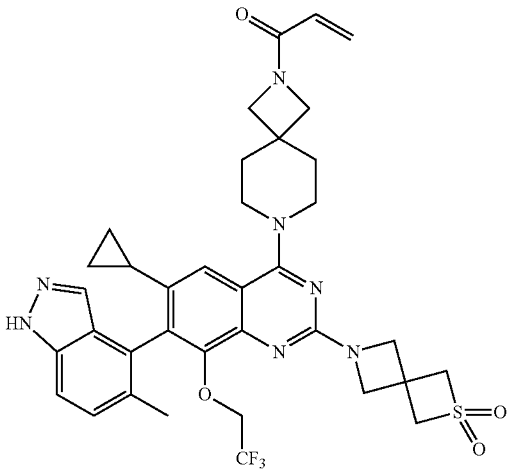 [SMILES: C=CC(=O)N1CC2(CCN(c3nc(N4CC5(C4)CS(=O)(=O)C5)nc4c(OCC(F)(F)F)c(-c5c(C)ccc6[nH]ncc56)c(C5CC5)cc34)CC2)C1] | 750.3 |
| 308 | 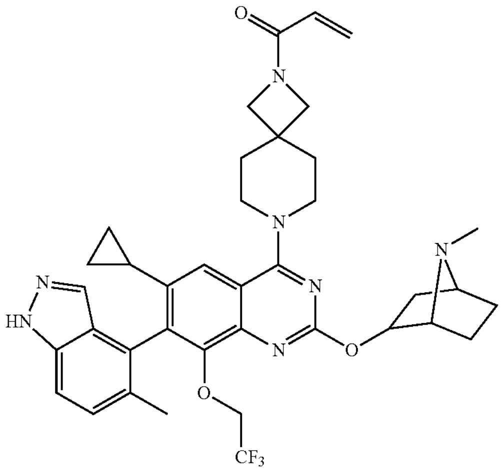 [SMILES: C=CC(=O)N1CC2(CCN(c3nc(OC4CC5CCC4N5C)nc4c(OCC(F)(F)F)c(-c5c(C)ccc6[nH]ncc56)c(C5CC5)cc34)CC2)C1] | 702.3 |
| 309 | 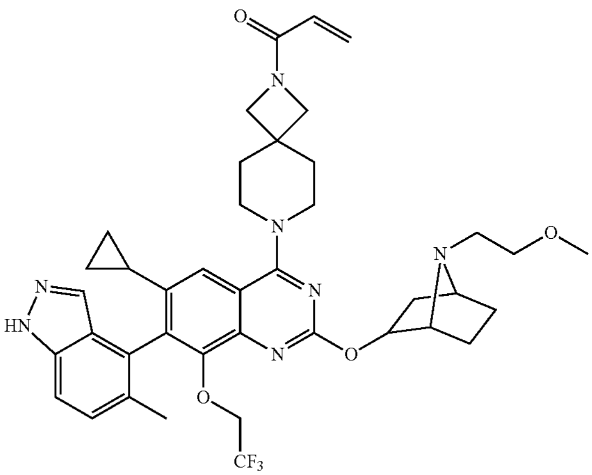 [SMILES: C=CC(=O)N1CC2(CCN(c3nc(OC4CC5CCC4N5CCOC)nc4c(OCC(F)(F)F)c(-c5c(C)ccc6[nH]ncc56)c(C5CC5)cc34)CC2)C1] | 746.3 |

TABLE 1-continued
| Compound | Compound structure | [M + H]+ |
| --- | --- | --- |
| 310 | 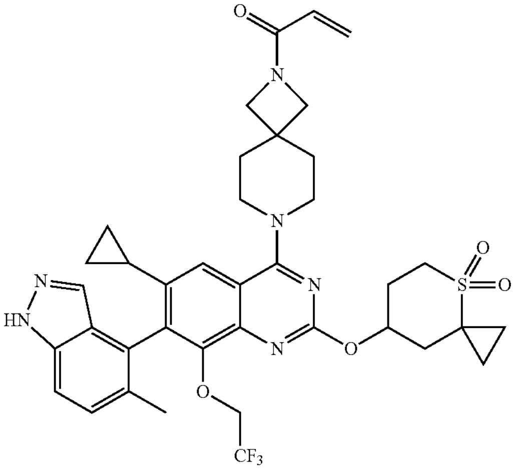 [SMILES: C=CC(=O)N1CC2(CCN(c3nc(OC4CCS(=O)(=O)C5(CC5)C4)nc4c(OCC(F)(F)F)c(-c5c(C)ccc6[nH]ncc56)c(C5CC5)cc34)CC2)C1] | 751.3 |
| 311 | 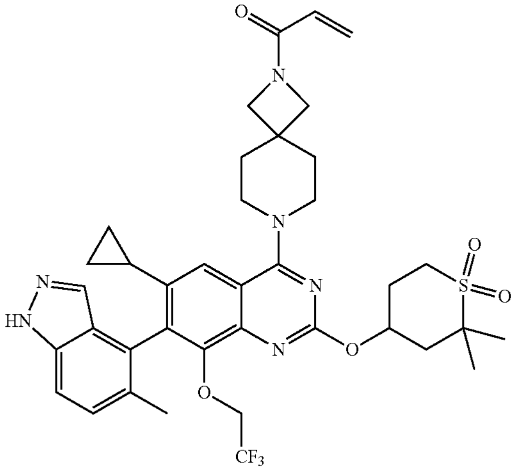 [SMILES: C=CC(=O)N1CC2(CCN(c3nc(OC4CCS(=O)(=O)C(C)(C)C4)nc4c(OCC(F)(F)F)c(-c5c(C)ccc6[nH]ncc56)c(C5CC5)cc34)CC2)C1] | 753.3 |
| 312 | 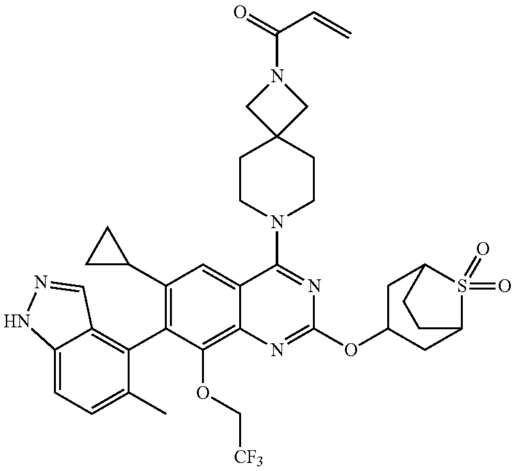 [SMILES: C=CC(=O)N1CC2(CCN(c3nc(OC4CC5CCC(C4)S5(=O)=O)nc4c(OCC(F)(F)F)c(-c5c(C)ccc6[nH]ncc56)c(C5CC5)cc34)CC2)C1] | 751.3 |

TABLE 1-continued
| Compound | Compound structure | [M + H]$^+$ |
|---|---|---|
| 313 | 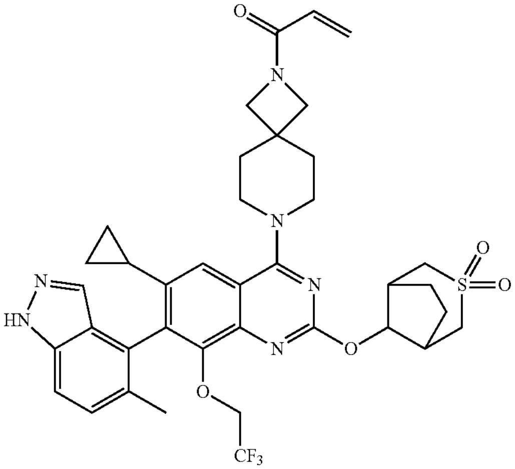 [SMILES: C=CC(=O)N1CC2(CCN(c3nc(OC4C5CCC4CS(=O)(=O)C5)nc4c(OCC(F)(F)F)c(-c5c(C)ccc6[nH]ncc56)c(C5CC5)cc34)CC2)C1] | 751.3 |
| 314 | 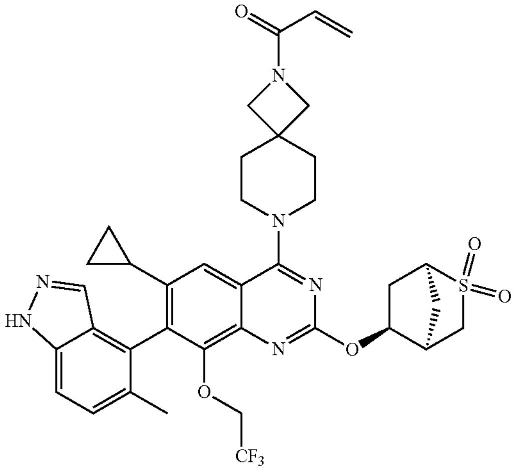 [SMILES: C=CC(=O)N1CC2(CCN(c3nc(O[C@H]4C[C@@H]5C[C@H]4CS5(=O)=O)nc4c(OCC(F)(F)F)c(-c5c(C)ccc6[nH]ncc56)c(C5CC5)cc34)CC2)C1] | 737.3 |
| 315 | 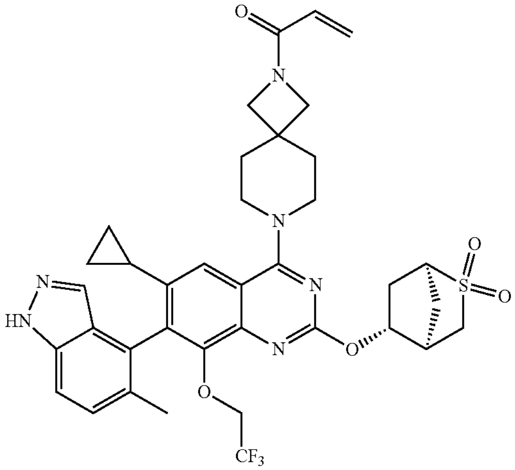 [SMILES: C=CC(=O)N1CC2(CCN(c3nc(O[C@@H]4C[C@@H]5C[C@H]4CS5(=O)=O)nc4c(OCC(F)(F)F)c(-c5c(C)ccc6[nH]ncc56)c(C5CC5)cc34)CC2)C1] | 737.3 |

TABLE 1-continued
| Compound | Compound structure | [M + H]+ |
| --- | --- | --- |
| 316 | 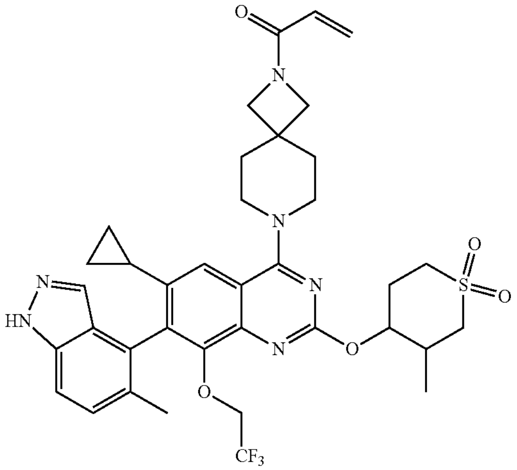 [SMILES: C=CC(=O)N1CC2(CCN(c3nc(OC4CCS(=O)(=O)CC4C)nc4c(OCC(F)(F)F)c(-c5c(C)ccc6[nH]ncc56)c(C5CC5)cc34)CC2)C1] | 739.3 |
| 317 | 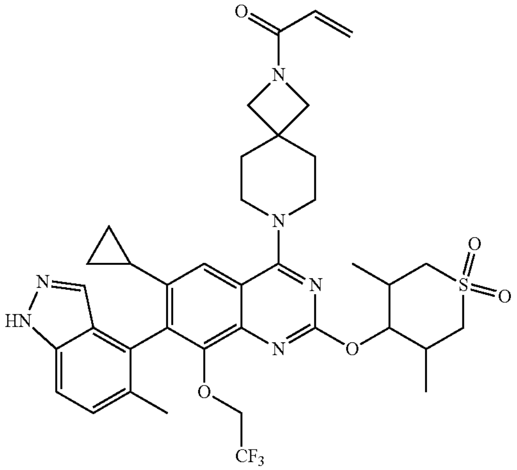 [SMILES: C=CC(=O)N1CC2(CCN(c3nc(OC4C(C)CS(=O)(=O)CC4C)nc4c(OCC(F)(F)F)c(-c5c(C)ccc6[nH]ncc56)c(C5CC5)cc34)CC2)C1] | 753.3 |
| 318 | 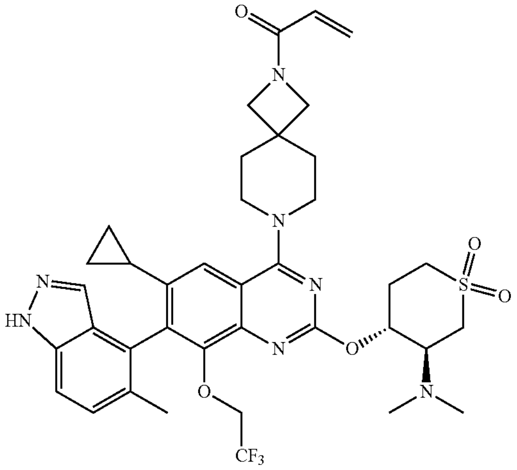 [SMILES: C=CC(=O)N1CC2(CCN(c3nc(O[C@@H]4CCS(=O)(=O)C[C@H]4N(C)C)nc4c(OCC(F)(F)F)c(-c5c(C)ccc6[nH]ncc56)c(C5CC5)cc34)CC2)C1] | 768.3 |

TABLE 1-continued
| Compound | Compound structure | [M + H]+ |
|---|---|---|
| 319 | 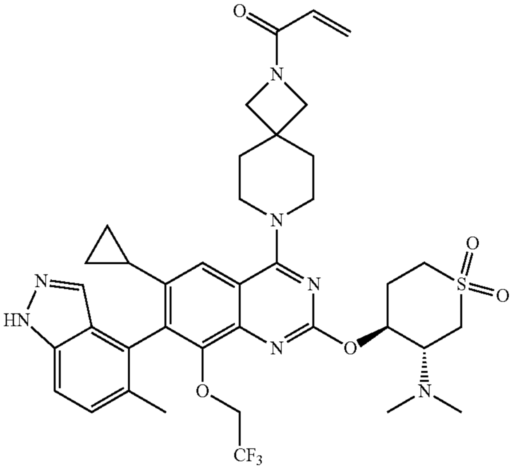 [SMILES: C=CC(=O)N1CC2(CCN(c3nc(O[C@H]4CCS(=O)(=O)C[C@@H]4N(C)C)nc4c(OCC(F)(F)F)c(-c5c(C)ccc6[nH]ncc56)c(C5CC5)cc34)CC2)C1] | 768.3 |
| 320 | 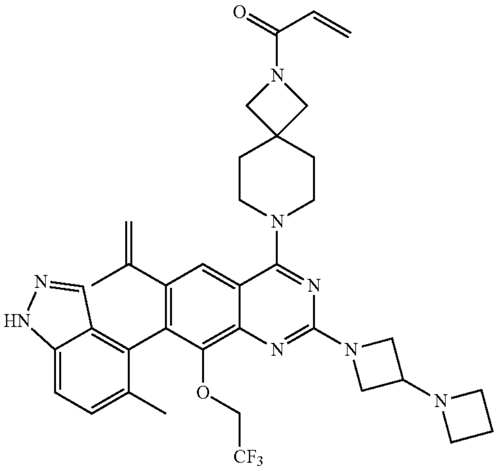 [SMILES: C=CC(=O)N1CC2(CCN(c3nc(N4CC(N5CCC5)C4)nc4c(OCC(F)(F)F)c(-c5c(C)ccc6[nH]ncc56)c(C(=C)C)cc34)CC2)C1] | 687.3 |
| 321 | 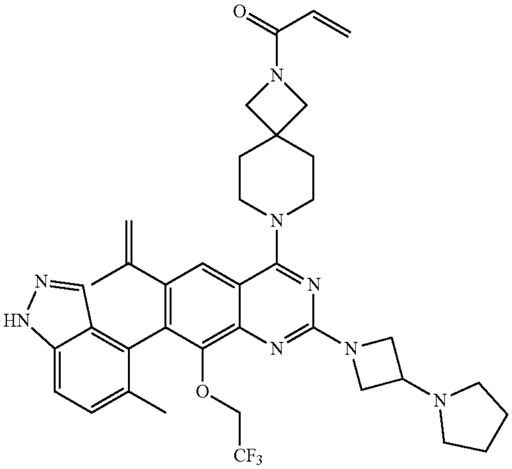 | 701.3 |

TABLE 1-continued
| Compound | Compound structure | [M + H]+ |
| --- | --- | --- |
| 322 | 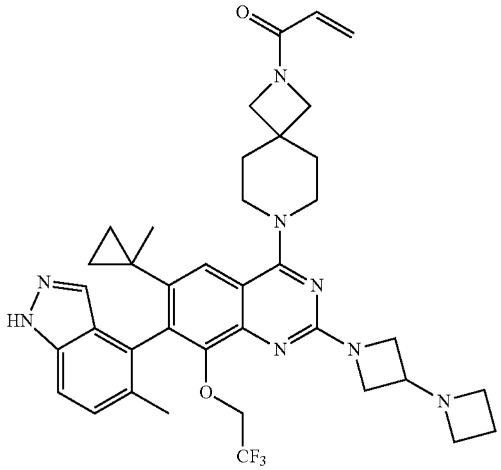 [SMILES: C=CC(=O)N1CC2(CCN(c3nc(N4CC(N5CCC5)C4)nc4c(OCC(F)(F)F)c(-c5c(C)ccc6[nH]ncc56)c(C5(C)CC5)cc34)CC2)C1] | 701.3 |
| 323 | 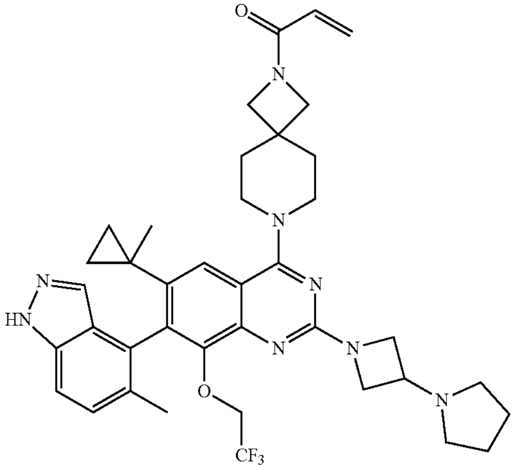 | 715.3 |
| 324 | 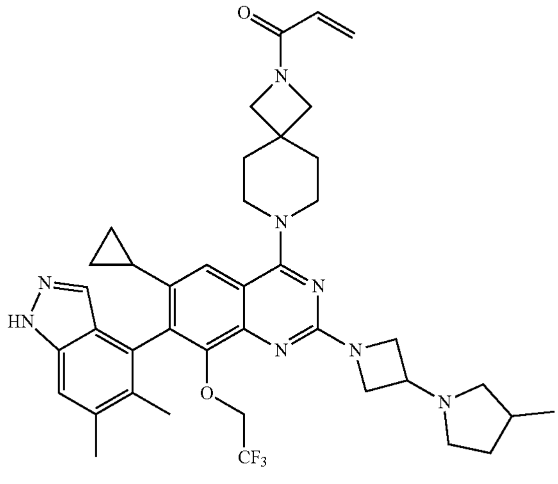 | 729.3 |

TABLE 1-continued
| Compound | Compound structure | [M + H]+ |
|---|---|---|
| 325 | 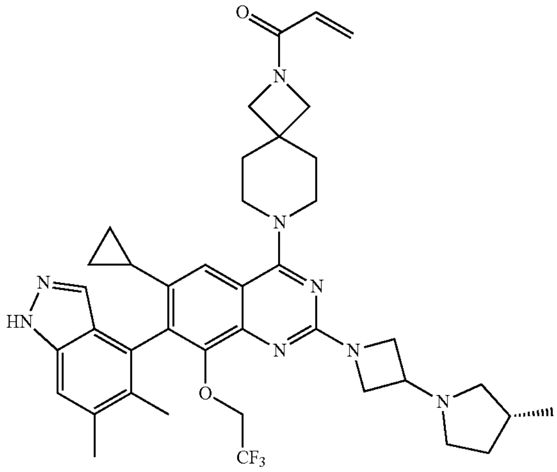 [SMILES: C=CC(=O)N1CC2(CCN(c3nc(N4CC(N5CC[C@@H](C)C5)C4)nc4c(OCC(F)(F)F)c(-c5c(C)c(C)cc6[nH]ncc56)c(C5CC5)cc34)CC2)C1] | 729.3 |
| 326 | 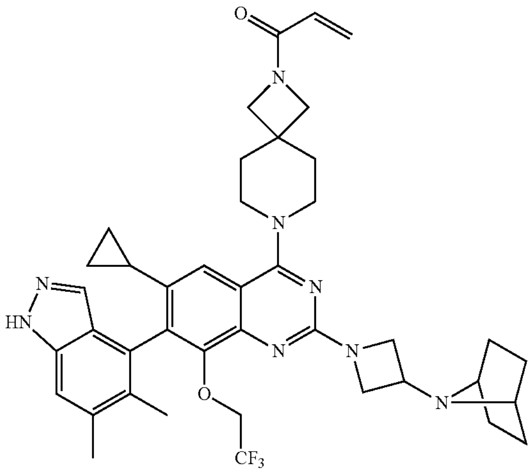 [SMILES: C=CC(=O)N1CC2(CCN(c3nc(N4CC(N5C6CCC5CC6)C4)nc4c(OCC(F)(F)F)c(-c5c(C)c(C)cc6[nH]ncc56)c(C5CC5)cc34)CC2)C1] | 741.4 |
| 327 | 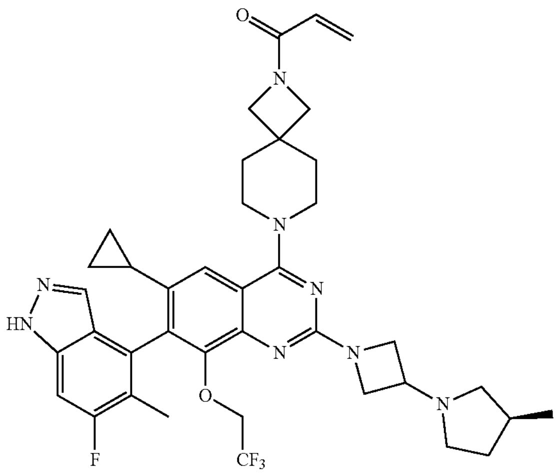 [SMILES: C=CC(=O)N1CC2(CCN(c3nc(N4CC(N5CC[C@H](C)C5)C4)nc4c(OCC(F)(F)F)c(-c5c(C)c(F)cc6[nH]ncc56)c(C5CC5)cc34)CC2)C1] | 733.4 |

TABLE 1-continued
| Compound | Compound structure | [M + H]+ |
|---|---|---|
| 328 | 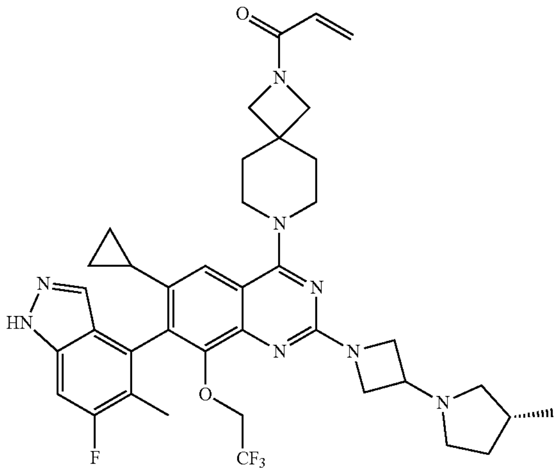 | 733.4 |
| 329 | 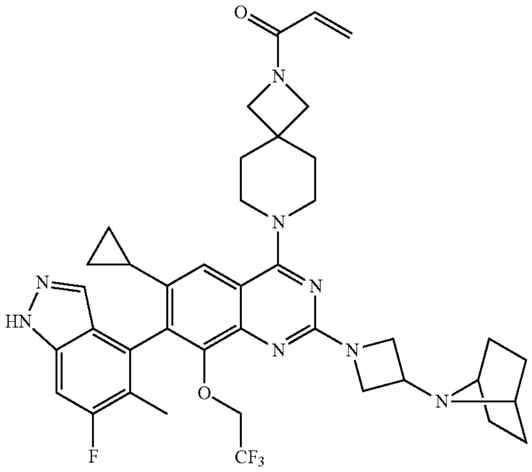 | 745.4 |
| 330 | 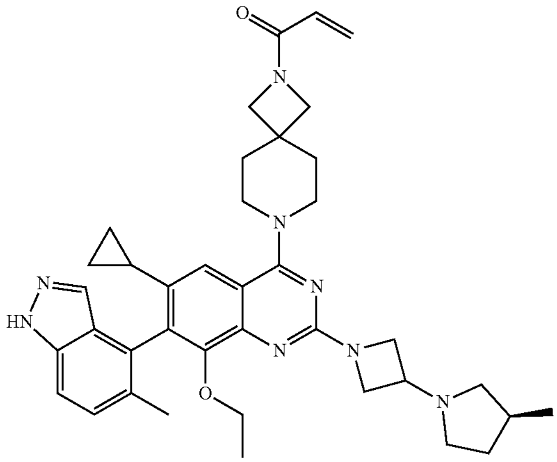 [SMILES: C=CC(=O)N1CC2(CCN(c3nc(N4CC(N5CC[C@H](C)C5)C4)nc4c(OCC)c(-c5c(C)ccc6[nH]ncc56)c(C5CC5)cc34)CC2)C1] | 661.4 |

TABLE 1-continued
| Compound | Compound structure | [M + H]$^+$ |
|---|---|---|
| 331 | 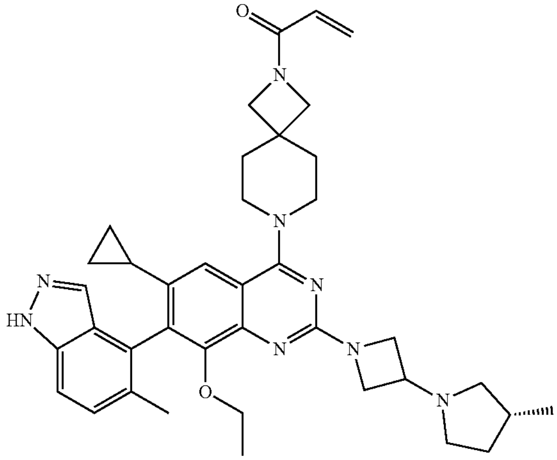 [SMILES: C=CC(=O)N1CC2(CCN(c3nc(N4CC(N5CC[C@@H](C)C5)C4)nc4c(OCC)c(-c5c(C)ccc6[nH]ncc56)c(C5CC5)cc34)CC2)C1] | 661.4 |
| 332 | 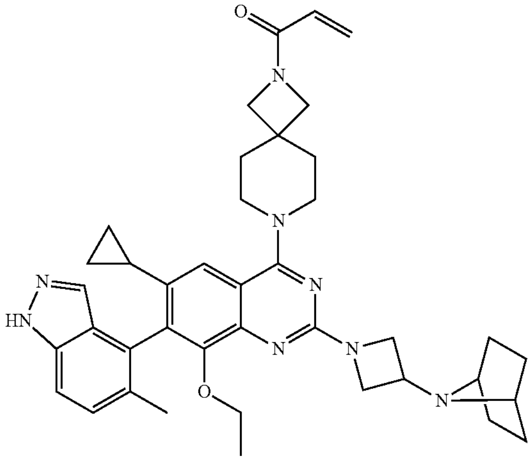 [SMILES: C=CC(=O)N1CC2(CCN(c3nc(N4CC(N5C6CCC5CC6)C4)nc4c(OCC)c(-c5c(C)ccc6[nH]ncc56)c(C5CC5)cc34)CC2)C1] | 673.4 |
| 333 | 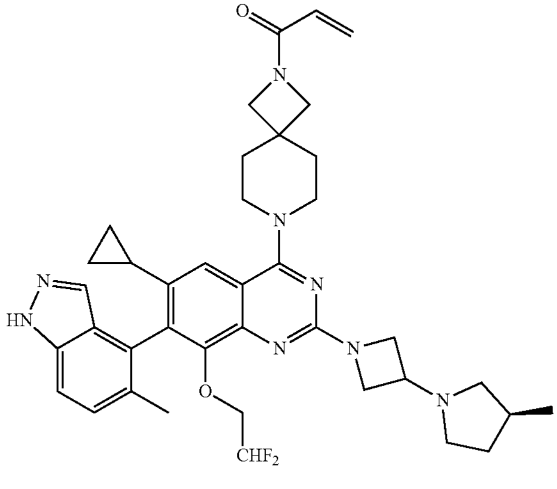 [SMILES: C=CC(=O)N1CC2(CCN(c3nc(N4CC(N5CC[C@H](C)C5)C4)nc4c(OCC(F)F)c(-c5c(C)ccc6[nH]ncc56)c(C5CC5)cc34)CC2)C1] | 697.4 |

TABLE 1-continued
| Compound | Compound structure | [M + H]+ |
| --- | --- | --- |
| 334 | 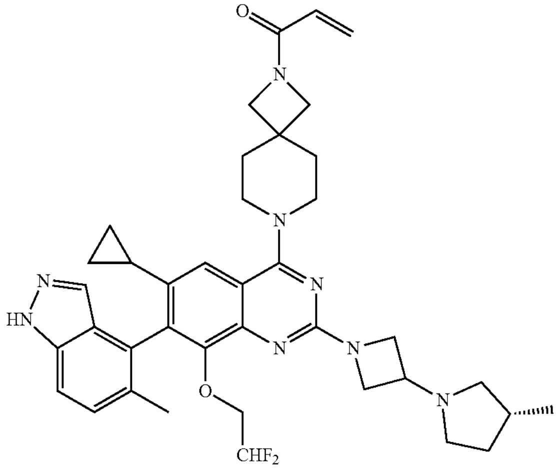 [SMILES: C=CC(=O)N1CC2(CCN(c3nc(N4CC(N5CC[C@@H](C)C5)C4)nc4c(OCC(F)F)c(-c5c(C)ccc6[nH]ncc56)c(C5CC5)cc34)CC2)C1] | 697.4 |
| 335 | 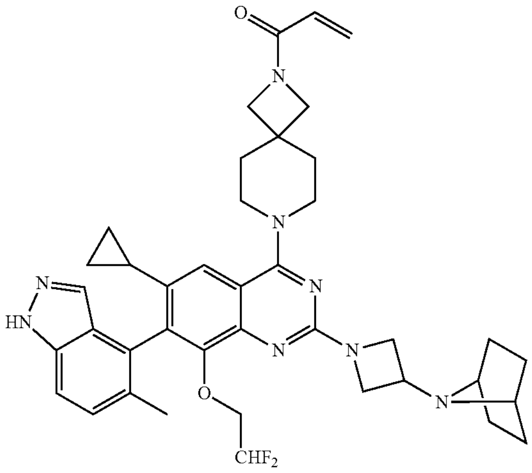 [SMILES: C=CC(=O)N1CC2(CCN(c3nc(N4CC(N5C6CCC5CC6)C4)nc4c(OCC(F)F)c(-c5c(C)ccc6[nH]ncc56)c(C5CC5)cc34)CC2)C1] | 709.4 |
| 336 | 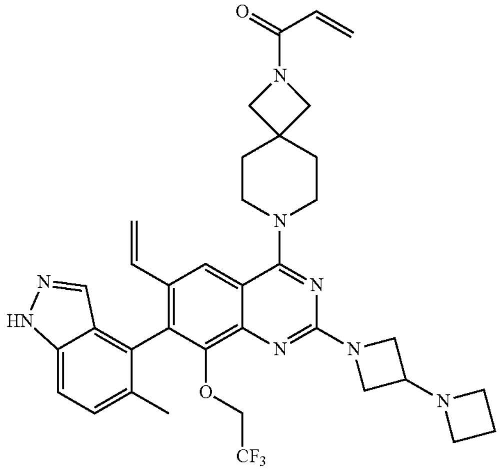 [SMILES: C=CC(=O)N1CC2(CCN(c3nc(N4CC(N5CCC5)C4)nc4c(OCC(F)(F)F)c(-c5c(C)ccc6[nH]ncc56)c(C=C)cc34)CC2)C1] | 673.3 |

TABLE 1-continued
| Compound | Compound structure | [M + H]+ |
|---|---|---|
| 337 | 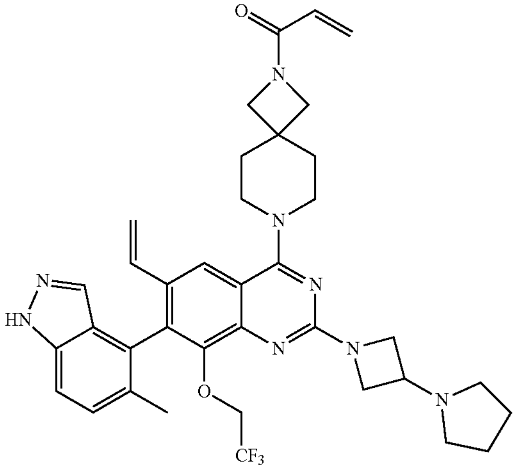 [SMILES: C=CC(=O)N1CC2(CCN(c3nc(N4CC(N5CCCC5)C4)nc4c(OCC(F)(F)F)c(-c5c(C)ccc6[nH]ncc56)c(C=C)cc34)CC2)C1] | 687.4 |
| 338 | 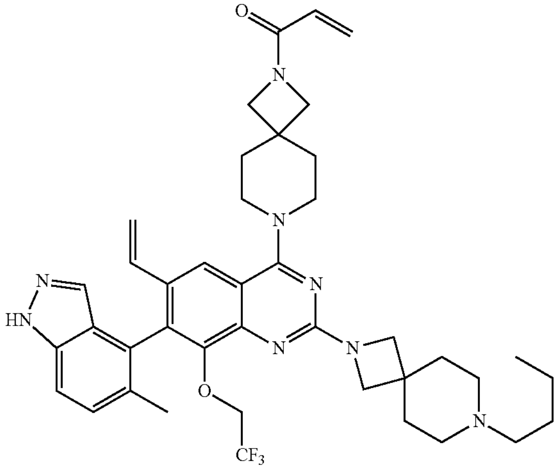 [SMILES: C=CC(=O)N1CC2(CCN(c3nc(N4CC5(CCN(CCCC)CC5)C4)nc4c(OCC(F)(F)F)c(-c5c(C)ccc6[nH]ncc56)c(C=C)cc34)CC2)C1] | 745.4 |
| 339 | 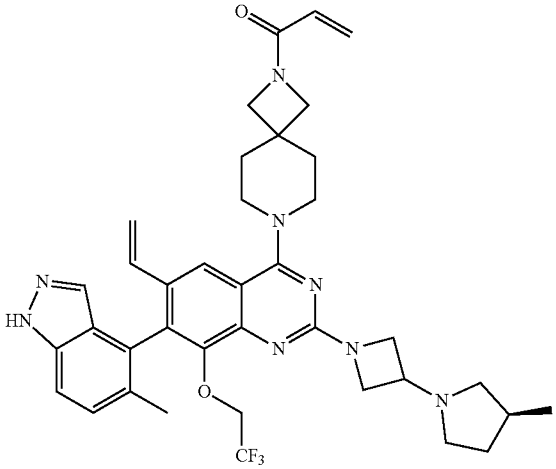 | 701.4 |

TABLE 1-continued

| Compound | Compound structure | [M + H]$^+$ |
|---|---|---|
| 340 | 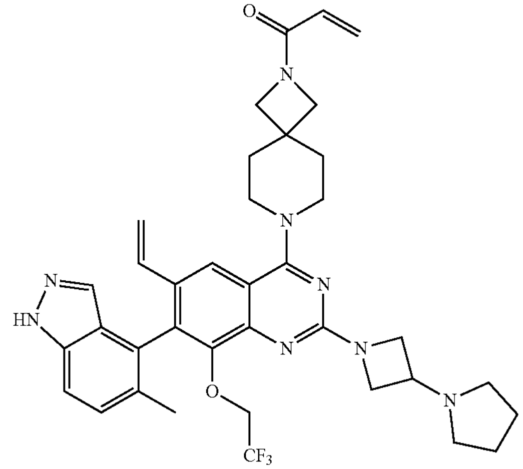 [SMILES: C=CC(=O)N1CC2(CCN(c3nc(N4CC(N5CCCC5)C4)nc4c(OCC(F)(F)F)c(-c5c(C)ccc6[nH]ncc56)c(C=C)cc34)CC2)C1] | 701.4 |
| 341 | 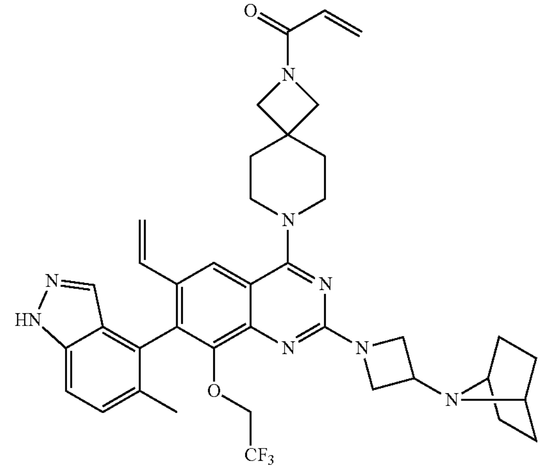 [SMILES: C=CC(=O)N1CC2(CCN(c3nc(N4CC(N5C6CCC5CC6)C4)nc4c(OCC(F)(F)F)c(-c5c(C)ccc6[nH]ncc56)c(C=C)cc34)CC2)C1] | 713.4 |

Example 342: Chiral Resolution of Compound 142

The compounds of the present application may have axial chirality. Compounds with axial chirality can be resolved to obtain two chiral isomers.

Compound 142 (50 mg) was dissolved in ethanol (2 mL) at a concentration of 25 mg/mL. The volume for each injection was 500 μL. Conditions for preparative chromatography: CHIRALPAK AD-H (20×250 mm, 5 μm) chromatography column; mobile phase: ethanol-n-hexane (40/60); flow rate: 12 mL/min; wavelength of detection: 254 nm. The stepwise eluate was concentrated by rotary evaporation and dried to obtain two chiral isomers 142-a and 142-b of compound 142:

- a first chiral isomer: 142-a; retention time on the chromatography column: 6.662 min; and
- a second chiral isomer: 142-b; retention time on the chromatography column: 10.831 min.

Compounds 171, 174 and 270 were chirally resolved using a similar resolution procedure to obtain their two chiral isomers 171-a/171-b, 174-a/174-b and 270-a/270-b, respectively. Their retention times on the chromatography column are as follows:

TABLE 2

Conditions for and results of chiral resolution of compounds 171, 174 and 270

| Compound | Conditions for resolution | Results of resolution |
|---|---|---|
| 171 | Same as those for compound 142 | a first chiral isomer: 171-a; retention time on the chromatography column: 7.481 min; and<br>a second chiral isomer: 171-b; retention time on the chromatography column: 12.770 min. |
| 174 | Same as those for compound 142 | a first chiral isomer: 174-a; retention time on the chromatography column: 8.994 min; and<br>a second chiral isomer: 174-b; retention time on the chromatography column: 14.583 min. |

TABLE 2-continued

| Conditions for and results of chiral resolution of compounds 171, 174 and 270 | | |
|---|---|---|
| Compound | Conditions for resolution | Results of resolution |
| 270 | Same as those for compound 142 except that the mobile phase is ethanol-n-hexane (30/70) | a first chiral isomer: 270-a; retention time on the chromatography column: 7.280 min; and a second chiral isomer: 270-b; retention time on the chromatography column: 12.962 min. |

Other compounds in the present application can also be chirally resolved using a similar method.

Example 343: pERK and ERK Protein Content Assay in 11358 Cells by Compounds

H358 cells were seeded in a 24-well plate. After one day of growth, a test compound (at a concentration of 1 μM) was added. After 24 h of action of the compound, the cells were lysed, and the cell lysate was transferred to a 96-well ELISA plate. The levels of pERK and ERK in the lysate were measured using an ELISA kit (abcam 176660). The ratio of pERK to ERK was calculated and compared with that of the DMSO group, and the percentage of inhibition of pERK activity by the compound was calculated. The results are shown in Table 3 below.

TABLE 3

Inhibitory activity of the compounds of the present invention against the pERK level in H358 cells

| Compound | Inhibition rate (%) | Compound | Inhibition rate (%) | Compound | Inhibition rate (%) |
|---|---|---|---|---|---|
| 1 | +++ | 2 | +++ | 3 | +++ |
| 4 | +++ | 5 | +++ | 6 | +++ |
| 7 | ++ | 8 | ++ | 9 | +++ |
| 10 | ++ | 11 | +++ | 12 | +++ |
| 13 | +++ | 14 | +++ | 15 | +++ |
| 16 | ++ | 17 | +++ | 18 | ++ |
| 19 | ++ | 20 | +++ | 21 | +++ |
| 22 | ++ | 23 | +++ | 24 | ++ |
| 25 | +++ | 26 | ++ | 27 | ++ |
| 28 | ++ | 29 | +++ | 30 | +++ |
| 31 | +++ | 32 | +++ | 33 | +++ |
| 34 | +++ | 35 | +++ | 36 | +++ |
| 37 | ++ | 38 | +++ | 39 | +++ |
| 40 | +++ | 41 | +++ | 42 | +++ |
| 43 | +++ | 44 | +++ | 45 | +++ |
| 46 | +++ | 47 | +++ | 48 | +++ |
| 49 | +++ | 50 | +++ | 51 | +++ |
| 52 | +++ | 53 | +++ | 54 | +++ |
| 55 | +++ | 56 | +++ | 57 | +++ |
| 58 | +++ | 59 | +++ | 60 | +++ |
| 61 | +++ | 62 | +++ | 63 | +++ |
| 64 | ++ | 65 | +++ | 66 | ++ |
| 67 | ++ | 68 | ++ | 69 | +++ |
| 70 | +++ | 71 | +++ | 72 | +++ |
| 73 | +++ | 74 | +++ | 75 | +++ |
| 76 | +++ | 77 | ++ | 78 | ++ |
| 79 | ++ | 80 | ++ | 81 | +++ |
| 82 | +++ | 83 | +++ | 84 | +++ |
| 85 | +++ | 86 | ++ | 87 | +++ |
| 88 | ++ | 89 | +++ | 90 | +++ |
| 91 | +++ | 92 | +++ | 93 | +++ |
| 94 | +++ | 95 | +++ | 96 | +++ |
| 97 | ++ | 98 | ++ | 99 | +++ |
| 100 | +++ | 101 | +++ | 102 | +++ |
| 103 | +++ | 104 | ++ | 105 | +++ |
| 106 | ++ | 107 | ++ | 108 | ++ |
| 109 | +++ | 110 | +++ | 111 | +++ |
| 112 | ++ | 113 | +++ | 114 | +++ |
| 115 | ++ | 116 | ++ | 117 | +++ |
| 118 | +++ | 119 | ++ | 120 | ++ |
| 121 | ++ | 122 | ++ | 123 | +++ |
| 124 | +++ | 125 | +++ | 126 | +++ |
| 127 | +++ | 128 | +++ | 129 | +++ |
| 130 | +++ | 131 | +++ | 132 | +++ |
| 133 | +++ | 134 | +++ | 135 | ++ |
| 136 | ++ | 137 | +++ | 138 | +++ |
| 139 | +++ | 140 | +++ | 141 | +++ |
| 142 | +++ | 143 | +++ | 144 | +++ |
| 145 | +++ | 146 | +++ | 147 | +++ |

TABLE 3-continued

Inhibitory activity of the compounds of the present invention against the pERK level in H358 cells

| Compound | Inhibition rate (%) | Compound | Inhibition rate (%) | Compound | Inhibition rate (%) |
|---|---|---|---|---|---|
| 148 | ++ | 149 | ++ | 150 | +++ |
| 151 | +++ | 152 | +++ | 153 | +++ |
| 154 | +++ | 155 | ++ | 156 | +++ |
| 157 | +++ | 158 | +++ | 159 | +++ |
| 160 | +++ | 161 | +++ | 162 | +++ |
| 163 | +++ | 164 | +++ | 165 | +++ |
| 166 | +++ | 167 | +++ | 168 | +++ |
| 169 | ++ | 170 | ++ | 171 | +++ |
| 172 | +++ | 173 | +++ | 174 | +++ |
| 175 | +++ | 176 | ++ | 177 | +++ |
| 178 | +++ | 179 | +++ | 180 | +++ |
| 181 | +++ | 182 | +++ | 183 | +++ |
| 184 | +++ | 185 | +++ | 186 | +++ |
| 187 | +++ | 188 | +++ | 189 | +++ |
| 190 | +++ | 191 | +++ | 192 | +++ |
| 193 | +++ | 194 | +++ | 195 | +++ |
| 196 | +++ | 197 | +++ | 198 | +++ |
| 199 | +++ | 200 | +++ | 201 | +++ |
| 202 | +++ | 203 | +++ | 204 | +++ |
| 205 | ++ | 206 | ++ | 207 | +++ |
| 208 | +++ | 209 | +++ | 210 | +++ |
| 211 | +++ | 212 | +++ | 213 | ++ |
| 214 | ++ | 215 | +++ | 216 | +++ |
| 217 | +++ | 218 | +++ | 219 | +++ |
| 220 | +++ | 221 | +++ | 222 | +++ |
| 223 | +++ | 224 | +++ | 225 | +++ |
| 226 | +++ | 227 | +++ | 228 | +++ |
| 229 | +++ | 230 | ++ | 231 | ++ |
| 232 | +++ | 233 | +++ | 234 | +++ |
| 235 | +++ | 236 | +++ | 237 | +++ |
| 238 | +++ | 239 | ++ | 240 | +++ |
| 241 | ++ | 242 | +++ | 243 | +++ |
| 244 | +++ | 245 | +++ | 246 | +++ |
| 247 | +++ | 248 | +++ | 249 | ++ |
| 250 | ++ | 251 | +++ | 252 | +++ |
| 253 | +++ | 254 | +++ | 255 | +++ |
| 256 | +++ | 257 | +++ | 258 | +++ |
| 259 | +++ | 260 | +++ | 261 | +++ |
| 262 | +++ | 263 | +++ | 264 | +++ |
| 265 | +++ | 266 | +++ | 267 | +++ |
| 268 | +++ | 269 | +++ | 270 | +++ |
| 271 | +++ | 272 | +++ | 273 | +++ |
| 274 | +++ | 275 | +++ | 276 | +++ |
| 277 | +++ | 278 | +++ | 279 | +++ |
| 280 | +++ | 281 | +++ | 282 | +++ |
| 283 | ++ | 284 | +++ | 285 | ++ |
| 286 | +++ | 287 | +++ | 288 | +++ |
| 289 | +++ | 290 | +++ | 291 | +++ |
| 292 | +++ | 293 | +++ | 294 | +++ |
| 295 | +++ | 296 | +++ | 297 | +++ |
| 298 | +++ | 299 | +++ | 300 | +++ |
| 301 | +++ | 302 | +++ | 303 | +++ |
| 304 | ++ | 305 | ++ | 306 | +++ |
| 307 | +++ | 308 | +++ | 309 | +++ |
| 310 | ++ | 311 | +++ | 312 | +++ |
| 313 | +++ | 314 | +++ | 315 | +++ |
| 316 | +++ | 317 | +++ | 318 | +++ |
| 319 | +++ | 320 | +++ | 321 | +++ |
| 322 | +++ | 323 | +++ | 324 | +++ |
| 325 | +++ | 326 | +++ | 327 | +++ |
| 328 | +++ | 329 | +++ | 330 | +++ |
| 331 | +++ | 332 | +++ | 333 | +++ |
| 334 | +++ | 335 | +++ | 336 | +++ |
| 337 | +++ | 338 | +++ | 339 | +++ |
| 340 | +++ | 341 | +++ | 142-a | +++ |
| 142-b | ++ | 171-a | +++ | 171-b | +++ |
| 174-a | +++ | 174-b | ++ | 270-a | +++ |
| 270-b | +++ | B | +++ | C | +++ |

+ indicates an inhibition rate less than or equal to 50%
++ indicates an inhibition rate from 50% to 90%
+++ indicates an inhibition rate greater than 90%.

Example 344: Antiproliferative Activity of Compounds Against 11358 Cells

2500 H358 cells were seeded in a 96-well ultra-low attachment plate (corning, 7007). After one day of growth, a serially diluted compound (a maximum concentration of 5 μM, 5-fold dilution, a total of five doses) was added. Three days after the addition of the compound, Cell Titer Glow (Promega, G9681) was added to evaluate pellet growth, and the $IC_{50}$ value was calculated. The results are shown in Table 4 below.

TABLE 4

Antiproliferative activity of the compounds of the present invention against H358 cells

| Compound | $IC_{50}$ | Compound | $IC_{50}$ | Compound | $IC_{50}$ |
|---|---|---|---|---|---|
| 1 | +++ | 2 | +++ | 3 | +++ |
| 4 | +++ | 5 | +++ | 6 | +++ |
| 7 | ++ | 8 | ++ | 9 | +++ |
| 10 | ++ | 11 | +++ | 12 | +++ |
| 13 | ++ | 14 | ++ | 15 | +++ |
| 16 | ++ | 17 | +++ | 18 | ++ |
| 19 | ++ | 20 | +++ | 21 | +++ |
| 22 | ++ | 23 | +++ | 24 | ++ |
| 25 | +++ | 26 | ++ | 27 | ++ |
| 28 | ++ | 29 | +++ | 30 | +++ |
| 31 | +++ | 32 | +++ | 33 | +++ |
| 34 | +++ | 35 | +++ | 36 | +++ |
| 37 | ++ | 38 | ++ | 39 | +++ |
| 40 | +++ | 41 | +++ | 42 | ++ |
| 43 | +++ | 44 | +++ | 45 | +++ |
| 46 | +++ | 47 | +++ | 48 | ++ |
| 49 | +++ | 50 | +++ | 51 | +++ |
| 52 | +++ | 53 | +++ | 54 | +++ |
| 55 | +++ | 56 | +++ | 57 | +++ |
| 58 | +++ | 59 | +++ | 60 | +++ |
| 61 | +++ | 62 | +++ | 63 | +++ |
| 64 | ++ | 65 | +++ | 66 | ++ |
| 67 | ++ | 68 | ++ | 69 | +++ |
| 70 | ++ | 71 | +++ | 72 | +++ |
| 73 | +++ | 74 | +++ | 75 | +++ |
| 76 | +++ | 77 | ++ | 78 | ++ |
| 79 | ++ | 80 | ++ | 81 | +++ |
| 82 | +++ | 83 | +++ | 84 | +++ |
| 85 | ++ | 86 | ++ | 87 | +++ |
| 88 | ++ | 89 | +++ | 90 | +++ |
| 91 | +++ | 92 | +++ | 93 | +++ |
| 94 | +++ | 95 | +++ | 96 | +++ |
| 97 | ++ | 98 | ++ | 99 | +++ |
| 100 | +++ | 101 | +++ | 102 | +++ |
| 103 | +++ | 104 | ++ | 105 | +++ |
| 106 | ++ | 107 | ++ | 108 | ++ |
| 109 | +++ | 110 | +++ | 111 | +++ |
| 112 | ++ | 113 | +++ | 114 | +++ |
| 115 | ++ | 116 | ++ | 117 | +++ |
| 118 | +++ | 119 | +++ | 120 | ++ |
| 121 | +++ | 122 | ++ | 123 | +++ |
| 124 | +++ | 125 | +++ | 126 | +++ |
| 127 | +++ | 128 | +++ | 129 | +++ |
| 130 | +++ | 131 | +++ | 132 | +++ |
| 133 | +++ | 134 | +++ | 135 | ++ |
| 136 | ++ | 137 | +++ | 138 | +++ |
| 139 | +++ | 140 | +++ | 141 | +++ |
| 142 | +++ | 143 | +++ | 144 | +++ |
| 145 | +++ | 146 | +++ | 147 | +++ |
| 148 | ++ | 149 | ++ | 150 | +++ |
| 151 | ++ | 152 | +++ | 153 | +++ |
| 154 | +++ | 155 | ++ | 156 | +++ |
| 157 | +++ | 158 | +++ | 159 | +++ |
| 160 | +++ | 161 | +++ | 162 | +++ |
| 163 | +++ | 164 | +++ | 165 | +++ |
| 166 | +++ | 167 | ++ | 168 | +++ |
| 169 | ++ | 170 | ++ | 171 | +++ |
| 172 | +++ | 173 | +++ | 174 | +++ |
| 175 | +++ | 176 | ++ | 177 | +++ |
| 178 | +++ | 179 | +++ | 180 | ++ |
| 181 | +++ | 182 | +++ | 183 | +++ |
| 184 | +++ | 185 | +++ | 186 | +++ |
| 187 | +++ | 188 | +++ | 189 | +++ |
| 190 | +++ | 191 | +++ | 192 | +++ |
| 193 | +++ | 194 | +++ | 195 | +++ |
| 196 | +++ | 197 | +++ | 198 | +++ |
| 199 | ++ | 200 | ++ | 201 | +++ |
| 202 | +++ | 203 | ++ | 204 | ++ |

TABLE 4-continued

Antiproliferative activity of the compounds of the present invention against H358 cells

| Compound | $IC_{50}$ | Compound | $IC_{50}$ | Compound | $IC_{50}$ |
|---|---|---|---|---|---|
| 205 | ++ | 206 | ++ | 207 | +++ |
| 208 | +++ | 209 | +++ | 210 | +++ |
| 211 | +++ | 212 | +++ | 213 | ++ |
| 214 | ++ | 215 | +++ | 216 | +++ |
| 217 | +++ | 218 | +++ | 219 | +++ |
| 220 | +++ | 221 | +++ | 222 | +++ |
| 223 | +++ | 224 | +++ | 225 | +++ |
| 226 | +++ | 227 | +++ | 228 | +++ |
| 229 | +++ | 230 | ++ | 231 | ++ |
| 232 | +++ | 233 | +++ | 234 | +++ |
| 235 | +++ | 236 | +++ | 237 | +++ |
| 238 | ++ | 239 | ++ | 240 | +++ |
| 241 | ++ | 242 | +++ | 243 | +++ |
| 244 | +++ | 245 | +++ | 246 | +++ |
| 247 | +++ | 248 | +++ | 249 | ++ |
| 250 | ++ | 251 | +++ | 252 | +++ |
| 253 | ++ | 254 | ++ | 255 | +++ |
| 256 | +++ | 257 | ++ | 258 | ++ |
| 259 | +++ | 260 | +++ | 261 | +++ |
| 262 | +++ | 263 | +++ | 264 | +++ |
| 265 | +++ | 266 | +++ | 267 | +++ |
| 268 | +++ | 269 | +++ | 270 | +++ |
| 271 | +++ | 272 | +++ | 273 | +++ |
| 274 | +++ | 275 | +++ | 276 | +++ |
| 277 | +++ | 278 | +++ | 279 | +++ |
| 280 | +++ | 281 | +++ | 282 | +++ |
| 283 | ++ | 284 | +++ | 285 | ++ |
| 286 | +++ | 287 | +++ | 288 | +++ |
| 289 | +++ | 290 | +++ | 291 | +++ |
| 292 | +++ | 293 | +++ | 294 | +++ |
| 295 | +++ | 296 | +++ | 297 | +++ |
| 298 | +++ | 299 | +++ | 300 | +++ |
| 301 | +++ | 302 | +++ | 303 | +++ |
| 304 | ++ | 305 | ++ | 306 | +++ |
| 307 | +++ | 308 | +++ | 309 | +++ |
| 310 | ++ | 311 | +++ | 312 | +++ |
| 313 | +++ | 314 | +++ | 315 | +++ |
| 316 | +++ | 317 | +++ | 318 | +++ |
| 319 | +++ | 320 | +++ | 321 | +++ |
| 322 | +++ | 323 | +++ | 324 | +++ |
| 325 | +++ | 326 | +++ | 327 | +++ |
| 328 | +++ | 329 | +++ | 330 | +++ |
| 331 | +++ | 332 | +++ | 333 | +++ |
| 334 | +++ | 335 | +++ | 336 | +++ |
| 337 | +++ | 338 | +++ | 339 | +++ |
| 340 | +++ | 341 | +++ | 142-a | +++ |
| 142-b | ++ | 171-a | +++ | 171-b | +++ |
| 174-a | +++ | 174-b | ++ | 270-a | +++ |
| 270-b | +++ | B | +++ | C | +++ |

+ indicates the $IC_{50}$ of the compound is greater than 1 μM

++ indicates the $IC_{50}$ of the compound is from 0.3 to 1 μM

+++ indicates the $IC_{50}$ of the compound is less than 0.3 μM.

As can be seen from the data in Tables 3 and 4, the antiproliferative activity of most of the compounds of the present invention against H358 cells is less than 0.3 μM, and when $R^5$ (or $R^{5a}$ or $R^{5b}$) is a spiro ring or other substituted heterocyclic ring, the compounds have very high K-RAS G12C inhibitory activity. Compounds 131, 142 and 171 all have good antiproliferative activity against H358 cells, with their $IC_{50}$ values being 1.5 nM, 2.5 nM and 1.4 nM, respectively, while the $IC_{50}$ values of the reference compounds B and C were 4.6 nM and 5.1 nM, respectively, indicating that the cell activity of the compounds was greatly improved after cyclization of the amino groups on the side chains of the compounds. In addition, when position 2 (substituent $R^4$) of acrylamide is substituted with a F atom that is small in size, the compounds also have very high K-RAS G12C inhibitory activity.

Example 345: Pharmacokinetic Evaluation in Mice

The compounds were administered by intravenous injection at a dose of 2 mg/kg and oral gavage at a dose of 10 mg/kg (0.5% CMC-Na suspension). 15 male ICR mice were selected for each group, and each mouse was subjected to blood collection at 3 discrete time points, with 3 mice per time point. The time points of sampling were as follows: before the administration, and at 5 min, 15 min, 30 min, 1 h, 3 h, 5 h, 8 h, 12 h and 24 h after the administration. 80 μL of blood was collected from the eye sockets or the hearts of the mice at each of the time points after the administration. All whole blood samples were collected in tubes containing EDTA $K_2$ and centrifuged (1500-1600 rmp) at 4° C. for 10 min to isolate plasma, which was then stored in a refrigerator at −90 to −60° C. for sample analysis. The compound concentration in the plasma was determined by liquid chromatography-tandem mass spectrometry, and the corresponding pharmacokinetic parameters were obtained according to a plasma concentration-time curve.

TABLE 5

| Pharmacokinetic parameters of compounds in mice | | | | | | | | | |
|---|---|---|---|---|---|---|---|---|---|
| Compound | Route of administration | Dose (mg/kg) | $t_{1/2}$ (h) | $T_{max}$ (h) | $C_{max}$ (ng/mL) | $AUC_{0-t}$ (ng · h/L) | Vss (mL/kg) | Cl (mL/h/kg) | F (%) |
| 1 | iv | 2 | 4.31 | 1 | 2557 | 13987 | 782 | 140 | NA |
| | po | 10 | 6.94 | 4 | 1543 | 20304 | NA | NA | 29.0 |
| 131 | iv | 2 | 4.12 | 0.5 | 2346 | 11340 | 2104 | 112 | NA |
| | po | 10 | 5.86 | 2 | 1824 | 22315 | NA | NA | 39.4 |
| 142 | iv | 2 | 3.31 | 0.083 | 13067 | 51995 | 187 | 38.5 | NA |
| | po | 10 | 3.89 | 2 | 6730 | 45952 | NA | NA | 17.7% |
| 171 | iv | 2 | 4.85 | 0.083 | 4910 | 26500 | 505 | 75.6 | NA |
| | po | 10 | 3.93 | 2 | 3320 | 35700 | NA | NA | 26.9 |
| B | iv | 2 | 4.47 | 0.083 | 2883 | 7822 | 1010 | 252 | NA |
| | po | 10 | 3.74 | 2 | 1300 | 10348 | -NA | NA | 26.5 |
| C | iv | 2 | 4.02 | 0.083 | 3210 | 20200 | 481 | 99 | NA |
| | po | 10 | 3.38 | 0.5 | 3110 | 24800 | NA | NA | 24.6 |

NA indicates data are not available;

As can be seen from the above table, compared to compound B, compound 131 has good oral absorption properties, and has improved metabolic parameters such as half-life ($t_{1/2}$), maximum plasma concentration ($C_{max}$), area under the drug-time curve ($AUC_{0-t}$), and oral bioavailability. It should be particularly noted that, compared to the reference compound C in the patent (Example 65 of WO2018/143315), compound 171 has better metabolic parameters, and compound 142 also has significantly improved metabolic parameters such as $C_{max}$ and $AUC_{0-t}$, indicating that the metabolic properties of the compound are well improved after the amino groups on the side chain are cyclized. The metabolic properties of the compounds similar to compounds 131 and 171 in the present application are also significantly improved. Good oral absorption properties are of great significance in improving the efficacy of drugs, reducing the dose of administration and reducing the costs.

Example 346: Evaluation of Antitumor Activity in Mice

Human pancreatic cancer Mia PaCa-2 cells were cultured conventionally in 1640 medium containing 10% fetal bovine serum in a 37° C./5% $CO_2$ incubator. After passage, the cells were collected when they reached the desired amount. $1\times10^7$ Mia PaCa-2 cells were injected into the left dorsal side of each nude mouse, and the animals were randomly grouped for administration after tumors grew to 150 mm3. The groups are as follows: 1) a solvent control group of 8 mice; and 2) compound 1 group, compound 2 group, compound 5 group, compound 31 group, compound 131 group, compound 142 group, compound 171 group, compound B group and compound C group, with 8 mice per group. Mice in the solvent control group were subjected to intragastric administration of 0.5% CMC-Na once daily; mice in compound 1 group, compound 2 group, compound 5 group, compound 31 group, compound 131 group, compound 142 group, compound 171 group, compound B group and compound C group were subjected to intragastric administration of a suspension of a compound in 0.5% CMC-Na once daily. On Tuesday and Thursday each week, tumor volumes and body weight of the mice were measured, and the nude mice were sacrificed on day 21 of administration. The test results are shown in Table 6 below.

TABLE 6

| Experimental therapeutic effects of compounds on graft tumors of human pancreatic cancer Mia PaCa-2 in nude mice | | | |
|---|---|---|---|
| Compound | Dose (mg/kg) | Administration regimen | Anti-tumor effect |
| 1 | 10 | qd*21 | 39% regression |
| 2 | 10 | qd*21 | 23% regression |
| 5 | 10 | qd*21 | 30% regression |
| 31 | 10 | qd*21 | 32% regression |
| 131 | 10 | qd*21 | 37% regression |
| 142 | 10 | qd*21 | 35% regression |
| 171 | 10 | qd*21 | 38% regression |
| B | 10 | qd*21 | 25% regression |
| C | 10 | qd*21 | 8% regression |

As can be seen from the data in the table above, the compounds of the present invention have high in vivo antitumor activity; a tumor can regress after 21 consecutive days of administration at 10 mg/kg/day; compounds 1, 5, 31, 131, 142 and 171 have higher in vivo activity than reference compound B and compound C, and compounds 142 and 171 have significantly higher in vivo activity than compound C, indicating the in vivo activity of the compound is also greatly improved after the amino groups on the side chain of the compound are cyclized.

Example 346: pERK Level Assay by Western Blot

H358 cells were plated on to a 24-well plate at $2\times10^5$ cells/well. Serially diluted compounds including AMG510, MRTX849, compound 142 and compound 171 were added. After overnight incubation, cells were lysed, and proteins were quantified and subjected to gel electrophoresis. The results of the phosphorylated ERK (pERK) level assay by western blot are shown in FIG. 1. As can be seen from the results in FIG. 1, the compounds 142 and 171 of the present invention shows stronger inhibition of the phosphorylated ERK (pERK) level in cells than the reference drugs AMG510 and MRTX849 when at the same concentration.

The invention claimed is:

1. A compound with a structure as shown in general formula (1), optical isomers thereof, pharmaceutically acceptable salts thereof, hydrates thereof or solvates thereof:

(1)

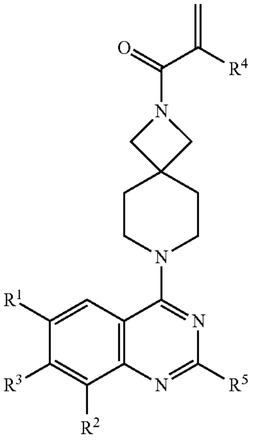

wherein in formula (1):

$R^1$ is H, halogen, C1-C3 alkyl, C2-C4 alkenyl, C2-C4 alkynyl or C3-C6 cycloalkyl;

$R^2$ is C1-C3 alkoxy, C1-C3 haloalkoxy or $-NR^aR^b$, wherein $R^a$ and $R^b$ are independently H, C1-C3 alkyl or C1-C3 haloalkyl, or $R^a$ and $R^b$, together with a N atom, form a 4-7 membered heterocycloalkyl group, wherein the heterocycloalkyl group may be substituted with 1-3 halogen atoms;

$R^3$ is

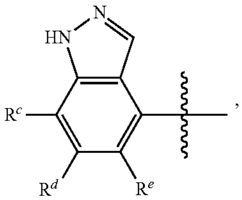

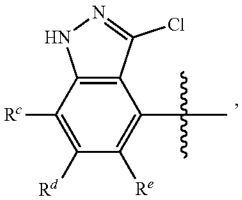

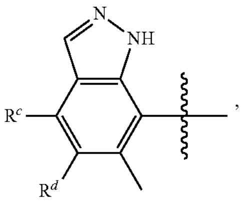

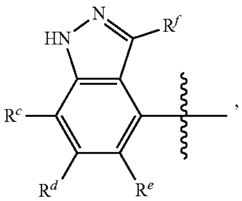

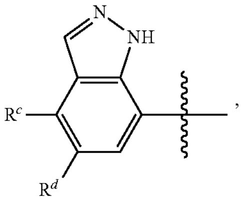

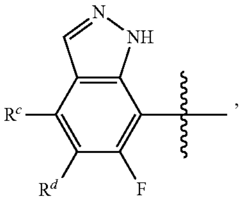

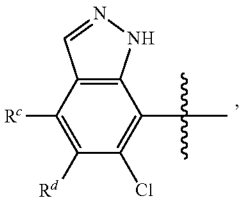

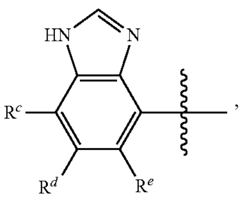

-continued

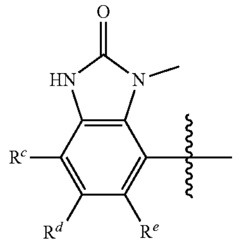

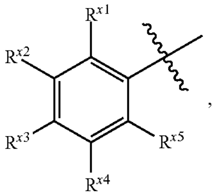

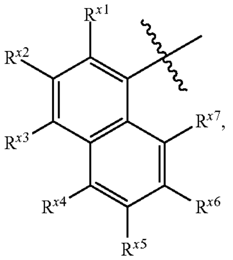

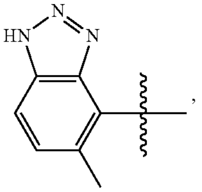

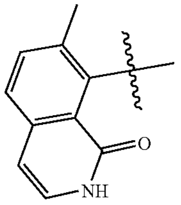

or

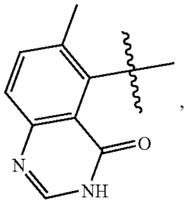

wherein $R^c$ is H or F; $R^d$ is H, F, Cl or Me; $R^e$ is H, F, Cl or Me; $R^f$ is F, $NH_2$, Me or cyclopropyl; $R^{x1}$, $R^{x2}$, $R^{x3}$, $R^{x4}$, $R^{x5}$, $R^{x6}$ and $R^{x7}$ are independently H, F, Cl, OH, OMe, $NH_2$, $CF_3$, C1-C3 alkyl or C3-C6 cycloalkyl;

$R^4$ is H, halogen, CN, C1-C3 alkyl, C1-C3 haloalkyl or heteroaryl; and when $R^3$ is

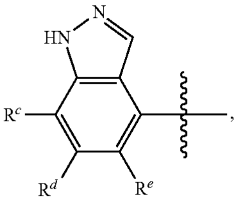

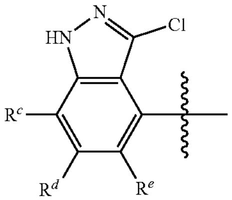

or

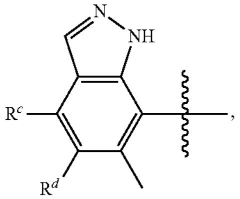

and $R^4$ is H, $R^5$ is:

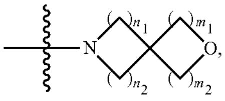

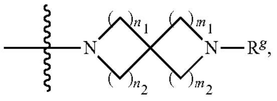

-continued

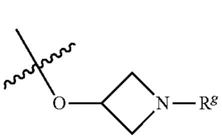,
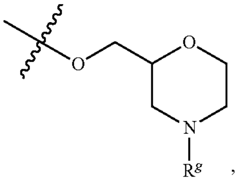,
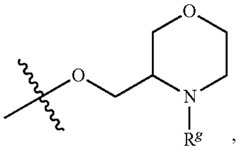,
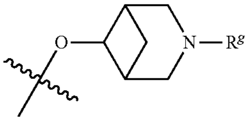,
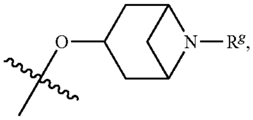
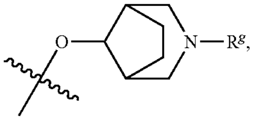
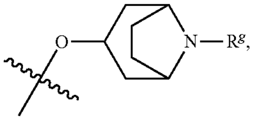
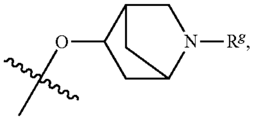
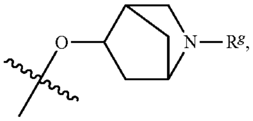
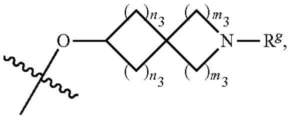
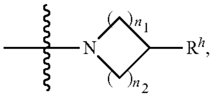
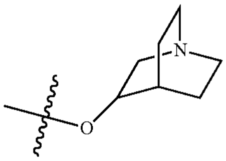,
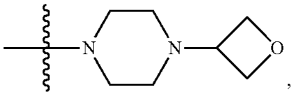,
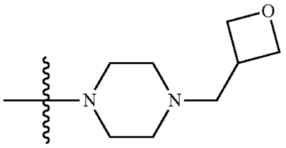
or
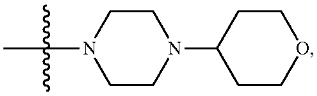

wherein $n_1$, $n_2$, $n_3$, $m_1$, $m_2$ and $m_3$ are independently integers of 1 or 2; $R^g$ is C1-C3 alkyl, C3-C6 cycloalkyl, (C1-C3) alkoxy-(C2-C3)alkyl-, (halogenated C1-C3)alkoxy-(C2-C3) alkyl-, (C3-C6) cycloalkyl-(C1-C3)alkyl-, heterocycloalkyl, heterocycloalkyl-(C1-C3)alkyl-, C1-C3 haloalkyl or cyano-substituted C1-C3 alkyl; $R^h$ is

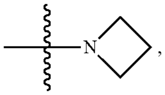,
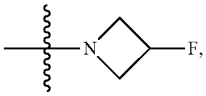
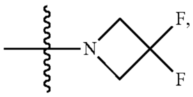
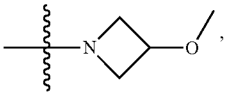,

-continued

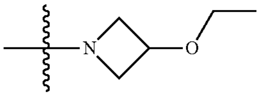,
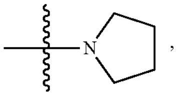,
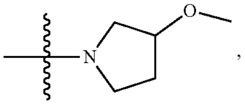,
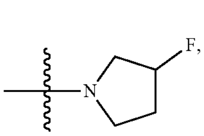
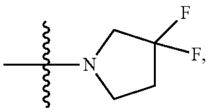
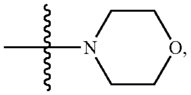
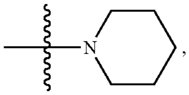,
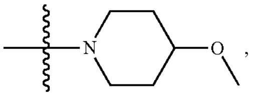,
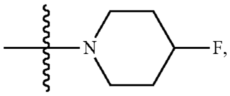
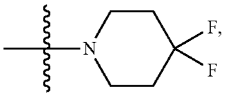
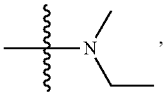,
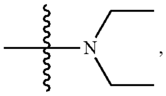,
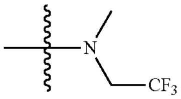
or
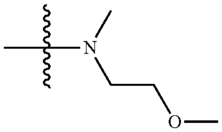;

when $R^3$ is

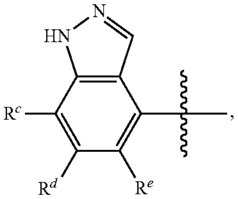,
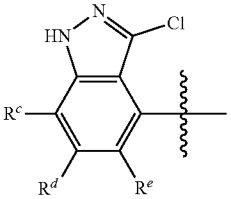
or
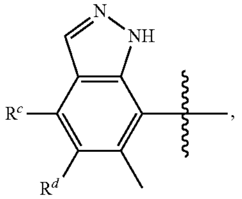, and $R^4$ is halogen, CN, C1-C3 alkyl, C1-C3 haloalkyl or heteroaryl; or, when $R^3$ is

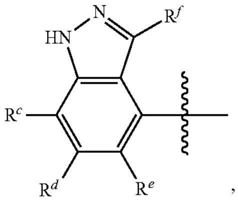
,
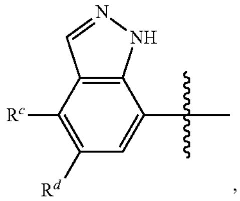
,
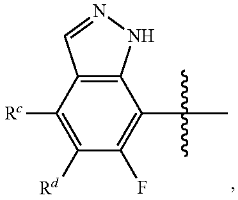
,
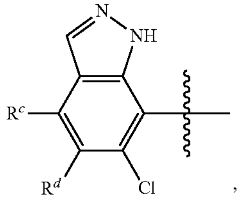
,
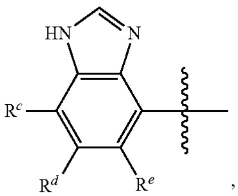
,
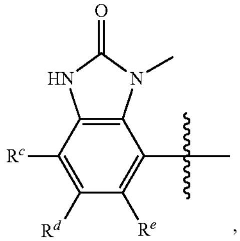
,
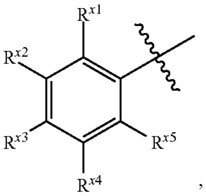
,
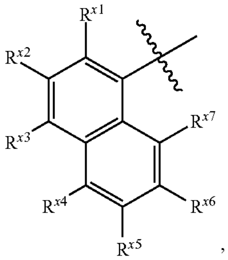
,
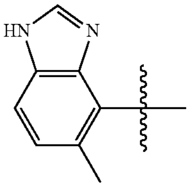
,
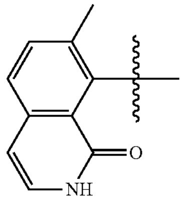
or
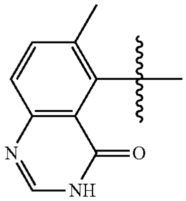
, $R^5$ is:
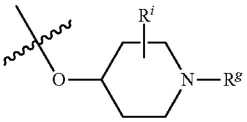
,
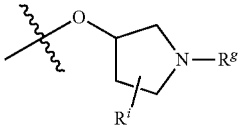
,
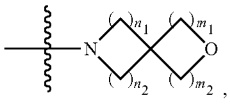
,
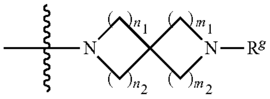
,
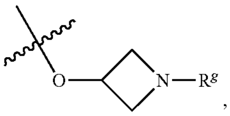
,
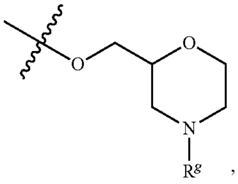
,
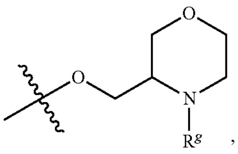
,
-continued
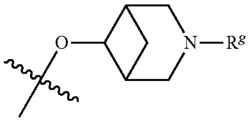
,
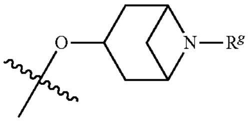
,
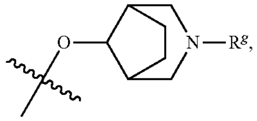
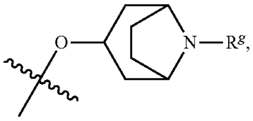
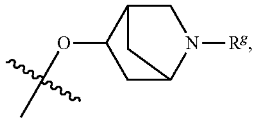
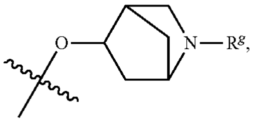
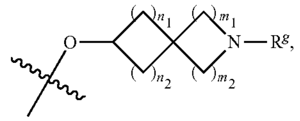
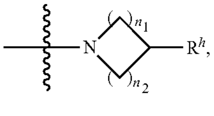
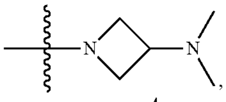
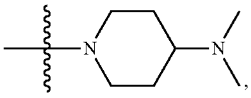
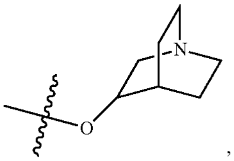
,
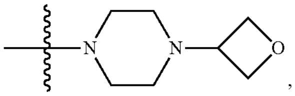
,
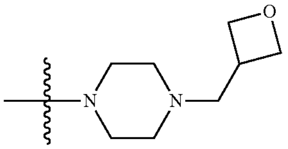
or
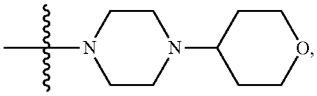
wherein $n_1$, $n_2$, $n_3$, $m_1$, $m_2$ and $m_3$ are independently integers of 1 or 2; $R^g$ is C1-C3 alkyl, C3-C6 cycloalkyl, (C1-C3) alkoxy-(C2-C3)alkyl-, (halogenated C1-C3)alkoxy-(C2-C3) alkyl-, (C3-C6) cycloalkyl-(C1-C3)alkyl-, heterocycloalkyl, heterocycloalkyl-(C1-C3)alkyl-, C1-C3 haloalkyl or cyano-substituted C1-C3alkyl; $R^h$ is
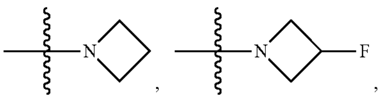
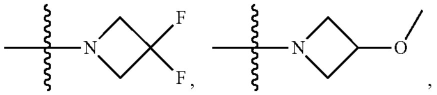
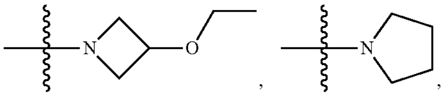
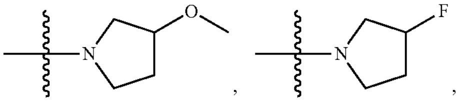
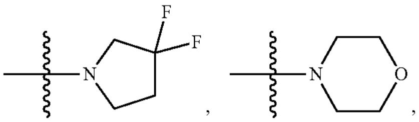

-continued
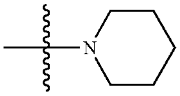, 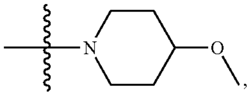,
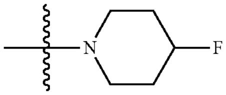, 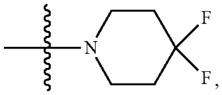,
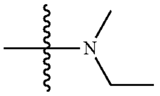, 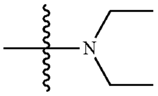, 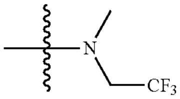 or
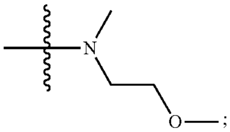;
$R^i$ is H, halogen, methyl or cyano.
2. The compound according to claim 1, wherein in the general formula (1), $R^1$ is H, F, Cl, Me, Et, isopropyl, vinyl, ethynyl or cyclopropyl.
3. The compound according to claim 1, wherein in the general formula (1), $R^2$ is $CH_3O$—, $CH_3CH_2O$—, $CF_3CH_2O$—, $CHF_2CH_2O$—,
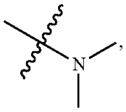, 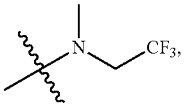, 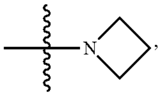,
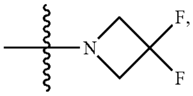, 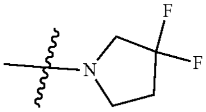 or
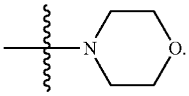.
4. The compound according to claim 1, wherein in the general formula (1), $R^3$ is
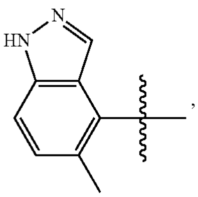, 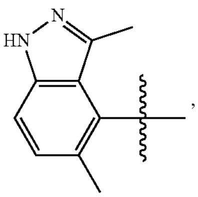,
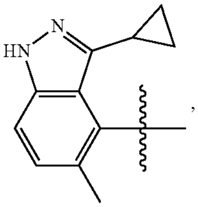, 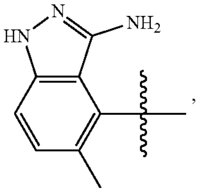,
-continued
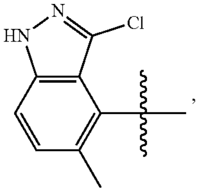, 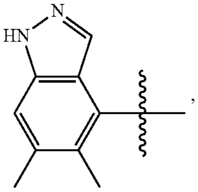,
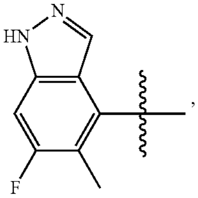, 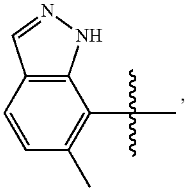,
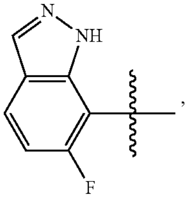, 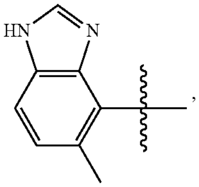,
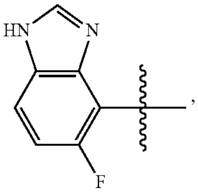, 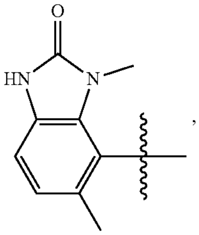,
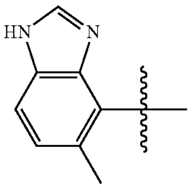, 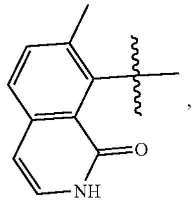,
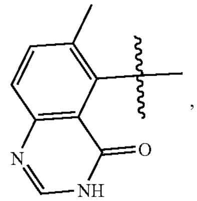, 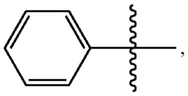,
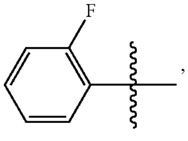, 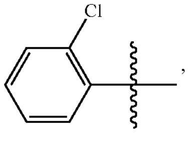,
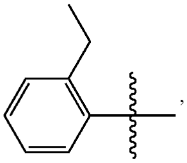, 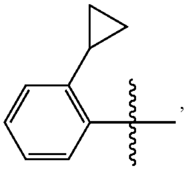,
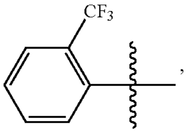, 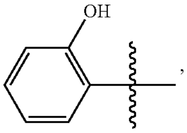, -continued
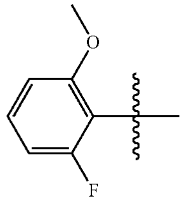,
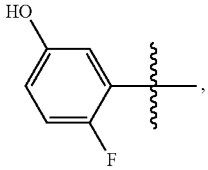,
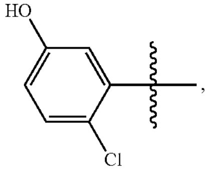,
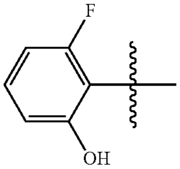,
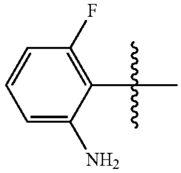,
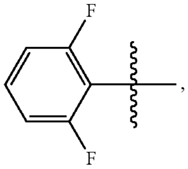,
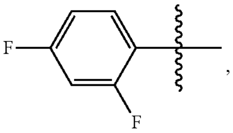,
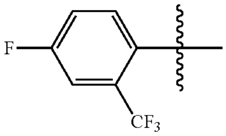,
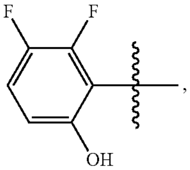,
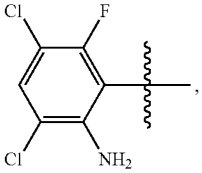,
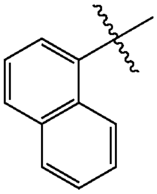,
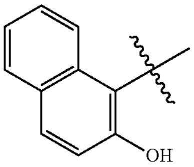
or 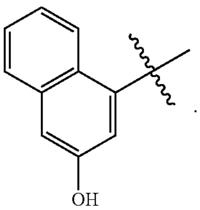.
5. The compound according to claim 1, wherein in the general formula (1), $R^4$ is H, F, CN, Me, $CF_3$,
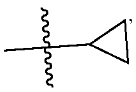,
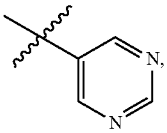
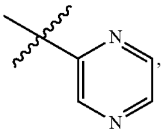,
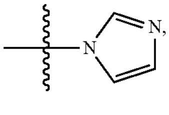
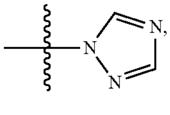
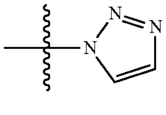 or
-continued
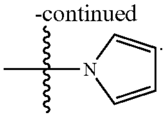.
6. The compound according to claim 1, wherein in the general formula (1), when $R^3$ is
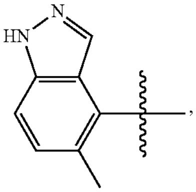,
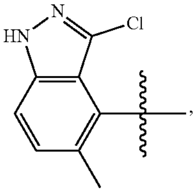,
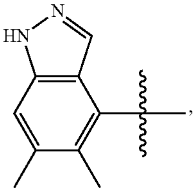,
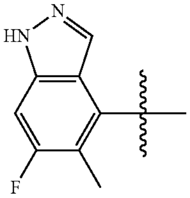 or
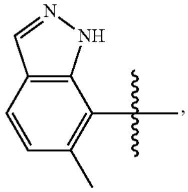,
and $R^4$ is H, $R^5$ is:
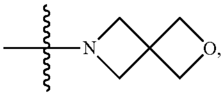
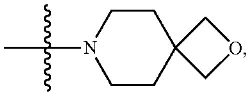
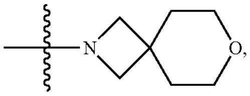
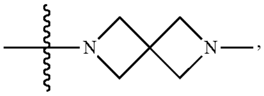,
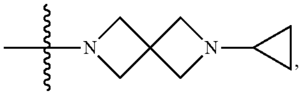,
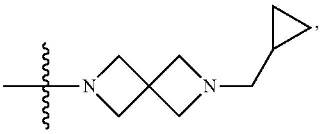,
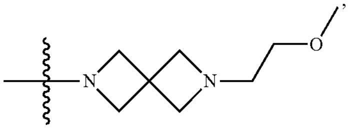,
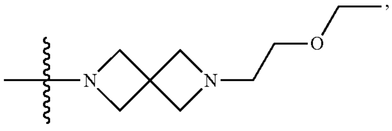,
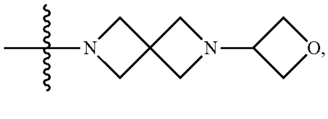

-continued
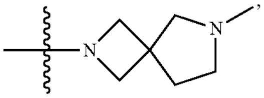
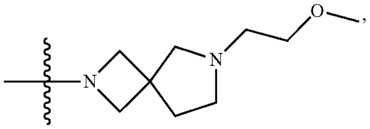
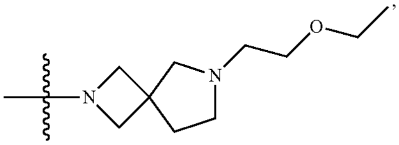
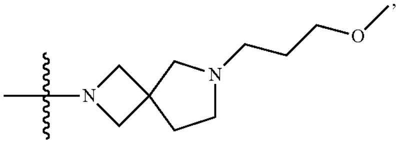
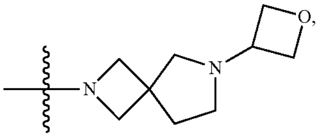
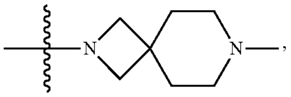
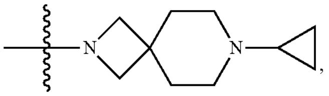
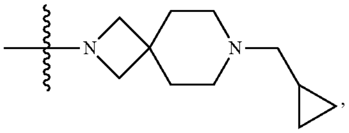
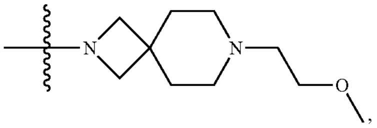
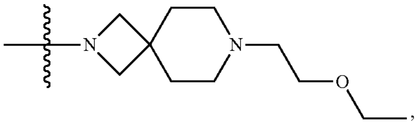
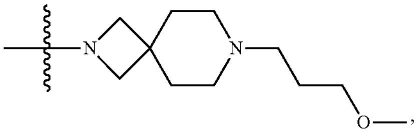
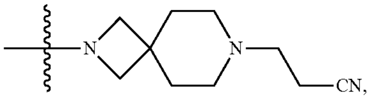
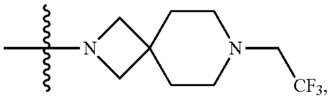
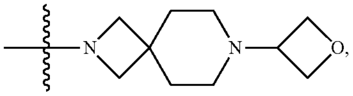
-continued
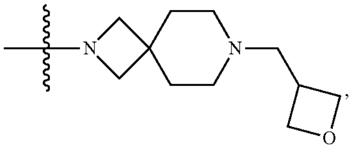
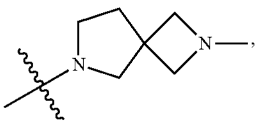
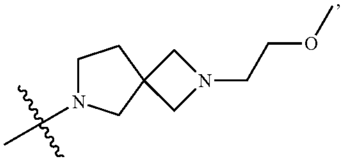
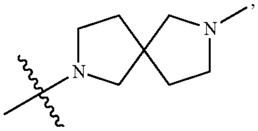
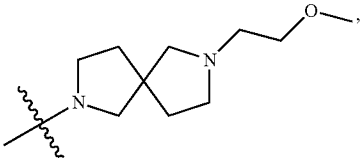
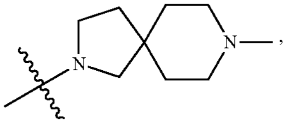
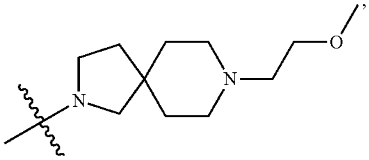
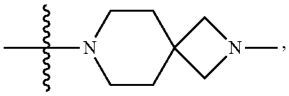
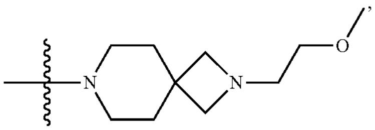
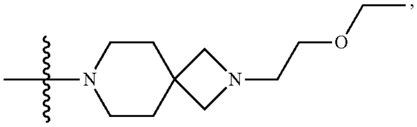
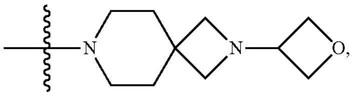
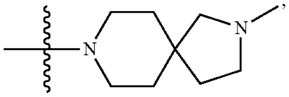

-continued
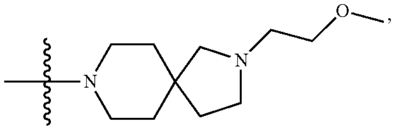
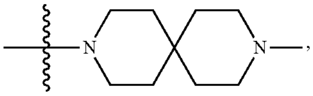
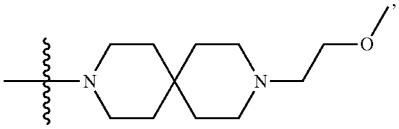
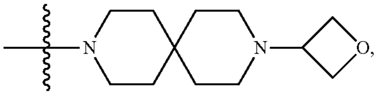
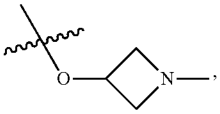
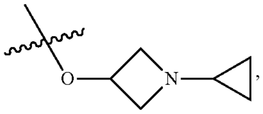
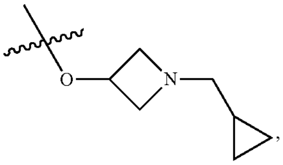
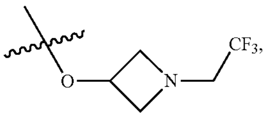
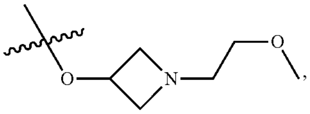
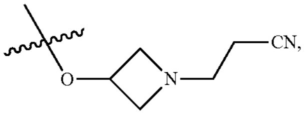
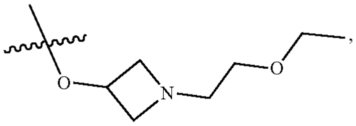
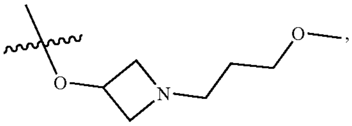
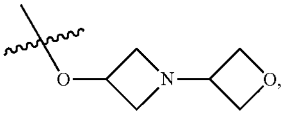
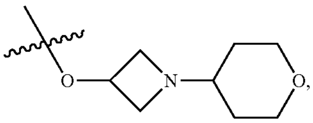
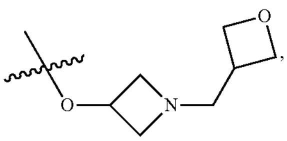
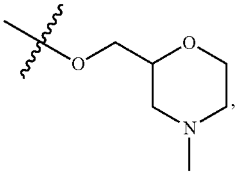
-continued
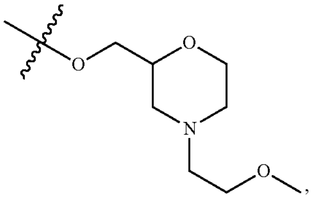
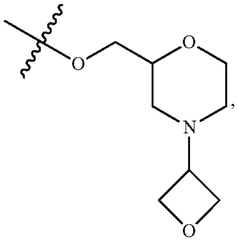
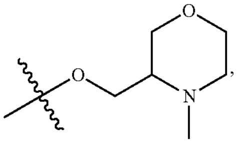
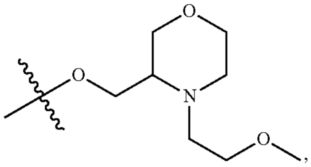
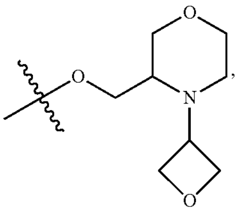
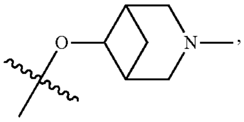
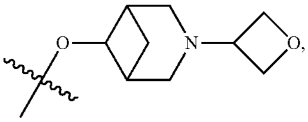
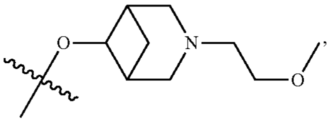
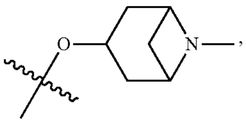
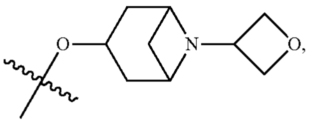
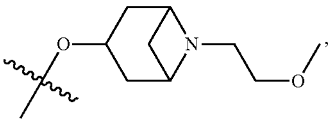
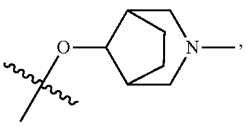
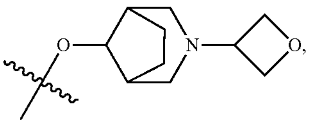
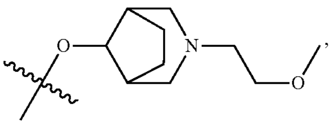
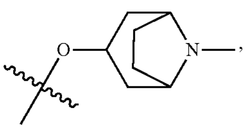
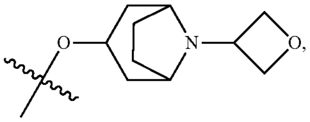

-continued
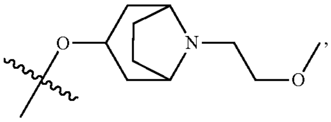
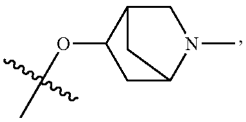
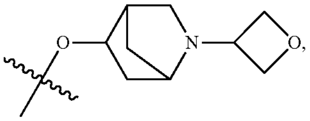
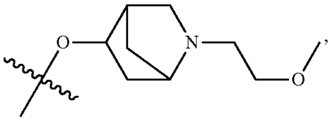
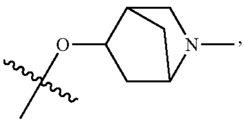
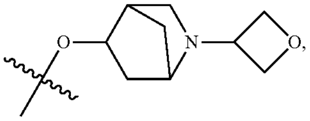
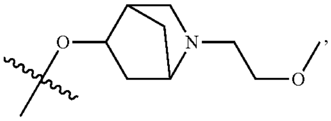
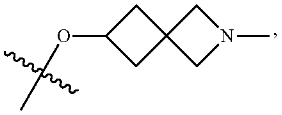
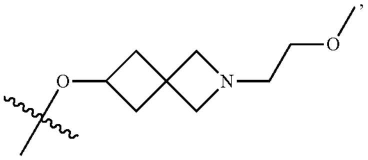
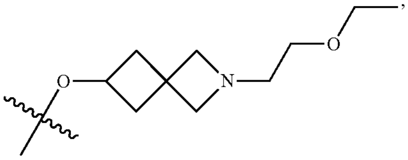
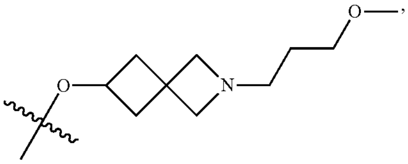
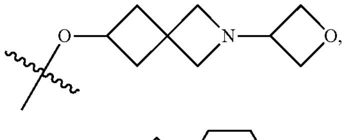
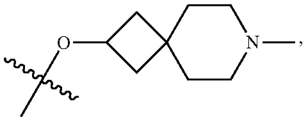
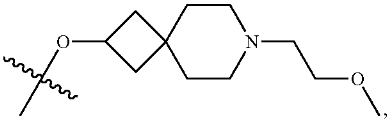
-continued
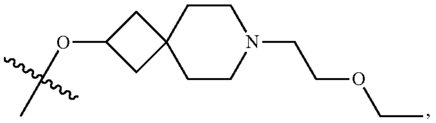
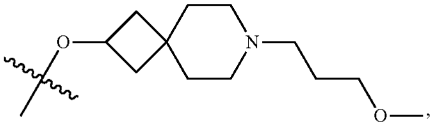
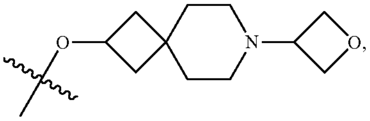
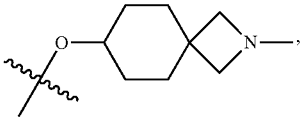
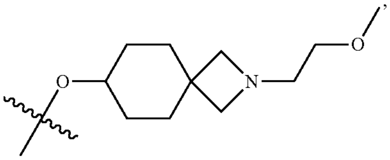
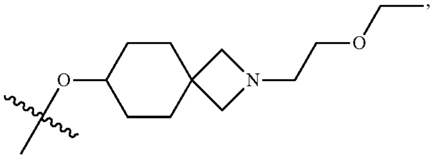
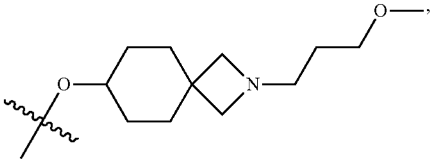
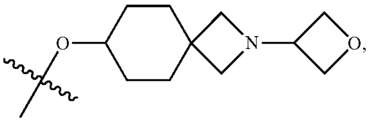
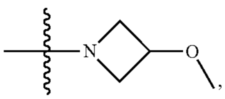
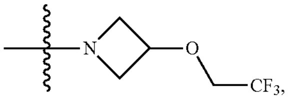
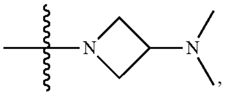
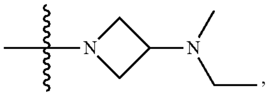
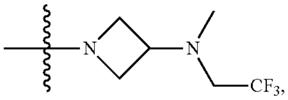
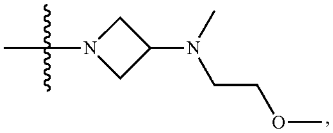

-continued
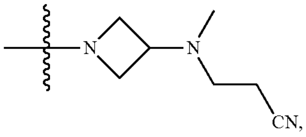
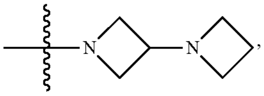
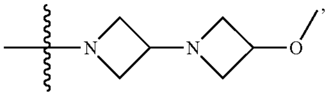
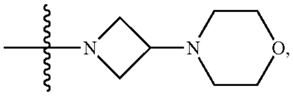
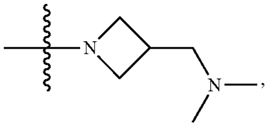
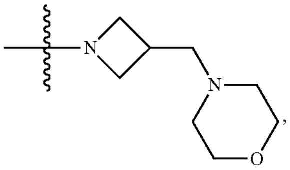
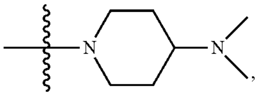
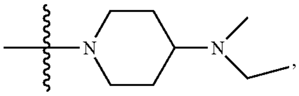
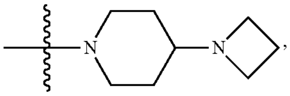
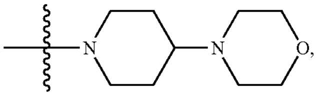
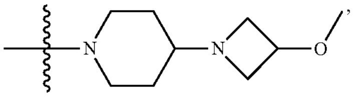
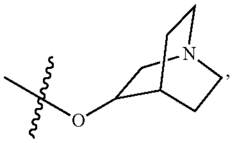
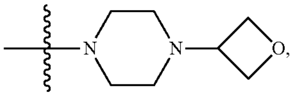
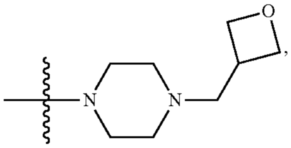
or
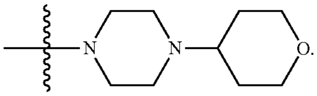
7. The compound according to claim 1, wherein in the general formula (1), when $R^3$ is
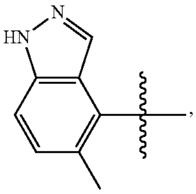
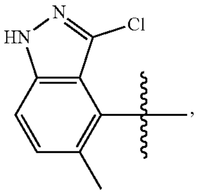
-continued
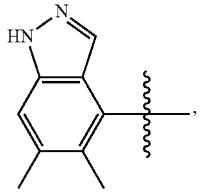
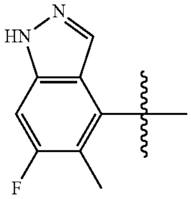
or
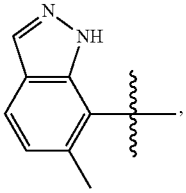
and $R^4$ is F, CN, Me, $CF_3$,
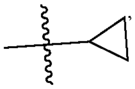
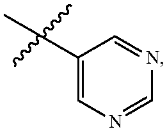
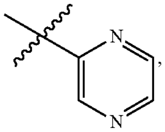
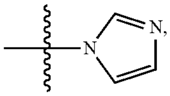
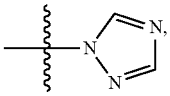
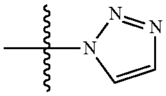
or
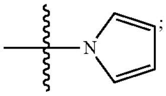
or, when $R^3$ is
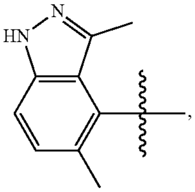
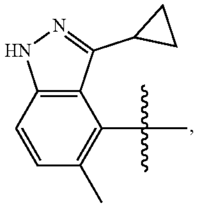
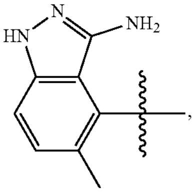
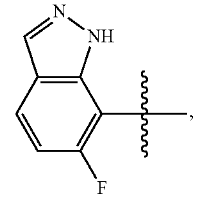
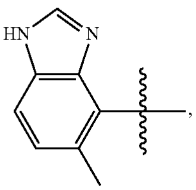
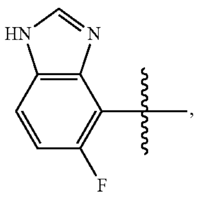

-continued
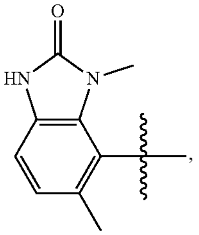
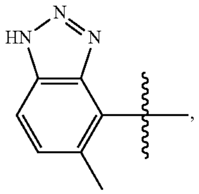
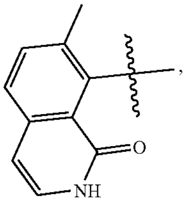
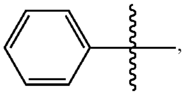
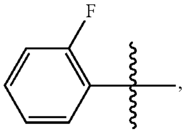
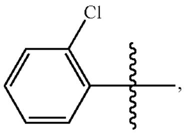
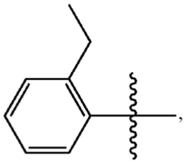
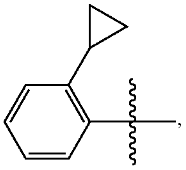
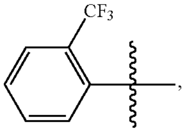
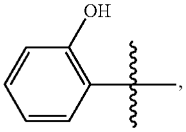
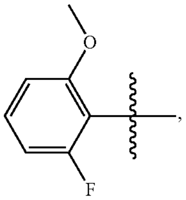
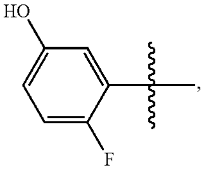
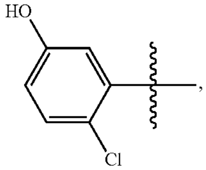
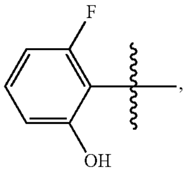
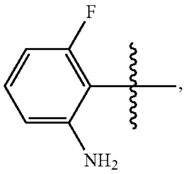
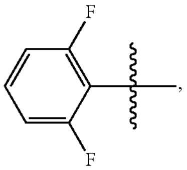
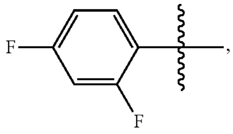
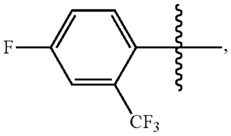
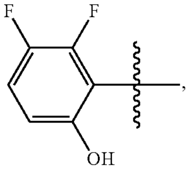
or
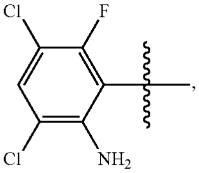
-continued
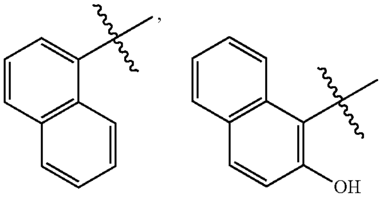
R⁵ is:
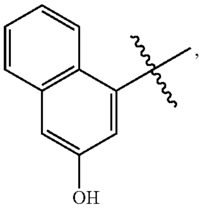
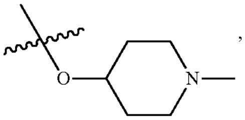
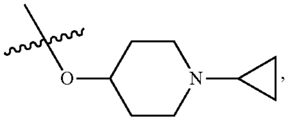
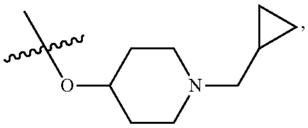
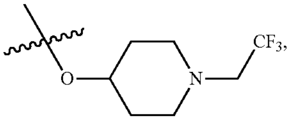
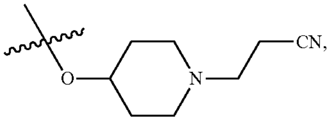
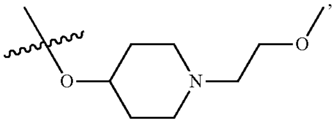
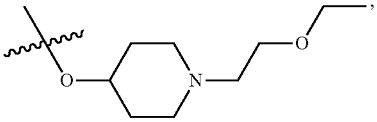
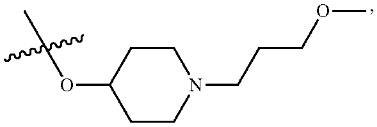
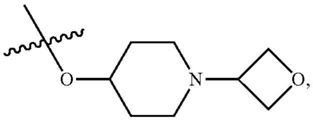
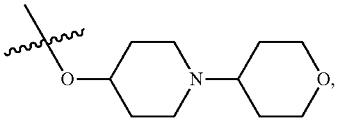
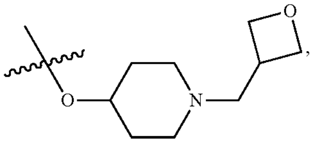
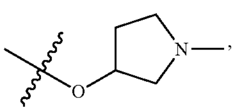
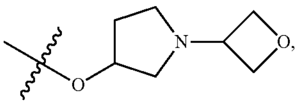

-continued
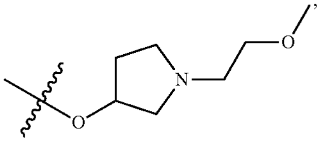
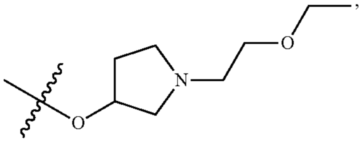
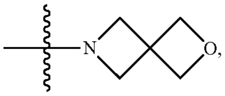
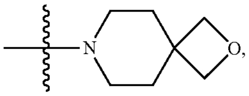
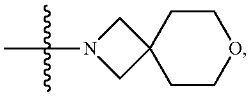
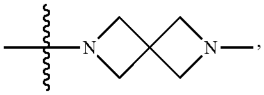
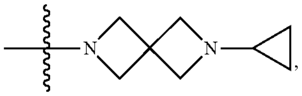
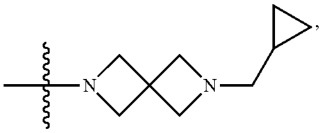
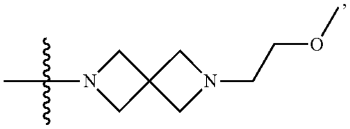
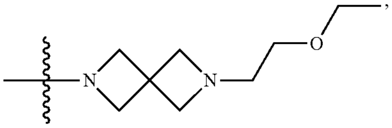
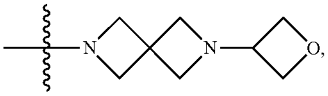
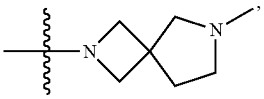
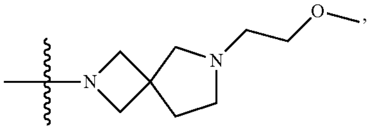
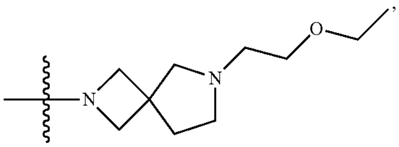
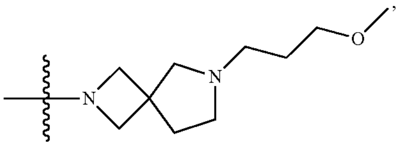
-continued
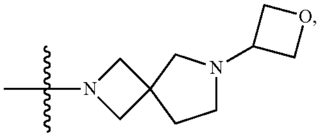
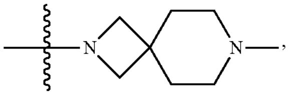
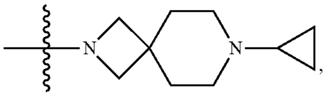
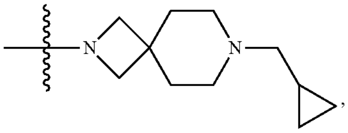
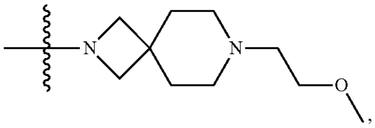
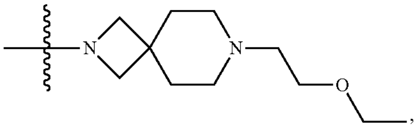
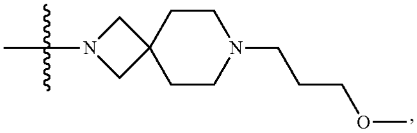
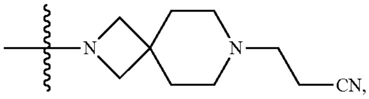
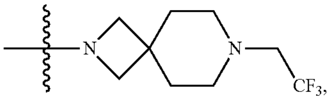
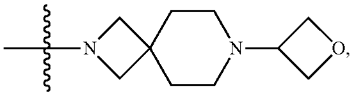
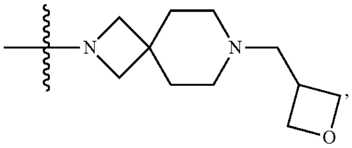
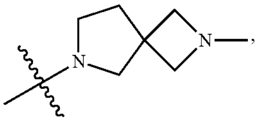
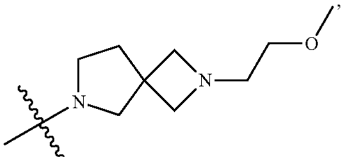

-continued
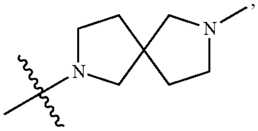
,
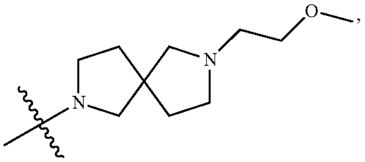
,
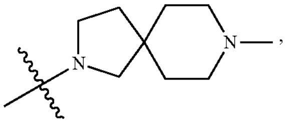
,
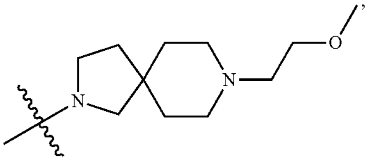
,
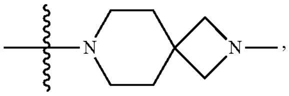
,
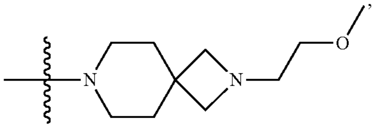
,
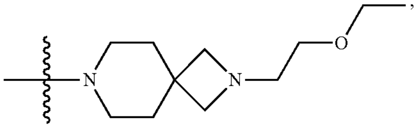
,
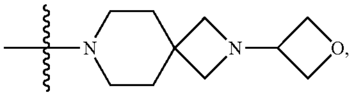
,
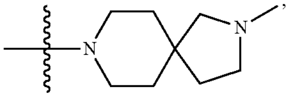
,
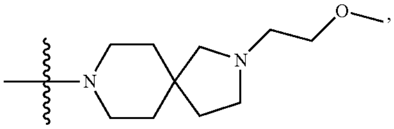
,
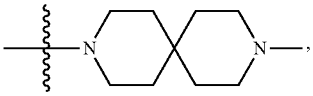
,
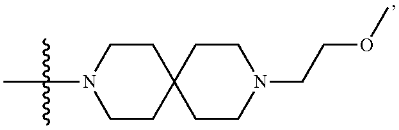
,
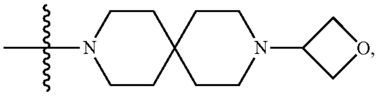
,
-continued
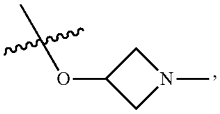
,
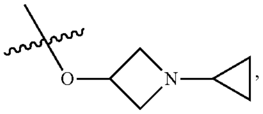
,
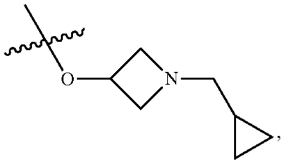
,
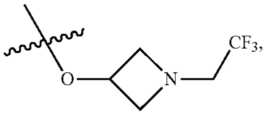
,
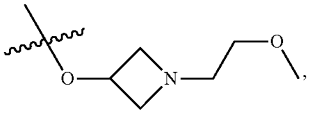
,
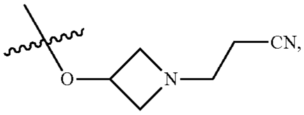
,
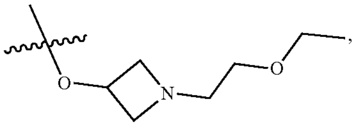
,
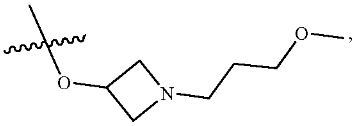
,
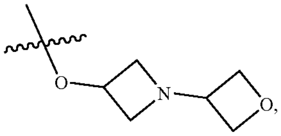
,
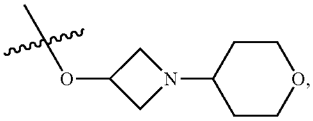
,
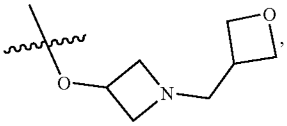
,
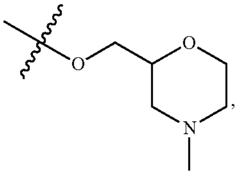
,
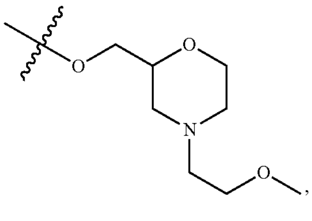
,
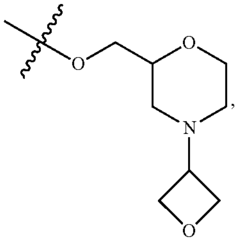
, -continued
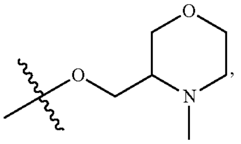
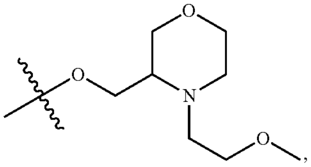
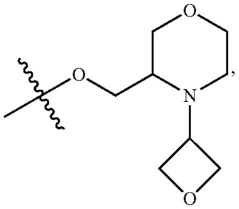
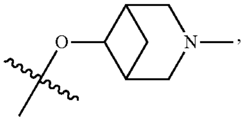
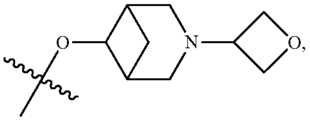
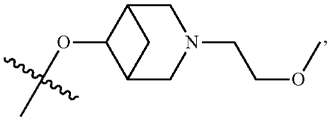
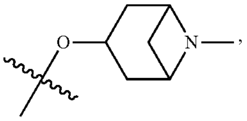
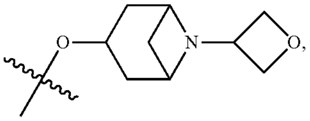
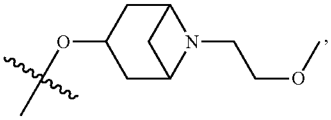
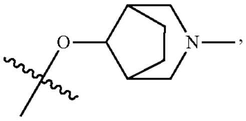
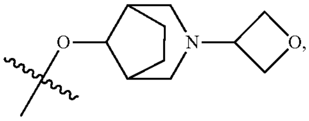
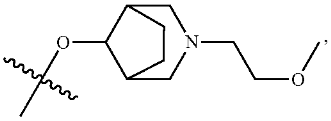
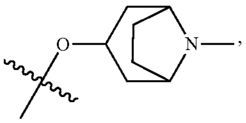
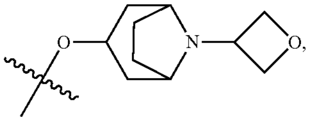
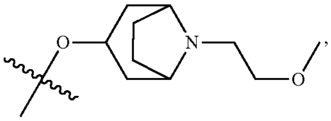
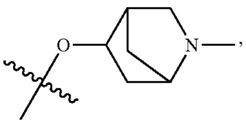
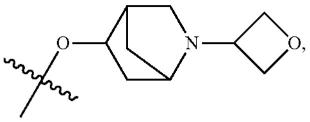
-continued
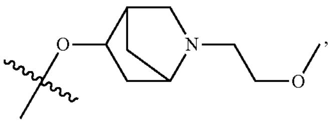
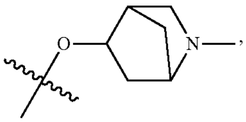
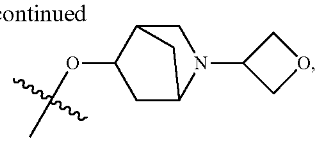
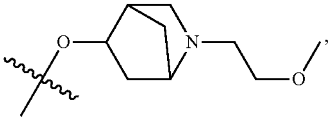
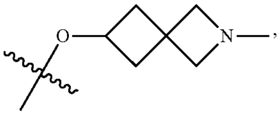
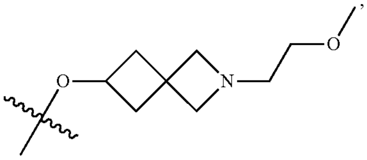
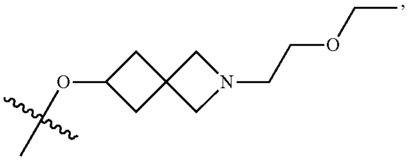
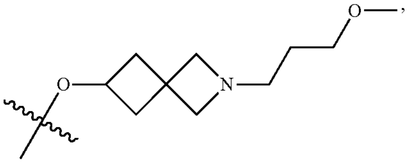
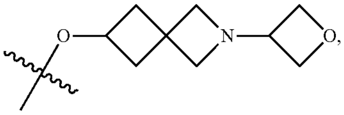
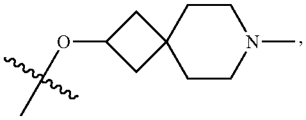
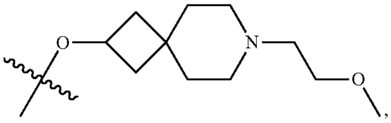
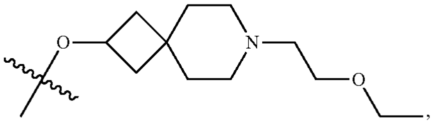
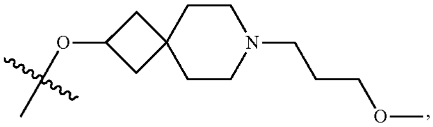
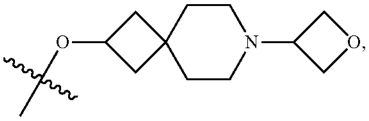

-continued
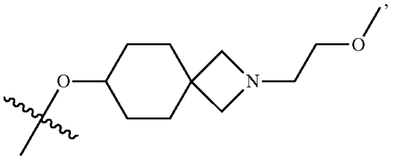
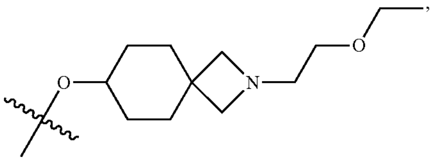
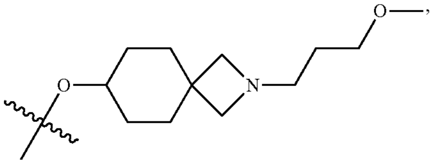
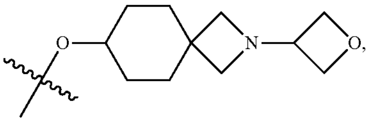
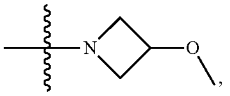
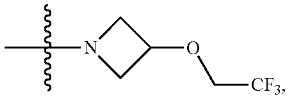
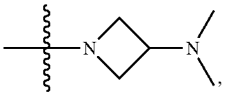
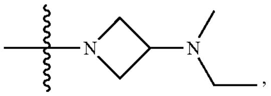
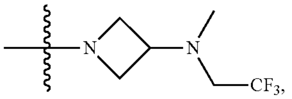
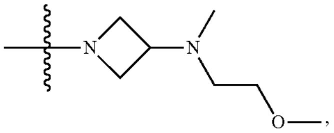
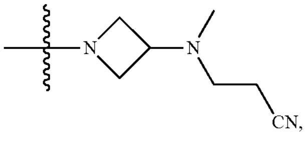
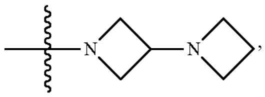
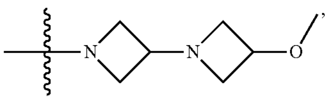
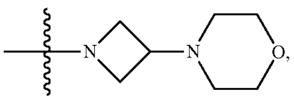
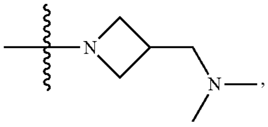
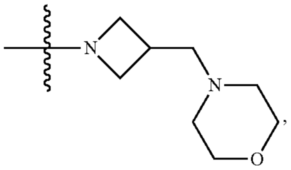
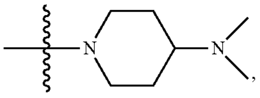
-continued
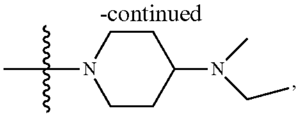
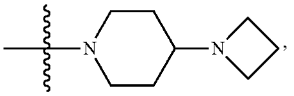
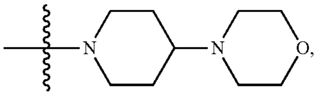
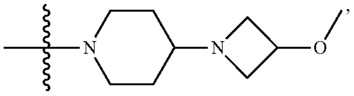
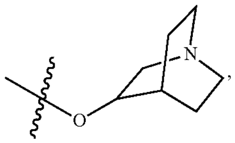
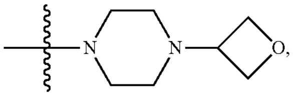
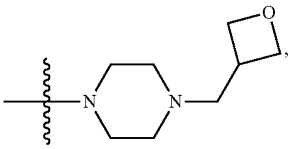
or
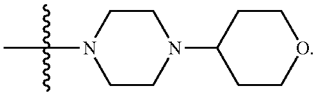
8. The compound according to claim 1, wherein in the general formula (1), $R^5$ is:
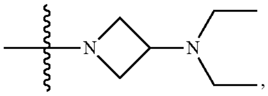
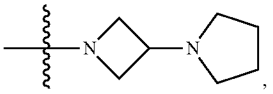
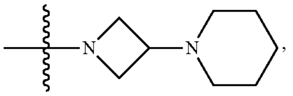
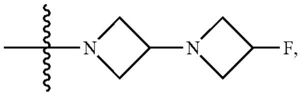
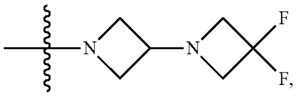
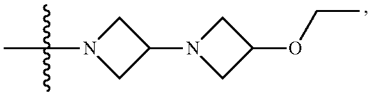
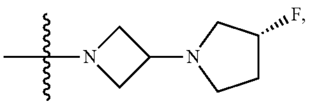
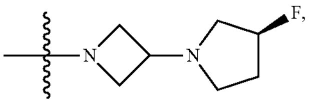
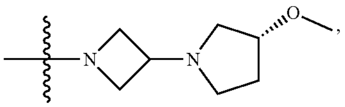

-continued
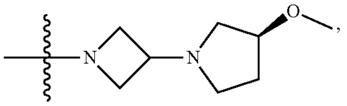
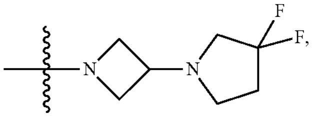
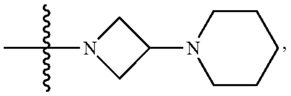
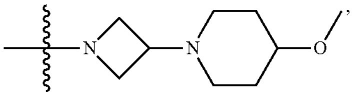
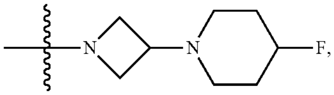
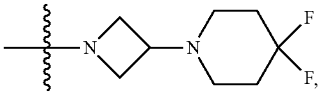
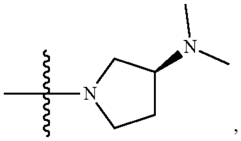
,
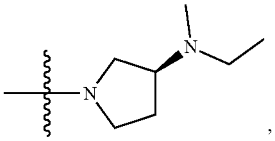
,
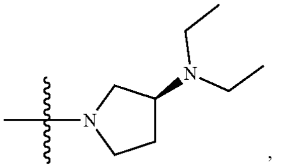
,
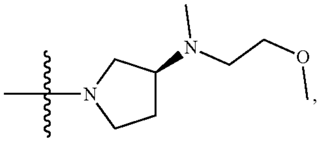
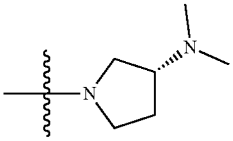
,
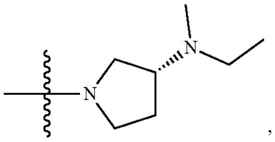
,
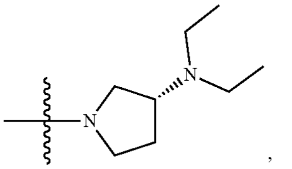
,
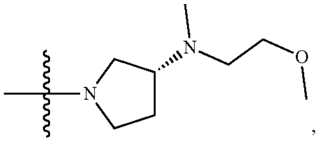
,
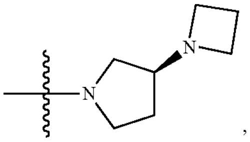
,
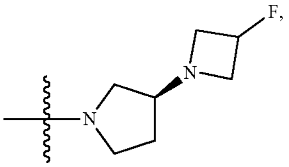
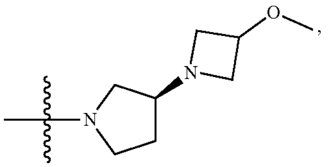
-continued
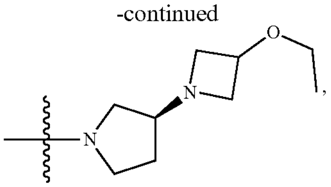
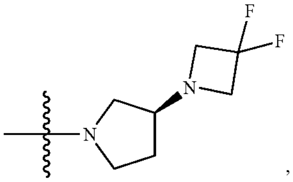
,
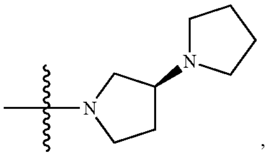
,
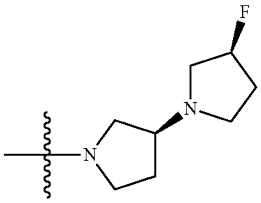
,
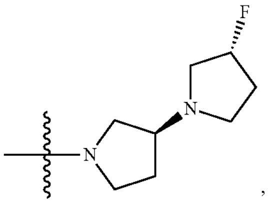
,
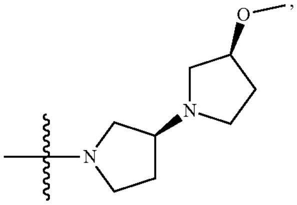
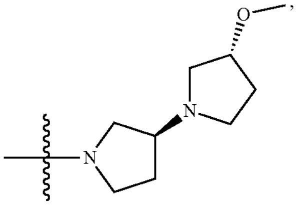
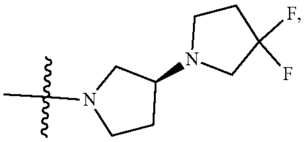
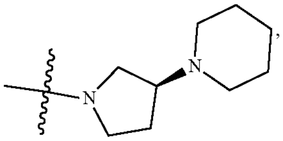
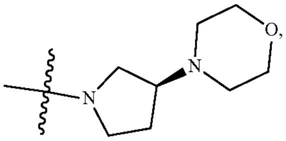
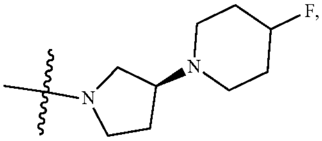
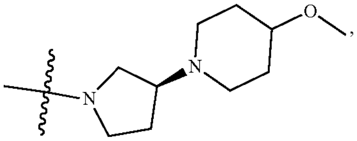
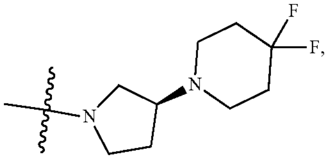

-continued
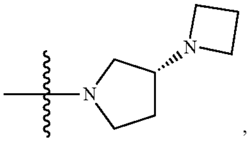
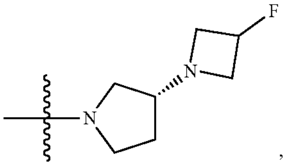
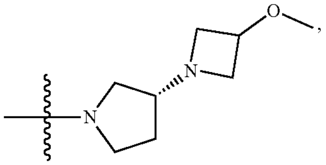
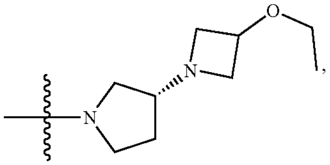
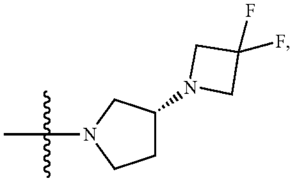
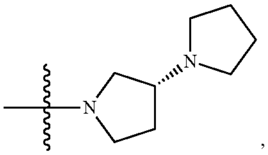
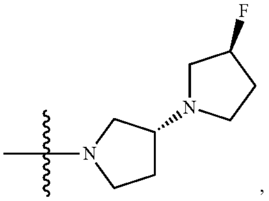
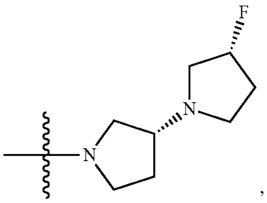
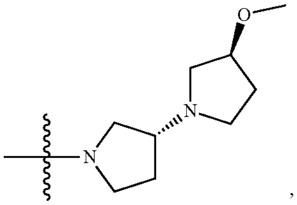
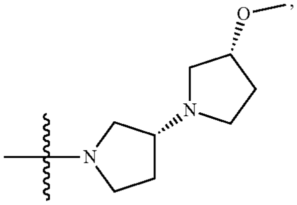
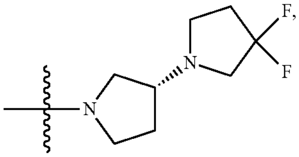
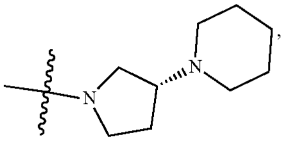
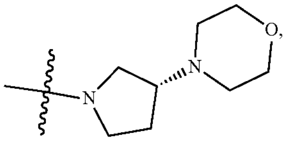
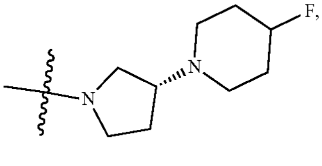
-continued
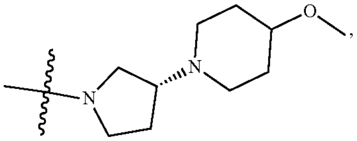
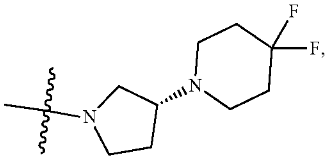
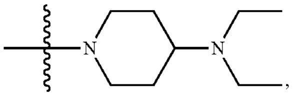
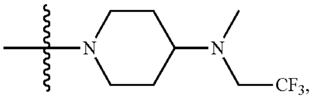
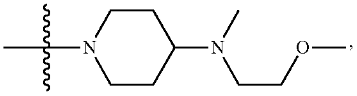
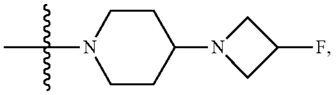
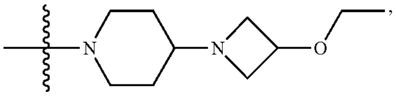
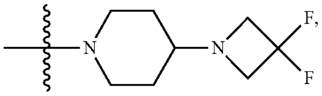
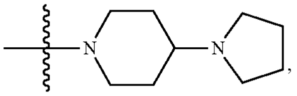
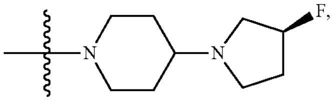
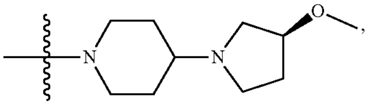
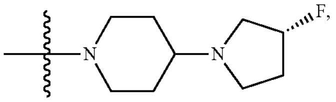
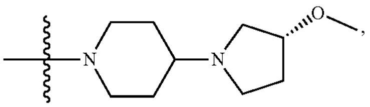
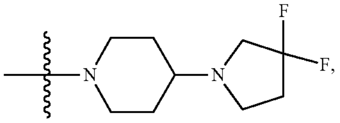
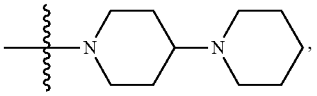
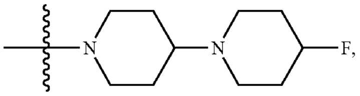

-continued
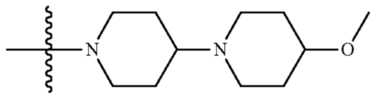
or
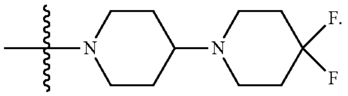
9. The compound, the optical isomers thereof, the pharmaceutically acceptable salts thereof, the hydrates thereof or the solvates thereof according to claim 1, wherein the compound has one of the following structures:
1
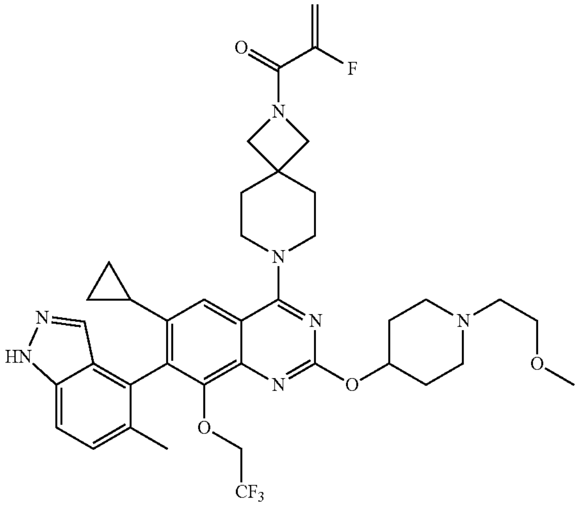
2
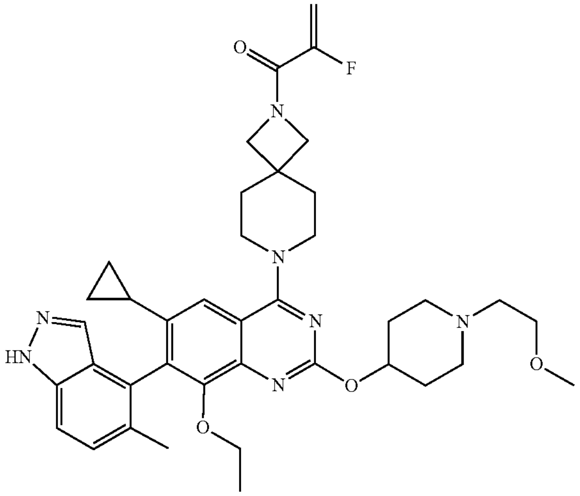
-continued
3
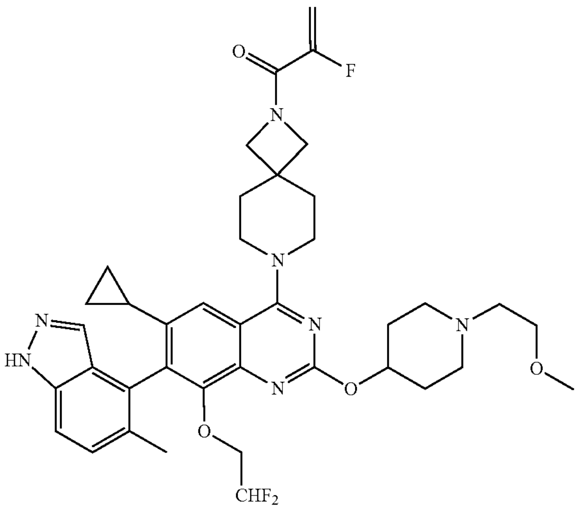
4
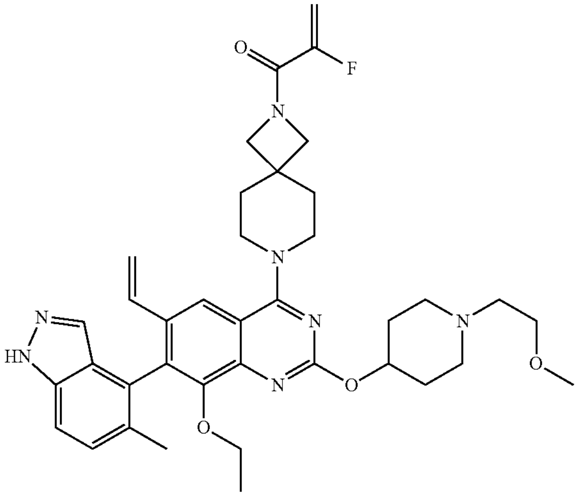
5
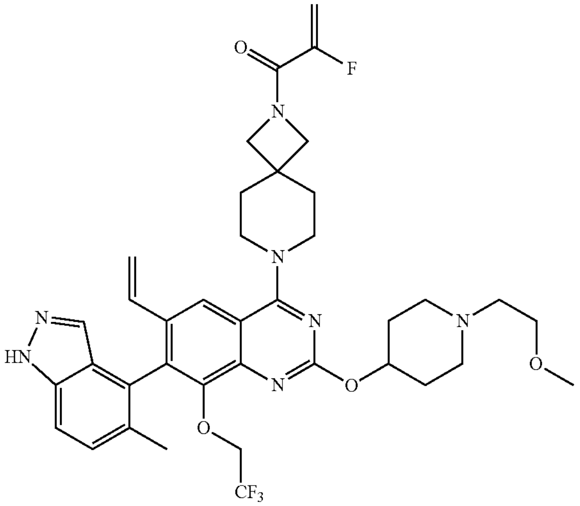

-continued
6
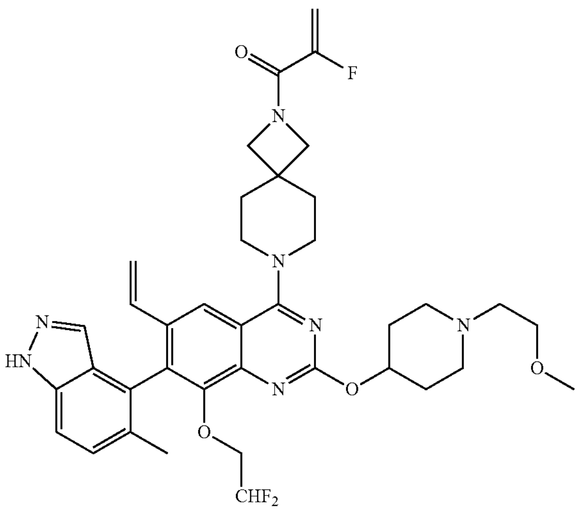
7
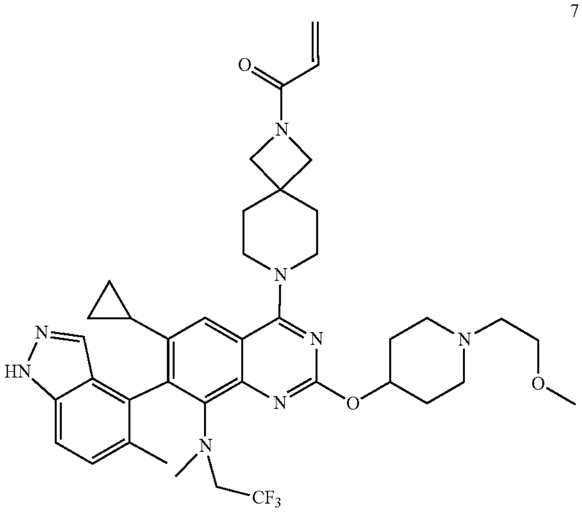
8
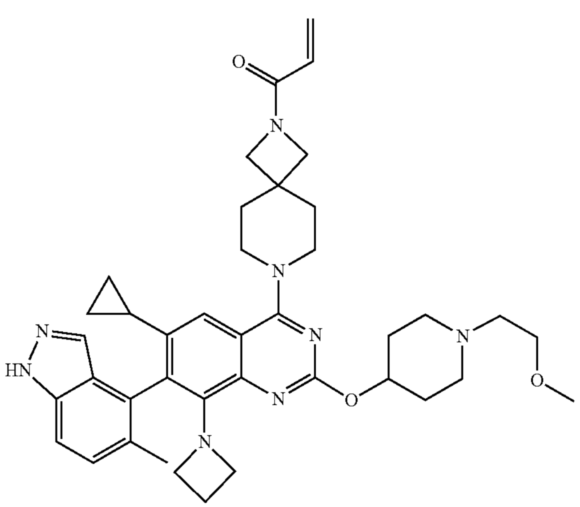
-continued
9
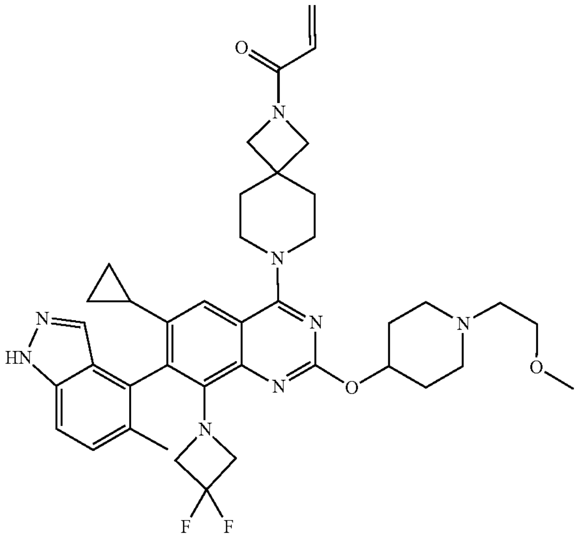
10
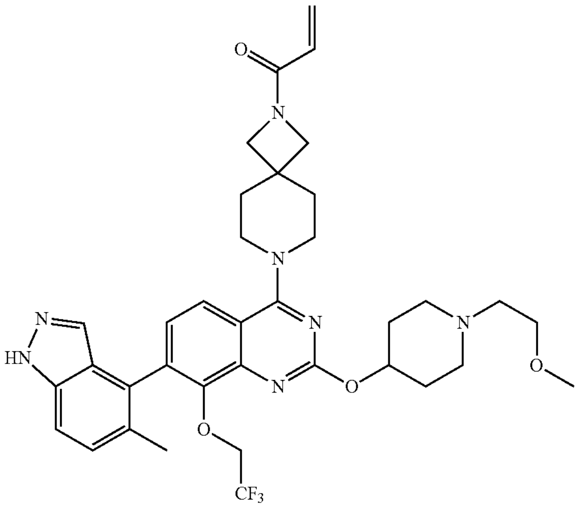
11
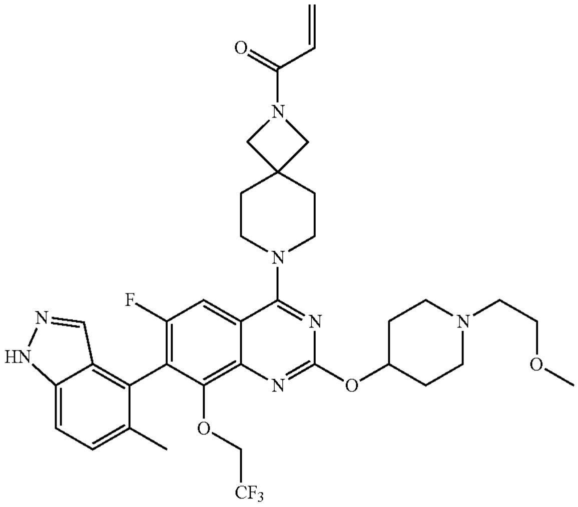

-continued
12
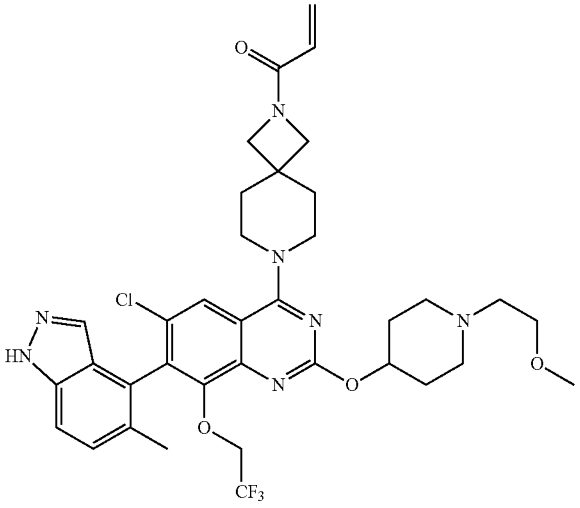
13
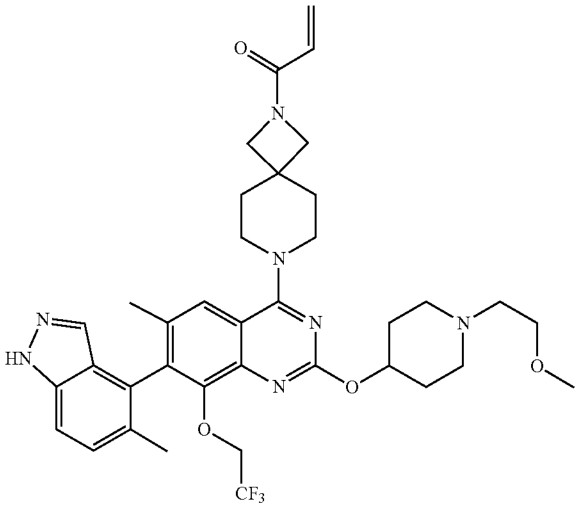
14
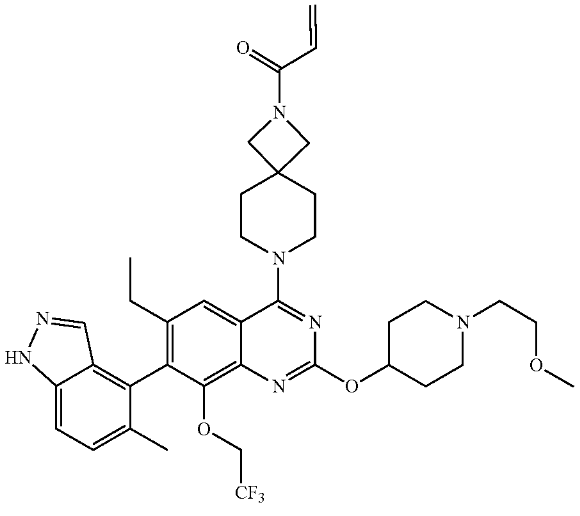
-continued
15
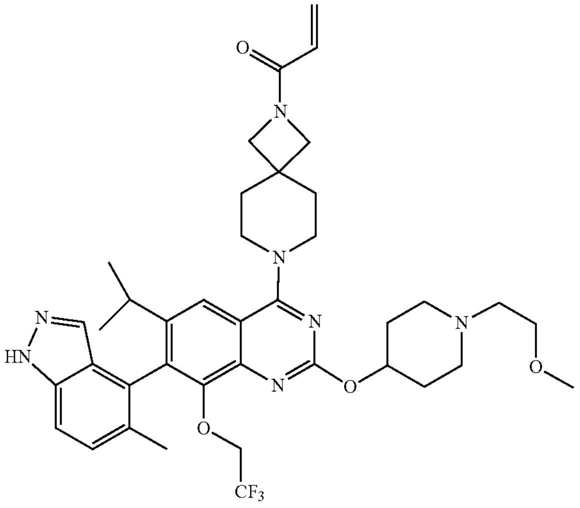
16
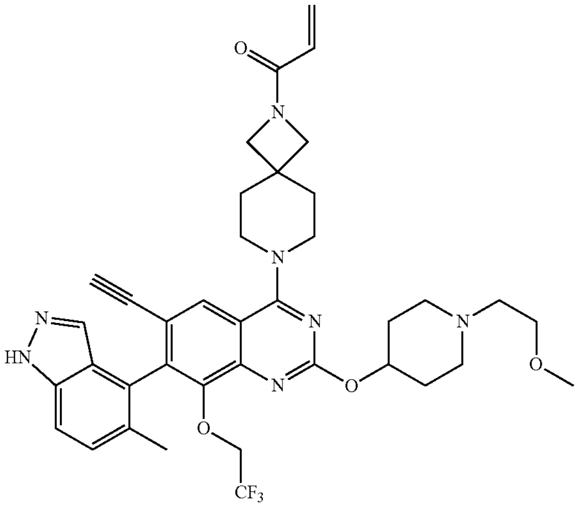
17
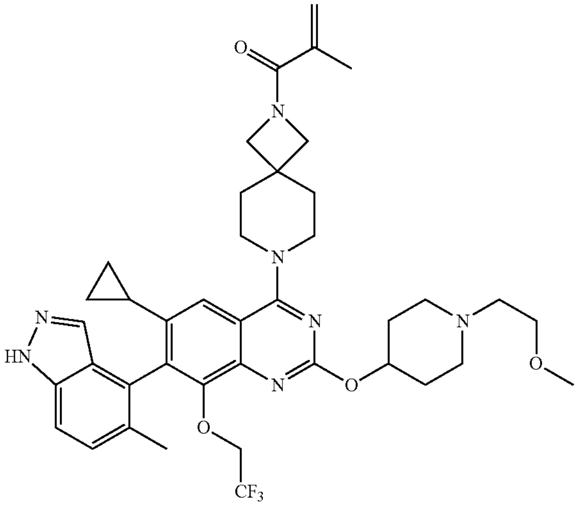

18
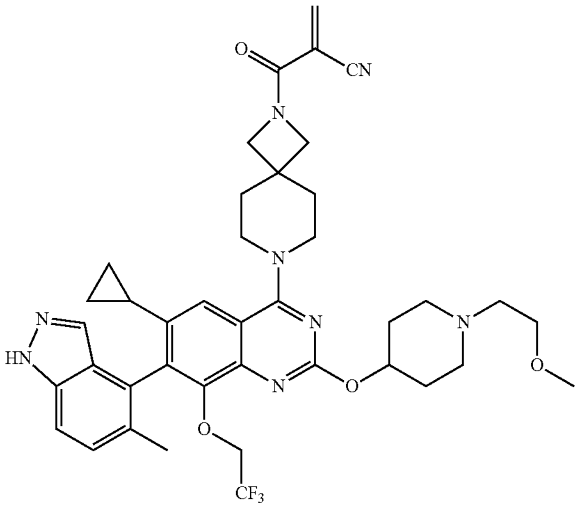
19
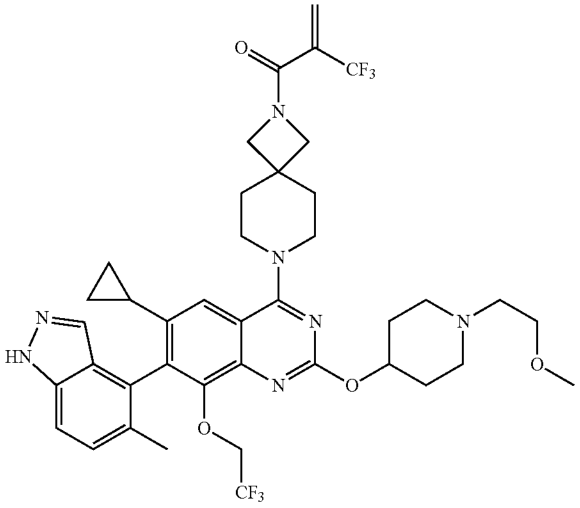
20
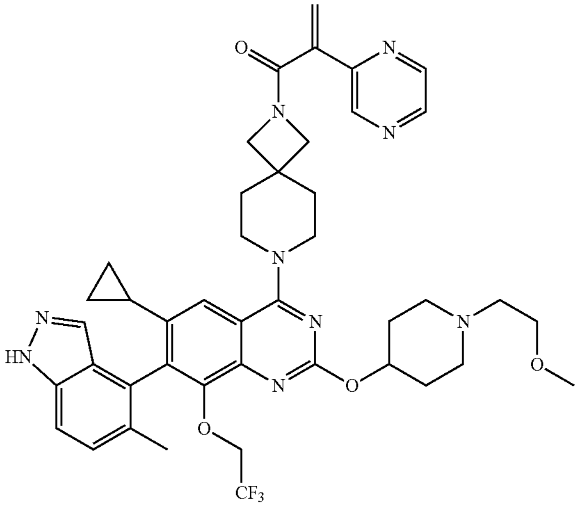
21
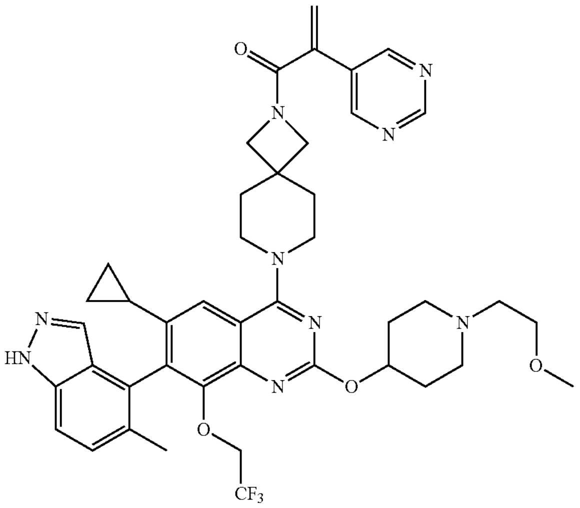
22
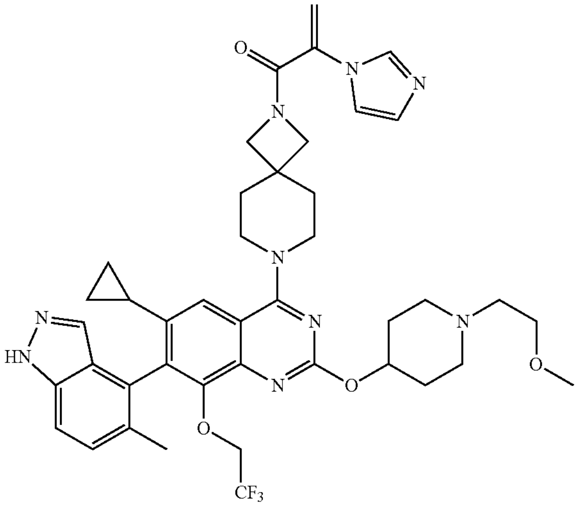
23
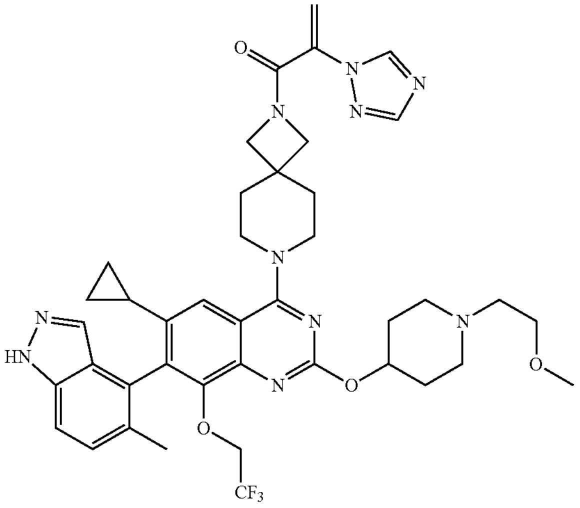

-continued
24
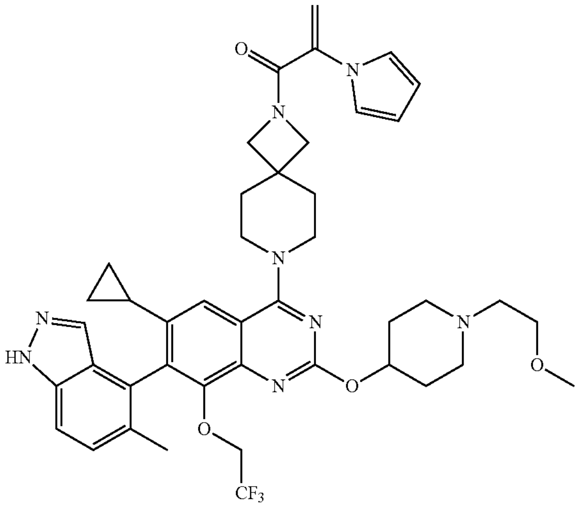
25
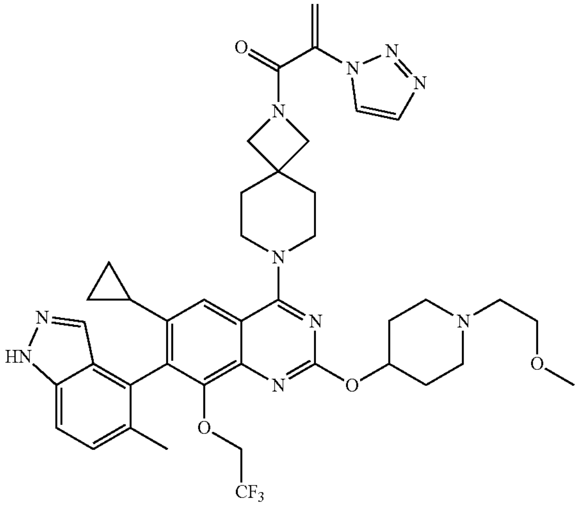
26
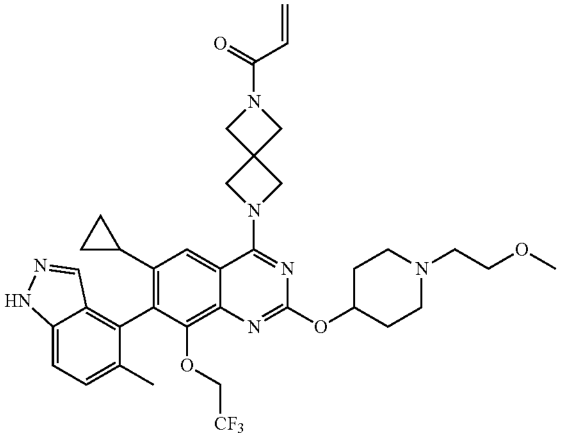
-continued
27
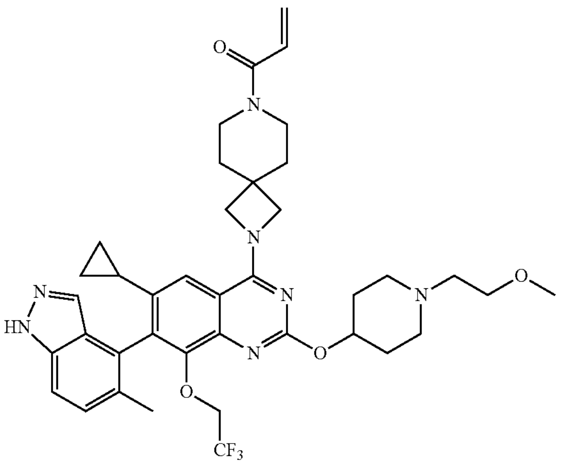
28
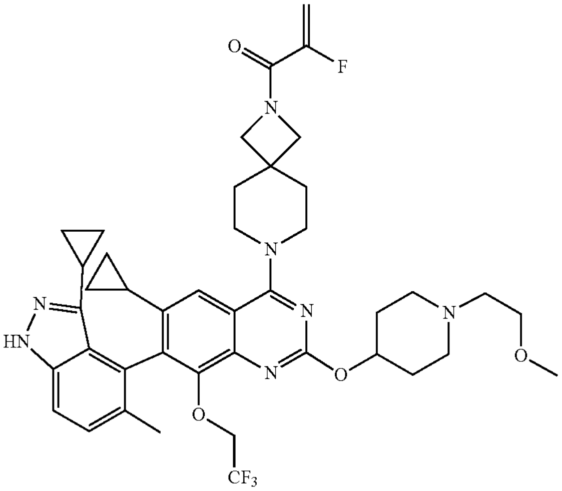
29
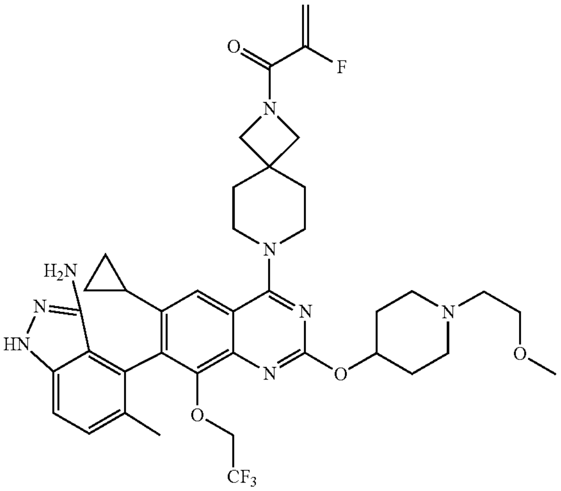

-continued
30
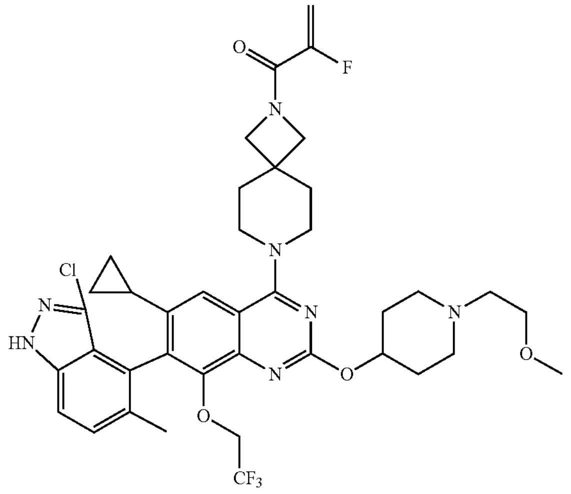
31
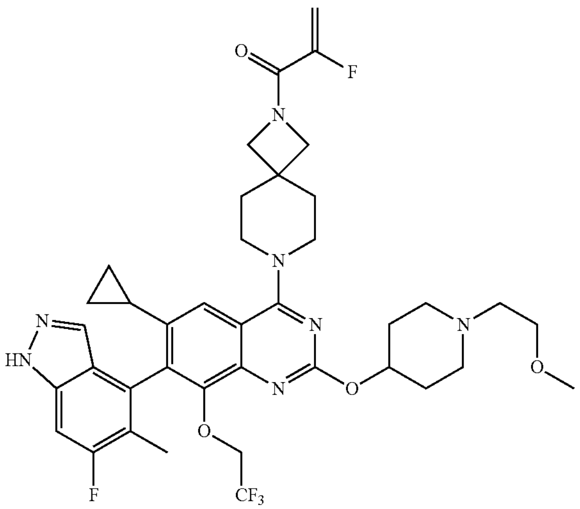
32
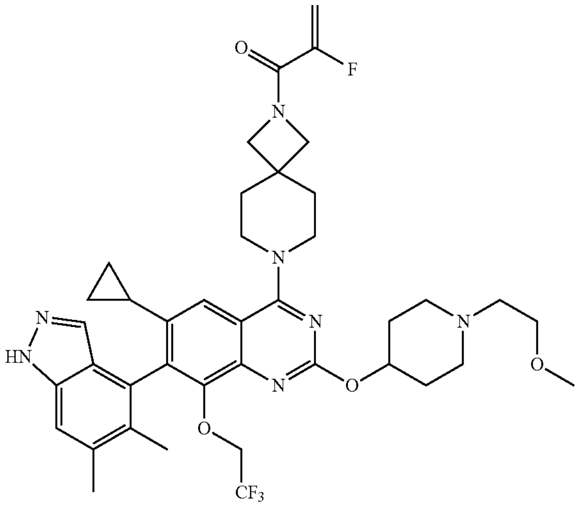
-continued
33
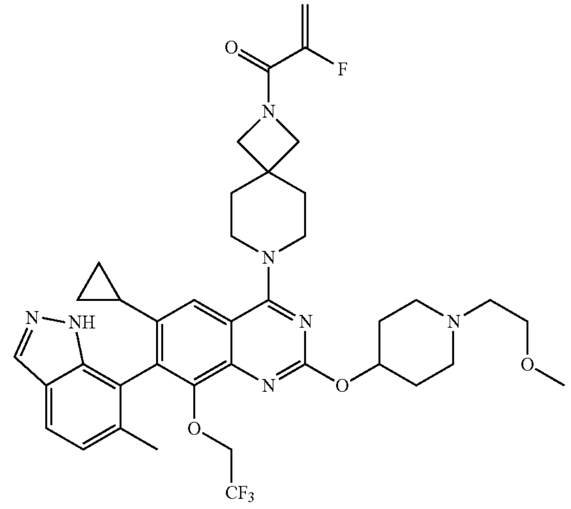
34
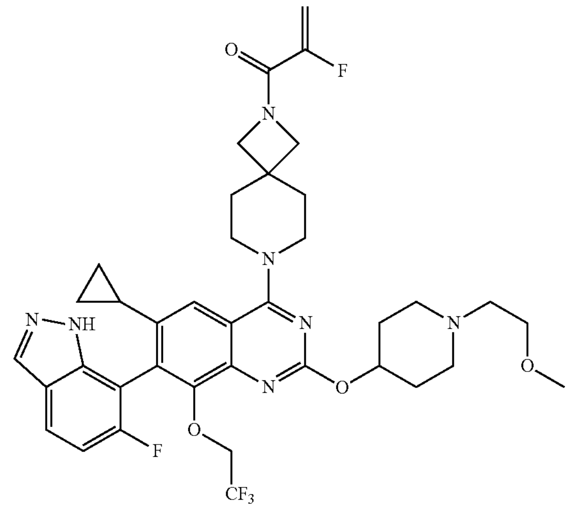
35
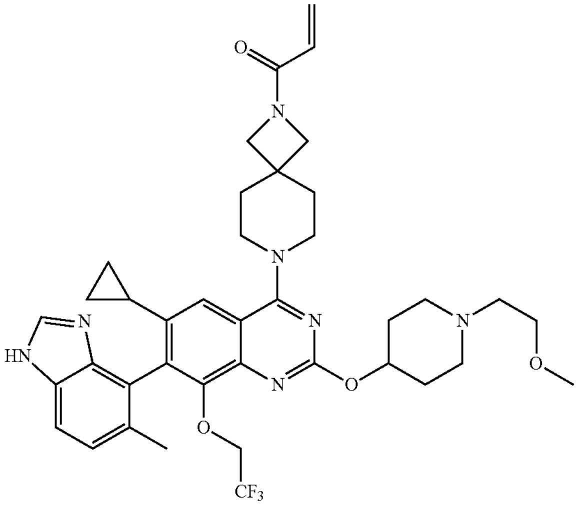

-continued
36
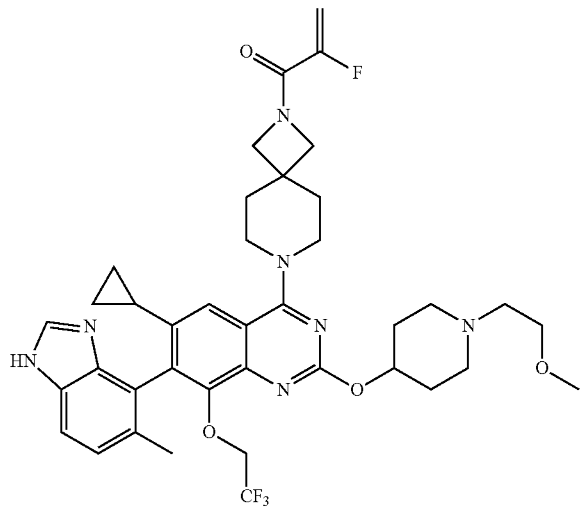
37
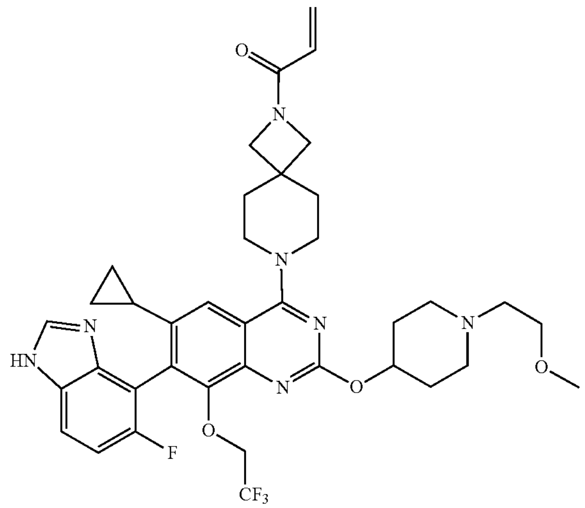
38
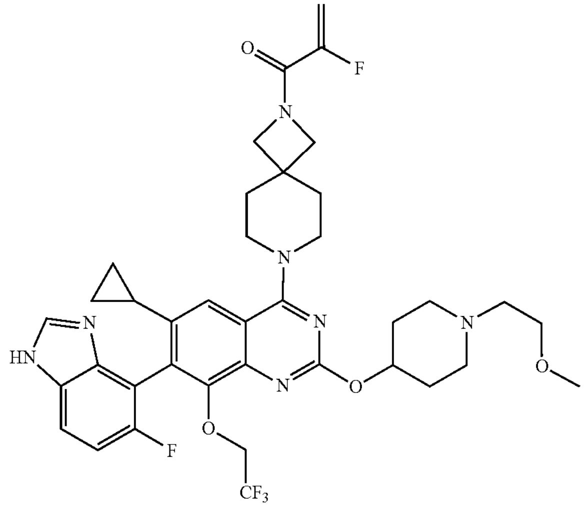
-continued
39
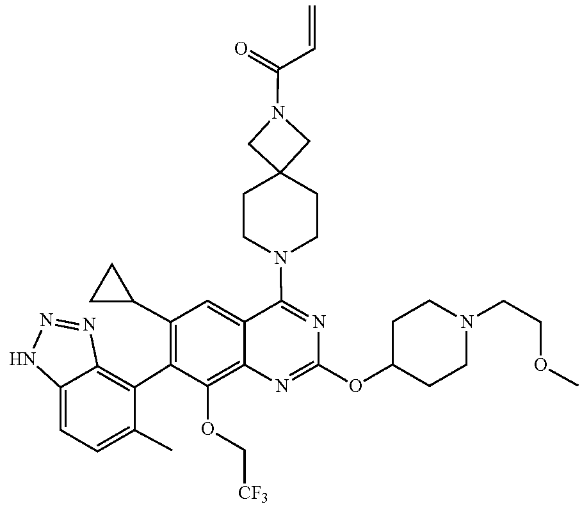
40
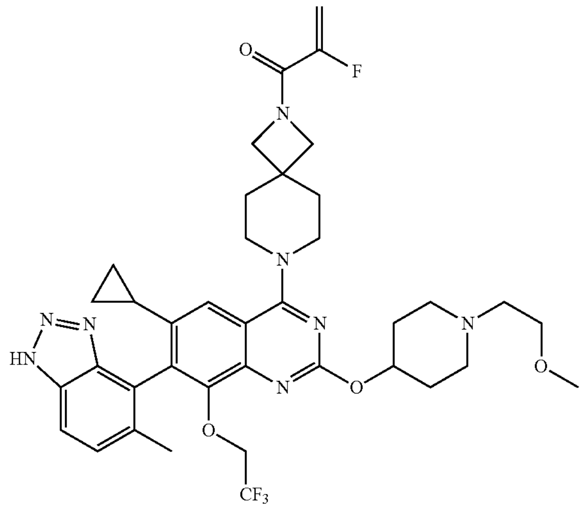
41
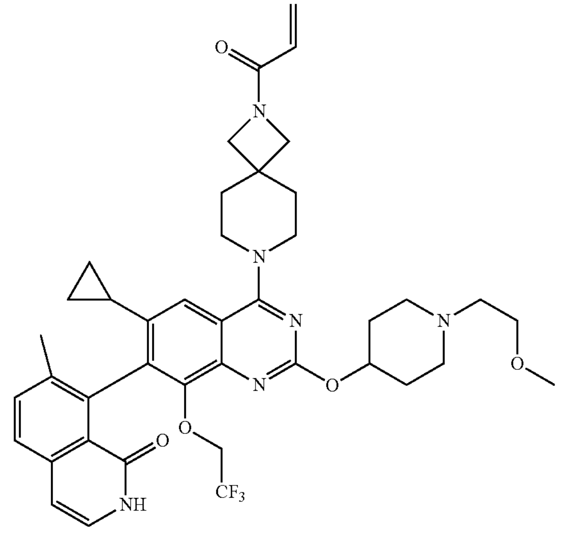

-continued
42
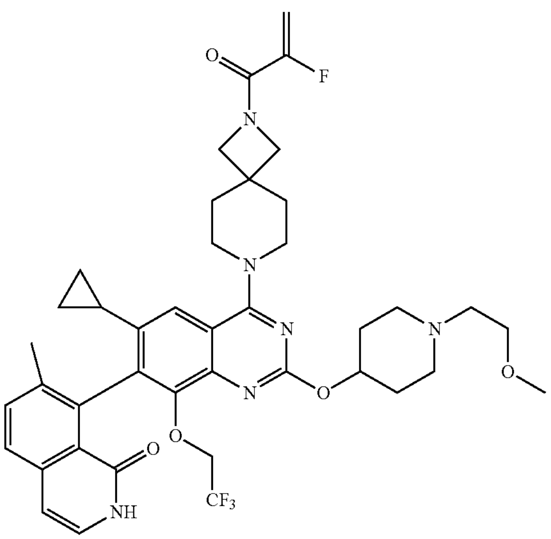
43
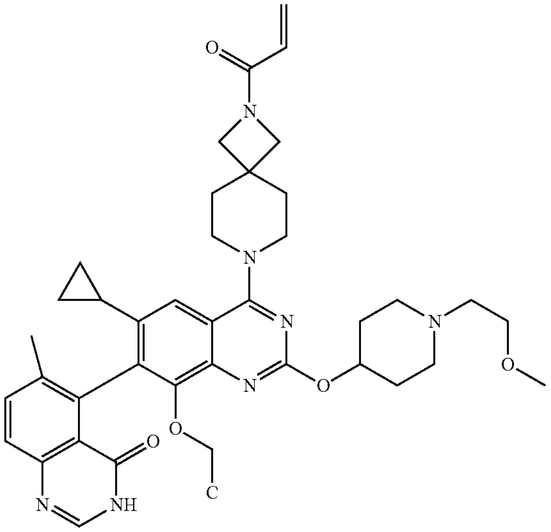
44
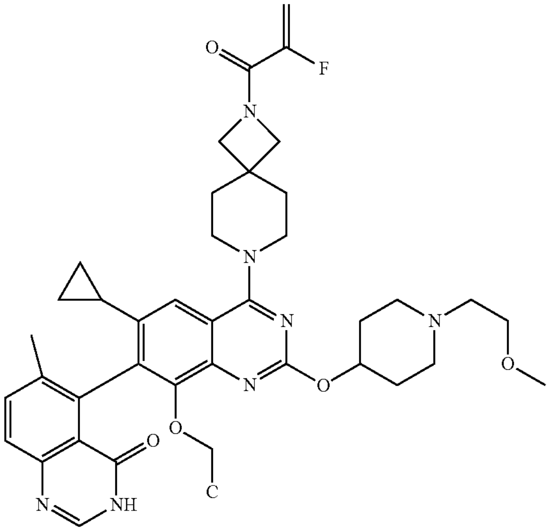
-continued
45
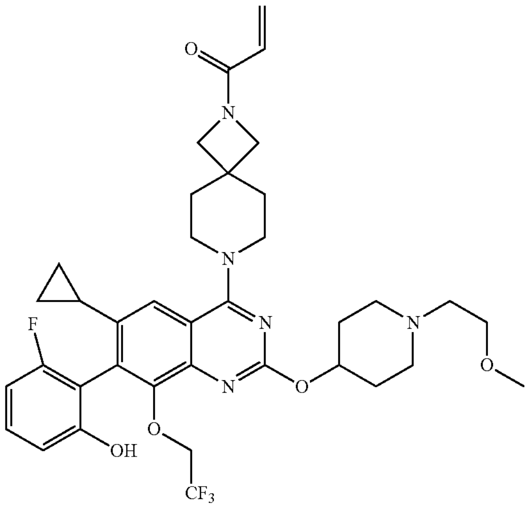
46
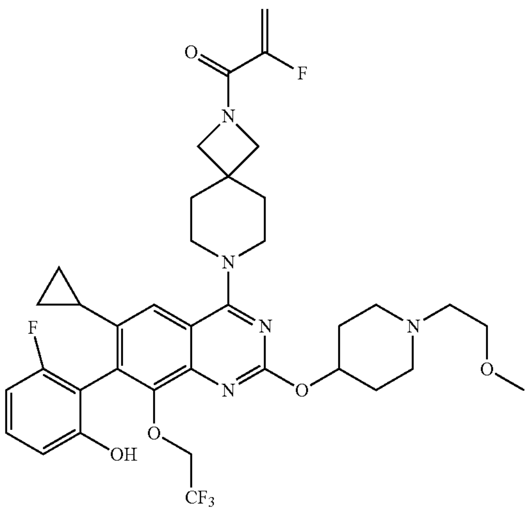
47
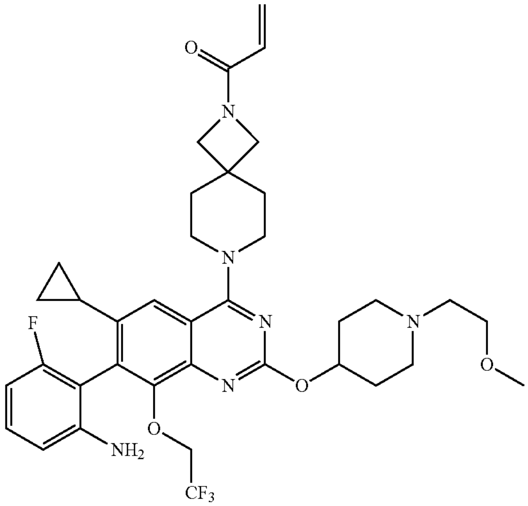

-continued
48
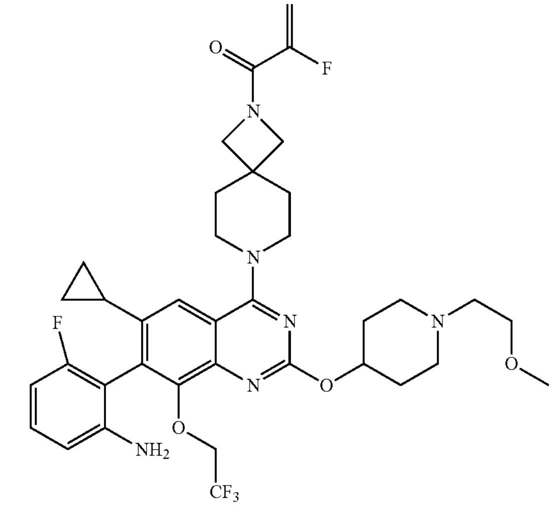
49
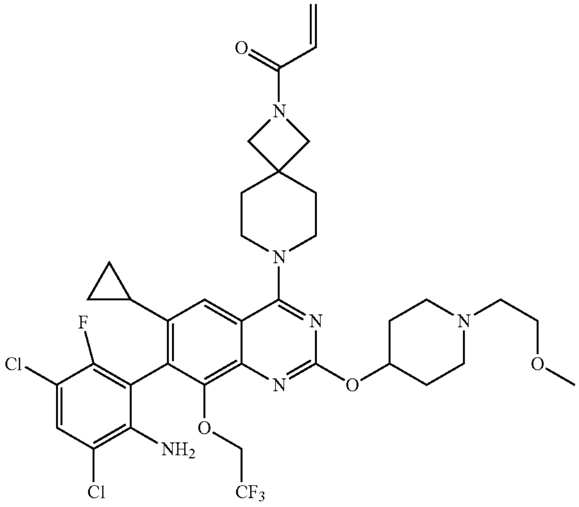
50
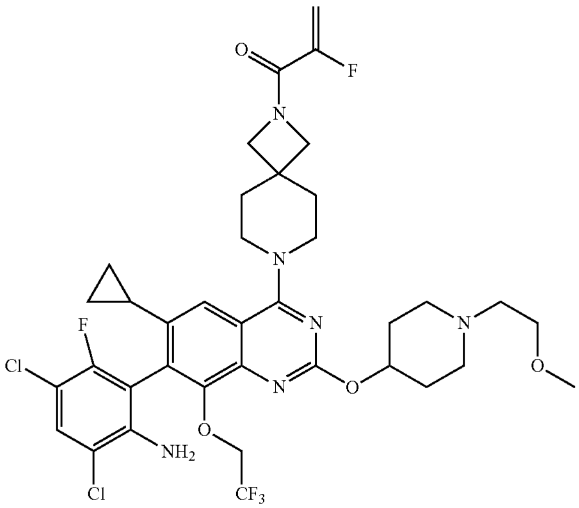
-continued
51
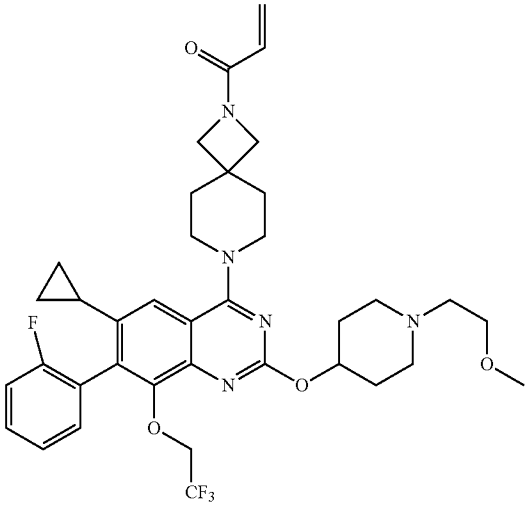
52
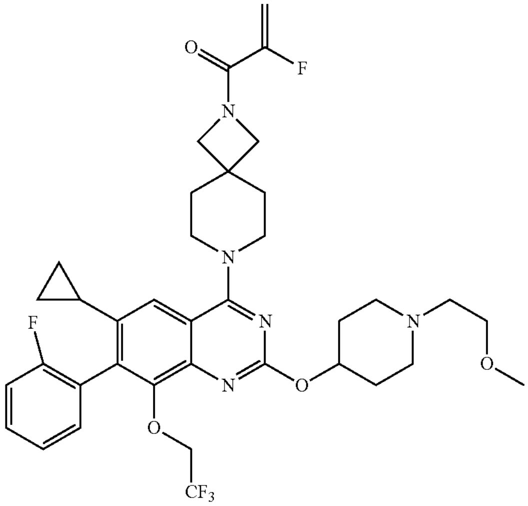
53
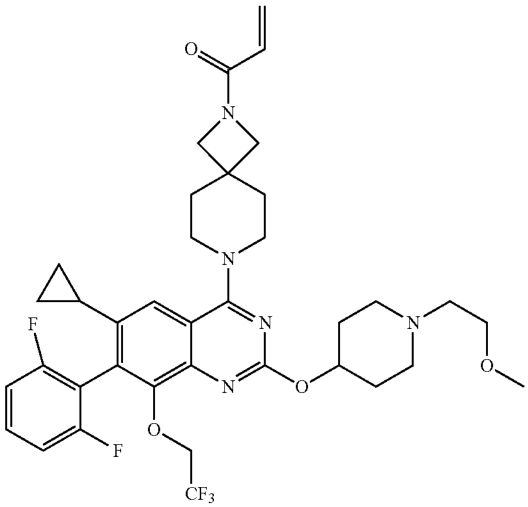

-continued
54
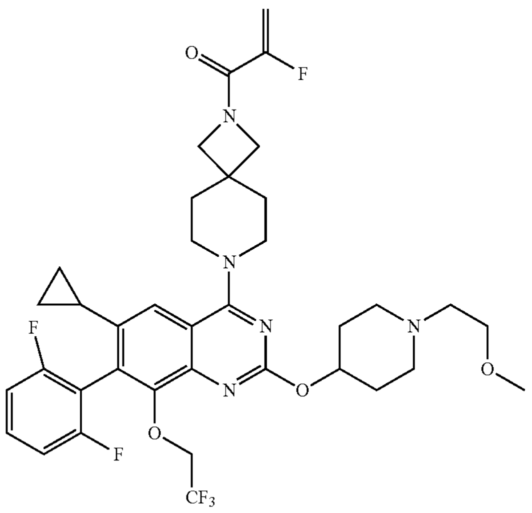
55
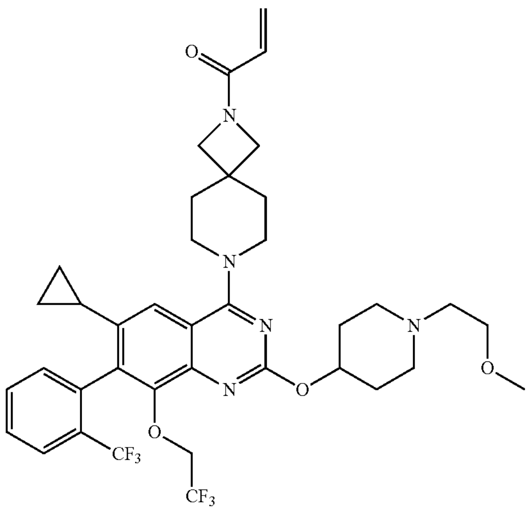
56
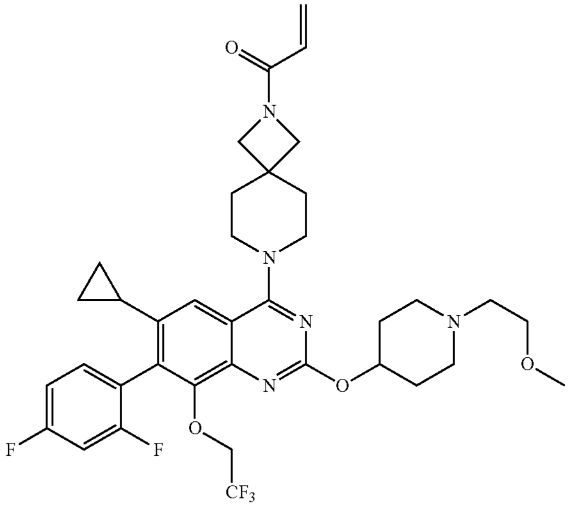
-continued
57
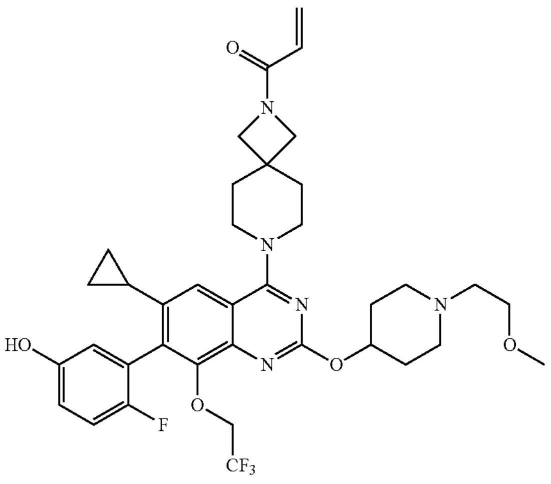
58
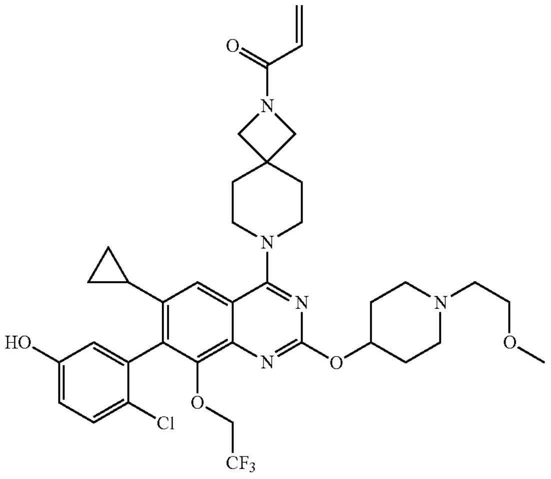
59
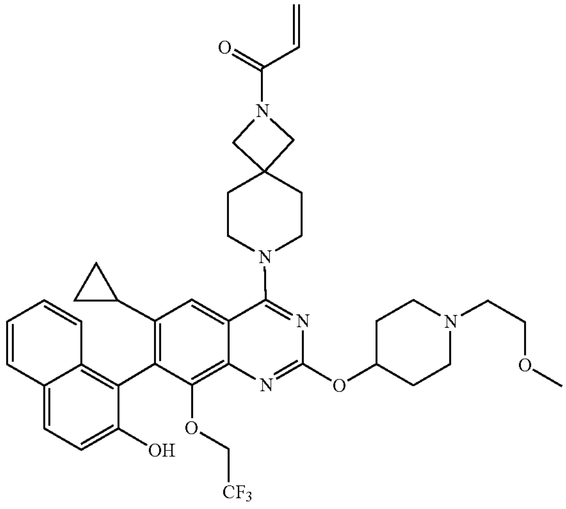

-continued
60
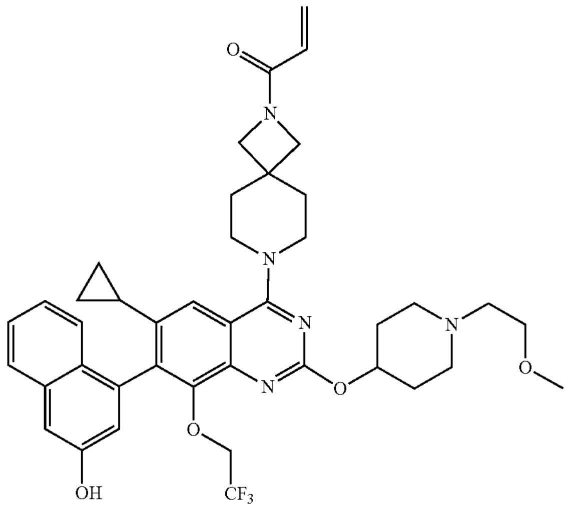
61
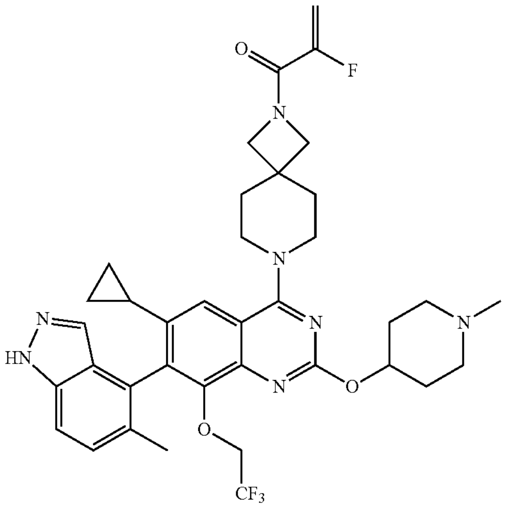
62
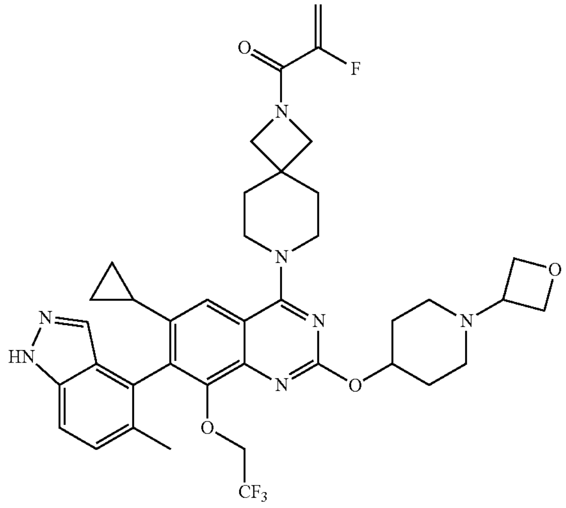
-continued
63
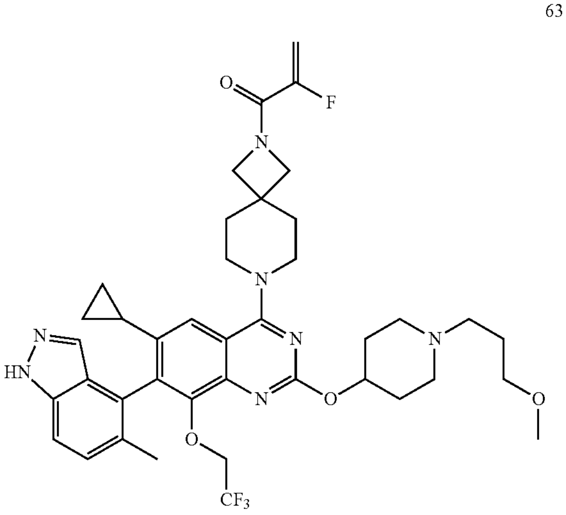
64
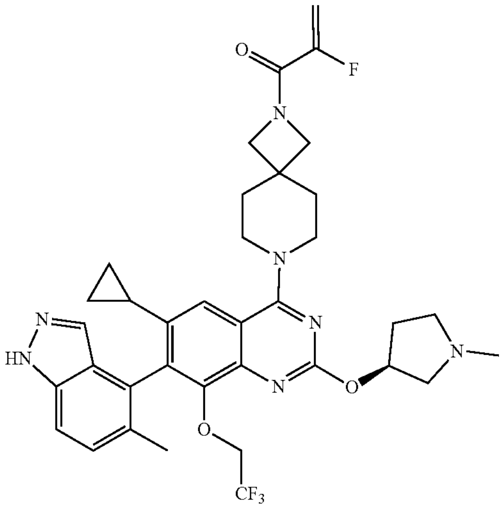
65
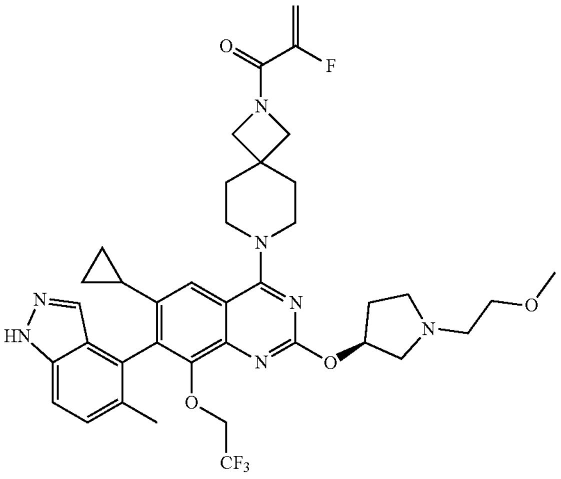

-continued
66
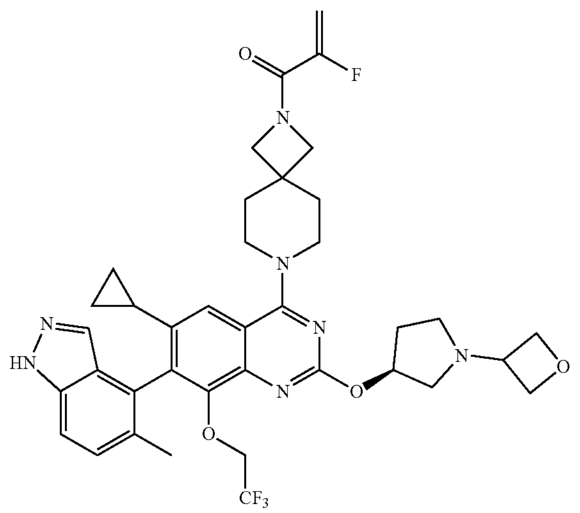
67
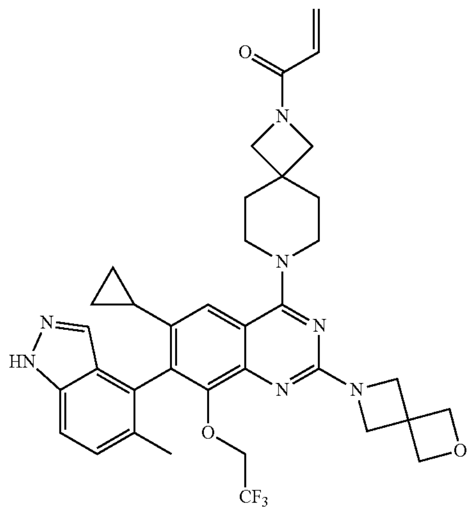
68
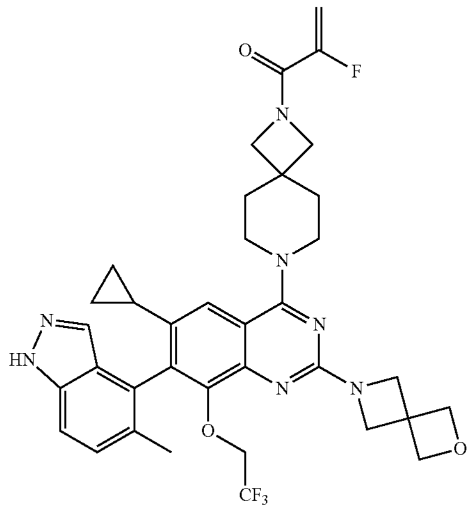
-continued
69
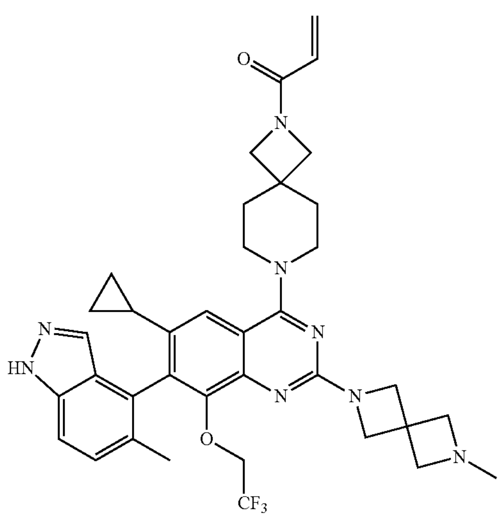
70
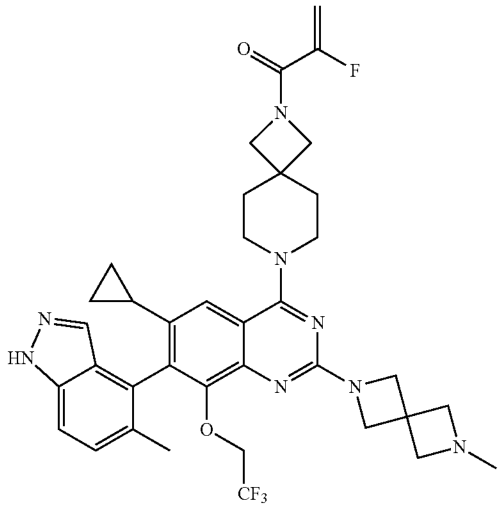
71
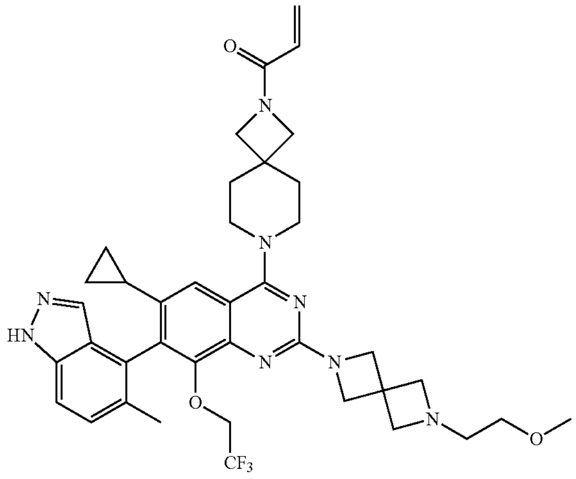

-continued
72
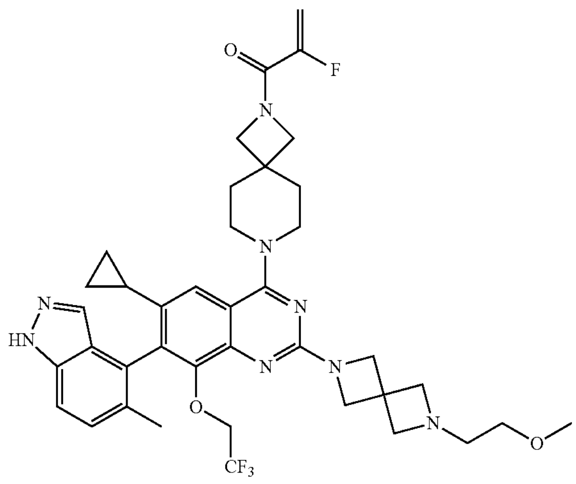
73
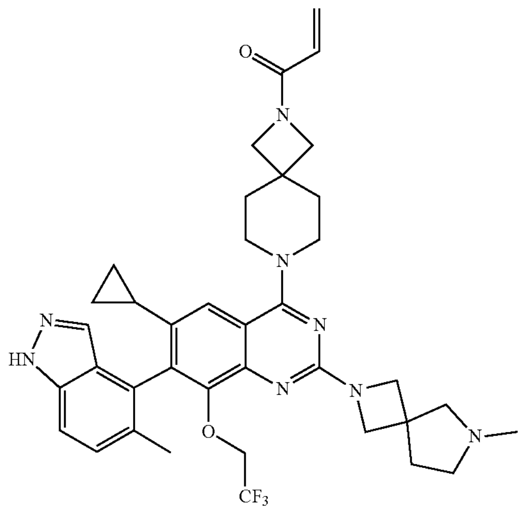
74
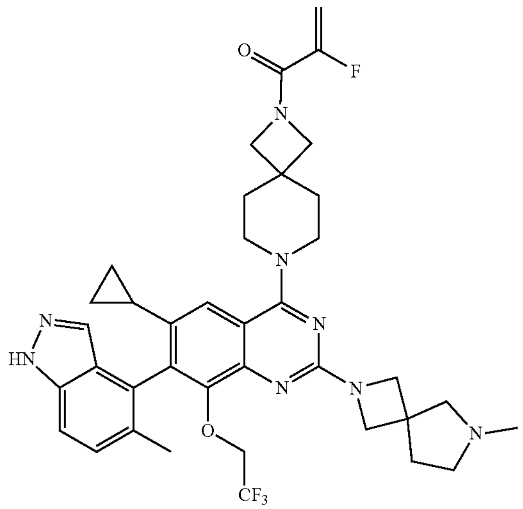
-continued
75
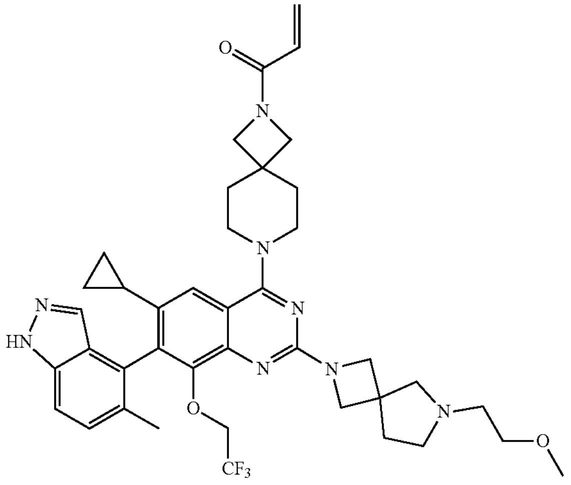
76
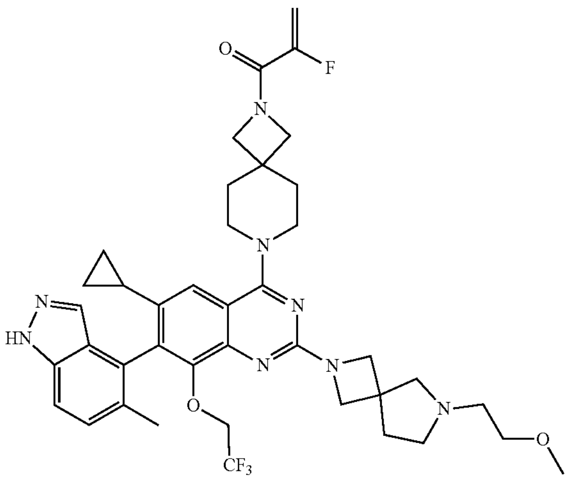
77
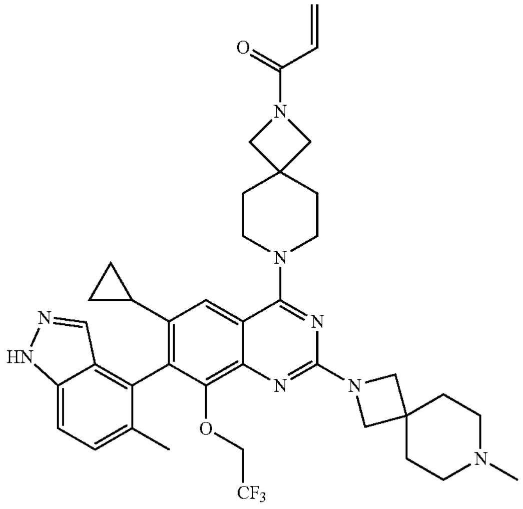

-continued
78
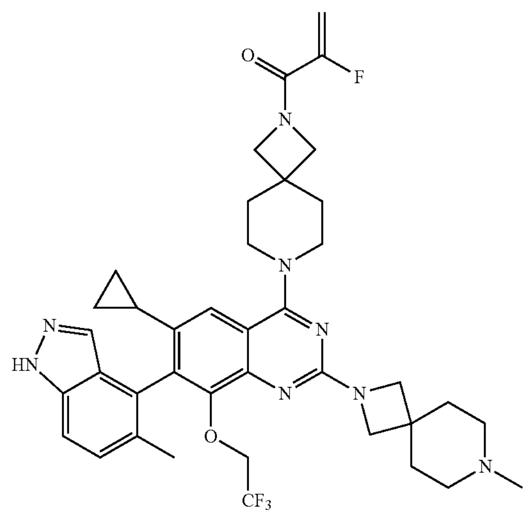
79
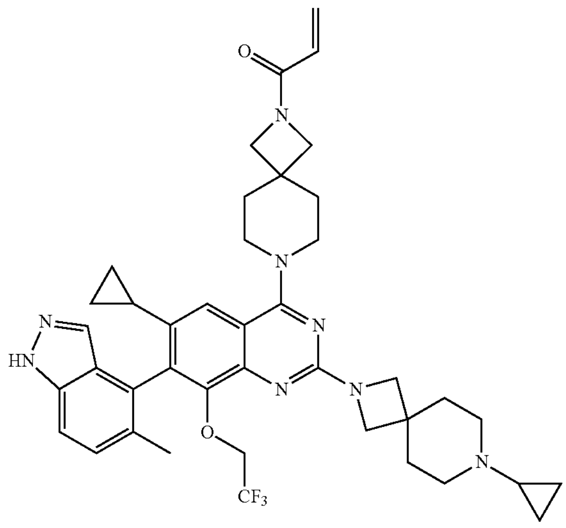
80
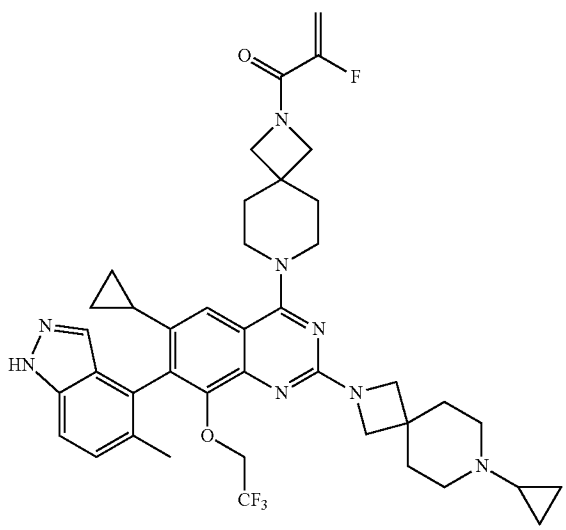
-continued
81
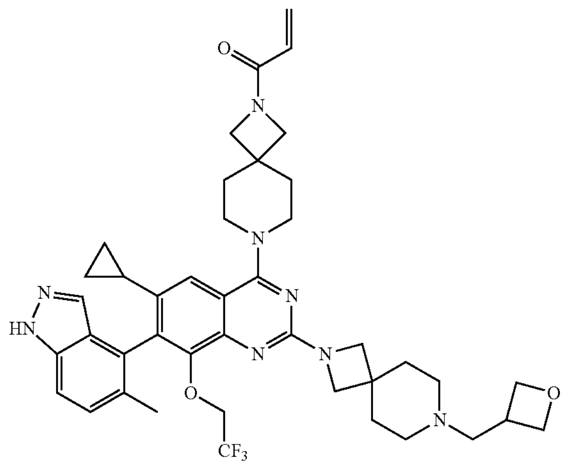
82
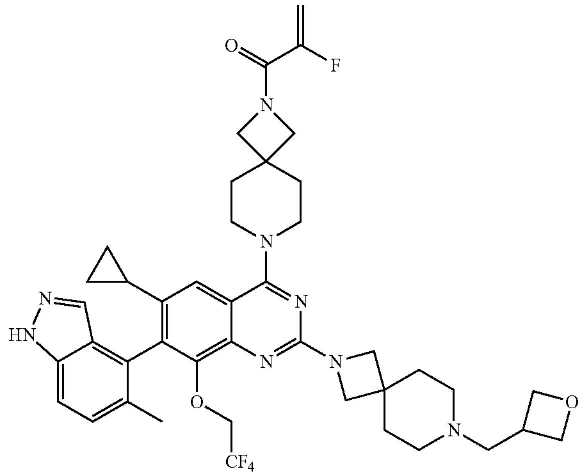
83
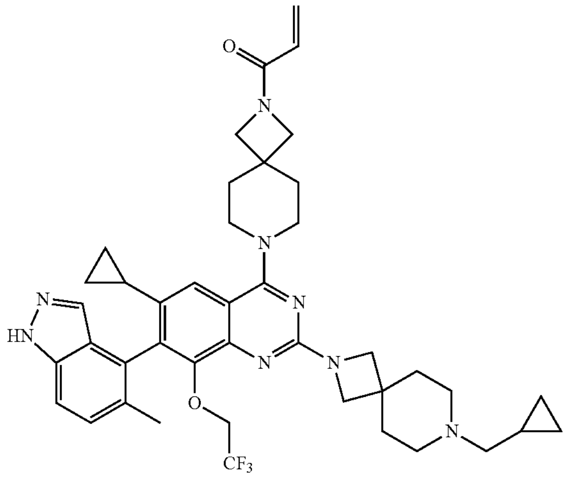

-continued
84
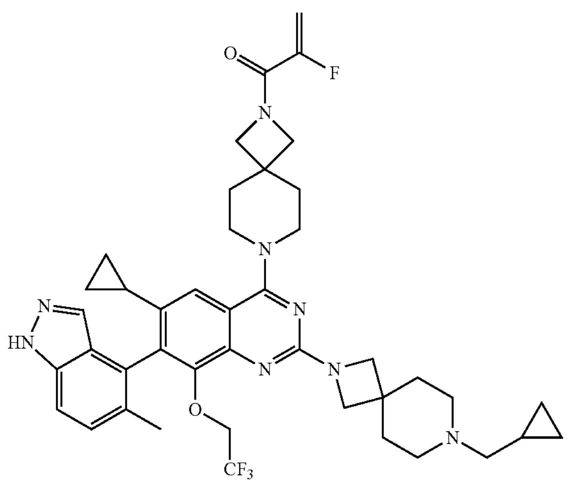
85
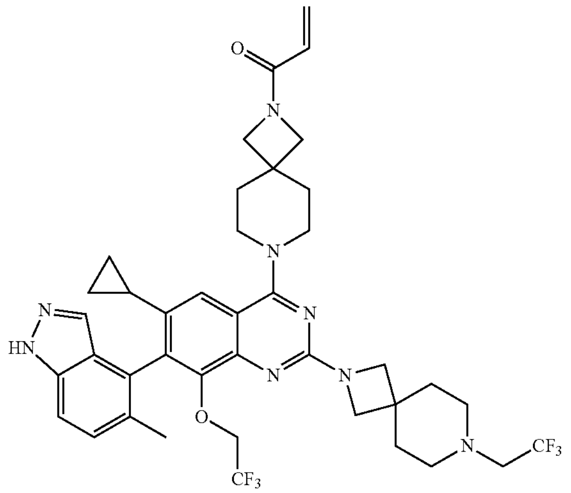
86
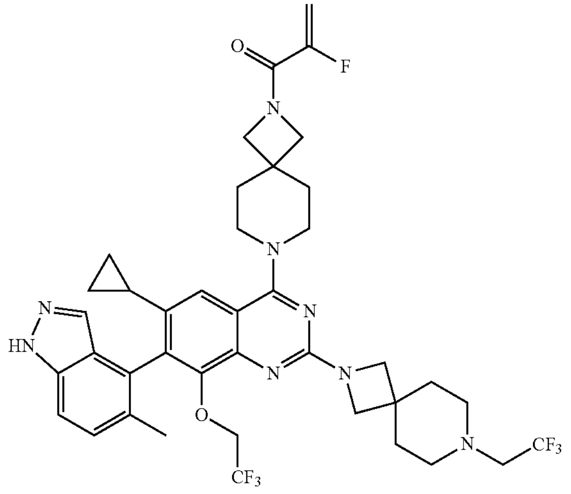
-continued
87
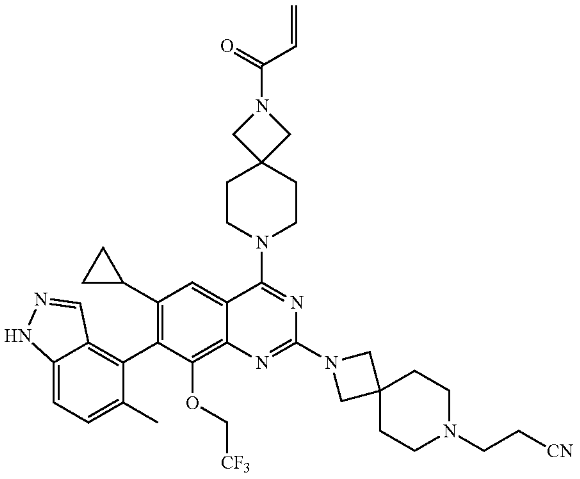
88
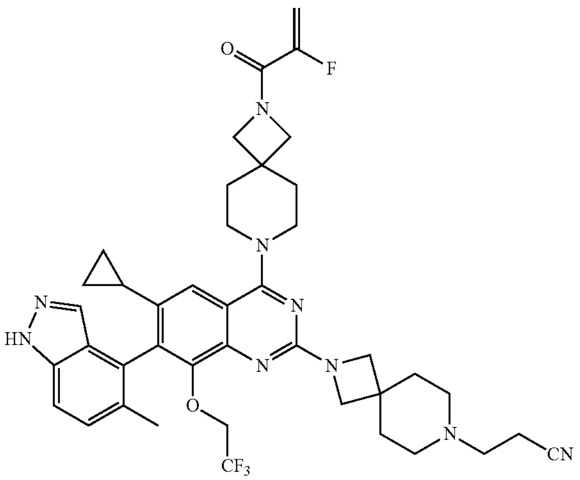
89
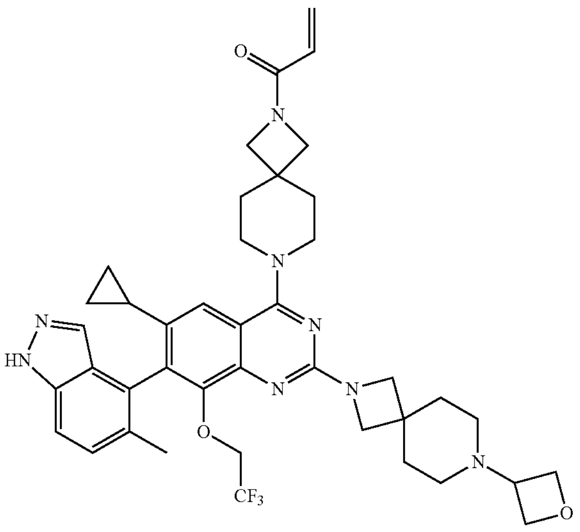

-continued
90
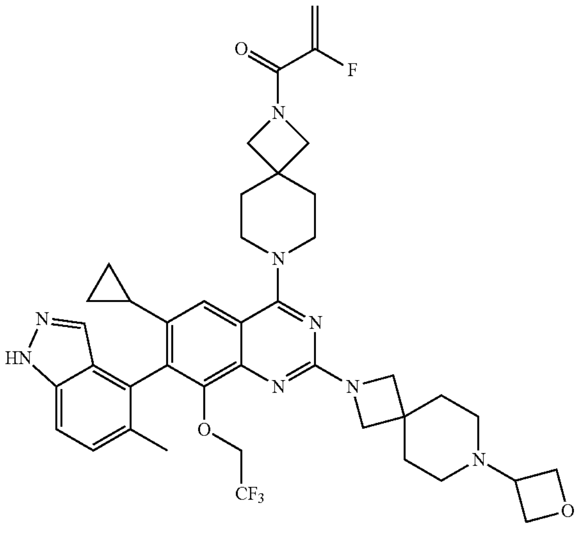
91
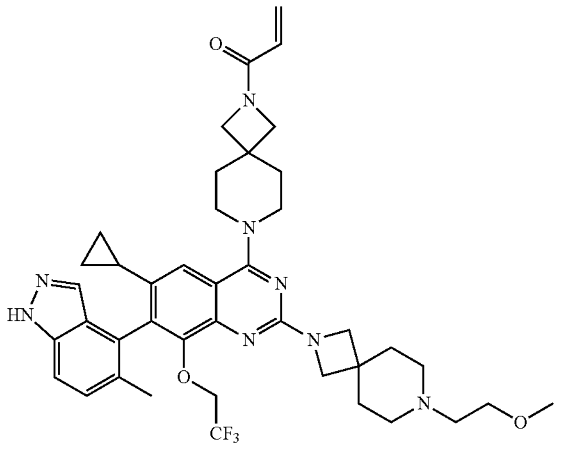
92
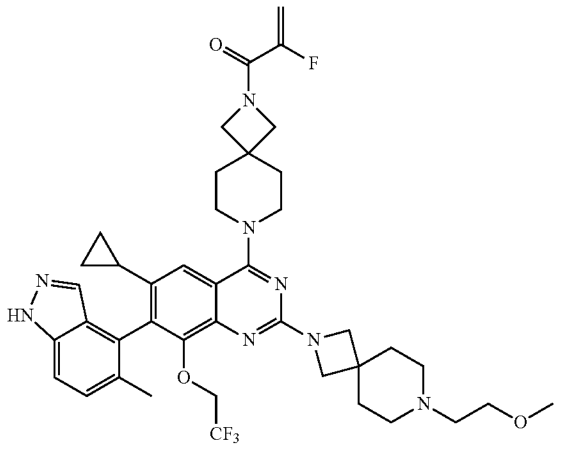
-continued
93
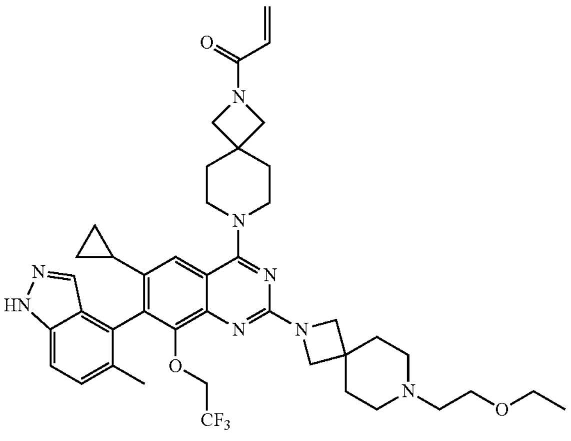
94
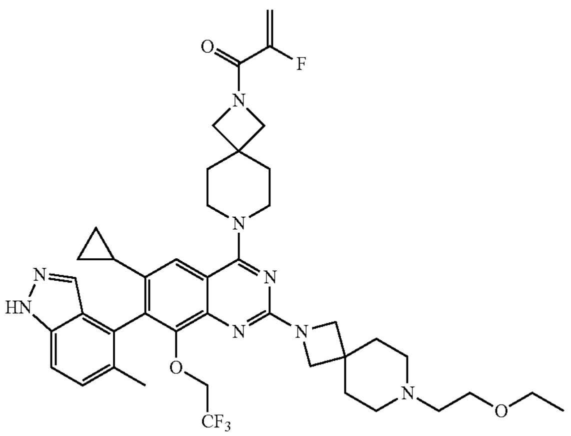
95
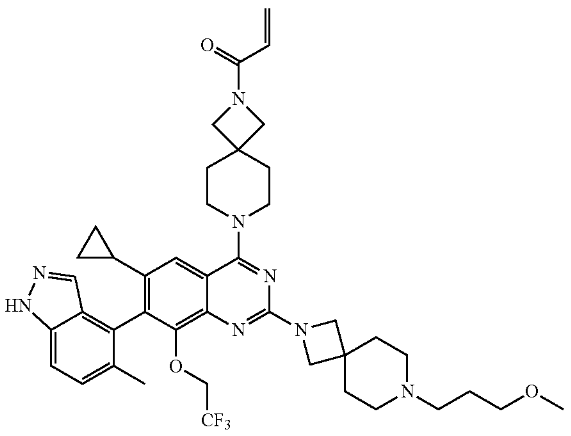

96
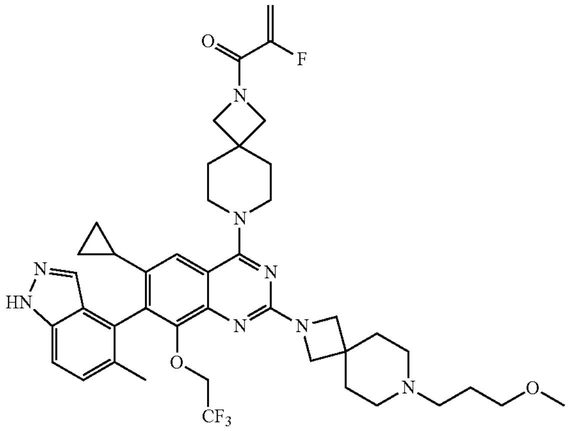
97
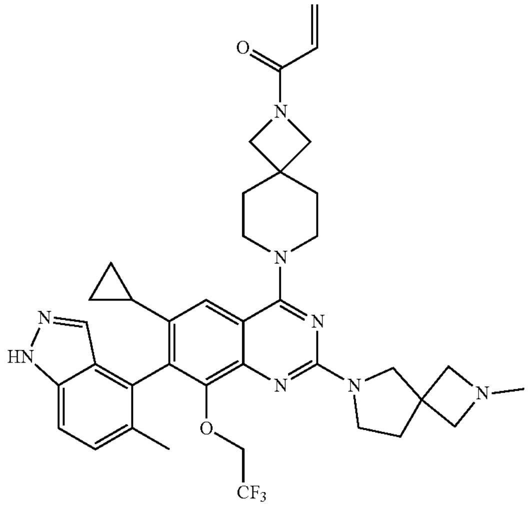
98
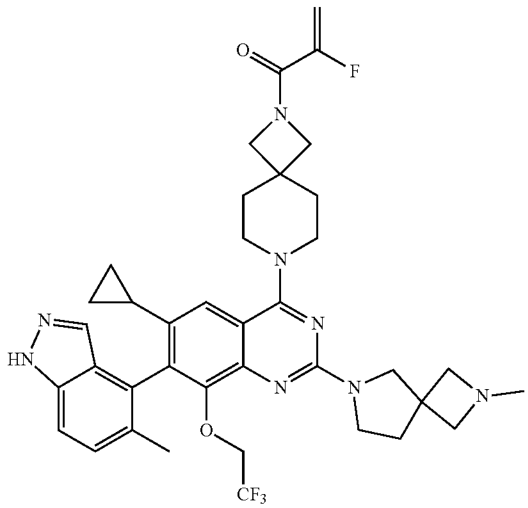
99
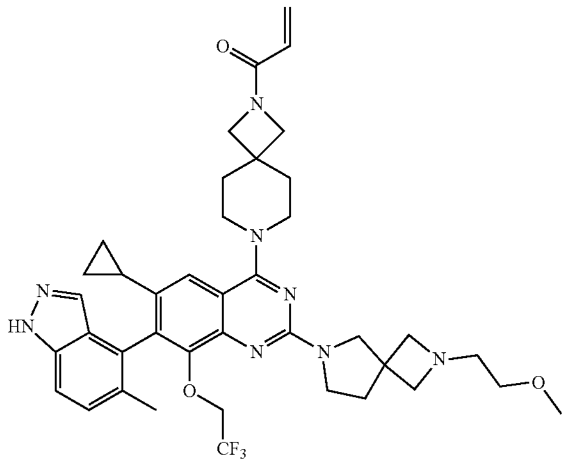
100
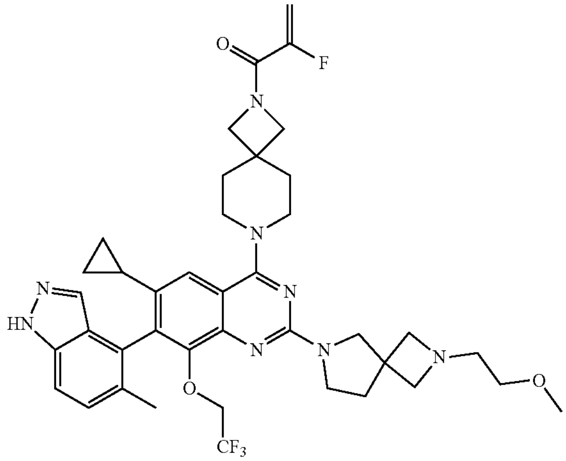
101
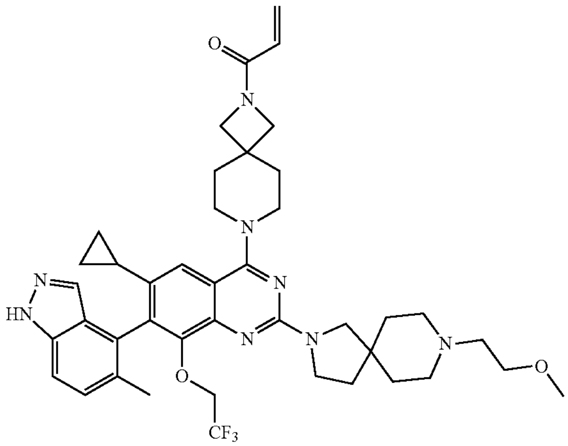

-continued
102
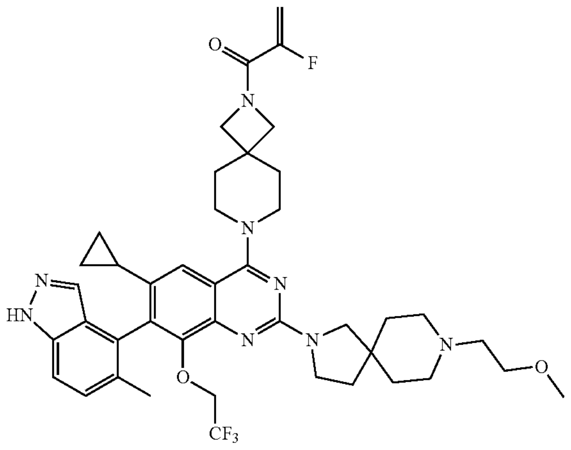
103
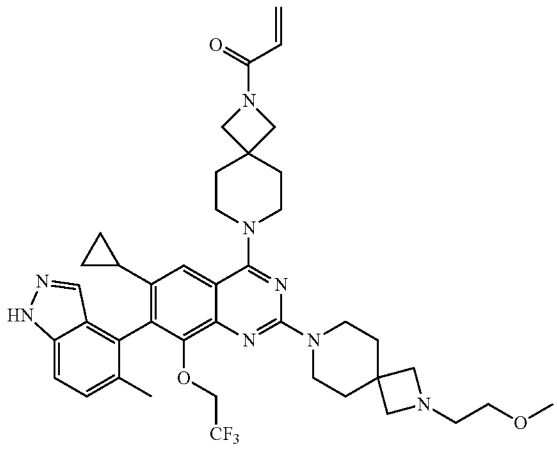
104
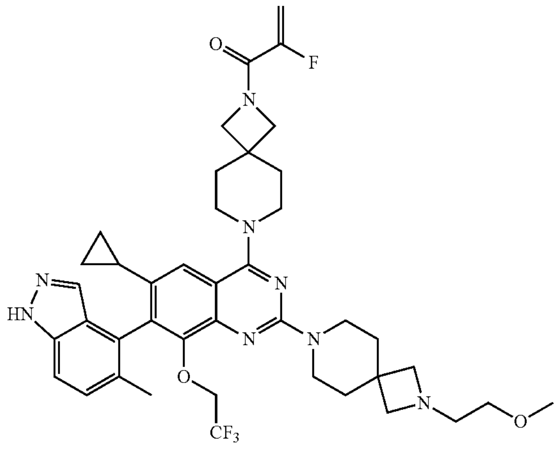
-continued
105
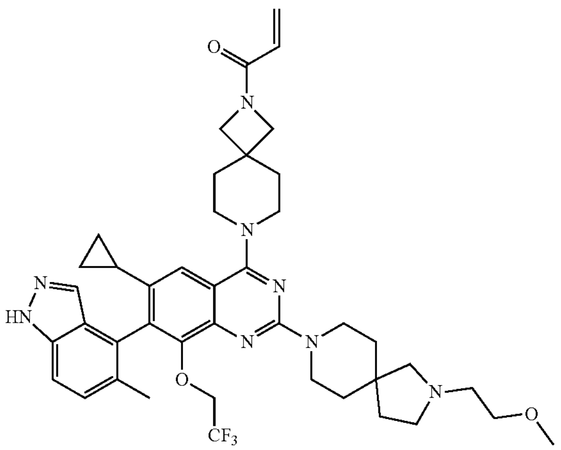
106
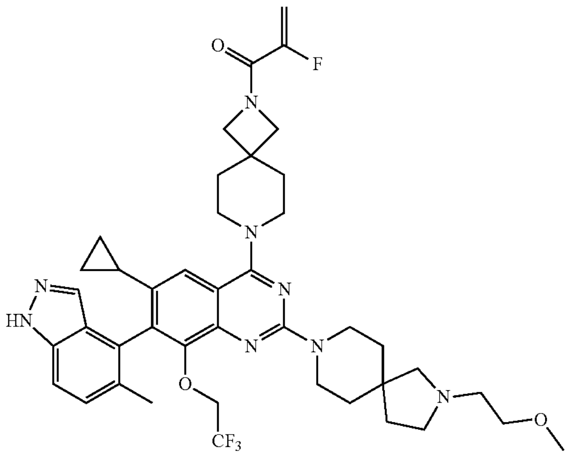
107
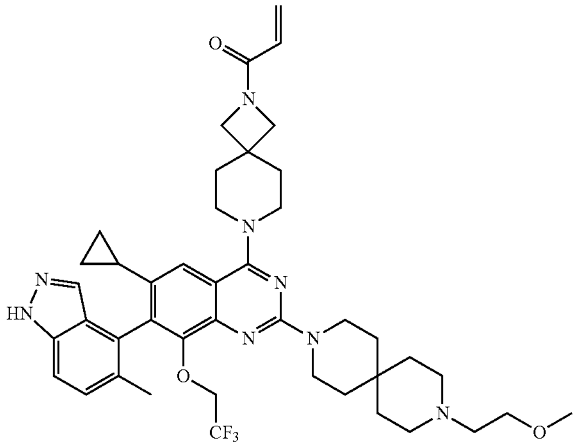

-continued
108
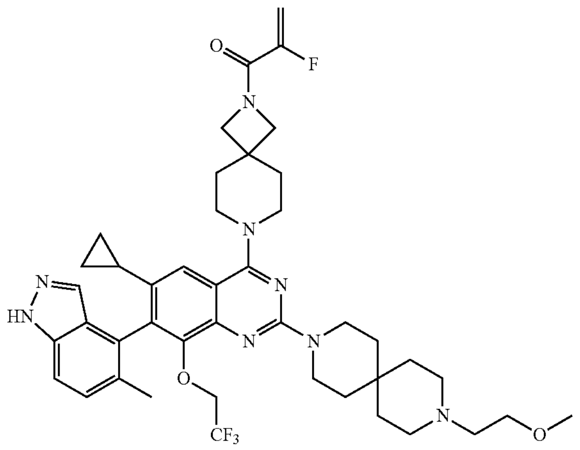
109
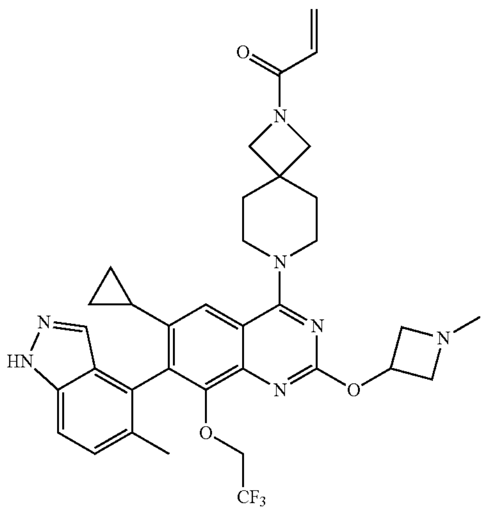
110
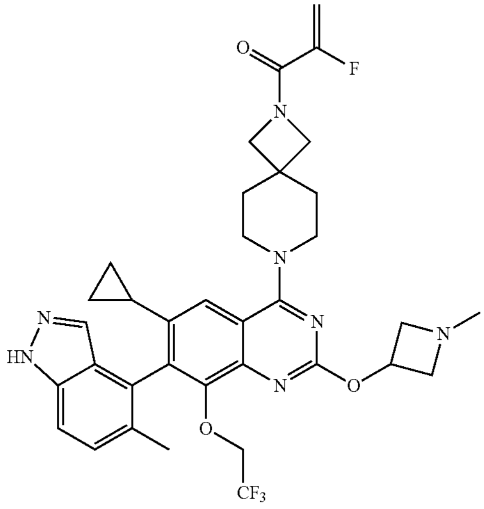
-continued
111
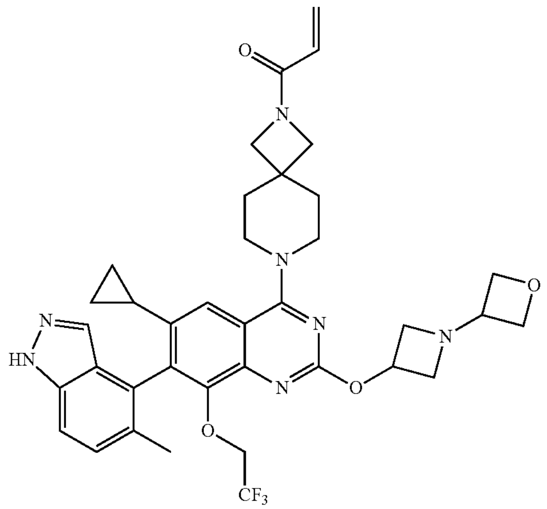
112
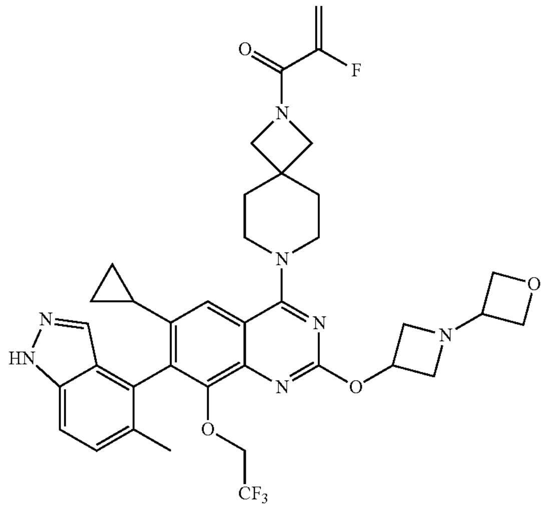
113
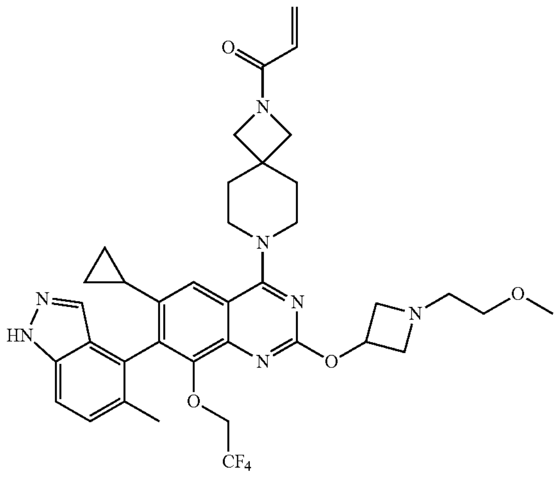

-continued
114
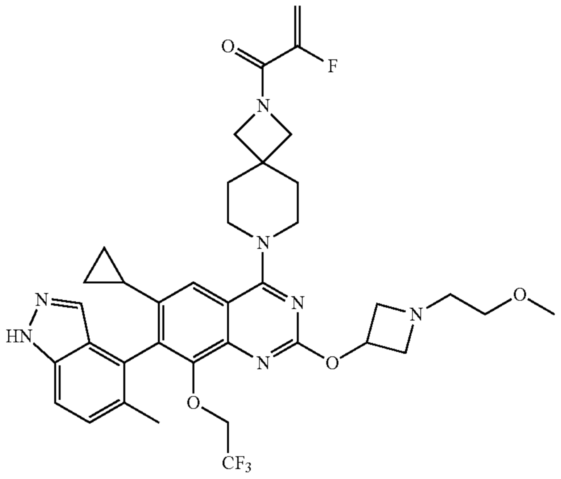
115
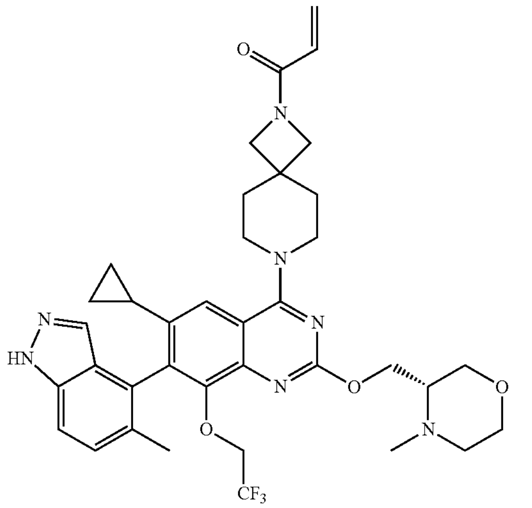
116
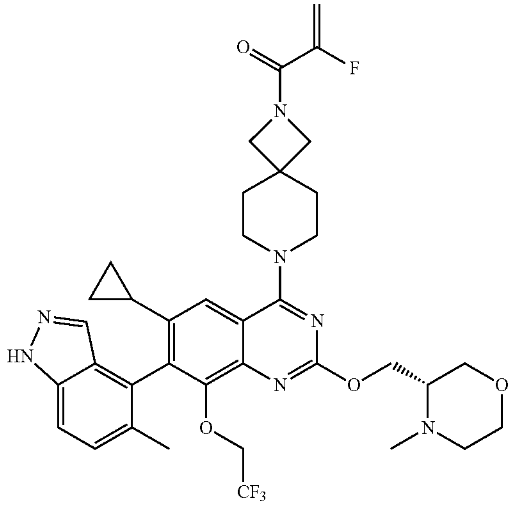
-continued
117
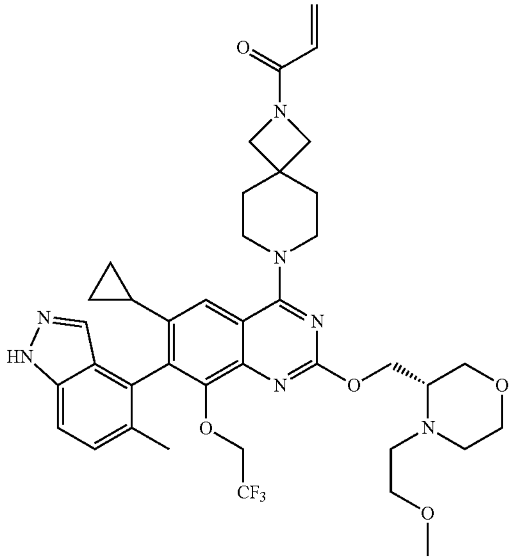
118
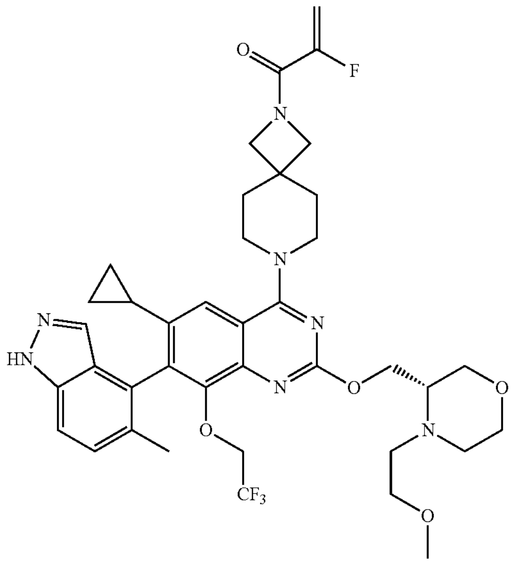
119
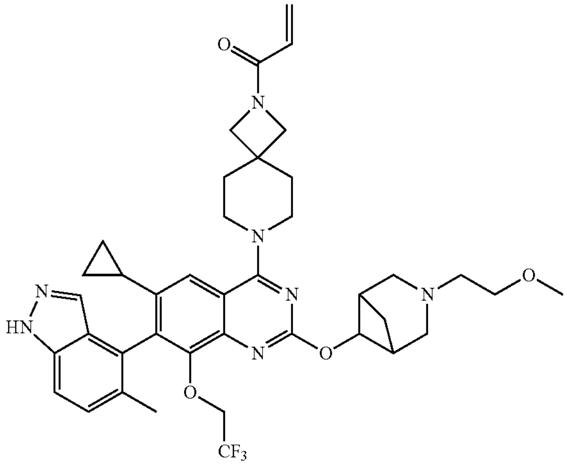

-continued
120
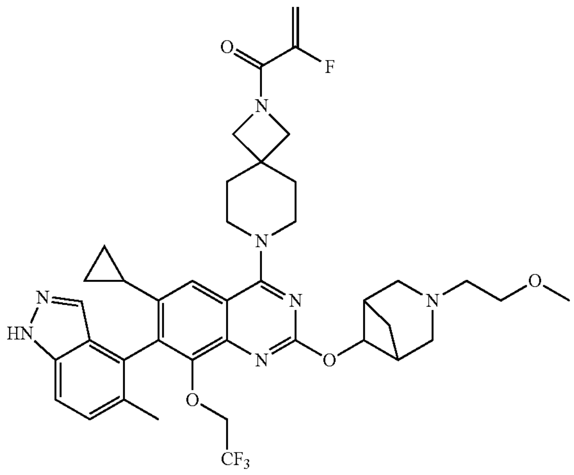
121
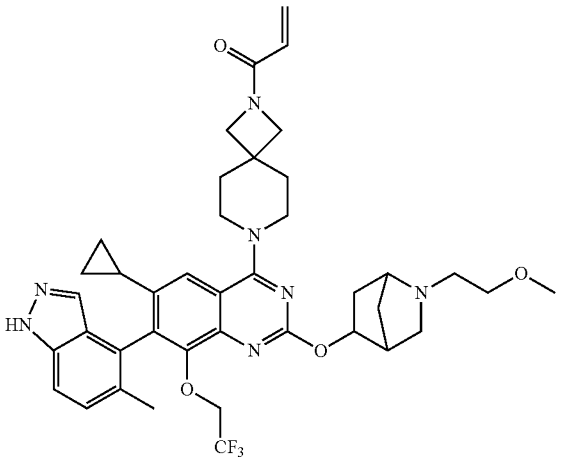
122
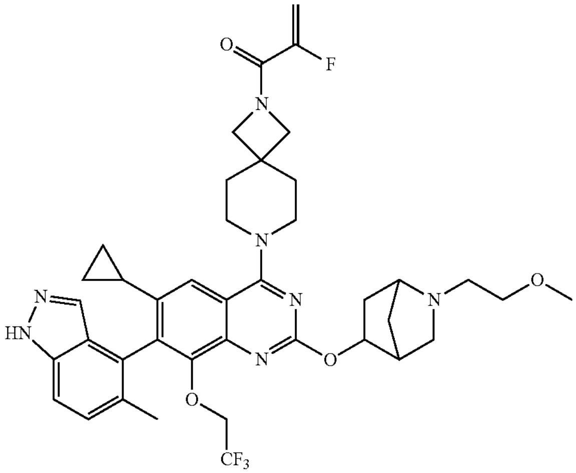
-continued
123
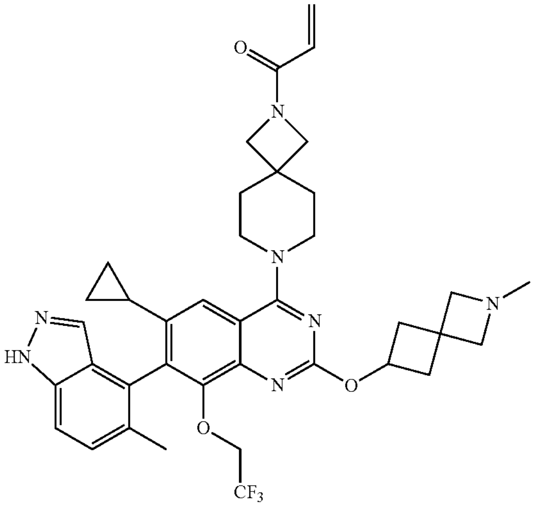
124
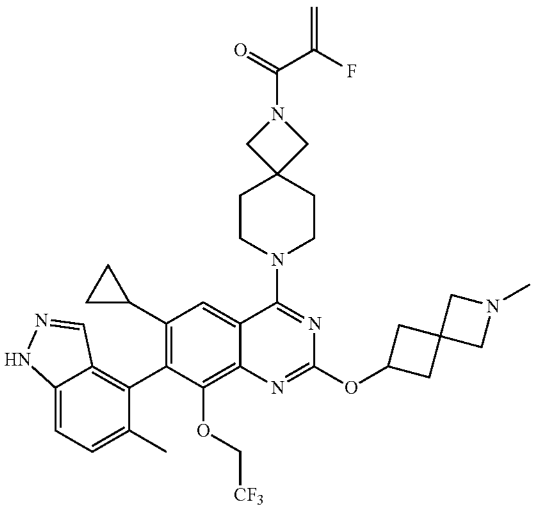
125
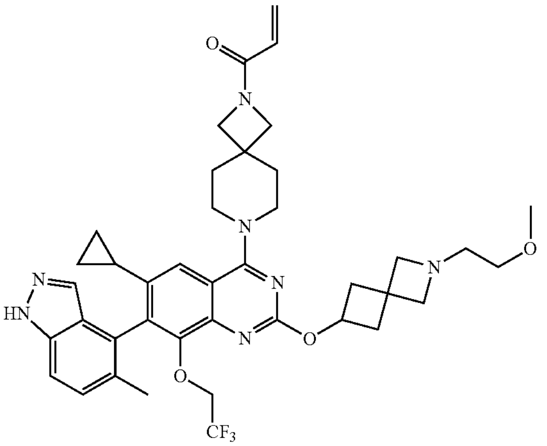

-continued
126
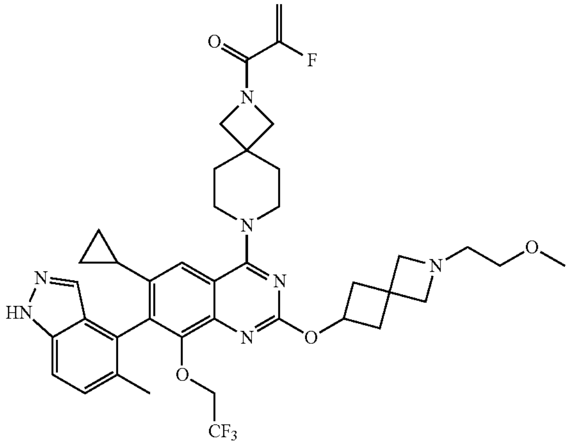
127
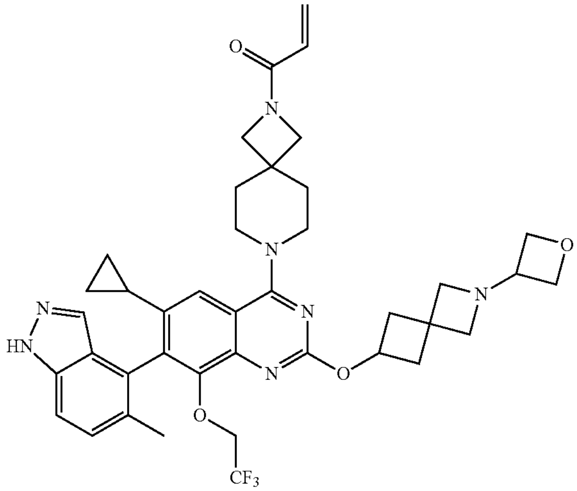
128
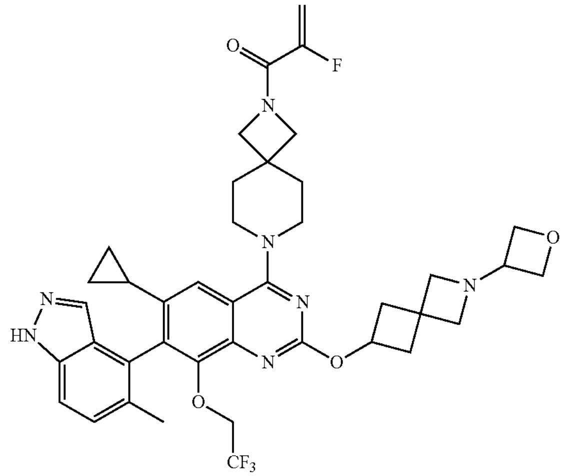
-continued
129
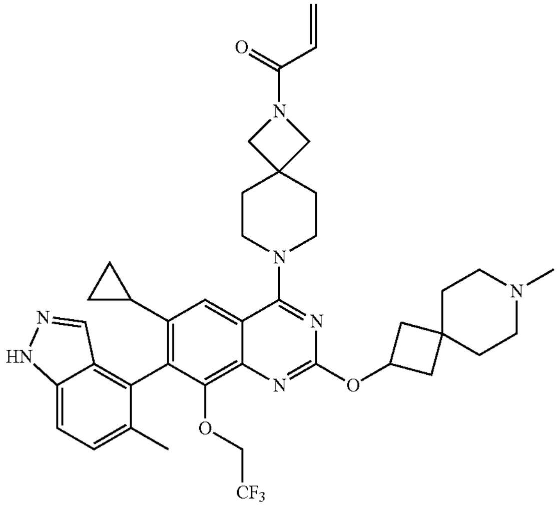
130
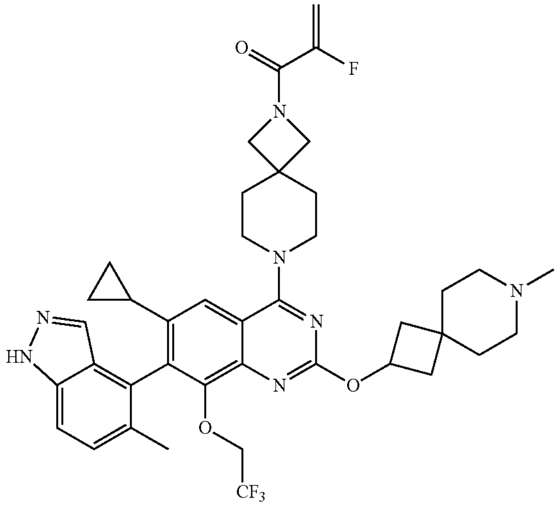
131
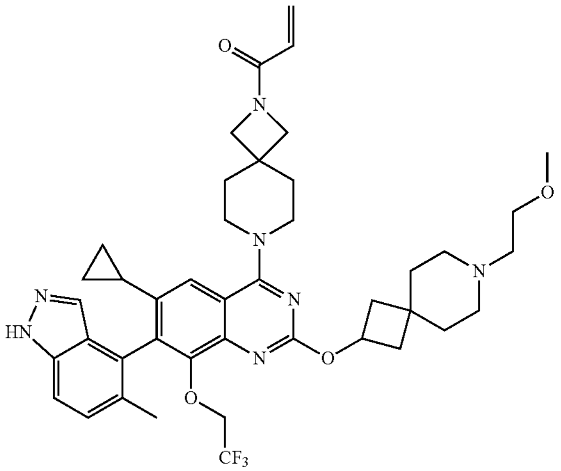

132
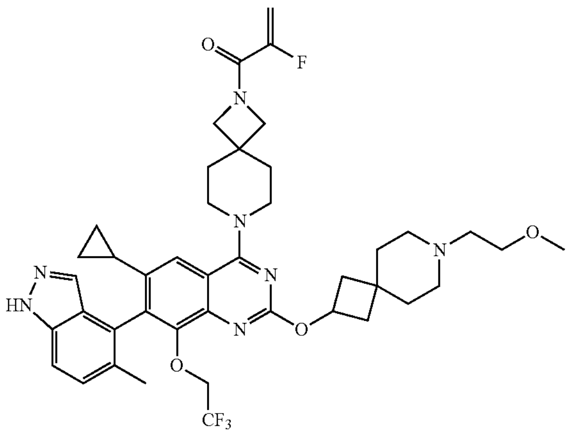
133
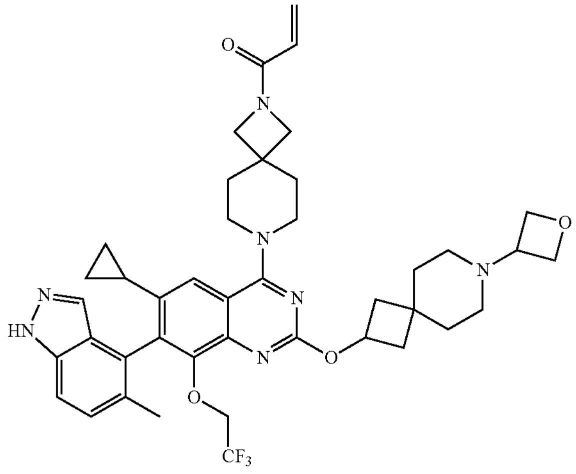
134
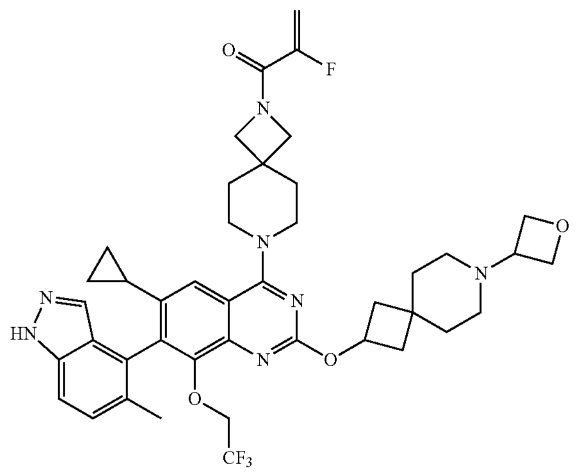
135
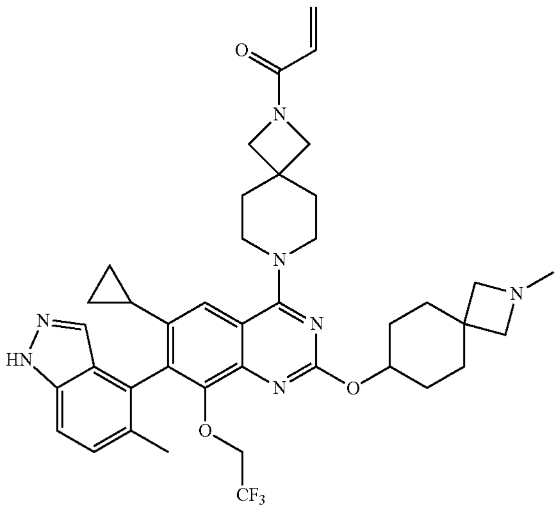
136
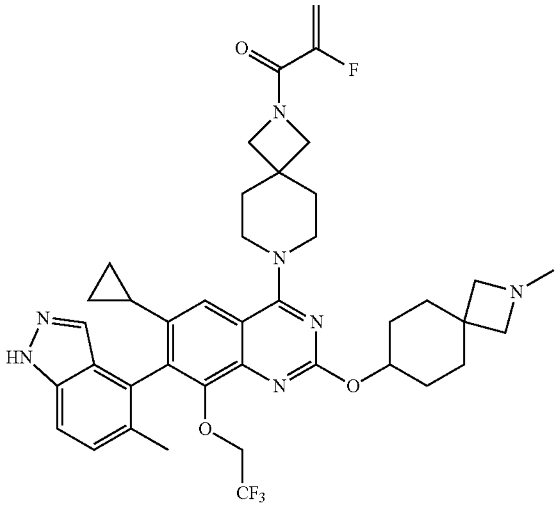
137
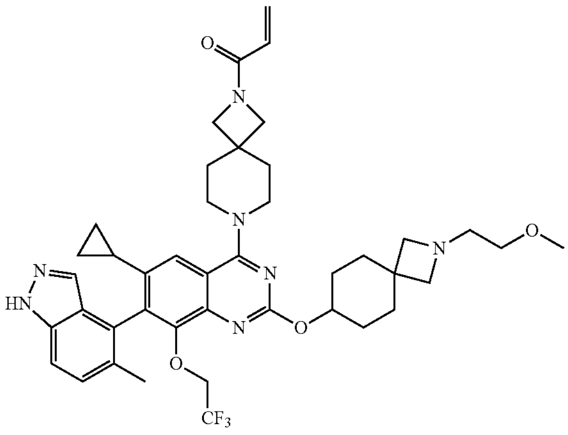

-continued
138
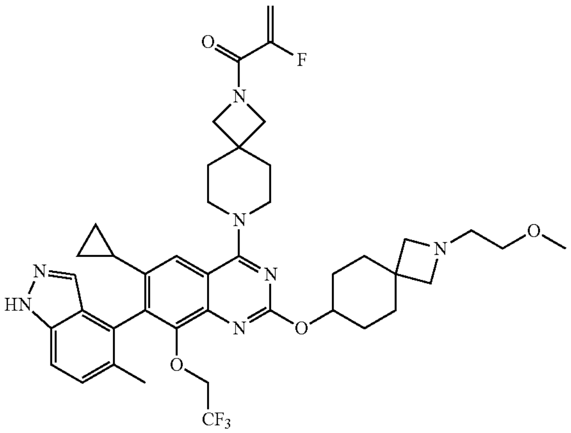
139
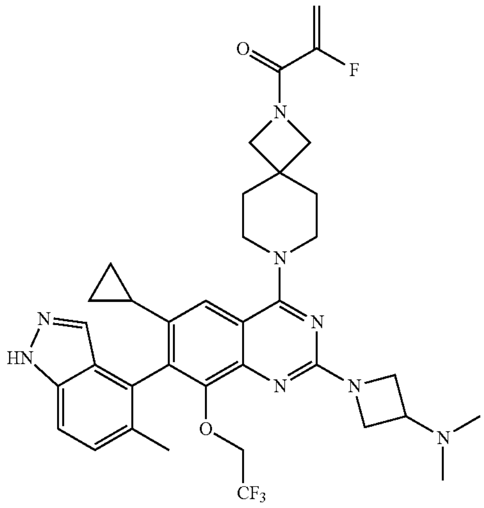
140
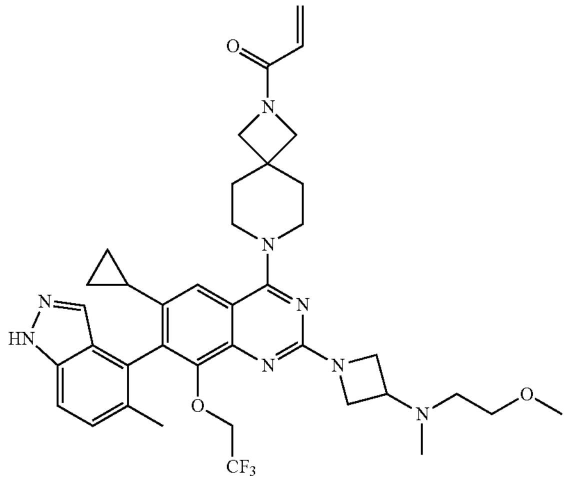
-continued
141
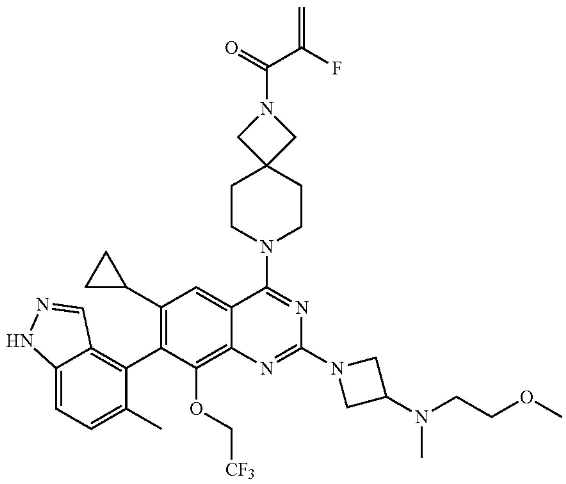
142
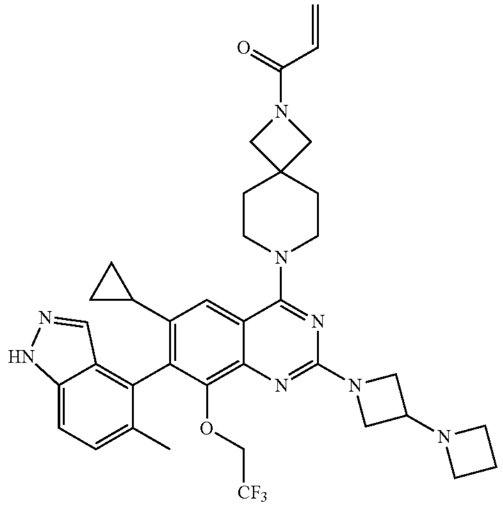
143
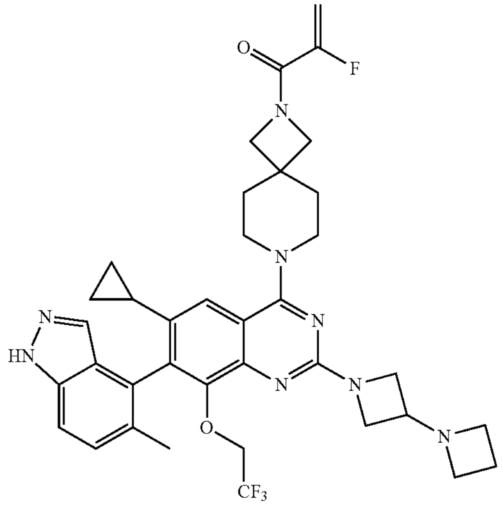

-continued
144
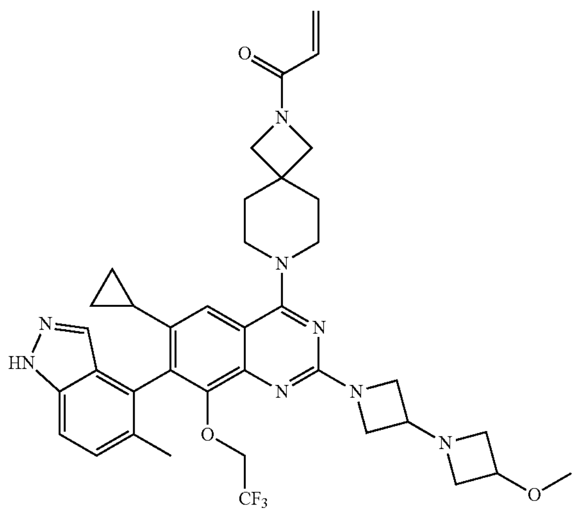
145
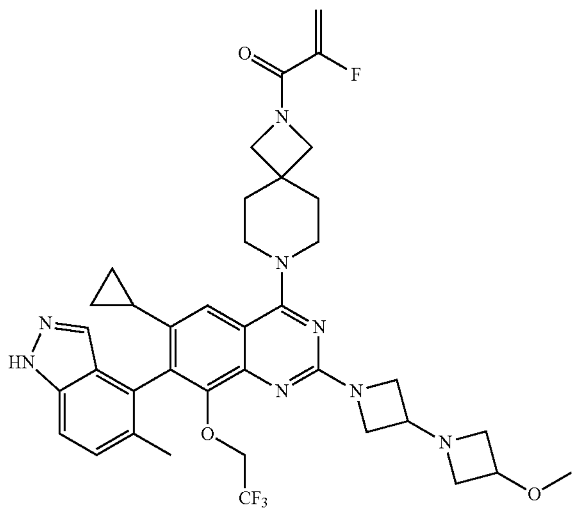
146
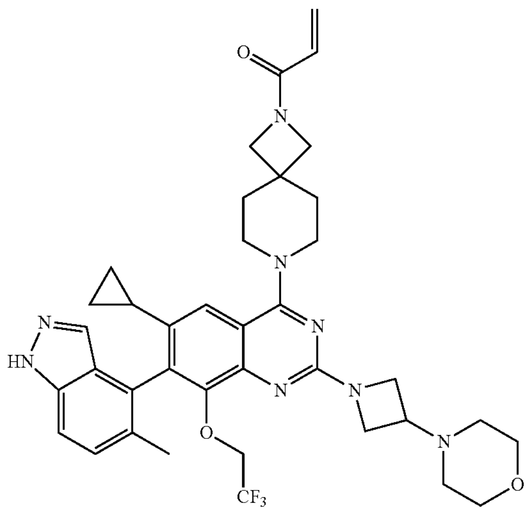
-continued
147
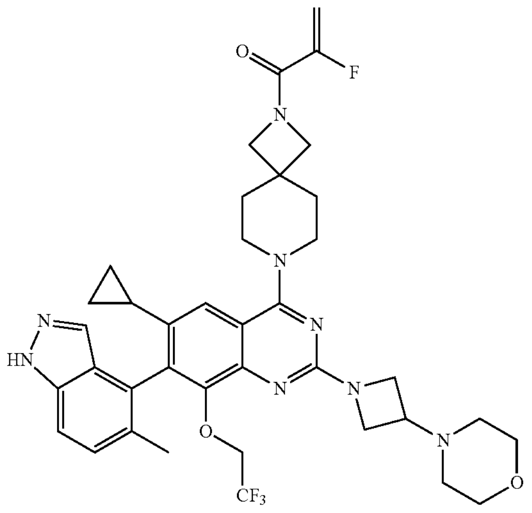
148
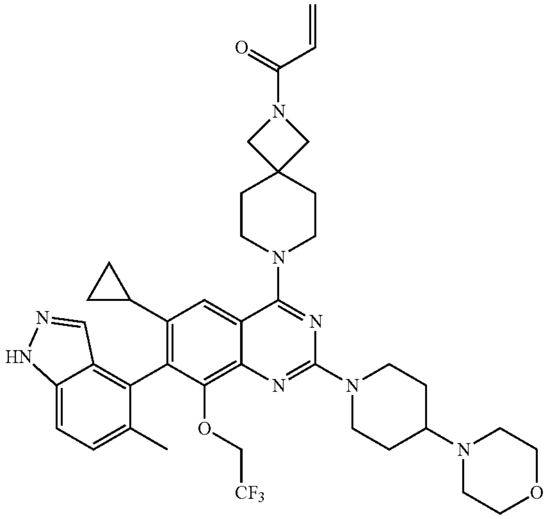
149
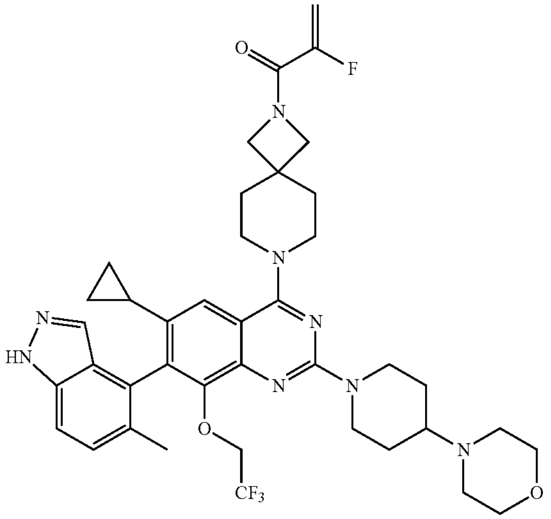

-continued
150
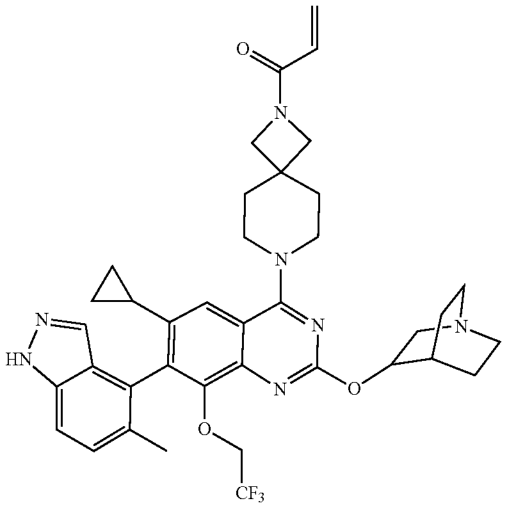
151
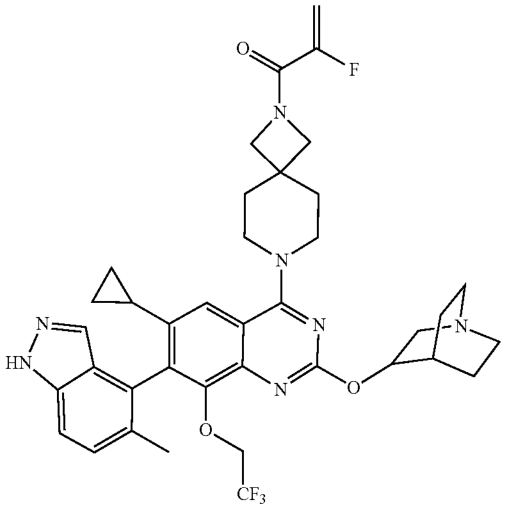
152
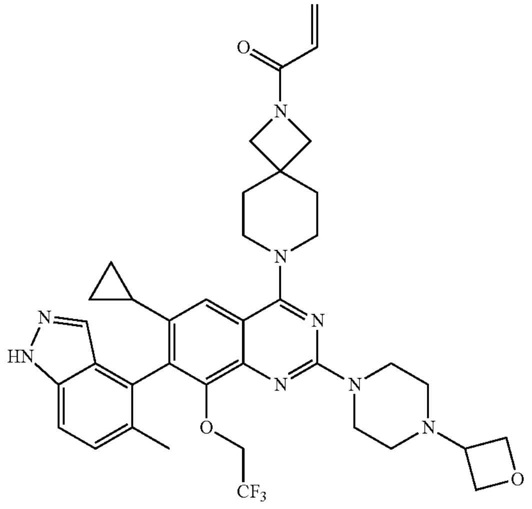
-continued
153
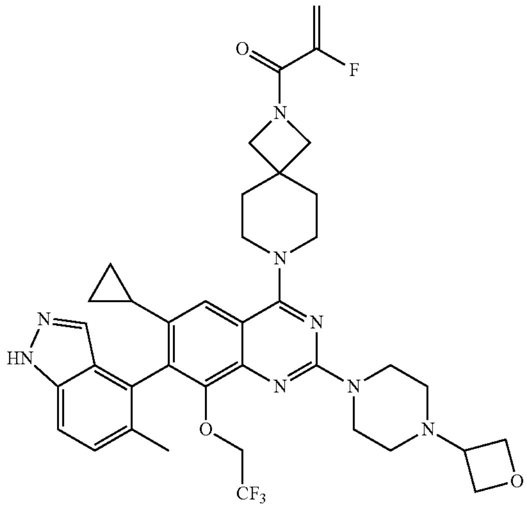
154
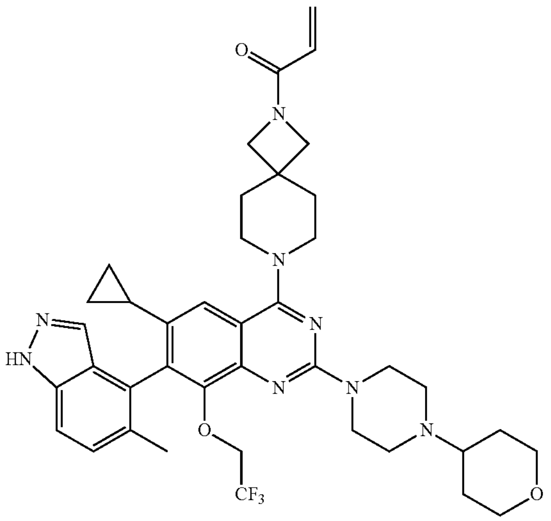
155
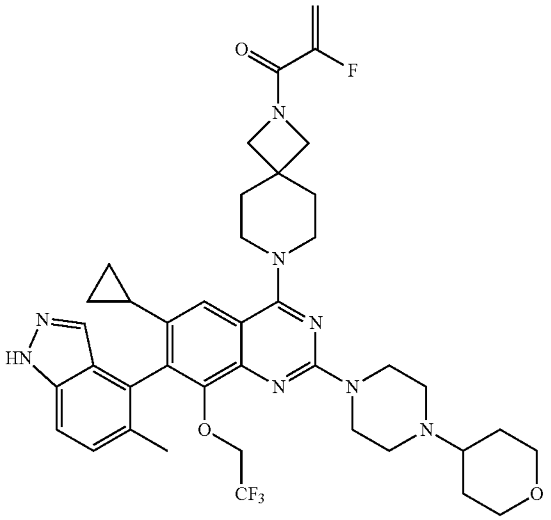

-continued
156
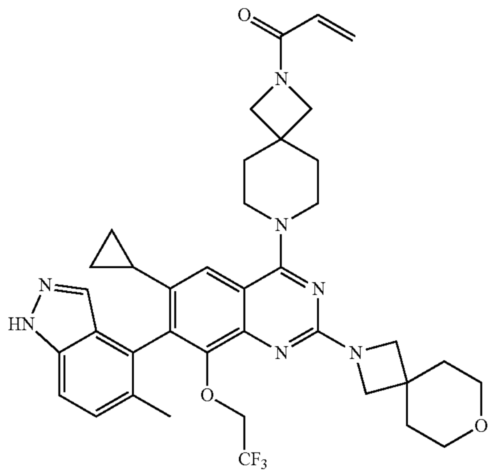
157
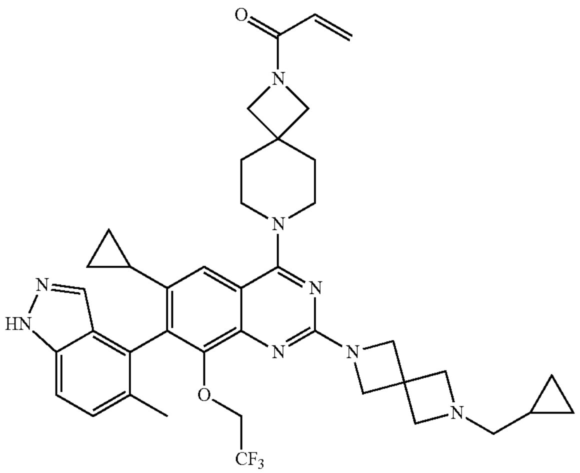
158
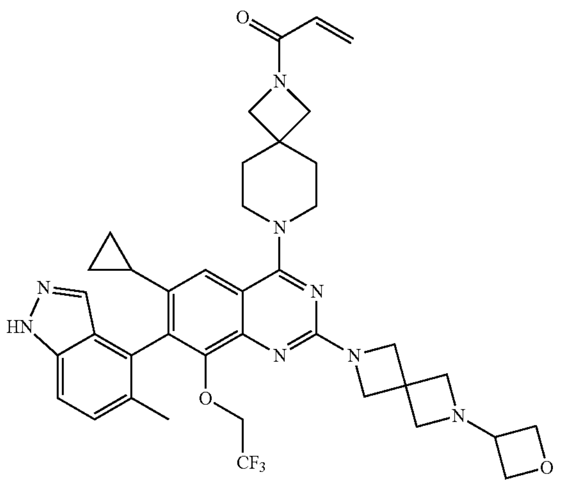
-continued
159
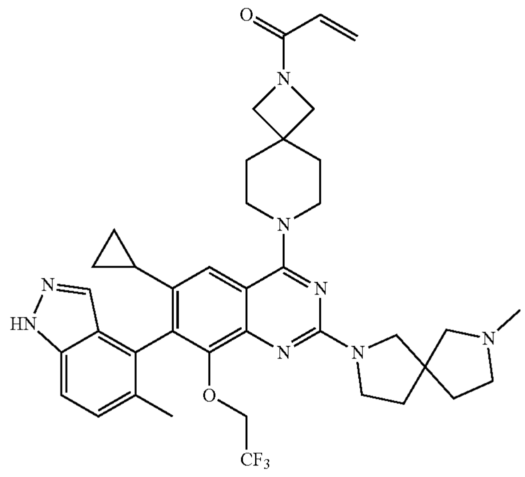
160
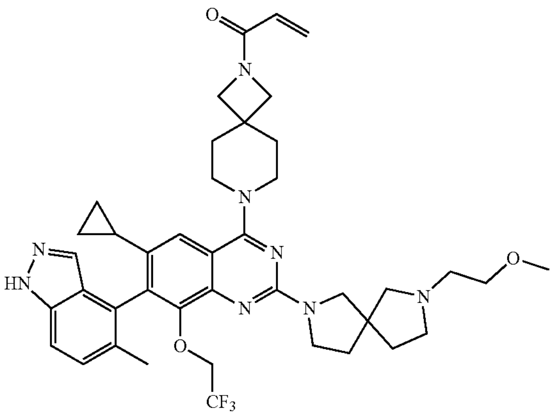
161
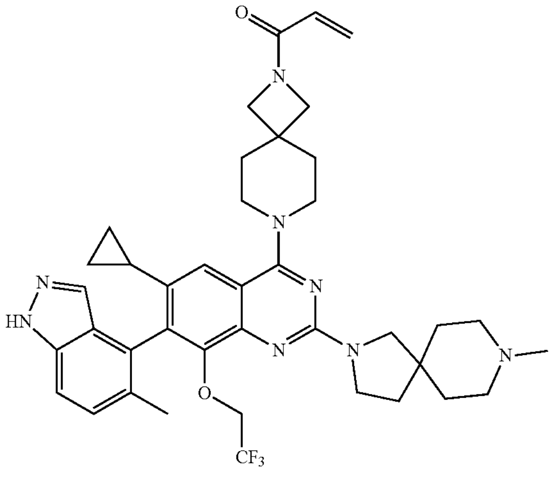

-continued
162
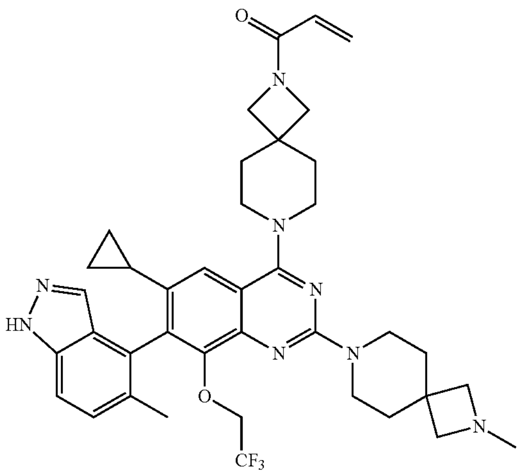
163
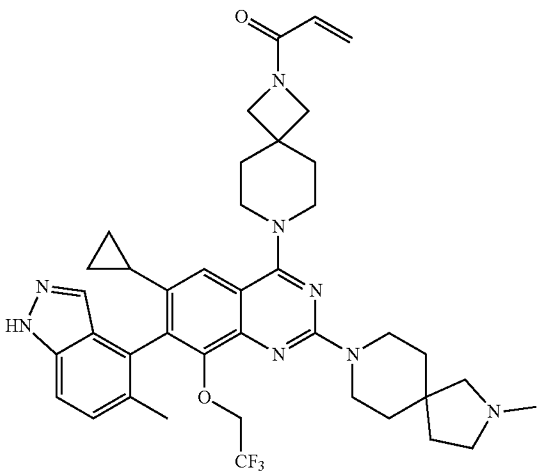
164
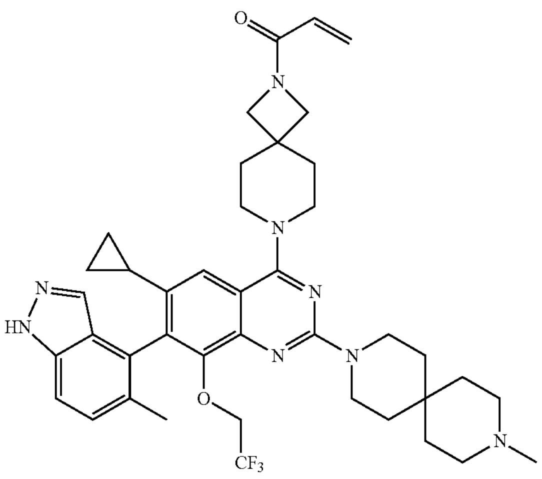
-continued
165
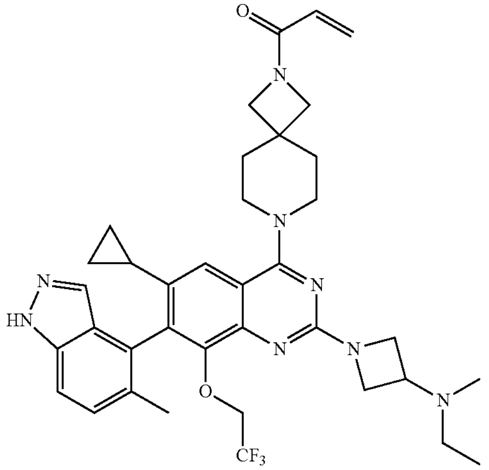
166
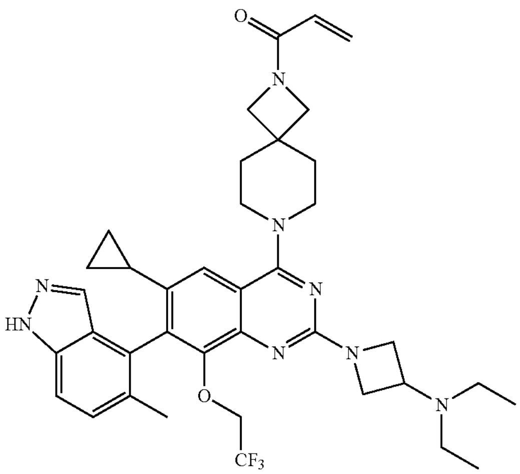
167
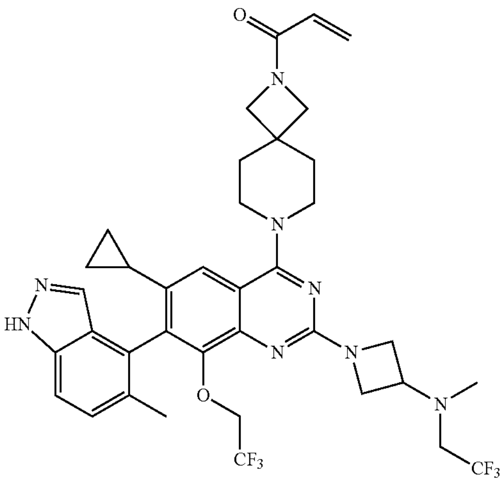

168
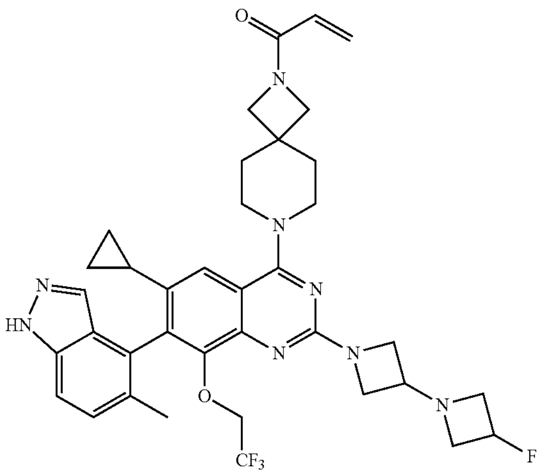
169
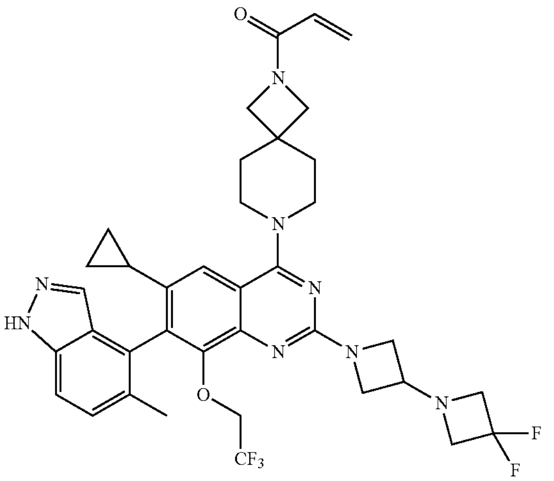
170
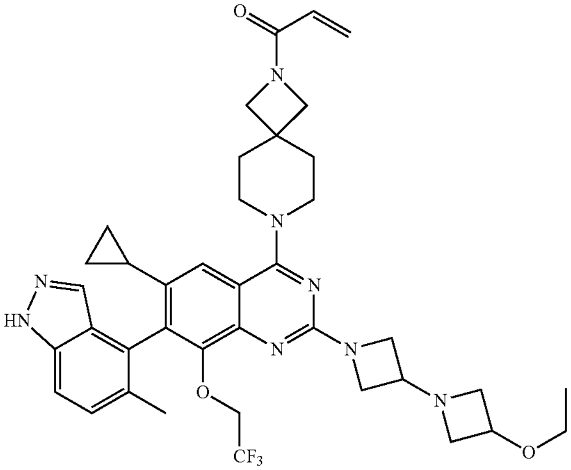
171
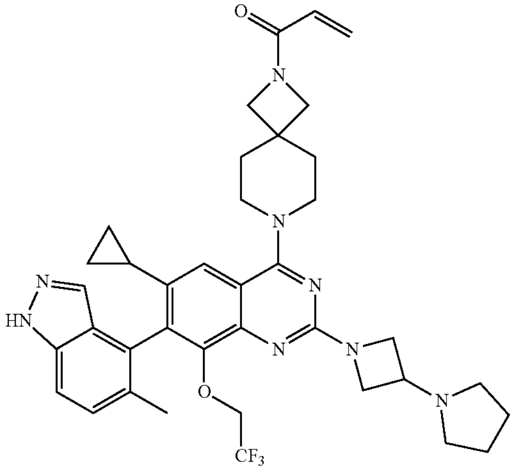
172
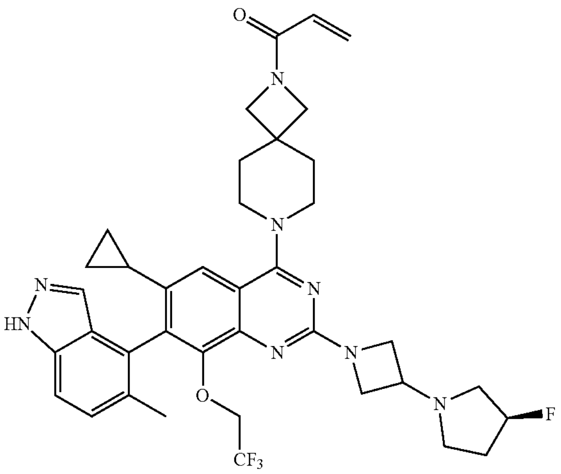
173
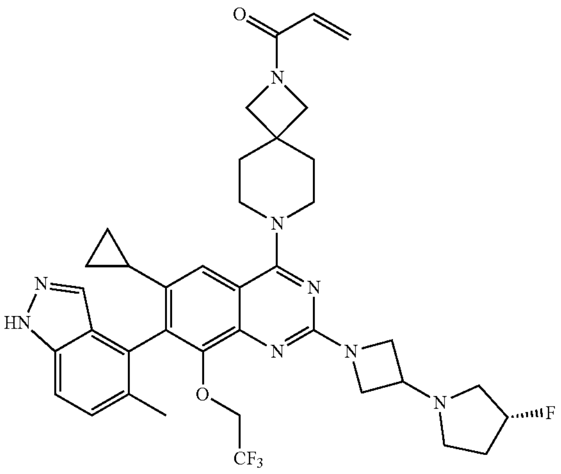

-continued
174
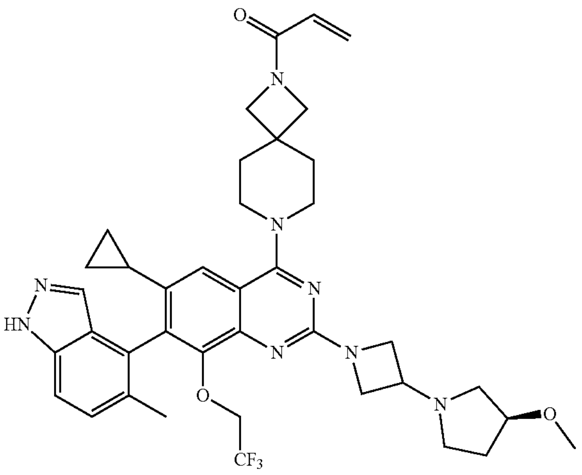
175
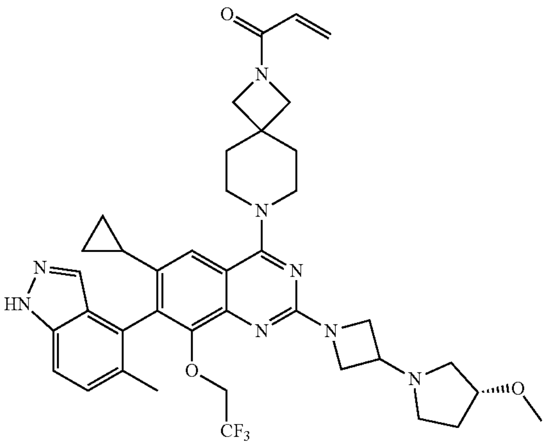
176
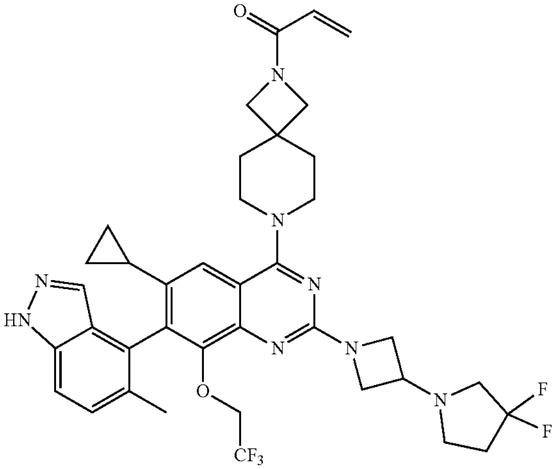
-continued
177
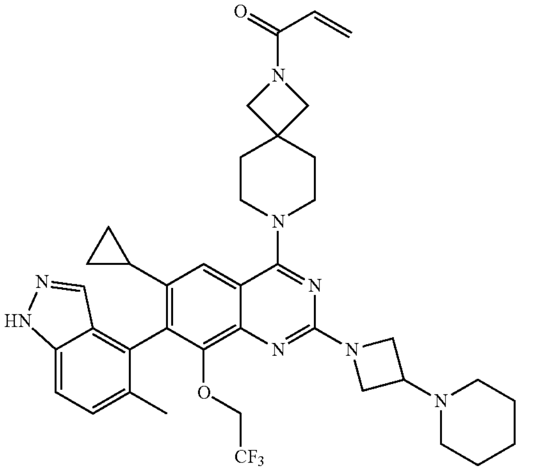
178
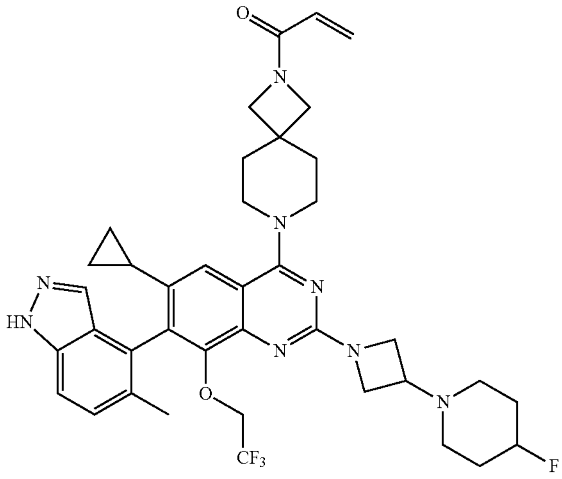
179
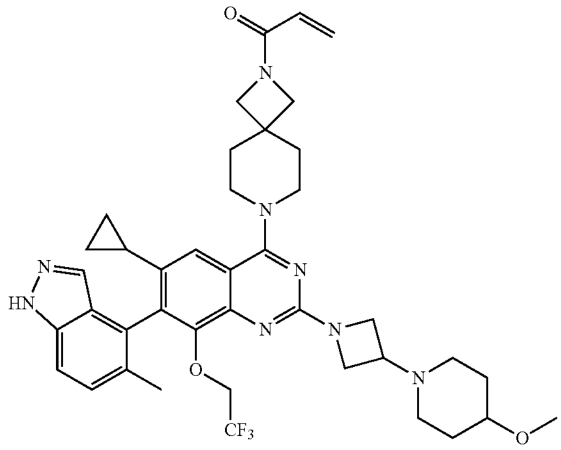

-continued
180
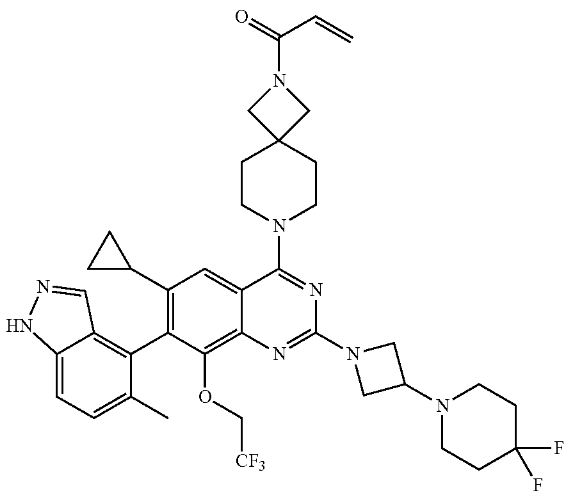
181
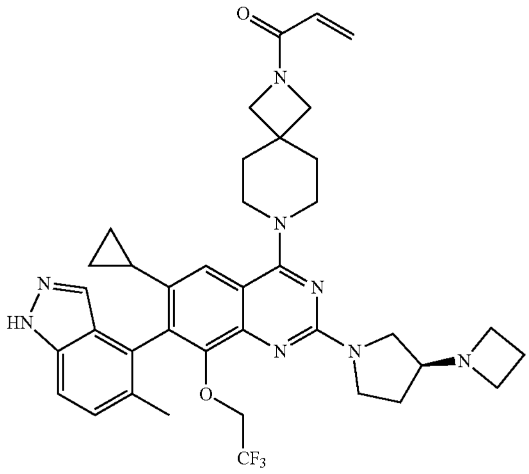
182
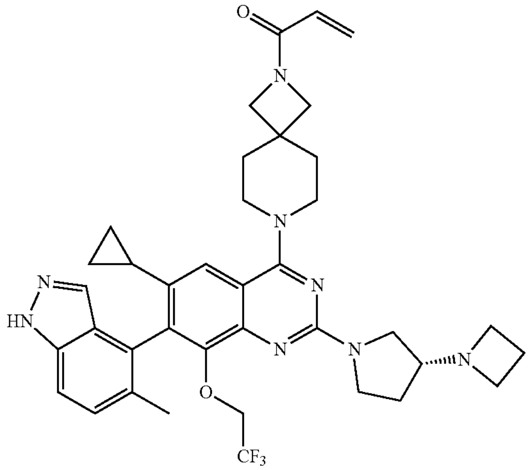
-continued
183
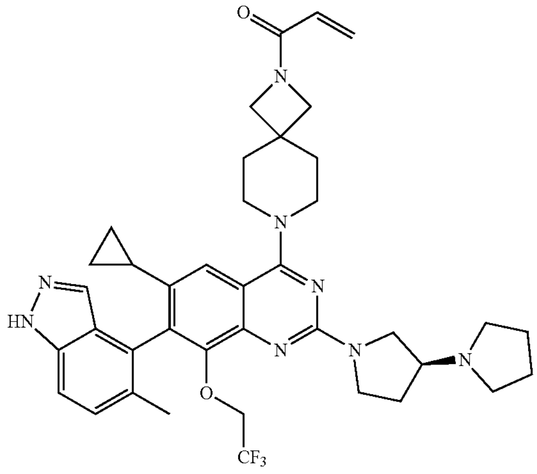
184
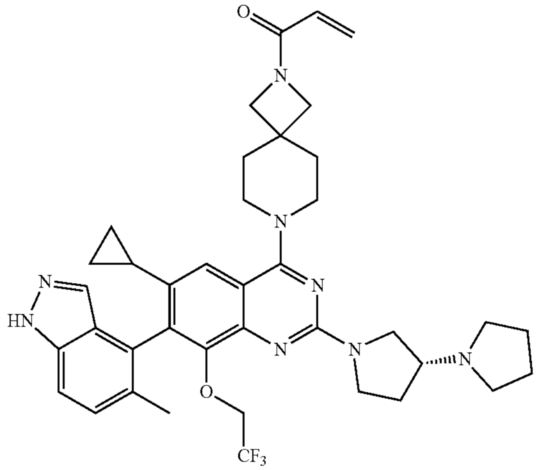
185
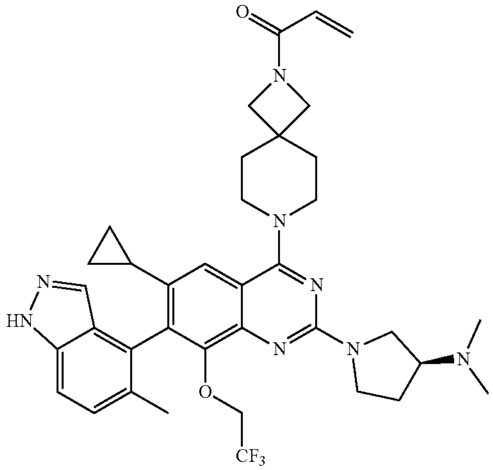

-continued
186
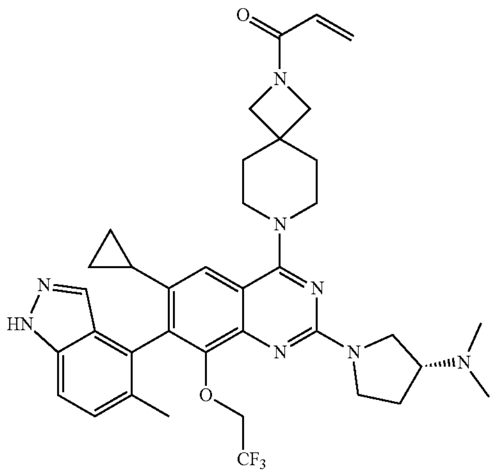
187
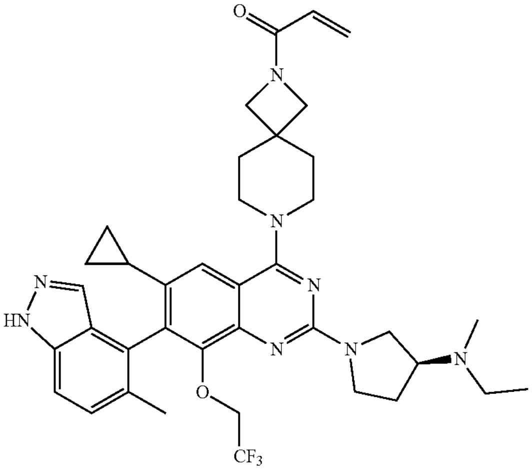
188
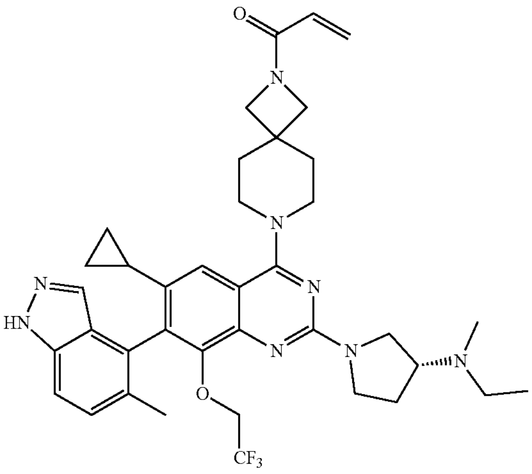
-continued
189
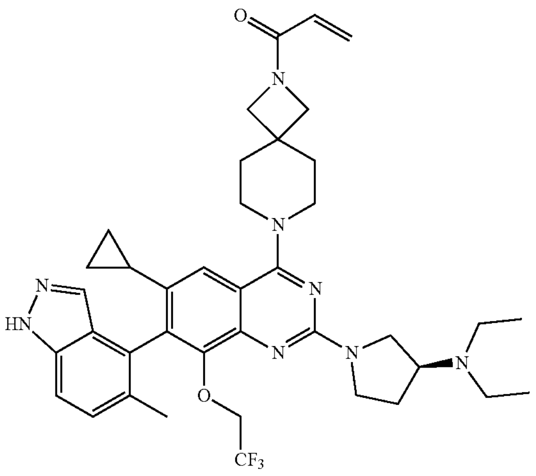
190
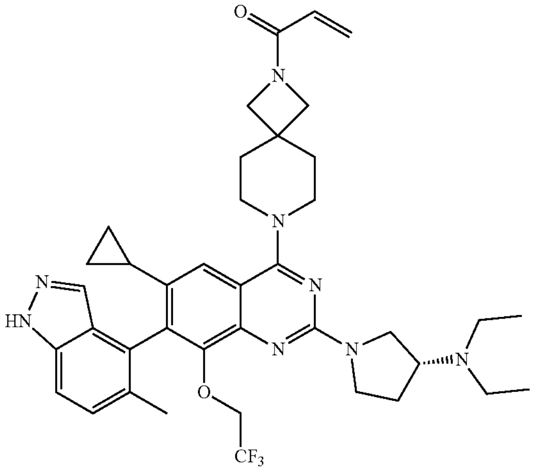
191
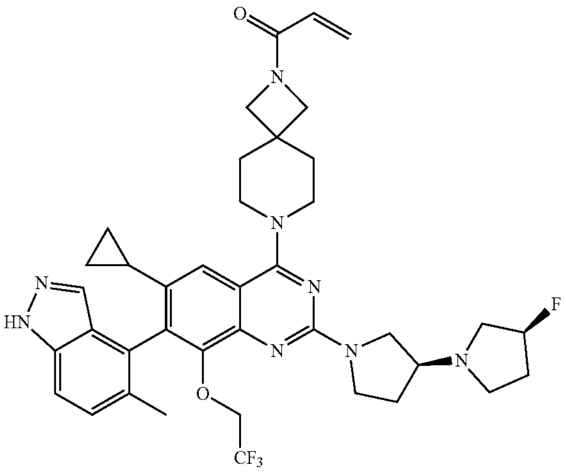

192
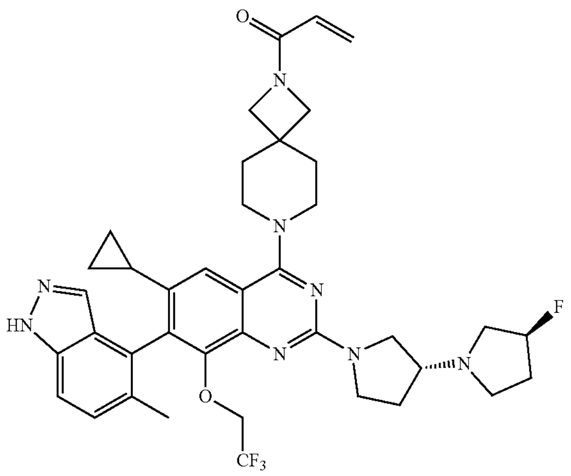
193
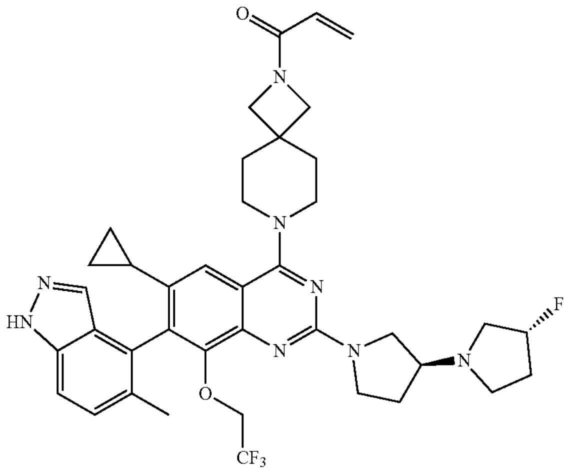
194
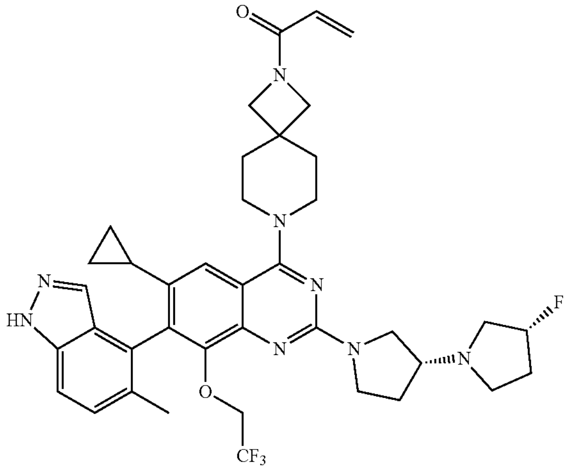
195
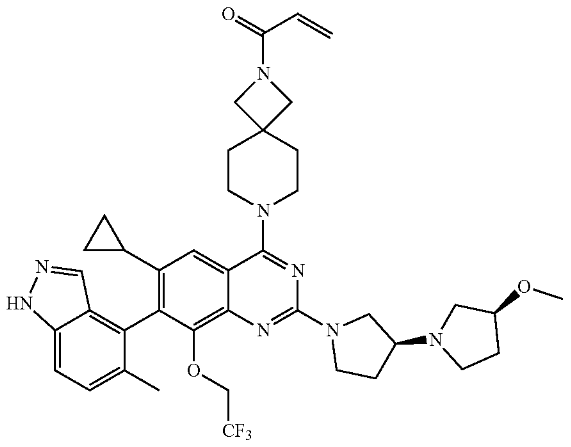
196
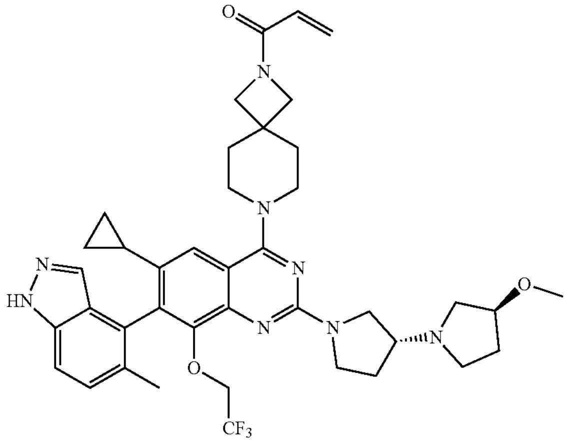
197
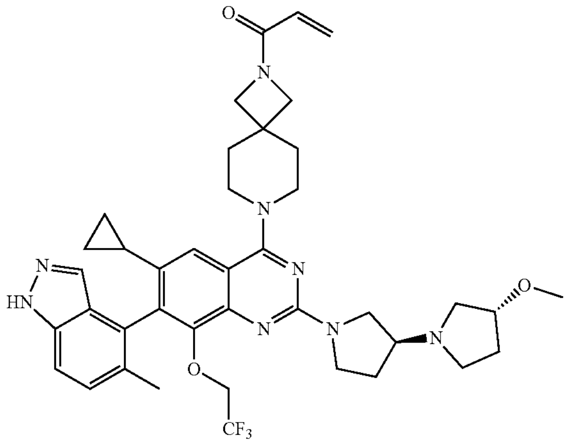

-continued
198
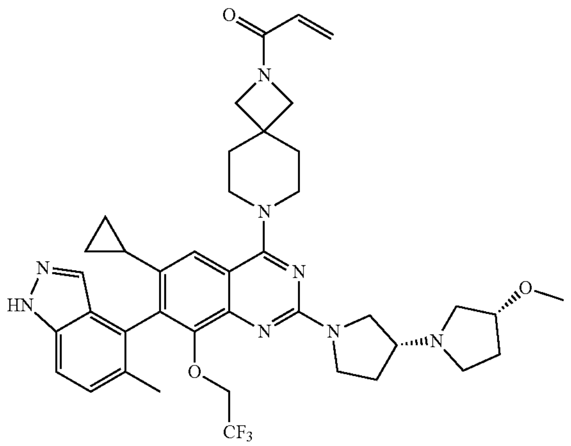
199
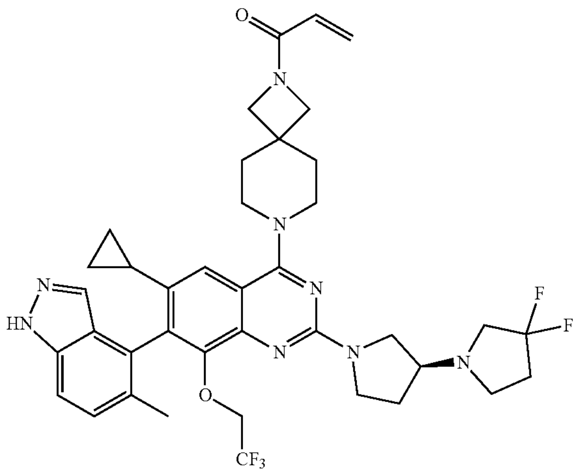
200
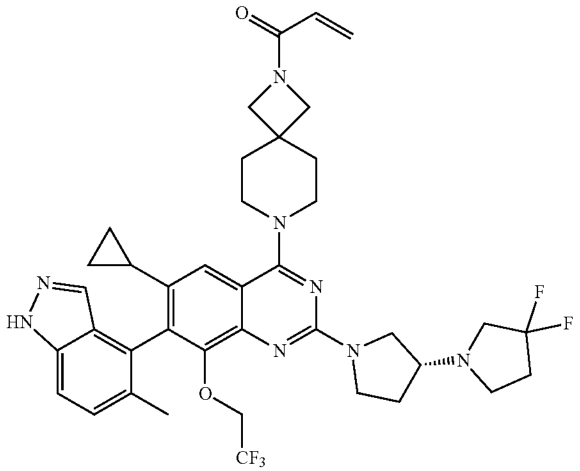
-continued
201
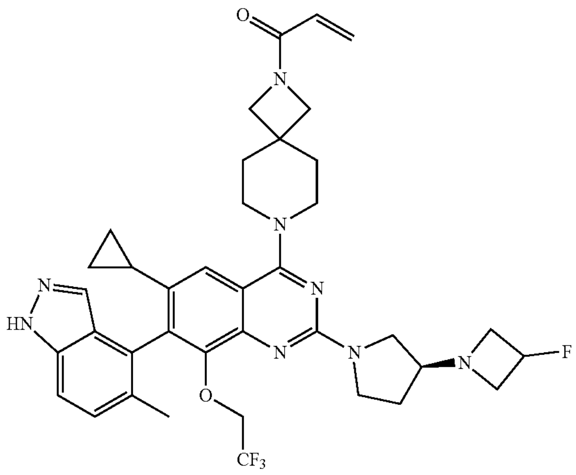
202
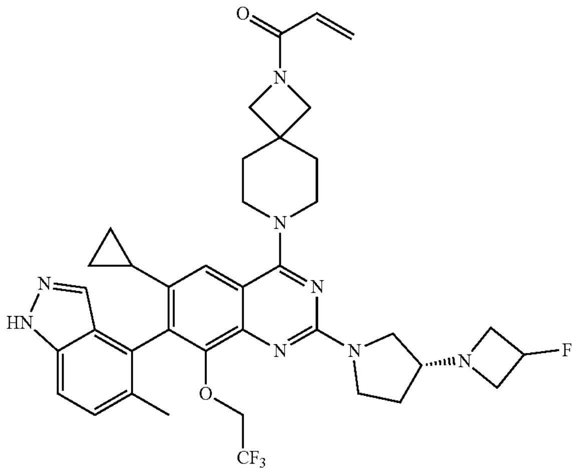
203
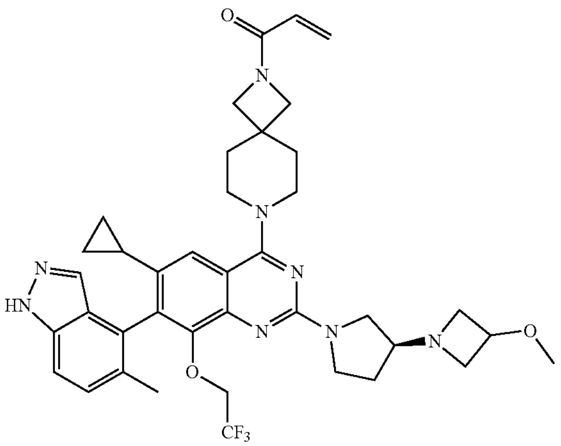

-continued
204
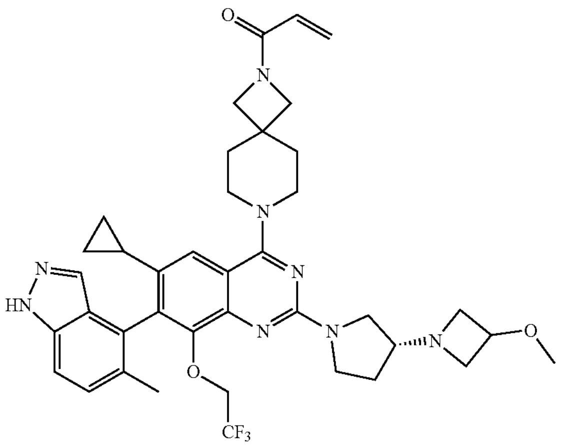
205
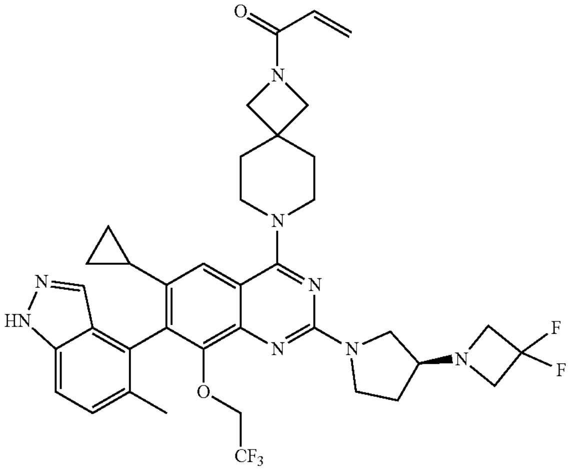
206
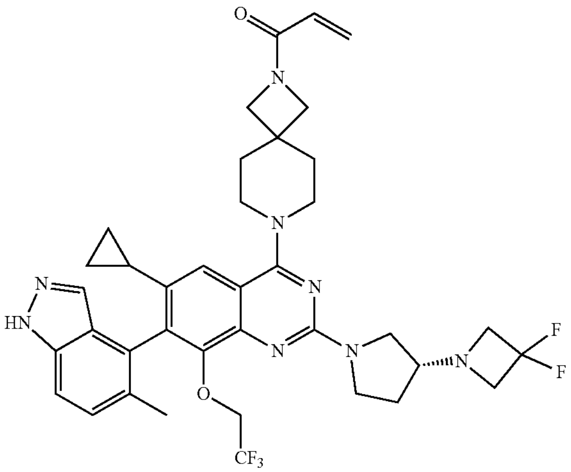
-continued
207
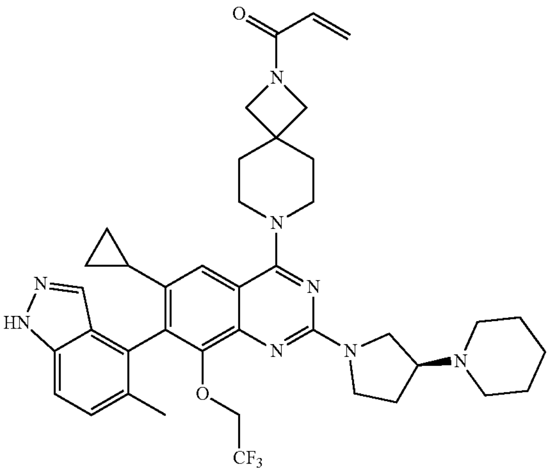
208
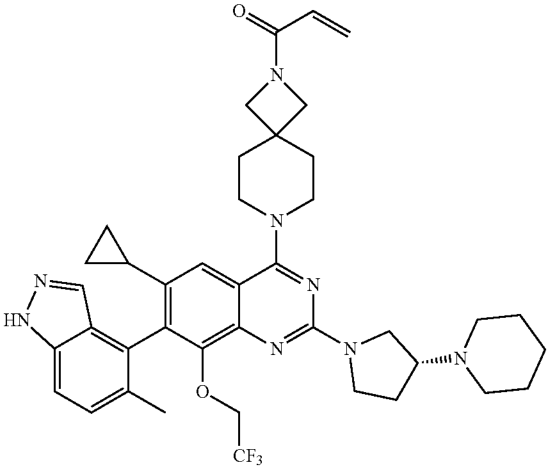
209
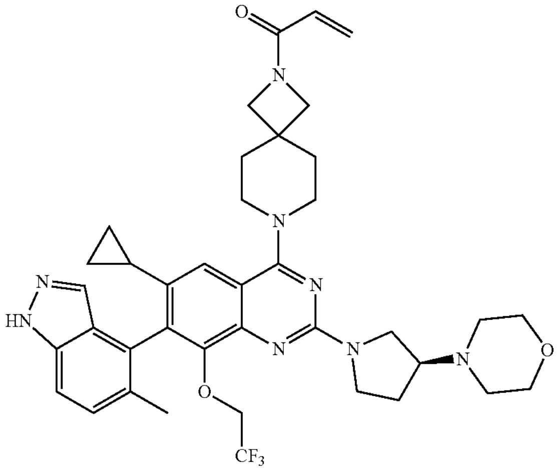

-continued
210
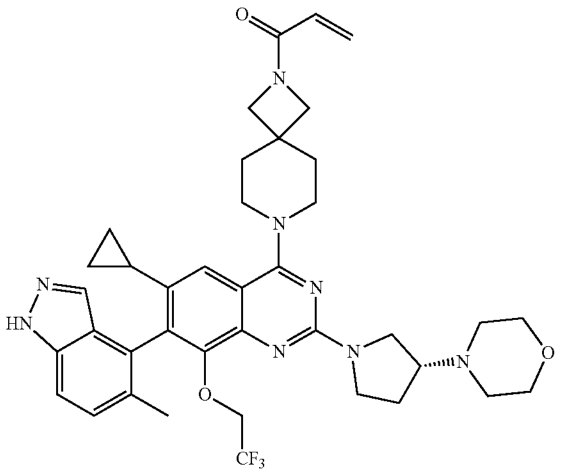
211
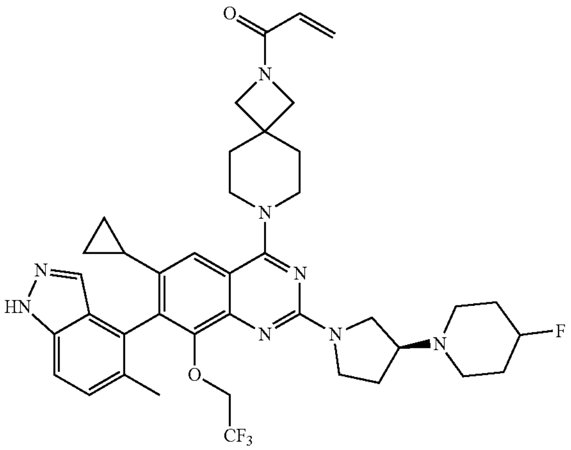
212
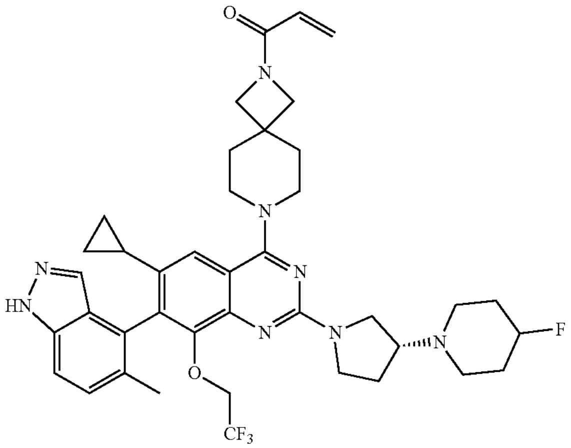
-continued
213
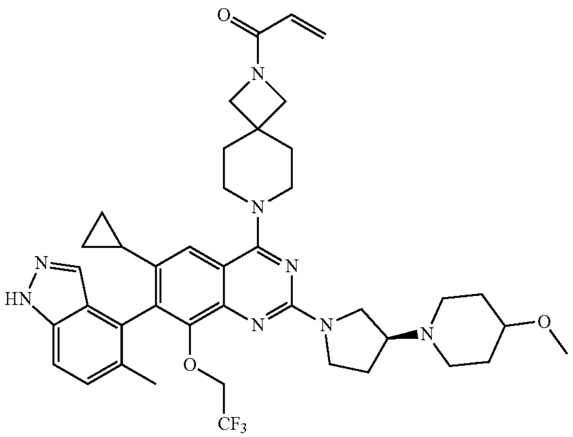
214
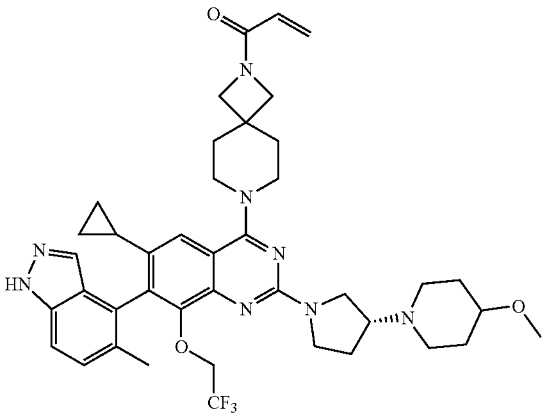
215
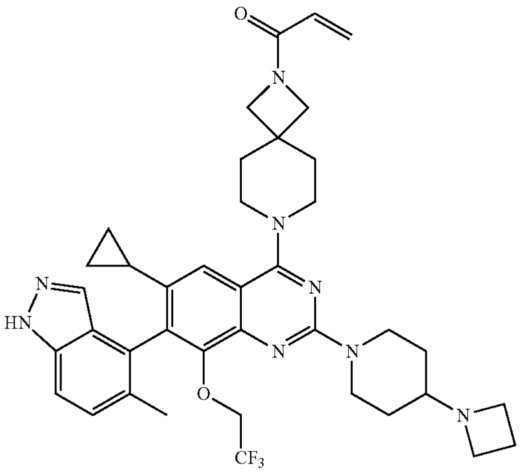

-continued
-continued
216
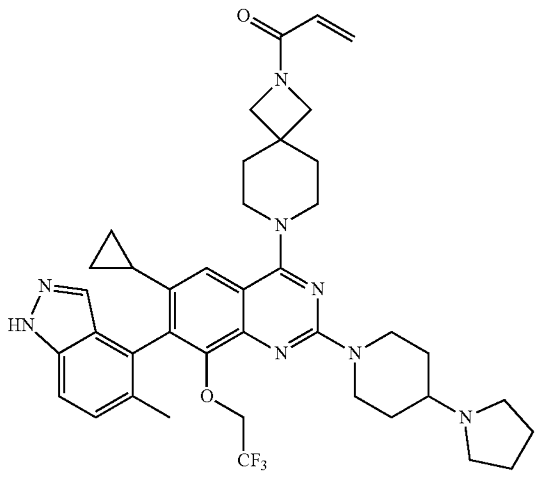
219
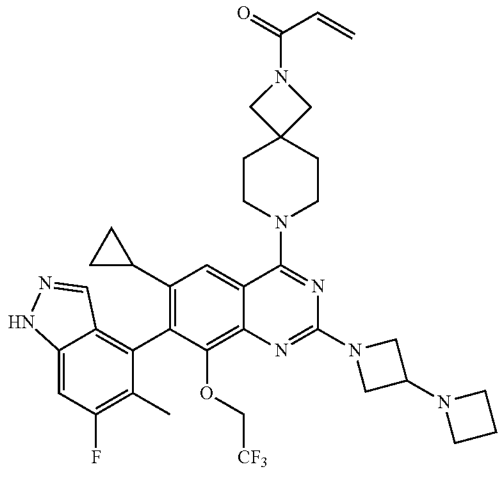
217
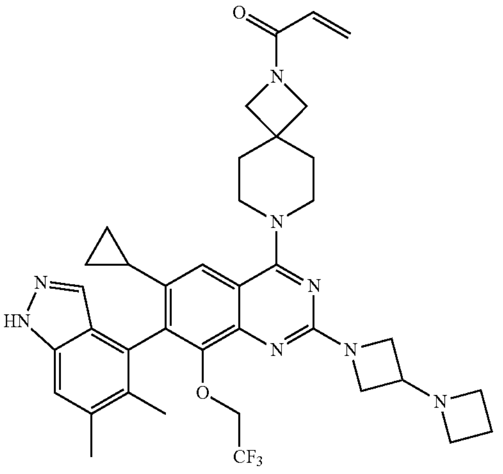
220
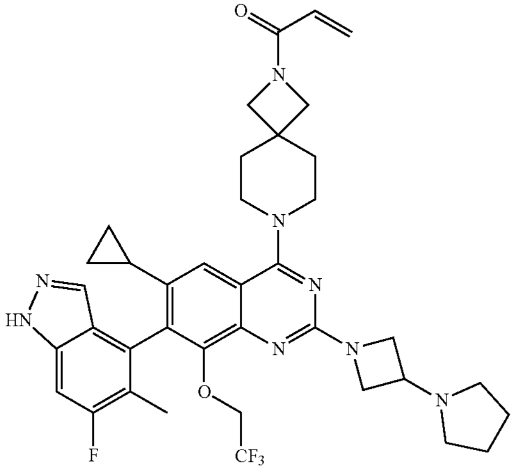
218
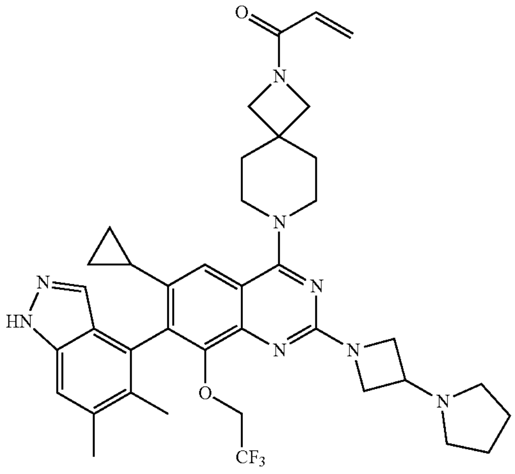
221
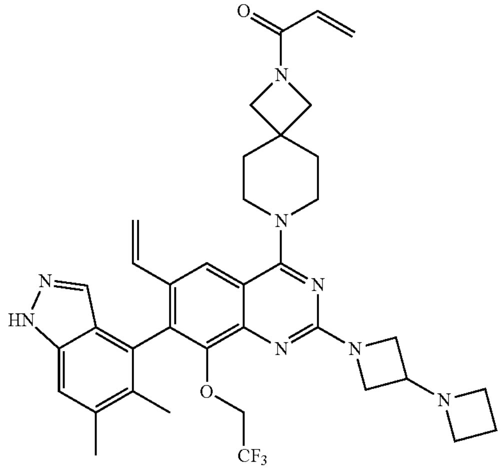

-continued
222
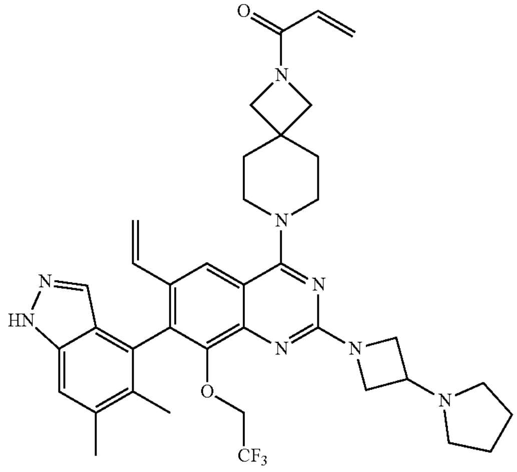
223
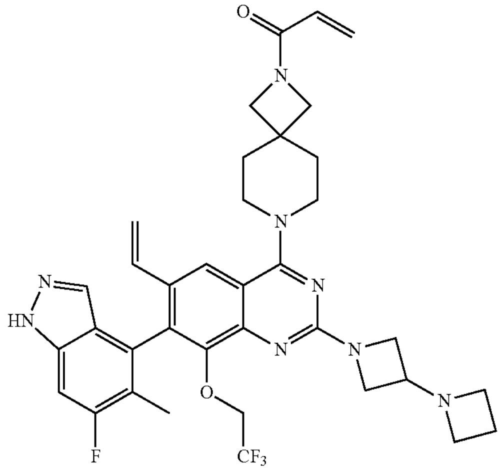
224
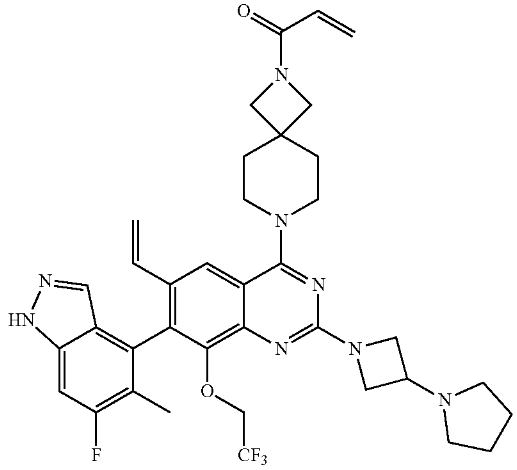
10. A compound with a structure as shown in general formula (2), optical isomers thereof, pharmaceutically acceptable salts thereof, hydrates thereof or solvates thereof:
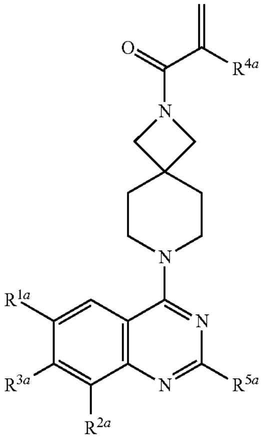
(2)
wherein in general formula (2):
$R^{1a}$ is
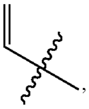,
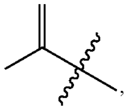,
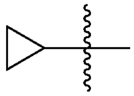 or 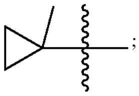;
$R^{2a}$ is $CH_3O$—, $CH_3CH_2O$—, $CF_3CH_2O$- or $CHF_2CH_2O$—;
$R^{3a}$ is
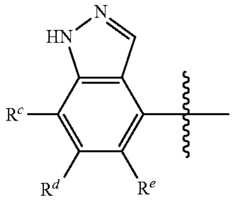,
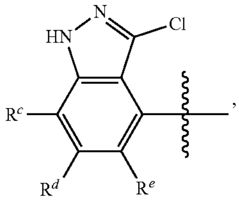,
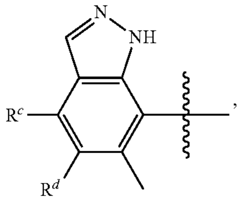,
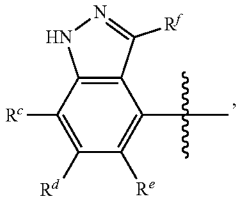,
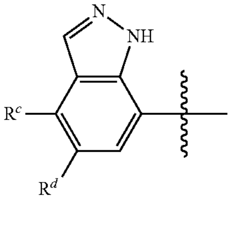,
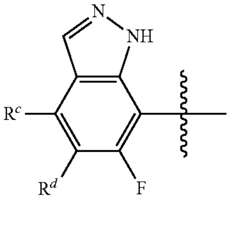, -continued

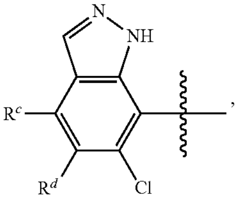
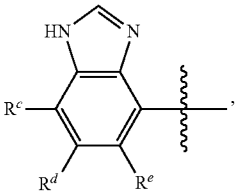
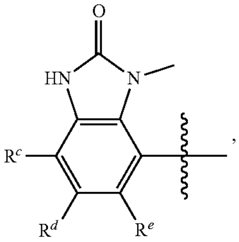
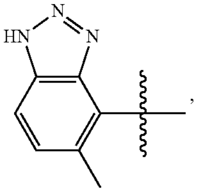
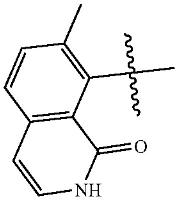
or
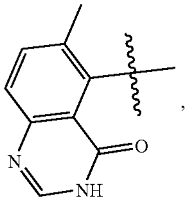

wherein $R^c$ is H or F, $R^d$ is H, F, Cl or Me, $R^e$ is H, F, Cl or Me, and $R^f$ is F, $NH_2$, Me or cyclopropyl;

$R^{4a}$ is H or F; and $R^{5a}$ is: H,

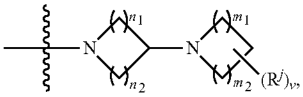
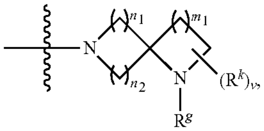
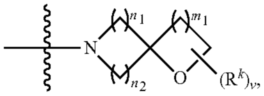
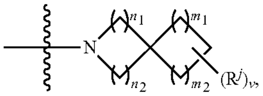
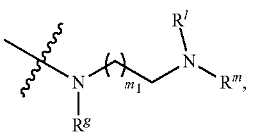
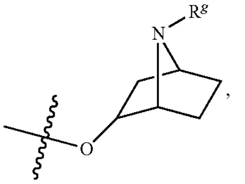
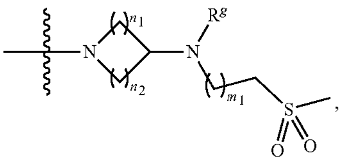

-continued

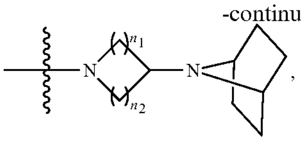
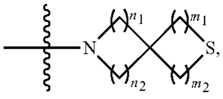
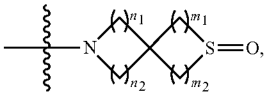
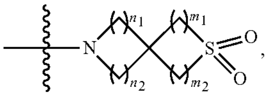
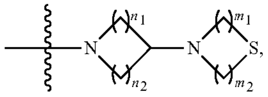
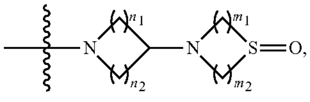
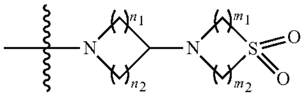
or
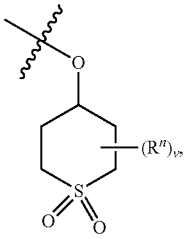

wherein $n_1$, $n_2$, $n_3$, $m_1$, $m_2$ and $m_3$ are independently integers of 1 or 2; v is an integer of 1, 2 or 3; $R^g$ is C1-C3 alkyl, C3-C6 cycloalkyl, (C1-C3)alkoxy-(C2-C3)alkyl-, (halogenated C1-C3)alkoxy-(C2-C3)alkyl-, (C3-C6) cycloalkyl-(C1-C3)alkyl-, heterocycloalkyl, heterocycloalkyl-(C1-C3) alkyl-, C1-C3 haloalkyl or cyano-substituted C1-C3 alkyl; $R^j$ is independently halogen, CN, $SO_2Me$, C1-C3 alkyl, C1-C3 haloalkyl, C1-C3 alkoxy, C1-C3 haloalkoxy, hydroxy-substituted C1-C3 alkyl, cyano-substituted C1-C3 alkyl, C3-C6cycloalkyl or

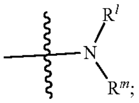

$R^k$ is independently halogen, CN, OH, C1-C3 alkyl, C1-C3 alkoxy, C3-C6 cycloalkyl or

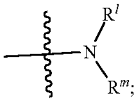

$R^n$ is independently halogen, CN, OH, C1-C3 alkyl, C1-C3 alkoxy or C3-C6 cycloalkyl, two $R^n$ groups, together with one carbon atom, form a spiro ring, or two $R^n$ groups, together with different carbon atoms, form a bridged ring; $R^1$ and $R^m$ are independently C1-C3 alkyl, C1-C3 haloalkyl, hydroxy-substituted C1-C3 alkyl, cyano-substituted C1-C3 alkyl, C3-C6 cycloalkyl, (C1-C3)alkoxy-(C2-C3)alkyl-, (halogenated C1-C3)alkoxy-(C2-C3)alkyl-, (C3-C6) cycloalkyl-(C1-C3)alkyl-, or $R^1$ and $R^m$, together with a N atom, form a 3-8 membered heterocycloalkyl group, wherein the 3-8 membered heterocycloalkyl group may be substituted with 1-3 groups selected from OH, halogen, cyano, C1-C3 alkyl, C3-C6 cycloalkyl, heterocycloalkyl, (C1-C3)alkoxy or (halogenated C1-C3)alkoxy.

11. The compound according to claim 10, wherein in the general formula (2), $R^{3a}$ is

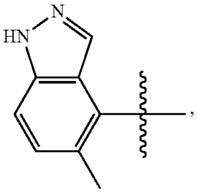,
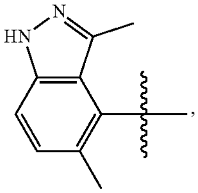,
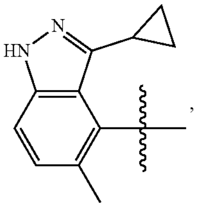,
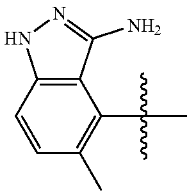,
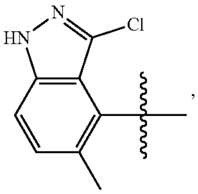,
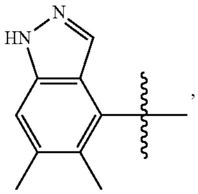,
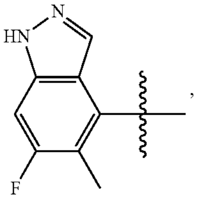,
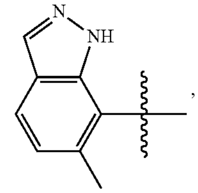,
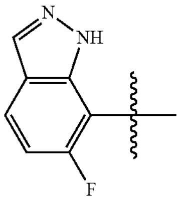,
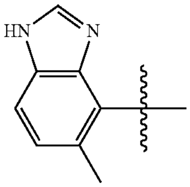,
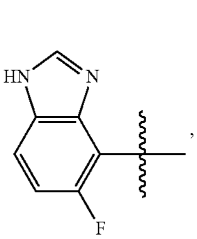,
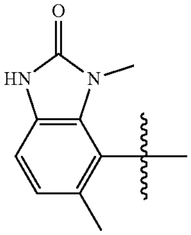,
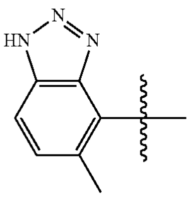,
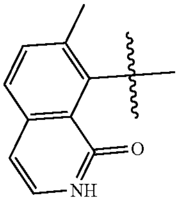
or -continued

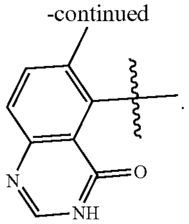.

12. The compound according to claim 10, wherein in the general formula (2), $R^{5a}$ is: H,

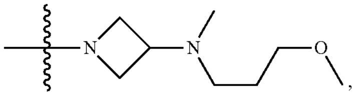,
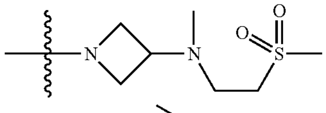,
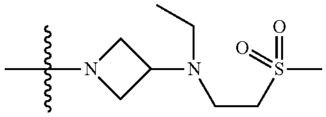,
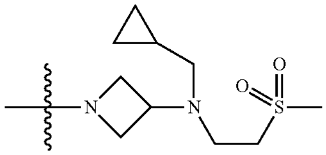,
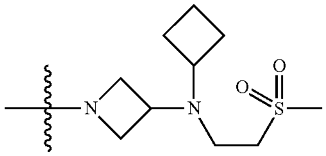,
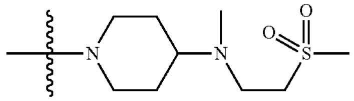,
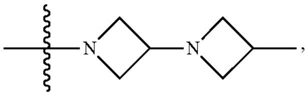,
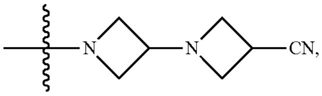
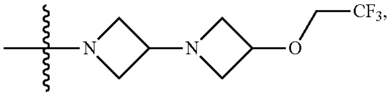
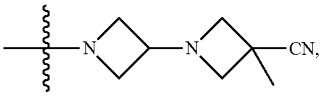
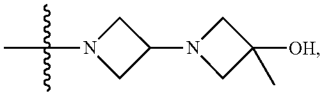
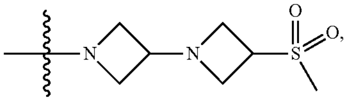
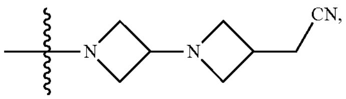

553
-continued
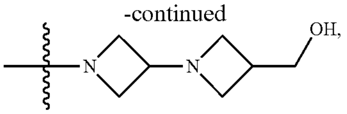
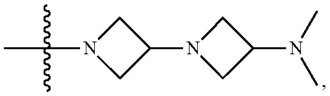
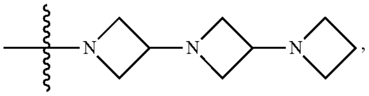
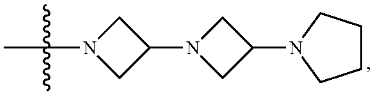
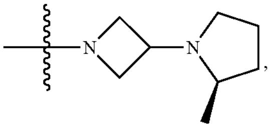
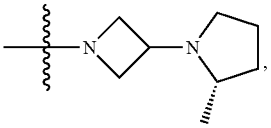
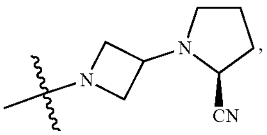
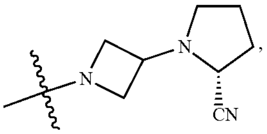
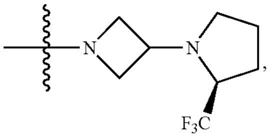
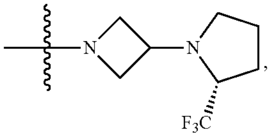
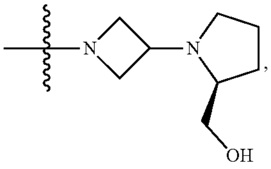
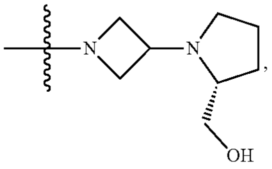
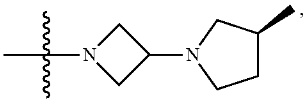
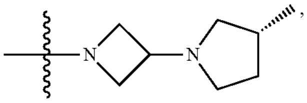
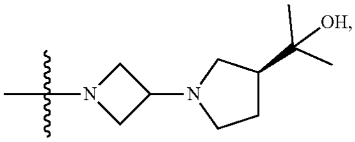
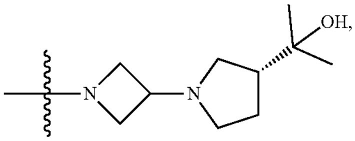
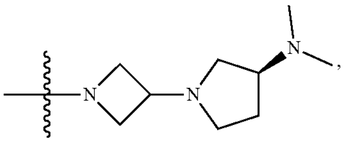
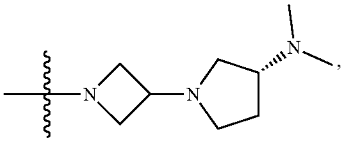
554
-continued
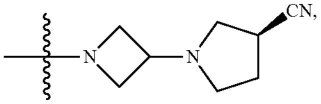
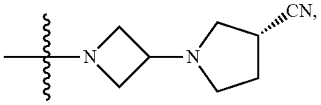
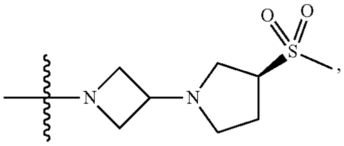
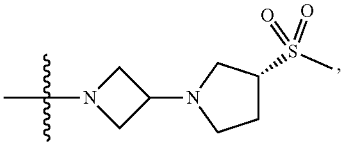
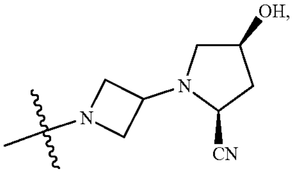
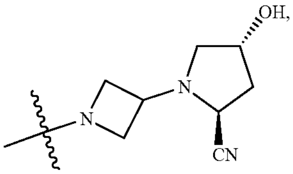
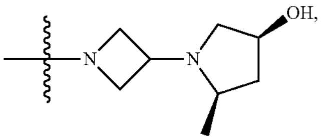
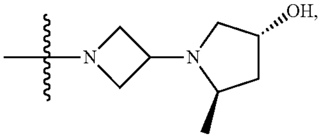
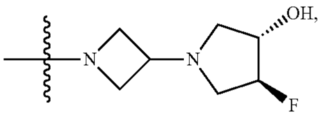
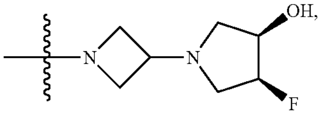
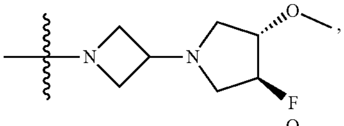
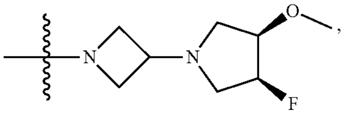
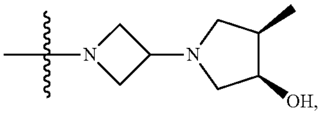

-continued
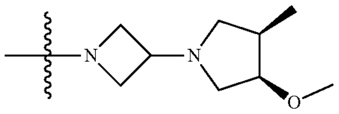,
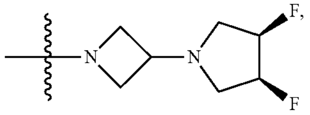
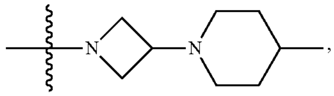,
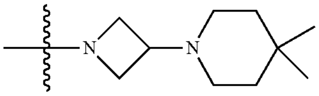,
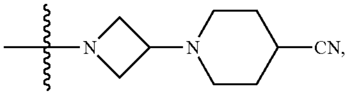
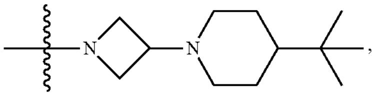,
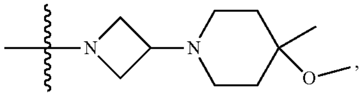,
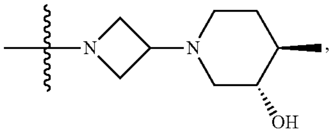,
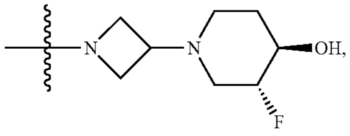
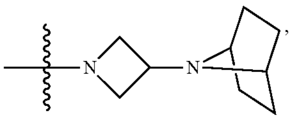,
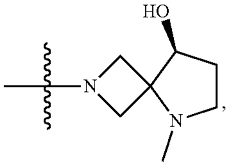,
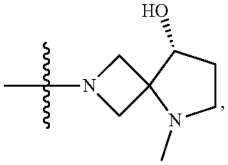,
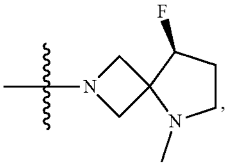,
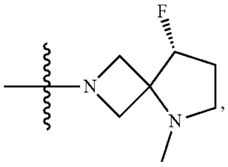,
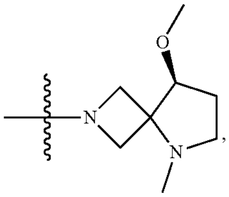,
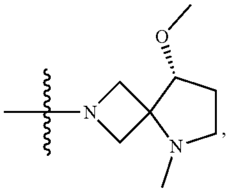,
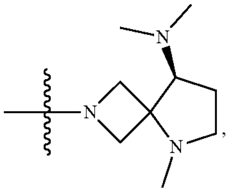,
-continued
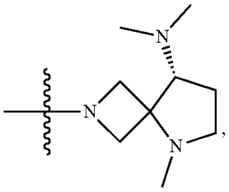,
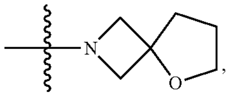,
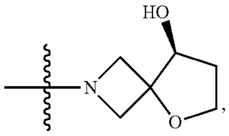,
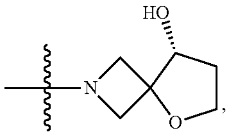,
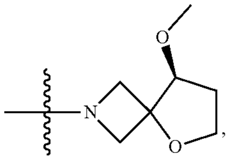,
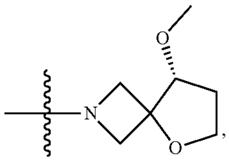,
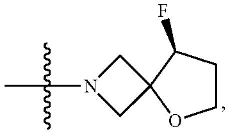,
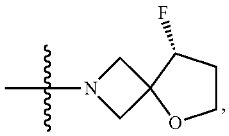,
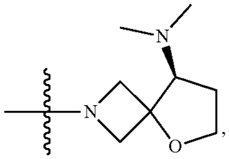,
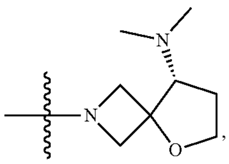,
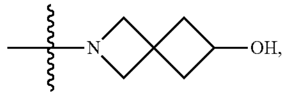
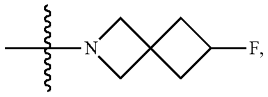
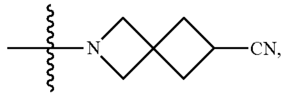
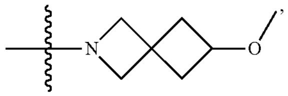
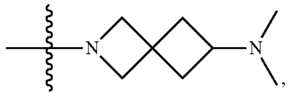
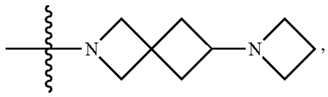,
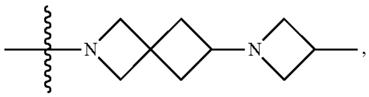,
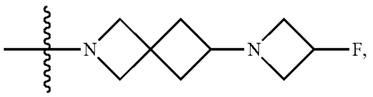
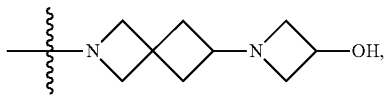
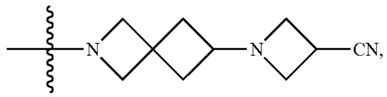
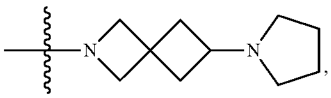, -continued
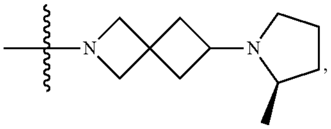
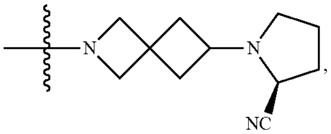
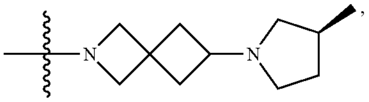
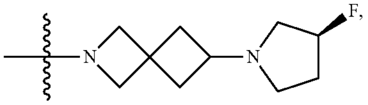
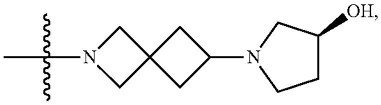
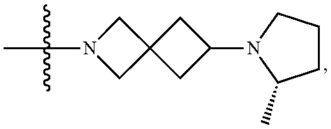
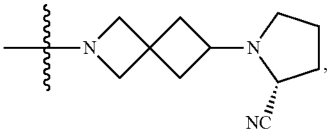
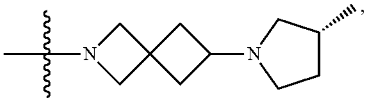
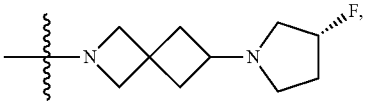
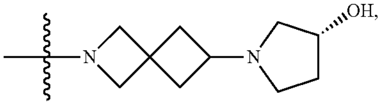
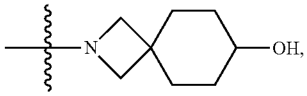
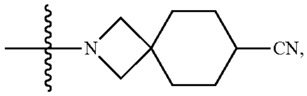
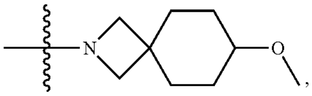
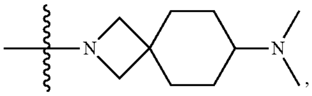
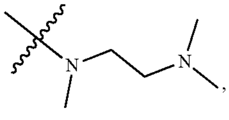
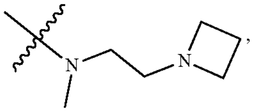
-continued
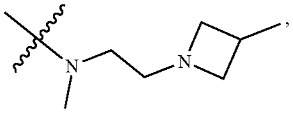
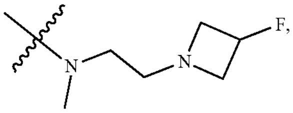
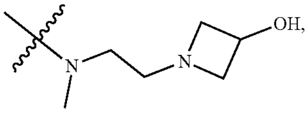
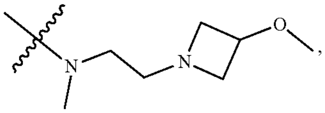
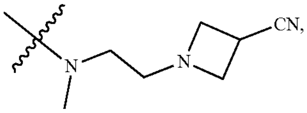
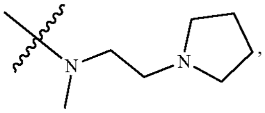
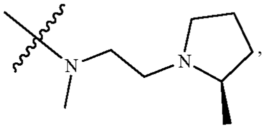
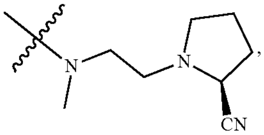
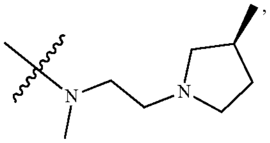
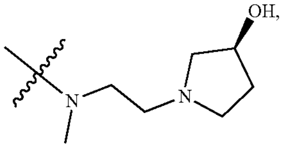
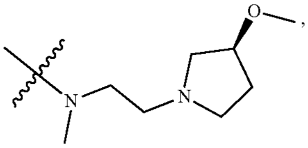
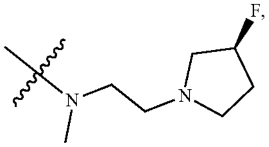
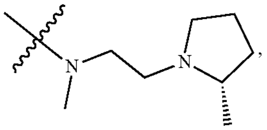
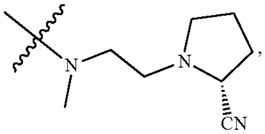
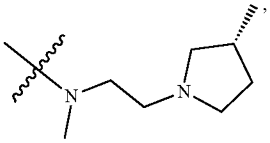

-continued
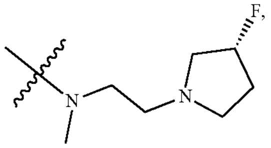
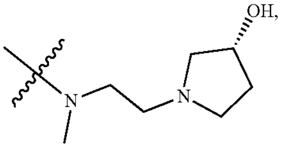
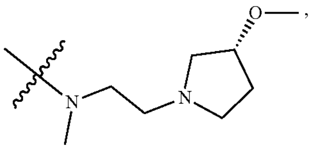
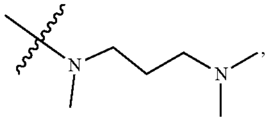
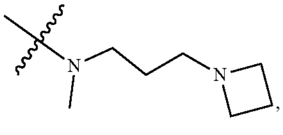
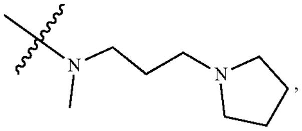
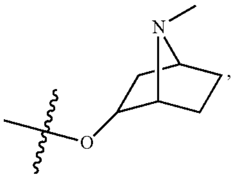
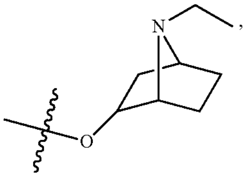
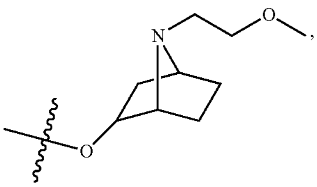
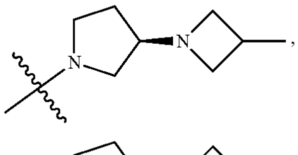
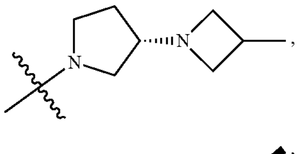
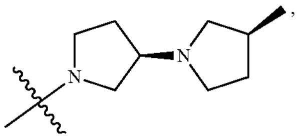
-continued
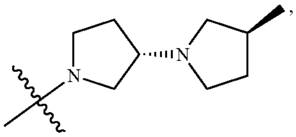
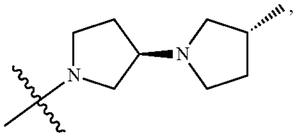
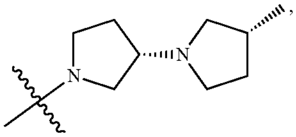
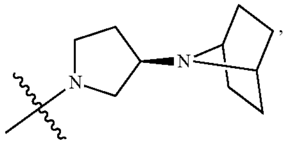
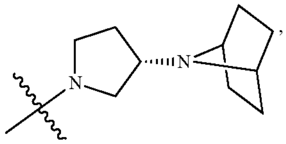
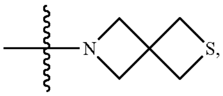
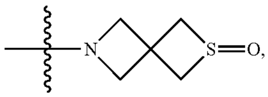
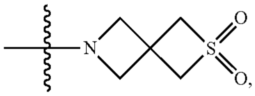
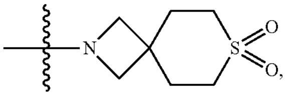
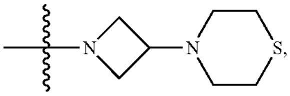
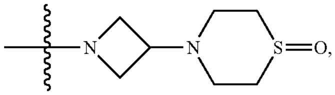
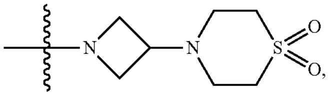
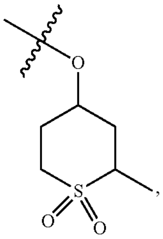
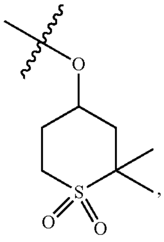
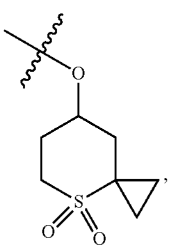
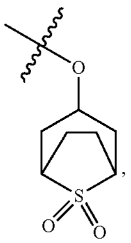

-continued
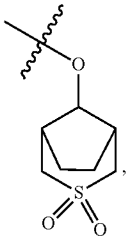,
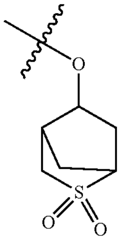,
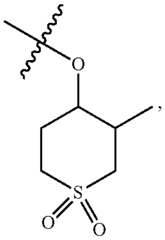,
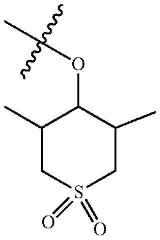
or
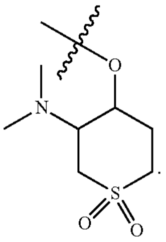.
13. The compound, the optical isomers thereof, the pharmaceutically acceptable salts thereof, the hydrates thereof or the solvates thereof according to claim 10, wherein the compound has one of the following structures:
225
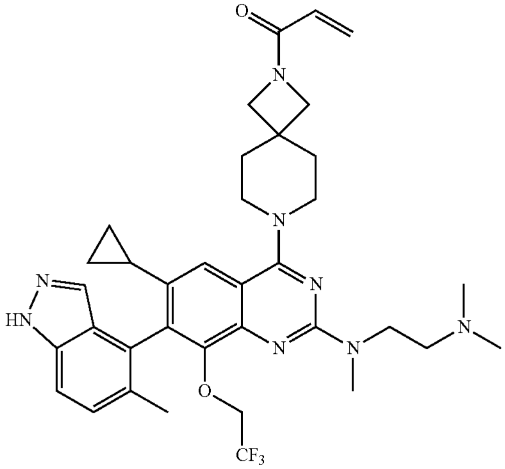
-continued
226
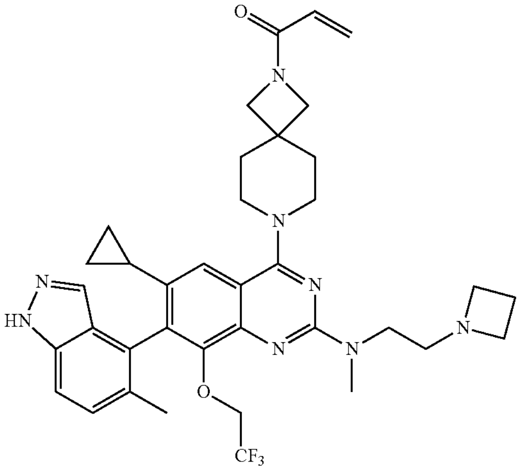
227
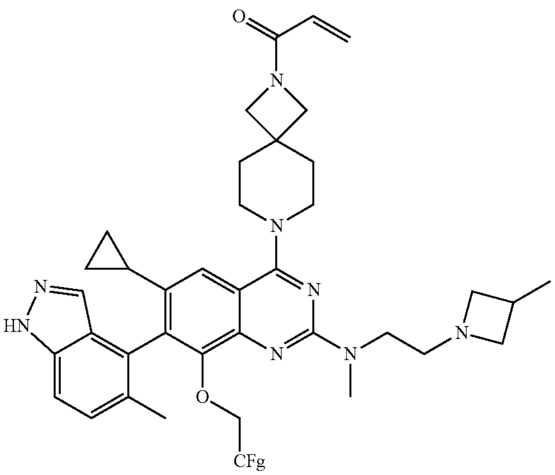
228
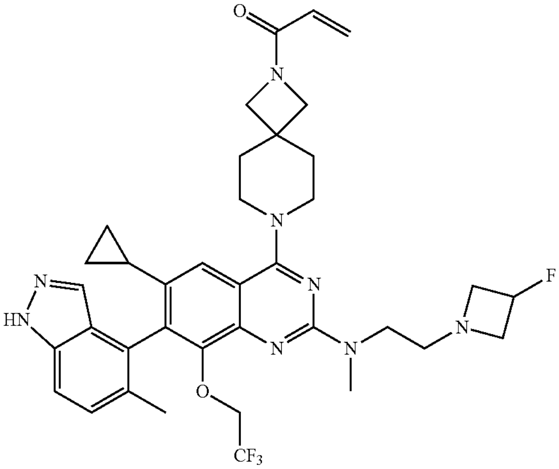

-continued
229
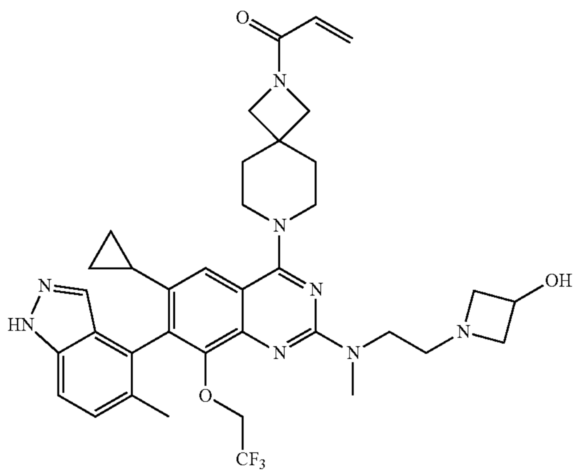
230
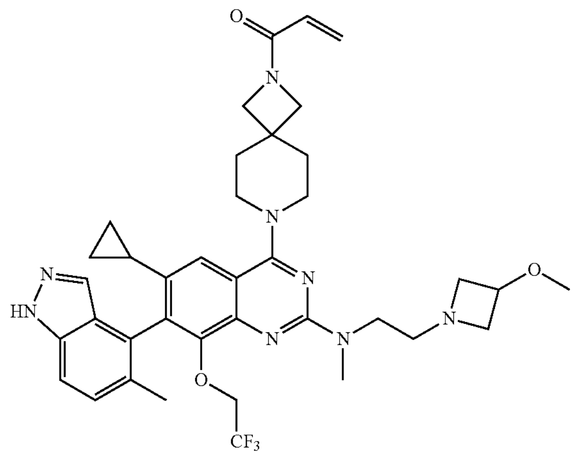
231
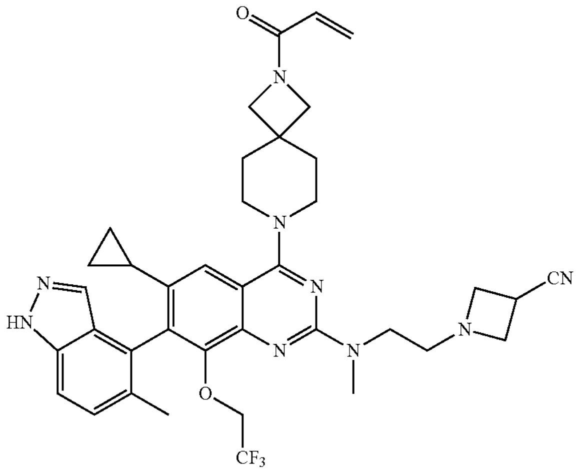
-continued
232
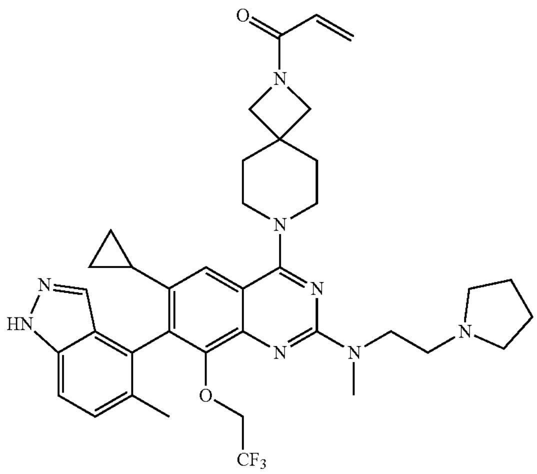
233
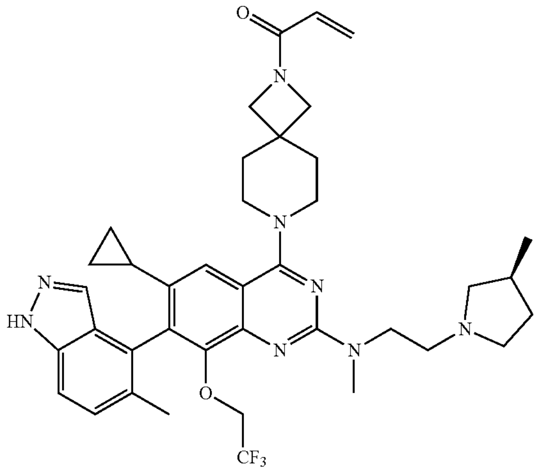
234
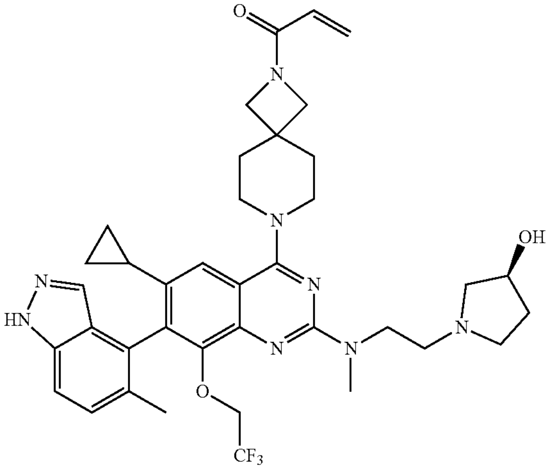

-continued
235
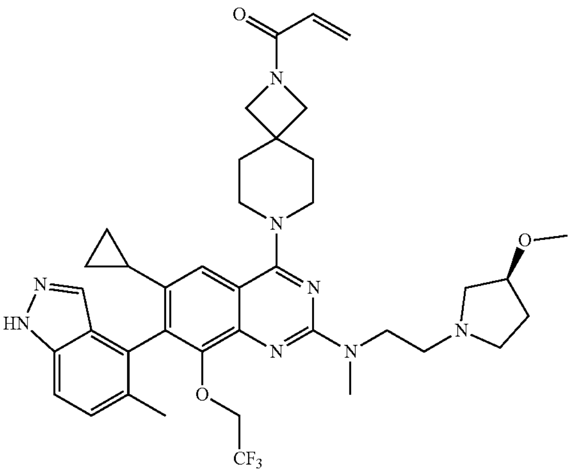
236
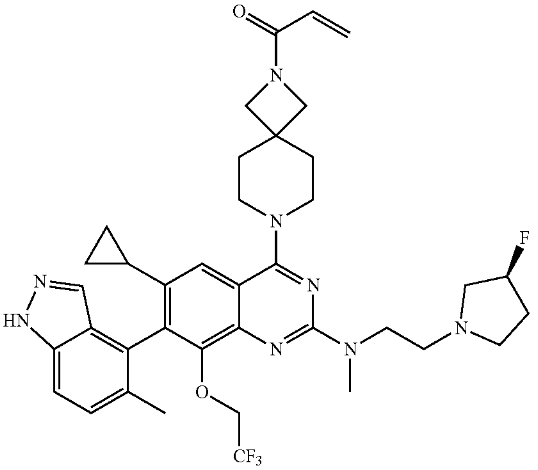
237
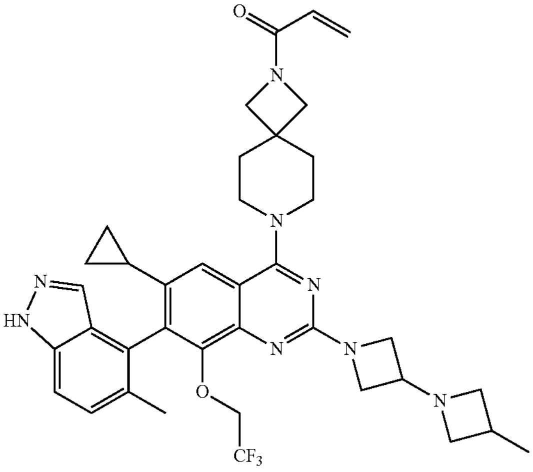
-continued
238
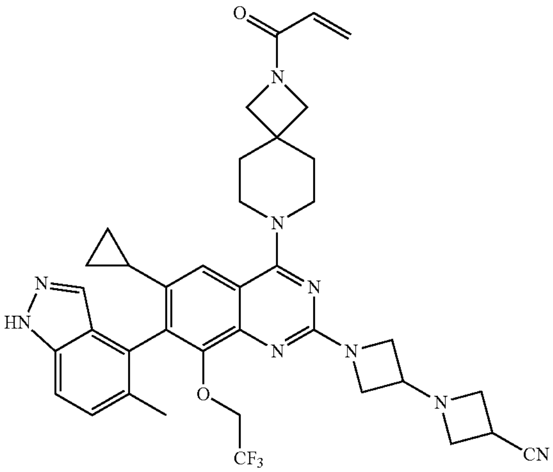
239
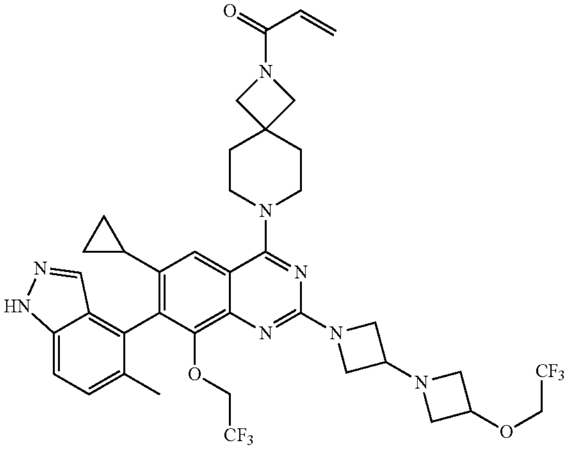
240
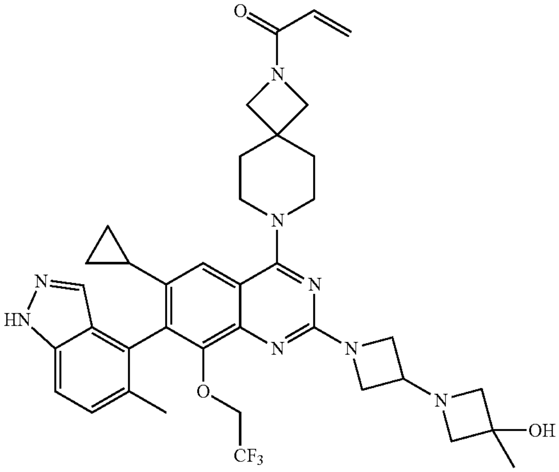

-continued
241
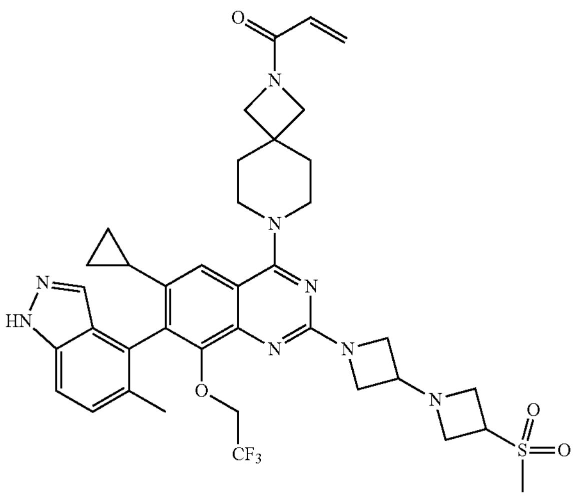
242
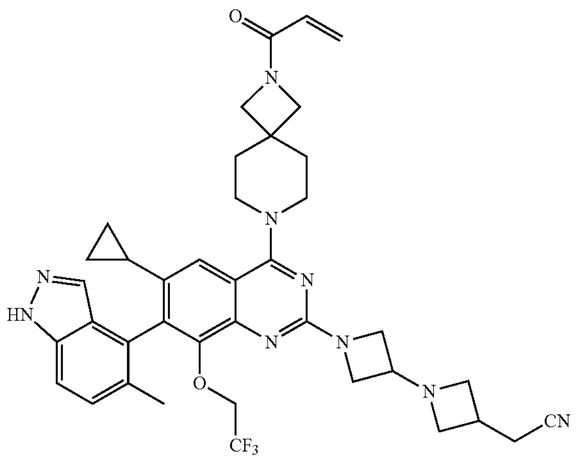
243
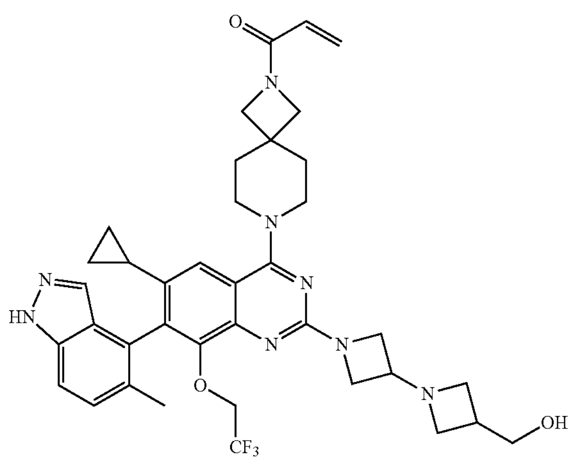
-continued
244
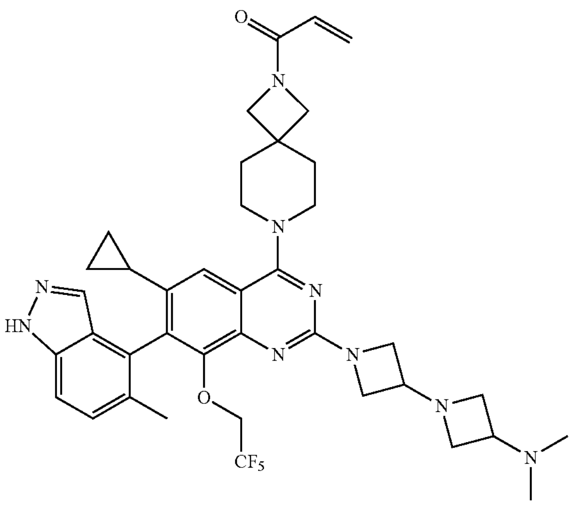
245
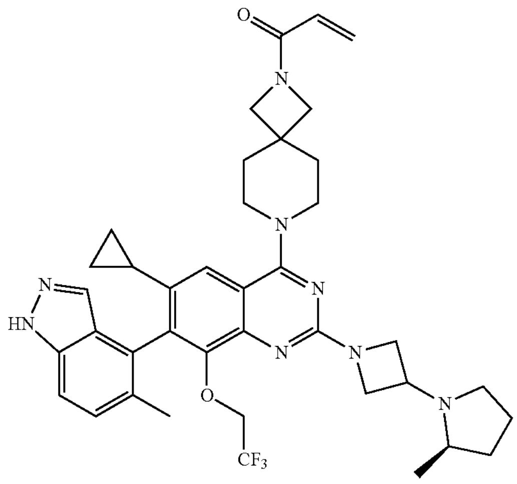
246
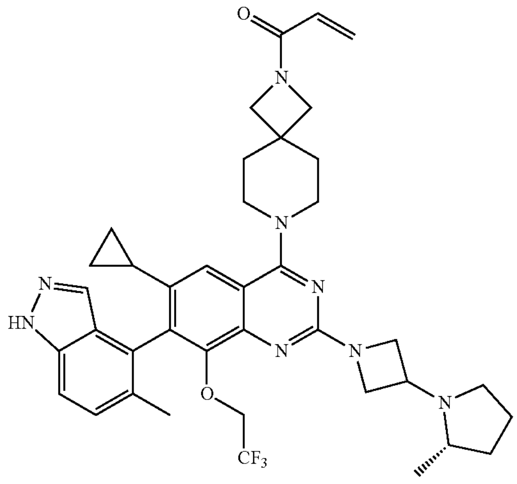

-continued
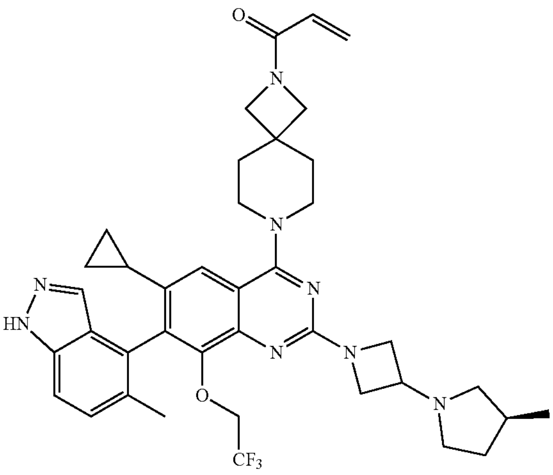
247
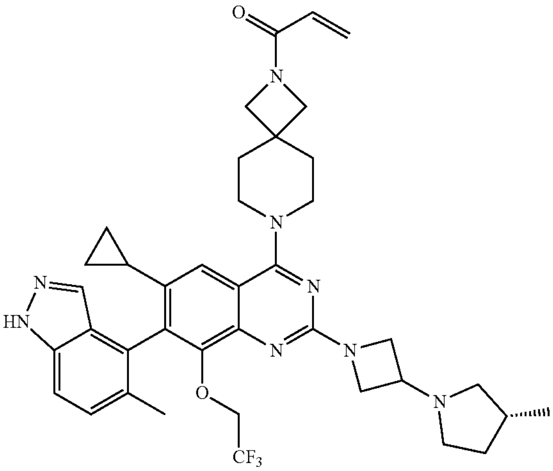
248
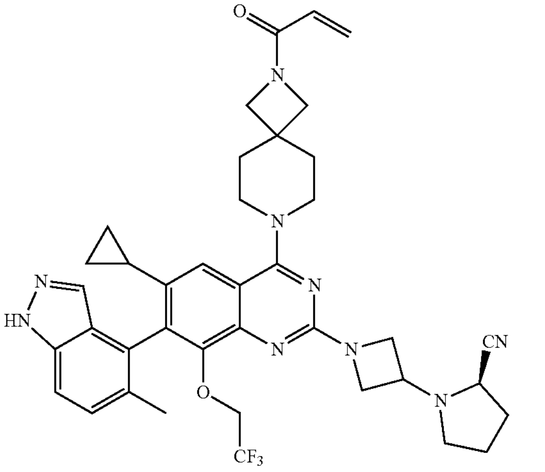
249
-continued
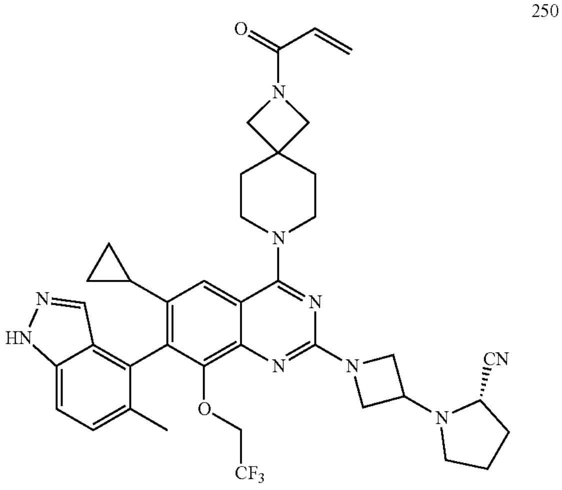
250
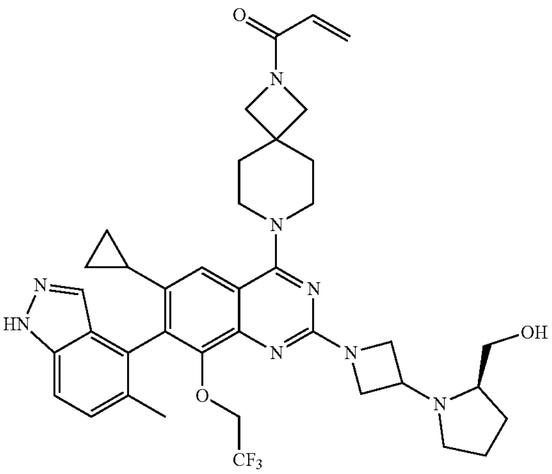
251
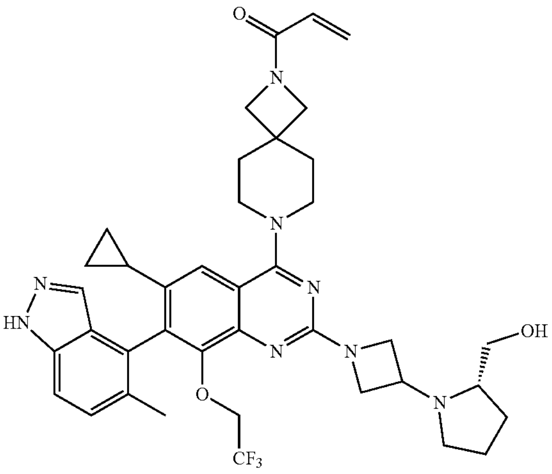
252

-continued
253
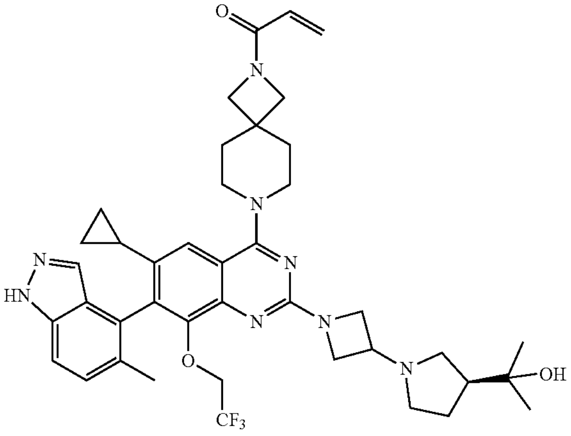
254
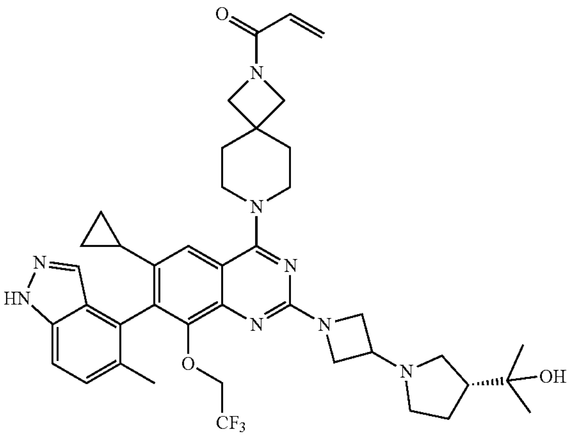
255
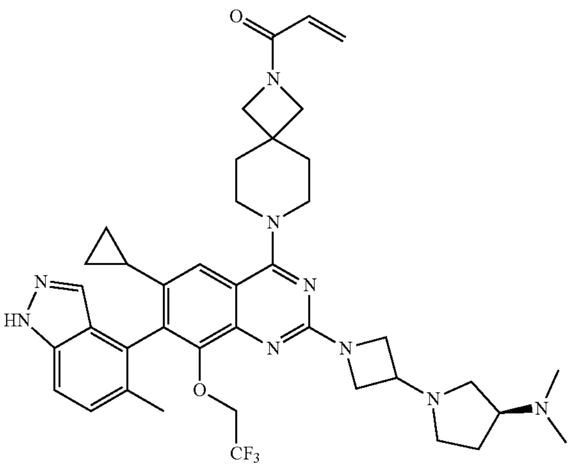
-continued
256
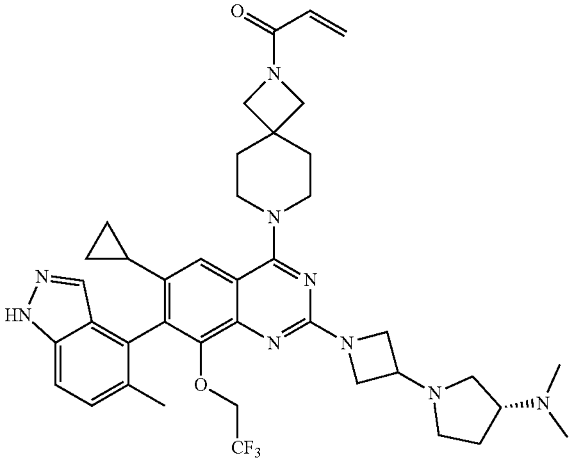
257
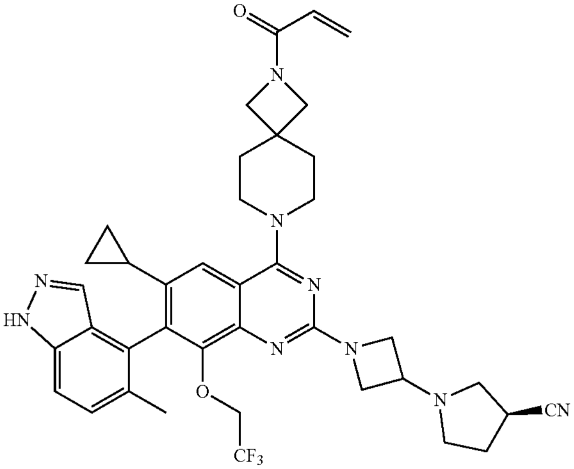
258
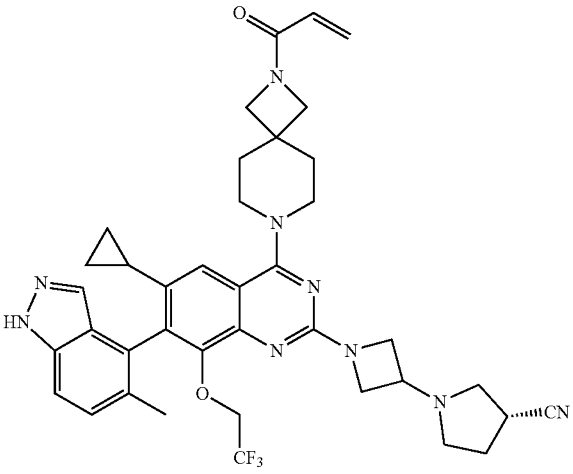

-continued
259
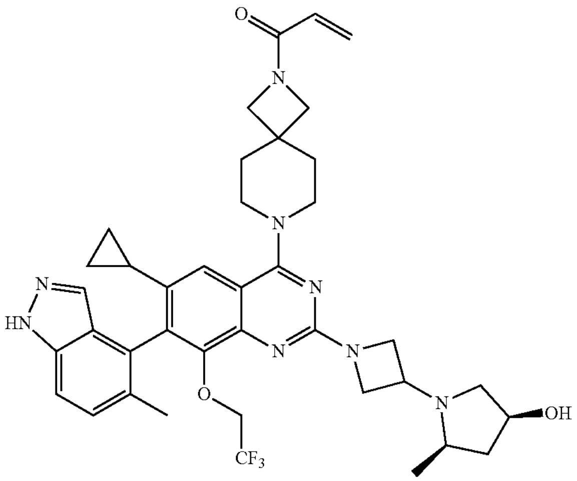
260
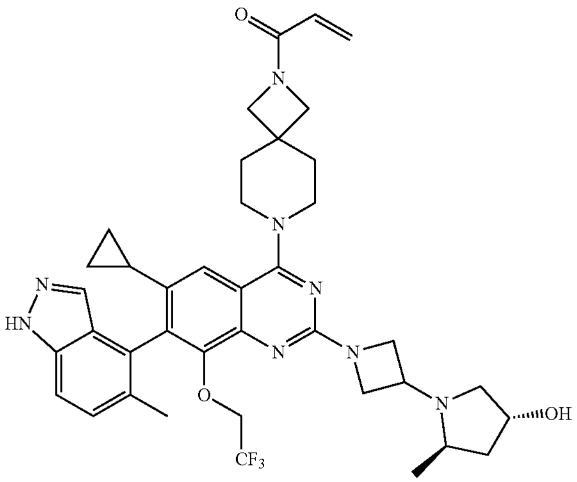
261
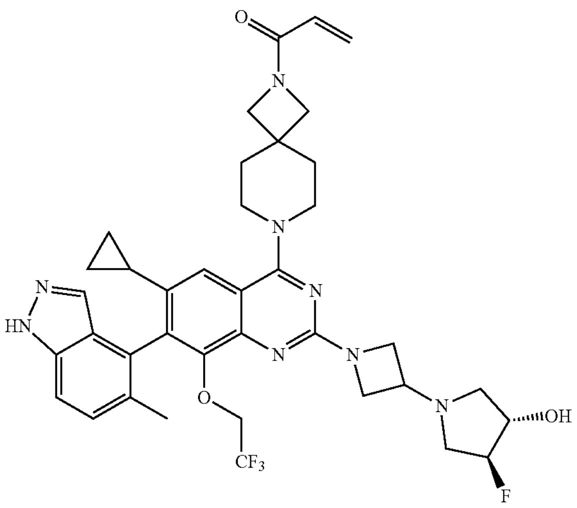
-continued
262
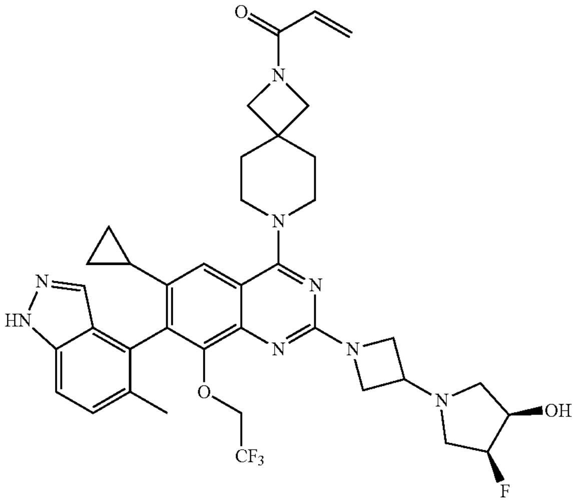
263
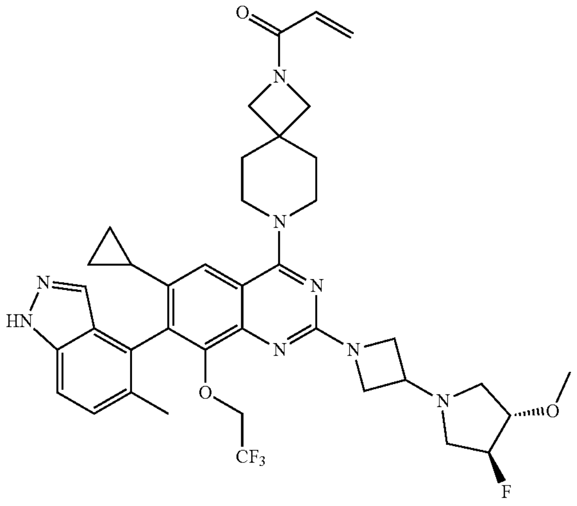
264
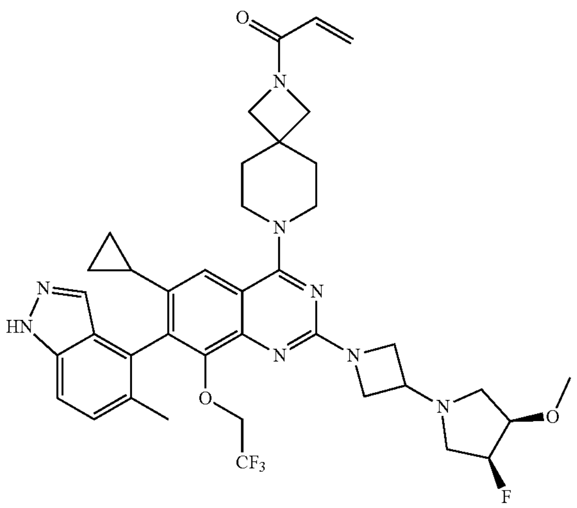

-continued
265
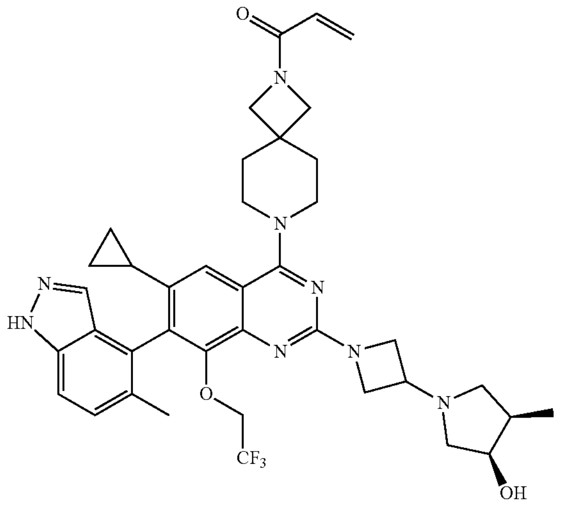
266
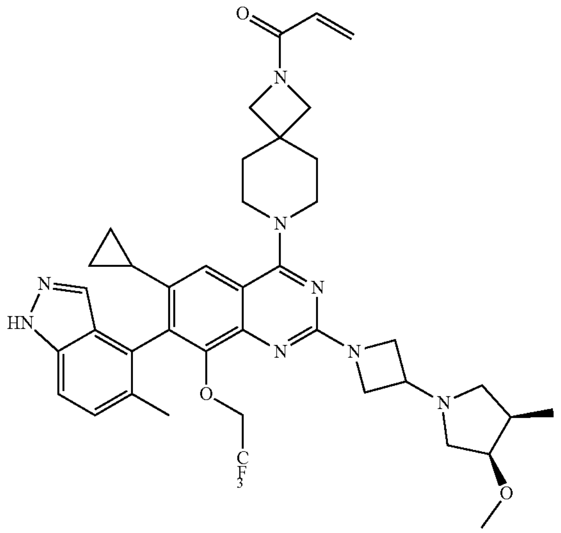
267
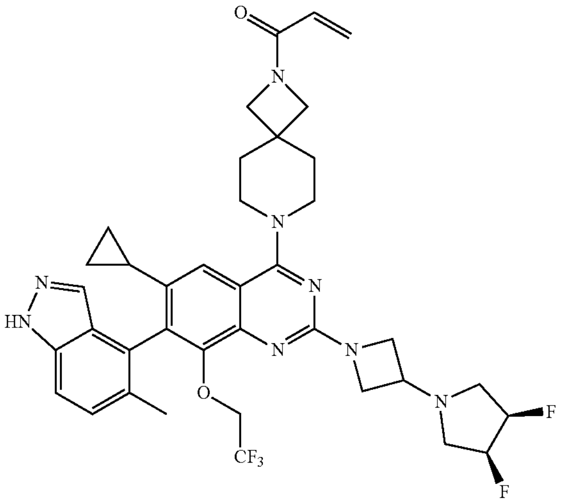
-continued
268
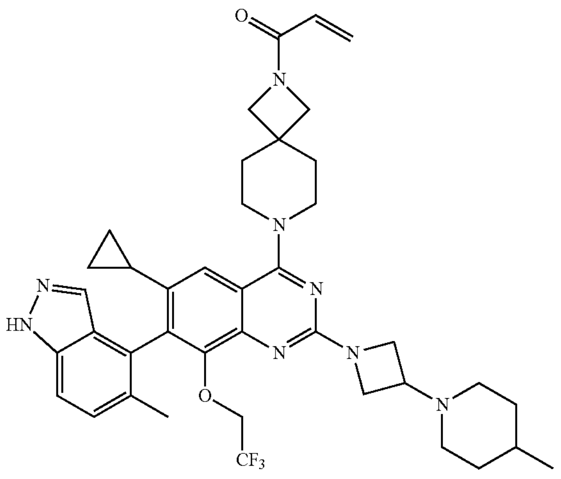
269
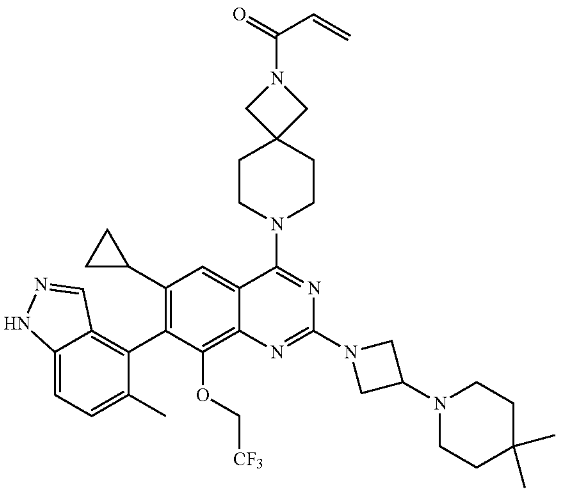
270
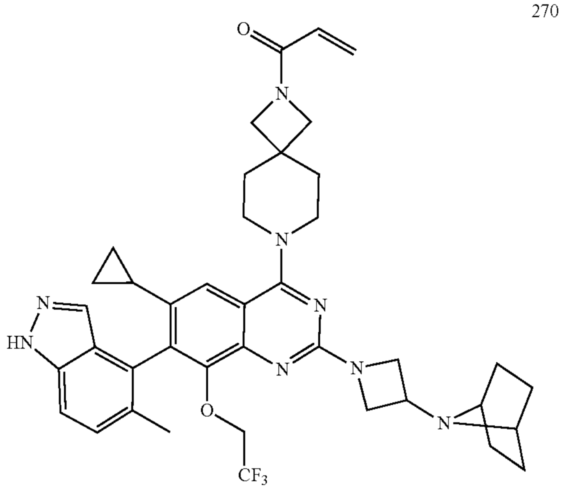

271
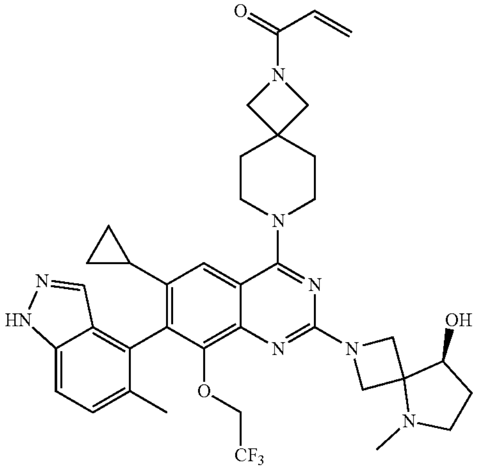
272
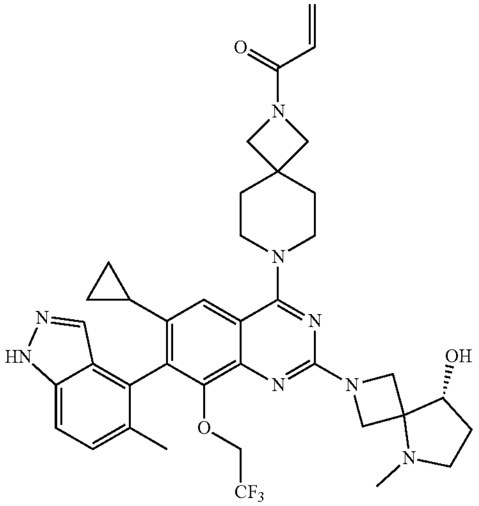
273
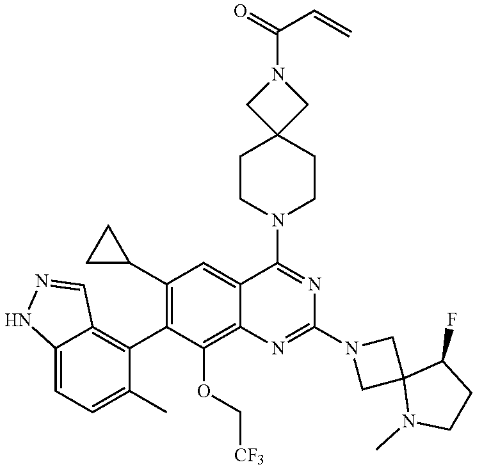
274
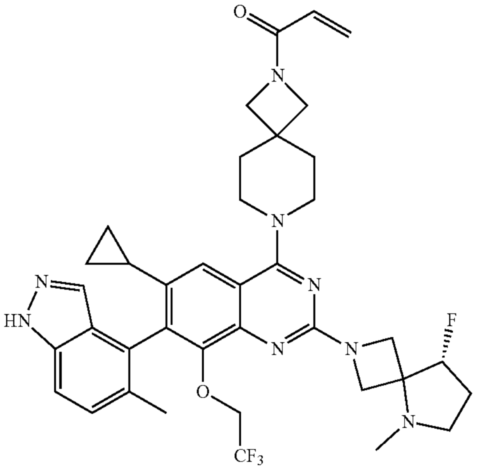
275
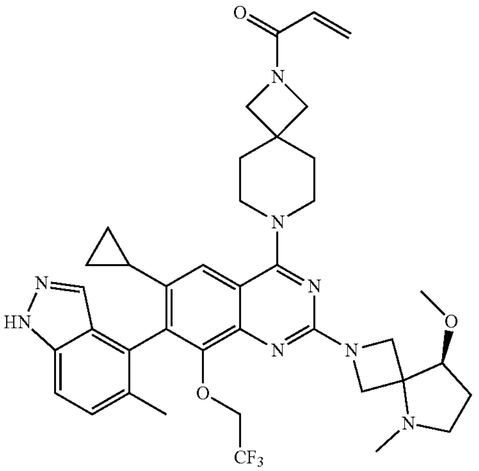
276
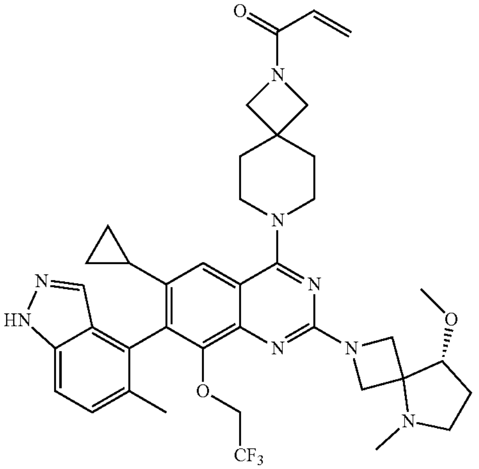

-continued
277
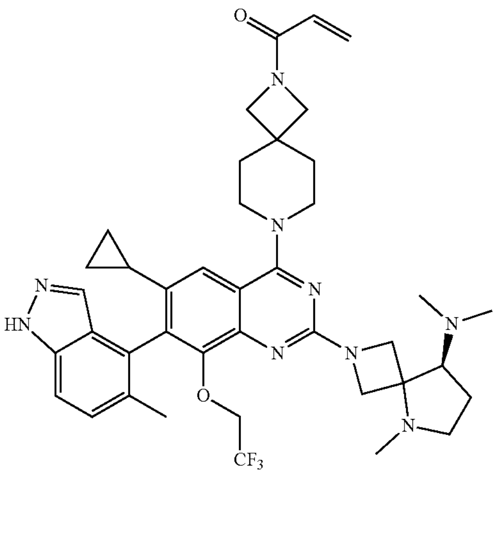
278
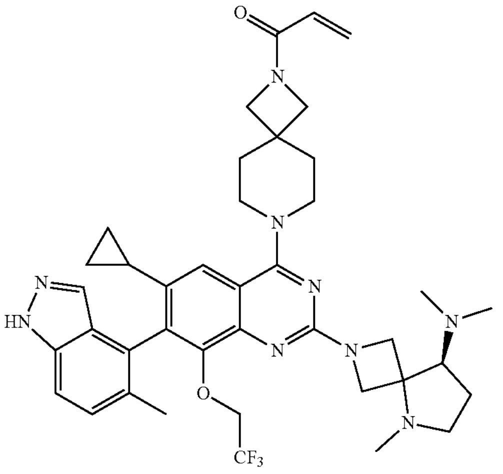
279
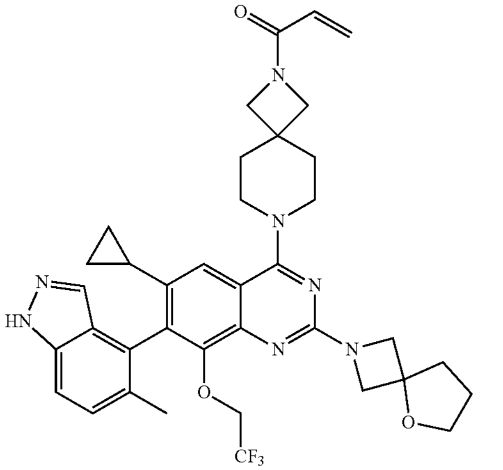
-continued
280
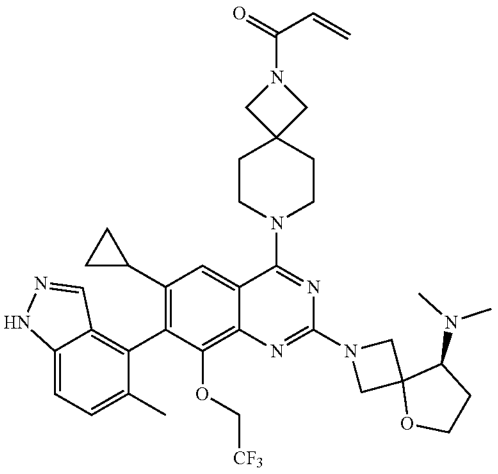
281
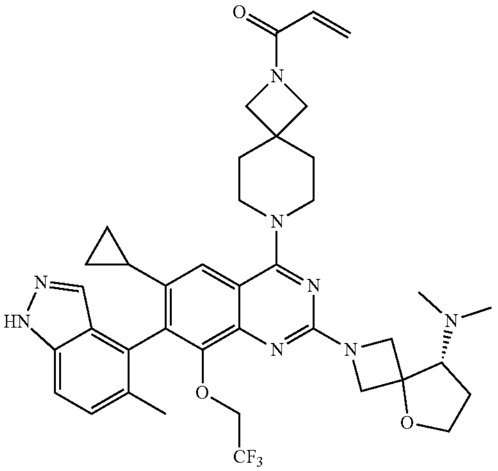
282
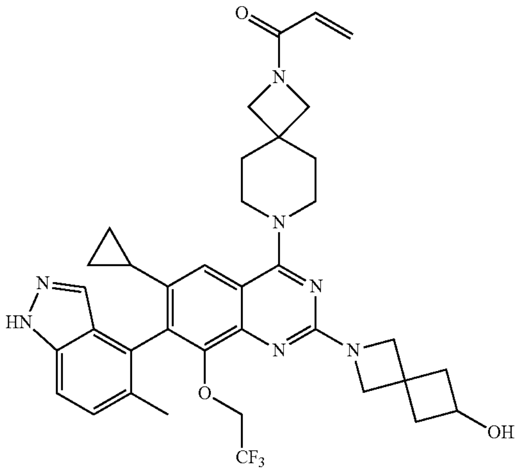

-continued
283
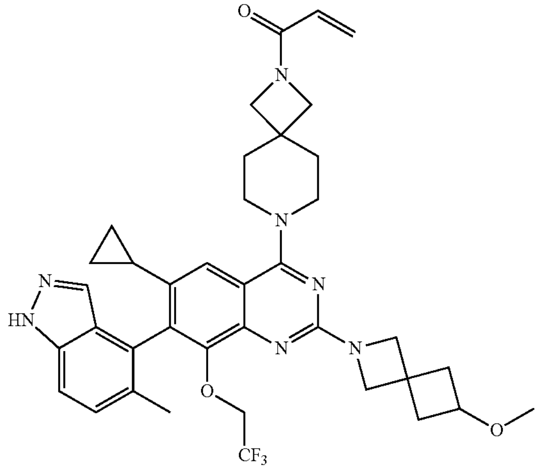
284
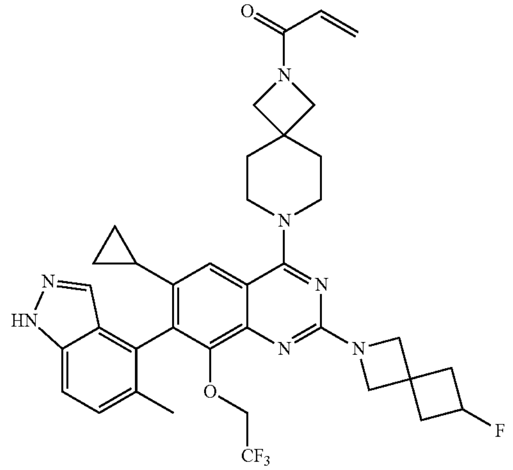
285
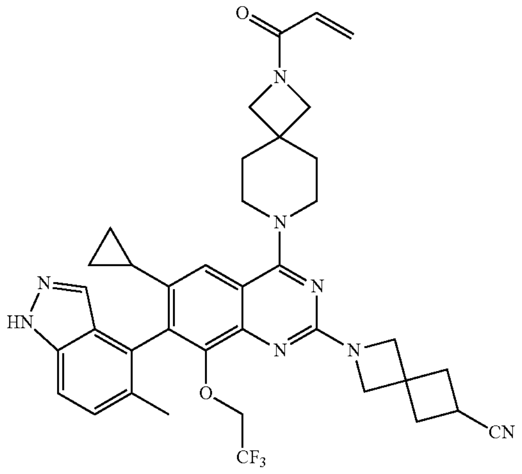
-continued
286
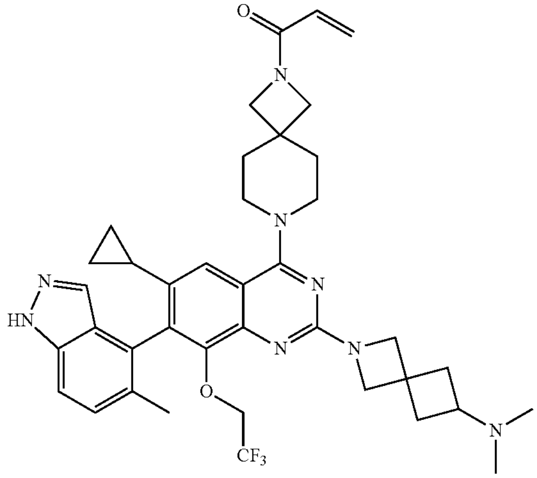
287
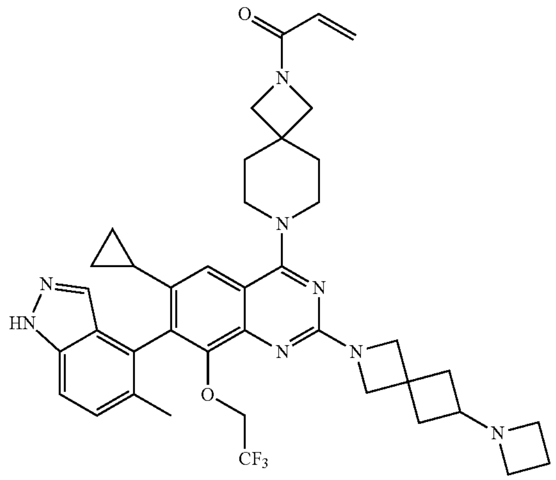
288
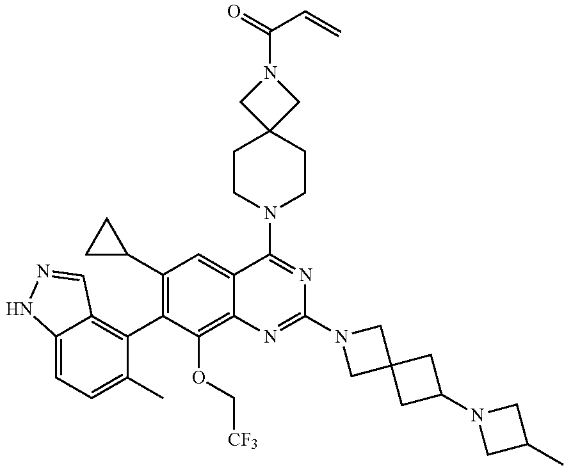

-continued
289
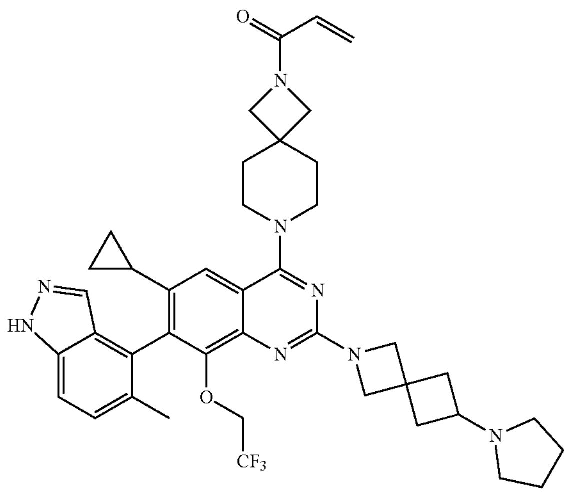
290
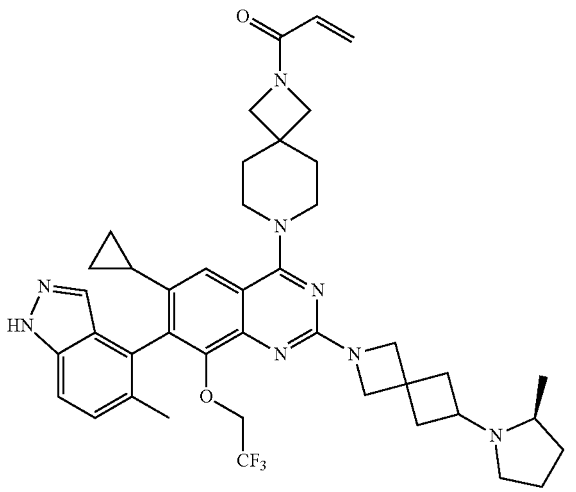
291
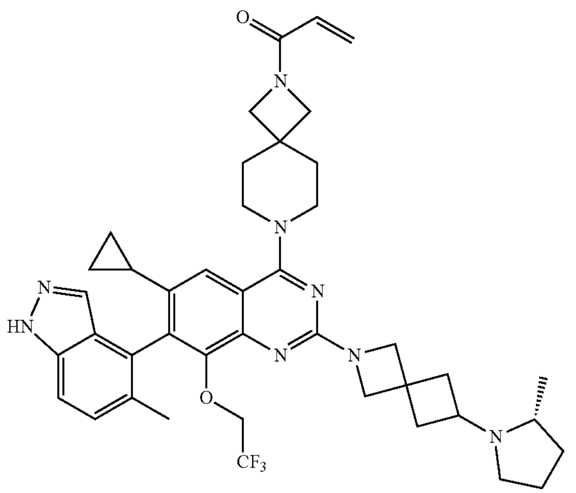
-continued
292
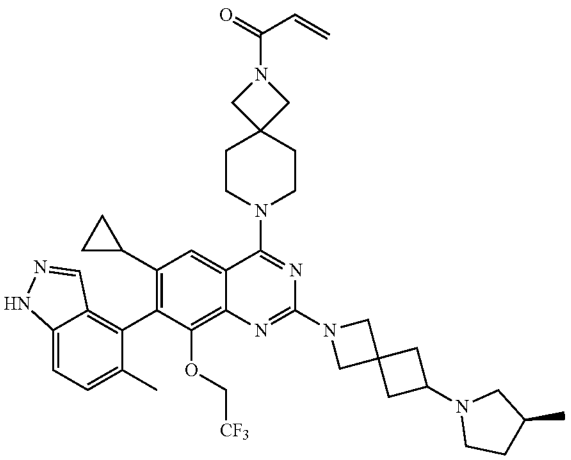
293
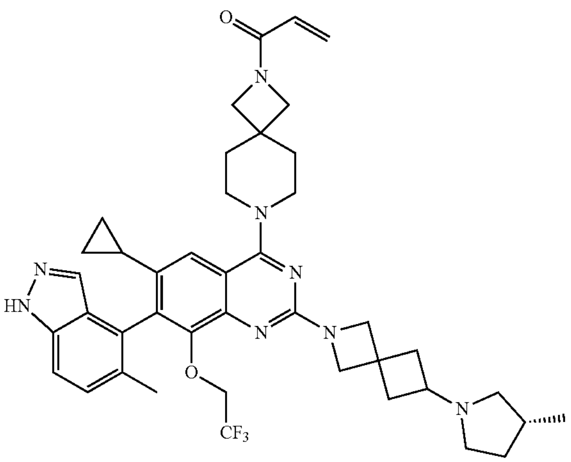
294
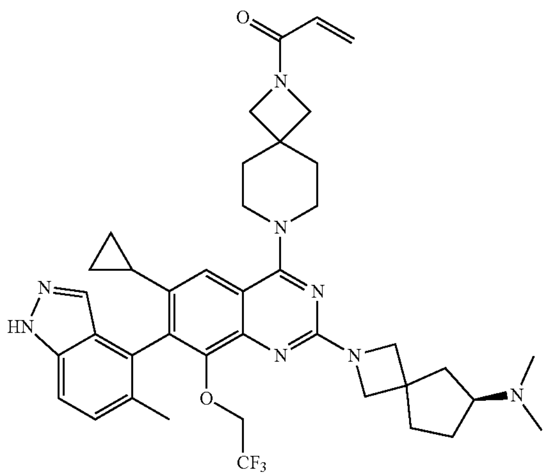

-continued
295
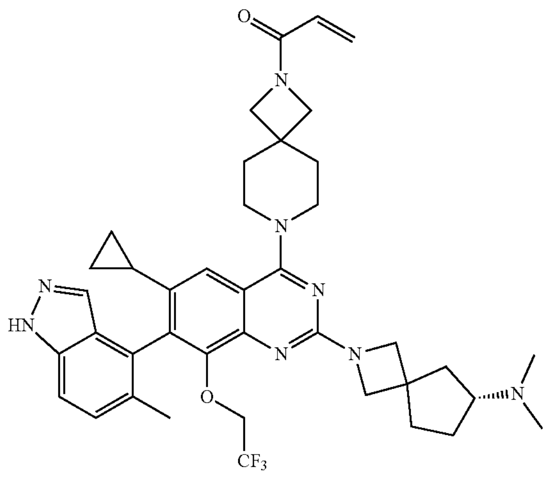
296
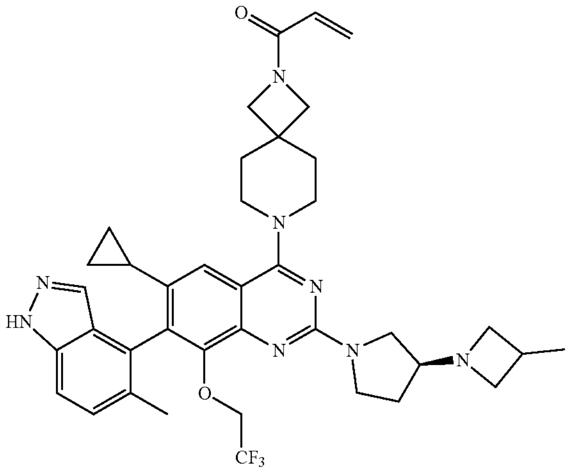
297
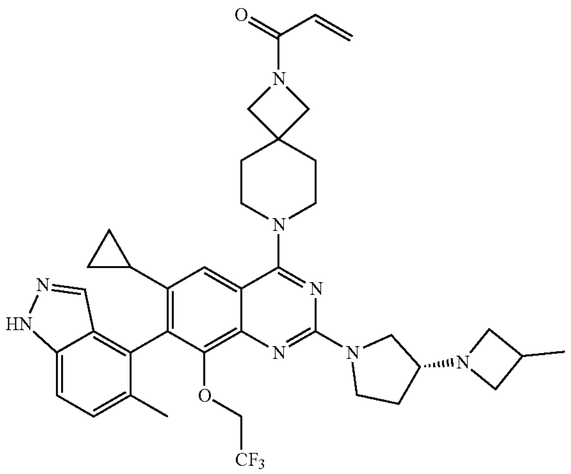
-continued
298
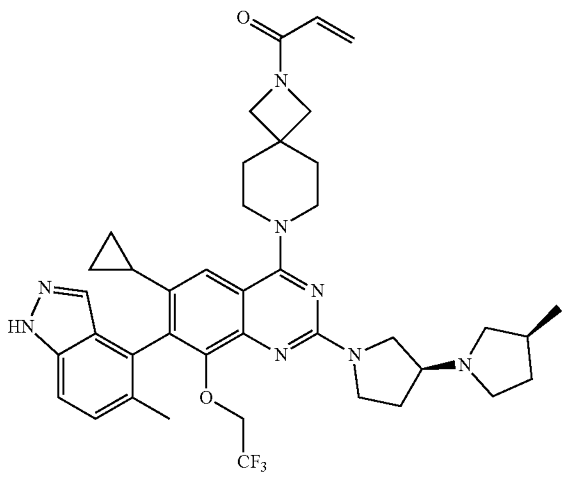
299
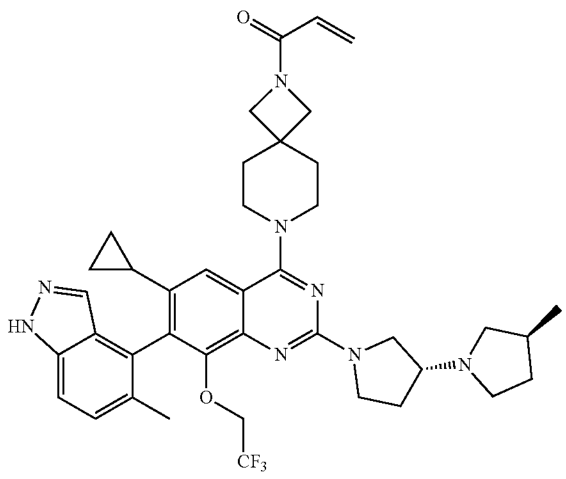
300
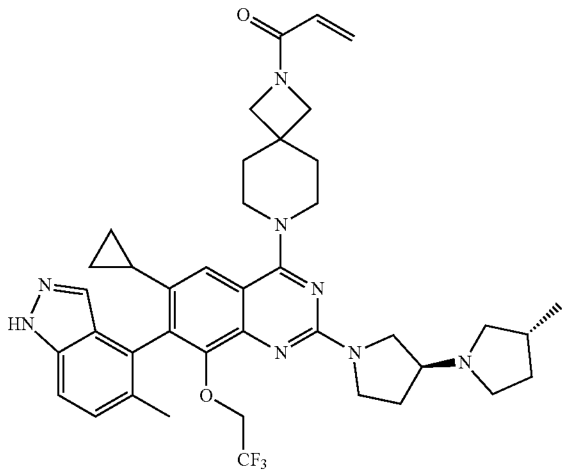

-continued
301
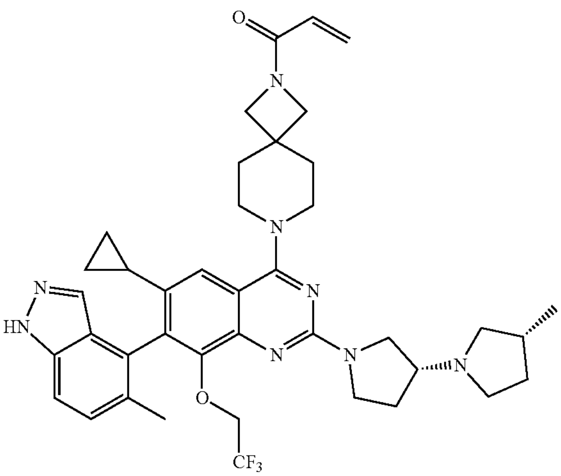
302
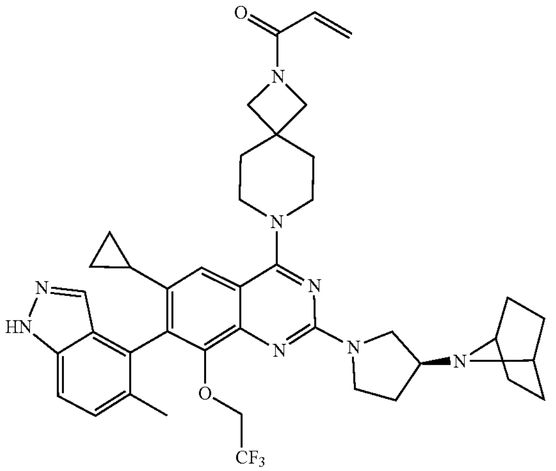
303
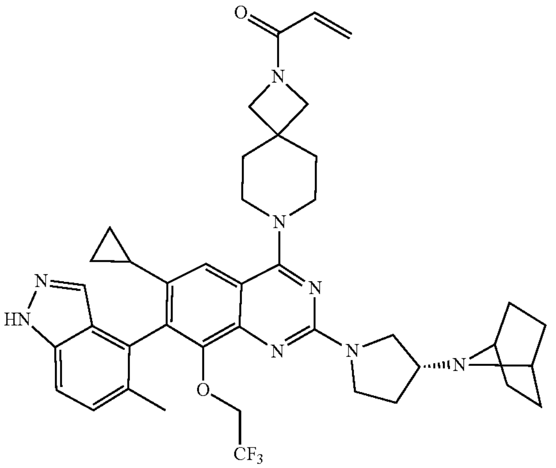
-continued
304
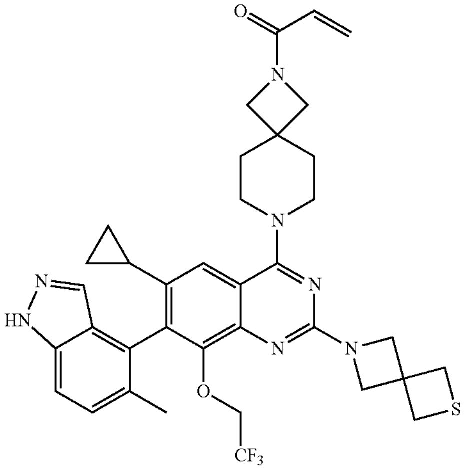
305
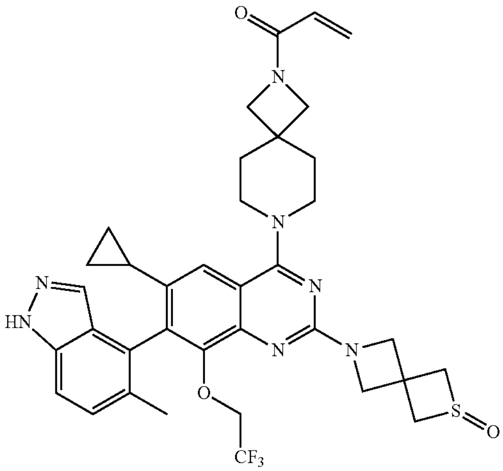
306
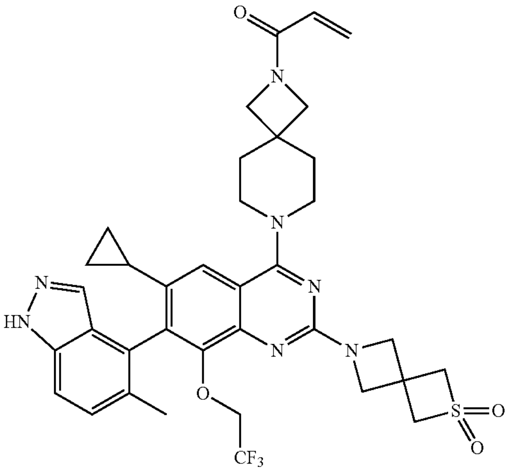

-continued
307
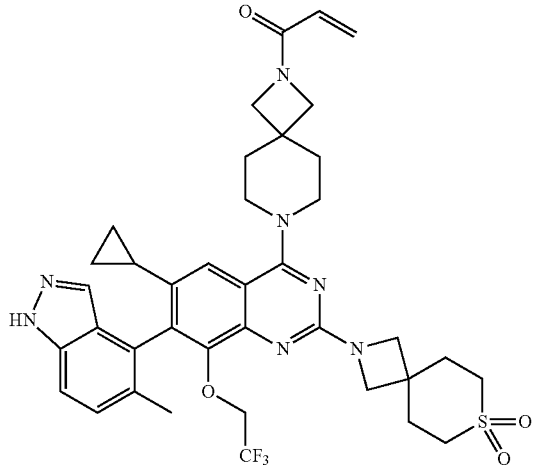
308
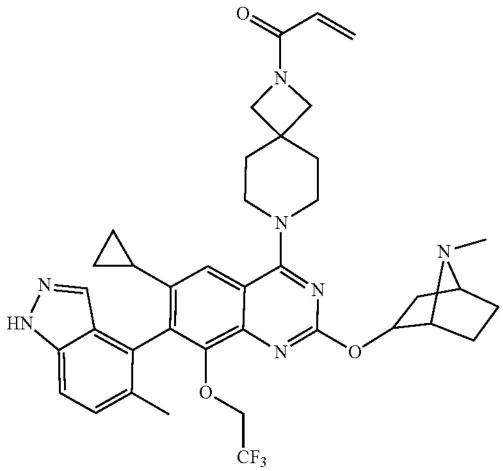
309
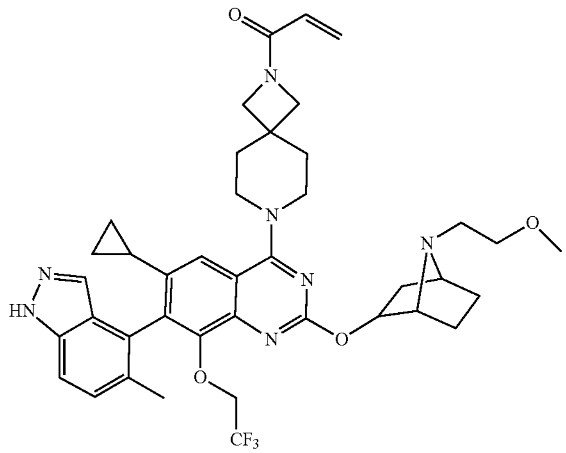
-continued
310
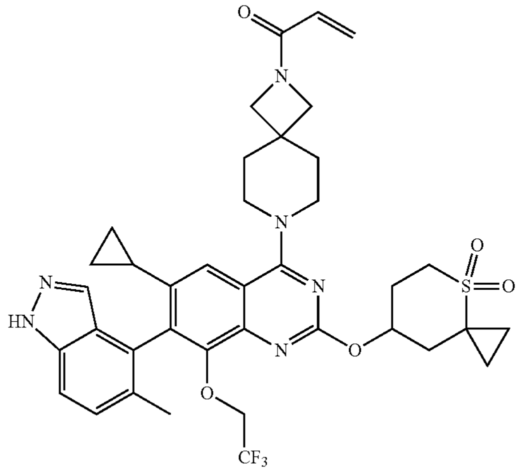
311
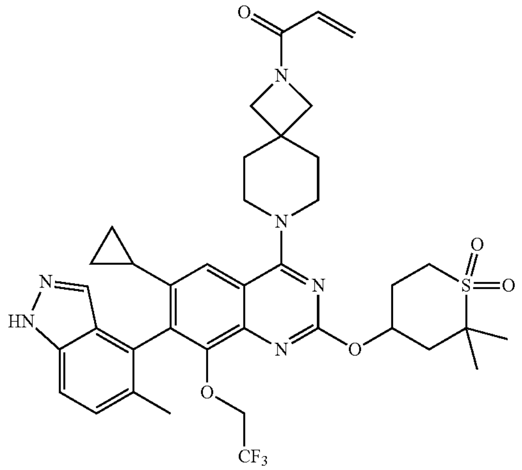
312
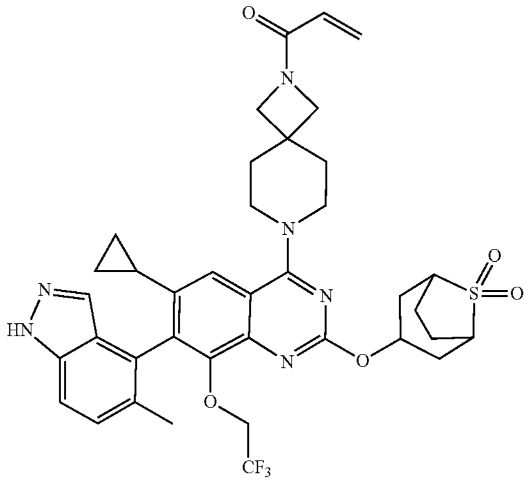

-continued
313
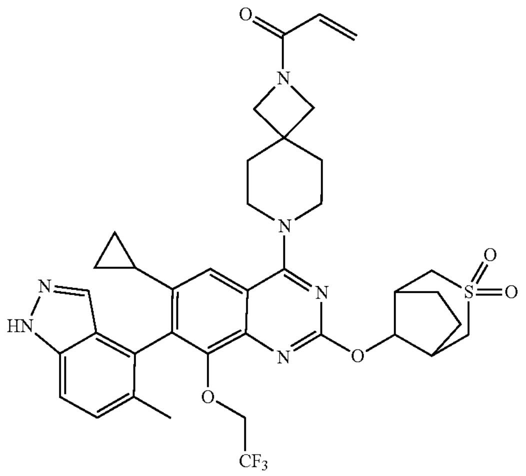
314
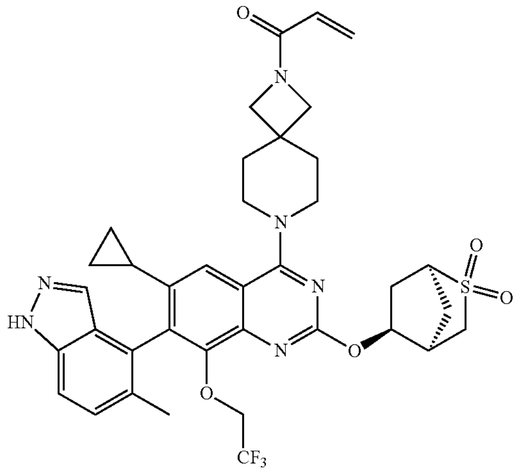
315
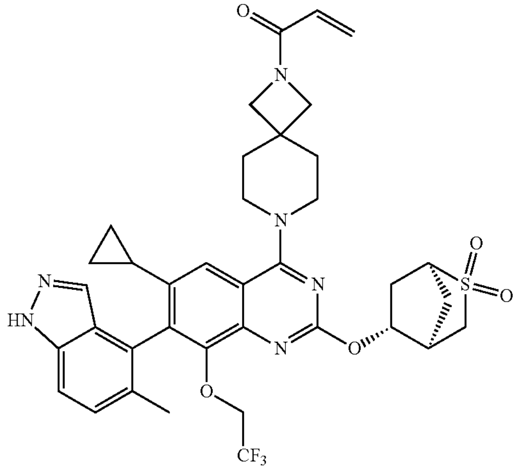
-continued
316
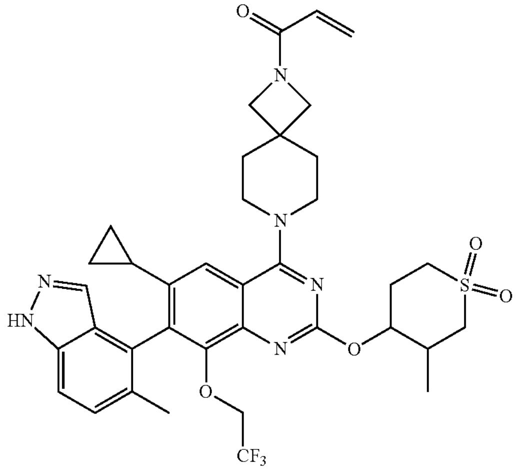
317
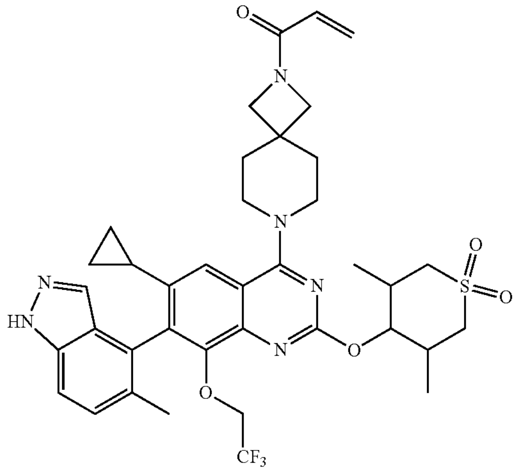
318
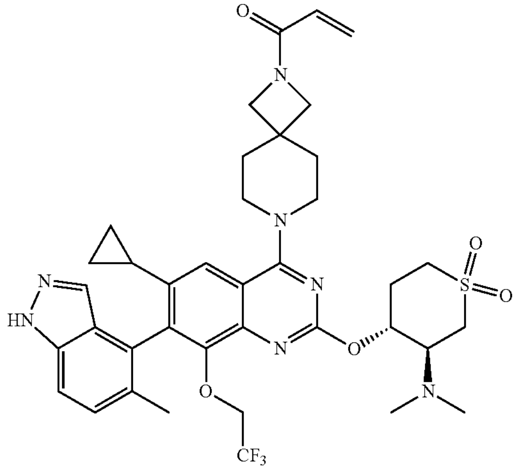

-continued
319
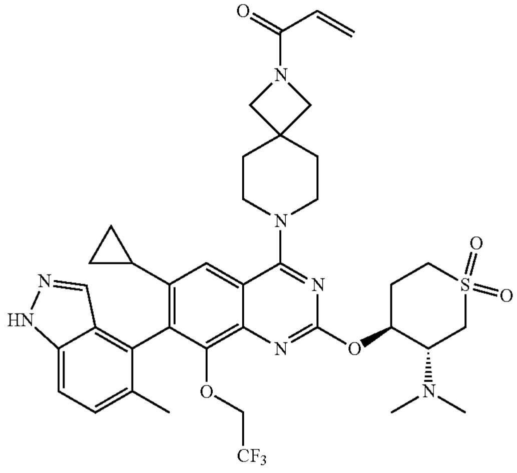
320
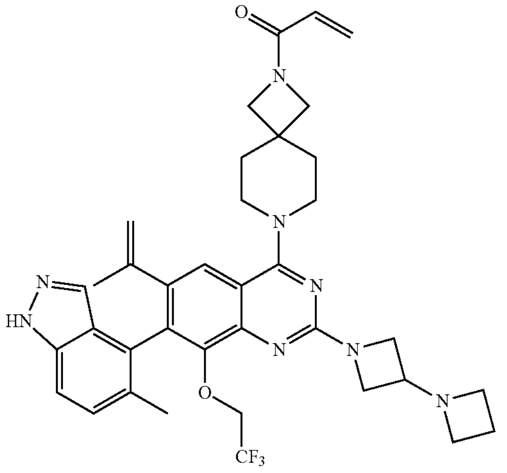
321
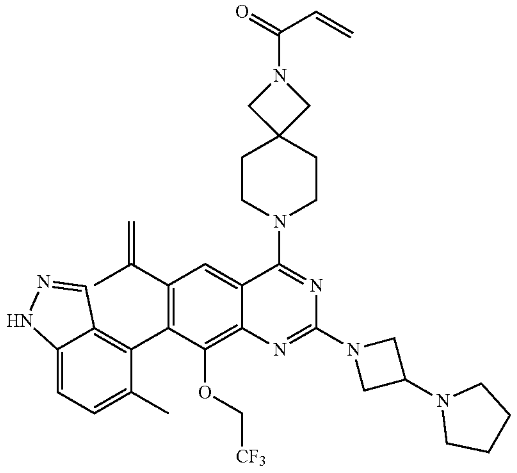
-continued
322
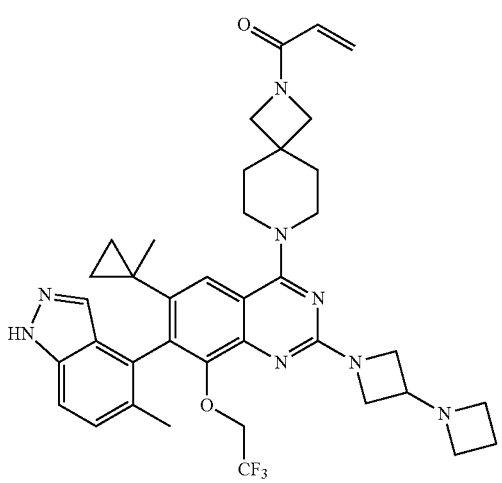
323
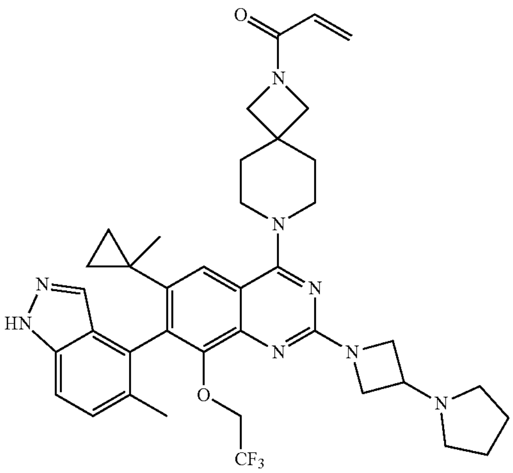
324
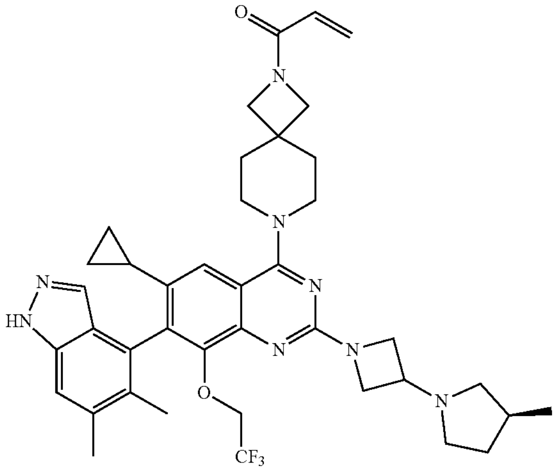

325
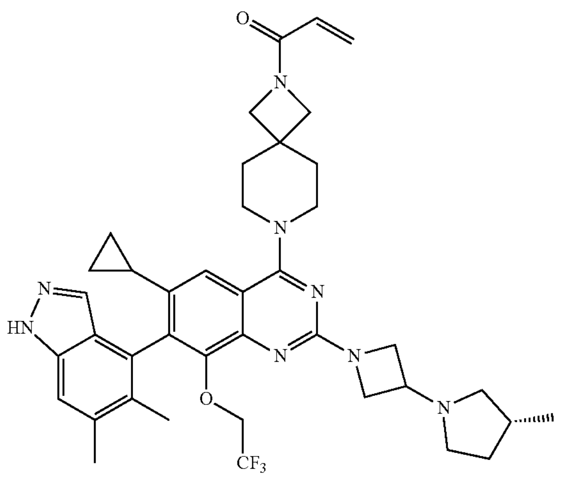
326
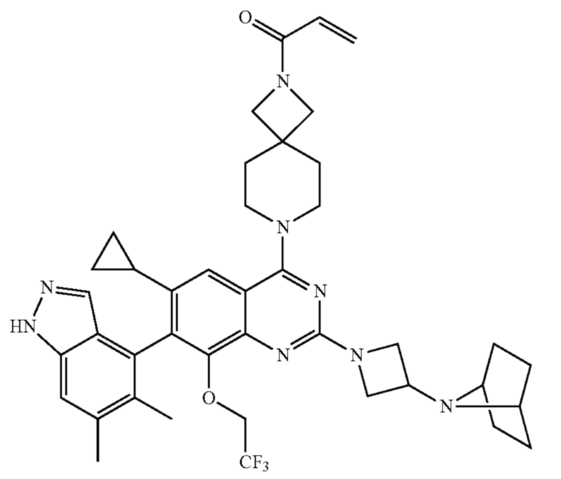
327
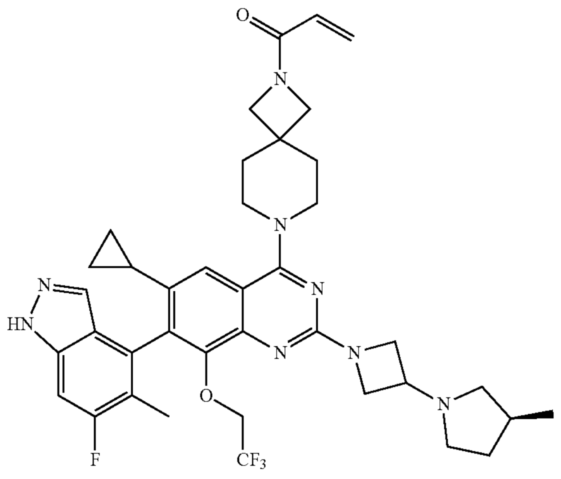
328
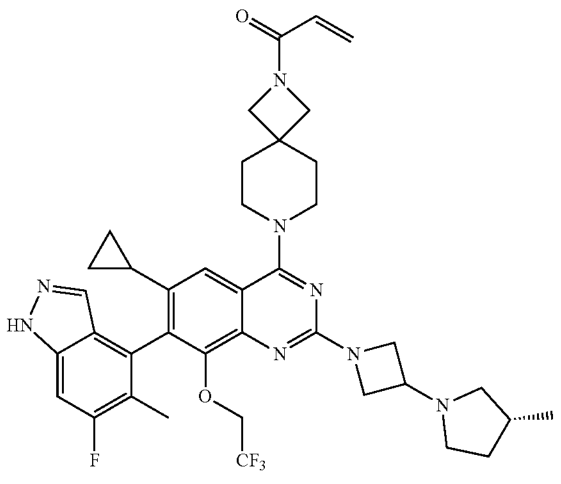
329
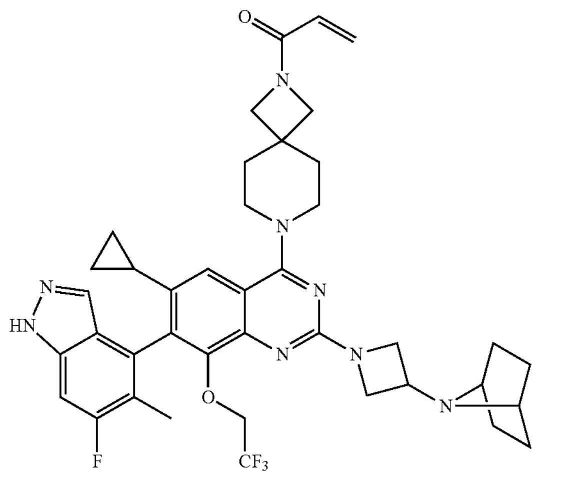
330
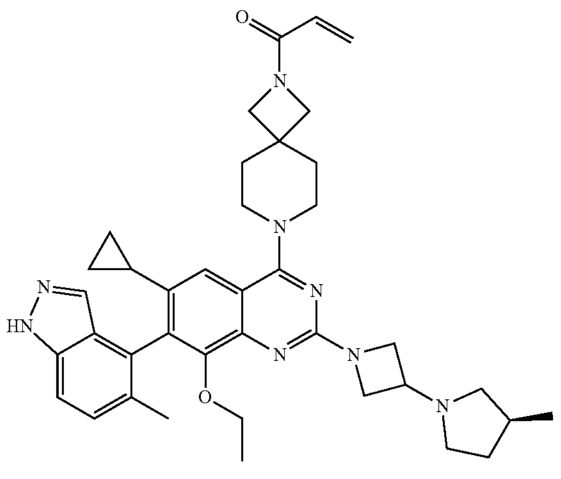

-continued
331
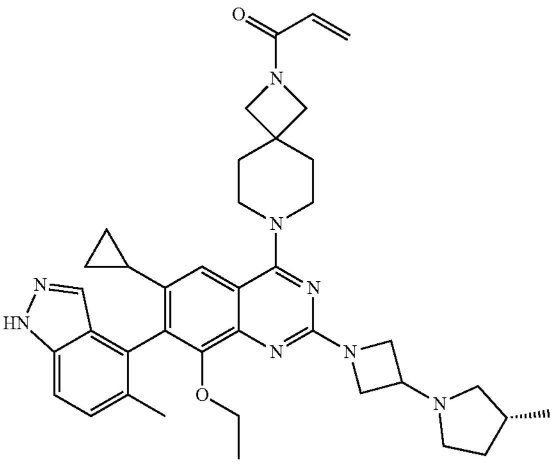
332
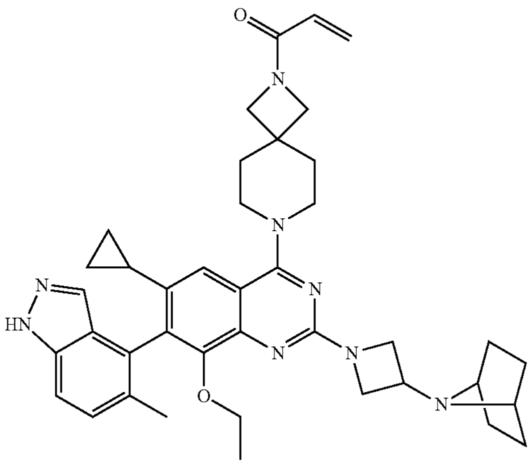
333
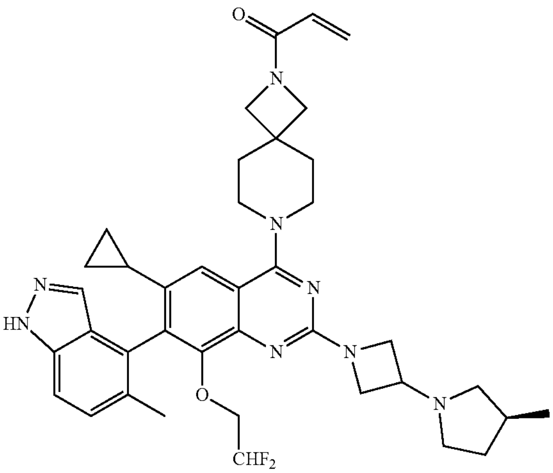
-continued
334
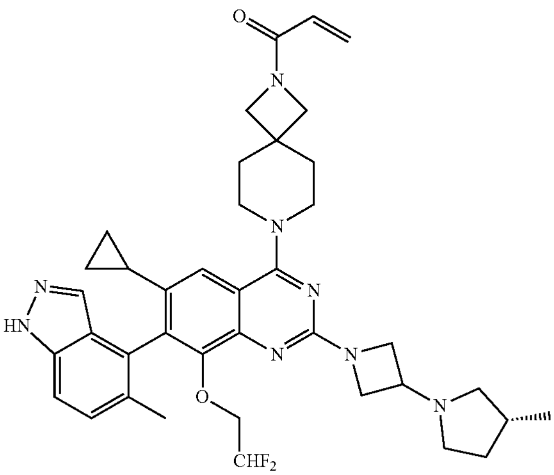
335
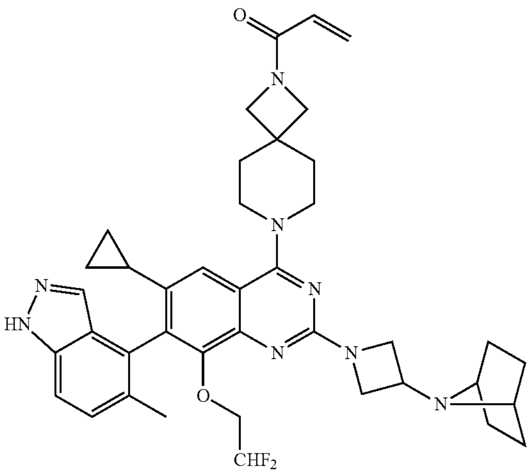
336
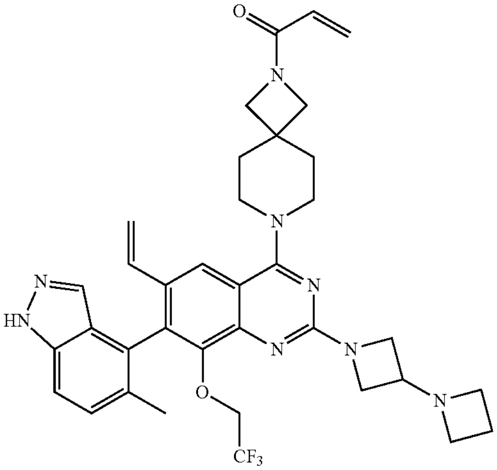

-continued
337
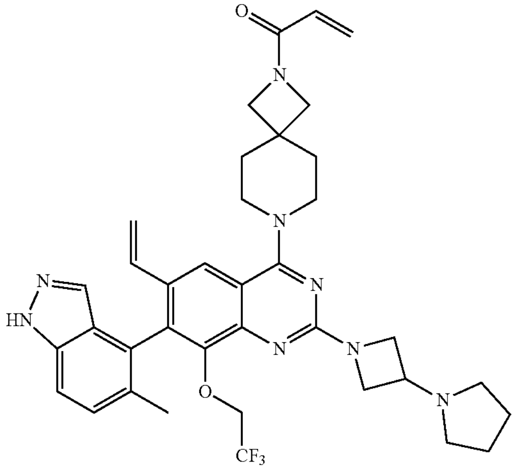
338
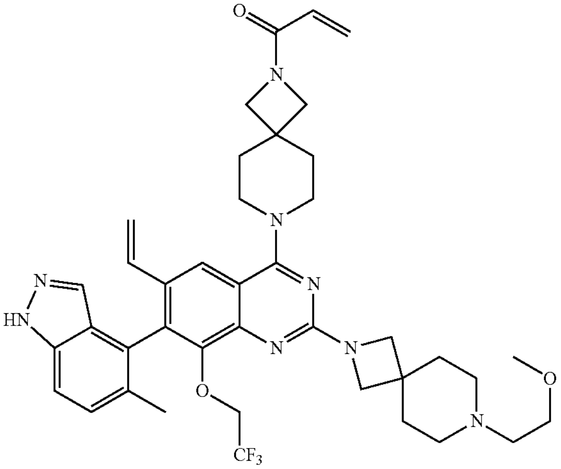
339
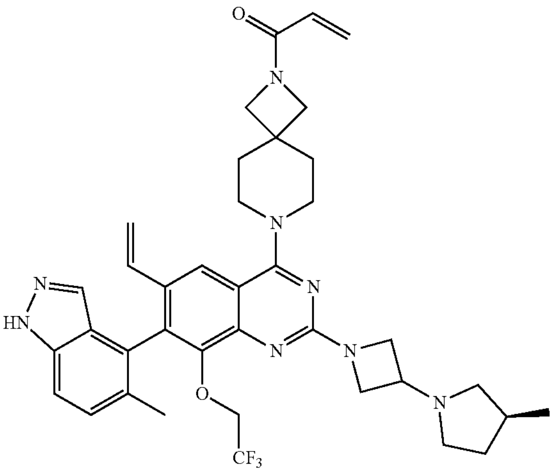
-continued
340
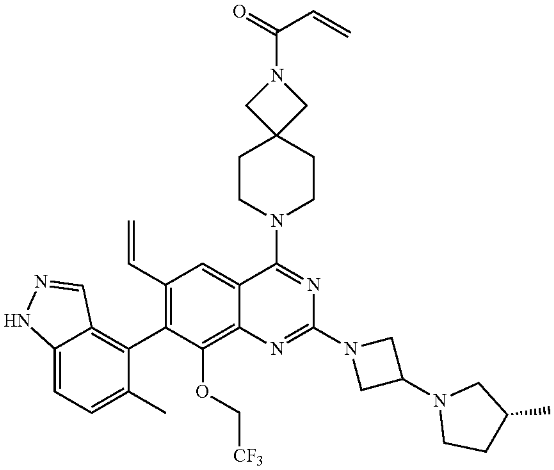
341
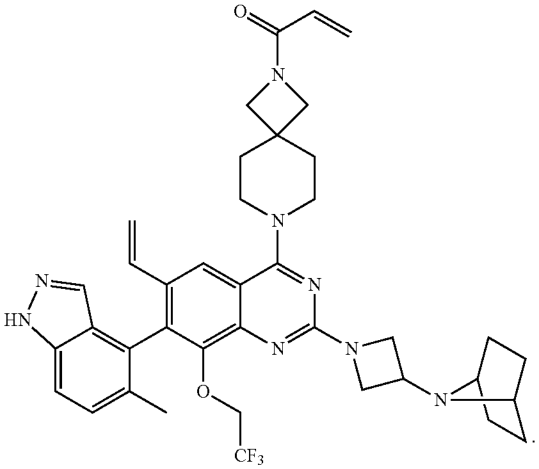
14. A compound with a structure as shown in general formula (3), optical isomers thereof, pharmaceutically acceptable salts thereof, hydrates thereof or solvates thereof:

-continued
(3)
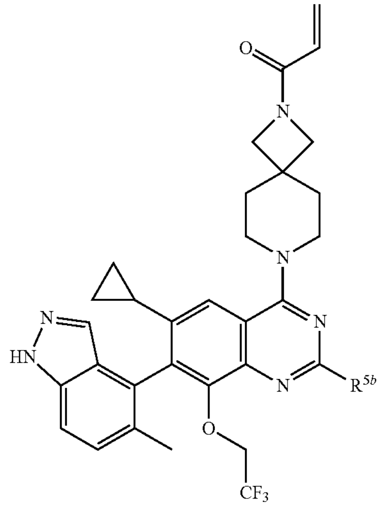
wherein, $R^{5b}$ is:
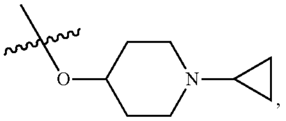
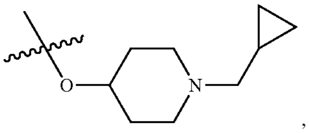
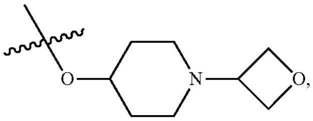
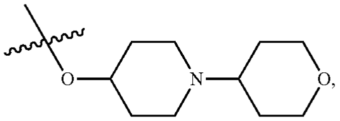
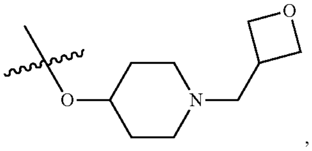
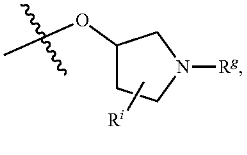
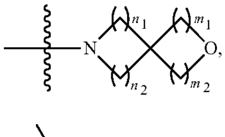
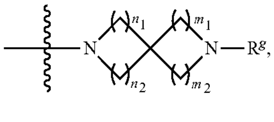
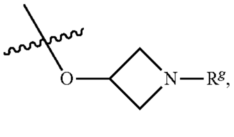
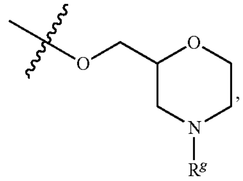
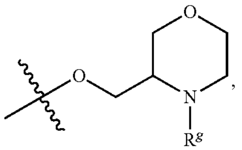
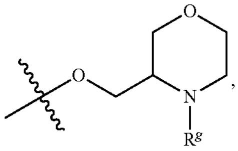
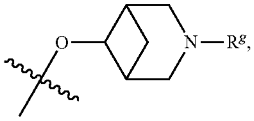
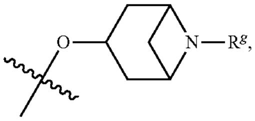
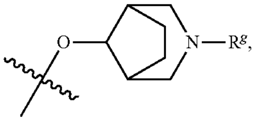
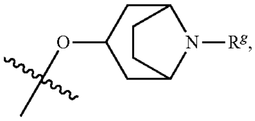
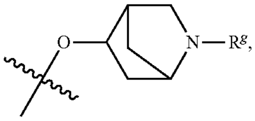
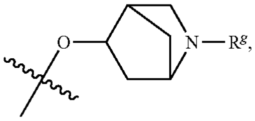
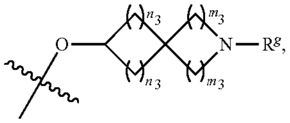
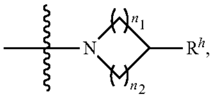
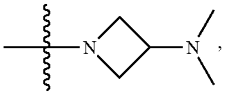
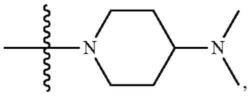
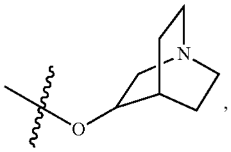
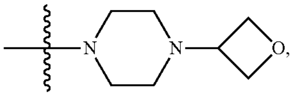
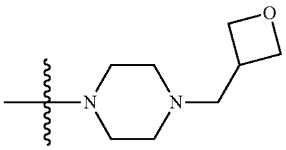
or
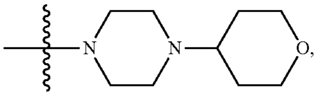
wherein $n_1$, $n_2$, $n_3$, $m_1$, $m_2$ and $m_3$ are independently integers of 1 or 2; $R^g$ is C1-C3 alkyl, C3-C6 cycloalkyl, (C1-C3) alkoxy-(C2-C3)alkyl-, (halogenated C1-C3)alkoxy-(C2-C3) alkyl-, (C3-C6) cycloalkyl-(C1-C3)alkyl-, heterocycloalkyl, heterocycloalkyl-(C1-C3)alkyl-, C1-C3 haloalkyl or cyano-substituted C1-C3 alkyl; $R^h$ is
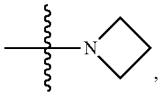
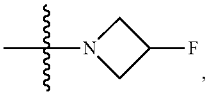
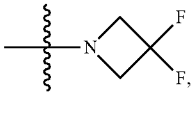
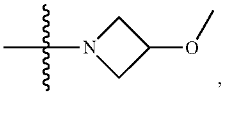
, -continued

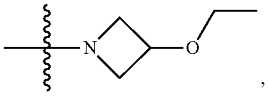, 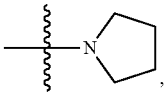,

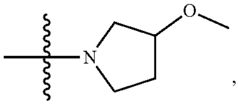, 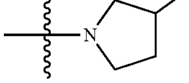,

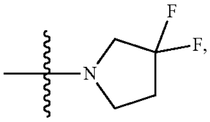 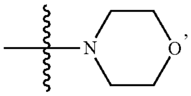

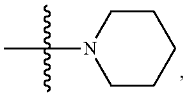, 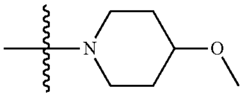,

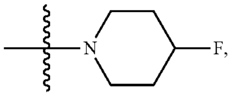 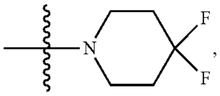,

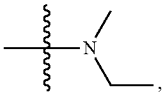, 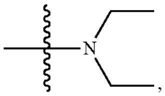, 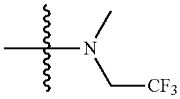 or

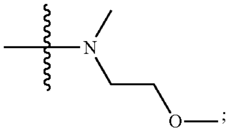

$R^i$ is H, halogen, methyl or cyano; or $R^{5b}$ is: H,

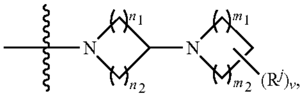

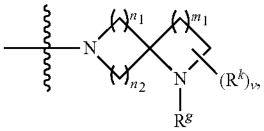

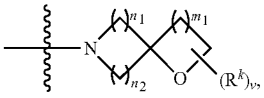

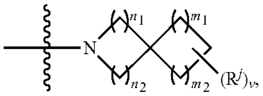

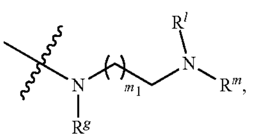 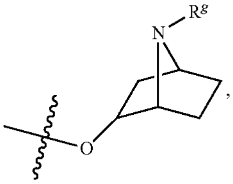,

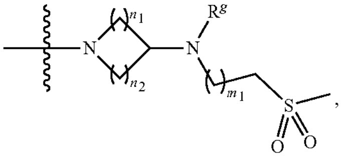

-continued

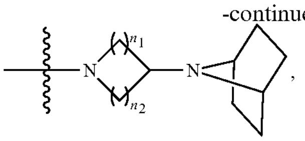, 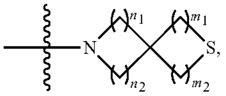

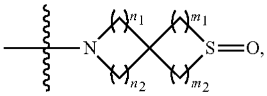 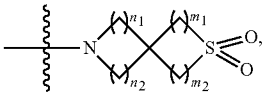

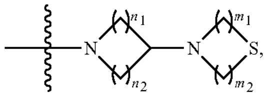

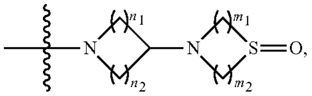

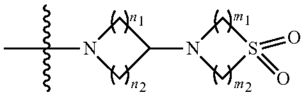 or

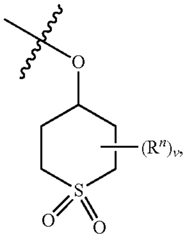

wherein $n_1$, $n_2$, $n_3$, $m_1$, $m_2$ and $m_3$ are independently integers of 1 or 2; v is an integer of 1, 2 or 3; $R^g$ is C1-C3 alkyl, C3-C6 cycloalkyl, (C1-C3)alkoxy-(C2-C3)alkyl-, (halogenated C1-C3)alkoxy-(C2-C3)alkyl-, (C3-C6) cycloalkyl-(C1-C3)alkyl-, heterocycloalkyl, heterocycloalkyl-(C1-C3) alkyl-, C1-C3 haloalkyl or cyano-substituted C1-C3 alkyl; $R^j$ is independently halogen, CN, $SO_2Me$, C1-C3 alkyl, C1-C3 haloalkyl, C1-C3 alkoxy, C1-C3 haloalkoxy, hydroxy-substituted C1-C3 alkyl, cyano-substituted C1-C3 alkyl, C3-C6cycloalkyl or

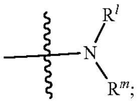

$R^k$ is independently halogen, CN, OH, C1-C3 alkyl, C1-C3 alkoxy, C3-C6 cycloalkyl or

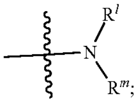

$R^n$ is independently halogen, CN, OH, C1-C3 alkyl, C1-C3 alkoxy or C3-C6 cycloalkyl, two $R^n$ groups, together with one carbon atom, form a spiro ring, or two $R^n$ groups, together with different carbon atoms, form a bridged ring; $R^1$ and $R^m$ are independently C1-C3 alkyl, C1-C3 haloalkyl, hydroxy-substituted C1-C3 alkyl, cyano-substituted C1-C3 alkyl, C3-C6 cycloalkyl, (C1-C3)alkoxy-(C2-C3)alkyl-, (halogenated C1-C3)alkoxy-(C2-C3)alkyl-, (C3-C6) cycloalkyl-(C1-C3)alkyl-, or $R^1$ and $R^m$, together with a N atom, form a 3-8 membered heterocycloalkyl group, wherein the 3-8 membered heterocycloalkyl group may be substituted with 1-3 groups selected from OH, halogen, cyano, C1-C3 alkyl, C3-C6 cycloalkyl, heterocycloalkyl, (C1-C3)alkoxy or (halogenated C1-C3)alkoxy.
15. The compound according to claim 14, wherein
$R^{5b}$ is: H,
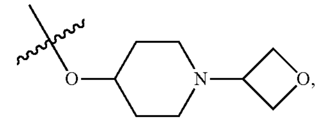
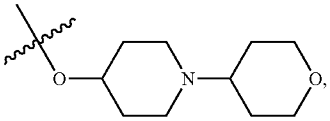
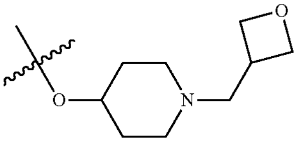
,
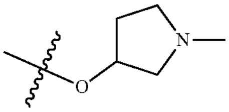
,
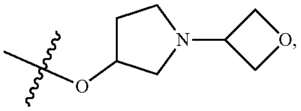
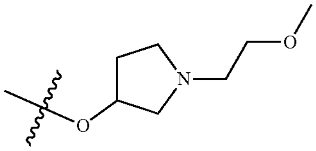
,
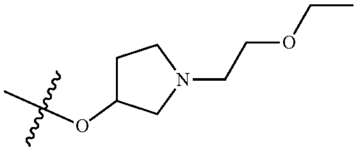
,
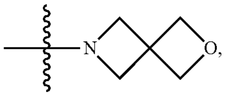
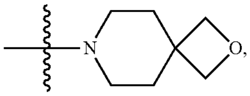
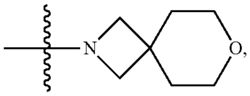
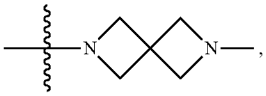
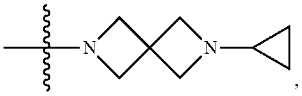
,
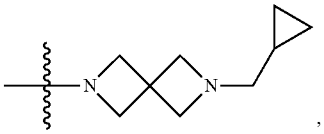
,
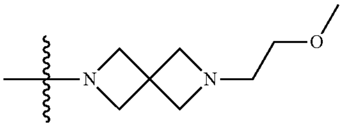
,
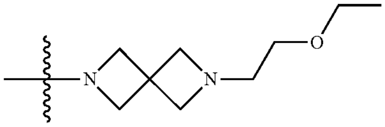
,
-continued
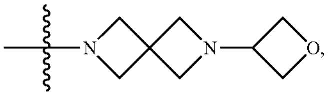
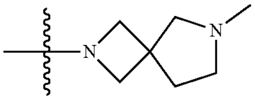
,
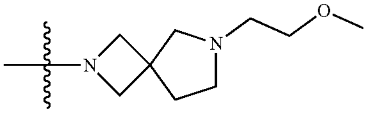
,
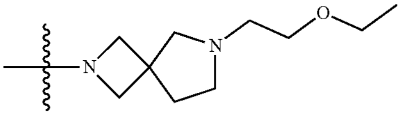
,
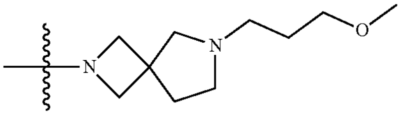
,
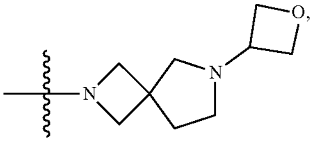
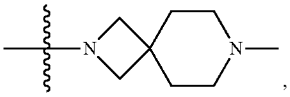
,
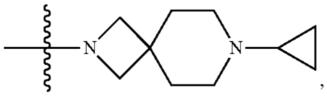
,
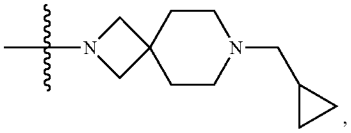
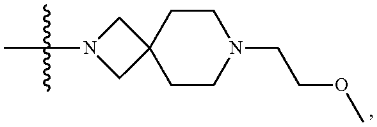
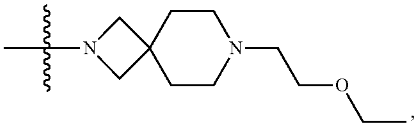
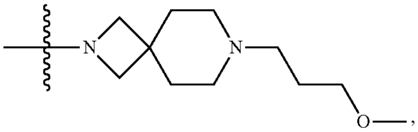
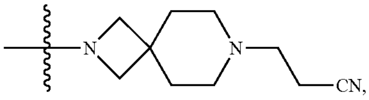
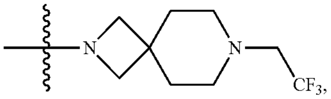
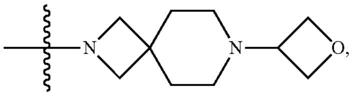

-continued
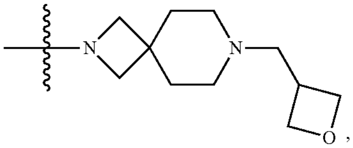,
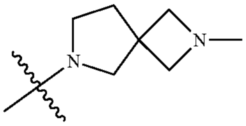,
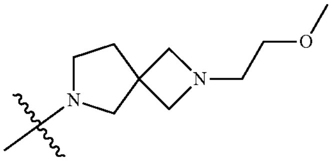,
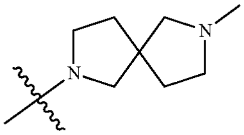,
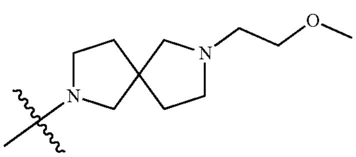,
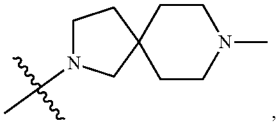,
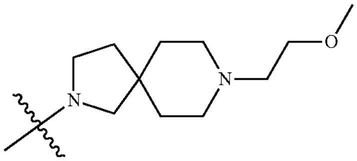,
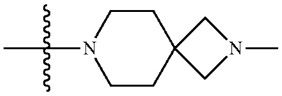,
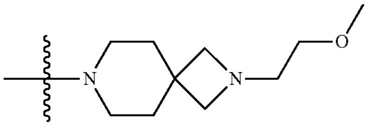,
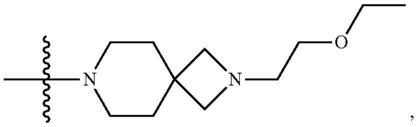,
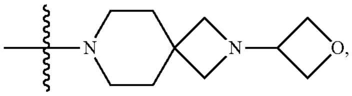,
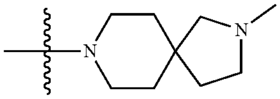,
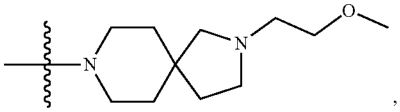,
-continued
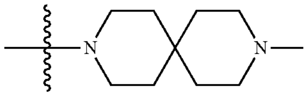,
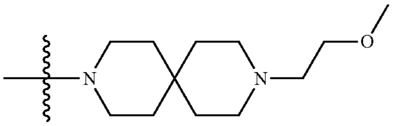,
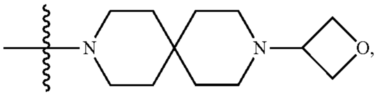,
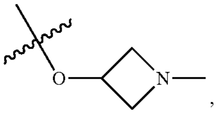, 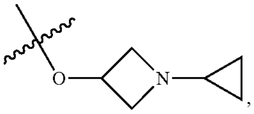,
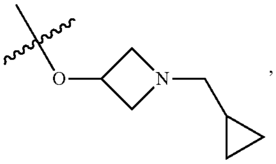, 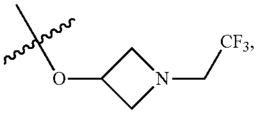,
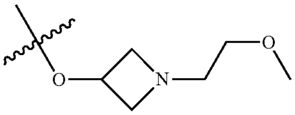,
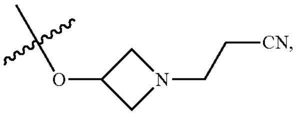,
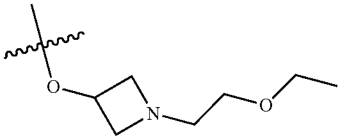,
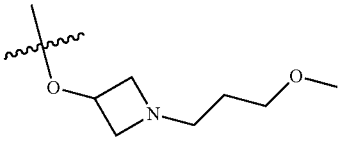,
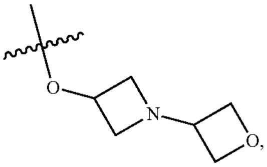,
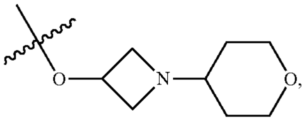,
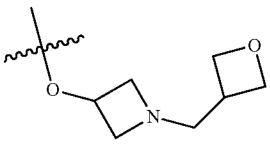, 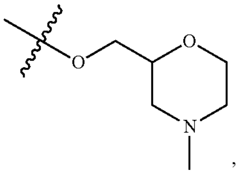, -continued
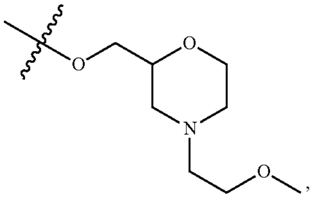,
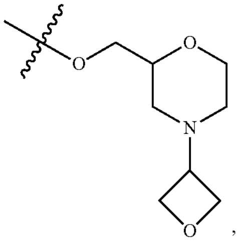,
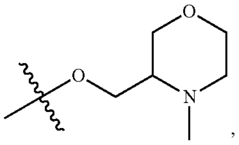,
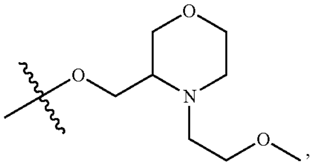,
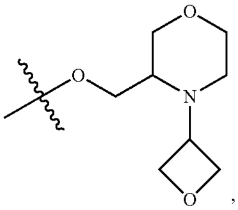,
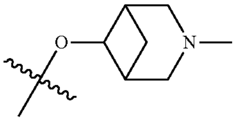,
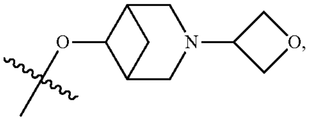,
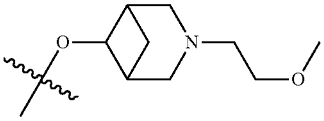,
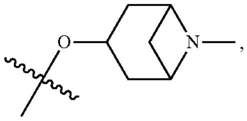,
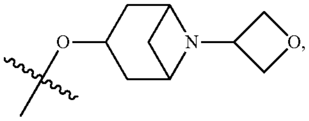,
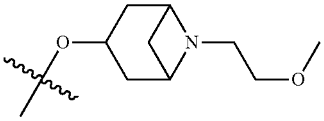,
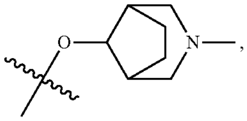,
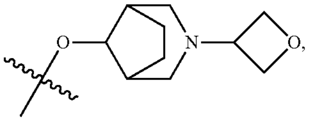,
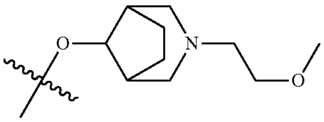,
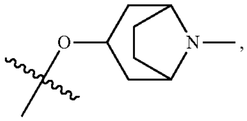,
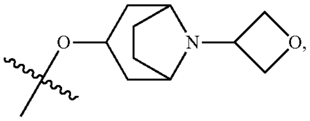,
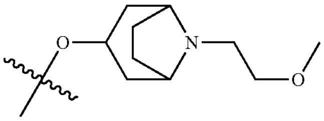,
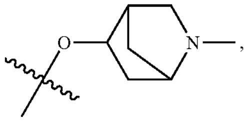,
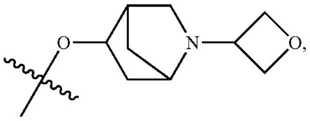,
-continued
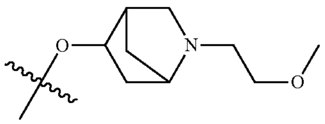,
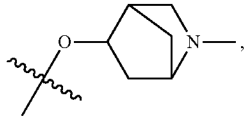,
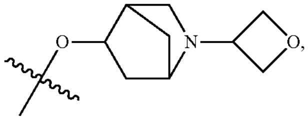,
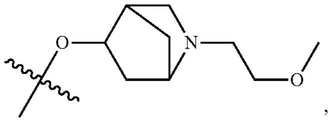,
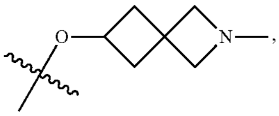,
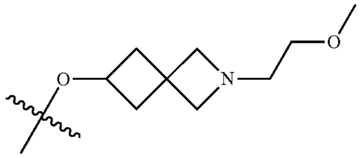,
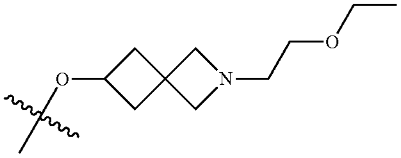,
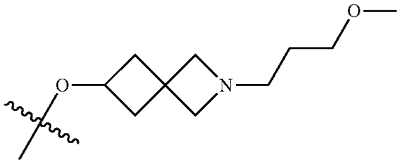,
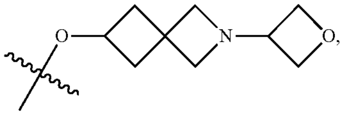,
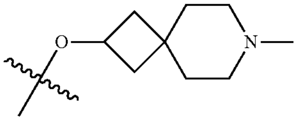,
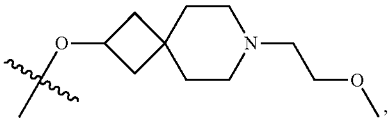,
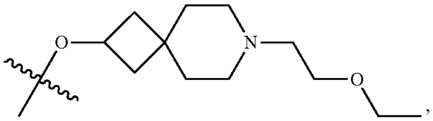,
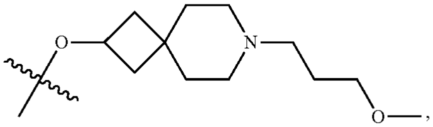,
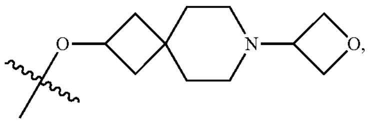, -continued
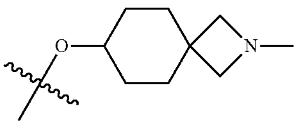,
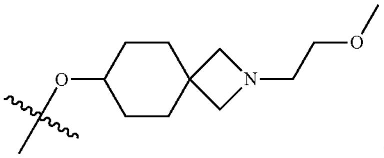,
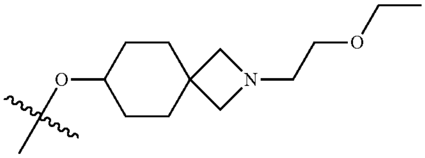,
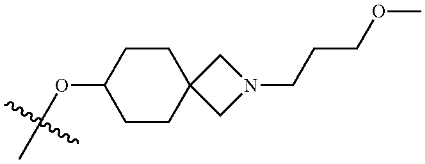,
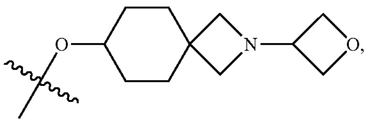,
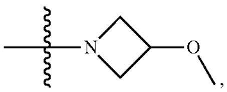, 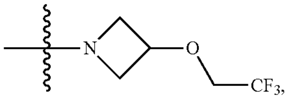,
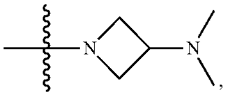, 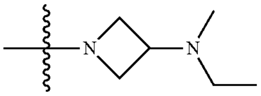,
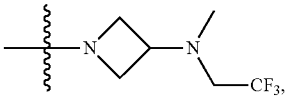,
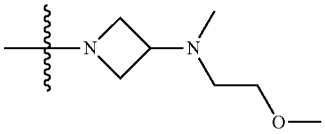,
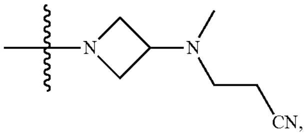,
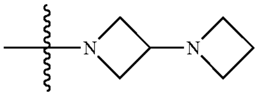,
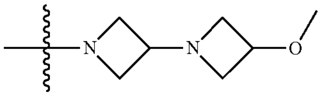,
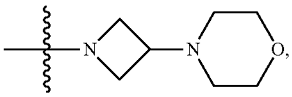, 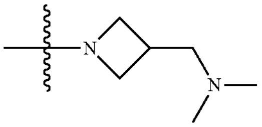,
-continued
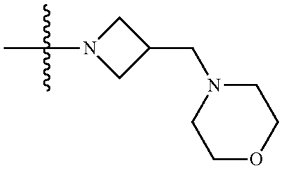, 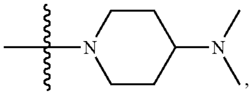,
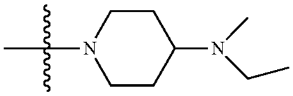,
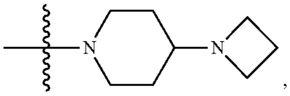,
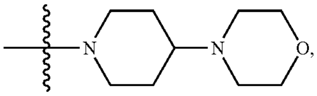,
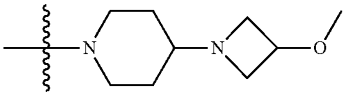,
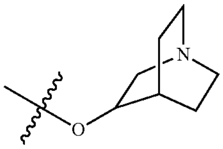, 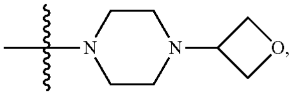,
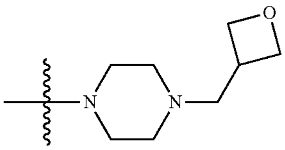,
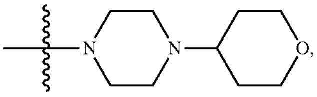,
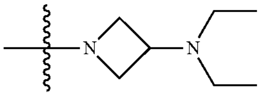, 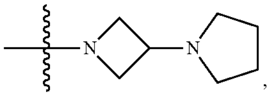,
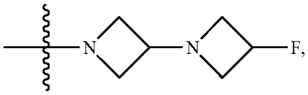,
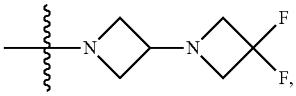,
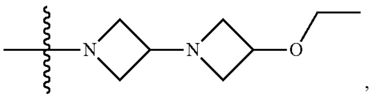,
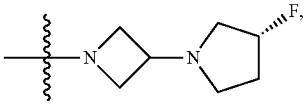,
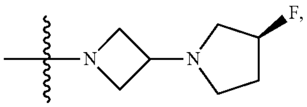,
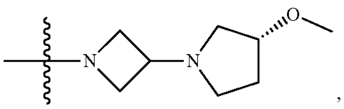, -continued
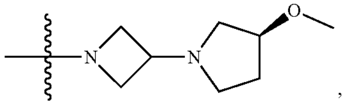
,
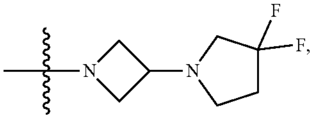
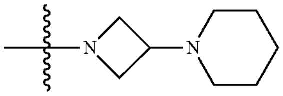
,
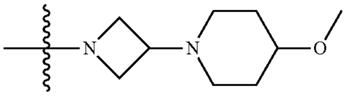
,
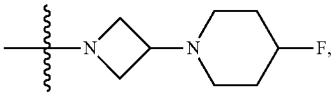
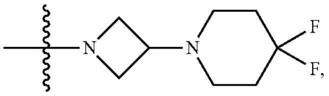
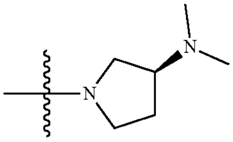
,
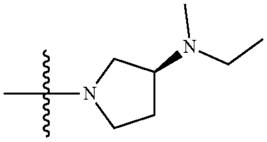
,
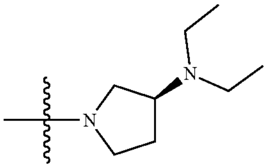
,
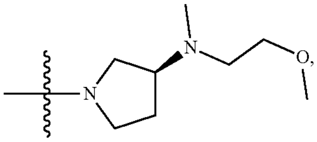
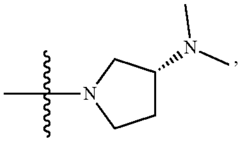
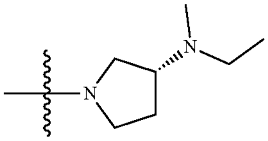
,
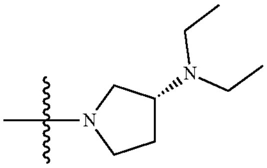
,
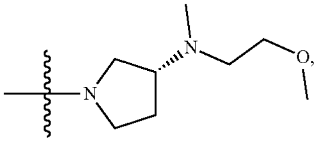
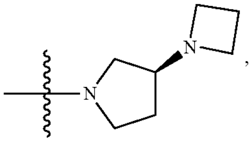
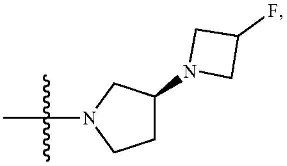
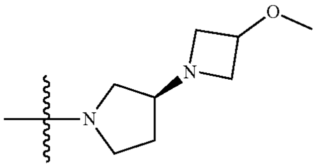
,
-continued
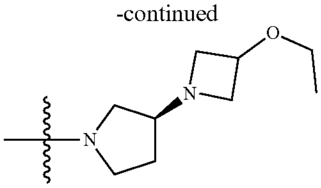
,
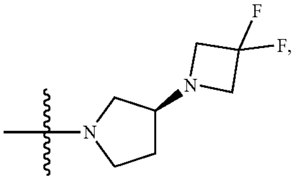
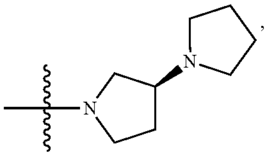
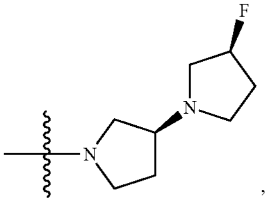
,
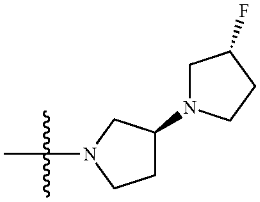
,
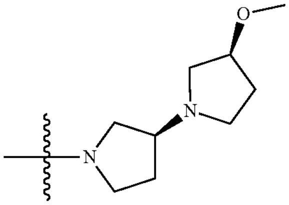
,
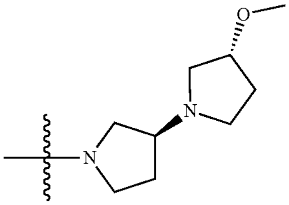
,
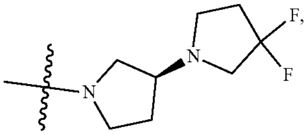
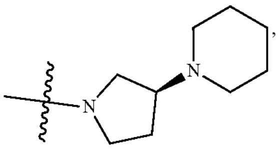
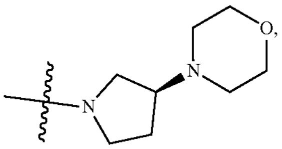
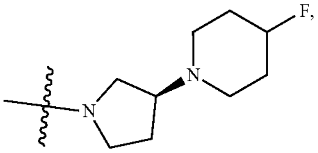
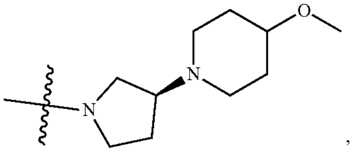
,
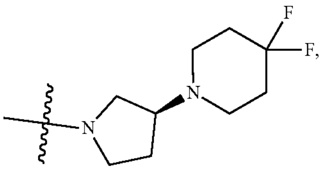

-continued
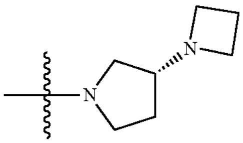
,
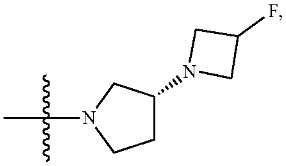
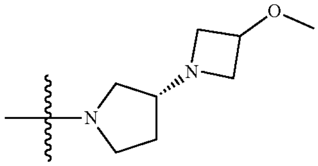
,
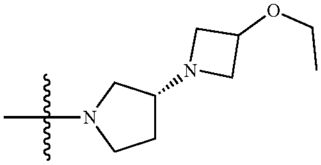
,
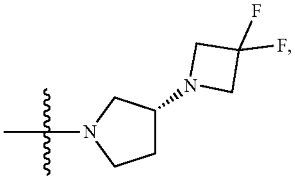
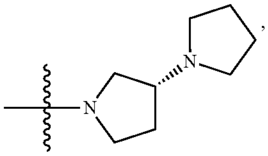
,
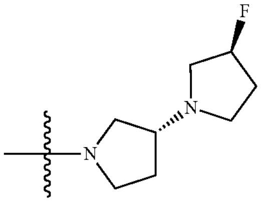
,
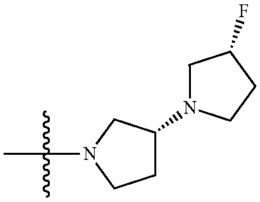
,
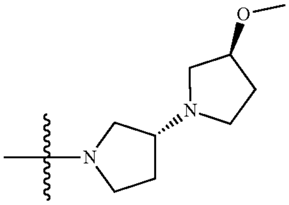
,
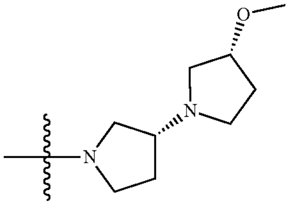
,
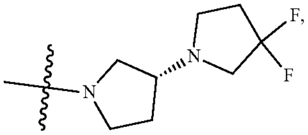
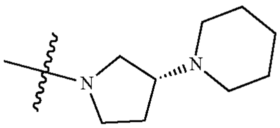
,
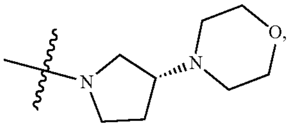
-continued
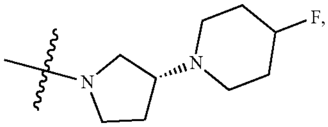
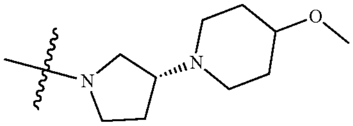
,
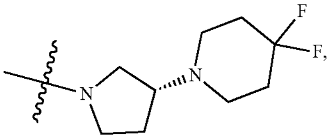
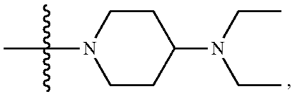
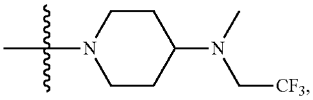
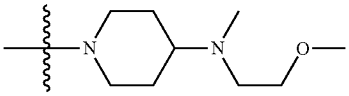
,
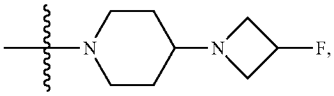
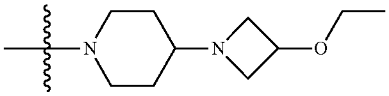
,
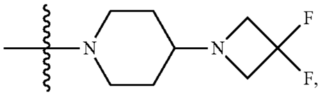
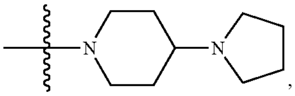
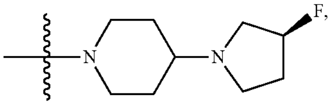
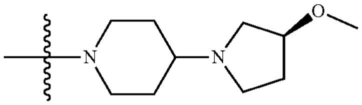
,
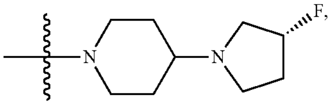
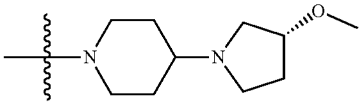
,
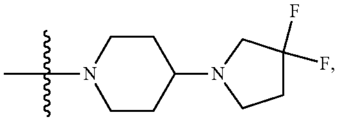
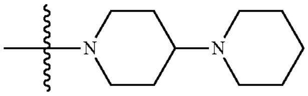
, -continued
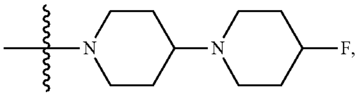
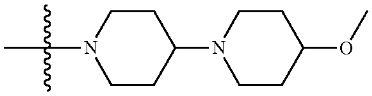
,
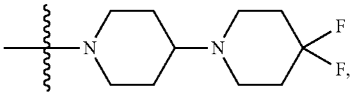
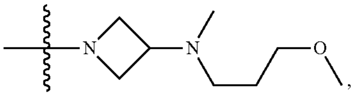
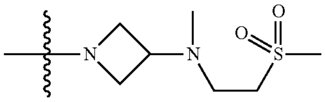
,
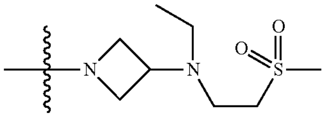
,
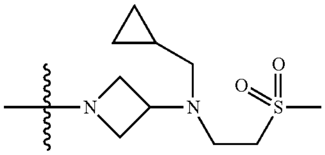
,
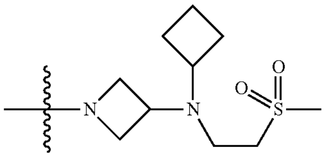
,
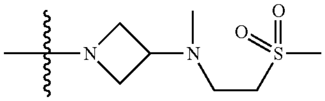
,
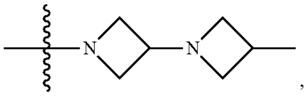
,
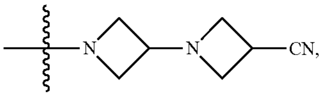
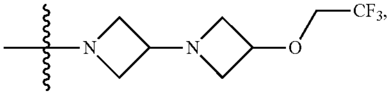
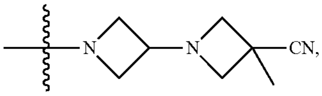
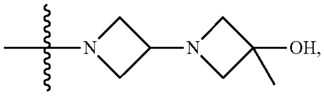
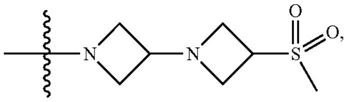
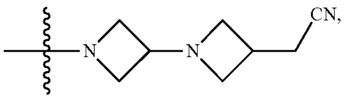
-continued
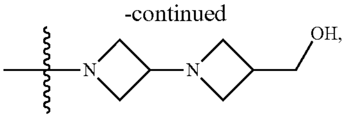
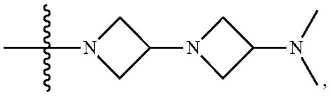
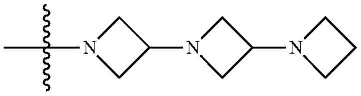
,
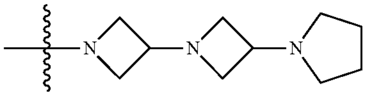
,
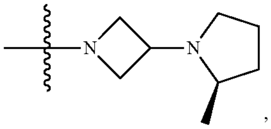
,
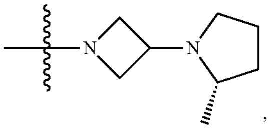
,
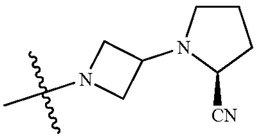
,
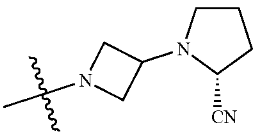
,
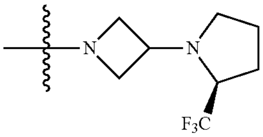
,
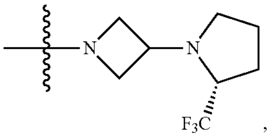
,
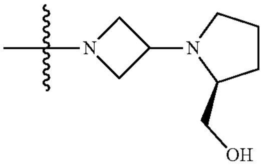
,
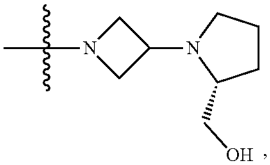
,
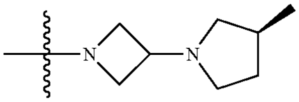
,
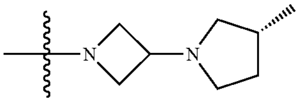
,
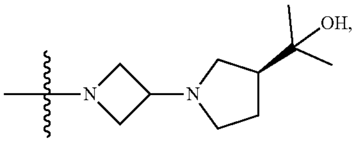
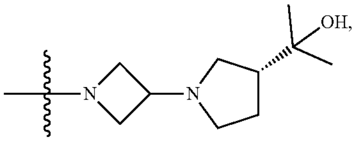
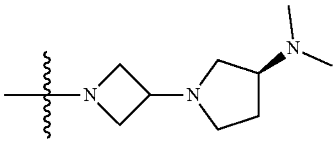
,
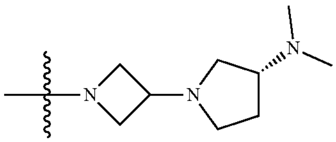
, -continued
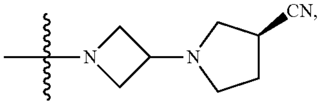
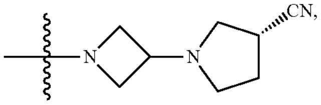
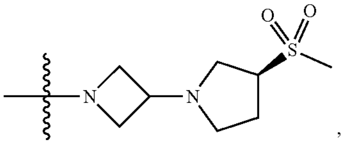
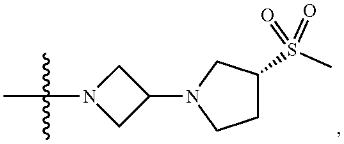
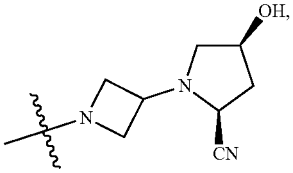
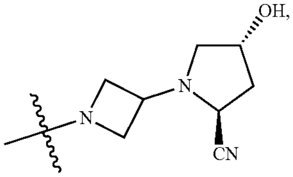
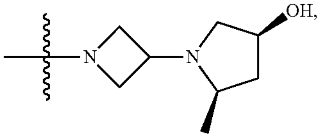
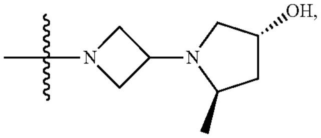
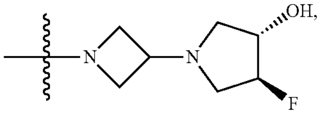
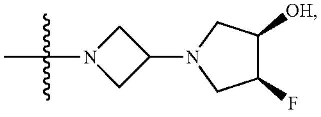
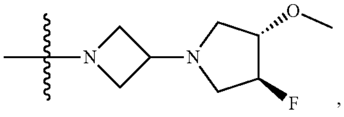
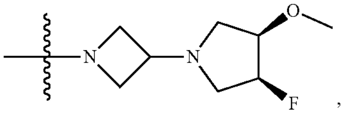
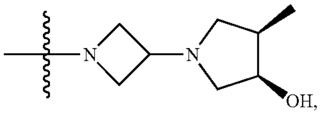
-continued
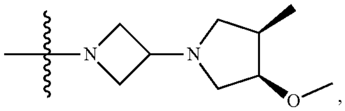
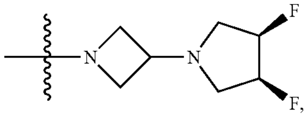
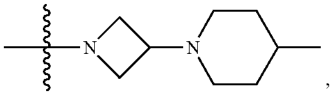
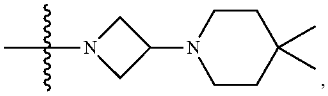
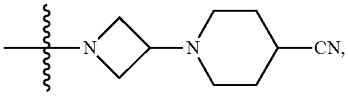
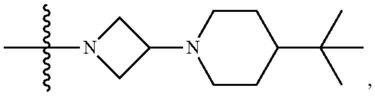
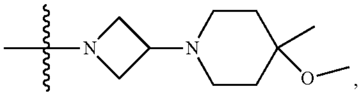
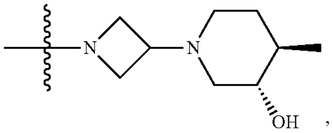
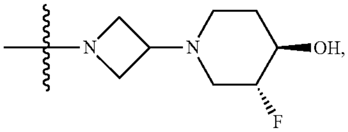
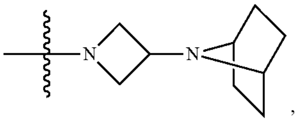
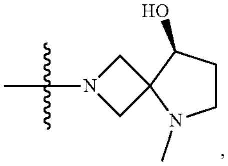
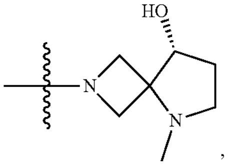
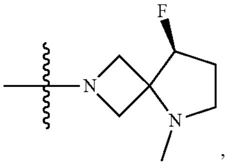
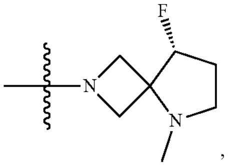
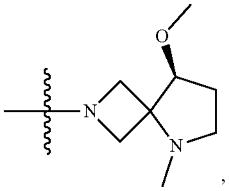
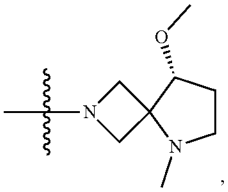
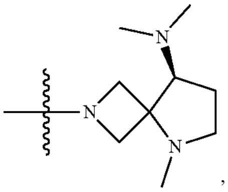

-continued
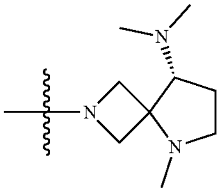,
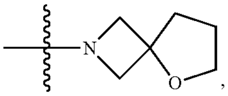,
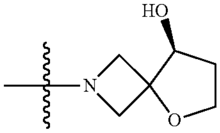,
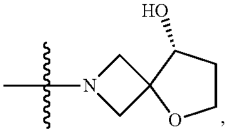,
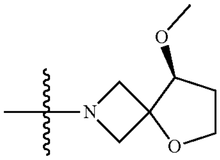,
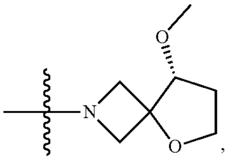,
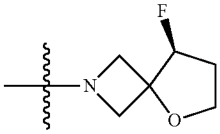,
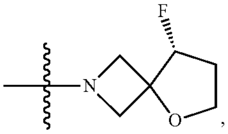,
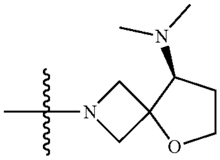,
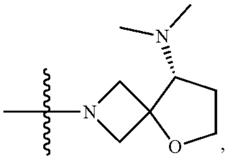,
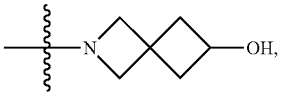,
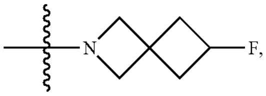,
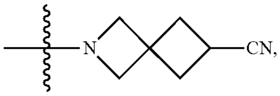,
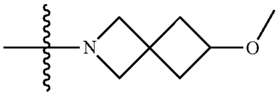,
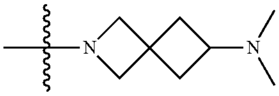,
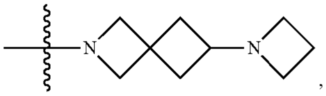,
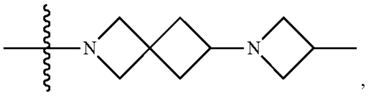,
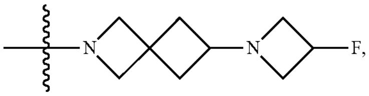,
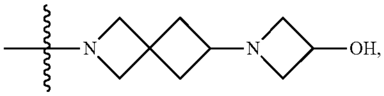,
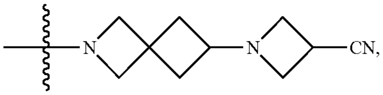,
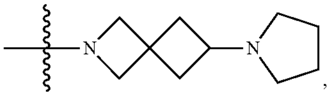,
-continued
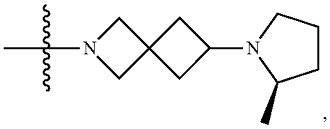,
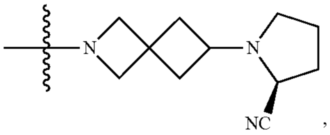,
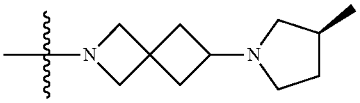,
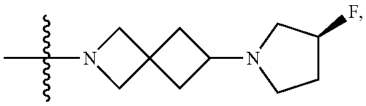,
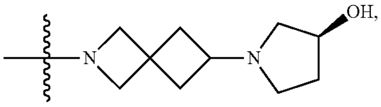,
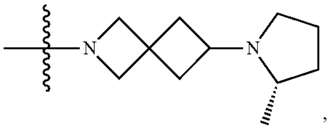,
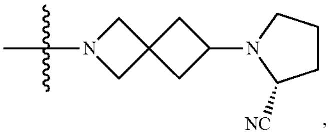,
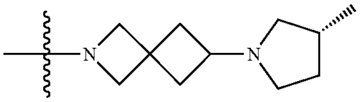,
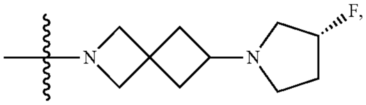,
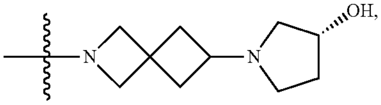,
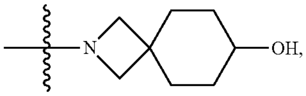,
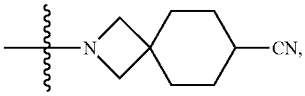,
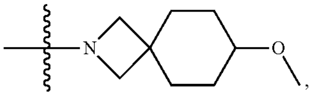,
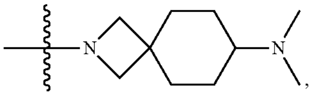,
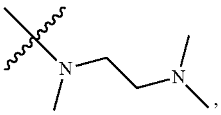,
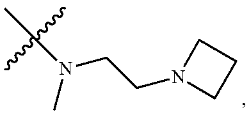, -continued
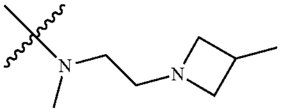
,
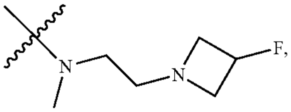
,
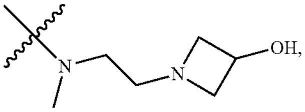
,
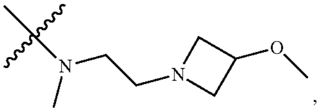
,
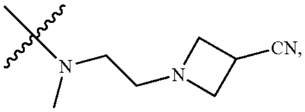
,
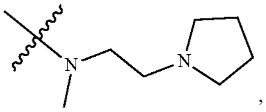
,
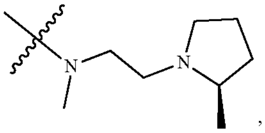
,
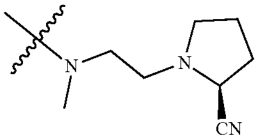
,
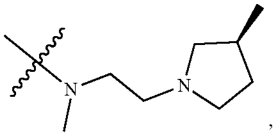
,
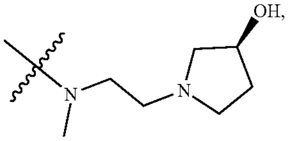
,
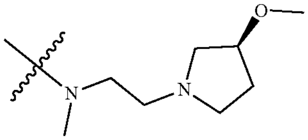
,
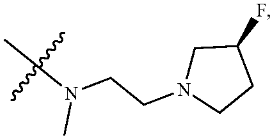
,
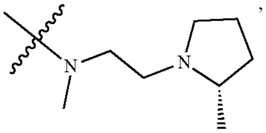
,
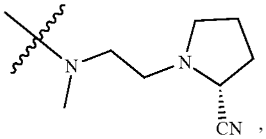
,
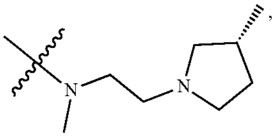
,
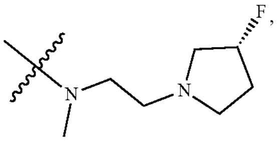
,
-continued
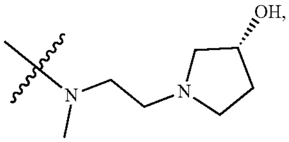
,
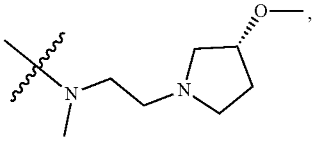
,
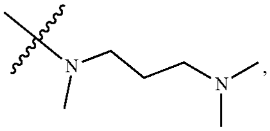
,
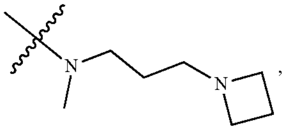
,
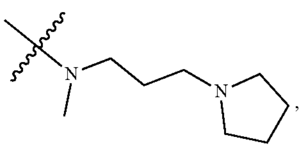
,
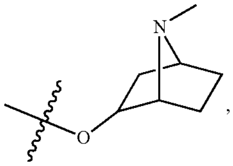
,
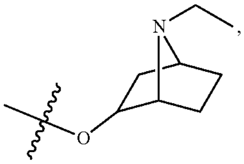
,
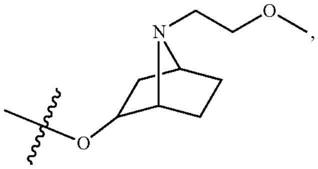
,
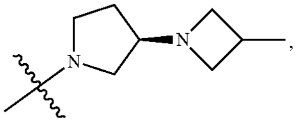
,
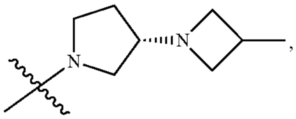
,
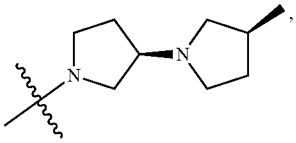
,
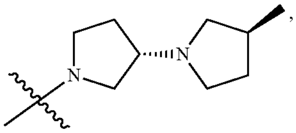
,
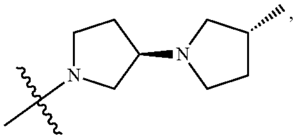
,
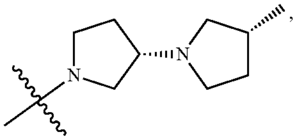
,
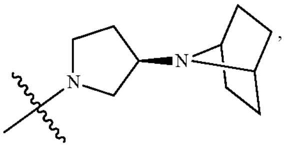
,
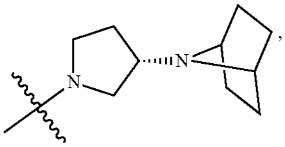
, -continued

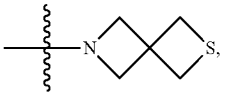

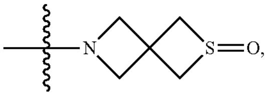

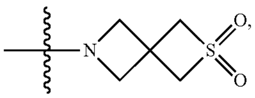

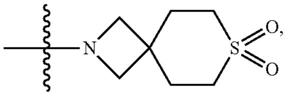

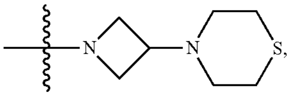

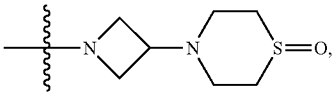

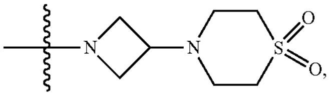

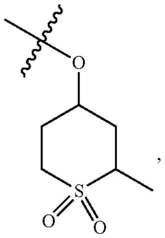

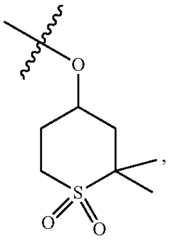

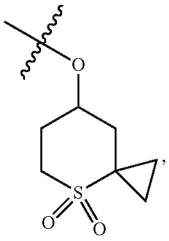

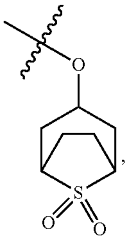

-continued

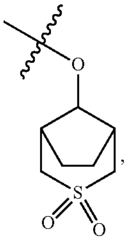

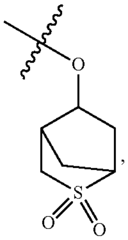

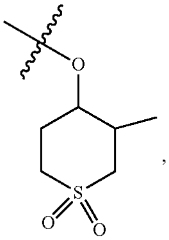

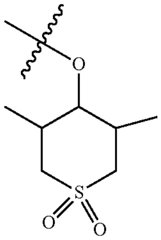

or

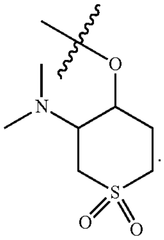

16. A pharmaceutical composition comprising a pharmaceutically acceptable excipient or carrier, and the compounds of general formula (1), the optical isomers thereof, the pharmaceutically acceptable salts thereof, the hydrates thereof or the solvates thereof according to claim 1 as active ingredients.

17. A pharmaceutical composition comprising a pharmaceutically acceptable excipient or carrier, and the compounds of general formula (2), the optical isomers thereof, the pharmaceutically acceptable salts thereof, the hydrates thereof or the solvates thereof according to claim 10 as active ingredients.

18. A pharmaceutical composition comprising a pharmaceutically acceptable excipient or carrier, and the compounds of general formula (3), the optical isomers thereof, the pharmaceutically acceptable salts thereof, the hydrates thereof or the solvates thereof according to claim 14 as active ingredients.

* * * * *